US009884832B2

(12) United States Patent
DeGrado et al.

(10) Patent No.: US 9,884,832 B2
(45) Date of Patent: Feb. 6, 2018

(54) INHIBITORS TARGETING DRUG-RESISTANT INFLUENZA A

(71) Applicant: The Trustees of The University of Pennsylvania, Philadelphia, PA (US)

(72) Inventors: William F. DeGrado, San Francisco, CA (US); Jizhou Wang, Eagleville, PA (US); Jun Wang, Philadelphia, PA (US); Hyunil Jo, Bryn Mawr, PA (US); Belgin Canturk, Burlington, NJ (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 14/363,116

(22) PCT Filed: Dec. 6, 2012

(86) PCT No.: PCT/US2012/068163

§ 371 (c)(1),
(2) Date: Jun. 5, 2014

(87) PCT Pub. No.: WO2013/086131

PCT Pub. Date: Jun. 13, 2013

(65) Prior Publication Data

US 2015/0191439 A1 Jul. 9, 2015

Related U.S. Application Data

(60) Provisional application No. 61/567,328, filed on Dec. 6, 2011, provisional application No. 61/705,310, filed on Sep. 25, 2012.

(51) Int. Cl.

| | |
|---|---|
| *C07D 413/04* | (2006.01) |
| *A61K 31/422* | (2006.01) |
| *C07D 271/06* | (2006.01) |
| *C07D 207/335* | (2006.01) |
| *A61K 31/417* | (2006.01) |
| *A61K 45/06* | (2006.01) |
| *C07C 215/50* | (2006.01) |
| *A61K 31/137* | (2006.01) |
| *A61K 31/155* | (2006.01) |
| *A61K 31/15* | (2006.01) |
| *C07C 211/38* | (2006.01) |
| *C07C 271/28* | (2006.01) |
| *A61K 31/27* | (2006.01) |
| *C07C 255/58* | (2006.01) |
| *A61K 31/26* | (2006.01) |
| *C07D 257/04* | (2006.01) |
| *A61K 31/41* | (2006.01) |
| *A61K 31/4245* | (2006.01) |
| *C07D 213/38* | (2006.01) |
| *A61K 31/4402* | (2006.01) |
| *C07D 233/88* | (2006.01) |

(Continued)

(52) U.S. Cl.

CPC .......... *C07D 271/06* (2013.01); *A61K 31/137* (2013.01); *A61K 31/15* (2013.01); *A61K 31/155* (2013.01); *A61K 31/26* (2013.01); *A61K 31/27* (2013.01); *A61K 31/41* (2013.01); *A61K 31/417* (2013.01); *A61K 31/4245* (2013.01); *A61K 31/4402* (2013.01); *A61K 31/505* (2013.01); *A61K 31/5377* (2013.01); *A61K 45/06* (2013.01); *C07C 211/27* (2013.01); *C07C 211/38* (2013.01); *C07C 211/49* (2013.01); *C07C 215/50* (2013.01); *C07C 217/58* (2013.01); *C07C 219/28* (2013.01); *C07C 233/43* (2013.01); *C07C 235/20* (2013.01); *C07C 237/30* (2013.01); *C07C 255/24* (2013.01); *C07C 255/58* (2013.01); *C07C 271/28* (2013.01); *C07C 317/32* (2013.01); *C07C 323/32* (2013.01); *C07D 207/335* (2013.01); *C07D 213/38* (2013.01); *C07D 233/88* (2013.01); *C07D 257/04* (2013.01); *C07D 261/08* (2013.01); *A61K 31/422* (2013.01); *C07C 2601/02* (2017.05); *C07C 2603/74* (2017.05); *C07D 413/04* (2013.01)

(58) Field of Classification Search

CPC ............................ A61K 31/422; C07D 413/04
See application file for complete search history.

(56) References Cited

U.S. PATENT DOCUMENTS

| | | | |
|---|---|---|---|
| 3,328,251 | A | 6/1967 | Smith |
| 3,567,829 | A | 3/1971 | Gagneux |

(Continued)

FOREIGN PATENT DOCUMENTS

| | | |
|---|---|---|
| WO | WO 1999/22735 | 5/1999 |
| WO | WO 2006/022454 | 3/2006 |

(Continued)

OTHER PUBLICATIONS

Registry No. 56916-85-9 (published Nov. 16, 1984).*

(Continued)

*Primary Examiner* — Robert Havlin
(74) *Attorney, Agent, or Firm* — Baker & Hostetler LLP

(57) ABSTRACT

Provided are compounds according to formula (Ia) or (Ib) as described herein, that are capable of modulating the activity of influenza viruses (e.g., influenza A virus), for example, via interaction with the M2 transmembrane protein, and other similar viroporins. Also provided are methods for treating an influenza A-affected disease state or infection comprising administering a composition comprising one or more compounds according to according to formulas (Ia') or (Ib), as described herein.

1 Claim, No Drawings

(51) Int. Cl.
| | |
|---|---|
| A61K 31/505 | (2006.01) |
| C07D 261/08 | (2006.01) |
| A61K 31/5377 | (2006.01) |
| C07C 211/27 | (2006.01) |
| C07C 211/49 | (2006.01) |
| C07C 217/58 | (2006.01) |
| C07C 219/28 | (2006.01) |
| C07C 233/43 | (2006.01) |
| C07C 235/20 | (2006.01) |
| C07C 237/30 | (2006.01) |
| C07C 255/24 | (2006.01) |
| C07C 317/32 | (2006.01) |
| C07C 323/32 | (2006.01) |

(56) References Cited

U.S. PATENT DOCUMENTS

| | | | | |
|---|---|---|---|---|
| 4,005,224 | A | | 1/1977 | Tankersley |
| 4,024,274 | A | * | 5/1977 | Druckrey et al. ............ 514/466 |
| 6,117,880 | A | | 9/2000 | Guo et al. |
| 7,145,037 | B2 | | 12/2006 | Makovec et al. |
| 7,951,816 | B2 | | 5/2011 | Kokubo et al. |
| 2008/0108050 | A1 | | 5/2008 | Montelione et al. |
| 2008/0293685 | A1 | | 11/2008 | Kong et al. |
| 2010/0063080 | A1 | | 3/2010 | Press et al. |
| 2010/0069420 | A1 | | 3/2010 | Degrado et al. |
| 2010/0093702 | A1 | * | 4/2010 | Barbay et al. ............ 514/217.06 |
| 2011/0065762 | A1 | | 3/2011 | Wang et al. |
| 2011/0065766 | A1 | | 3/2011 | Wang et al. |
| 2011/0236881 | A1 | | 9/2011 | Degrado et al. |
| 2011/0288111 | A1 | | 11/2011 | Degrado et al. |
| 2011/0294785 | A1 | | 12/2011 | Degrado et al. |
| 2012/0270917 | A1 | | 10/2012 | Degrado et al. |
| 2012/0283249 | A1 | * | 11/2012 | Lopez .................. A61K 31/167 514/220 |

FOREIGN PATENT DOCUMENTS

| | | |
|---|---|---|
| WO | WO 2007/136737 | 11/2007 |
| WO | WO2009153457 | * 12/2009 |
| WO | WO 2009153457 | * 12/2009 |
| WO | WO 2010/019712 | 2/2010 |
| WO | WO 2010/033339 | 3/2010 |
| WO | WO 2010/033340 | 3/2010 |
| WO | WO 2011/022191 | 2/2011 |
| WO | WO 2013/086131 | 6/2013 |

OTHER PUBLICATIONS

Machine Tranlation (partial) of WO2009153457 (Dec. 2009).*
Aldrich et al. (Journal of Medicinal Chemistry, 1971, vol. 14, No. 6, p. 535-543).*
Banik et al. (CAPLUS Abstract of: Indian Journal of Chemistry, Section B: Organic Chemistry Including Medicinal Chemistry (2001), 40B(11), 1134-1139).*
Cannon, "Analog Design" in Burger's Medicinal Chemistry and Drug Discovery, 6th ed. 2003, Wiley, pp. 687-714.*
Vaczi et al. (CAPLUS Abstract of: Acta Microbiologica Academiae Scientiarum Hungaricae (1973), 20(3), 241-7).*
Ma et al. (CAPLUS Abstract of: Science in China, Series B: Chemistry (2004), 47(4), 301-310).*
Duque et al.; "2. Inhibitors of the M2 channel of influenza A virus"; Recent Advances in Pharmaceutical Sciences; 2011; p. 35-64.
Abdel-Magid et al., "Reductive Amination of Aldehydes and Ketones with Sodium Triacetoxyborohydride. Studies on Direct and Indirect Reductive Amination Procedures", J. Org. Chem., May 31, 1996, 61(11), 3849-3862.
Acharya, et al., "Influenza A Virus Employs Water Clusters to Sequester Charge in a Biological Membrane", Submitted to Science on Jun. 9, 2009, 1-41.

Adcock et al, "Transmission of Ploar Substitutent Effects in the Adamantanering System as Monitored by 19F NMR", Magn, Reson. Chem., Mar. 1998, 36(3), 181-194.
Anderson, A. C., "The Process of Structure-Based Drug Design", Chemistry & Biology, Sep. 2003, 10(9), 787-797.
Balannik, et al., "Design and pharmacological characterization of inhibitors of amantadine-resistant mutants of the M2 ion channel of influenza A virus", Biochemistry, Dec. 22, 2009, 48(50), 11872-11882.
Betakova et al., "Influence of Residue 44 on the Activity of the M2 Proton Channel of Influenza A Virus", J. Gen. Virology, Jan. 2005, 86(Part 1), 181-184.
Braslau, et al., "The Synthesis and Evaluation of New a-Hydrogen Nitroxides for 'Living' Free Radical Polymerization", Synthesis—Stuttgart, Jun. 2005, 2005(9), 1496-1506.
Bright et al, "Incidence of Adamantane Resistance Among Influenza A (H3N2) Viruses Isolated Worldwide From 1994 to 2005: A Cause for Concern", Lancet, Oct. 1, 2005, 366(9492), 1175-1181.
Bright et al., "Adamantane Resistance Among Influenza A Viruses Isolated Early During the 2005-2006 Influenza Season in the United States", J. Am. Med. Assoc., Feb. 22, 2006, 295(8), 891-894.
Chang et al, "Membrane Permeabilization by Small Hydrophobic Nonstructural Proteins of Japanese Encephalitis Virus", Journal of Virology,1999, 73(8), 6257-6264.
Ciampor et al, "Influenza Virus M2 Protein and Haemagglutinin Conformation Changes During Intracellular Transport", Acta Virologica, 1995, 39, 171-181.
Deyde et al., "Surveillance of Resistance to Adamantanes Among Influenza A(H3N2) and A(H1N1) Viruses Isolated Worldwide", J. Infect. Dis., Jul. 15, 2007: Epub: Jun. 7, 2007, 196(2), 249-257.
Du et al., "Designing Inhibitors of M2 Proton Channel Against H1N1 Swine Influenza Virus", PLoS One, 2010, 5(2), 1-7.
Ettmayer, et al., "Lessons Learned From Marketed and Investigational Prodrugs", Journal of Medicinal Chemistry, May 6, 2004, 47(10), 2394-2404.
Fischer et al., "204. Die Synthese von 1 ,3-disubstituierten Adamantanen", Helv. Chim. Acta., Sep. 29, 1976, 59(6), 1953-1962 (English Abstract Included).
Flaugh et al., "Acid-catalyzed annelation of a-alkylaldehydes and a,l-unsaturated ketones. A one-pot synthesis of 4,4-dimethyl-2-cyclohexen-1-one", J. Org. Chem., Dec. 1980, 45(26), 5399-5400.
Geluk, et al., "Hydride Transfer Reactions of the Adamantyl Cation (IV): Synthesis of 1,4- and2,6-substituted Adamantanes by Oxidation With Sulfuric Acid", Recueil des Travaux Chimiques des Pays-Bas, 1971, 90(5), 516-520.
GenBank Accession No. AA046668, "Membrane ion channel M2 [Influenza A virus (NHong Kong/16/1968(H3N2))]", http://www.ncbi.nlm.nih.gov/protein/37933009?report=gpwithparts&log =segview#sequence37933009>, May 31, 2005, 4 pages (See Sequence on p. 3).
Gonzalez, M.E. and Carrasco, L., "Viroporins", FEBS Letters, Jul. 2003, 552, 28-34.
Grambas et al., "Influence of Amantadine Resistance Mutations on the pH Regulatory Function of the M2 Protein of Influenza A Viruses", Virology, Dec. 1992, 191(2), 541-549.
Greene et al., "Protective Groups in Organic Synthesis", Wiley & Sons 2nd edition, 1991, 1-405.
Han et al., "Biochemical and Functional Characterization of the Ebola Virus VP24 Protein: Implications for a Role in Virus Assembly and Budding", J. of Virology, Feb. 2003, 77(3), 1793-1800.
Han, Z. and Harty, R., "The NS3 Protein of Bluetongue Virus Exhibits Viroporin-like Properties", The Journal of Biological Chemistry, 279(41), Oct. 8, 2004, 43092-43097.
Han, J., "Advances in Characterization of Pharmaceutical Hydrates", Trends in Bio/PharmaceuticalIndustry, Mar. 2006, 25-29.
Hayden, et al., "Plaque Inhibition Assay for Drug Susceptibility Testing on Influenza Viruses", Antimicrobial Agents and Chemotherapy, May 1980, 17(5), 865-870.
Hayden, F.G., "Antiviral Resistance in Influenza Viruses—Implications for Management and Pandemic Response", N. Eng, J. Med., Feb. 23, 2006, 354(8), 785-788.

(56) References Cited

OTHER PUBLICATIONS

Higuchi et al., "Pro-drugs as Novel Drug Delivery Systems", A.C.S. Symposium Series, 14, Jun. 1, 1975, 1-115.
Hu, et al., "Backbone Structure of the Amantadine-Blocked Trans-Membrane Domain M2Proton Channel from Influenza A Virus", Biophysical Journal, Jun. 15, 2007, 92(12), 4335-4343.
International Patent Application No. PCT/US 12/68163: International Search Report and Written Opinion dated Feb. 15, 2013, 19 pages.
Ito et al, "Evolutionary Analysis of the Influenza A Virus M Gene With Comparison of the M1 and M2 Proteins", Journal of Virology, Oct. 1991, 65(10), 5491-5498.
Jefferson et al, "Antivirals for Influenza in Healthy Adults: Systematic Review", The Lancet, 2006, 367(9507), 303-313.
Jing et al., "Functional Studies Indicate Amantadine Binds to the Pore of the Influenza A Virus M2 Proton-Selective Ion Channel", PNAS USA, Aug. 5, 2008, 105(31), 10967-10972.
Kalir, et al., "2-phenyl-2-adamantanamine hydrochloride-[Tricyclo[3.3.1.13,7]decan-2-amine, 2-phenyl, hydrochloride]", Organic Syntheses, 1981, 60, 104-108.
Khan et al, "Workgroup, Planning, Biological and Chemical Terrorism: Strategic Plan for Preparedness and Response", MMWR, Apr. 21, 2000, 49(RR-4), 1-14.
Kiso et al, "Resistant Influenza A Viruses in Children Treated With Oseltamivir: Descriptive Study", The Lancet, Aug. 28, 2004, 364(9436), 759-765.
Kolocouris et al., "Interaction Between an Amantadine Analogue and the Transmembrane Portion of the Influenza A M2 protein in Liposomes Probed by 1H NMR Spectroscopy of the Ligand," J. Med. Chem., Sep. 23, 2004, 47(20), 4975-4978.
Kolocouris et al., "Design and Synthesis of Bioactive Adamantane Spiro Heterocycles", Bioorganic & Med. Chem. Lett., Aug. 2007, 17(15), 4358-4362.
Kurtz et al., "Growth Impairment Resulting From Expression of Influenza Virus M2 Protein in *Saccharomyces cerevisiae*: Identification of a Novel Inhibitor of Influenza Virus", Antimicrob. Agents Chemotherapy., Oct. 1995, 39(10), 2204-2209.
Lamb et al, "The Influenza A Virus M2 Ion Channel Protein and Its Role in the Influenza Virus Life Cycle, Receptor-Mediated Virus Entry into Cells", Cold Spring harbor, N.Y., Cold Spring Harbor Press, 1994, 303-321.
Lamb et al., "The Proton Selective Ion Channels of Influenza A and B Viruses", Cold Spring Harbor, NY, 1994, Chapter 3, 65-93.
Law et al., Salt-Bridge Dynamics Control Substrate-Induced Conformational Change in the Membrane Transporter GlpT, 2008, Journal of Molecular Biology, 378, 828-839.
Ma, et al., "Identification of the Functional Core of the Influenza A virus NM2 Proton-Selective Ion Channel", PNAS, Jul. 28, 2009, 106(30), 12283-12288.
Majerski, et al., "Rearrangement of Bridgehead Alcohols to Polycyclic Ketones by Fragmentation-cyclization: 4-protoadamantanone (tricyclo-[4.3.1.03,8]decan-4-one)", Organic Syntheses, 1979, 59, 147-152.
Morissette, et al., "High-Throughput Crystallization: Polymorphs, Salts, Co-Crystals and Solvates of Pharmaceutical Solids", Advanced Drug Delivery Reviews, Feb. 2004, 56(3), 275-300.
Moss, et al., "Conversion of 'Obstinate' Nitriles to Amidines by Garigipati's Reaction", Tetrahedron Letters, Nov. 27, 1995, 36(48), 8761-8764.
Nasr, et al., "Rigid Multivalent Scaffolds Based on Adamantane", J. Organic Chemistry, Feb. 1, 2008, 73(3), 1056-1060.
Okada, et al., "Protonation of Histidine and Histidine-Tryptophan Interaction in the Activation of the M2 ion Channel from Influenza A Virus", Biochemistry, May 22, 2001, 40(20), 6053-6060.
Palandoken, et al., "A facile synthesis of (tert-alkoxy)amines", Tetrahedron Letters, Sep. 26, 2005, 46(39), 6667-6669.
Pinto, et al., "A Functionally Defined Model for the M2 Proton Channel of Influenza A Virus Suggests a Mechanism for Its Ion Selectivity", PNAS, Oct. 14, 1997, 94(21), 11301-11306.

Ramaiah, et al., "1-Trifluoromethyi-1-Cyclohexanol-[Cyclohexanol, 1-(trifluoromethyl)-]", Organic Syntheses, 1995, 72, 232-240.
Remington's Pharmaceutical Sciences, 1ih edition, Mack Publishing Company, Easton, PA, 1985, 1418-1419.
Rohde et al., "Discovery and Metabolic Stabilization of Potent and Selective 2-amino-N-(adamant-2-yl) Acetamide 11beta-hydroxysteroid Dehydrogenase Type 1 Inhibitors", Journal of Med. Chem., Jan. 2007, 50(1), 149-164.
Schnell et al., Supplementary Information, 2005, Nature, 451(31): s1-s16.
Schnell et sl., "Structure and Mechanism of the M2 Proton Channel of Influenza A Virus", Nature, Jan. 31, 2008, 451(7178), 591-595.
Scholtissek et al., "How to Overcome Resistance of Influenza A Viruses Against Adamantine Derivatives", 1998, Antiviral Research, 37:83-95.
Schulz et al., "SSM-Based Electrophysiology", Methods, Oct. 2008, 46(2), 97-103.
Setaki et al., "Synthesis, Conformational Characteristics and Anti-Influenza Virus A Activity of Some 2-adamantylsubstituted Azacycles," Bioorganic Chemistry, Oct. 2006, 34(5), 248-273.
Shimbo, et al., "Ion Selectivity and Activation of the M2 Ion Channel of Influenza Virus", Biophysical Journal, Mar. 1996, 70(3), 1335-1346.
Stella et al., "Prodrugs: Challenges and Rewards Part 1", Biotechnology: Pharmaceutical Aspects, Springer, 2007, p. 24 of Part 1.1: A Case for Prodrugs.
Stella, Valentino J., "Prodrugs as Therapeutics", Expert Opinion on Therapeutic Patents, Mar. 2004, 14(3), 277-280.
Stouffer, et al., "Structural Basis for the Function and Inhibition of an Influenza Virus Proton Channel", Nature, Jan. 31, 2008, 451(7178), 596-599.
Stouffer, et al., "Structural Basis for the Function and Inhibition of an Influenza Virus Proton Channel", Nature Corrigendum, Mar. 20, 2008, 452(7185), 380.
Thiel, K. A., "Structure-Aided Drug Design's Next Generation", Nature Biotechnol., May 2004, 22(5), 513-519.
Testa, Bernard, "Prodrug Research: Futile or Fertile?", Biochemical Pharmacology, Dec. 2004, 68(11), 2097-2106.
Tian, et al., "Initial Structural and Dynamic Characterization of the M2 Protein Transmembrane and Amphipathic Helices in Lipid Bilayers", Protein Science, Nov. 2003, 12(11), 2597-2605.
Tu et al., "Characterization of Inhibition of M2 Ion Channel Activity by BL-1743, An Inhibitor of Influenza A virus", J. Viral., Jul. 1996, 70(7), 4246-4252.
Turner et al., "A facile route to imidazol-4-yl Anions and Their Reaction With Carbonyl Compounds", J. Org. Chem., Sep. 1991, 56(20), 5739-5740.
Van Niekerk, et al, "Membrane Association of African Horsesickness Virus Nonstructural Protein NS3 Determines Its Cytotoxicity", Virology, Jan. 20, 2001, 279(2), 499-508.
Venkataraman et al., "Chemical Rescue of Histidine Selectivity Filter Mutants of the M2 Ion Channel of Influenza A virus", J. Bioi. Chem., Jun. 3, 2005, 280(22), 21463-21472.
Vippagunta, et al., "Crystalline solids", Adv. Drug Delivery Reviews, May 2001, 48(1), 3-26.
Wang et al., "Discovery of Spiro-Piperidine Inhibitors and Their Modulation of the Dynamics of the M2 Proton Channel From Influenza A Virus", J. Am. Chem. Soc., Jun. 17, 2009; Epub Mar. 26, 2009, 131(23), 8066-8076.
Wareing, et al., "CXCR2 Is Required for Neutrophil Recruitment to the Lung During Influenza Virus Infection, But Is Not Essential for Viral Clearance", Viral Immunology, Sep. 2007, 20(3), 369-377.
Winum et al, "N-(tert-butoxycarbonyi)-N-[4-(dimethylazaniumylidene)-1,4-dihydropyridin-1-ylsulfonyl]azanide: A New Sulfamyolating Agent. Structure and Reactivity Toward Amines", Org. Letters, Jul. 12, 2001,3(14), 2241-2243.
Wolff, et al., "Metabolic Considerations in Prodrug Design", Burger's Medicinal Chemistry and Drug Discovery, John Wiley & Sons, 5[1] edition, vol. 1: Principles and Practice, Feb. 1995, 975-977.

(56) References Cited

OTHER PUBLICATIONS

Yi et al., "A Secondary Gate as a Mechanism for Inhibition of the M2 Proton Channel by Amantadine", J. Phys. Chem. B., Jul. 10, 2008; Epub May 14, 2008, 112(27), 7977-7799.
Zhao et al, "Discovery of Highly Potent Agents Against Influenza A Virus", European Journal of Medicinal Chemistry, 46(1), Jan. 2011, 52-57.

* cited by examiner

US 9,884,832 B2

INHIBITORS TARGETING DRUG-RESISTANT INFLUENZA A

CROSS-REFERENCE TO RELATED APPLICATIONS

This application is the National Stage of International Application No. PCT/US2012/068163, filed Dec. 6, 2012, which claims the benefit of and priority to U.S. Provisional Application No. 61/567,328, filed Dec. 6, 2011, and U.S. Provisional Application No. 61/705,310, filed Sep. 25, 2012, the entireties of which applications are incorporated herein by reference for any and all purposes.

GOVERNMENT RIGHTS

Research leading to the disclosed invention was funded, in part, by the U.S. National Institutes of Health, Bethesda, Md., GM56423 and AI74571 (both to William F. DeGrado). Accordingly, the United States Government may have rights in the invention described herein.

TECHNICAL FIELD

The present invention relates, in part, to methods of treatment, prevention, and inhibition of viral disorders. In one aspect, the present invention relates to inhibition of the M2 proton channel of influenza viruses (e.g., influenza A virus and/or influenza B virus) and other similar viroporins (e.g., VP24 of Ebola and Marburg viruses; and NS3 protein of Bluetongue). The present invention further relates to compounds which have been shown to possess antiviral activity, in particular, inhibiting the M2 proton channel (e.g., wild type and/or drug resistant influenza such as S31N or V27A influenza or other drug-resistant influenza strains) of influenza viruses and other similar viroporins.

BACKGROUND

Viroporins are a growing class of membrane proteins that are important for viral replication and packaging. These proteins also affect cellular functions, including the cell vesicle system, glycoprotein trafficking and membrane permeability (Gonzalez et al., FEBS Lett., 2003, 552, 28-34). The M2 proton channel is a prototype for this class of proteins that is essential to the survival of the virus (Lamb et al., Wimmer E, editor, Receptor-Mediated Virus Entry into Cells, Cold Spring Harbor, N. Y, Cold Spring Harbor Press, 1994, p. 303-321).

Viroporins are essential components of a variety of viruses including Ebola, Marburg, Bluetongue, African horse sickness, foot and mouth disease, and Japanese encephalitis viruses. In particular, Ebola and Marburg viruses pose a particularly serious threat to human health and are classified as category A biowarfare agents by the Center for Disease Control (CDC) (Khan et al., MMWR, 2000, 49, RR-4, 1-14). VP24 from Ebola and Marburg viruses is an integral membrane protein that possesses viroporin activity similar to the M2 protein (Han et al., J. Virology, 2003, 77(3), 793-800). NS3 protein of Bluetongue is a viroporin that is critical for virus release (Han et al., J. Biol. Chem., 2004, 279, 41, 43092-43097). In addition, picronaviruses (Gonzalez et al., FEBS Lett., 2003, 552, 28-34), African horse sickness, and Japanese encephalitis encode proteins with viroporin activity that play central roles in viral pathogenesis (Van Niekerk et al., Virology, 2001, 279, 499-508; Chang et al., J. Vivol., 1999, 73(8), 6257-6264).

Influenza viruses infect the upper and lower respiratory tracts and cause substantial morbidity and mortality annually. Influenza A viruses, which also infect a wide number of avian and mammalian species, pose a considerable public health burden with epidemic and pandemic potential. Influenza together with complications of the virus is consistently among the top 10 common causes of death, ranking higher than some other much more widely publicized killers, such as the HIV virus that causes AIDS. It is estimated that in annual influenza epidemics, 5-15% of the world's population contracts influenza, resulting in an estimated 3-5 million cases of severe illness and 250,000 to 500,000 deaths around the world from influenza-associated complications. In the U.S., 10%-20% of the population is infected with the flu every year, with an average 0.1% mortality. The flu causes 36,000 deaths each year in the U.S., and 114,000 hospitalizations. The cost of influenza epidemics to the U.S. economy is estimated at $3-15 billion. Approximately 20% to 40% of the world's population became ill during the catastrophic "Spanish" flu pandemic in 1918, which killed an estimated 40 to 50 million people worldwide and 675,000 people in the United States. The "Asian" flu pandemic of 1957 resulted in the deaths of approximately 69,800 people in the United States and 2.0 to 7.4 million worldwide. The H1N1 swine flu pandemic in 2009 has caused about 3,000 deaths worldwide to date.

Tamiflu (oseltamivir), which targets neuraminidase protein, is the only remaining orally administered anti-flu drug on the market and resistance to the drug is increasing with oseltamivir-resistant viruses arising during clinical use of the drug in children (Kiso et al., Lancet, 2004, 364, 759-65). Oseltamivir has been used for treatment of infected individuals and although it is FDA-approved for prophylaxis its usefulness for prophylactic treatment has been questioned in a recent systematic analysis of data from 51 controlled trials (Jefferson et al., Lancet, 2006, 367, 303-13). Thus, there is an immediate need to develop additional agents that inhibit the M2 proton channel and its drug-resistant forms, and in particular the most prevalent mutant form, S31N, but also in others including L26, V27, A30, and G34.

Influenza A and B viruses each encode a small oligomeric integral membrane protein, M2 of influenza A virus and BM2 of influenza B virus, each of which is a proton-selective ion channel. The M2 protein plays an important role during the early and late stages of the viral life cycle. Early in the cycle, the virus enters cells by receptor-mediated endocytosis, which places the virus into endosomal vesicles. Proton-pumping ATP-ases in the endosomal membrane lower the internal pH, which triggers the fusion of the viral envelope with the endosomal membrane and the release of the viral RNA into the cytoplasm. However, unless the inside of the virus is acidified prior to fusion, the RNA remains encapsulated by a matrix protein known as M1 (Ito et al., J. Virol., 1981, 65, 5491-8). The M2 protein provides a conduit for passage of protons into the interior of the virus, thereby promoting the dissociation of RNA from its matrix protein. This is a crucial step in uncoating of the virus and exposing its content to the cytoplasm of the host cell. In some strains of influenza A virus, the M2 protein is also important for equilibrating the pH of the lumen of the Golgi apparatus with the cytoplasm, thus preventing a premature conformational change in the viral hemagglutinin at the wrong time and in the wrong place (Ciampor et al., Acta Virologica, 1995, 39, 171-181) Inhibition of M2 at this later stage of the viral life cycle prevents viral maturation and release from the host cell.

Several features make M2 an excellent target for an anti-influenza drug. It is essential and present in all known isolates of influenza A virus, and it is already validated as a drug target. Although a variety of mutations occur naturally and can be isolated in cell culture, one mutant in particular, S31N, predominates in more than 98% of the transmissible resistant viral strains isolated from patients in the last decade (Bright et al., *Lancet*, 2005, 366, 1175-1181).

Thus, there is a great need for additional compositions and methods of treatment based on the use of antiviral compounds against key viral pathogens and, optionally, less prone to the development of resistance by those pathogens. Moreover, there is a great need for additional compositions and methods of treatment based on the use of antiviral compounds that are effective in the treatment of viral pathogens that have already developed resistance to existing antiviral agents. In particular, there is a great need for effective compositions and methods for the treatment of viral infections such as influenza, Ebola, Marburg, bluetongue, foot and mouth disease, African horse sickness, and Japanese encephalitis (including the strains that have already developed resistance to existing antiviral agents). The present invention is directed to these and other important ends

SUMMARY

The present invention provides, in part, compounds according to formula (Ia):

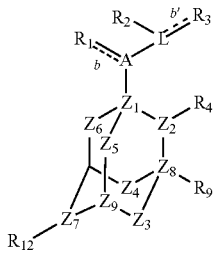

(Ia)

or a stereoisomer, isotopically substituted analogue, or pharmaceutically acceptable salt thereof, wherein each of the variable groups are as defined herein.

The present disclosure also pertains to compounds according to formula (Ib):

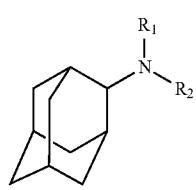

(Ib)

or a stereoisomer, isotopically substituted analogue, or pharmaceutically acceptable salt thereof, wherein $R_1$ and $R_2$ are as defined herein.

Also disclosed are compounds according to formula (Ia'):

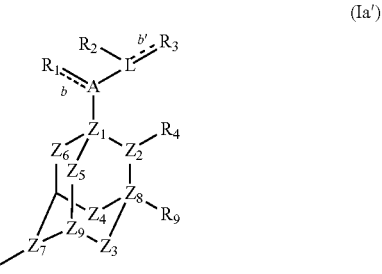

(Ia')

or a stereoisomer, isotopically substituted analogue, or pharmaceutically acceptable salt thereof, wherein each of the variable groups are as defined herein.

The present invention is also directed to methods for treating a viral infection, such as influenza (e.g., wild-type influenza, such as wild-type influenza A or B, or one or more mutant varieties of influenza such as S31N influenza), Ebola, Marburg, bluetongue, foot and mouth disease, African horse sickness, and Japanese encephalitis, in a patient (including a human or an animal) comprising administering to a subject in need thereof a composition comprising a compound of Formula (Ia), (Ia'), or (Ib) as defined herein.

Also provided are compositions comprising a compound according to Formula (Ia), (Ia'), or (Ib) or a pharmaceutically acceptable salt, isotopically substituted analogue, or stereoisomer thereof, and a pharmaceutically acceptable carrier, diluent, or excipient.

DETAILED DESCRIPTION OF ILLUSTRATIVE EMBODIMENTS

The present invention may be understood more readily by reference to the following detailed description taken in connection with the accompanying figures and examples, which form a part this disclosure. It is to be understood that this invention is not limited to the specific products, methods, conditions or parameters described and/or shown herein, and that the terminology used herein is for the purpose of describing particular embodiments by way of example only and is not intended to be limiting of the claimed invention.

The disclosures of each patent, patent application, and publication cited or described in this document are hereby incorporated herein by reference, in their entirety.

As employed above and throughout the disclosure, the following terms and abbreviations, unless otherwise indicated, shall be understood to have the following meanings.

In the present disclosure the singular forms "a," "an," and "the" include the plural reference, and reference to a particular numerical value includes at least that particular value, unless the context clearly indicates otherwise. Thus, for example, a reference to "a compound" is a reference to one or more of such compounds and equivalents thereof known to those skilled in the art, and so forth. Furthermore, when indicating that a certain chemical moiety "may be" X, Y, or Z, it is not intended by such usage to exclude in all instances other choices for the moiety; for example, a statement to the effect that $R_1$ "may be alkyl, aryl, or amino" does not necessarily exclude other choices for $R_1$, such as halo, aralkyl, and the like.

When values are expressed as approximations, by use of the antecedent "about," it will be understood that the particular value forms another embodiment. As used herein, "about X" (where X is a numerical value) preferably refers to ±10% of the recited value, inclusive. For example, the phrase "about 8" refers to a value of 7.2 to 8.8, inclusive; as another example, the phrase "about 8%" refers to a value of 7.2% to 8.8%, inclusive. Where present, all ranges are inclusive and combinable. For example, when a range of "1 to 5" is recited, the recited range should be construed as including ranges "1 to 4", "1 to 3", "1-2", "1-2 & 4-5", "1-3 & 5", and the like. In addition, when a list of alternatives is positively provided, such listing can be interpreted to mean that any of the alternatives may be excluded, e.g., by a negative limitation in the claims. For example, when a range of "1 to 5" is recited, the recited range may be construed as including situations whereby any of 1, 2, 3, 4, or 5 are negatively excluded; thus, a recitation of "1 to 5" may be construed as "1 and 3-5, but not 2", or simply "wherein 2 is not included." In another example, when a listing of possible substituents including "hydrogen, alkyl, and aryl" is provided, the recited listing may be construed as including situations whereby any of "hydrogen, alkyl, and aryl" is negatively excluded; thus, a recitation of "hydrogen, alkyl, and aryl" may be construed as "hydrogen and aryl, but not alkyl", or simply "wherein the substituent is not alkyl".

As used herein, the terms "component," "composition of compounds," "compound," "drug," "pharmacologically active agent," "active agent," "therapeutic," "therapy," "treatment," or "medicament" are used interchangeably herein to refer to a compound or compounds or composition of matter which, when administered to a subject (human or animal) induces a desired pharmacological and/or physiologic effect by local and/or systemic action.

The abbreviations in the specification correspond to units of measure, techniques, properties, or compounds as follows: "min" means minute(s), "g" means gram(s), "mg" means milligram(s), "µg" means microgram(s), "eq" means equivalent(s), "h" means hour(s), "µL" means microliter(s), "mL" means milliliter(s), "mM" means millimolar, "M" means molar, "mmol" or "mmole" means millimole(s), "cm" means centimeters, "SEM" means standard error of the mean, and "IU" means International Units. "$IC_{50}$ value" or "$IC_{50}$" means dose of the compound which results in 50% alleviation or inhibition of the observed condition or effect.

As used herein, "alkyl" refers to an optionally substituted, saturated straight, or branched, hydrocarbon radical having from about 1 to about 20 carbon atoms (and all combinations and subcombinations of ranges and specific numbers of carbon atoms therein). Where appropriate, "alkyl" can mean "alkylene"; for example, if X is —$R_1R_2$, and $R_1$ is said to be "alkyl", then "alkyl" may correctly be interpreted to mean "alkylene".

"Amino" refers to —$NH_2$ and may include one or more substituents that replace hydrogen. "Amino" is used interchangeably with amine and is also intended to include any pharmaceutically acceptable amine salts. For example, amino may refer to —$NH^+(X)(Y)Cl^-$, wherein X and Y are preferably and independently hydrogen or alkyl, wherein alkyl may include one or more halo substitutions.

As used herein, "aryl", "arene", and "aromatic" each refer to an optionally substituted, saturated or unsaturated, monocyclic, polycyclic, or other homo-, carbo- or heterocyclic aromatic ring system having from about 3 to about 50 ring members (and all combinations and subcombinations of ranges and specific numbers of carbon atoms therein), with from about 5 to about 10 ring atom members being preferred. Such moieties encompass (include) "heteroaryl" and "heteroarene" as defined infra. Where appropriate, "aryl" can mean "arene"; for example, if X is —$R_1R_2$, and $R_1$ is said to be "aryl", then "aryl" may correctly be interpreted to mean "arene".

As used herein, "alkenyl" refers to an alkyl radical having from about 2 to about 20 carbon atoms and one or more double bonds (and all combinations and subcombinations of ranges and specific numbers of carbon atoms therein), wherein alkyl is as previously defined. In some embodiments, it is preferred that the alkenyl groups have from about 2 to about 6 carbon atoms. Alkenyl groups may be optionally substituted.

As used herein, "aralkyl" refers to alkyl radicals bearing one or more aryl substituents and having from about 4 to about 50 carbon atoms (and all combinations and subcombinations of ranges and specific numbers of carbon atoms therein), wherein aryl and alkyl are as previously defined. In some preferred embodiments, the alkyl moieties of the aralkyl groups have from about 1 to about 4 carbon atoms. In other preferred embodiments, the alkyl moieties have from about 1 to about 3 carbon atoms. Aralkyl groups may be optionally substituted.

"Alkylamino" signifies alkyl-(NH)—, wherein alkyl is as previously described and NH is defined in accordance with the provided definition of amino. "Arylamino" represents aryl-(NH)—, wherein aryl is as defined herein and NH is defined in accordance with the provided definition of amino. Likewise, "aralkylamino" is used to denote aralkyl-(NH)—, wherein aralkyl is as previously defined and NH is defined in accordance with the provided definition of amino. "Alkylamido" refers to alkyl-CH(=O)NH—, wherein alkyl is as previously described. "Alkoxy" as used herein refers to the group R—O— where R is an alkyl group, and alkyl is as previously described. "Aralkoxy" stands for R—O—, wherein R is an aralkyl group as previously defined. "Alkylsulfonyl" means alkyl-$SO_2$—, wherein alkyl is as previously defined. "Aminooxy" as used herein refers to the group amino-(O)—, wherein amino is defined as above. "Aralkylaminooxy" as used herein is used to denote aryl-akyl-aminooxy-, wherein aryl, alkyl, and aminooxy are respectively defined as provided previously.

As used herein, "alkylene" refers to an optionally branched or substituted bivalent alkyl radical having the general formula —$(CH_2)_n$—, where n is 1 to 10. Non-limiting examples include methylene, trimethylene, pentamethylene, and hexamethylene.

"Alkyleneamino" refers to —$(CH_2)_n$—NH—, where n is 1 to 10 and wherein the bivalent alkyl radical may be optionally branched or substituted, and the amino group may include one or more substituents that replace hydrogen.

As used herein, "heteroaryl" or "heteroarene" refers to an aryl radical wherein in at least one of the rings, one or more of the carbon atom ring members is independently replaced by a heteroatom group selected from the group consisting of S, O, N, and NH, wherein aryl is as previously defined. Heteroaryl/heteroarene groups having a total of from about 3 to about 14 carbon atom ring members and heteroatom ring members are preferred. Likewise, a "heterocyclic ring" is an aryl radical wherein one or more of the carbon atom ring members may be (but are not necessarily) independently replaced by a heteroatom group selected from the group consisting of S, O, N, and NH. Heterocyclic rings having a total from about 3 to about 14 ring members and heteroatom ring members are preferred, but not necessarily present; for example, "heterocyclohexyl" may be a six-membered aryl radical with or without a heteroatom group.

"Halo" and "halogen" each refers to a fluoro, chloro, bromo, or iodo moiety, with fluoro, chloro, or bromo being preferred.

"Haloalkyl" signifies halo-alkyl- wherein alkyl and halo, respectively, are as previously described.

The phrase reading "[moiety] is absent" may mean that the substituents to which the moiety is attached are directly attached to each other.

Typically, substituted chemical moieties include one or more substituents that replace hydrogen. As used herein, a "substituent" or "substitution" refers to halo (e.g., F, Cl, Br, I), alkyl, cycloalkyl, alkylcycloalkyl, cycloalkylalkyl, alkenyl, alkynyl, aralkyl, aryl, heteroaryl, heteroaralkyl, spiroalkyl, heterocycloalkyl, hydroxyl (—OH), nitro (—$NO_2$), cyano (—CN), amino (—$NH_2$), —N-substituted amino (—NHR"), —N,N-disubstituted amino (—N(R")R"), oxo (=O), carboxy (—COOH), —O—C(=O)R", —C(=O)R", —OR", —C(=O)OR", -(alkylene)-C(=O)—OR", —NHC(=O)R", aminocarbonyl (—C(=O)$NH_2$), —N-substituted aminocarbonyl (—C(=O)NHR"), —N,N-disubstituted aminocarbonyl (—C(=O)N(R")R"), thiol, thiolato (—SR"), sulfonic acid (—$SO_3$H), phosphonic acid (—$PO_3$H), —P(=O)(OR")OR", —S(=O)R", —S(=O)$_2$R", —S(=O)$_2$$NH_2$, —S(=O)$_2$ NHR", S(=O)$_2$NR"R", —NHS(=O)$_2$R", —NR"S(=O)$_2$R", —$CF_3$, —$CF_2$$CF_3$, —NHC(=O)NHR", —NHC(=O)NR"R", —NR"C(=O)NHR", —NR"C(=O)NR"R", or —NR"C(=O)R". In relation to the aforementioned substituents/substitutions, each moiety R" can be, independently, any of H, alkyl, cycloalkyl, alkenyl, aryl, aralkyl, heteroaryl, or heterocycloalkyl, for example.

As used herein, the terms "treatment" or "therapy" (as well as different word forms thereof) includes preventative (e.g., prophylactic), curative or palliative treatment.

As employed above and throughout the disclosure the term "effective amount" refers to an amount effective, at dosages, and for periods of time necessary, to achieve the desired result with respect to the treatment of the relevant disorder, condition, or side effect. It will be appreciated that the effective amount of components of the present invention will vary from patient to patient not only with the particular compound, component or composition selected, the route of administration, and the ability of the components to elicit a desired response in the individual, but also with factors such as the disease state or severity of the condition to be alleviated, hormone levels, age, sex, weight of the individual, the state of being of the patient, and the severity of the pathological condition being treated, concurrent medication or special diets then being followed by the particular patient, and other factors which those skilled in the art will recognize, with the appropriate dosage ultimately being at the discretion of the attendant physician. Dosage regimens may be adjusted to provide the improved therapeutic response. An effective amount is also one in which any toxic or detrimental effects of the components are outweighed by the therapeutically beneficial effects. As an example, the compounds useful in the methods of the present invention are administered at a dosage and for a time such that the level of activation and adhesion activity of platelets is reduced as compared to the level of activity before the start of treatment.

"Pharmaceutically acceptable" refers to those compounds, materials, compositions, and/or dosage forms which are, within the scope of sound medical judgment, suitable for contact with the tissues of human beings and animals without excessive toxicity, irritation, allergic response, or other problem complications commensurate with a reasonable benefit/risk ratio.

Within the present invention, the disclosed compounds may be prepared in the form of pharmaceutically acceptable salts. "Pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like. These physiologically acceptable salts are prepared by methods known in the art, e.g., by dissolving the free amine bases with an excess of the acid in aqueous alcohol, or neutralizing a free carboxylic acid with an alkali metal base such as a hydroxide, or with an amine.

Compounds described herein throughout, can be used or prepared in alternate forms. For example, many amino-containing compounds can be used or prepared as an acid addition salt. Often such salts improve isolation and handling properties of the compound. For example, depending on the reagents, reaction conditions and the like, compounds as described herein can be used or prepared, for example, as their hydrochloride or tosylate salts. Isomorphic crystalline forms, all chiral and racemic forms, N-oxide, hydrates, solvates, and acid salt hydrates, are also contemplated to be within the scope of the present invention.

Certain acidic or basic compounds of the present invention may exist as zwitterions. All forms of the compounds, including free acid, free base and zwitterions, are contemplated to be within the scope of the present invention. It is well known in art that compounds containing both amino and carboxy groups often exist in equilibrium with their zwitterionic forms. Thus, any of the compounds described herein throughout that contain, for example, both amino and carboxy groups, also include reference to their corresponding zwitterions.

"Hydrate" refers to a compound of the present invention which is associated with water in the molecular form, i.e., in which the H—OH bond is not split, and may be represented, for example, by the formula R.$H_2$O, where R is a compound of the invention. A given compound may form more than one hydrate including, for example, monohydrates (R.$H_2$O) or polyhydrates (R.n$H_2$O wherein n is an integer >1) including, for example, dihydrates (R.2$H_2$O), trihydrates (R.3$H_2$O), and the like, or hemihydrates, such as, for example, R.$n_{1/2}$$H_2$O, R.$n_{1/3}$$H_2$O, R.$n_{1/4}$$H_2$O and the like wherein n is an integer.

"Solvate" refers to a compound of the present invention which is associated with solvent in the molecular form, i.e., in which the solvent is coordinatively bound, and may be represented, for example, by the formula R.(solvent), where R is a compound of the invention. A given compound may form more than one solvate including, for example, monosolvates (R.(solvent)) or polysolvates (R.n(solvent)) wherein n is an integer >1) including, for example, disolvates (R.2(solvent)), trisolvates (R.3(solvent)), and the like, or hemisolvates, such as, for example, R.n/2(solvent), R.n/3(solvent), R.n/4(solvent) and the like wherein n is an integer. Solvents herein include mixed solvents, for example, methanol/water, and as such, the solvates may incorporate one or more solvents within the solvate.

"Acid hydrate" refers to a complex that may be formed through association of a compound having one or more base moieties with at least one compound having one or more acid moieties or through association of a compound having one or more acid moieties with at least one compound having one or more base moieties, said complex being further associated with water molecules so as to form a hydrate, wherein said hydrate is as previously defined and R represents the complex herein described above.

The term "stereoisomers" refers to compounds that have identical chemical constitution, but differ as regards the arrangement of the atoms or groups in space.

"Racemic" means having the capacity for resolution into forms of opposed optical activity.

As used herein, the term "partial stereoisomer" refers to stereoisomers having two or more chiral centers wherein at least one of the chiral centers has defined stereochemistry (i.e., R or S) and at least one has undefined stereochemistry (i.e., R or S). When the term "partial stereoisomers thereof" is used herein, it refers to any compound within the described genus whose configuration at chiral centers with defined stereochemistry centers is maintained and the configuration of each undefined chiral center is independently selected from R or S. For example, if a stereoisomer has three chiral centers and the stereochemical configuration of the first center is defined as having "S" stereochemistry, the term "or partial stereoisomer thereof" refers to stereoisomers having SRR, SRS, SSR, or SSS configurations at the three chiral centers, and mixtures thereof.

An "isotopically substituted analogue" is a compound of the present disclosure in which one or more atoms have been replaced with an isotope of that atom. For example, hydrogen (protium) may be substituted with deuterium or tritium. Other atoms that may be replaced with an isotope thereof in order to form an isotopically substituted analogue thereof include, for example, carbon (replaced with $C^{13}$), nitrogen (replaced with $N^{15}$), iodine (replaced with $I^{131}$), fluorine (replaced with $F^{18}$), or sulfur (replaced with $S^{31}$). Any available isotope may be used to form an isotopically substituted analogue thereof, and those of ordinary skill in the art will recognize available techniques for forming such analogues from a given compound.

"Prodrug" refers to compounds which are themselves inactive or minimally active for the activity desired, but through biotransformation can be converted into biologically active metabolites. For example, a prodrug of the present invention would include, inter alia, any compound which is convertible in vivo by metabolic means to a compound claimed or described in the present disclosure.

"N-oxide" refers to compounds wherein the basic nitrogen atom of either a heteroaromatic ring or tertiary amine is oxidized to give a quaternary nitrogen bearing a positive formal charge and an attached oxygen atom bearing a negative formal charge.

When any variable occurs more than one time in any constituent or in any formula, its definition in each occurrence is independent of its definition at every other occurrence. Combinations of substituents and/or variables are permissible only if such combinations result in stable compounds.

The term "administering" means either directly administering a compound or composition of the present invention, or administering a prodrug, derivative or analog which will form an equivalent amount of the active compound or substance within the body.

"Dosage unit" refers to physically discrete units suited as unitary dosages for the particular individual to be treated. Each unit may contain a predetermined quantity of active compound(s) calculated to produce the desired therapeutic effect(s) in association with the required pharmaceutical carrier. The specification for the dosage unit forms of the invention may be dictated by (a) the unique characteristics of the active compound(s) and the particular therapeutic effect(s) to be achieved, and (b) the limitations inherent in the art of compounding such active compound(s).

"Subject" or "patient" refers to an embryonic, immature, or adult animal, including the human species, that is treatable with the compositions, and/or methods of the present invention.

It has presently been discovered that certain adamantane variants are effective for inhibiting the respective viroporins of various virus species, including virus species in which a mutation of the viroporin and/or associated structures is present. As used herein, "inhibition" of a viroporin refers to the reduction of the viroporin's ability to function in a manner that is most consistent with the vitality of the virus of which the viroporin is a component.

Accordingly, in one aspect, the present invention provides compounds according to Formula Ia:

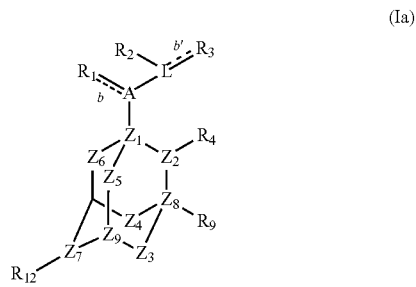

(Ia)

wherein

A is $C_{1-3}$ alkylene or a bond between L and the atom at position $Z_1$;

L is nitrogen;

$R_1$ is NH, $NH_2$, alkyl, or, if A is a bond, is absent;

dashed lines b and b' may independently represent a double bond;

$R_2$ is H, alkyl, -(D)(E), or is absent;

$R_3$ is —(X)(Y);

$R_4$ is —($R_5$)($R_6$), halo, or is absent;

$R_5$ is nitrogen or oxygen;

$R_6$ is hydrogen or —($R_7$)($R_8$)

$R_7$ is alkylene, —CH($R_{7a}$)—, —$(CH_2)_{0-6}$CH(OH)—, or represents a bond between $R_5$ and $R_8$;

$R_{7a}$ is alkyl;

$R_8$ is optionally substituted mono-, di-, or tricyclic ring system that optionally includes one or more heteroatoms;

$R_9$ is —($R_{10}$)($R_{11}$) or is absent;

$R_{10}$ is oxygen, nitrogen, alkyl, —$CF_3$, or alkylene;

$R_{11}$ is hydrogen, halo, or is absent;

R$_{12}$ is alkyl, alkoxy, halo, oxo, or hydroxyl;

D is alkylene, alkenylene, alkynylene, —CH(Q)-, carbonyl, or a bond;

E is an optionally substituted mono-, di-, or tricyclic ring system that optionally includes one or more heteroatoms;

X is alkylene, alkenylene, alkynylene, —CH(Q)-, carbonyl, or a bond;

Q is alkyl, —C(=O)O(CH$_2$)$_{1-3}$CH$_3$, or —(CH$_2$)$_{0-3}$OH;

Y is an optionally substituted mono-, di-, or tricyclic ring system that optionally includes one or more heteroatoms;

Z$_2$ is optionally substituted alkylene of which one or more carbon atoms is optionally replaced with N, O, or S, or represents a bond between Z$_1$ and Z$_8$;

Z$_3$ is optionally substituted alkylene of which one or more carbon atoms is optionally replaced with N, O, or S, or represents a bond between Z$_8$ and Z$_9$;

Z$_4$, Z$_5$, and Z$_6$ are independently alkylene, N, O, or S;

Z$_7$ is optionally substituted alkylene of which one or more carbon atoms is optionally replaced with N, O, or S;

or a stereoisomer, isotopically substituted analogue, or pharmaceutically acceptable salt thereof, with the proviso that (i) if A is a bond and R$_2$ is H or absent, except if X is alkynyl, then:

Y is not unsubstituted phenyl, pyridinyl, furanyl, thiophenyl, pyrrolyl, or benzodioxolyl;

if Y is mono-substituted furanyl, then the substituent on Y is not methyl, hydroxyl, methanolyl, alkoxy, acetylamino, nitro, bromo, chloro, or fluoro;

if Y is mono-substituted phenyl, then the substituent on Y is not methyl, hydroxyl, methanolyl, alkoxy, unsubstituted phenyl, methoxybenzyloxy, acetylamino, nitro, bromo, chloro, or fluoro;

if Y is mono-substituted thiopheneyl, then the substituent on Y is not methyl, ethyl, chloro, or bromo;

if Y is mono-substituted oxadiazolyl, then the substituent on Y is not methoxyphenyl;

if Y is mono-substituted thiazolyl, then the substituent on Y is not methyl;

if Y is mono-substituted naphthyl, then the substituent on Y is not 1-hydroxyl; and, if Y is di-substituted phenyl, then the substituents on Y may not both be alkoxy, and, (ii) if A is C$_1$ alkyl, R$_1$ is NH, and Y is mono-substituted phenyl, then the substituent is not hydroxyl.

In certain embodiments, A is a bond, R$_1$ is absent, X is alkylene or —CH(Q)-, and Y is a carbocyclic ring optionally substituted with one or more substituents independently selected from alkoxy, halo, alkyl, cycloalkyl, hydroxyl, aryl, trifluoromethoxy, trifluoromethyl, alkylsilanyl, alkylsulfanyl, aryloxy, aralkoxy, and hydroxyalkyl. For example, Y may be substituted with aryl, aryloxy, or aralkoxy, in which the aryl moiety of the aryl, aryloxy, or aralkoxy is optionally substituted phenyl, pyrrolidinyl, furanyl, thiopheneyl, oxazolyl, imidazolyl, pyridinyl, naphthyl. isoxazolyl, isoxazolinyl, isothiazolyl, isothiazolinyl, oxadiazolyl, thiadiazolyl, thiazolyl, triazolyl, tetrazolyl, morpholinyl, pyrimidinyl, pyridazinyl, pyrazinyl, pyrrolyl, cyclopropyl, cyclopentyl, or cyclohexyl.

In certain other embodiments, A is a bond, R$_1$ is absent, X is alkylene or —CH(Q)-, and Y is an unsubstituted mono-, di-, or tricyclic ring system that optionally includes one or more heteroatoms independently selected from oxygen, nitrogen, and sulfur. In such instances, Y may be, for example, Y is a six-membered carbocyclic ring that is ortho-fused with a six-membered heterocyclic ring; a six membered heterocyclic ring that is ortho-fused with a six-membered heterocyclic ring; a six membered heterocyclic ring that is ortho-fused with a five-membered heterocyclic ring; a six membered heterocyclic ring that is ortho-fused with a five-membered carbocyclic ring; a six-membered carbocyclic ring that is ortho-fused with a five-membered heterocyclic ring; a pair of ortho-fused five-membered heterocyclic rings; a pair of ortho-fused five-membered carbocyclic rings; or, a single three- to seven-membered carbo- or heterocyclic ring. For example, Y may be represented by the structure

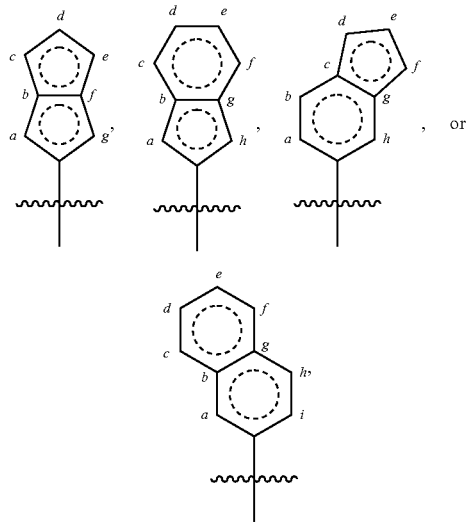

or any heterocyclic analog of which that includes one or more heteroatoms independently selected from oxygen, nitrogen, and sulfur at any of the positions labeled a, b, c, d, e, f, g, h, and i in the structures above. In some examples, Y is a single unsaturated, partially saturated, or fully saturated six-membered carbo- or heterocyclic ring; a single unsaturated, partially saturated, or fully saturated five-membered carbo- or heterocyclic ring; an unsaturated, partly-saturated, or fully-saturated thiophene ring that is ortho-fused to an unsaturated, partly-saturated, or fully-saturated thiophene, pyrrole, furan, imidazole, thiazole, or oxazole ring, an unsaturated, partly-saturated, or fully-saturated furan ring that is ortho-fused to an unsaturated, partly-saturated, or fully-saturated thiazole or oxazole ring; an unsaturated, partly-saturated, or fully-saturated pyrrole ring that is ortho-fused to an unsaturated, partly-saturated, or fully-saturated thiazole or oxazole ring; or, a phenyl ring that is ortho-fused to an unsaturated, partly-saturated, or fully-saturated thiophene, pyridine, imidazole, or furan ring. In such embodiments, when Y is a single unsaturated, partially saturated, or fully saturated six-membered carbo- or heterocyclic ring, or is a single unsaturated, partially saturated, or fully saturated five-membered carbo- or heterocyclic ring, Y may be, for example, isoxazolyl, isoxazolinyl, isothiazolyl, isothiazolinyl, oxadiazolyl, thiadiazolyl, oxazolyl, thiazolyl, triazolyl, tetrazolyl, imidazolyl, phenyl, morpholinyl, pyridinyl, pyrimidinyl, pyridazinyl, pyrazinyl, thiopheneyl, furanyl, pyrrolyl, cyclopropyl, cyclopentyl, or cyclohexyl.

In other embodiments of compounds according to formula (Ia), A is a bond, R$_1$ is absent, X is alkylene or —CH(Q)-, and Y is a substituted mono-, di-, or tricyclic ring system that includes one or more heteroatoms independently selected from oxygen, nitrogen, and sulfur. In such embodiments, Y may be, for example, a single three- to seven-membered heterocyclic ring; a single unsaturated, partially saturated, or fully saturated six-membered carbo- or heterocyclic ring; a single unsaturated, partially saturated, or fully saturated five-membered carbo- or heterocyclic ring; a pair of ortho-fused five-membered heterocyclic rings, wherein at least one of said rings is substituted; a pair of ortho-fused six-membered heterocyclic rings, wherein at least one of said rings is substituted; a six-membered heterocyclic ring that is ortho-fused with a six-membered carbocyclic ring, wherein at least one of said rings is substituted; a five-membered heterocyclic ring that is ortho-fused with a five-membered carbocyclic ring, wherein at least one of said rings is substituted; a five-membered heterocyclic ring that is ortho-fused with a six-membered carbocyclic ring, wherein at least one of said rings is substituted; or, a five-membered carbocyclic ring that is ortho-fused with a six-membered heterocyclic ring, wherein at least one of said rings is substituted. The substituents may independently be, for example, oxo, hydroxyl, halo, nitro, alkyl, trifluoromethyl, trifluoromethoxy, cycloalkyl, alkoxy, alkoxyalkyl, alkylsulfanyl, alkylsulfanylalkyl, trifluoromethylsulfanyl, cyano, amino, alkylamino, di-alkylamino, alkoxycarbonylalkyl(alkyl) amino, aryl, or aralkyl. In certain embodiments, Y may be represented by the structure

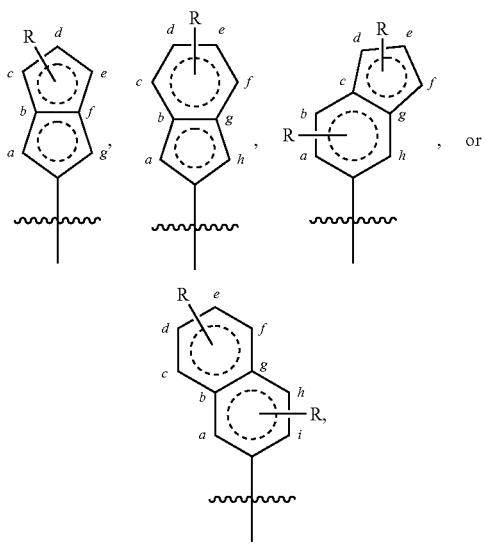

wherein R represents a substitution, or any heterocyclic analog of which that includes one or more heteroatoms independently selected from oxygen, nitrogen, and sulfur at any of the positions labeled a, b, c, d, e, f, g, h, and i in the structures above. In the structures above, each R may independently be oxo, hydroxyl, halo, nitro, alkyl, trifluoromethyl, trifluoromethoxy, cycloalkyl, alkoxy, alkylsulfanyl, trifluoromethylsulfanyl, cyano, amino, or aryl. When Y represents a single ring, Y may be, for example, isoxazolyl, isoxazolinyl, isothiazolyl, isothiazolinyl, oxadiazolyl, thiadiazolyl, oxazolyl, thiazolyl, triazolyl, tetrazolyl, imidazolyl, phenyl, morpholinyl, pyridinyl, pyrimidinyl, pyridazinyl, pyrazinyl, thiopheneyl, furanyl, pyrrolyl, cyclopropyl, cyclopentyl, or cyclohexyl, each with at least one substitution. The substitutions on Y when it is a single ring may be, for example, halo, thiopheneyl, alkylthiopheneyl, alkoxythiopheneyl, imidazolyl, imidazolyl substituted with one or both of methyl and trifluoromethyl, tetrahydrofuranyl, furanyl, alkylfuranyl, phenyl, pyridinyl, morpholinomethyl, cyclopropyl, cyclopentyl, cyclohexyl, alkoxy, alkoxyalkyl, alkyl, alkylsulfanyl, alkylsulfanylalkyl, alkylsilanyl, cyano, amino, alkylamino, di-alkylamino, alkoxycarbonylalkyl(alkyl)amino, nitro, alkoxyphenyl, alkylsulfanylphenyl, halophenyl, trifluoromethyl, trifluoromethylphenyl, trifluoromethoxyphenyl, thiazolyl substituted with one or both of methyl and trifluoromethyl, isoxazolyl optionally substituted with methyl, isoxazolinyl, isothiazolyl, isothiazolinyl, oxadiazolyl, thiadiazolyl, oxazolyl, thiazolyl, triazolyl, tetrazolyl, morpholinyl, pyrimidinyl, pyridazinyl, pyrrolidinyl, piperadinyl, pyrazinyl, or pyrrolyl. Any of the substitutions on Y may themselves be substituted.

In other embodiments of the compounds of formula (Ia), A is a bond, $R_1$ is absent, X is alkylene or —CH(Q)-, and $R_9$ is —$(R_{10})(R_{11})$. In still other embodiments, A is a bond, $R_1$ is absent, X is alkylene or —CH(Q)-, and $R_4$ is —$(R_5)(R_6)$. In yet other embodiments, A is a bond, $R_1$ is absent, X is alkylene or —CH(Q)-, and $R_2$ is -(D)(E). Other embodiments are such that A is a bond, $R_1$ is absent, X is alkylene or —CH(Q)-, and $Z_7$ is alkylene that is substituted with alkyl, hydroxyl, or halo. Still other embodiments are such that A is a bond, $R_1$ is absent, X is alkylene or —CH(Q)-, and $Z_7$ is alkylene of which one or more carbon atoms is replaced with N, O, or S. In other embodiments, A is a bond, $R_1$ is absent, X is alkylene or —CH(Q)-, and one or more of $Z_2$-$Z_7$ is N, O, or S. In yet other embodiments, A is a bond, $R_1$ is absent, X is alkenylene or alkynylene, and Y is optionally substituted aryl.

Exemplary compounds according to formula (Ia) include:

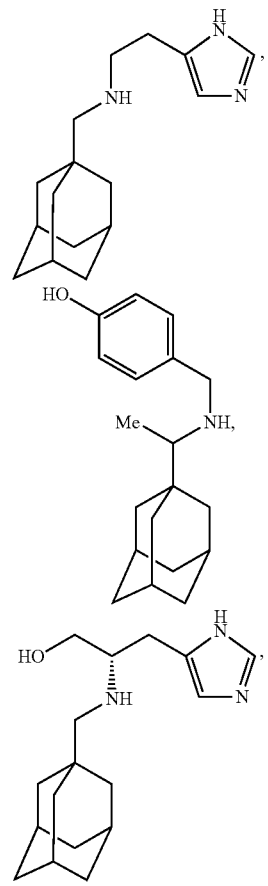

-continued
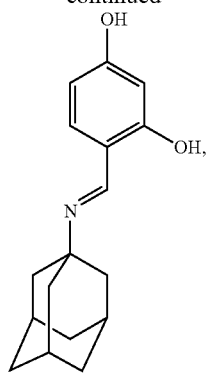
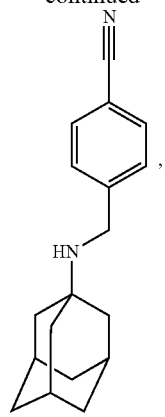

-continued
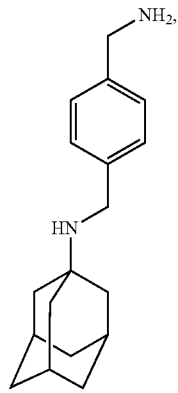
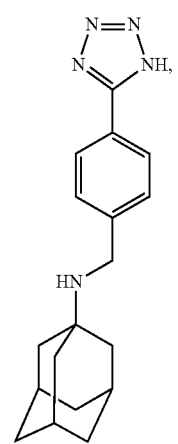
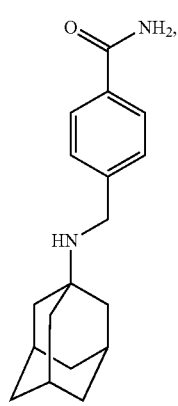
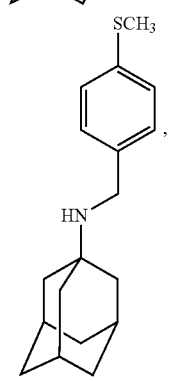
-continued
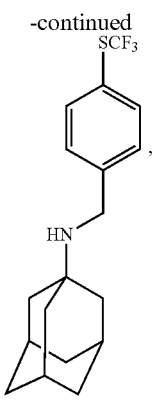
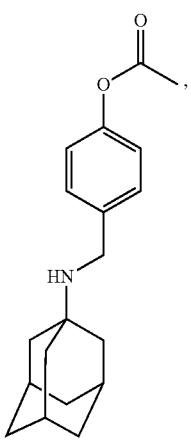
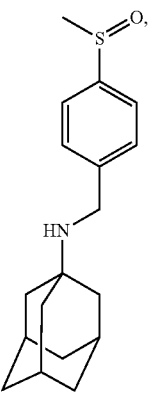
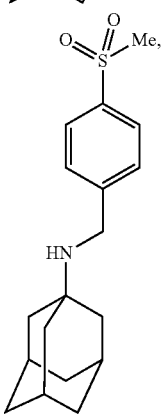

-continued
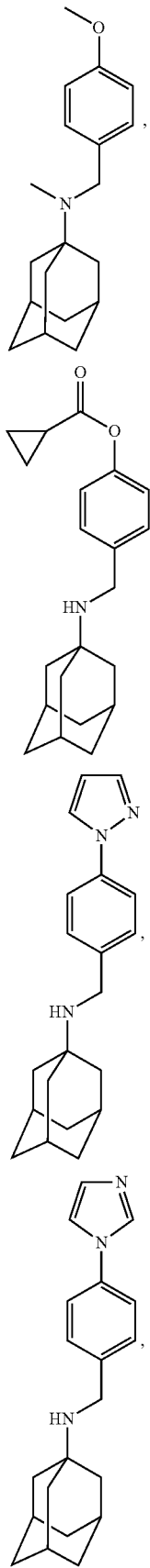
-continued
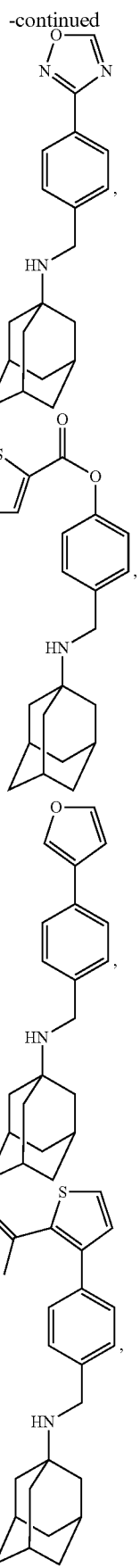

21
-continued
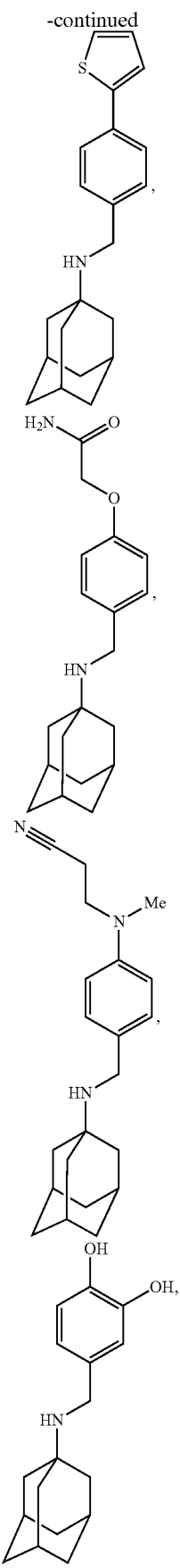
22
-continued
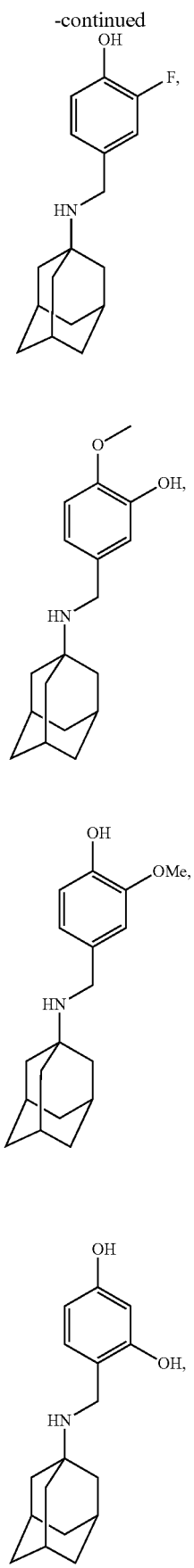

-continued
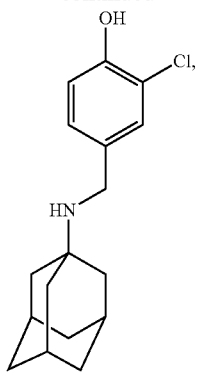
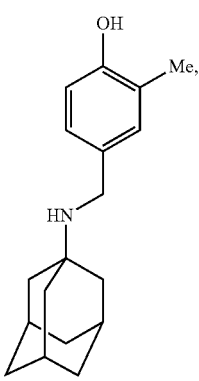
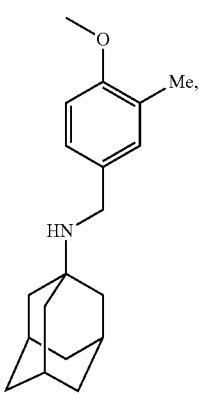
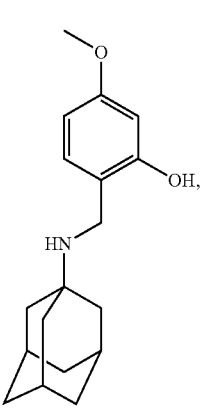
-continued
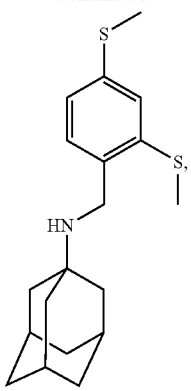
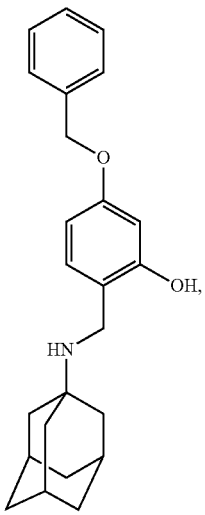
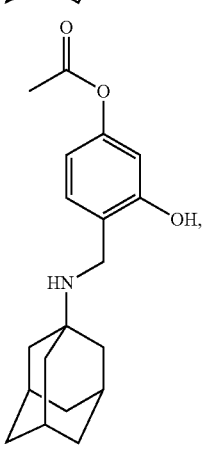
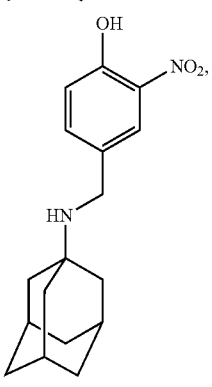

25
-continued
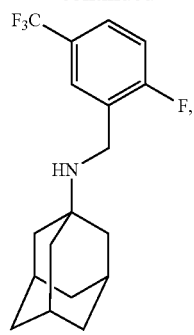
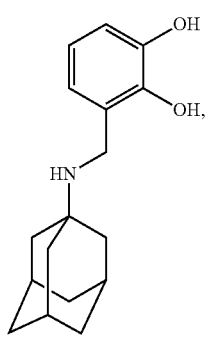
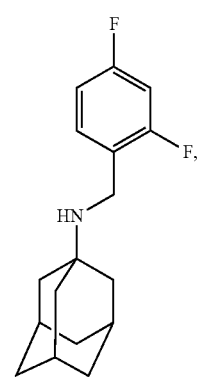
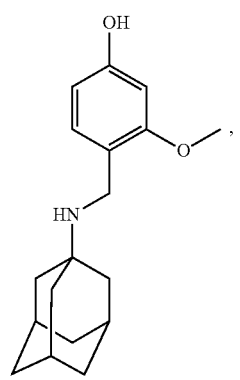
26
-continued
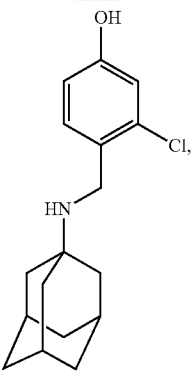
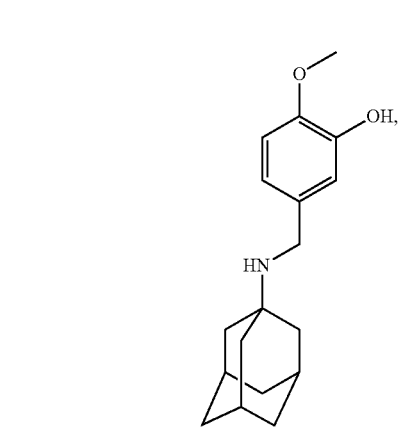
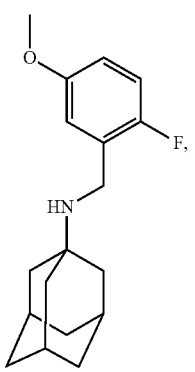
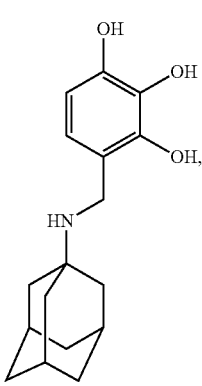

27
-continued

28
-continued

29
-continued
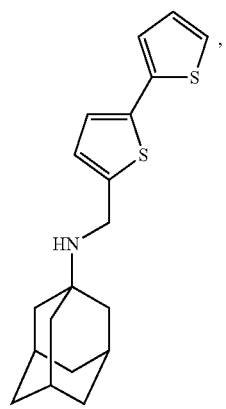
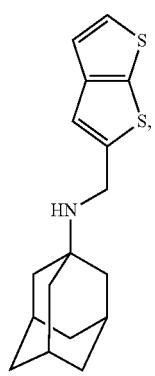
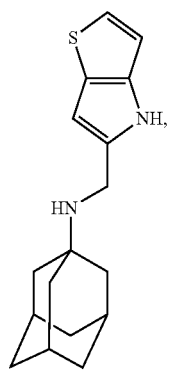
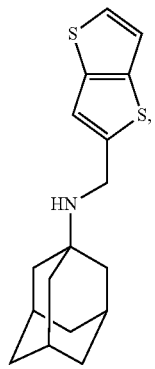
30
-continued
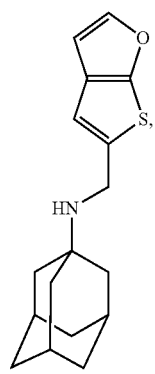
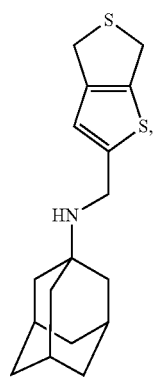
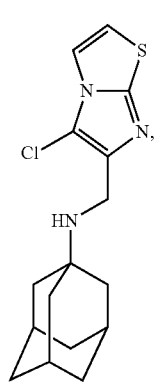
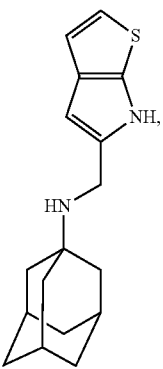

31
-continued
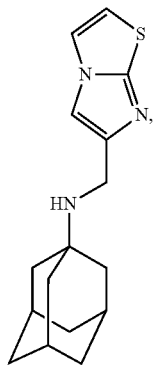
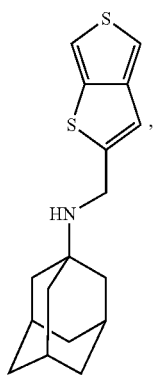
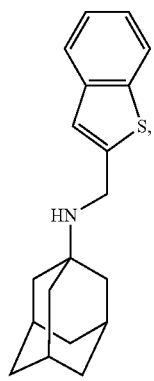
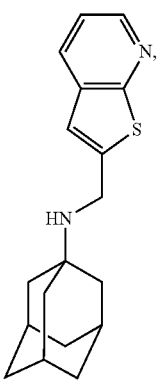
32
-continued
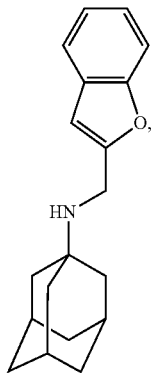
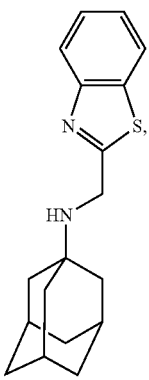
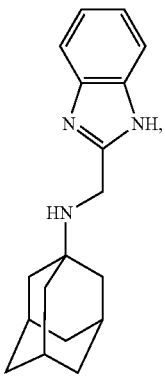
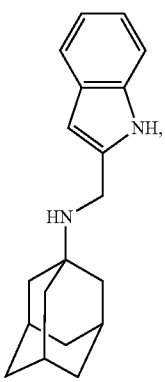

33
-continued
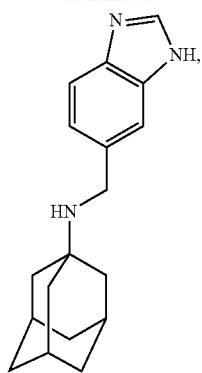
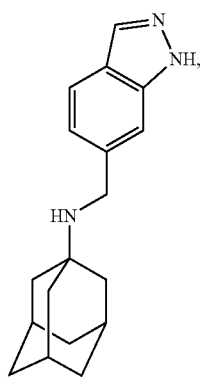
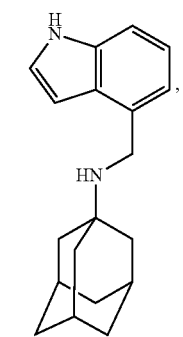
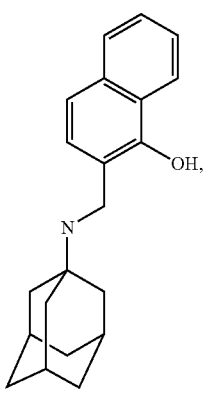
34
-continued
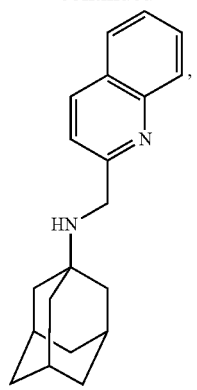
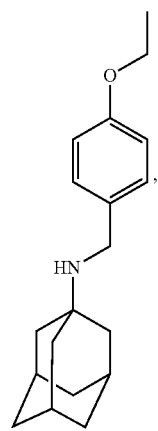
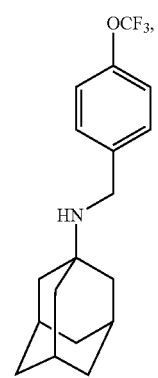
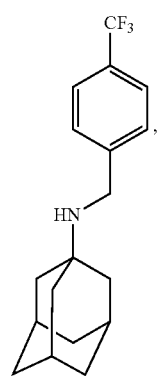

35
-continued
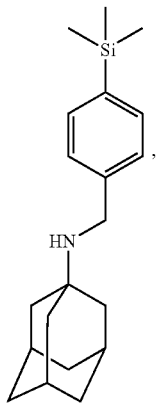
36
-continued
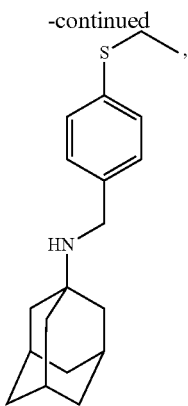
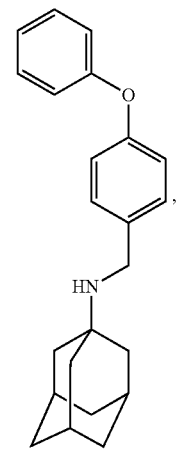
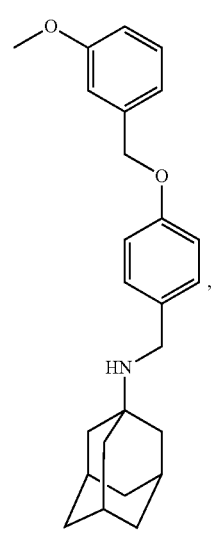

37
-continued
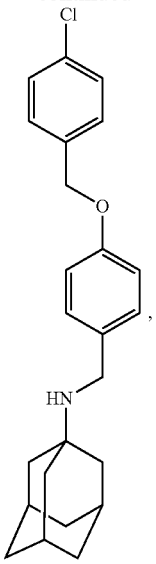
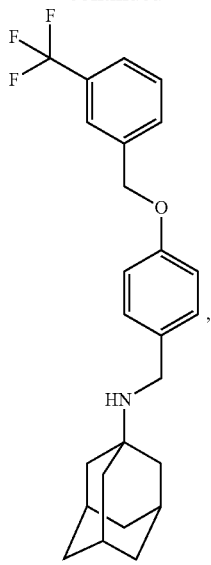
38
-continued

-continued
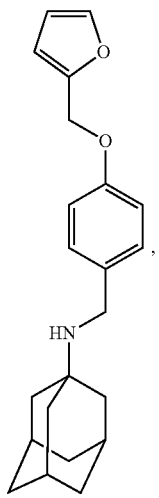
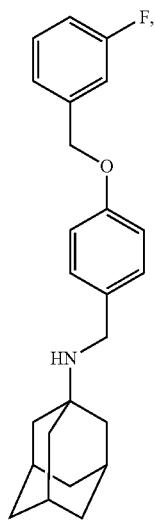
-continued
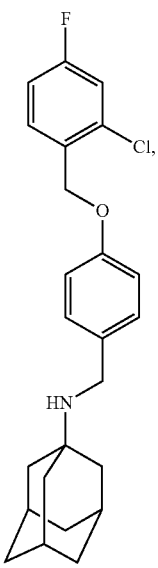
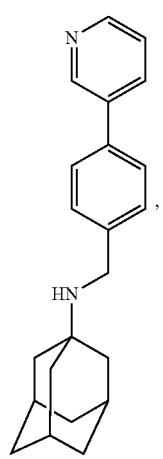
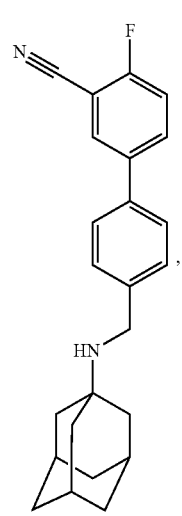

41
-continued
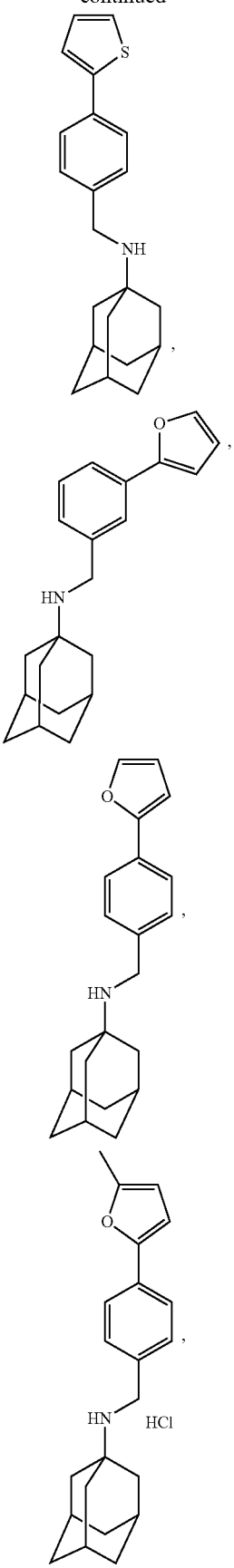
42
-continued
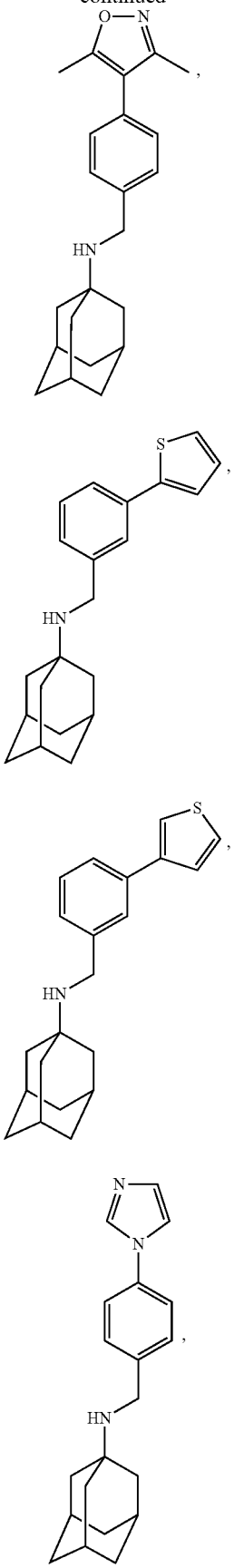

-continued
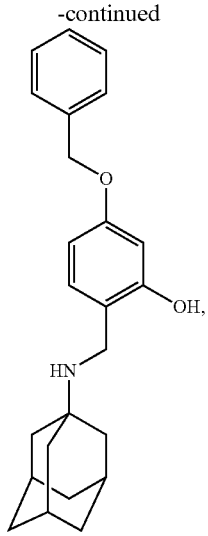
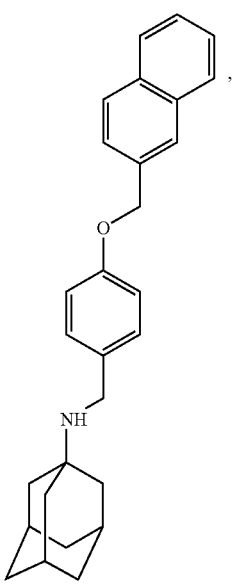
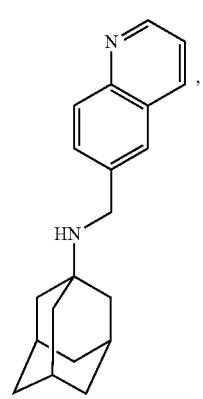
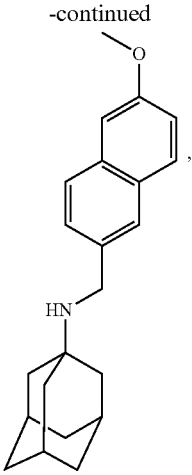
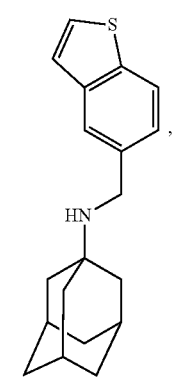
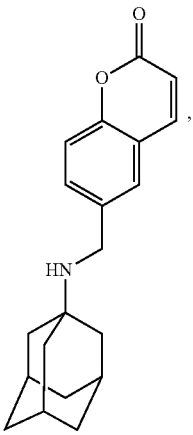
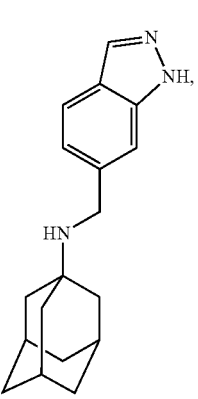

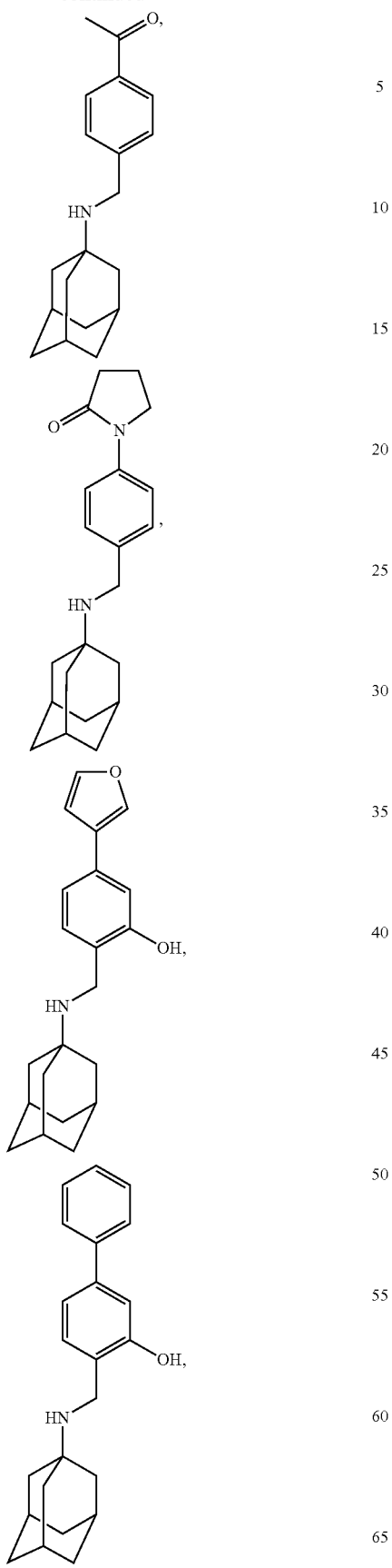
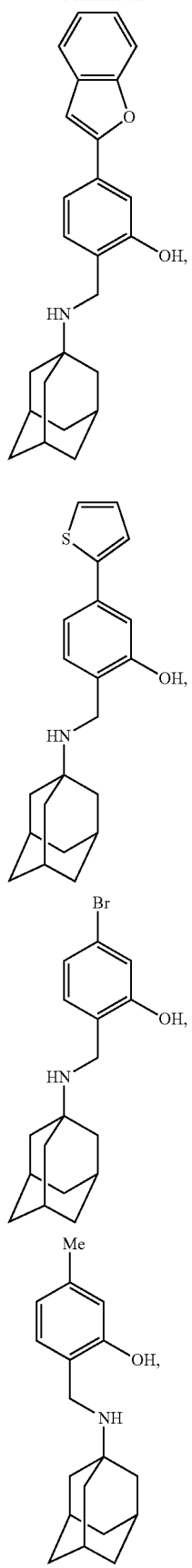

-continued
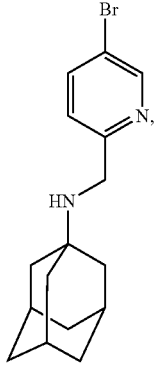
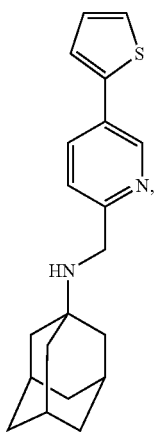
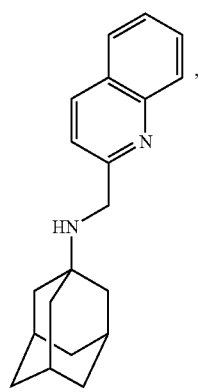
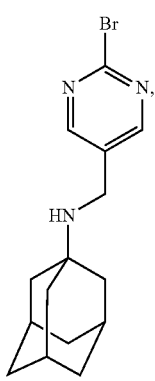
-continued
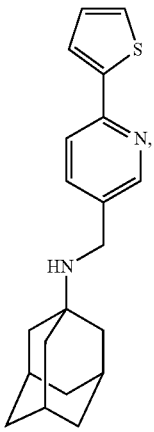
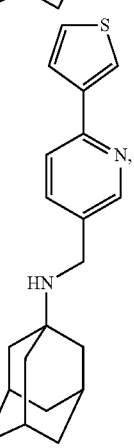
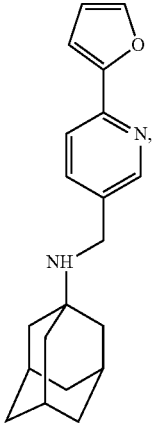
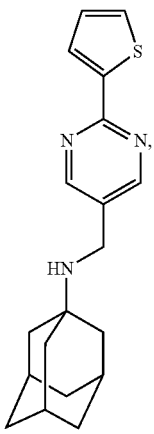

49
-continued
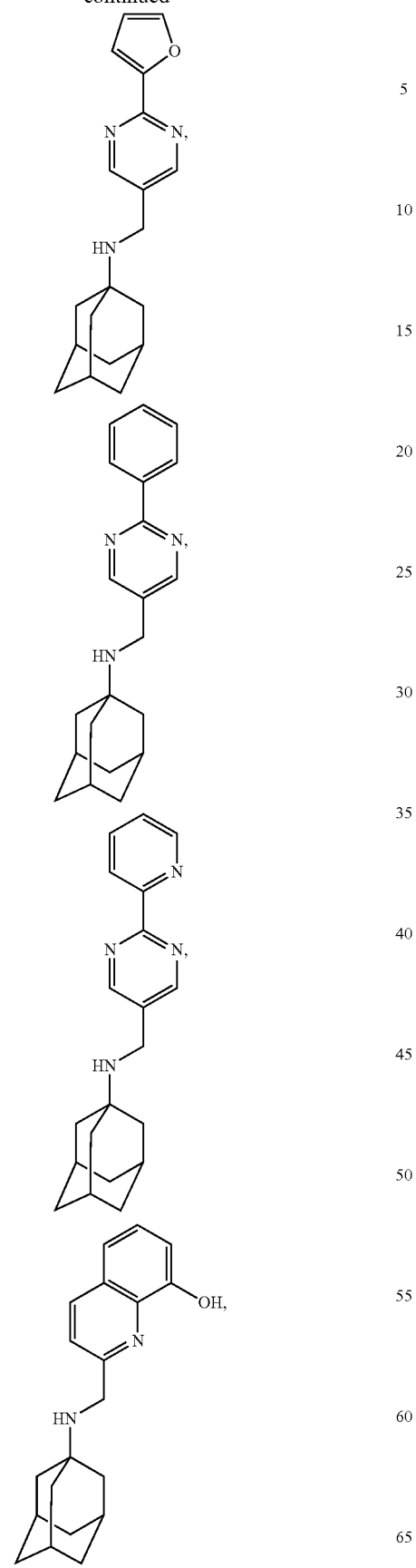
50
-continued
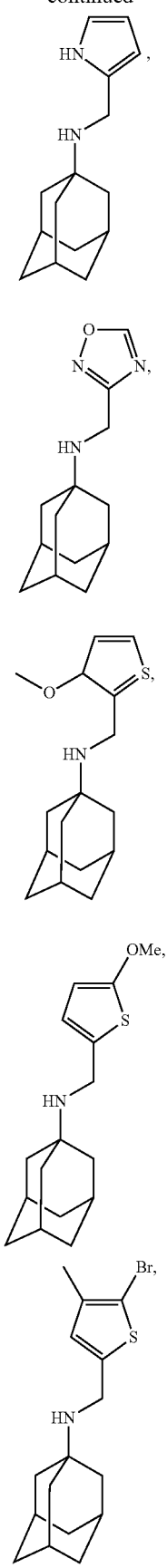

51
-continued
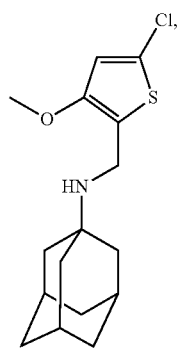
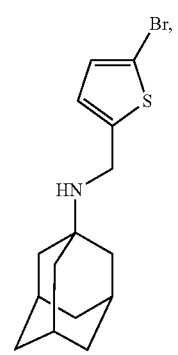
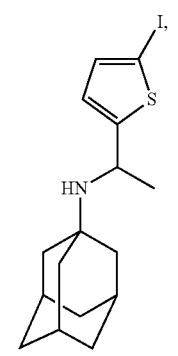
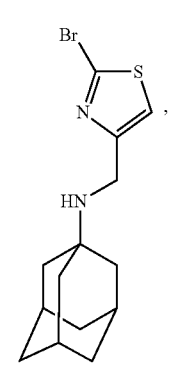
52
-continued
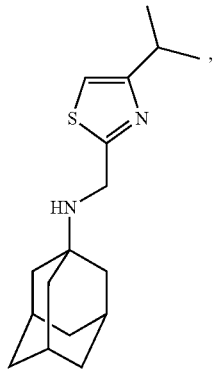
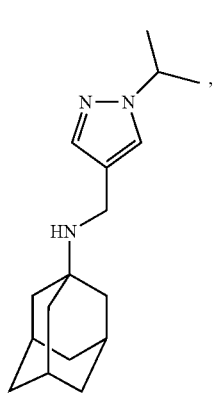
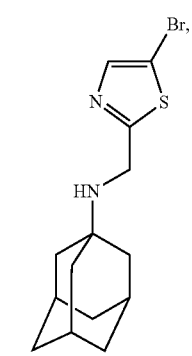
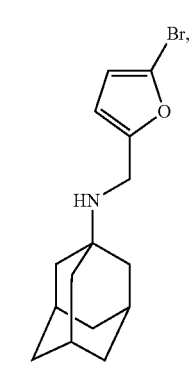

53
-continued
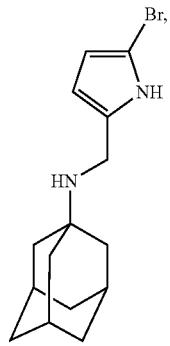
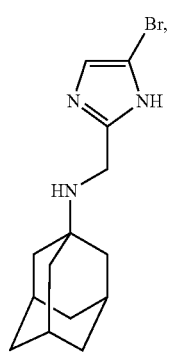
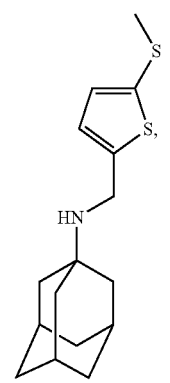
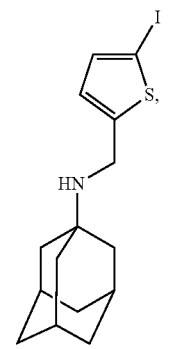
54
-continued
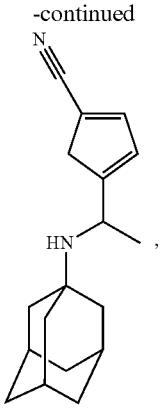
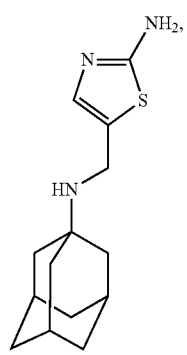
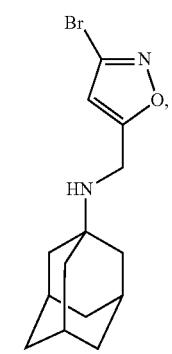
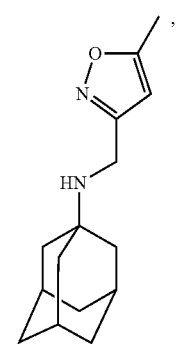

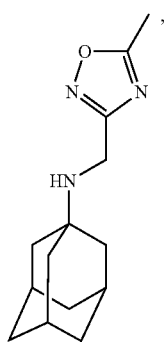
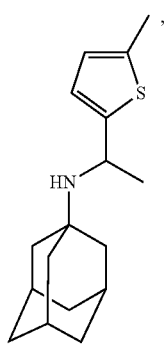
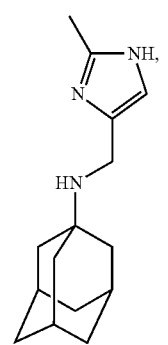
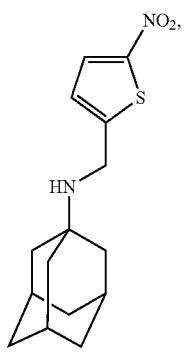
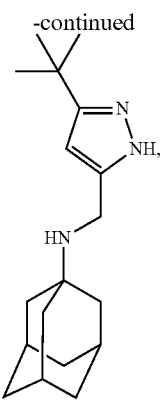
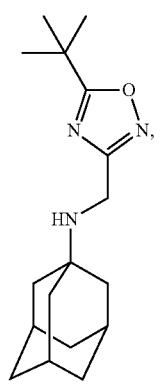
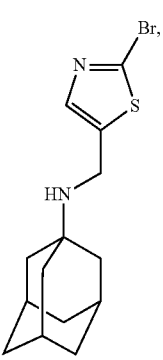
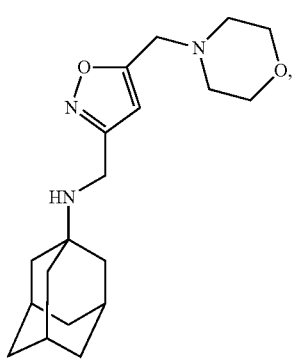

57
-continued
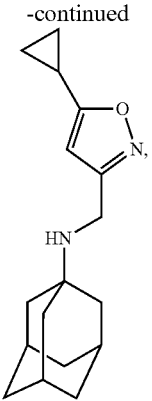
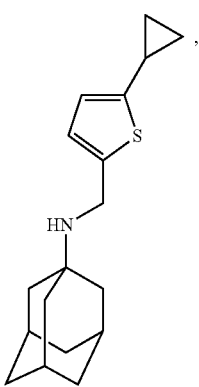
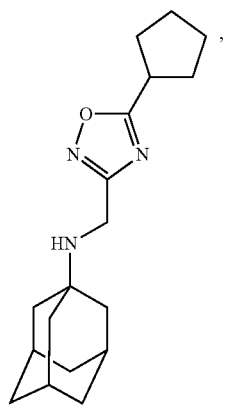
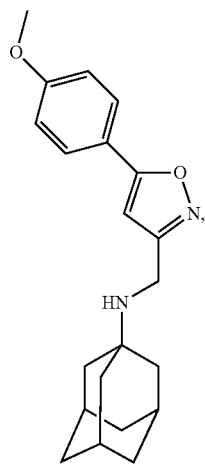
58
-continued
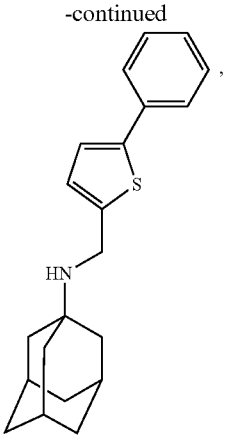
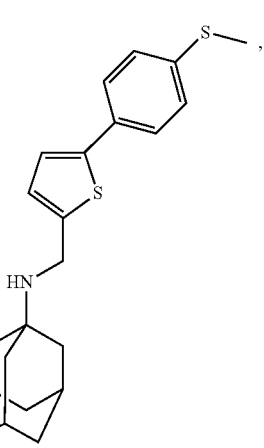
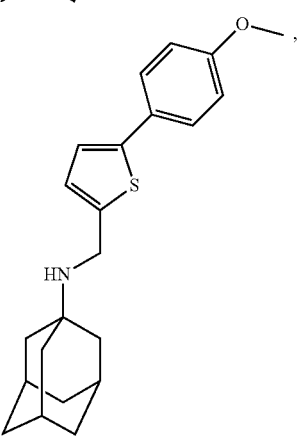
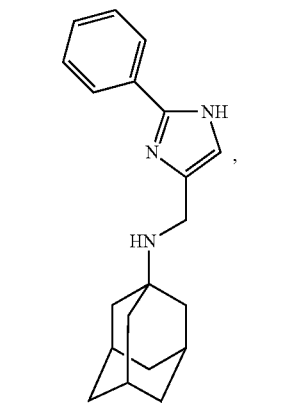

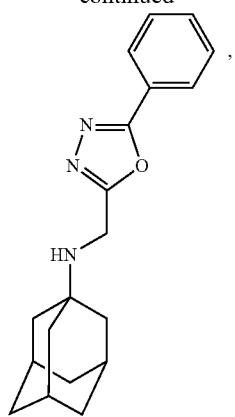
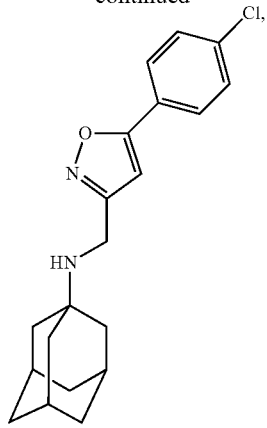
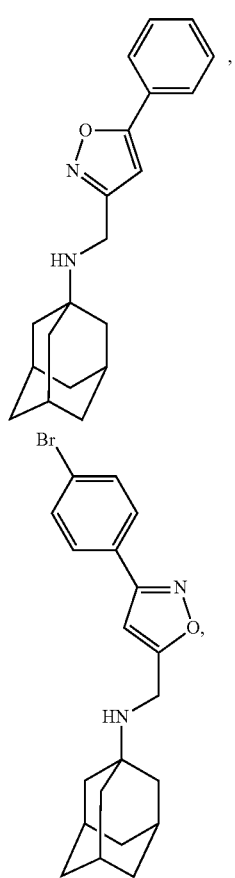
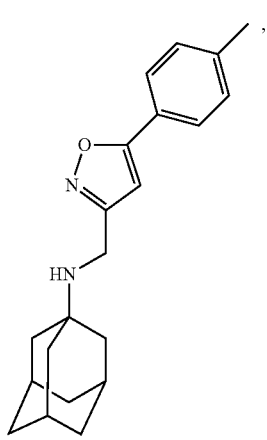
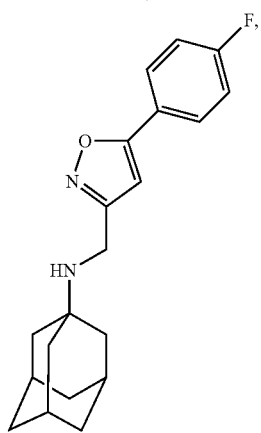
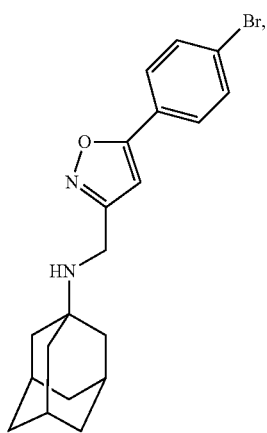

61
-continued
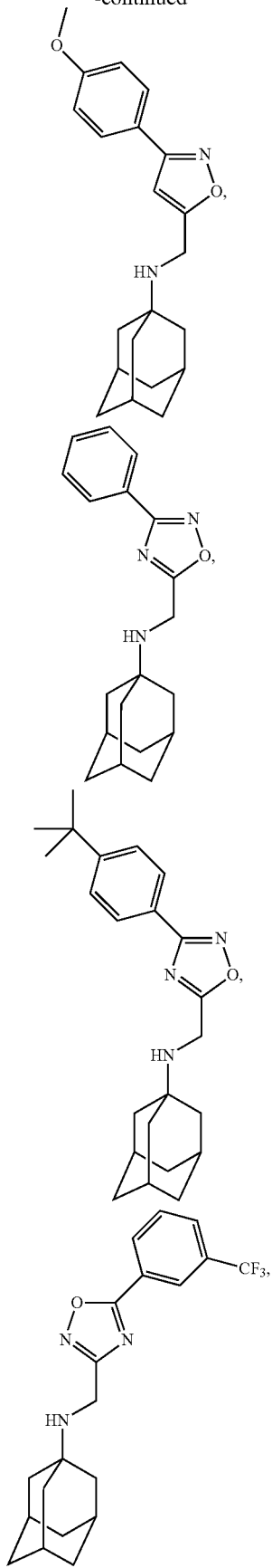
62
-continued
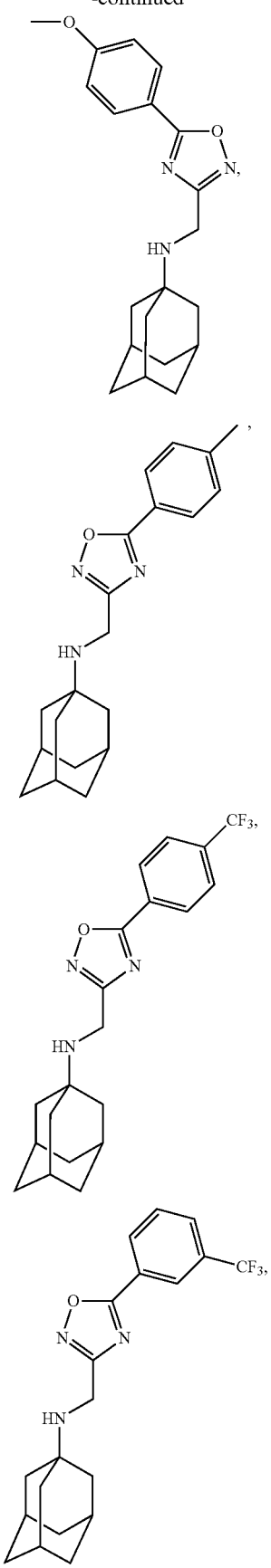

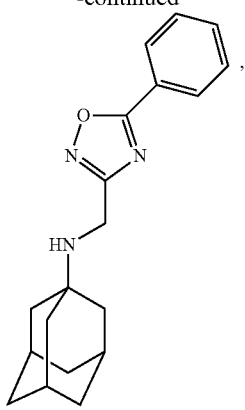
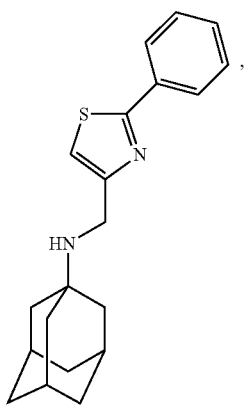
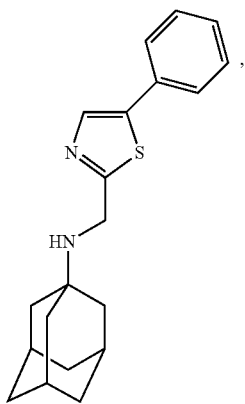
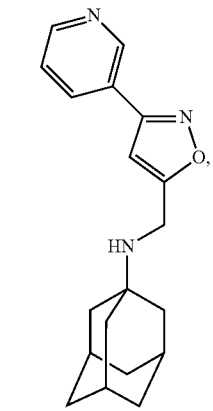
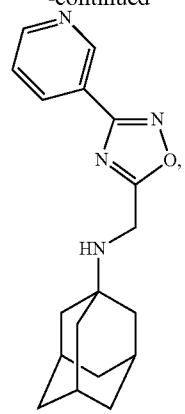
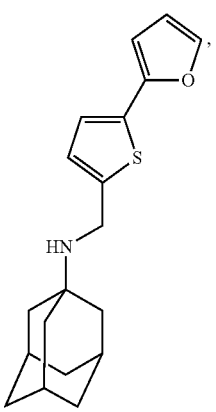
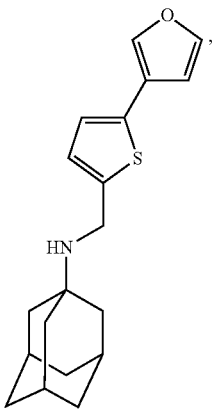
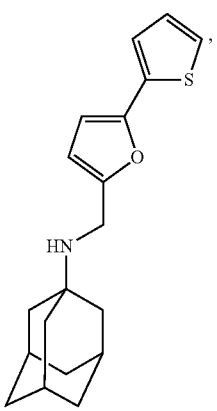

65
-continued
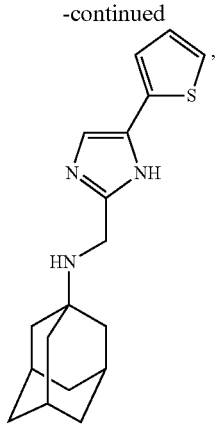
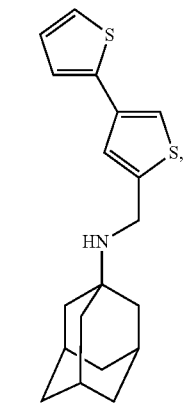
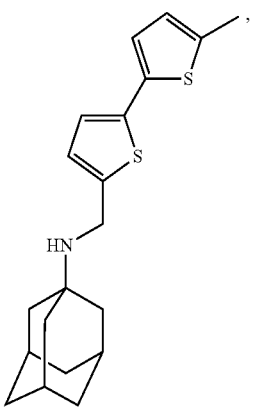
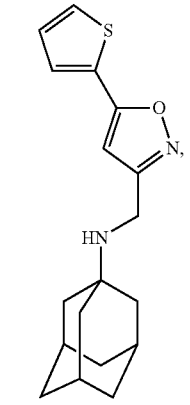
66
-continued
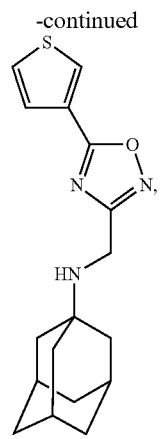
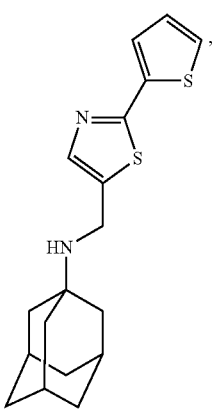
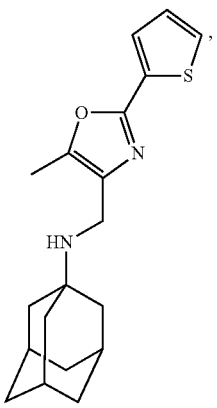
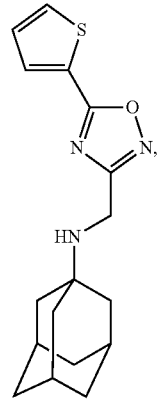

67
-continued
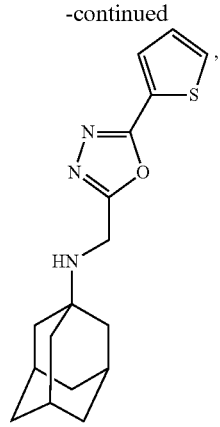
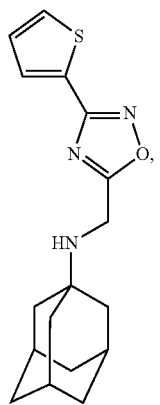
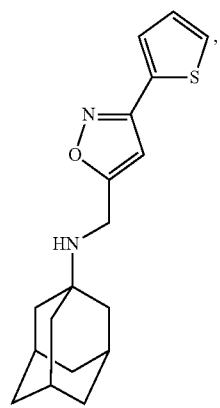
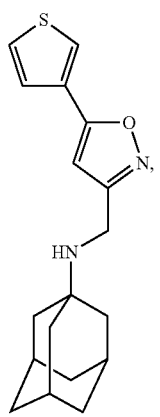
68
-continued
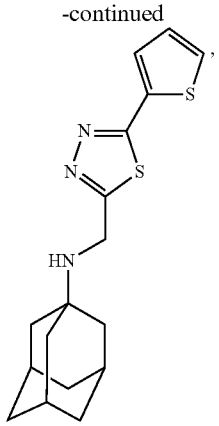
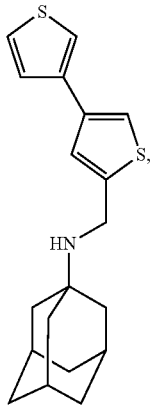
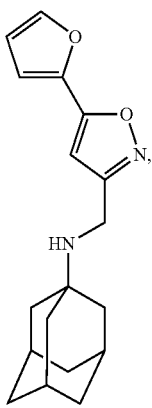
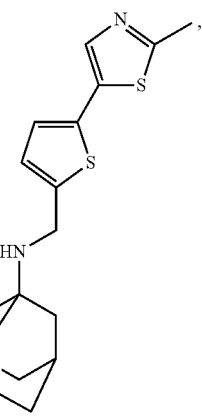

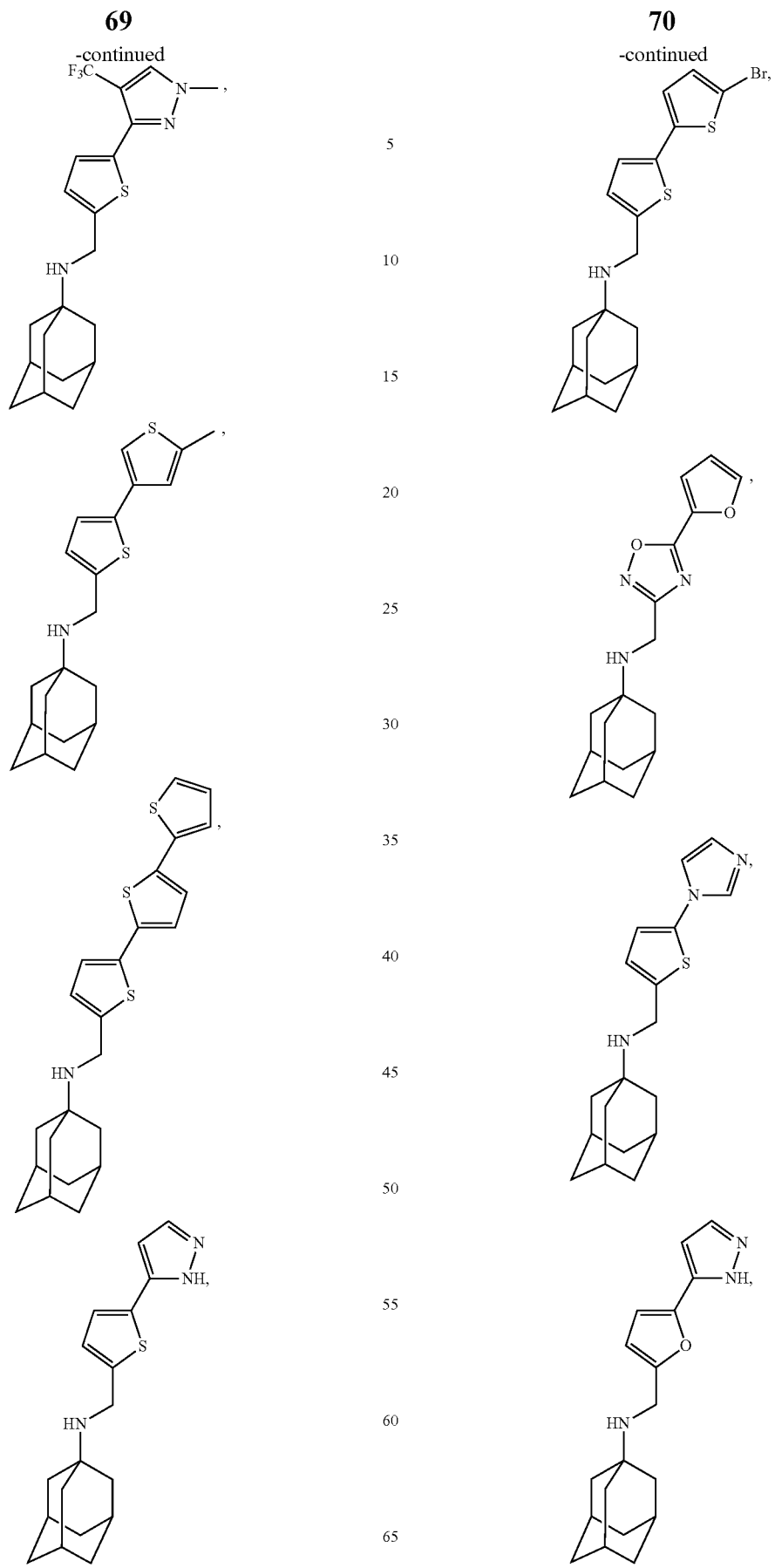

71
-continued
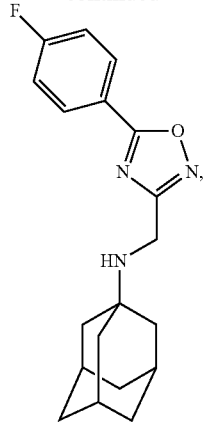
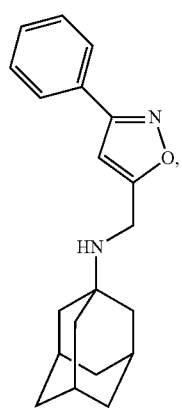
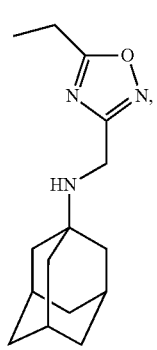
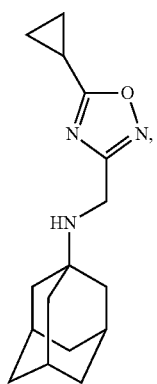
72
-continued
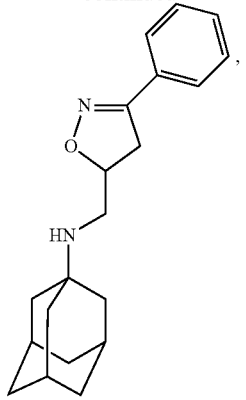
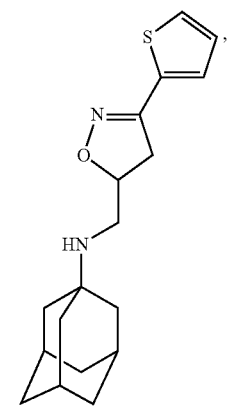
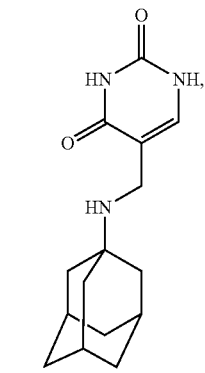
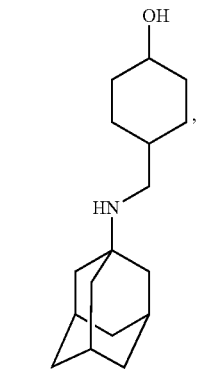

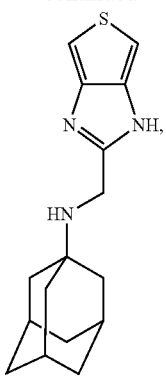
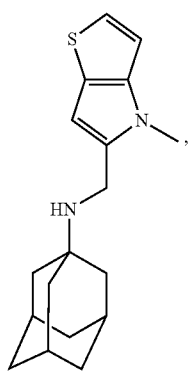
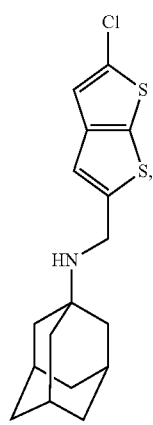
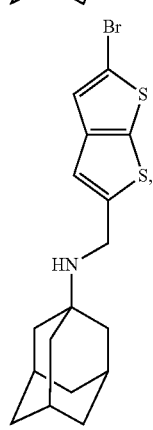
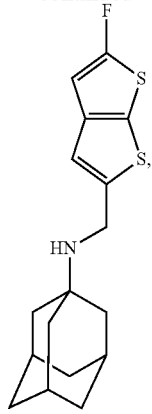
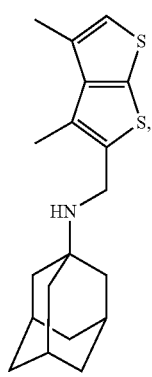
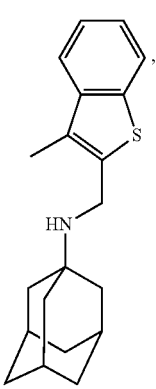
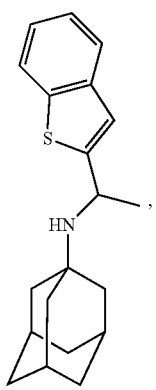

-continued
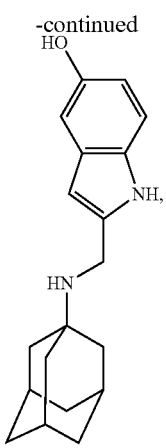
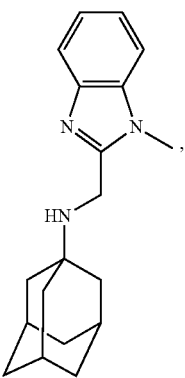
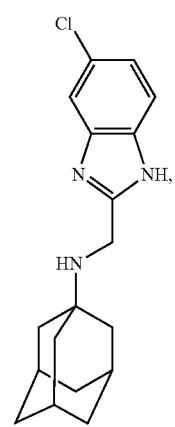
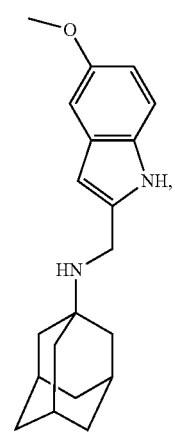
-continued
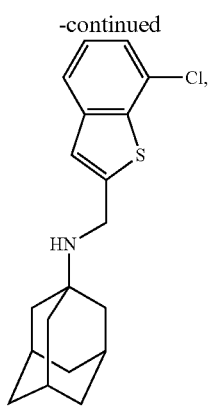
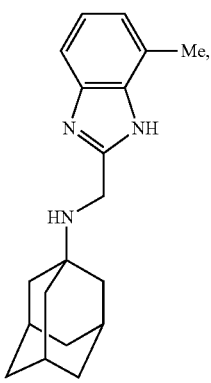
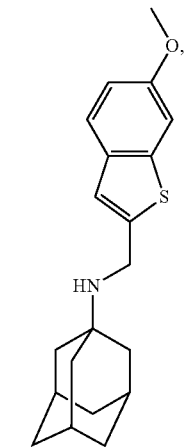
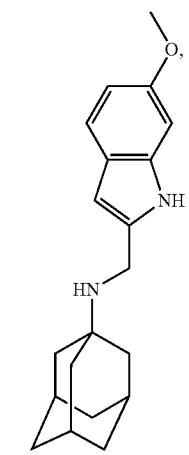

77
-continued
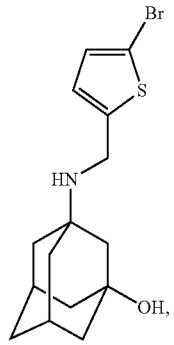
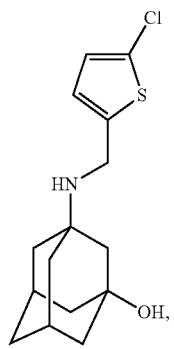
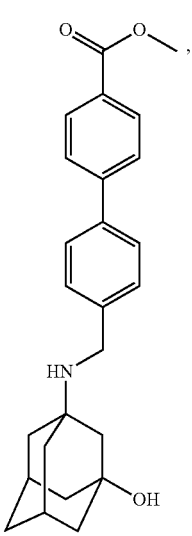
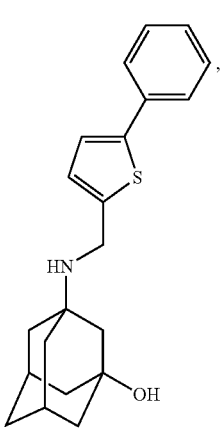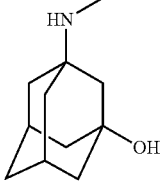
78
-continued
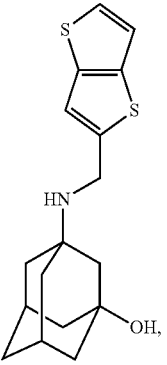
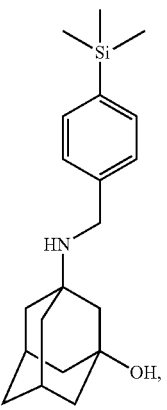
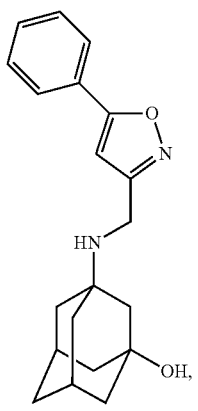
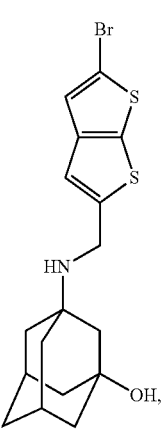

79
-continued
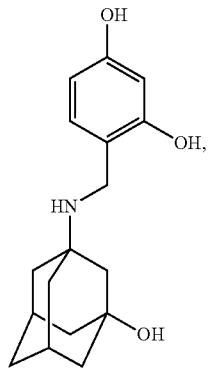
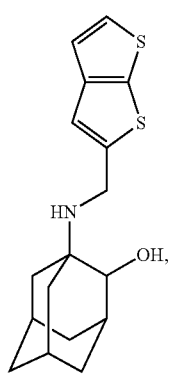
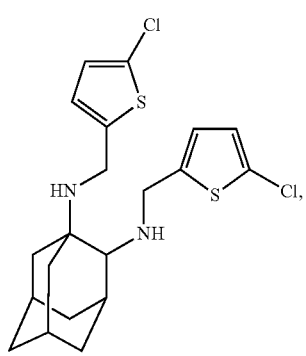
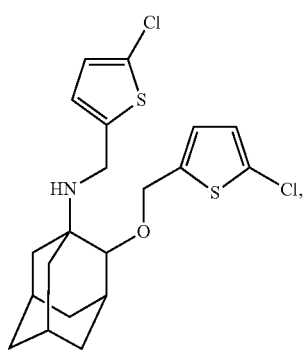
80
-continued
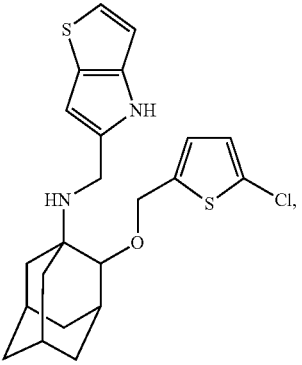
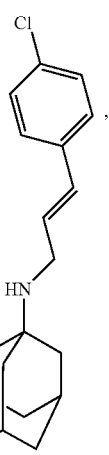
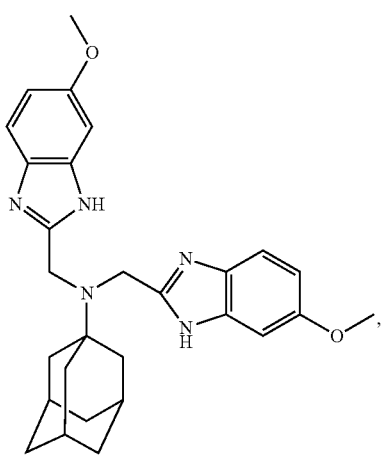
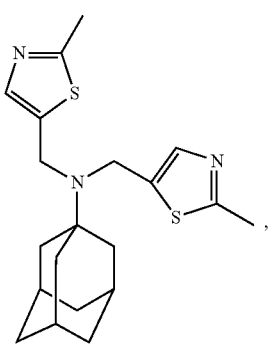

81
-continued
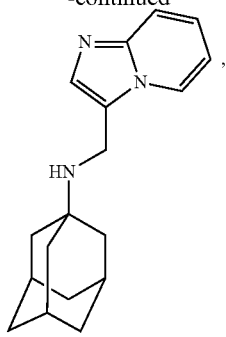
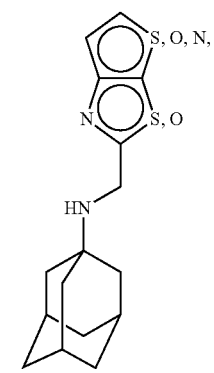
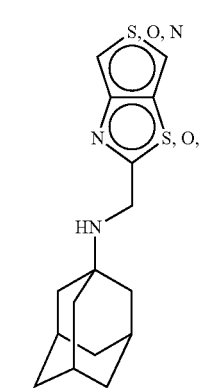
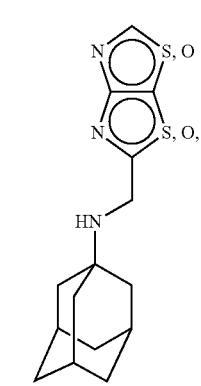
82
-continued
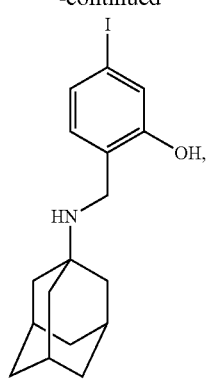
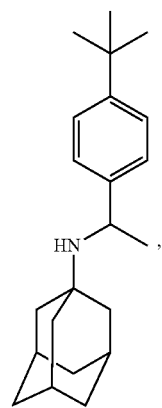
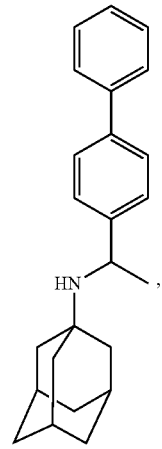
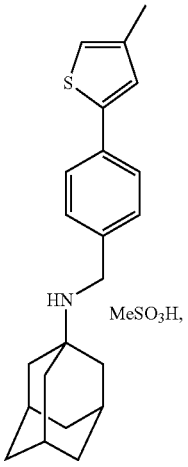
MeSO₃H, -continued
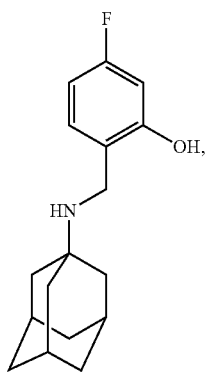
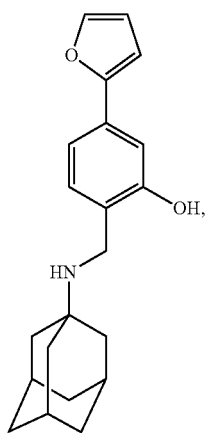
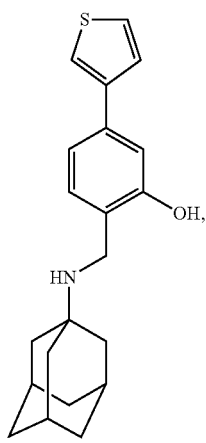

-continued
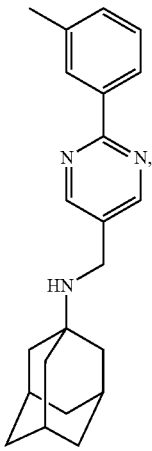
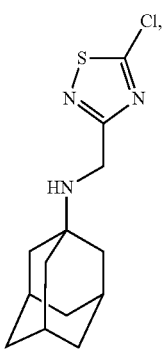
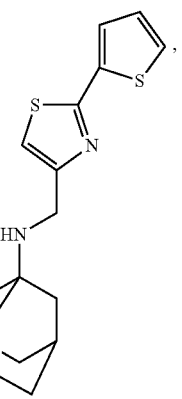
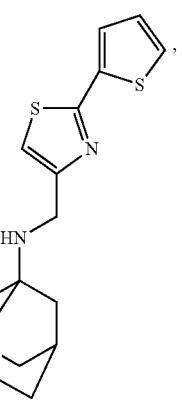

85
-continued
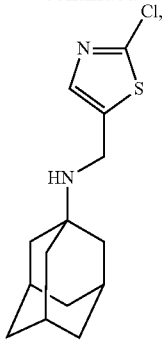
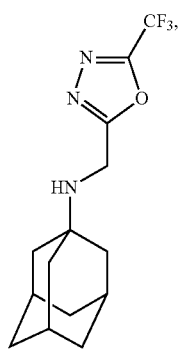
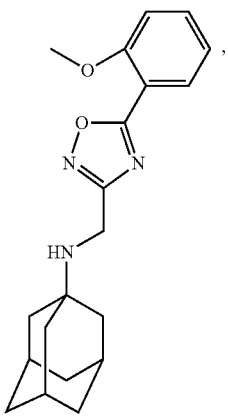
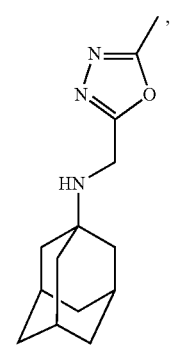
86
-continued
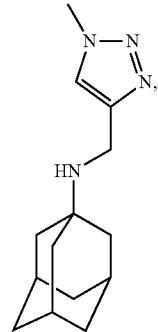
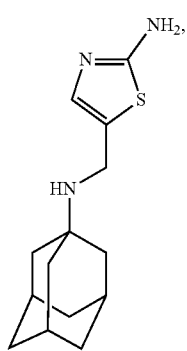
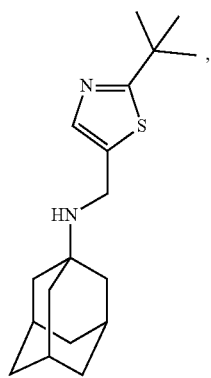
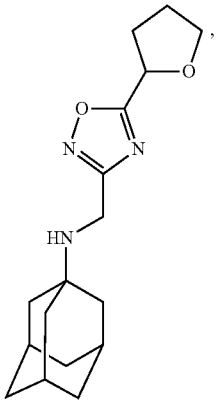

87
-continued
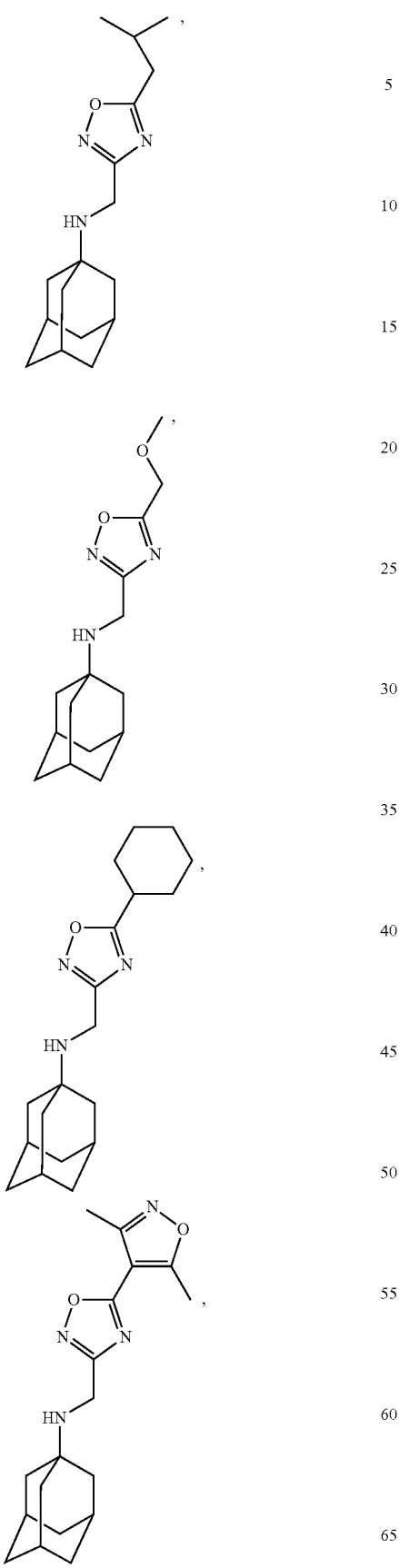
88
-continued
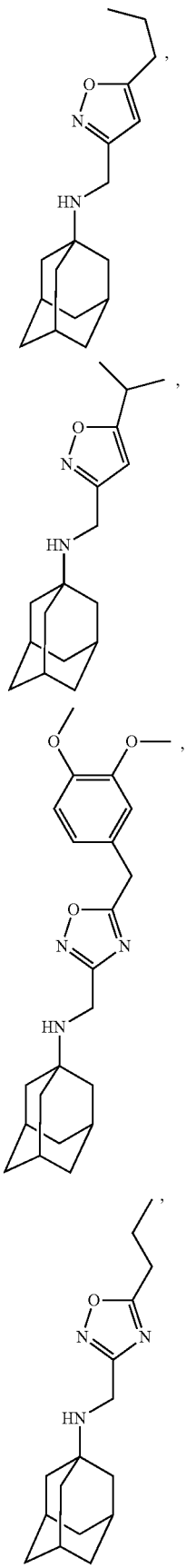

89
-continued
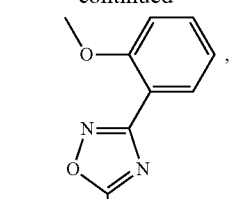
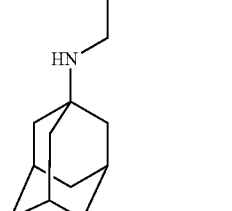
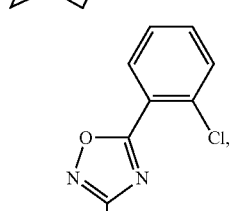
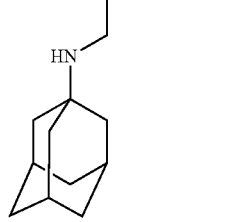
90
-continued
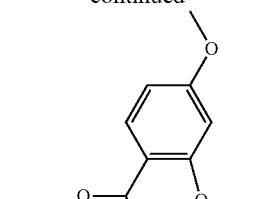
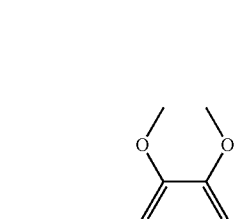
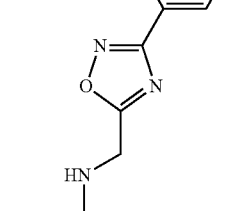
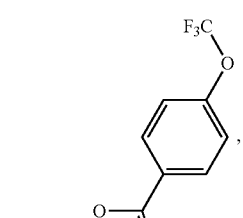

91
-continued
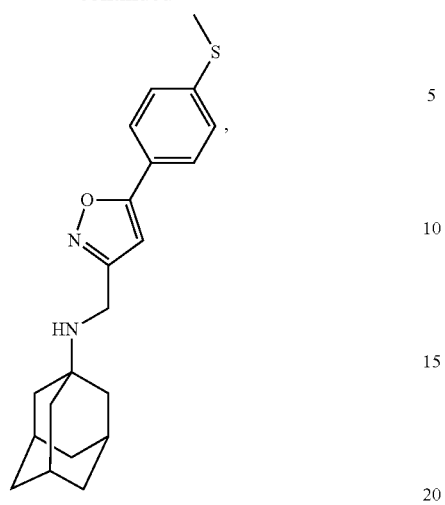
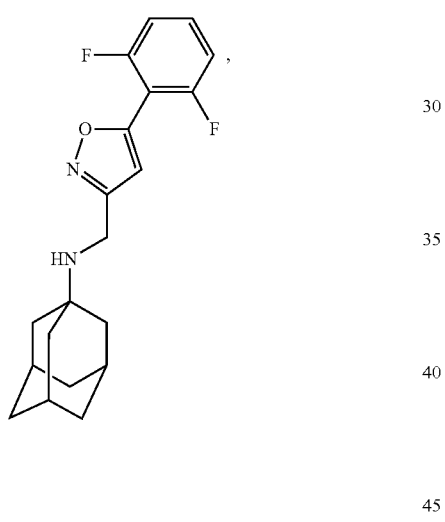
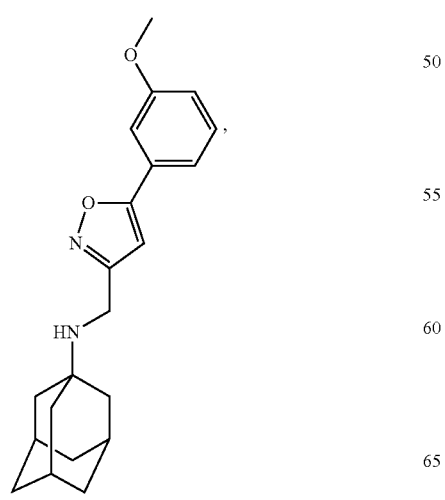
92
-continued
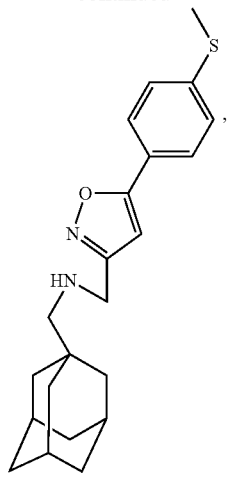
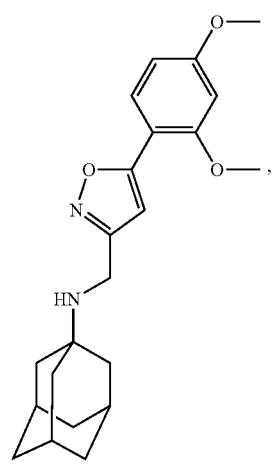
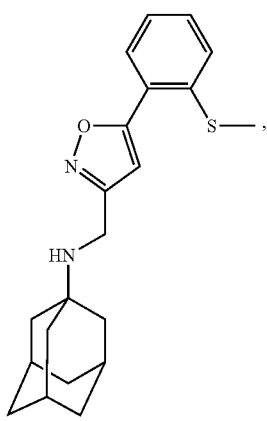

93
-continued
94
-continued
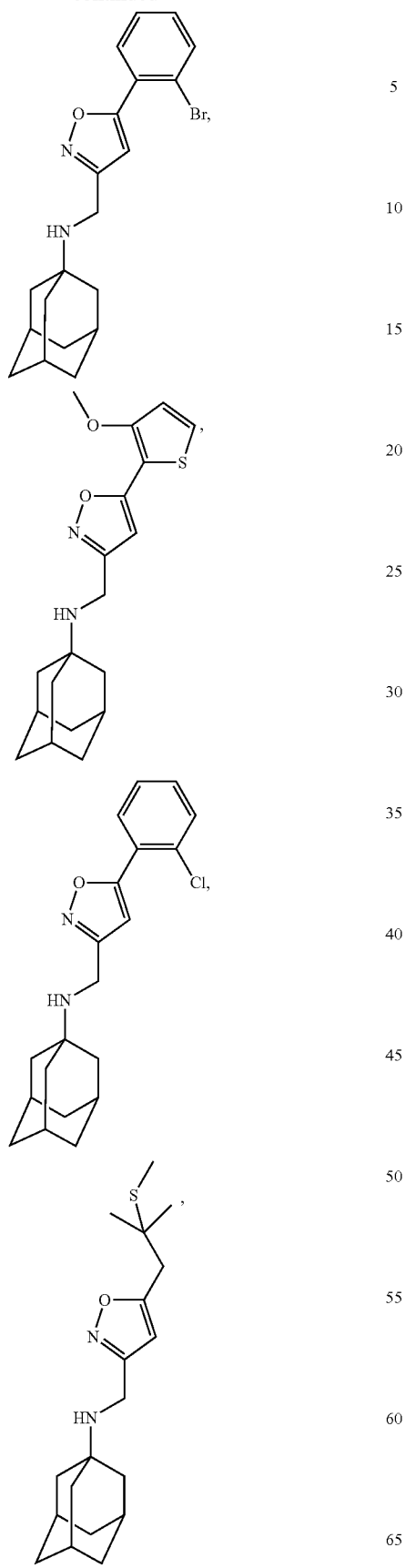
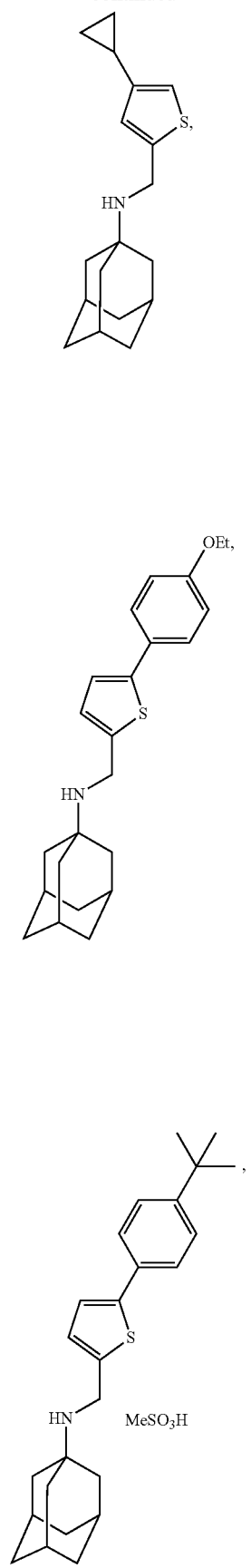

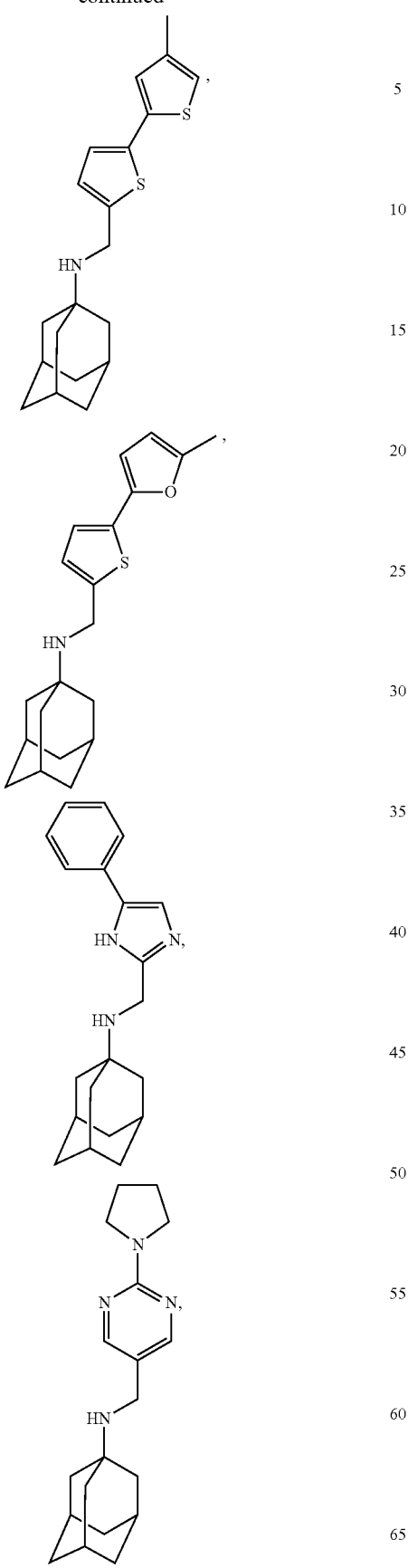
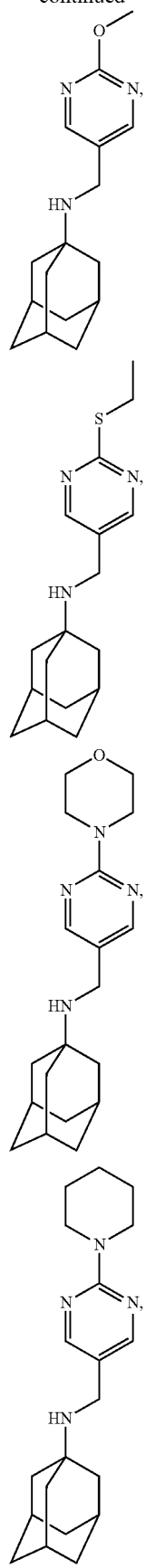

97
-continued
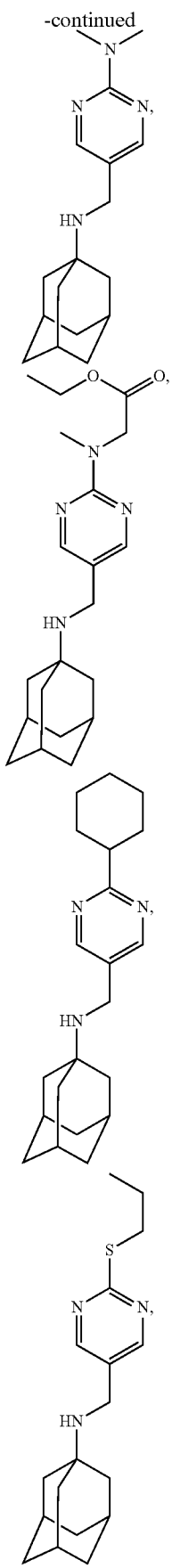
98
-continued
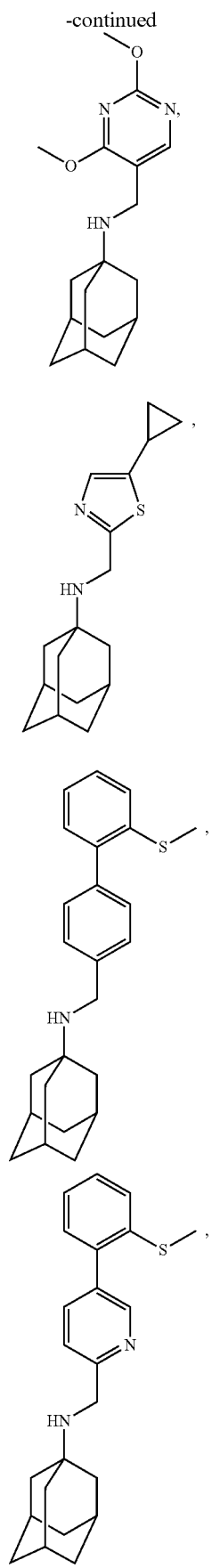

99
-continued
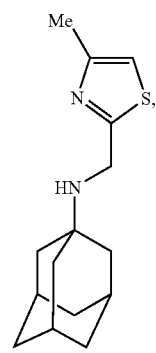
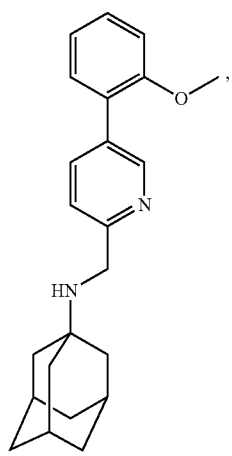
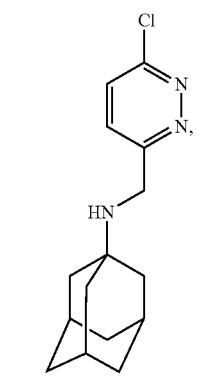
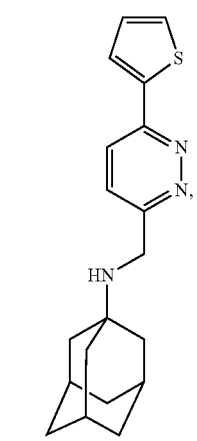
100
-continued
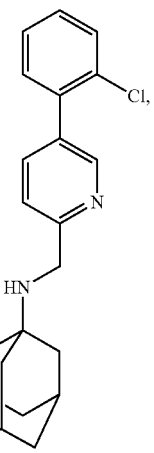
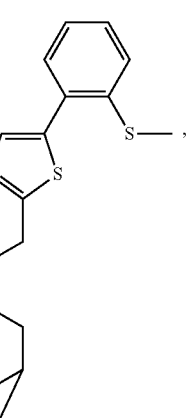
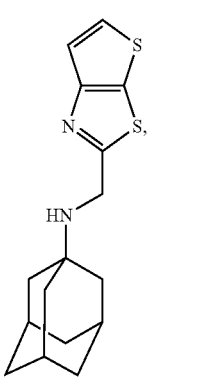
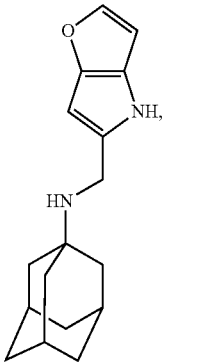

101
-continued
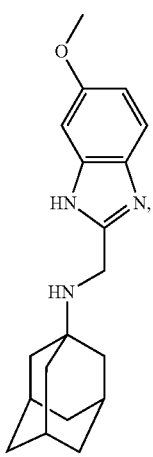
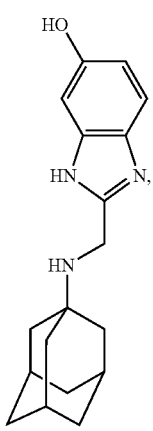
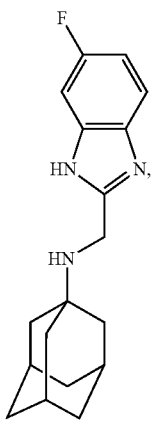
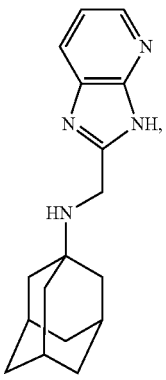
102
-continued
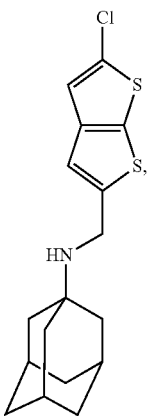
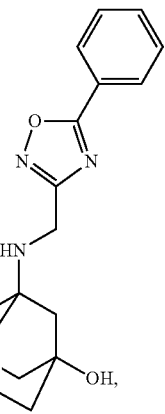
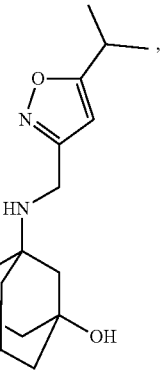
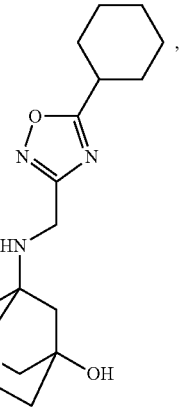

103
-continued
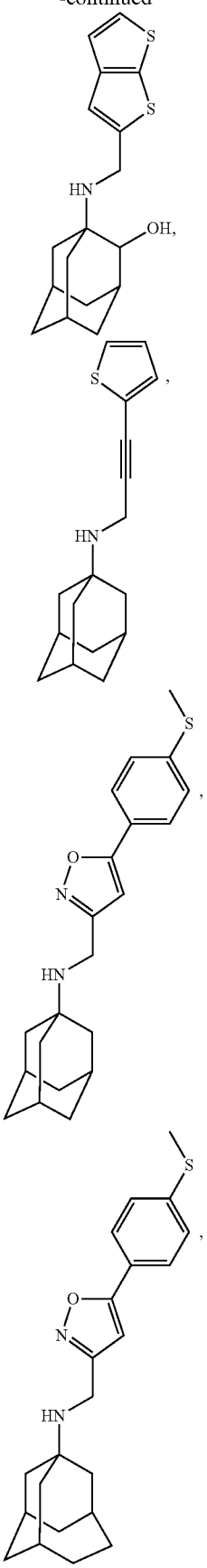
104
-continued
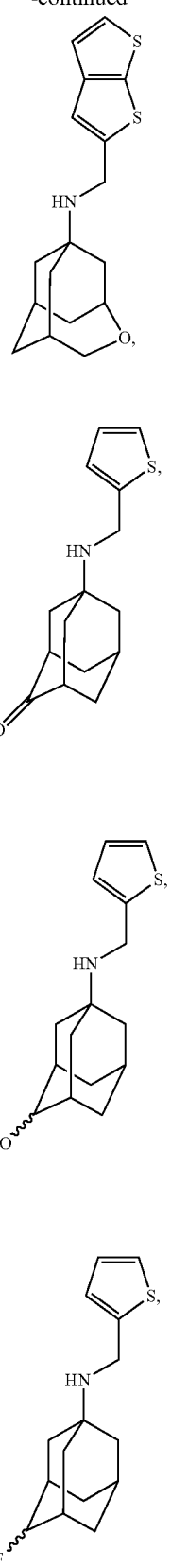
and stereoisomers, isotopically substituted analogues, or pharmaceutically acceptable salts thereof.

Also disclosed are compounds according to formula Ib

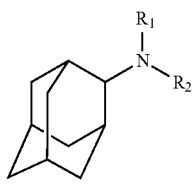

(Ib)

wherein

R₁ is hydrogen; and,

R₂ is —(R₃)(R₄);

R₃ is alkyl; and,

R₄ is a substituted mono-, di-, or tricyclic ring system, or,

R₁ together with R₂ and the atom to which they are both attached form an optionally substituted mono-, di-, or tricyclic ring system, or a stereoisomer, partial stereoisomer, isotopically substituted analogue, prodrug, pharmaceutically acceptable salt, hydrate, solvate, acid hydrate, or N-oxide thereof.

In some embodiments of the compounds according to formula Ib, R₄ is a substituted monocyclic ring. For example, R₄ may be a five- or six-membered carbocyclic or heterocyclic ring bearing one or more substituents independently selected from hydroxyl, halo, alkyl, alkoxy, trifluoromethyl, trifluoromethoxy, alkylsulfanyl, cycloalkyl, and aryl. In one example, R₄ is a five-membered heterocyclic ring bearing one or more aryl substituents.

In other embodiments of the compounds according to formula Ib, R₄ is a substituted dicyclic ring system that optionally includes one or more heteroatoms. For example, R₄ may be a a pair of ortho-fused heterocyclic rings.

Exemplary compounds according to formula Ib include

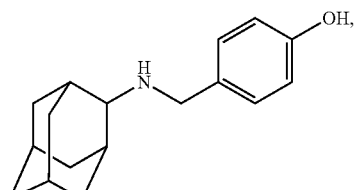

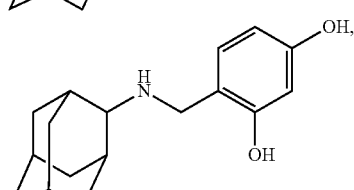

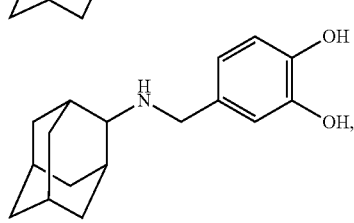

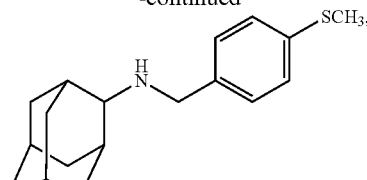

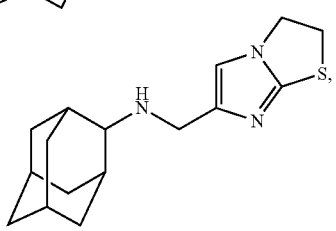

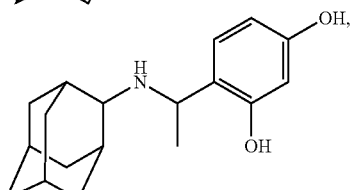

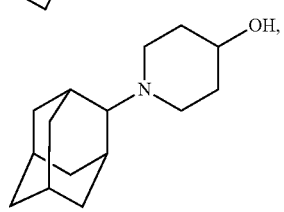

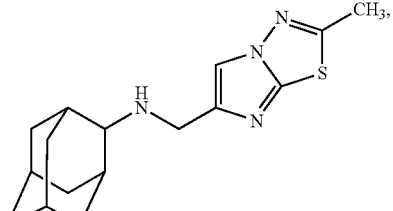

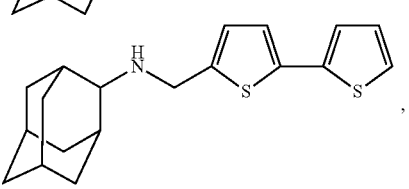

or a stereoisomer, isotopically substituted analogue, or pharmaceutically acceptable salt thereof.

The compounds employed in the present invention may exist in prodrug form. As used herein, "prodrug" is intended to include any covalently bonded carriers which release the active parent drug, for example, as according to the formulas or compounds employed in the methods of the present invention in vivo when such prodrug is administered to a subject. Since prodrugs are known to enhance numerous desirable qualities of pharmaceuticals (e.g., solubility, bioavailability, manufacturing, etc.) the compounds of the present invention may, if desired, be delivered in prodrug form. Thus, the present invention contemplates methods of delivering prodrugs. Prodrugs of the compounds employed in the present invention, for example, according to formula (Ia), (Ia') (described more fully infra), or (Ib) may be prepared by modifying functional groups present in the compound in such a way that the modifications are cleaved, either in routine manipulation or in vivo, to the parent compound.

Accordingly, prodrugs include, for example, compounds described herein in which a hydroxy, amino, or carboxy group is bonded to any group that, when the prodrug is administered to a mammalian subject, cleaves to form a free hydroxyl, free amino, or carboxylic acid, respectively. Examples include, but are not limited to, acetate, formate and benzoate derivatives of alcohol and amine functional groups; and alkyl, carbocyclic, aryl, and alkylaryl esters such as methyl, ethyl, propyl, iso-propyl, butyl, isobutyl, sec-butyl, tert-butyl, cyclopropyl, phenyl, benzyl, and phenethyl esters, and the like.

As will be readily understood, functional groups present may contain protecting groups during the course of synthesis. Protecting groups are known per se as chemical functional groups that can be selectively appended to and removed from functionalities, such as hydroxyl groups and carboxyl groups. These groups are present in a chemical compound to render such functionality in a room temperature to chemical reaction conditions to which the compound is exposed. Any of a variety of protecting groups may be employed with the present invention. Protecting groups that may be employed in accordance with the present invention may be described in Greene, T. W. and Wuts, P. G. M., *Protective Groups in Organic Synthesis* 2d. Ed., Wiley & Sons, 1991.

In a further aspect, the present disclosure relates to pharmaceutical compositions comprising a compound according to formula (Ia), (Ib), or a pharmaceutically acceptable salt, isotopically substituted analogue, or stereoisomer thereof and a pharmaceutically acceptable carrier, diluent, or excipient. The applicable carrier, diluent, or excipient may be selected on the basis of the chosen route of administration and standard pharmaceutical practice as described, for example, in *Remington's Pharmaceutical Sciences* (Mack Pub. Co., Easton, Pa., 1985), the disclosure of which is hereby incorporated by reference in its entirety. The pharmaceutical compositions may further comprise a therapeutically effective amount of a further agent that modulates an influenza virus. With respect to certain embodiments, the present compositions may further comprise a therapeutically effective amount of a further agent that modulates Influenza A virus, Influenza B virus, or another Viroporin-type virus. For example, the further agent that modulates virus may be a known anti-viral agents, such as Tamiflu®, Relenza®, or peramivir. In certain embodiments, the present compositions comprise a therapeutically effective amount of a compound according to formula (Ia) or (Ib) which is administered in combination with immunizations or vaccines that are effective in preventing or lessening the symptoms of influenza. Examples include antibodies, immune suppressants, anti-inflammatory agents, and the like.

The present disclosure also pertains to methods for treating an influenza A virus-affected disease state or infection comprising the step of administering to a subject in need thereof a composition comprising a compound according to formula (Ia')

(Ia')

wherein

A is $C_{1-3}$ alkylene or a bond between L and the atom at position $Z_1$;

L is nitrogen;

$R_1$ is NH, $NH_2$, alkyl, or, if A is a bond, is absent;

dashed lines b and b' may independently represent a double bond;

$R_2$ is H, alkyl, -(D)(E), or is absent;

$R_3$ is —(X)(Y);

$R_4$ is —$(R_5)(R_6)$, halo, or is absent;

$R_5$ is nitrogen or oxygen;

$R_6$ is hydrogen or —$(R_7)(R_8)$ $R_7$ is alkylene, —$CH(R_{7a})$—, —$(CH_2)_{0-6}CH(OH)$—, or represents a bond between $R_5$ and $R_8$;

$R_{7a}$ is alkyl;

$R_8$ is optionally substituted mono-, di-, or tricyclic ring system that optionally includes one or more heteroatoms;

$R_9$ is —$(R_{10})(R_{11})$ or is absent;

$R_{10}$ is oxygen, nitrogen, alkyl, —$CF_3$, or alkylene;

$R_{11}$ is hydrogen, halo, or is absent;

$R_{12}$ is alkyl, alkoxy, halo, oxo, or hydroxyl;

D is alkylene, alkenylene, alkynylene, —CH(Q)-, carbonyl, or a bond;

E is an optionally substituted mono-, di-, or tricyclic ring system that optionally includes one or more heteroatoms;

X is alkylene, alkenylene, alkynylene, —CH(Q)-, carbonyl, or a bond;

Q is alkyl, —C(═O)O$(CH_2)_{1-3}CH_3$, —$(CH_2)_{0-3}$OH, or —C(═O)—;

Y is an optionally substituted mono-, di-, or tricyclic ring system that optionally includes one or more heteroatoms;

$Z_2$ is optionally substituted alkylene of which one or more carbon atoms is optionally replaced with N, O, or S, or represents a bond between $Z_1$ and $Z_8$;

$Z_3$ is optionally substituted alkylene of which one or more carbon atoms is optionally replaced with N, O, or S, or represents a bond between $Z_8$ and $Z_9$;

$Z_4$, $Z_5$, and $Z_6$ are independently alkylene, N, O, or S;

$Z_7$ is optionally substituted alkylene of which one or more carbon atoms is optionally replaced with N, O, or S;

or a stereoisomer, partial stereoisomer, isotopically substituted analogue, prodrug, pharmaceutically acceptable salt, hydrate, solvate, acid hydrate, or N-oxide thereof, wherein each of the variable groups may be defined according to any of the embodiments described above in connection with the inventive compounds according to formula (Ia), albeit without the limiting provisos that are recited with respect to the compounds according to formula (Ia);

or, a compound according to formula (Ib)

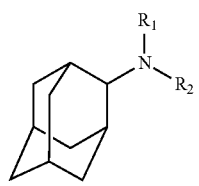

(Ib)

or a stereoisomer, partial stereoisomer, isotopically substituted analogue, prodrug, pharmaceutically acceptable salt, hydrate, solvate, acid hydrate, or N-oxide thereof, wherein $R_1$ and $R_2$ may be defined according to any of the embodiments described above in connection with the inventive compounds according to formula (Ib), or, a combination of two more compounds according to any of formula (Ia') and (Ib), and a pharmaceutically acceptable carrier, diluent, or excipient.

Exemplary compounds according to formula (Ia') include

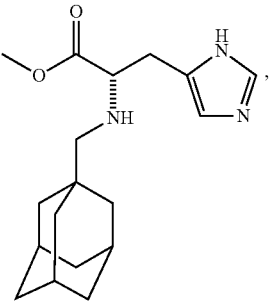

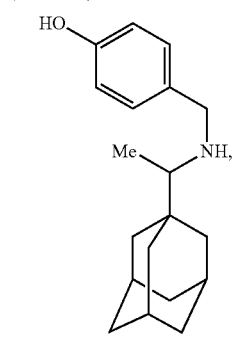

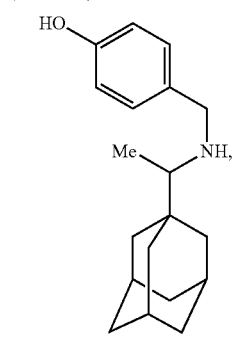

-continued

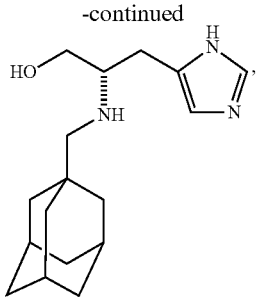

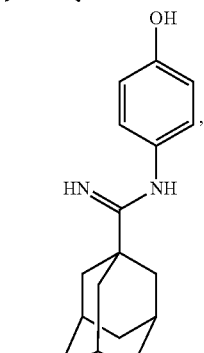

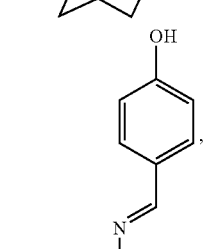

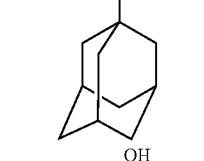

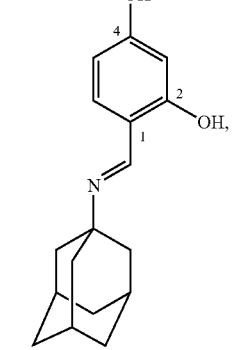

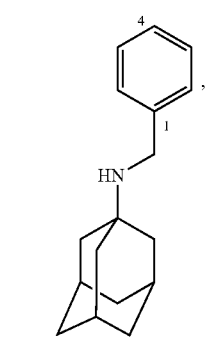

111
-continued
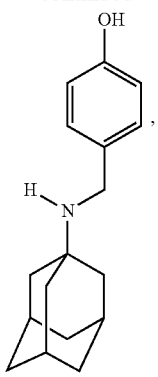
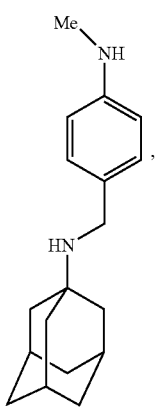
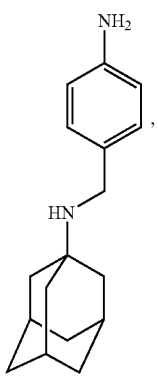
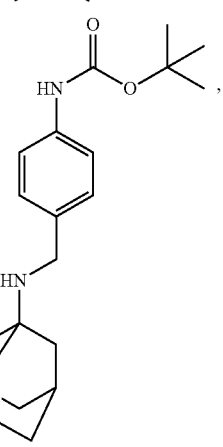
112
-continued
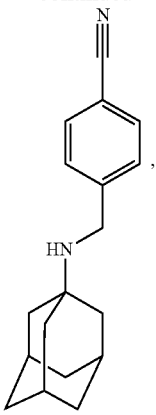
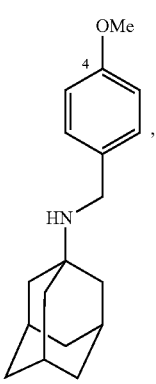
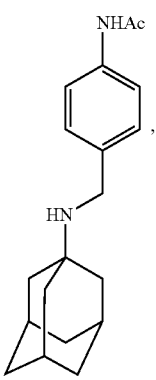
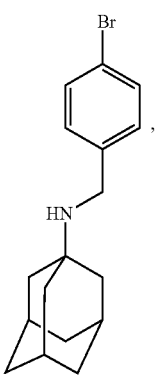

113
-continued
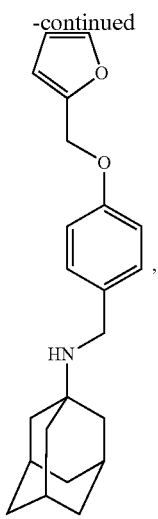
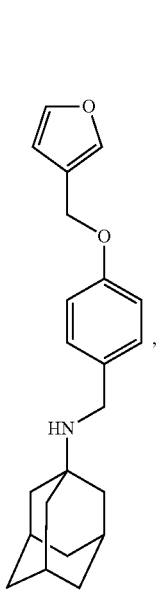
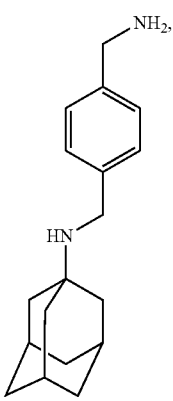
114
-continued
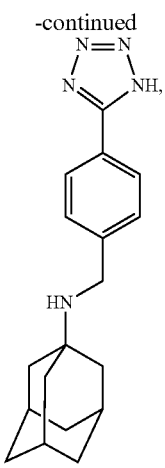
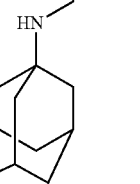
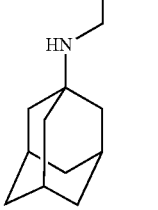
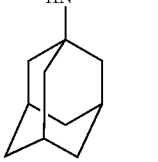

115
-continued
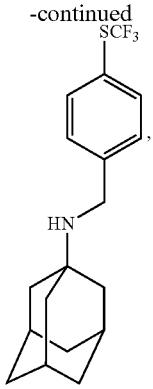
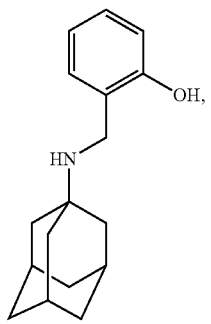
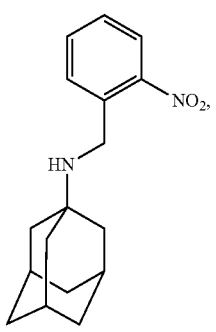
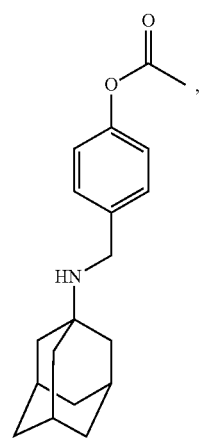
116
-continued
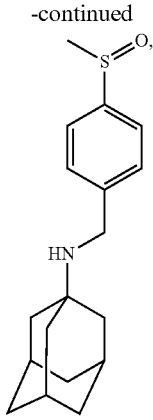
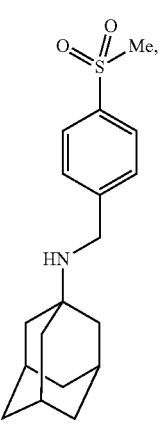
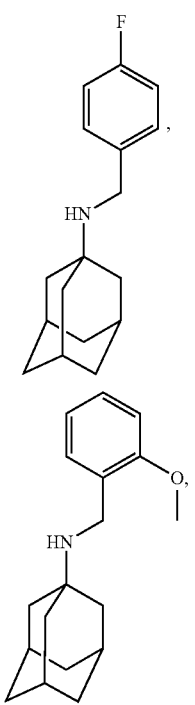

117
-continued
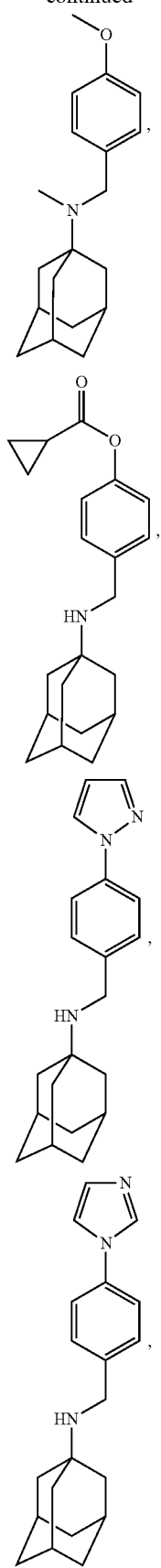
118
-continued
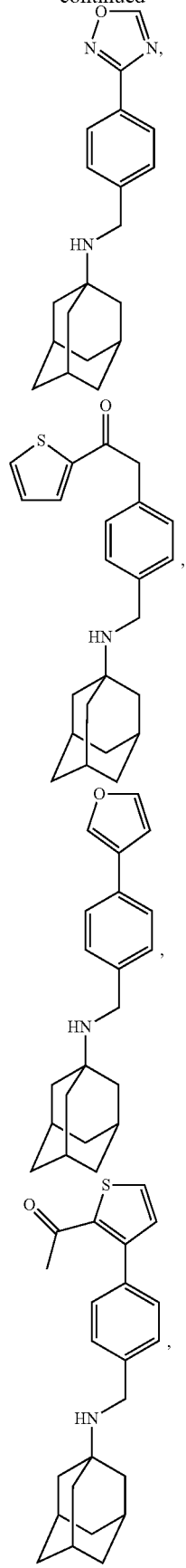

119
-continued
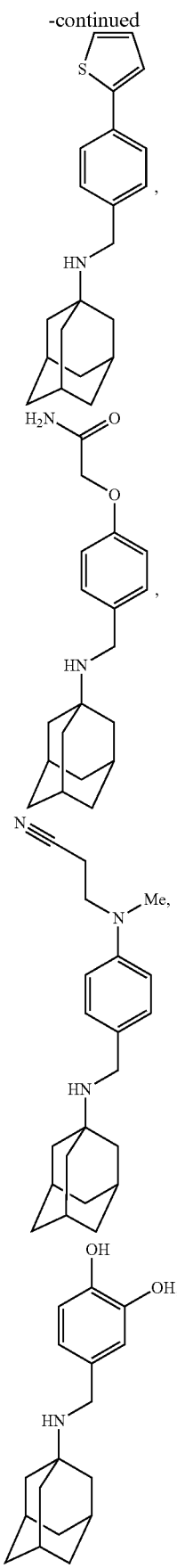
120
-continued
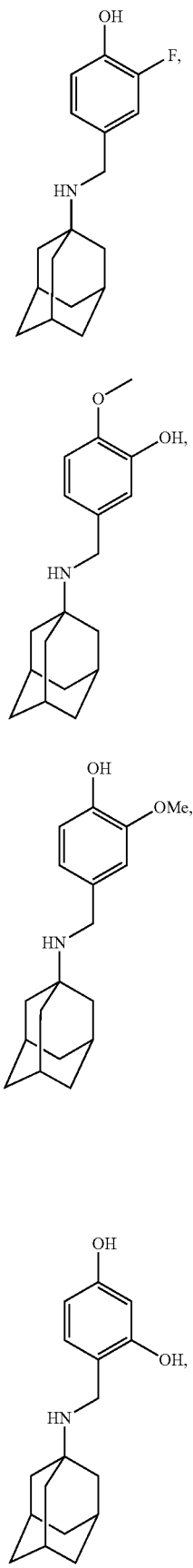

| 121 | 122 |
|---|---|
| -continued | -continued |
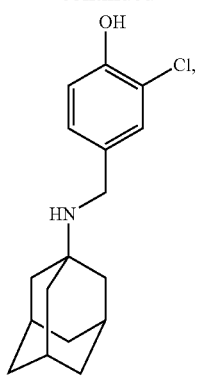
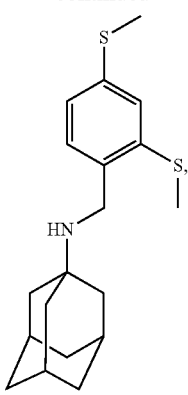
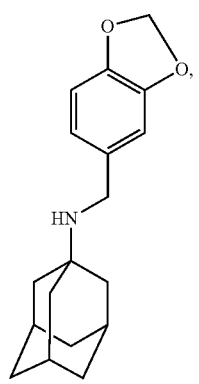
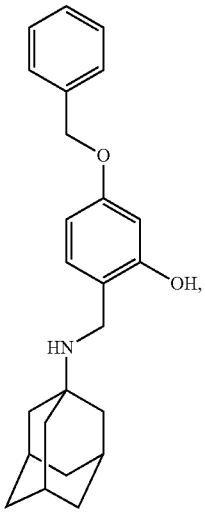
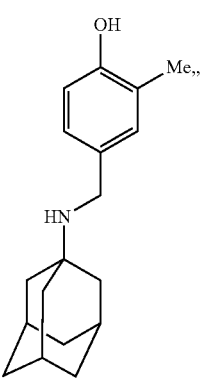
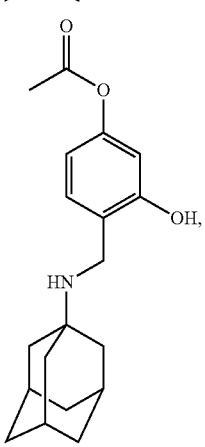
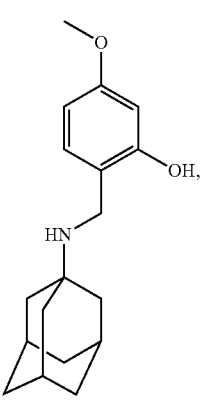
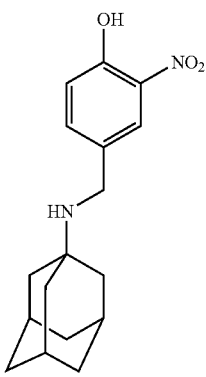

123
-continued
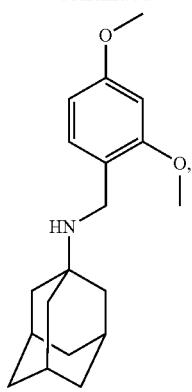
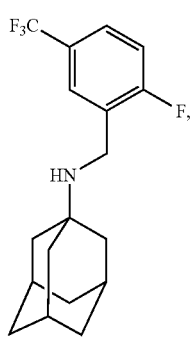
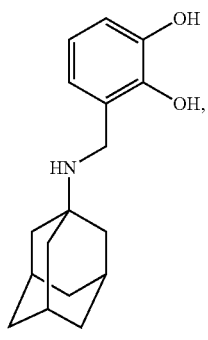
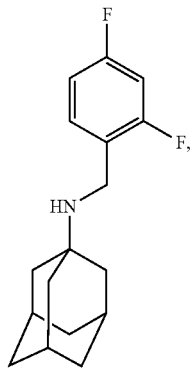
124
-continued
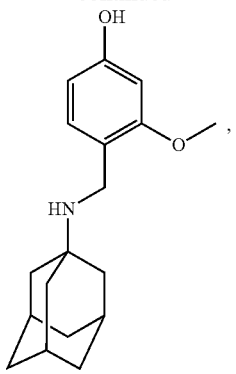
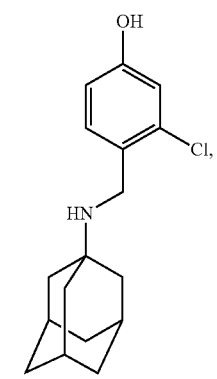
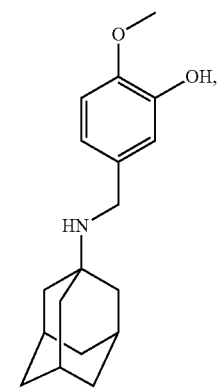
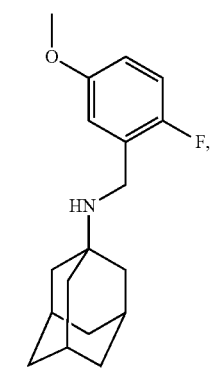

-continued
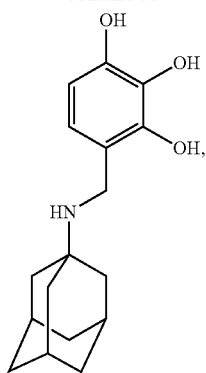
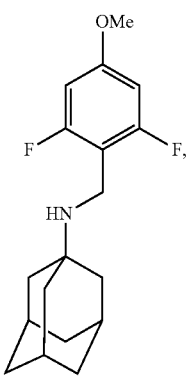
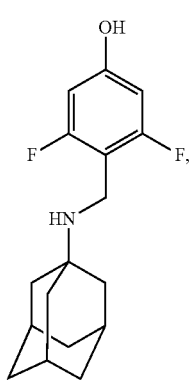
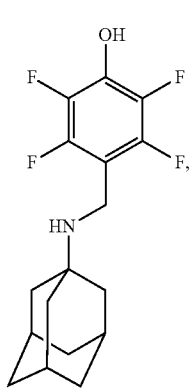
-continued
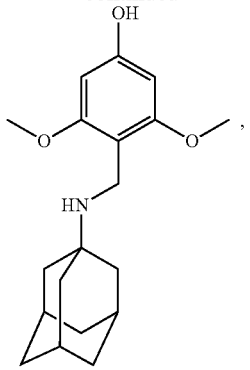
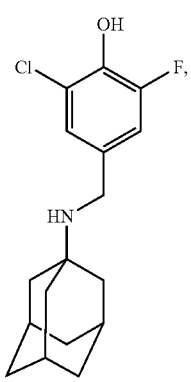
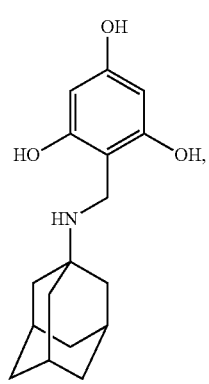
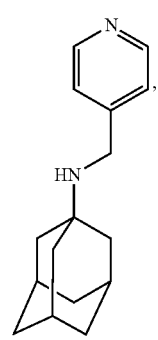

127
-continued
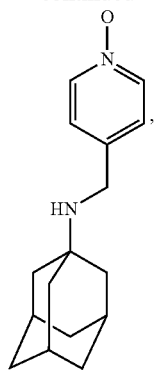
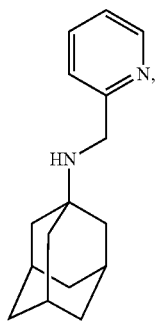
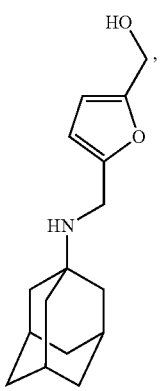
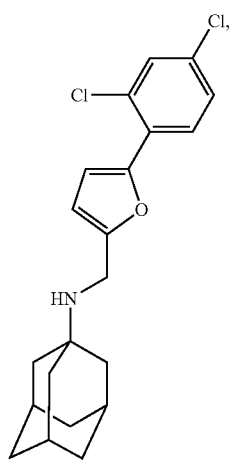
128
-continued
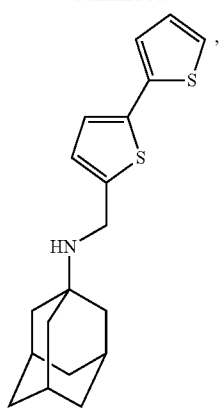
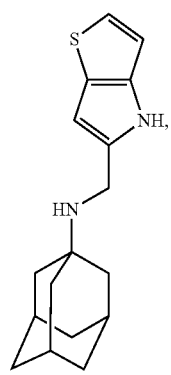
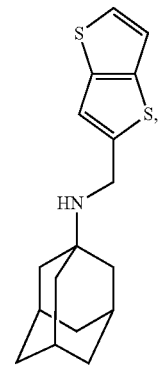
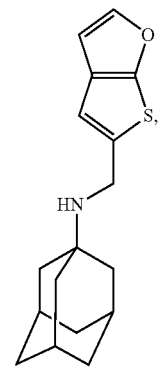

129
-continued
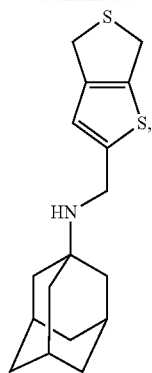
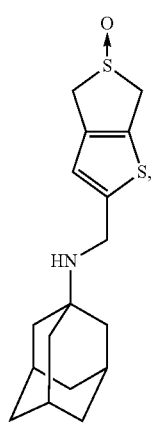
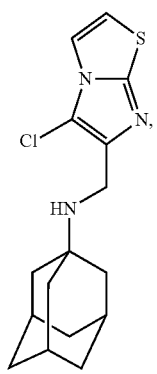
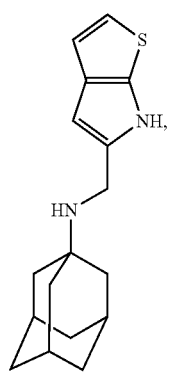
130
-continued
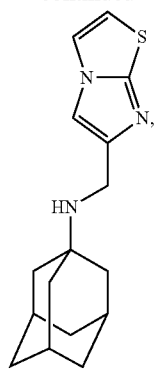
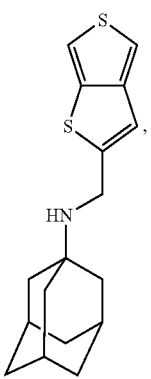
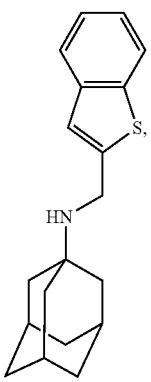
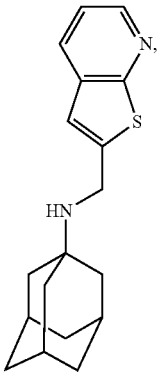

131
-continued
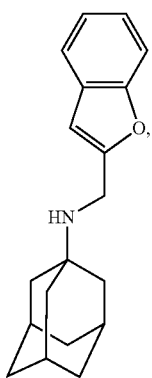
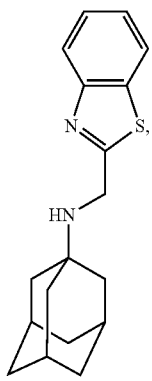
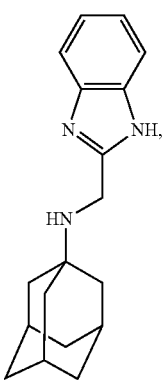
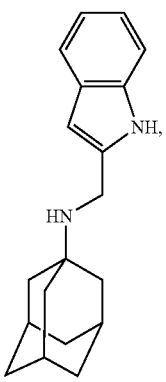
132
-continued
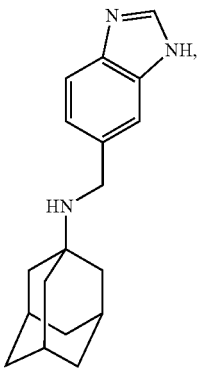
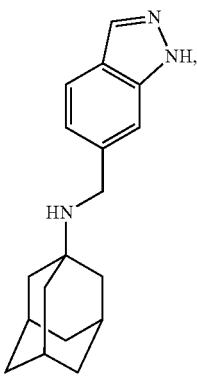
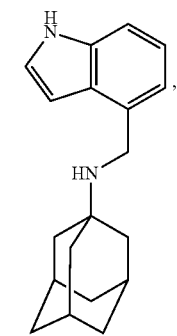
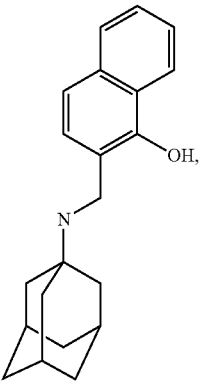

133
-continued
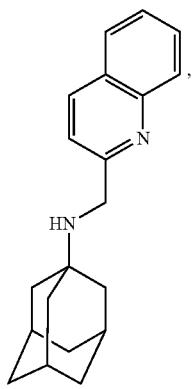,
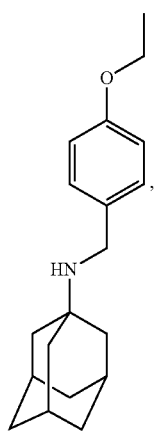,
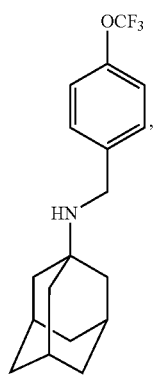,
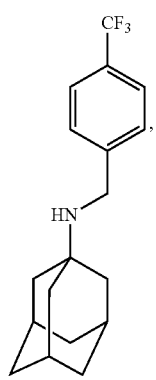,
134
-continued
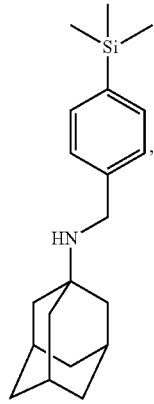,
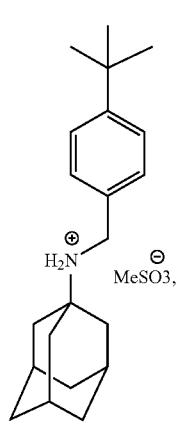,
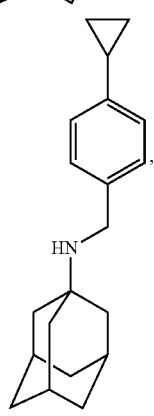,
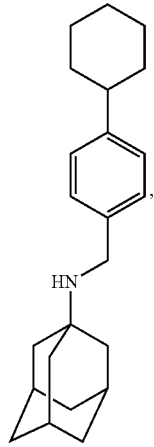, 135
-continued
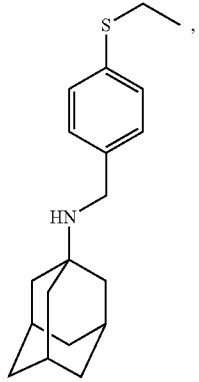
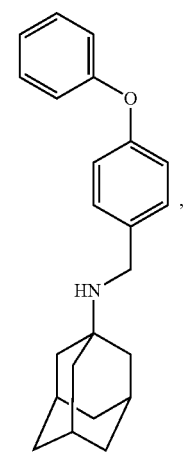
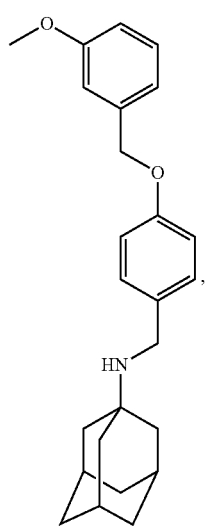
136
-continued
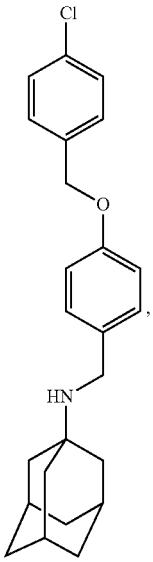
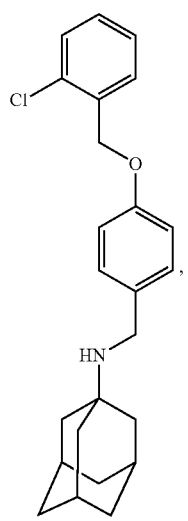
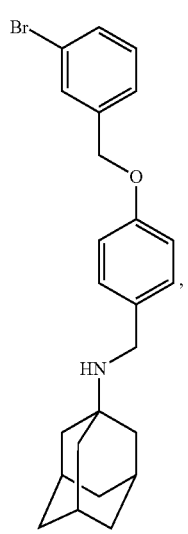

137
-continued
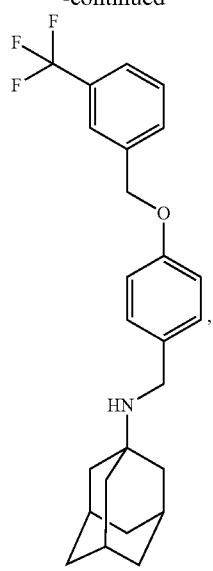
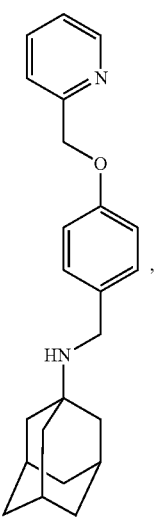
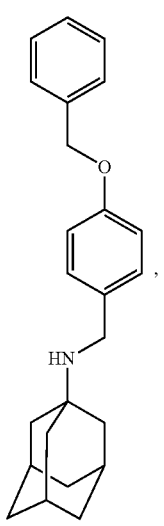
138
-continued
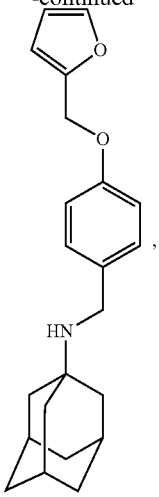
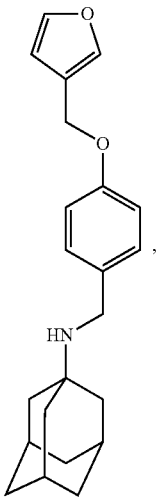
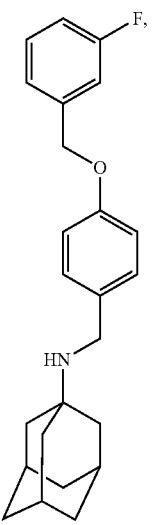

139
-continued
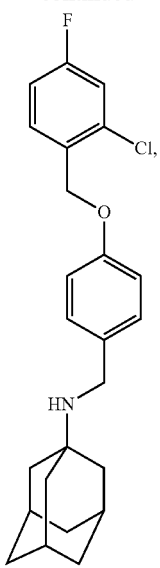
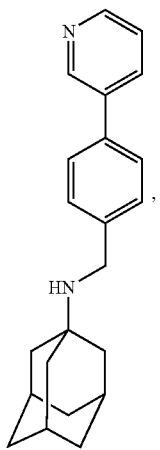
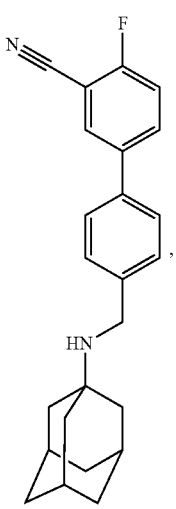
140
-continued
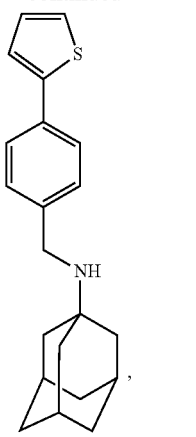
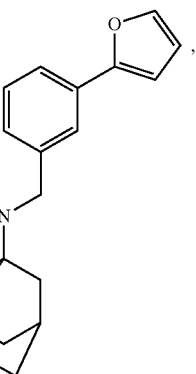
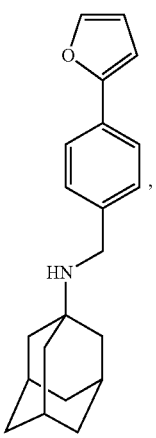
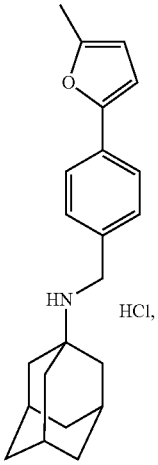

141
-continued
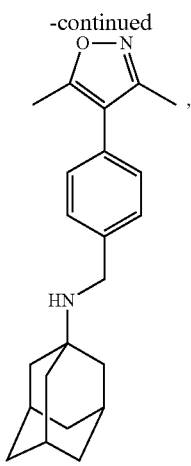
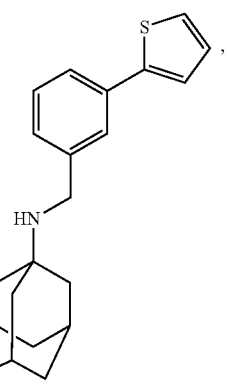
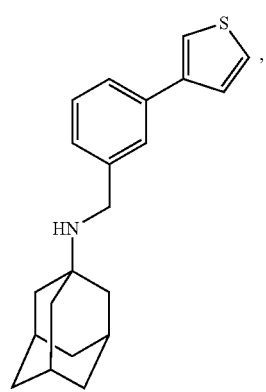
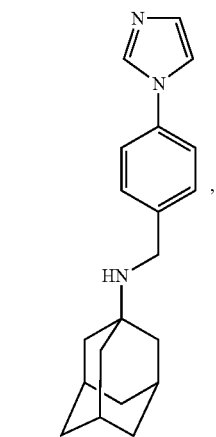
142
-continued
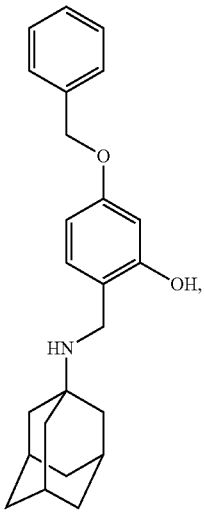
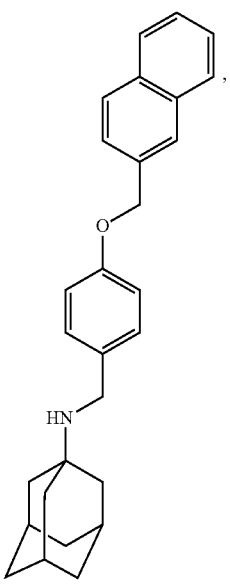
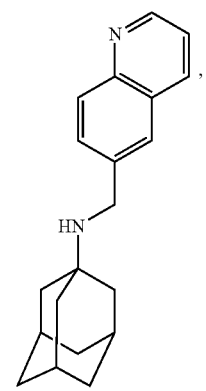

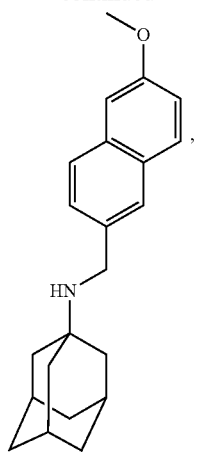,
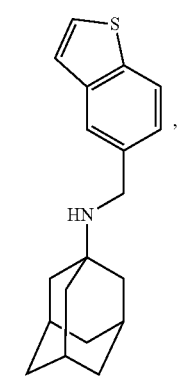,
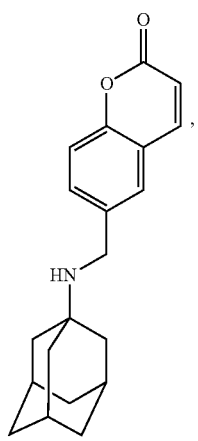,
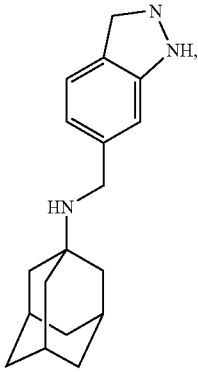,
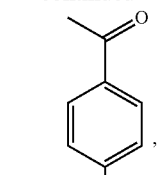,
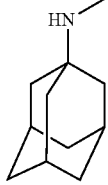,
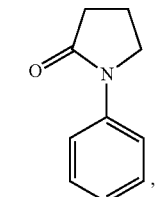,
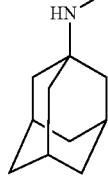,
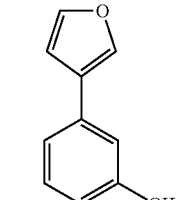,
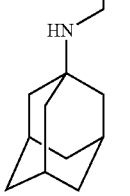,
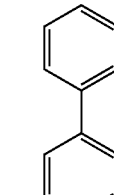,
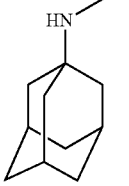

145
-continued
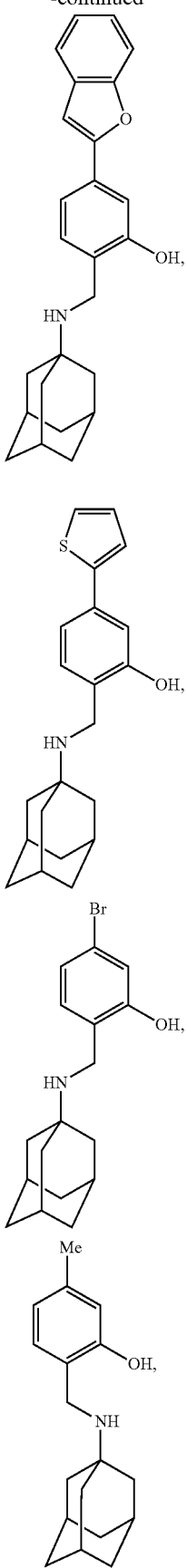
146
-continued
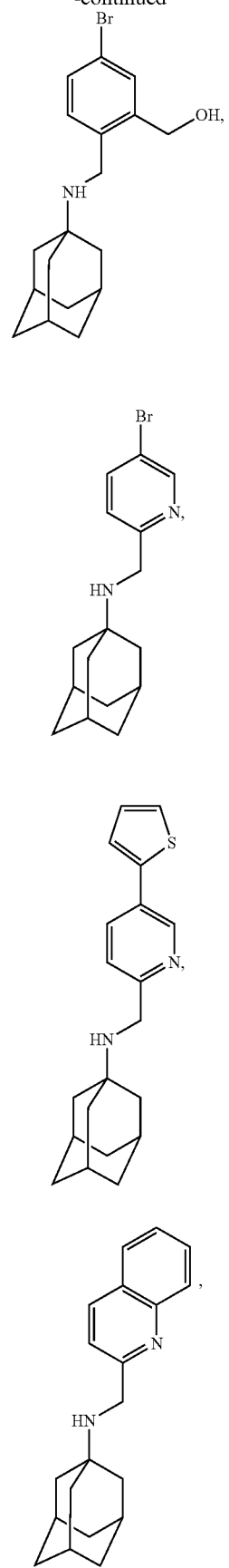

147
-continued
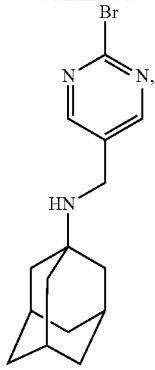
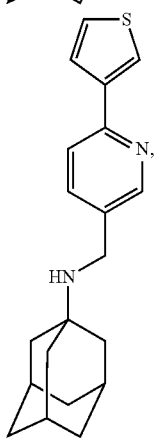
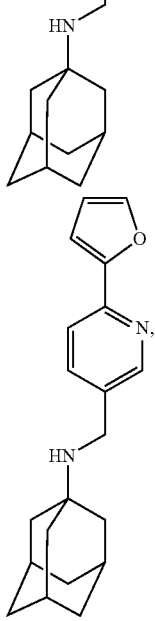
148
-continued
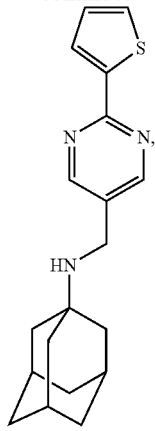
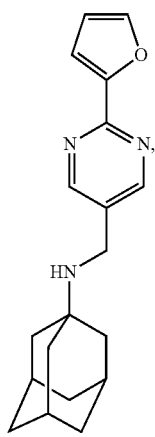
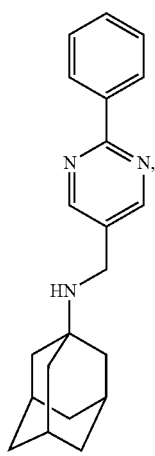

149
-continued
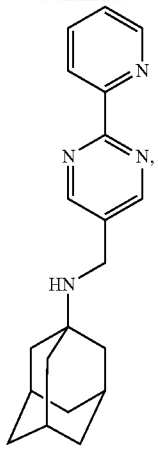
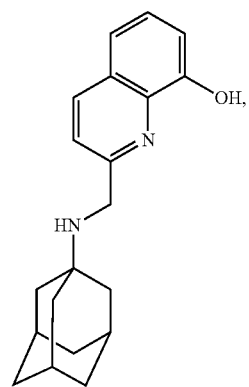
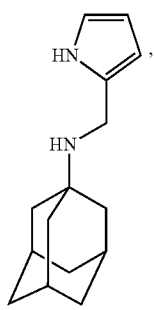
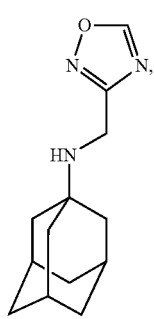
150
-continued
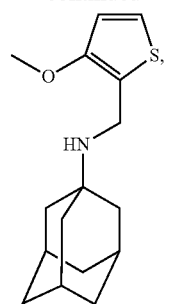
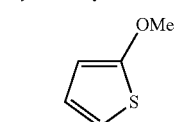
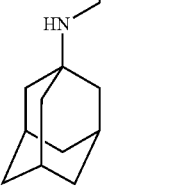
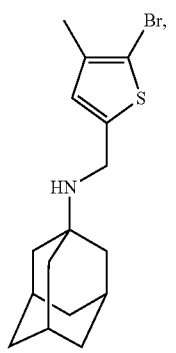
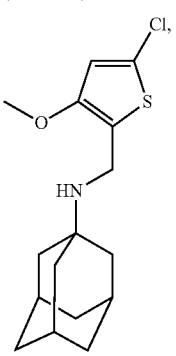
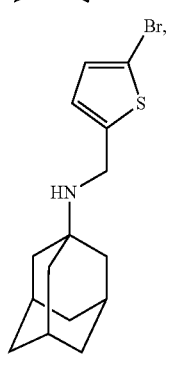

| 151 -continued | 152 -continued |
|---|---|
| 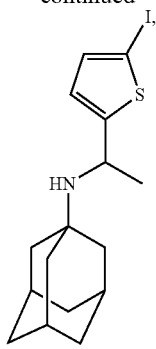 | 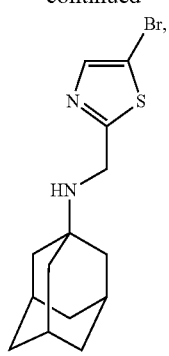 |
| 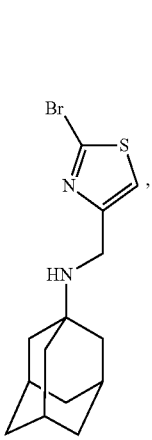 | 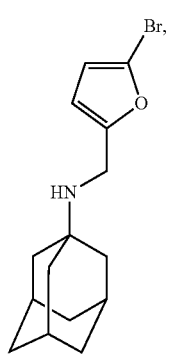 |
| 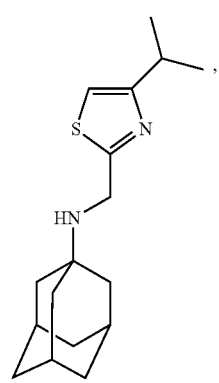 | 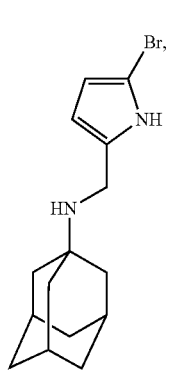 |
| 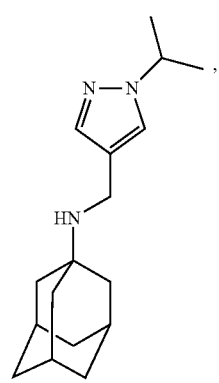 | 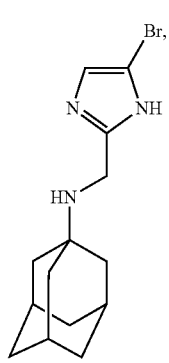 |

153
-continued
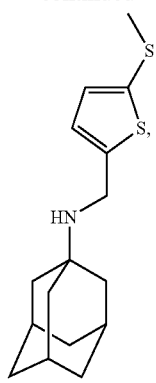
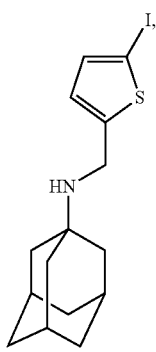
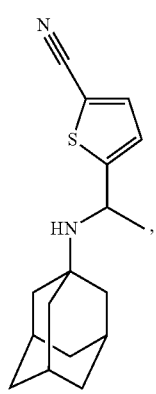
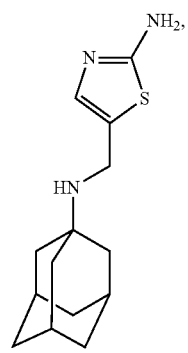
154
-continued
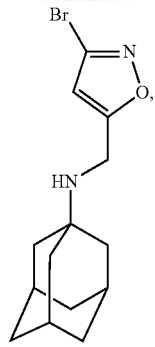
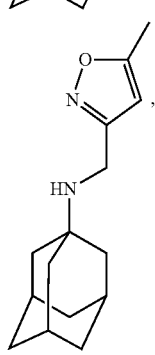
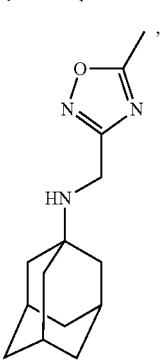
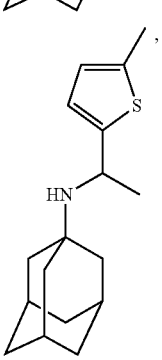
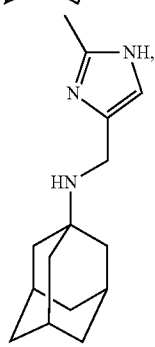

-continued
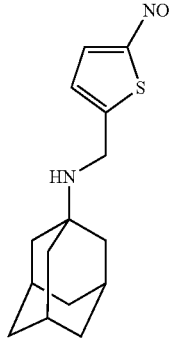
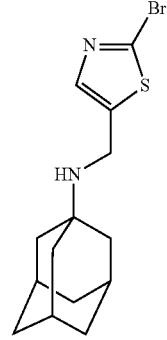
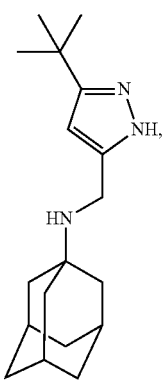
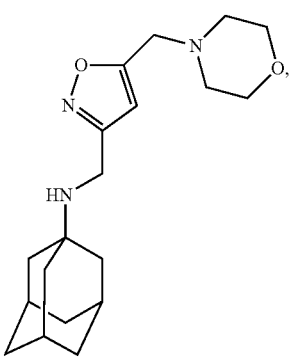
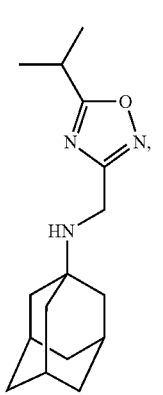
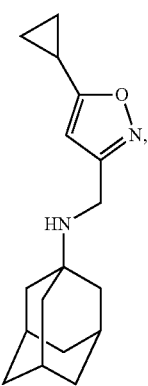
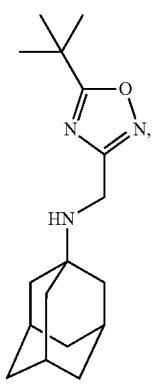
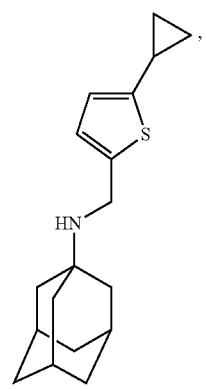

157
-continued
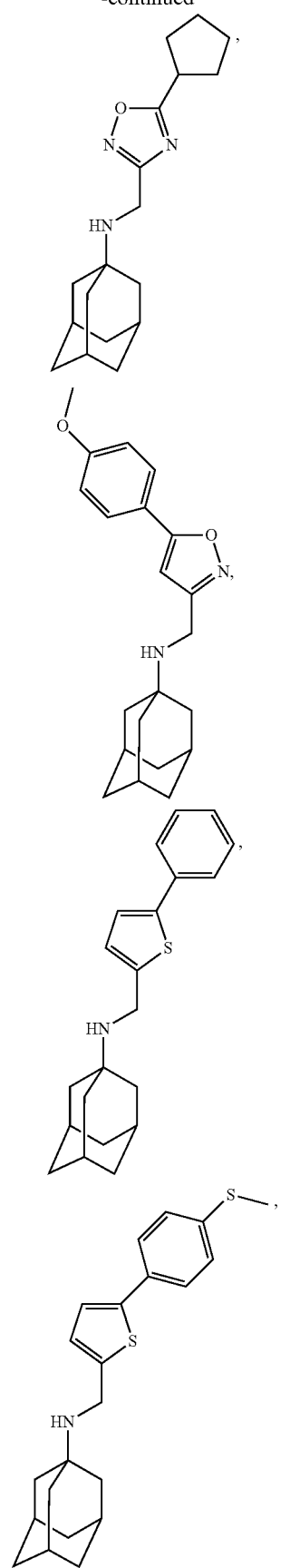
158
-continued
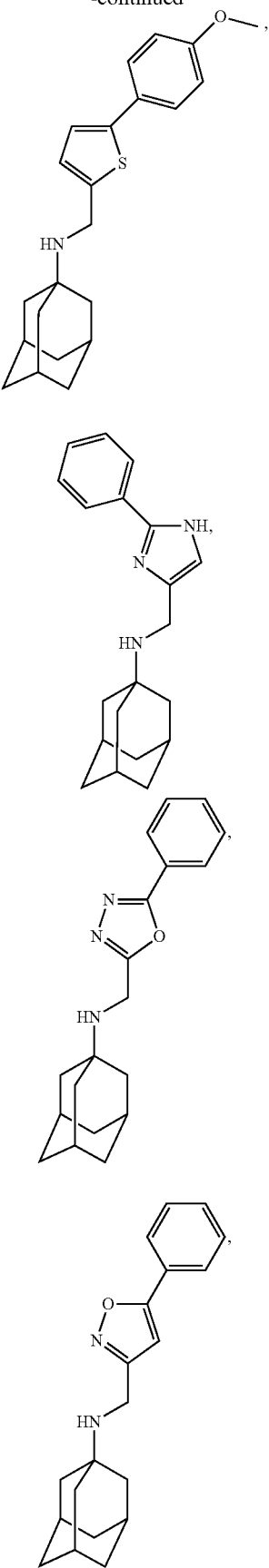

159
-continued
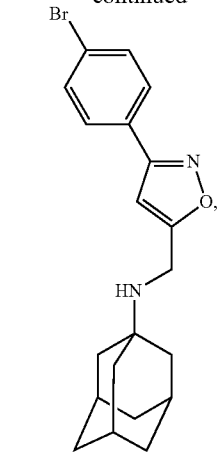
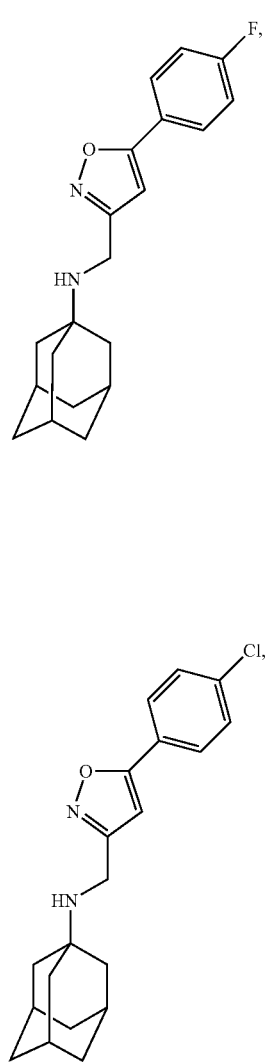
160
-continued
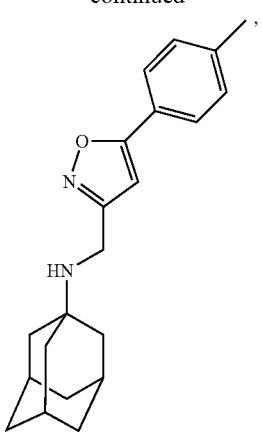
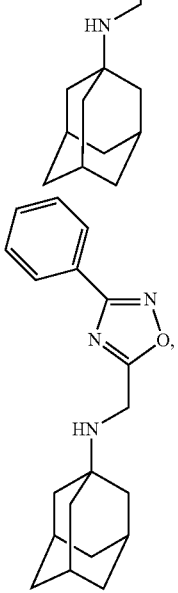

161
-continued
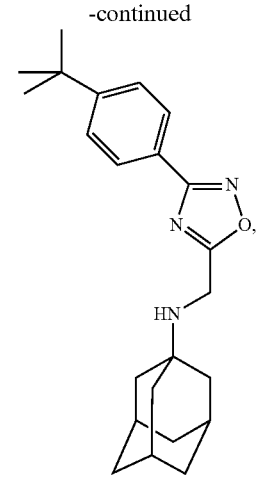
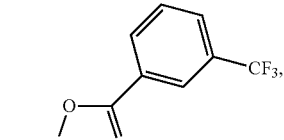
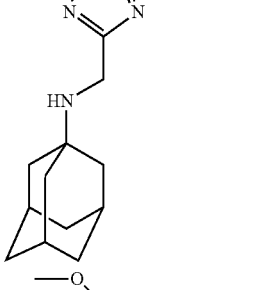
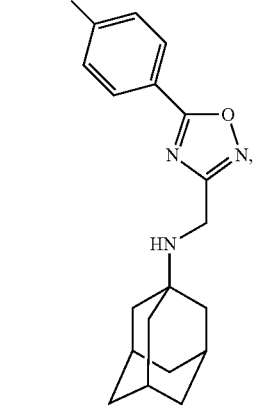
162
-continued
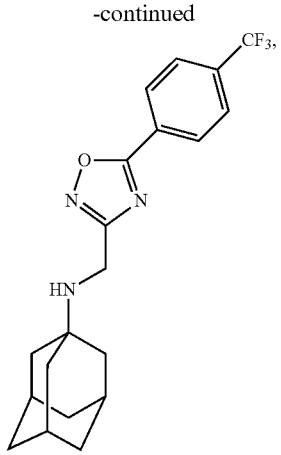
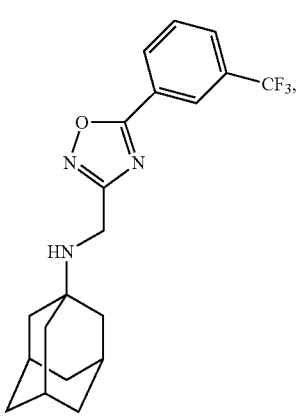
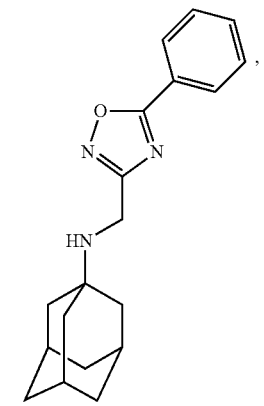
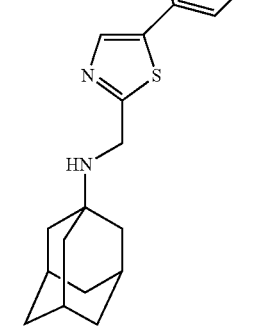

163
-continued
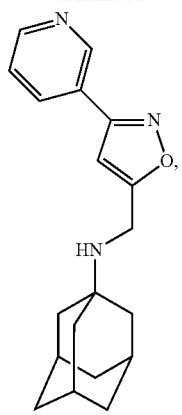
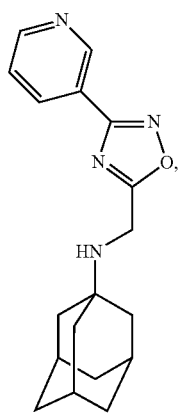
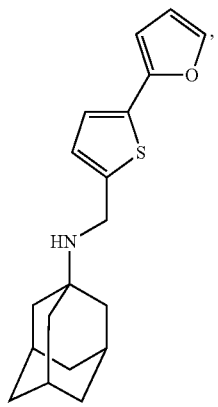
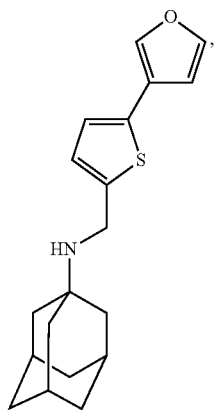
164
-continued
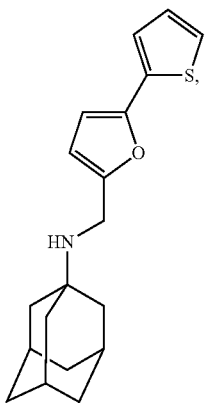
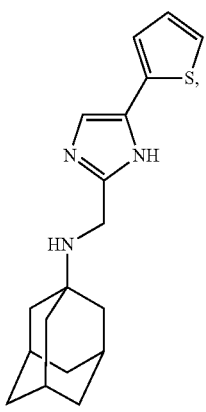
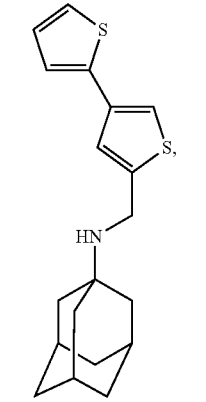
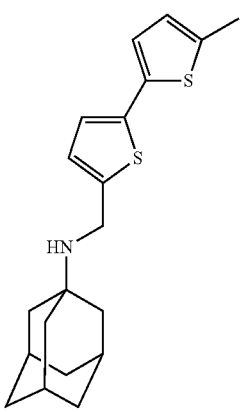

165
-continued
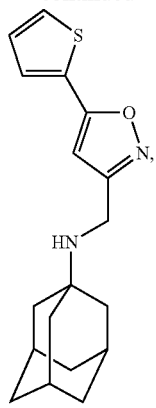
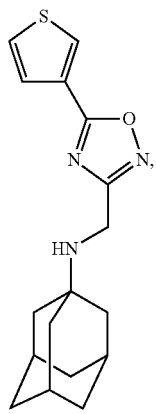
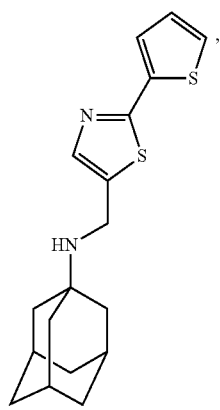
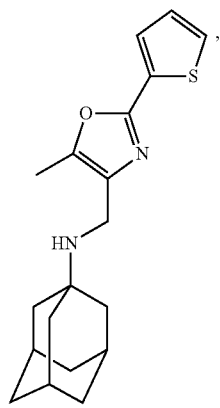
166
-continued
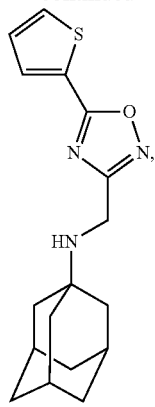
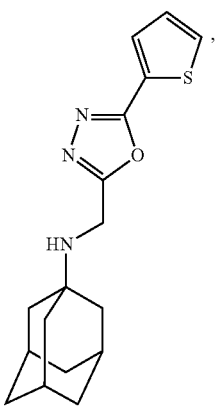
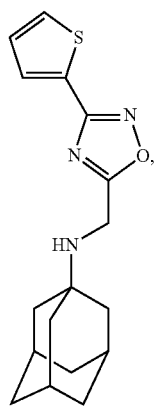
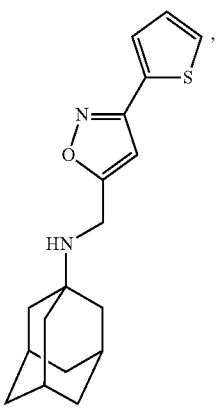

167
-continued
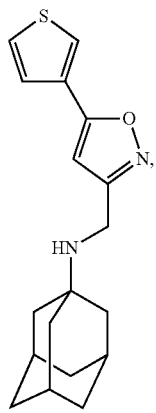
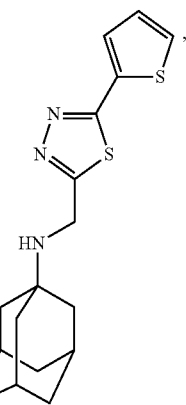
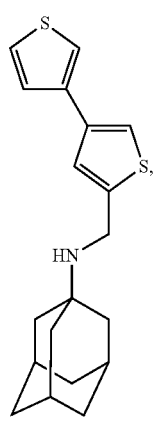
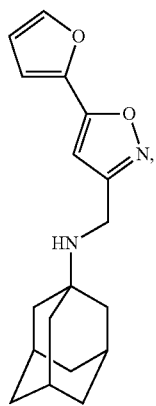
168
-continued
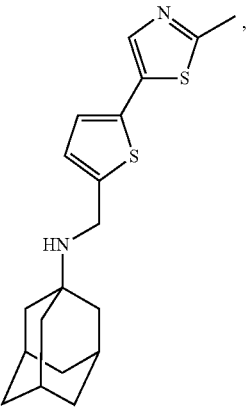
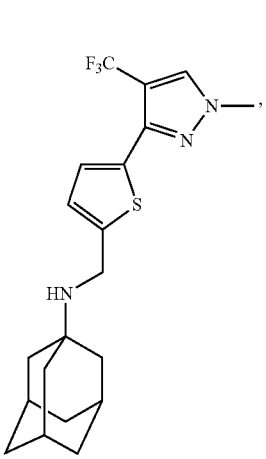
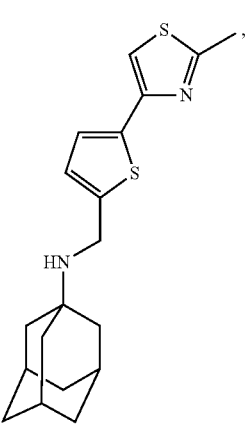

169
-continued
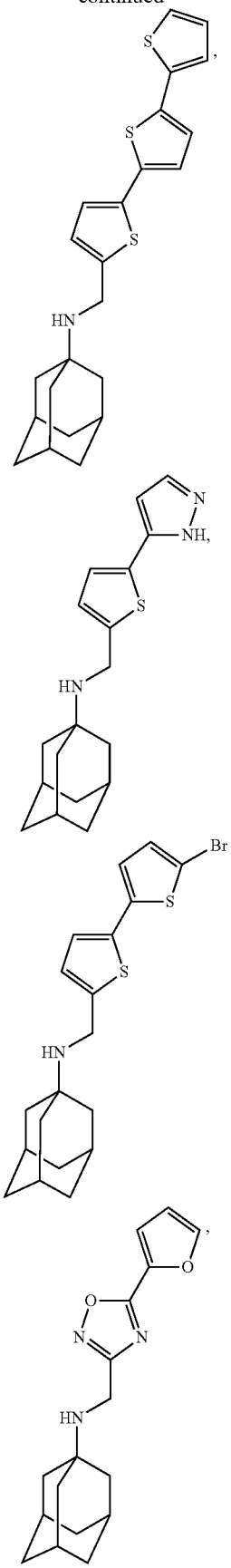
170
-continued
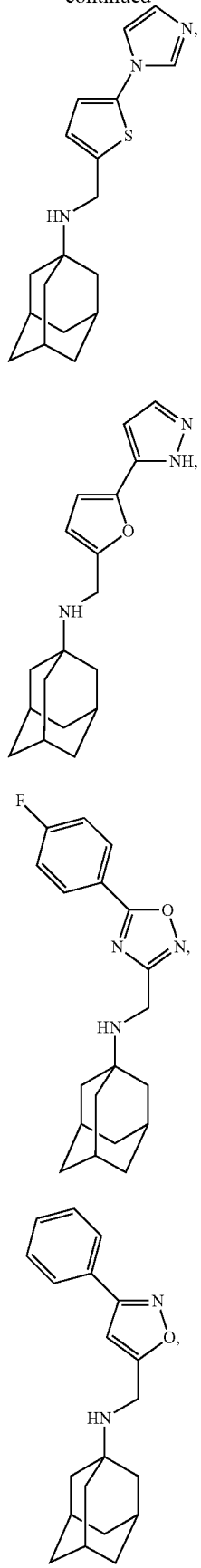

171
-continued
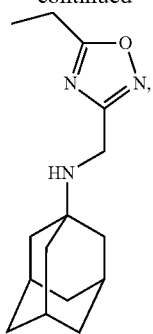
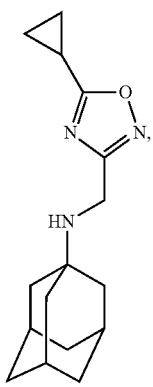
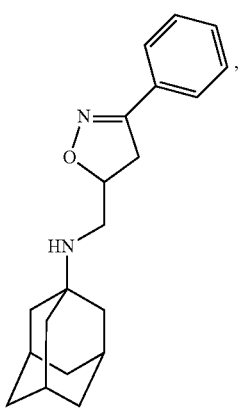
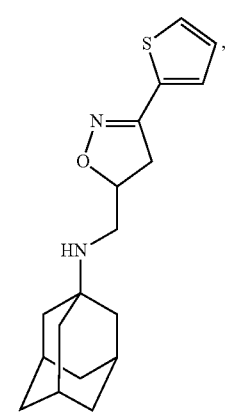
172
-continued
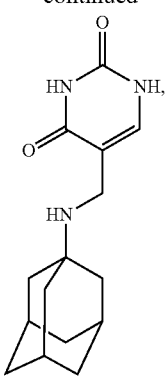
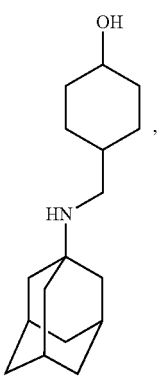
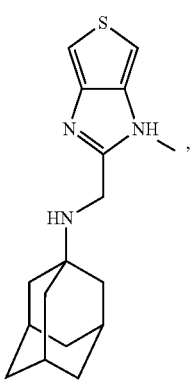
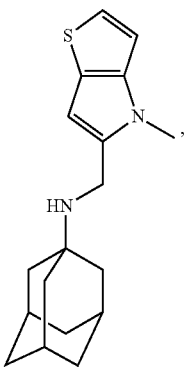

173
-continued
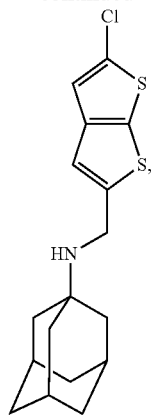
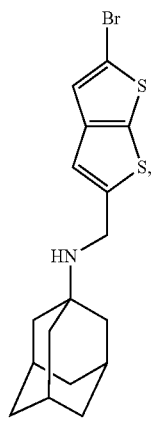
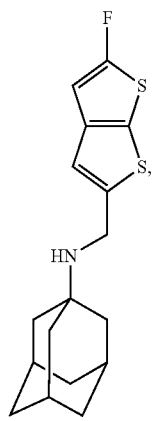
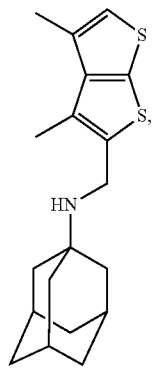
174
-continued
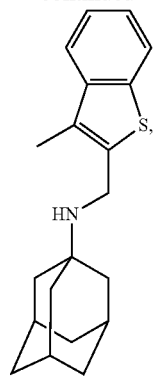
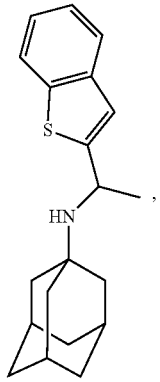
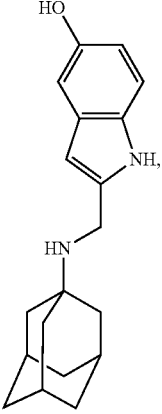
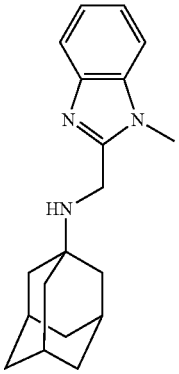

-continued
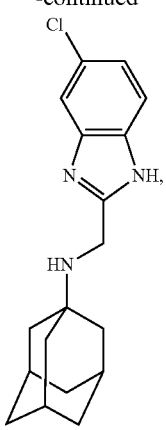
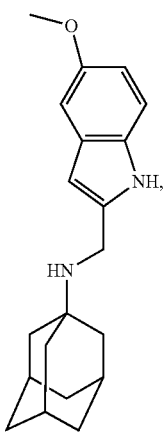
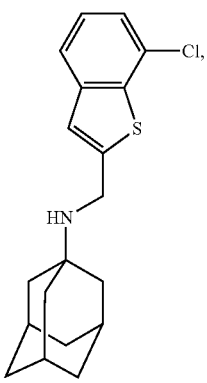
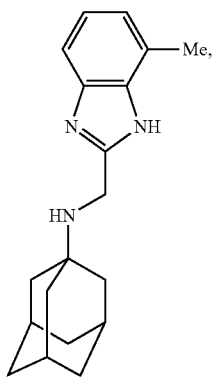
-continued
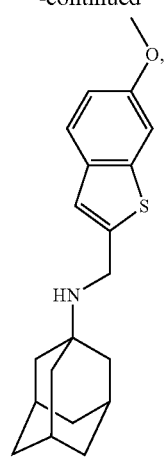
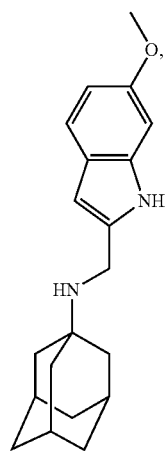
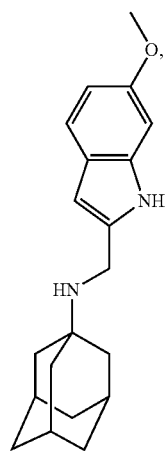
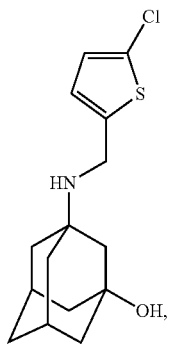

177
-continued
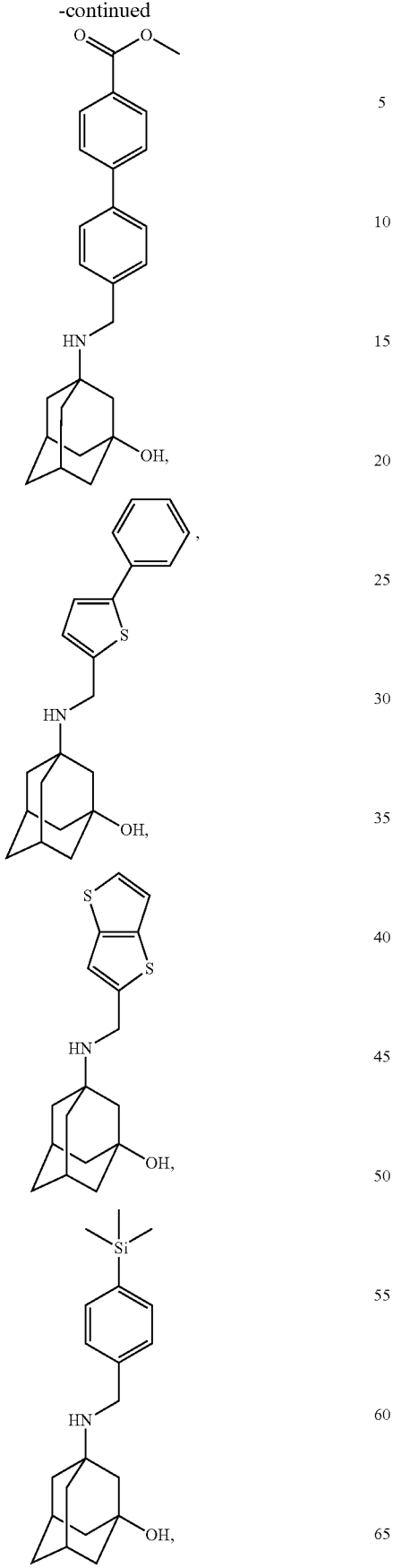
178
-continued
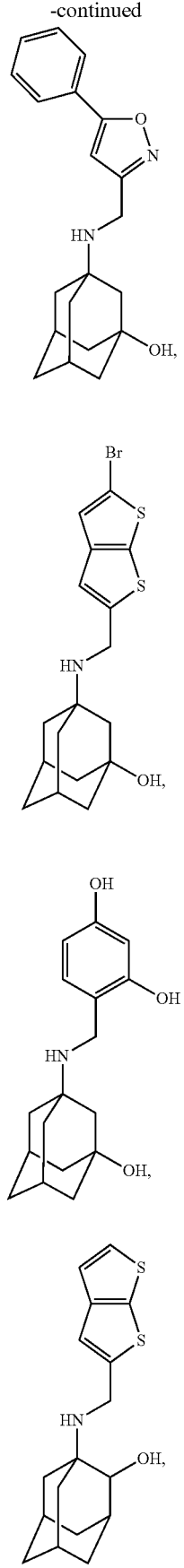

179
-continued
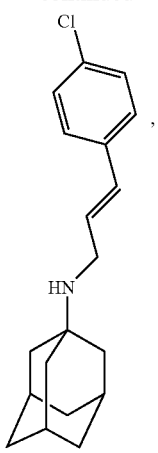
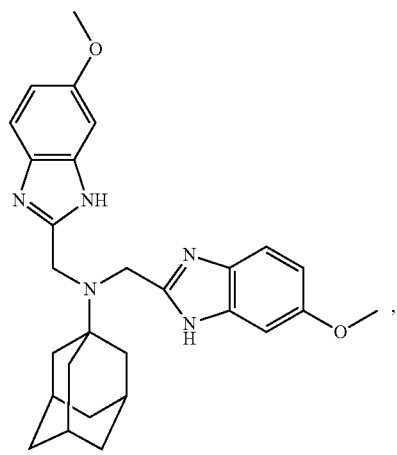
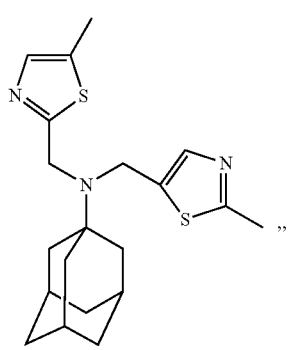
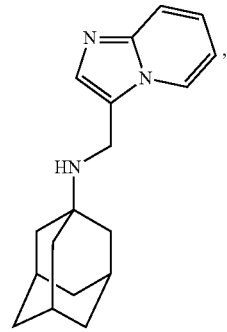
180
-continued
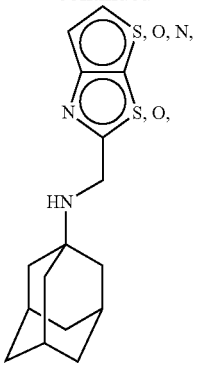
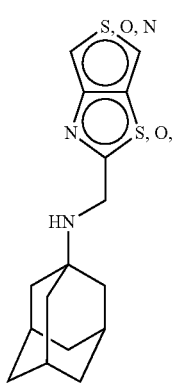
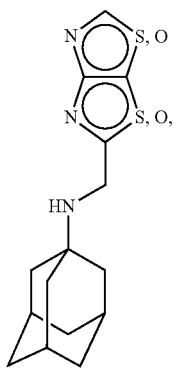
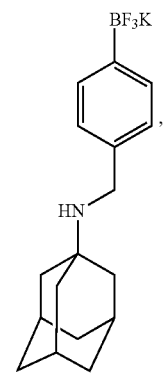

181
-continued
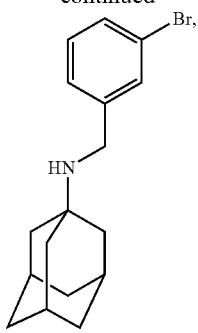
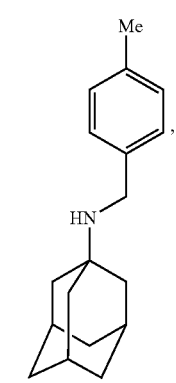
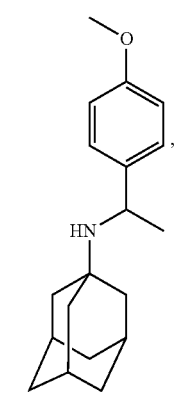
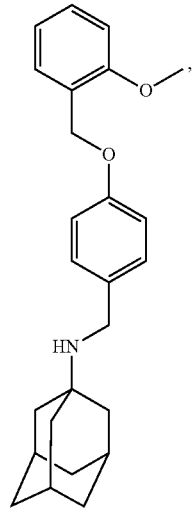
182
-continued
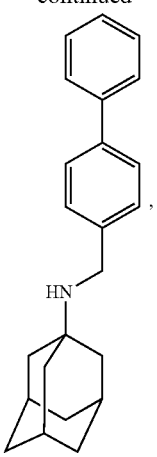
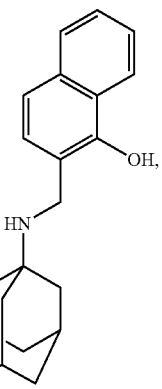
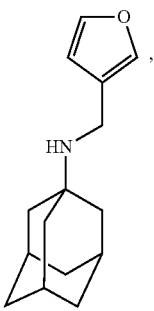
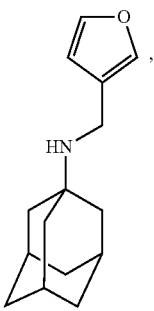

-continued
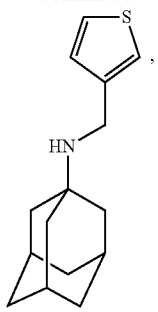
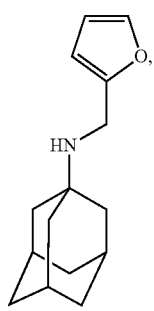
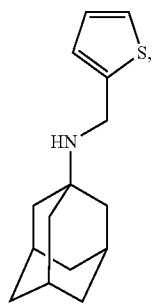
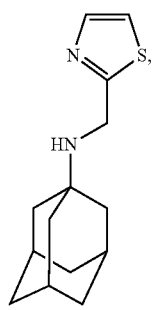
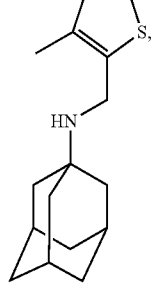
-continued
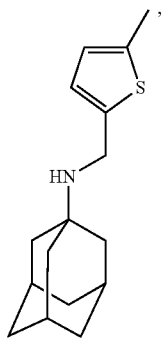
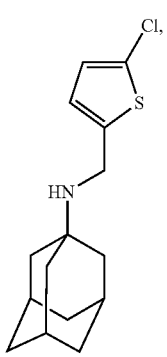
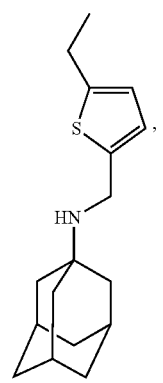
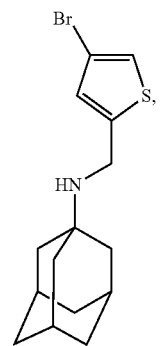

185
-continued
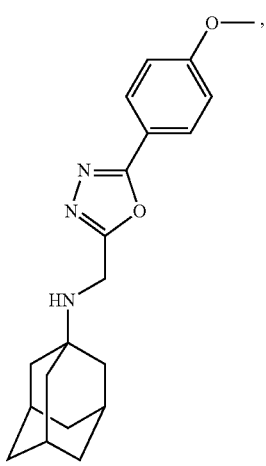
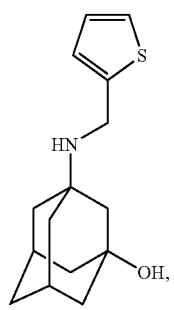
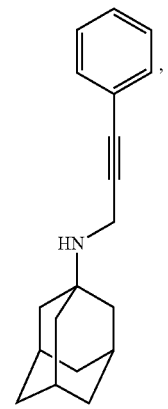

186
-continued
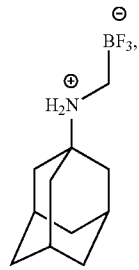
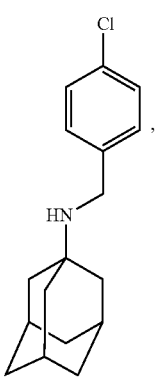
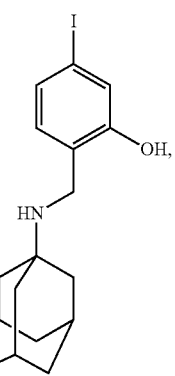
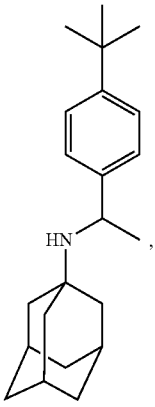

187
-continued
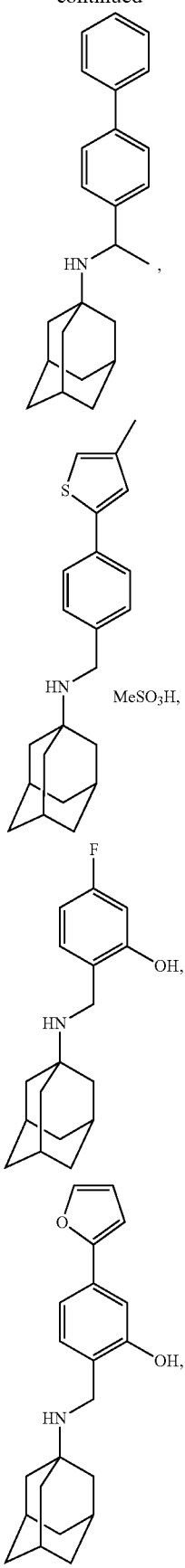
188
-continued
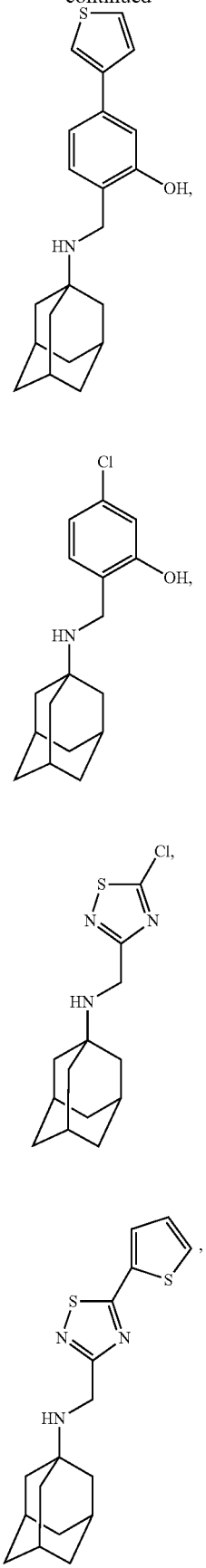

189
-continued
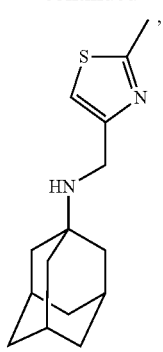
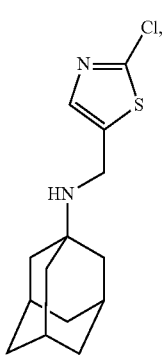
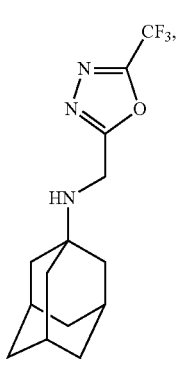
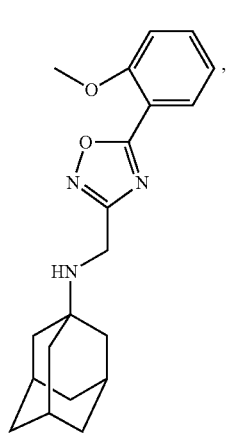
190
-continued
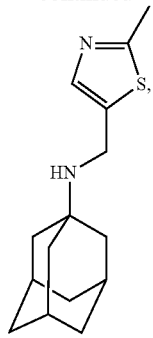
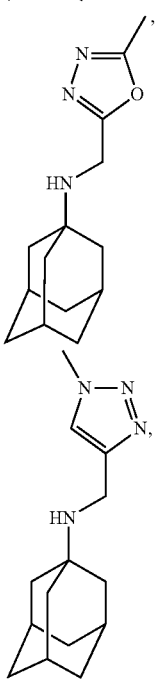
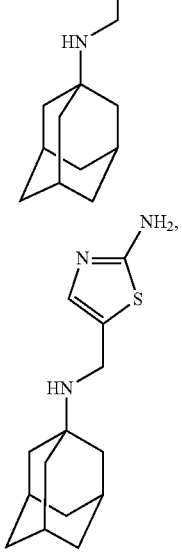
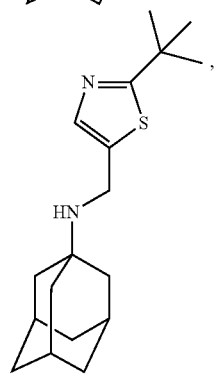

191 -continued
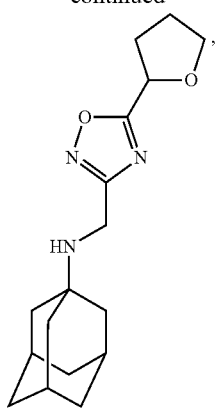
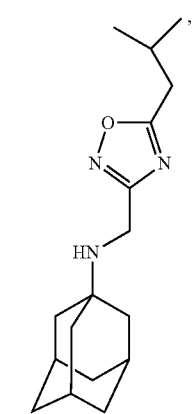
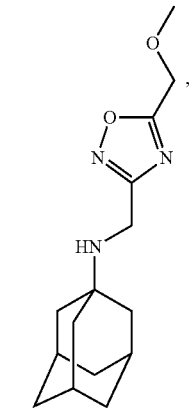
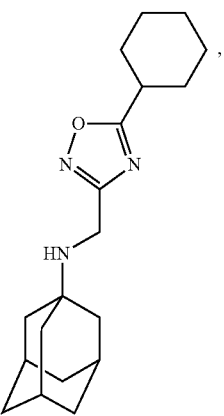
192 -continued
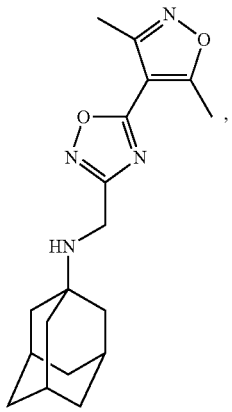
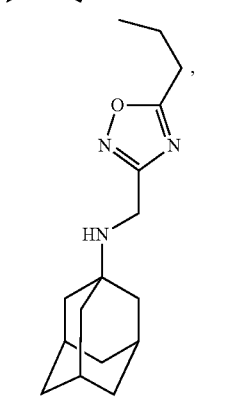
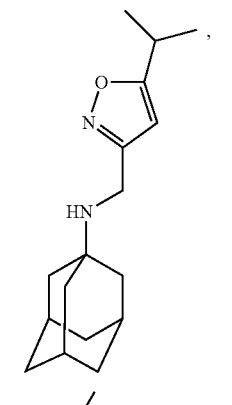
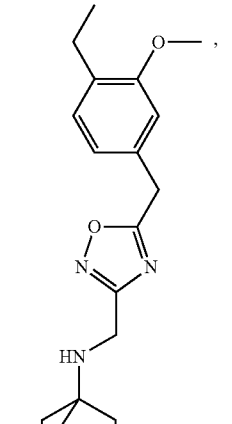

193
-continued
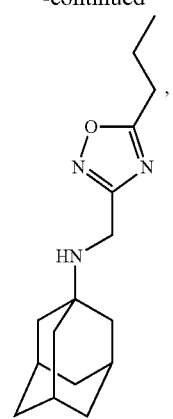
,
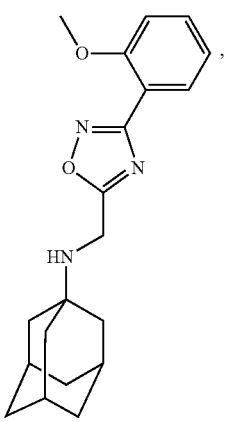
,
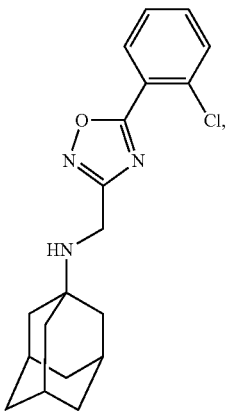
,
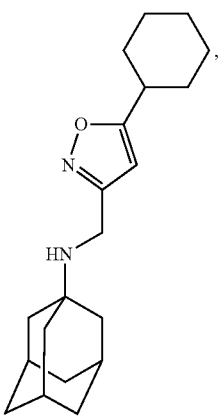
,
194
-continued
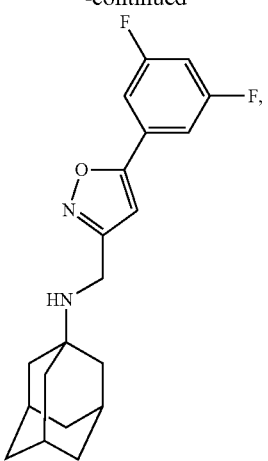
,
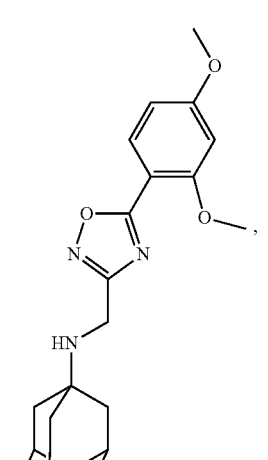
,
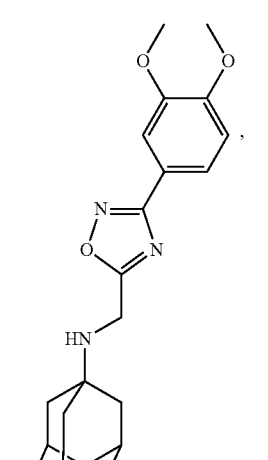
,

195
-continued
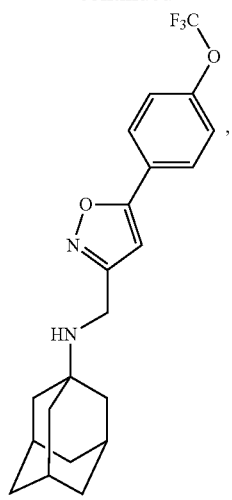
,
196
-continued
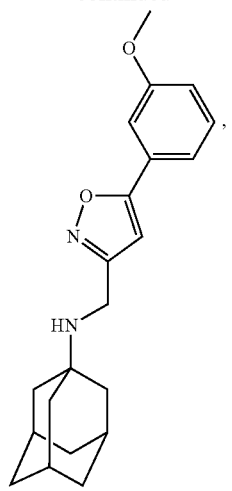
,
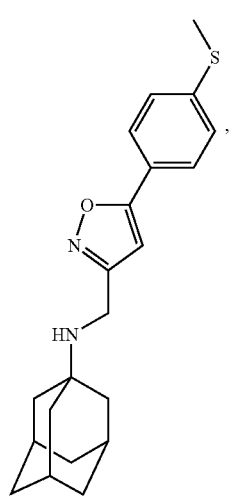
,
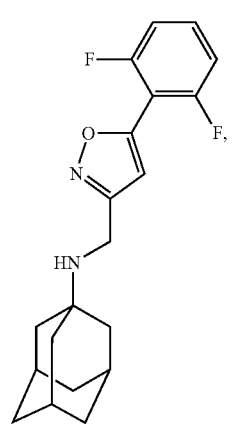
,
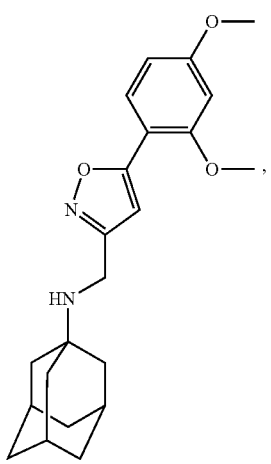
,

197
-continued
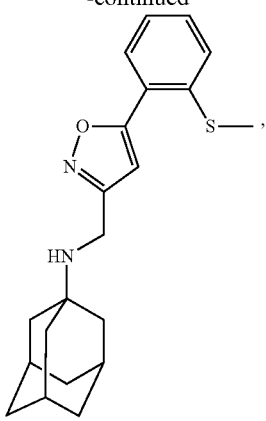
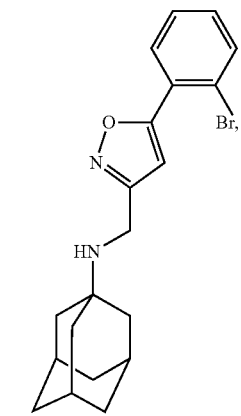
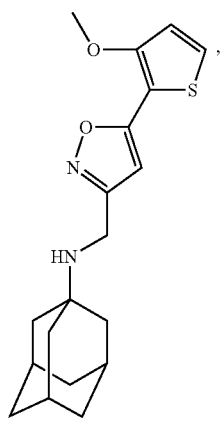
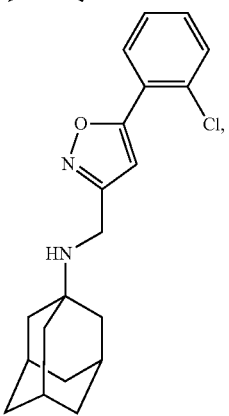
198
-continued
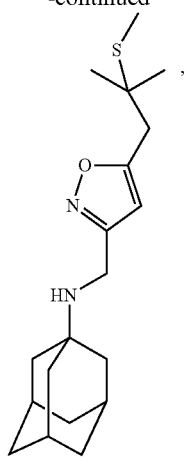
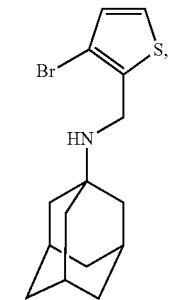
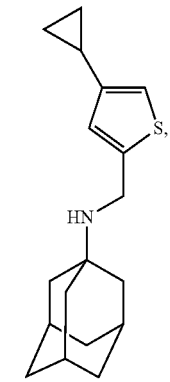
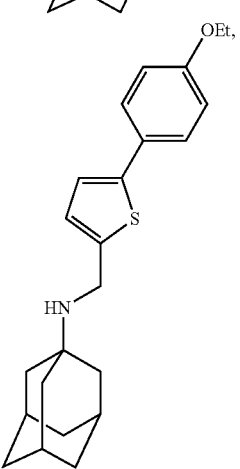

199
-continued
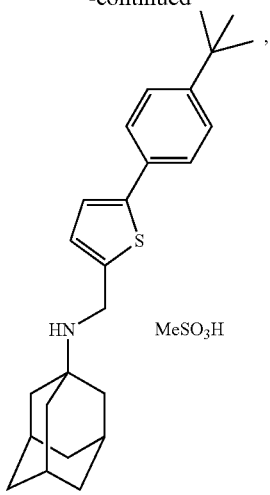
200
-continued
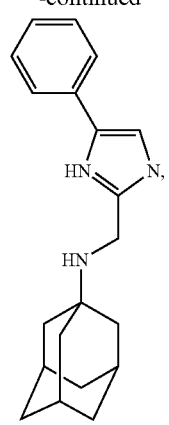
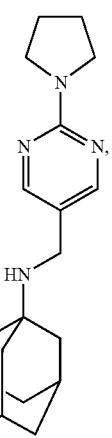
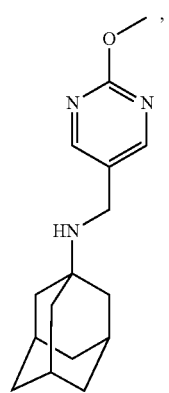
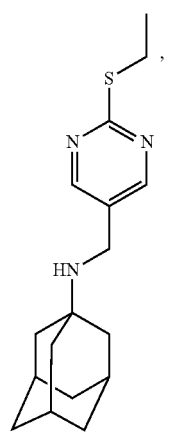

201
-continued
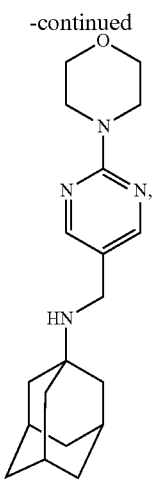
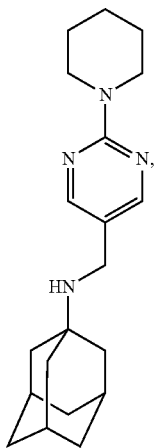
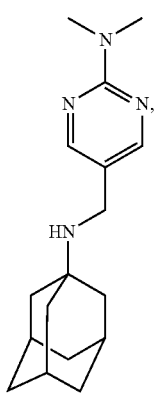
202
-continued
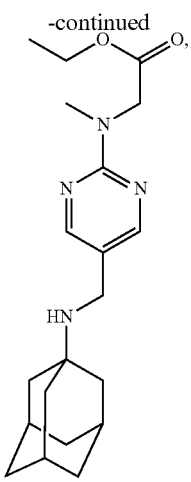
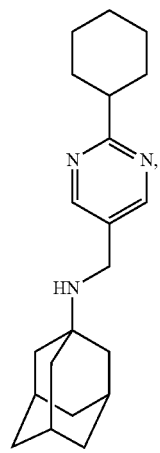
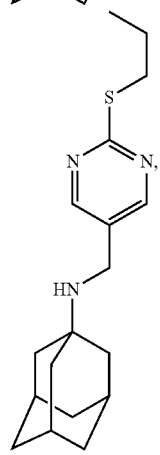
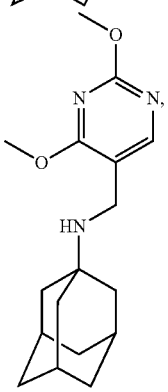

203
-continued
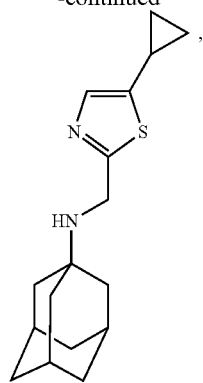
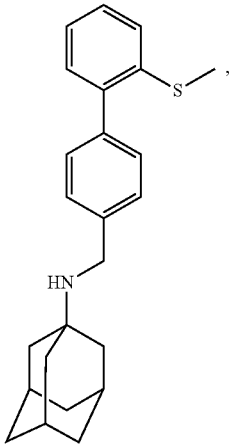
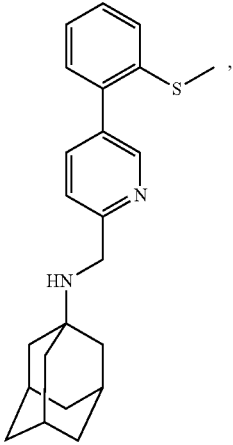
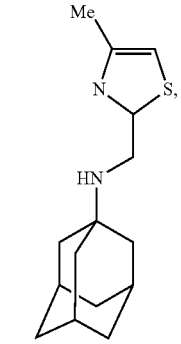
204
-continued
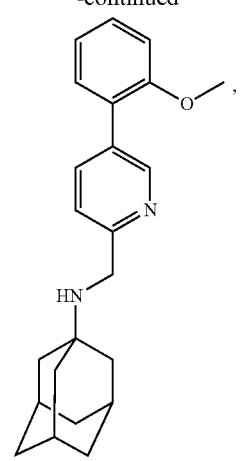
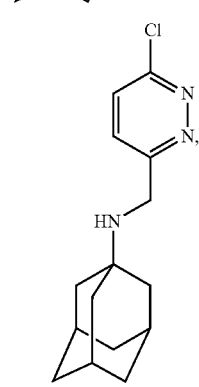
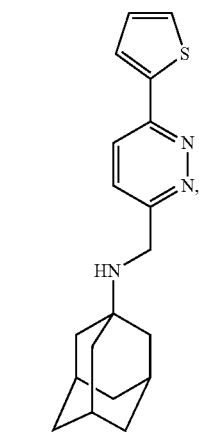
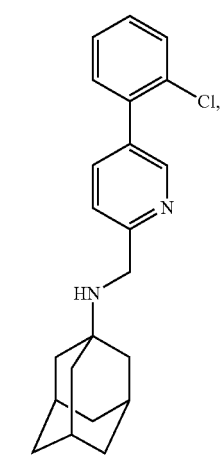

205
-continued

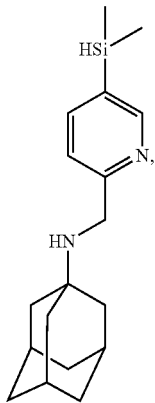
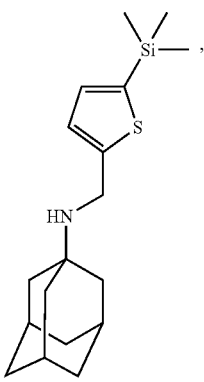
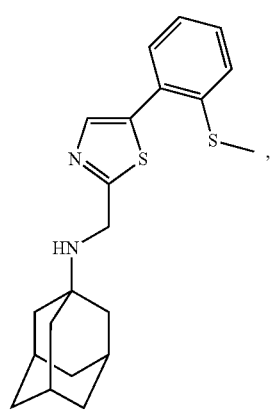
206
-continued
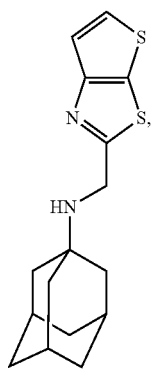
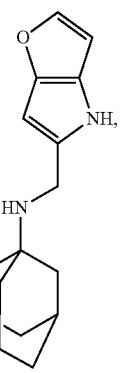
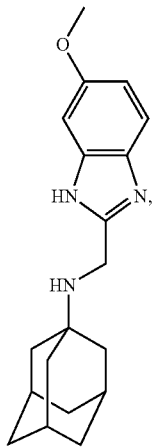
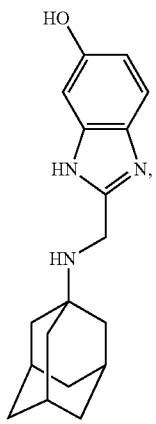

207
-continued
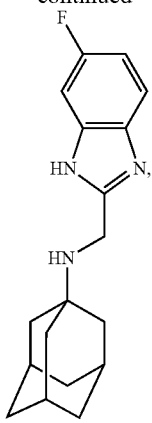
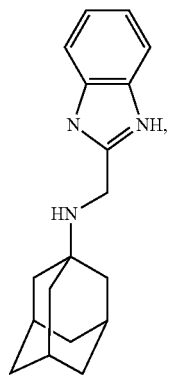
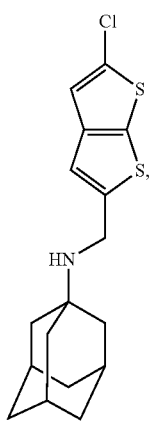
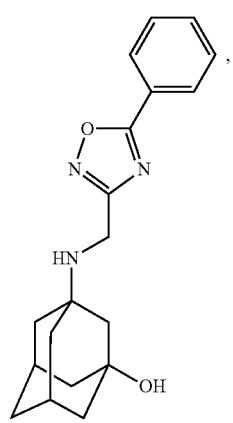
208
-continued
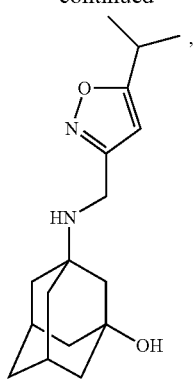
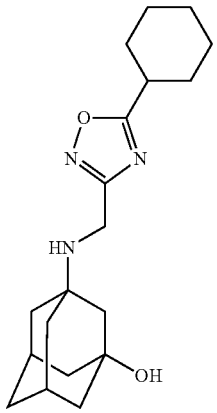
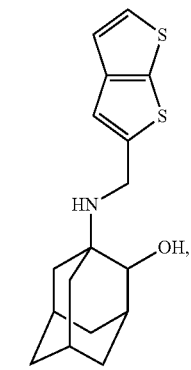
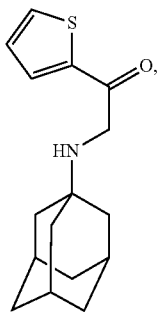

or a stereoisomer, partial stereoisomer, isotopically substituted analogue, prodrug, pharmaceutically acceptable salt, hydrate, solvate, acid hydrate, or N-oxide thereof.

In some embodiments, the methods provided herein inhibit an M2 proton channel (i.e., M2 protein or M2) of an influenza virus (including M2 of an influenza A virus and/or BM2 of an influenza B virus). In some embodiments, the M2 belongs to a wild type influenza virus. In some embodiments, the M2 belongs to an influenza virus strain that is resistant to the existing anti-influenza drugs (such as amantadine and/or rimantadine), for example, a S31N mutant. The mutant virus may comprise an influenza virus having the L26F mutation; may comprise an influenza virus having the V27G mutation, the V27I mutation, the V27T mutation, the V27S mutation, or the V27A mutation; may comprise an influenza virus having the A30T mutation; may comprise an influenza virus having the S31A mutation or the S31N mutation; may an influenza virus having the G34E mutation or the G34A mutation; may comprise an influenza virus having the L38F mutation; may comprise an influenza virus having the W41L mutation or the W41Y mutation; may comprise an influenza virus having the D44N mutation or the D44H mutation; and/or may comprise an influenza virus having the R45K mutation or the R45H mutation.

In some embodiments, the methods provided herein inhibit VP24 of an Ebola or a Marburg virus.

In some embodiments, the methods provided herein inhibit NS3 protein of a Bluetongue virus.

In some embodiments, the methods provided herein inhibit a viroporin of a picornavirus, foot and mouth disease virus, African horse sickness virus, or Japanese encephalitis virus.

In some embodiments, the compounds and/or salts provided herein can inhibit (i.e., decrease activity of) an M2 proton channel of an influenza virus (including M2 of an influenza A virus; BM2 of an influenza B virus, M2 of a wild type influenza virus, and/or M2 of a drug resistant influenza such as S31N influenza or other drug-resistant strains) by, for example, binding to the transmembrane region of M2 and interfering with proton conduction inside the virus and ultimately preventing the replication of the virus. In some embodiments, the compounds and/or salts provided herein can inhibit M2 and prevent viral maturation and release from the host cell. Accordingly, in some embodiments, the present invention provides a method for treating influenza (including wild type influenza and/or drug resistant influenza such as S31N influenza or other drug-resistant strains) in a patient (including a human or another animal) comprising contacting the patient with a therapeutically effective amount of a compound of formula (Ia'), (Ib), or (II) as defined herein. In some embodiments, the method is a method for treating influenza that is a wild type. In some embodiments, the method is for treating influenza that is resistant to one or more of the existing anti-influenza drugs. In some embodiments, the method is a method for treating influenza that is resistant to amantadine and/or rimantadine.

In some embodiments, the compounds and/or salts provided herein can inhibit other integral membrane proteins that possess viroporin activity similar to the M2 protein (for example, VP24 of Ebola and Marburg viruses, NS3 protein of a Bluetongue virus, and a viroporin of a picornavirus, foot and mouth disease virus, African horse sickness virus, or Japanese encephalitis virus). Accordingly, in some embodiments, the present invention provides methods for treating Ebola, Marburg, bluetongue, foot and mouth disease, African horse sickness, and Japanese encephalitis in a patient (including a human or another animal) comprising contacting the patient with a therapeutically effective amount of the compound of formula (Ia'), (Ib), or (II) as defined herein. In some embodiments, the method is a method for treating Ebola or Marburg in a patient. In some embodiments, the method is a method for treating Bluetongue in a patient. In some embodiments, the method is a method of treating a picornavirus infection, foot and mouth disease, African horse sickness, or Japanese encephalitis in a patient.

Methods of measuring inhibition of M2 protein of an influenza virus (or other integral membrane proteins that possess viroporin activity similar to the M2 protein (for example, VP24 of Ebola and Marburg viruses, NS3 protein of a Bluetongue virus, and a viroporin of a picornavirus, foot and mouth disease, African horse sickness virus, or Japanese encephalitis virus) are routine in the art.

The present invention further provides methods for treating viral infections such as influenza, Ebola, Marburg, bluetongue, foot and mouth disease, African horse sickness, and Japanese encephalitis in an individual (e.g., patient) by administering to the individual in need of such treatment a therapeutically effective amount or dose of a compound of formula (Ia'), (Ib), or (II) as defined herein or a pharmaceutical composition thereof.

As used herein, the term "cell" is meant to refer to a cell that is in vitro, ex vivo or in vivo. In some embodiments, an ex vivo cell can be paroom temperature of a tissue sample excised from an organism such as a mammal. In some embodiments, an in vitro cell can be a cell in a cell culture. In some embodiments, an in vivo cell is a cell living in an organism such as a mammal.

As used herein, the term "contacting" refers to the bringing together of indicated moieties in an in vitro system or an in vivo system. For example, "contacting" the M2 protein (i.e., the M2 proton channel) of an influenza virus with a compound in the invention may include the administration of a compound in the present invention to an individual or patient, such as a human, having an influenza infection, as well as, for example, introducing a compound of the invention into a sample containing a cellular or purified preparation containing the M2 protein.

As used herein, the term "individual" or "patient," used interchangeably, refers to any animal, including mammals, such as mice, rats, other rodents, rabbits, dogs, cats, swine, cattle, sheep, horses, or primates, such as humans.

As used herein, the phrase "therapeutically effective amount" refers to the amount of active compound or pharmaceutical agent that elicits the biological or medicinal response that is being sought in a tissue, system, animal, individual or human by a researcher, veterinarian, medical doctor or other clinician, which includes one or more of the following:

(1) preventing the disease; for example, preventing a disease, condition or disorder in an individual who may be predisposed to the disease, condition or disorder but does not yet experience or display the pathology or symptomatology of the disease;

(2) inhibiting the disease; for example, inhibiting a disease, condition or disorder in an individual who is experiencing or displaying the pathology or symptomatology of the disease, condition or disorder (i.e., including arresting further development of the pathology and/or symptomatology); and (3) ameliorating the disease; for example, ameliorating a disease, condition or disorder in an individual who is experiencing or displaying the pathology or symptomatology of the disease, condition or disorder (i.e., including reversing the pathology and/or symptomatology).

A subject or patient in whom administration of the therapeutic compound is an effective therapeutic regimen for a disease or disorder is preferably a human, but can be any animal, including a laboratory animal in the context of a clinical trial or screening or activity experiment. Thus, as can be readily appreciated by one of ordinary skill in the art, the methods, compounds and compositions of the present invention are particularly suited to administration to any animal, particularly a mammal, and including, but by no means limited to, humans, domestic animals, such as feline or canine subjects, farm animals, such as but not limited to bovine, equine, caprine, ovine, and porcine subjects, wild animals (whether in the wild or in a zoological garden), research animals, such as mice, rats, rabbits, goats, sheep, pigs, dogs, cats, and the like, avian species, such as chickens, turkeys, songbirds, and the like, i.e., for veterinary medical use.

The compounds of this invention may be administered orally or parenterally, neat or in combination with conventional pharmaceutical carriers, diluents, or excipients, which may be liquid or solid. The applicable solid carrier, diluent, or excipient may function as, among other things, a binder, disintegrant, filler, lubricant, glidant, compression aid, processing aid, color, sweetener, preservative, suspending/dispersing agent, tablet-disintegrating agent, encapsulating material, film former or coating, flavors, or printing ink. Of course, any material used in preparing any dosage unit form is preferably pharmaceutically pure and substantially non-toxic in the amounts employed. In addition, the active compound may be incorporated into sustained-release preparations and formulations. Parenteral administration in this respect includes administration by, inter alia, the following routes: intravenous, intramuscular, subcutaneous, intraocular, intrasynovial, transepithelial including transdermal, ophthalmic, sublingual and buccal; topically including ophthalmic, dermal, ocular, rectal and nasal inhalation via insufflation, aerosol, and rectal systemic.

In powders, the carrier, diluent, or excipient may be a finely divided solid that is in admixture with the finely divided active ingredient. In tablets, the active ingredient is mixed with a carrier, diluent or excipient having the necessary compression properties in suitable proportions and compacted in the shape and size desired. For oral therapeutic administration, the active compound may be incorporated with the carrier, diluent, or excipient and used in the form of ingestible tablets, buccal tablets, troches, capsules, elixirs, suspensions, syrups, wafers, and the like. The amount of active compound(s) in such therapeutically useful compositions is preferably such that a suitable dosage will be obtained. The therapeutic compositions preferably contain up to about 99% of the active ingredient.

Liquid carriers, diluents, or excipients may be used in preparing solutions, suspensions, emulsions, syrups, elixirs, and the like. The active ingredient of this invention can be dissolved or suspended in a pharmaceutically acceptable liquid such as water, an organic solvent, a mixture of both, or pharmaceutically acceptable oils or fat. The liquid carrier, excipient, or diluent can contain other suitable pharmaceutical additives such as solubilizers, emulsifiers, buffers, preservatives, sweeteners, flavoring agents, suspending agents, thickening agents, colors, viscosity regulators, stabilizers, or osmo-regulators.

Suitable solid carriers, diluents, and excipients may include, for example, calcium phosphate, silicon dioxide, magnesium stearate, talc, sugars, lactose, dextrin, starch, gelatin, cellulose, methyl cellulose, ethylcellulose, sodium carboxymethyl cellulose, microcrystalline cellulose, polyvinylpyrrolidine, low melting waxes, ion exchange resins, croscarmellose carbon, acacia, pregelatinized starch, crospovidone, HPMC, povidone, titanium dioxide, polycrystalline cellulose, aluminum methahydroxide, agar-agar, tragacanth, or mixtures thereof.

Suitable examples of liquid carriers, diluents and excipients for oral and parenteral administration include water (particularly containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil), or mixtures thereof.

For parenteral administration, the carrier, diluent, or excipient can also be an oily ester such as ethyl oleate and isopropyl myristate. Also contemplated are sterile liquid carriers, diluents, or excipients, which are used in sterile liquid form compositions for parenteral administration. Solutions of the active compounds as free bases or pharmacologically acceptable salts can be prepared in water suitably mixed with a surfactant, such as hydroxypropylcellulose. A dispersion can also be prepared in glycerol, liquid polyethylene glycols, and mixtures thereof and in oils. Under ordinary conditions of storage and use, these preparations may contain a preservative to prevent the growth of microorganisms.

The pharmaceutical forms suitable for injectable use include, for example, sterile aqueous solutions or dispersions and sterile powders for the extemporaneous preparation of sterile injectable solutions or dispersions. In all cases, the form is preferably sterile and fluid to provide easy syringability. It is preferably stable under the conditions of manufacture and storage and is preferably preserved against the contaminating action of microorganisms such as bacteria and fungi. The carrier, diluent, or excipient may be a solvent or dispersion medium containing, for example, water, ethanol, polyol (for example, glycerol, propylene glycol, liquid polyethylene glycol and the like), suitable mixtures thereof, and vegetable oils. The proper fluidity can be maintained, for example, by the use of a coating, such as lecithin, by the maintenance of the required particle size in the case of a dispersion, and by the use of surfactants. The prevention of the action of microorganisms may be achieved by various antibacterial and antifungal agents, for example, parabens, chlorobutanol, phenol, sorbic acid, thimerosal and the like. In many cases, it will be preferable to include isotonic agents, for example, sugars or sodium chloride. Prolonged absorption of the injectable compositions may be achieved by the use of agents delaying absorption, for example, aluminum monostearate and gelatin.

Sterile injectable solutions may be prepared by incorporating the active compounds in the required amounts, in the appropriate solvent, with various of the other ingredients enumerated above, as required, followed by filtered sterilization. Generally, dispersions may be prepared by incorporating the sterilized active ingredient into a sterile vehicle which contains the basic dispersion medium and the required other ingredients from those enumerated above. In the case of sterile powders for the preparation of sterile injectable solutions, the preferred methods of preparation may include vacuum drying and the freeze drying technique that yields a powder of the active ingredient or ingredients, plus any additional desired ingredient from the previously sterile-filtered solution thereof.

The compounds of the invention may be administered in an effective amount by any of the conventional techniques well-established in the medical field. The compounds employed in the methods of the present invention including the compounds of formula (Ia'), (Ib), or (II), may be administered by any means that results in the contact of the active agents with the agents' site or sites of action in the body of a patient. The compounds may be administered by any conventional means available.

Preferably the pharmaceutical composition is in unit dosage form, e.g. as tablets, buccal tablets, troches, capsules, elixirs, powders, solutions, suspensions, emulsions, syrups, wafers, granules, suppositories, or the like. In such form, the composition is sub-divided in unit dose containing appropriate quantities of the active ingredient; the unit dosage forms can be packaged compositions, for example packeted powders, vials, ampoules, prefilled syringes or sachets containing liquids. The unit dosage form can be, for example, a capsule or tablet itself, or it can be the appropriate number of any such compositions in package form. In addition, dosage forms of the present invention can be in the form of capsules wherein one active ingredient is compressed into a tablet or in the form of a plurality of microtablets, particles, granules or non-perils. These microtablets, particles, granules or non-perils are then placed into a capsule or compressed into a capsule, possibly along with a granulation of the another active ingredient.

The dosage of the compounds of the present invention that will be most suitable for prophylaxis or treatment will vary with the form of administration, the particular compound chosen and the physiological characteristics of the particular patient under treatment. Generally, small dosages may be used initially and, if necessary, increased by small increments until the desired effect under the circumstances is reached. Generally speaking, oral administration may require higher dosages.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations. The dose may also be provided by controlled release of the compound, by techniques well known to those in the art.

Additional information regarding the preparation of the present compounds for administration and the formulation of compositions according to the present invention is provided infra.

The compounds useful in the methods of the present invention may be prepared in a number of ways well known to those skilled in the art. The compounds can be synthesized, for example, by the methods as described below, or variations thereon as appreciated by the skilled artisan. The reagents used in the preparation of the compounds of this invention can be either commercially obtained or can be prepared by standard procedures described in the literature. All processes disclosed in association with the present invention are contemplated to be practiced on any scale, including milligram, gram, multigram, kilogram, multikilogram or commercial industrial scale.

For compounds herein in which a variable appears more than once, each variable can be a different moiety selected from the Markush group defining the variable. For example, where a structure is described having two R groups that are simultaneously present on the same compound, the two R groups can represent different moieties selected from the Markush group defined for R.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

The present invention is further defined in the following Examples. It should be understood that these examples, while indicating preferred embodiments of the invention, are given by way of illustration only, and should not be construed as limiting the appended claims From the above discussion and these examples, one skilled in the art can ascertain the essential characteristics of this invention, and without departing from the spirit and scope thereof, can make various changes and modifications of the invention to adapt it to various usages and conditions.

EXAMPLES

General Synthesis.

The compounds of this invention can be prepared from readily available starting materials using the following general methods and procedures. It will be appreciated that where typical or suitable process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

The processes described herein can be monitored according to any suitable method known in the art. For example, product formation can be monitored by spectroscopic means, such as nuclear magnetic resonance spectroscopy (e.g., $^1$H or $^{13}$C NMR), infrared spectroscopy (IR), spectrophotometry (e.g., UV-visible), or mass spectrometry, or by chromatography such as high performance liquid chromatography (HPLC) or thin layer chromatography.

Preparation of compounds can involve the protection and deprotection of various chemical groups. The need for protection and deprotection, and the selection of appropriate protecting groups can be readily determined by one skilled in the art. The chemistry of protecting groups can be found, for example, in P. G. M. Wuts and T. Greene, *Greene's Protective Groups in Organic Synthesis*, 4th. Ed., Wiley & Sons, 2006, which is incorporated herein by reference in its entirety.

The reactions of the processes described herein can be carried out in suitable solvents which can be readily selected by one of skill in the art of organic synthesis. Suitable solvents can be substantially nonreactive with the starting materials (reactants), the intermediates, or products at the temperatures at which the reactions are carried out, i.e., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected. The compounds of the invention can be prepared, for example, using the reaction pathways and techniques as described below.

General Procedures

Procedure A:

Amine (1.2 equiv) and aldehyde/ketone (1.0 equiv) were mixed in methanol and then treated with sodium cyanoborohydride (3.0 eq). The mixture was stirred at room temperature under a $N_2$ atmosphere overnight. The reaction mixture was quenched by adding water, and the product was extracted with butanol. The combined organic layer was dried over $Na_2SO_4$, and concentrated under reduced pressure. The crude product was separated by flash column chromatography (1-10% $CH_3OH/CH_2Cl_2$).

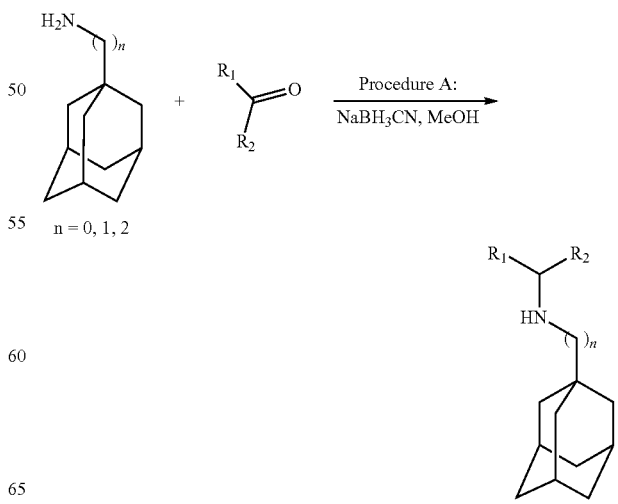

Procedure B:

Amine (1 equiv) and aldehyde/ketone (1 eq) were mixed in 1,2-dichloroethane and then treated with sodium triacetoxyborohydride (1.4 eq) and AcOH (1 eq). The mixture was stirred at room temperature under a $N_2$ atmosphere overnight. The reaction mixture was quenched by adding 1 N NaOH, and the product was extracted with DCM. The combined organic layer was dried over $MgSO_4$, and concentrated under reduced pressure after filtration. The crude product was separated by flash column chromatography (1-10% $CH_3OH/CH_2Cl_2$).

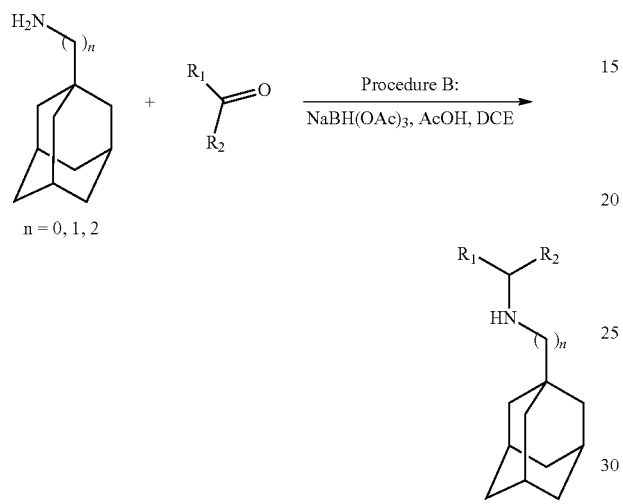

Procedure C:

Adamantane (1 eq) and aldehyde (1 eq) were mixed, and 2 ml of titanium (IV) isopropoxide was added. The resulting slurry was heated to 100° C. and stirred overnight. Then the solution was cooled down to 0° C. in ice bath, methanol was added and sodium boronhydride (4 eq) was added portionwise in 10 mins. The solution was warmed to room temperature and stirred overnight. The solvent was removed under reduced pressure, and the resulting residue was extracted with ethyl acetate and water. The organic layer was separated, dried over anhydrous magnesium sulfate, filtered and concentrated under reduced pressure. The mixture was then purified by silica gel flash column chromatography to give the final product (5-10% $CH_3OH/CH_2Cl_2$).

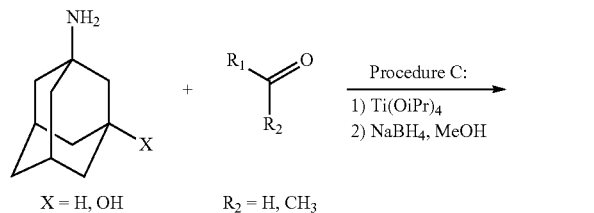

Procedure D:

The chloride/bromide (1 eq), amantadine (1.5 eq) was dissolved in isopropanol, CsI (0.1 eq) and triethyl amine (2 eq) were then added. The reaction mixture was heated to reflux overnight. The solvent was removed under reduced pressure, and the resulting residue was extracted with dichloromethane and water. The organic layer was separated, dried over anhydrous magnesium sulfate, filtered and concentrated under reduced pressure. The mixture was then purified by silica gel flash column chromatography to give the final product (5-10% $CH_3OH/CH_2Cl_2$).

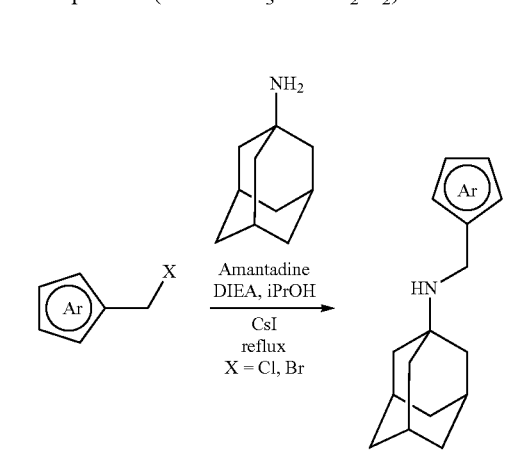

Procedure E:

Acid (1.0 equiv) was added to a solution (0.5 M) of HOAT (1.5 equiv) and EDCI (1.5 equiv) in anhydrous DMF and stirring was continued for 1 h. Then, amine (1.5 equiv) was added and the reaction mixture was stirred at room temperature overnight. After the solvent was removed under reduced pressure, the residue was purified by flash column chromatography (1-10% $CH_3OH/CH_2Cl_2$) to give the tile amid.

To a solution of above amide (1.0 equiv) in anhydrous THF was added dropwise of $LiAlH_4$ solution (2.0 M in THF) (4 equiv) at 0° C. The resulting solution was stirred for 10 h at reflux. The solution was then cooled to 0° C. and quenched by $H_2O/1N$ $NaOH/H_2O$ protocol. After the mixture was stirred for 1 h, the solid was removed by filtration. The resulting solution was evaporated to dryness and purified by flash column chromatography (1-10% $CH_3OH/CH_2Cl_2$).

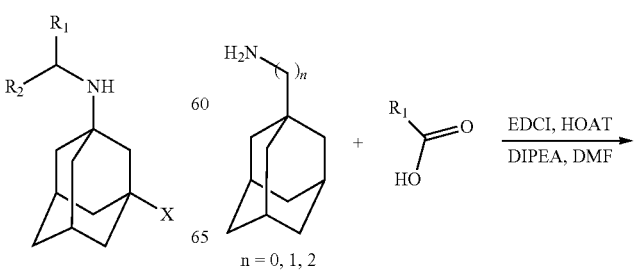

-continued

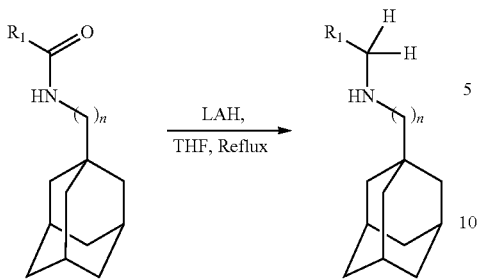

Procedure F:

A Biotage microwave vial was charged with Pd(OAc)₂ (3 mol %), RuPhos (6 mol %), halide (1 equiv), potassium trifluoroborate (1.3 equiv), and Na₂CO₃ (2 equiv). The test tube was sealed with a cap lined with a disposable Teflon septum, evacuated and purged (×3). Degassed ethanol (0.18 M) was added via syringe and the reaction was heated at 85° C. for 12 h. The reaction mixture was allowed to cool to room temperature and filtered through a thin pad of celite (elution with EtOAc). The solvent was removed in vacuo and the crude product was purified by flash column chromatography (0-10% MeOH/CH₂Cl₂).

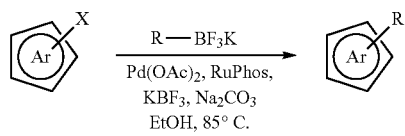

Procedure G:

A mixture of aryl halide (1.0 equiv), boronic acid (1.2 equiv), K₂CO₃ (2.0 equiv), and Pd(dppf)Cl₂ (10% mol) in dioxane/H₂O (v/v 5:1) was heated at 80° C. under inert environment for 2 h. The solution was evaporated to dryness and purified by flash column chromatography (1-10% CH₃OH/CH₂Cl₂) to give the title compound.

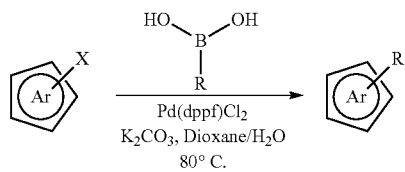

Procedure H:

A Biotage microwave vial was charged with Pd(OAc)₂ (3 mol %), XPhos (6 mol %), halide (1 equiv), potassium trifluoroborate (1.3 equiv), and K₂CO₃ (3 equiv). The vial was sealed with a cap lined with a disposable Teflon septum, evacuated and purged (×3). Degassed THF (3.8 mL) and H₂O (0.38 mL) were added via syringe, and the reaction was heated at 100° C. for 24 h. The reaction mixture was allowed to cool to rt and extracted with CH₂Cl₂ (×3) and dried over MgSO₄, filtered, and concentrated in vacuo. Unless otherwise specified, the crude product was purified by HPLC.

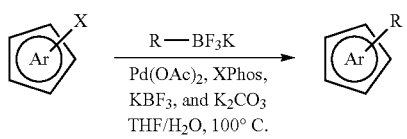

Procedure I:

The corresponding alcohol was dissolved in THF and triphenylphosphine (1 eq) was added. After cooling to −20° C. using 50% iPrOH/dry ice bath, NBS (1 eq) was added to the mixture. After 5 min stirring at the same temperature, adamantan-1-ylamine (2 eq) was added and the temperature was raised to rt and stirred for 2 h. The crude mixture was diluted with diethyl ether and filtered to remove triphenylphosphine oxide. The filtrated was concentrated and the product was isolated by RP-HPLC.

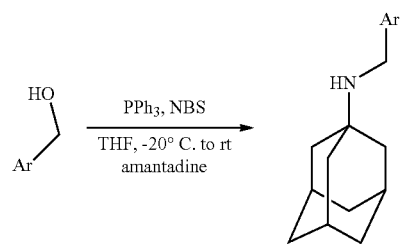

Procedure j:

2-chloro-N-hydroxyacetimidamide (1 eq) and acid chloride (1 eq) in DMF was cooled to 0° C. in ice bath, TEA (1 eq) was added dropwise. After addition, the mixture was heated to 135° C. for 4 hrs. Solvent was removed under reduced pressure, extracted with ethyl acetate and water. The combined organic phases was dried over MgSO₄, filtered and concentrated under reduced pressure. The intermediate chloride was used for the next step alkylation without further purification.

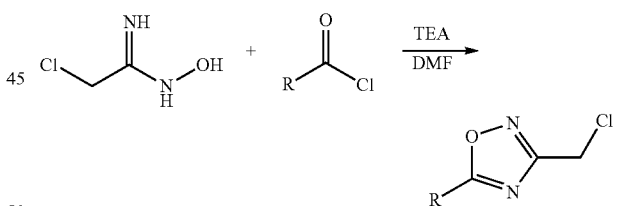

Procedure K:

A KOtBu (1.2 eq) was added dropwise to a stirred solution of dimethyl oxalate (1.1 eq) and ketone (1 eq) in toluene. The reaction was stirred at room temperature overnight. The reaction was quenched by 1N HCl, followed by concentration under reduced pressure. The resulting aqueous slurry was extracted with DCM. The combined organic phase was dried over MgSO₄, filtered and concentrated under reduced pressure. The crude ester (1 eq) was dissolved in MeOH, hydroxylamine hydrochloride (2 eq) was added, and the solution was heated to 50° C. for 4 hrs. The resulting isoxazole carboxylate was purified by flash column chromatography (60-100% DCM/Hexane). The ester was subsequently reduced by NaBH₄ (3 eq) in MeOH for 2 hrs at room temperature. The alcohol intermediate was used for the next step bromination without further purification. For bromination, the alcohol (1 eq) and CBr₄ (1.5 eq) in DCM was cooled to 0° C., PPh₃ (1.5 eq) was added and the solution was stirred at the same temperature for 2 hrs. The solvent was removed under reduced pressure. The residue was purified by flash column chromatography to give the desired bromide intermediate. Final alkylation was performed by following general procedure E.

General Procedure L.

A mixture of halophenol (1 eq), anhydrous magnesium dichloride (1.5 eq), and triethylamine (3.75 eq) in acetonitrile (0.32 M) was stirred at rt under $N_2$. Dry ($P_2O_5$) paraformaldehyde (6.8 eq) was added to the mixture dropwise and after the addition was complete, the mixture was refluxed for 72 h. Then the mixture was acidified with 5% HCl and extracted with diethyl ether (×3). The ethereal solution was washed with $H_2O$ (×2) and brine and then dried over MgSO4, filtered, and concentrated in vacuo. The crude product was purified by column chromatography (0-10% ethyl acetate/hexane) to give the title compound.

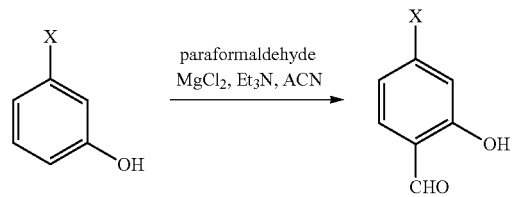

X = F, Cl, Br, I

Example 1/IMX559

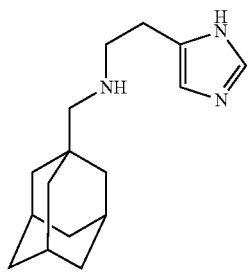 [SMILES: c1ncc(CCNCC23CC4CC(CC(C4)C2)C3)[nH]1]

Adamantan-1-ylmethyl-[2-(3H-imidazol-4-yl)-ethyl]-amine

Based on general procedure A, from adamantane-1-carbaldehyde and 2-(3H-Imidazol-4-yl)-ethylamine, a white solid (70%) is obtained. Data: LC/MS (ESR) m/z 260 [M+H]⁺.

Example 2/IMX563

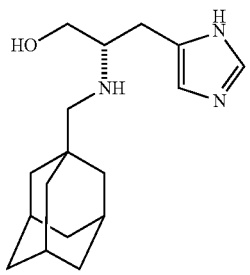

2-[(adamantan-1-ylmethyl)-amino]-3-(3H-imidazol-4-yl)-propan-1-ol

Based on general procedure A, from adamantane-1-carbaldehyde and 2-Amino-3-(3H-imidazol-4-yl)-propionic acid methyl ester, 2-[(Adamantan-1-ylmethyl)-amino]-3-(3H-imidazol-4-yl)-propionic acid methyl ester. Reduction of the ester with LAH gave the title compound. Data: LC/MS (ESR) m/z 290 [M+H]⁺.

Example 3/IMX558

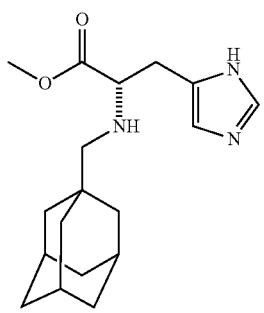

2-[(Adamantan-1-ylmethyl)-amino]-3-(3H-imidazol-4-yl)-propionic acid methyl ester Based on general procedure A, from adamantane-1-carbaldehyde and 2-Amino-3-(3H-imidazol-4-yl)-propionic acid methyl ester, a white solid (75%) is obtained. Data: LC/MS (ESR) m/z 318 [M+H]⁺.

Example 4/IMX574

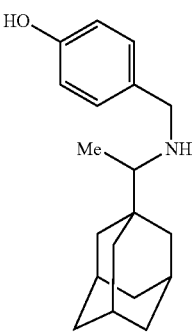

4-[(1-Adamantan-1-yl-ethylamino)-methyl]-phenol

Based on general procedure A, from 1-adamantan-1-yl-ethylamine and 4-Hydroxy-benzaldehyde, a white solid (71%) is obtained. Data: LC/MS (ESR) m/z 286 [M+H]$^+$.

Example 8/IMX583

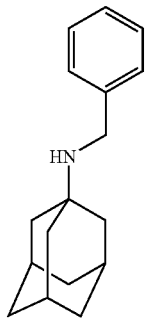 [SMILES: c1ccc(CNC23CC4CC(CC(C4)C2)C3)cc1]

Adamantan-1-yl-benzyl-amine

Based on general procedure A, from adamantan-1-ylamine and benzaldehyde, a white solid (80%) is obtained. Data: LC/MS (ESR) m/z 242 [M+H]$^+$.

Example 9/IMX 557

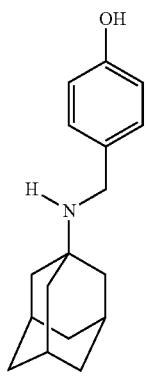 [SMILES: Oc1ccc(CNC23CC4CC(CC(C4)C2)C3)cc1]

4-(Adamantan-1-ylaminomethyl)-phenol

Based on general procedure A, from adamantan-1-ylamine and 4-hydroxy-benzaldehyde, an off-white solid (71%) is obtained. Data: LC/MS (ESR) m/z 258 [M+H]$^+$.

Example 10/IMX576

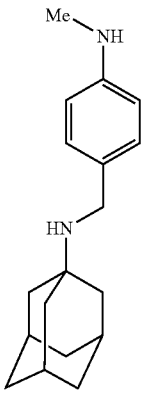 [SMILES: CNc1ccc(CNC23CC4CC(CC(C4)C2)C3)cc1]

Adamantan-1-yl-(4-methylamino-benzyl)-amine

Based on general procedure A, from adamantan-1-ylamine and (4-Formyl-phenyl)-methyl-carbamic acid tert-butyl ester, followed with deprotection with HCl, a white solid (75%) is obtained. Data: LC/MS (ESR) m/z 271 [M+H]$^+$.

Example 11/IMX 569

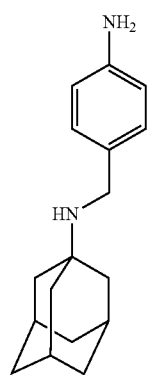

Adamantan-1-yl-(4-amino-benzyl)-amine

Based on general procedure A, from adamantan-1-ylamine and (4-Formyl-phenyl)-carbamic acid tert-butyl ester, followed with deprotection with HCl, an off-white solid (83%) is obtained. Data: LC/MS (ESR) m/z 257 [M+H]$^+$.

Example 12/IMX579

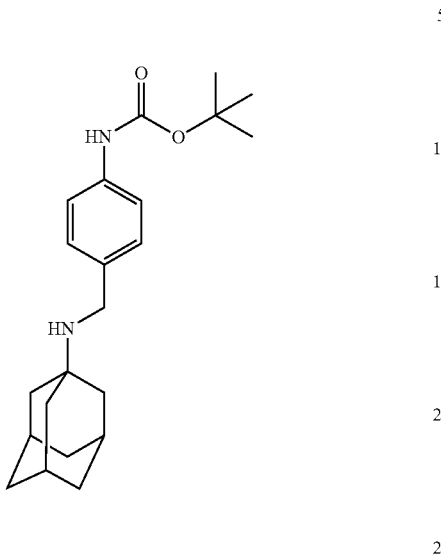

[4-(Adamantan-1-ylaminomethyl)-phenyl]carbamic acid tert-butyl ester

Based on general procedure A, from adamantan-1-ylamine and (4-Formyl-phenyl)-carbamic acid tert-butyl ester, an off-white solid (81%) is obtained. Data: LC/MS (ESR) m/z 357 [M+H]$^+$.

Example 13/IMX572

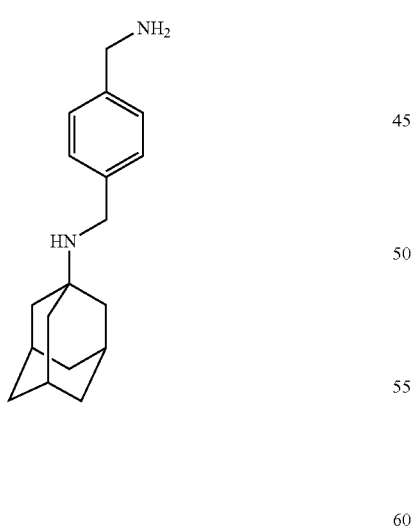

Adamantan-1-yl-(4-aminomethyl-benzyl)-amine

Based on general procedure A, from adamantan-1-ylamine and (4-Formyl-benzyl)-carbamic acid tert-butyl ester, followed with deprotection with HCl, an of-white solid (72%) is obtained. Data: LC/MS (ESR) m/z 271 [M+H]$^+$.

Example 14/IMX571

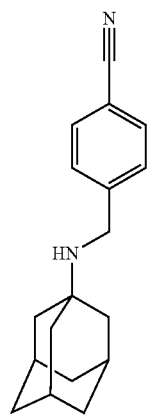 [SMILES: N#Cc1ccc(CNC23CC4CC(CC(C4)C2)C3)cc1]

4-(Adamantan-1-ylaminomethyl)-benzonitrile

Based on general procedure A, from adamantan-1-ylamine and 4-Formyl-benzonitrile, a white solid (78%) is obtained. Data: LC/MS (ESR) m/z 267 [M+H]$^+$.

Example 15/IMX570

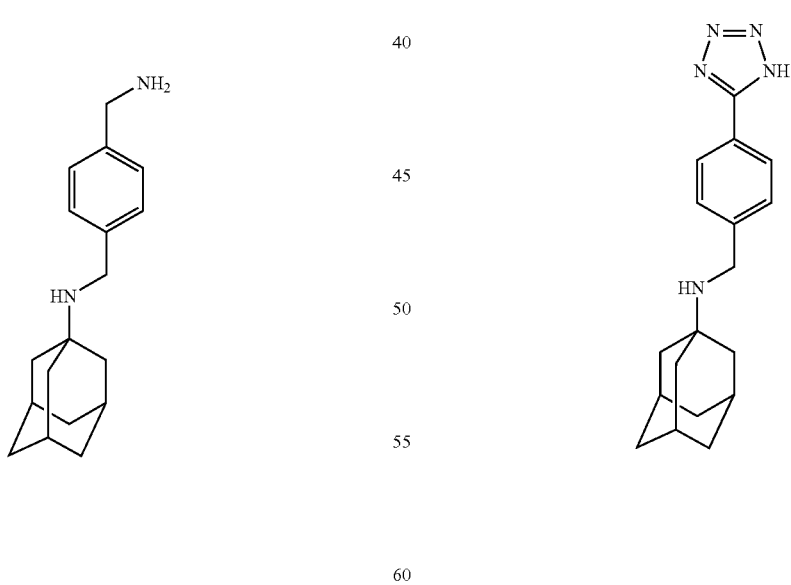

Adamantan-1-yl-[4-(1H-tetrazol-5-yl)-benzyl]amine

Based on general procedure A, from 4-(adamantan-1-ylaminomethyl)-benzonitrile (IMX571) with NaN3, an off-white solid (69%) is obtained. Data: LC/MS (ESR) m/z 310 [M+H]$^+$.

Example 16/IMX586

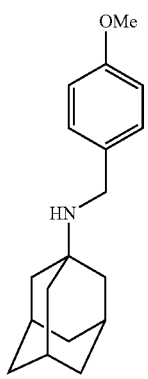

Adamantan-1-yl-(4-methoxy-benzyl)-amine

Based on general procedure A, from adamantan-1-ylamine and 4-Methoxy-benzaldehyde, a white solid (90%) is obtained. Data: LC/MS (ESR) m/z 272 [M+H]$^+$.

Example 17/IMX584

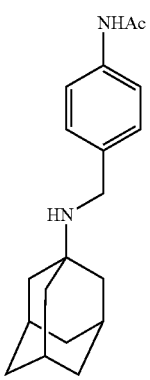 [SMILES: CC(=O)Nc1ccc(CNC23CC4CC(CC(C4)C2)C3)cc1]

N-[4-(Adamantan-1-ylaminomethyl)-phenyl]-acetamide

Based on general procedure A, from adamantan-1-ylamine and N-(4-Formyl-phenyl)-acetamide, a white solid (65%) is obtained. Data: LC/MS (ESR) m/z 242 [M+H]$^+$.

Example 18/IMX585

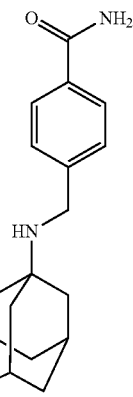

4-(Adamantan-1-ylaminomethyl)-benzamide

Based on general procedure A, from adamantan-1-ylamine and N-(4-Formyl-phenyl)-acetamide, a white solid (65%) is obtained. Data: LC/MS (ESR) m/z 285 [M+H]$^+$.

Example 19/IMX590/M2WJ261

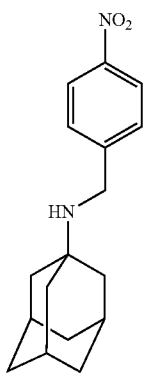

Adamantan-1-yl-(4-nitro-benzyl)-amine

Based on general procedure A, from adamantan-1-ylamine and 4-Nitro-benzaldehyde, an off-white solid (89%) is obtained. Data: LC/MS (ESR) m/z 287 [M+H]$^+$.

Example 20/IMX627

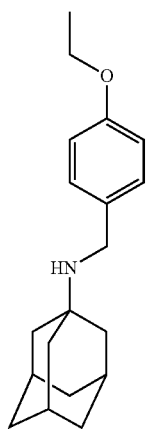 [SMILES: CCOc1ccc(CNC23CC4CC(CC(C4)C2)C3)cc1]

Adamantan-1-yl-(4-ethoxy-benzyl)-amine

Based on general procedure A, from adamantan-1-ylamine and 4-ethoxy-benzaldehyde, a white solid (83%) is obtained. Data: LC/MS (ESR) m/z 286 [M+H]$^+$.

Example 21/IMX629

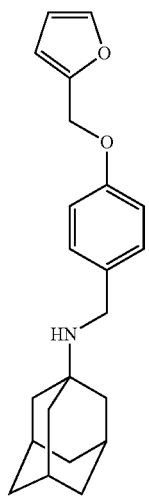 [SMILES: c1coc(COc2ccc(CNC34CC5CC(CC(C5)C3)C4)cc2)c1]

Adamantan-1-yl-[4-(furan-2-ylmethoxy)-benzyl]-amine

Based on general procedure A, from adamantan-1-ylamine and 4-(Furan-2-ylmethoxy)-benzaldehyde, a white solid (83%) is obtained. Data: LC/MS (ESR) m/z 338 [M+H]$^+$.

Example 22/IMX630

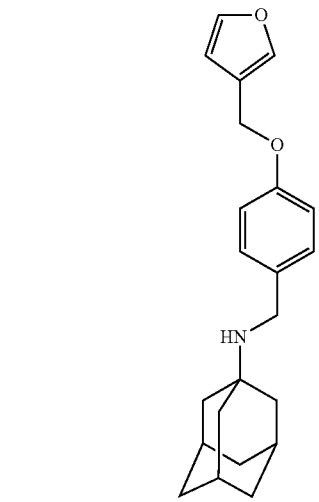 [SMILES: c1cc(COc2ccc(CNC34CC5CC(CC(C5)C3)C4)cc2)co1]

Adamantan-1-yl-[4-(furan-3-ylmethoxy)-benzyl]-amine

Based on general procedure A, from adamantan-1-ylamine and 4-(furan-3-ylmethoxy)-benzaldehyde, a white solid (83%) is obtained. Data: LC/MS (ESR) m/z 338 [M+H]$^+$.

Example 23/IMX613/M2WJ275

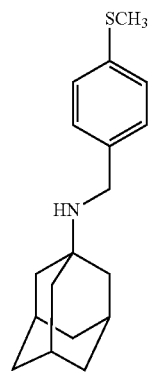

Adamantan-1-yl-(4-methylsulfanyl-benzyl)-amine

Based on general procedure A, from adamantan-1-ylamine and 4-methylsulfanyl-benzaldehyde, a white solid (72%) is obtained. Data: LC/MS (ESR) m/z 288 [M+H]$^+$.

Example 24/IMX614

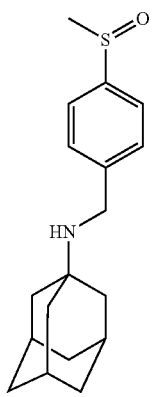 [SMILES: CS(=O)c1ccc(CNC23CC4CC(CC(C4)C2)C3)cc1]

Adamantan-1-yl-(4-methanesulfinyl-benzyl)-amine

Treating adamantan-1-yl-(4-methylsulfanyl-benzyl)-amine (based on general procedure A, from adamantan-1-ylamine and 4-methylsulfanyl-benzaldehyde) with mCPBA (1.1 equiv) at room temperature gave adamantan-1-yl-(4-methanesulfinyl-benzyl)-amine as a solid (90%). Data: LC/MS (ESR) m/z 304 [M+H]$^+$.

Example 25/M2WJ305

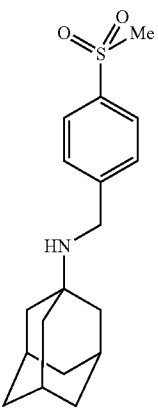 [SMILES: CS(=O)(=O)c1ccc(CNC23CC4CC(CC(C4)C2)C3)cc1]

Adamantan-1-yl-(4-methanesulfonyl-benzyl)-amine

Treatment of adamantan-1-yl-(4-methylsulfanyl-benzyl)-amine (based on general procedure B, from adamantan-1-ylamine and 4-methylsulfanyl-benzaldehyde) with mCPBA (2.3 equiv) at room temperature gave the title compound as a solid (yield: 82%). Data: LC/MS (ESR) m/z 320 [M+H]$^+$.

Example 26/IMX615/M2WJ300

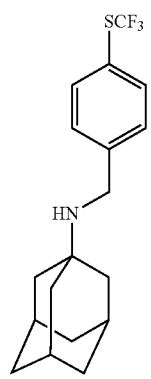

Adamantan-1-yl-(4-trifluoromethylsulfanyl-benzyl)-amine

Based on general procedure A, from adamantan-1-ylamine and 4-trifluoromethylsulfanyl-benzaldehyde, a off-white solid (73%) is obtained. Data: LC/MS (ESR) m/z 342 [M+H]$^+$.

Example 27/IMX6 00

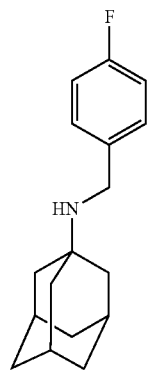

Adamantan-1-yl-(4-fluoro-benzyl)-amine

Based on general procedure A, from adamantan-1-ylamine and 4-Fluoro-benzaldehyde, a white solid (82%) is obtained. Data: LC/MS (ESR) m/z 260 [M+H]$^+$.

233

Example 28/IMX599

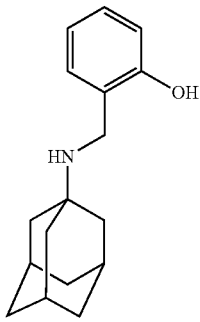 [SMILES: Oc1ccccc1CNC12CC3CC(CC(C3)C1)C2]

2-(Adamantan-1-ylaminomethyl)-phenol

Based on general procedure A, from adamantan-1-ylamine and 2-hydroxy-benzaldehyde, a white solid (76%) is obtained. Data: LC/MS (ESR) m/z 258 [M+H]$^+$.

Example 29/IMX598

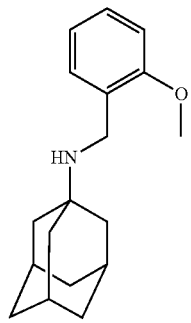

Adamantan-1-yl-(2-methoxy-benzyl)-amine

Based on general procedure A, from adamantan-1-ylamine and 2-methoxy-benzaldehyde, an off-white solid (80%) is obtained. Data: LC/MS (ESR) m/z 272 [M+H]$^+$.

Example 30/IMX591

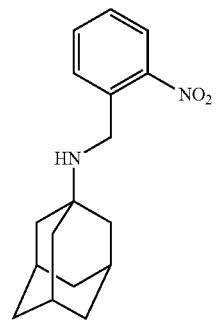 [SMILES: O=[N+]([O-])c1ccccc1CNC12CC3CC(CC(C3)C1)C2]

234

Adamantan-1-yl-(2-nitro-benzyl)-amine

Based on general procedure A, from adamantan-1-ylamine and 2-Nitro-benzaldehyde, an off-white solid (73%) is obtained. Data: LC/MS (ESR) m/z 287 [M+H]$^+$.

Example 31/IMX582

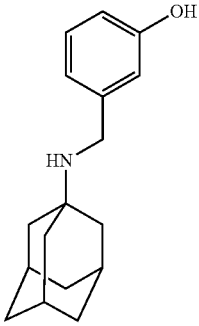 [SMILES: Oc1cccc(CNC23CC4CC(CC(C4)C2)C3)c1]

3-(Adamantan-1-ylaminomethyl)-phenol

Based on general procedure A, from adamantan-1-ylamine and 3-Hydroxy-benzaldehyde, an off-white solid (75%) is obtained. Data: LC/MS (ESR) m/z 258 [M+H]$^+$.

Example 32/IMX637

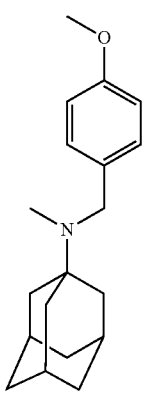 [SMILES: COc1ccc(CN(C)C23CC4CC(CC(C4)C2)C3)cc1]

Adamantan-1-yl-(4-methoxy-benzyl)-methyl-amine

Treatment of adamantan-1-yl-(4-methoxy-benzyl)-amine (1.00 equiv) (based on procedure A, from Adamantan-1-ylamine and 4-methoxy-benzaldehyde) with MeI (1.2 equiv) in DMF gave the title compound as a white solid (90%). Data: LC/MS (ESR) m/z 286 [M+H]$^+$.

Example 33/M2WJ280

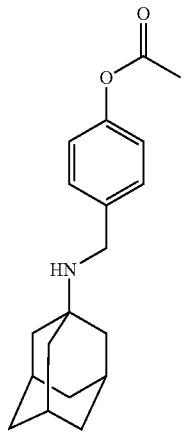 [SMILES: CC(=O)Oc1ccc(CNC23CC4CC(CC(C4)C2)C3)cc1]

Acetic acid 4-(adamantan-1-ylaminomethyl)-phenyl ester

Based on procedure B, from adamantan-1-ylamine and acetic acid 4-formyl-phenyl ester (yield: 64%). Data: MS m/z 300 [M+H]$^+$.

Example 34/M2WJ312

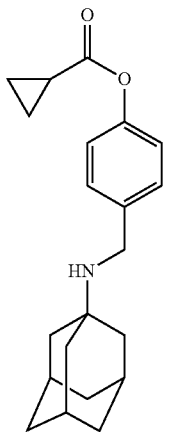 [SMILES: O=C(Oc1ccc(CNC23CC4CC(CC(C4)C2)C3)cc1)C1CC1]

Cyclopropanecarboxylic acid 4-(adamantan-1-ylaminomethyl)-phenyl ester

Based on procedure B, from adamantan-1-ylamine and Cyclopropanecarboxylic acid 4-formyl-phenyl ester (yield: 68%). Data: MS m/z 326 [M+H]$^+$.

Example 35/M2WJ308

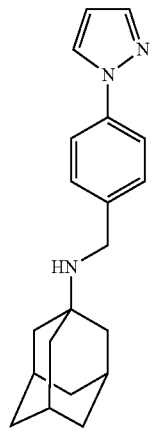 [SMILES: c1cnn(-c2ccc(CNC34CC5CC(CC(C5)C3)C4)cc2)c1]

Adamantan-1-yl-(4-pyrazol-1-yl-benzyl)-amine

Based on procedure B, from adamantan-1-ylamine and 4-pyrazol-1-yl-benzaldehyde (yield: 82%). Data: MS m/z 308 [M+H]$^+$.

Example 36/M2WJ309

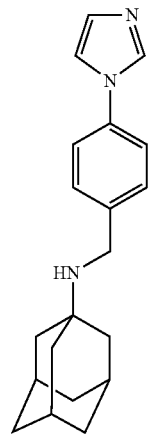 [SMILES: c1cn(-c2ccc(CNC34CC5CC(CC(C5)C3)C4)cc2)cn1]

Adamantan-1-yl-(4-imidazol-1-yl-benzyl)-amine

Based on procedure B, from adamantan-1-ylamine and 4-Imidazol-1-yl-benzaldehyde (yield: 78%). Data: MS m/z 308 [M+H]$^+$.

Example 37 M2WJ313

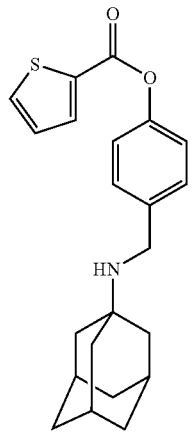 [SMILES: O=C(Oc1ccc(CNC23CC4CC(CC(C4)C2)C3)cc1)c1cccs1]

Thiophene-2-carboxylic acid 4-(adamantan-1-ylaminomethyl)-phenyl ester

Based on procedure B, from adamantan-1-ylamine and Thiophene-2-carboxylic acid 4-formyl-phenyl ester (yield: 74%). Data: MS m/z 368 [M+H]$^+$.

Example 38/BC001

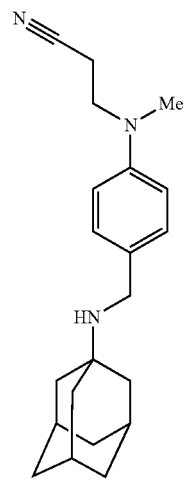 [SMILES: CN(CCC#N)c1ccc(CNC23CC4CC(CC(C4)C2)C3)cc1]

3-((4-((Adamantan-1-ylamino)methyl)phenyl)(methyl)amino)propanenitrile

Based on general procedure B, from adamantan-1-ylamine and 3-((4-formylphenyl)(methyl)amino)-propanenitrile, a white solid was obtained. Data: LC/MS (ESCi) m/z 324.28 [M+H]$^+$.

Example 39/BC002

2-(4-((Adamantan-1-ylamino)methyl)phenoxy)acetamide

Based on general procedure B, from adamantan-1-ylamine and 2-(4-formylphenoxyl)acetamide, a white solid was obtained. Data: LC/MS (ESCi) m/z 315.09 [M+H]$^+$.

Example 40/BC004

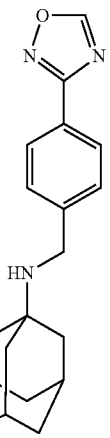

Adamantan-1-yl-(4-[1,2,4]oxadiazol-3-yl-benzyl)-amine

Based on general procedure A, from adamantan-1-ylamine and 4-(1,2,4-oxadiazol-3-yl)benzaldehyde, a white solid was obtained. Data: LC/MS (ESCi) m/z 310.00 [M+H]$^+$.

Example 41/BC005

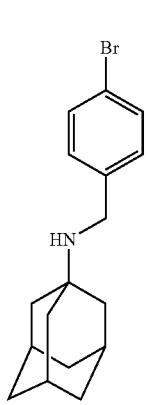 [SMILES: Brc1ccc(CNC23CC4CC(CC(C4)C2)C3)cc1]

N-(4-Bromobenzyl)adamantan-1-amine

Based on general procedure 2, from adamantan-1-ylamine and 4-bromobenzaldehyde, a light yellow solid was obtained. Data: LC/MS (ESCi) m/z 320.13 and 322.27 [M+H]$^+$.

Example 42/BC015

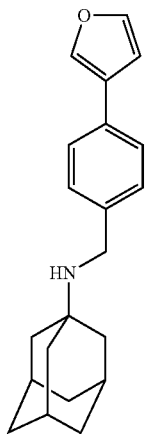 [SMILES: c1cc(-c2ccc(CNC34CC5CC(CC(C5)C3)C4)cc2)co1]

N-(4-(Furan-3-yl)benzyl)adamantan-1-amine

Based on general procedure 3, from N-(4-bromobenzyl) adamantan-1-amine and potassium furan-2-yltrifluoroborate, a white solid was obtained. Data: LC/MS (ESCi) m/z 308.04 [M+H]$^+$.

Example 43/BC016

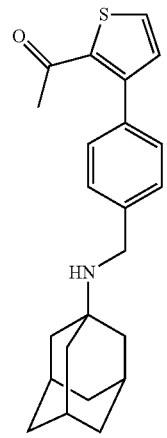 [SMILES: CC(=O)c1sccc1-c1ccc(CNC23CC4CC(CC(C4)C2)C3)cc1]

1-(3-(4-((Adamantan-1-ylamino)methyl)phenyl)
thiophen-2-yl)ethanone

Based on general procedure D, from N-(4-bromobenzyl) adamantan-1-amine and potassium (2-acetylthiophen)-3-yl-trifluoroborate, after an HLPC purification a white solid was obtained. Data: LC/MS (ESCi) m/z 366.14 [M+H]$^+$.

Example 44/BC018

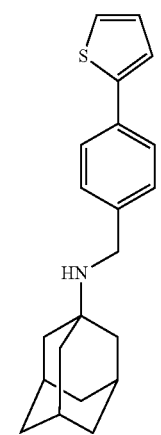

N-(4-(Thiophen-2-yl)benzyl)adamantan-1-amine

Based on general procedure D, from N-(4-bromobenzyl) adamantan-1-amine and potassium thiophen-2-yltrifluoroborate, after an HPLC purification a yellow solid was obtained. Data: LC/MS (ESCi) m/z 324.16 [M+H]$^+$.

Example 45/IMX564

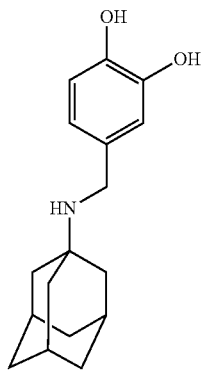 [SMILES: Oc1ccc(CNC23CC4CC(CC(C4)C2)C3)cc1O]

4-(Adamantan-1-ylaminomethyl)-benzene-1,2-diol

Based on general procedure A, from adamantan-1-ylamine and 3,4-Dihydroxy-benzaldehyde, a white solid (82%) is obtained. Data: LC/MS (ESR) m/z 274 [M+H]$^+$.

Example 46/IMX589

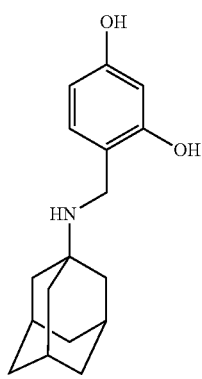

4-(Adamantan-1-ylaminomethyl)-benzene-1,3-diol

Based on general procedure A, from adamantan-1-ylamine and 2,4-Dihydroxy-benzaldehyde, a white solid (70%) is obtained. Data: LC/MS (ESR) m/z 274 [M+H]$^+$.

Example 47/IMX 566

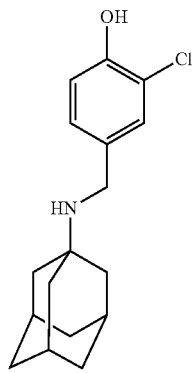

4-(Adamantan-1-ylaminomethyl)-2-chloro-phenol

Based on general procedure A, from adamantan-1-ylamine and 3-Chloro-4-hydroxy-benzaldehyde, a off-white solid (65%) is obtained. Data: LC/MS (ESR) m/z 292 [M+H]$^+$.

Example 48/IMX 573

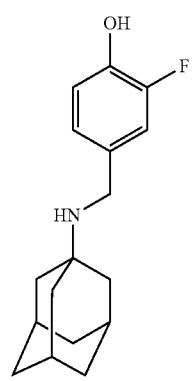 [SMILES: Oc1ccc(CNC23CC4CC(CC(C4)C2)C3)cc1F]

4-(Adamantan-1-ylaminomethyl)-2-fluoro-phenol

Based on general procedure A, from adamantan-1-ylamine and 3-Fluoro-4-hydroxy-benzaldehyde, a white solid (71%) is obtained. Data: LC/MS (ESR) m/z 276 [M+H]$^+$.

243

Example 49/IMX580

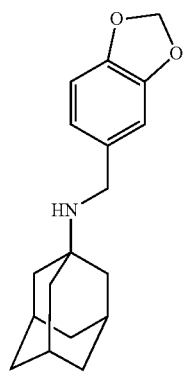 [SMILES: c1cc2c(cc1CNC13CC4CC(CC(C4)C1)C3)OCO2]

[4-(Adamantan-1-ylaminomethyl)-phenyl]carbamic acid tert-butyl ester

Based on general procedure A, from adamantan-1-ylamine and Benzo[1,3]dioxole-5-carbaldehyde, a white solid (71%) is obtained. Data: LC/MS (ESR) m/z 286 [M+H]$^+$.

Example 50/IMX581

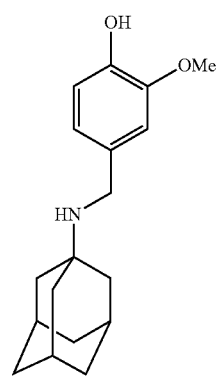 [SMILES: COc1cc(CNC23CC4CC(CC(C4)C2)C3)ccc1O]

4-(Adamantan-1-ylaminomethyl)-2-methoxy-phenol

Based on general procedure A, from adamantan-1-ylamine and 4-Hydroxy-3-methoxy-benzaldehyde, a white solid (73%) is obtained. Data: LC/MS (ESR) m/z 288 [M+H]$^+$.

244

Example 51/IMX567

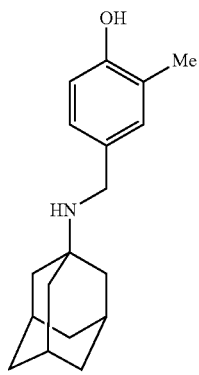 [SMILES: Cc1cc(CNC23CC4CC(CC(C4)C2)C3)ccc1O]

4-(Adamantan-1-ylaminomethyl)-2-methyl-phenol

Based on general procedure A, from adamantan-1-ylamine and 4-Hydroxy-3-methyl-benzaldehyde, a white solid (65%) is obtained. Data: LC/MS (ESR) m/z 272 [M+H]$^+$.

Example 52/M2WJ25

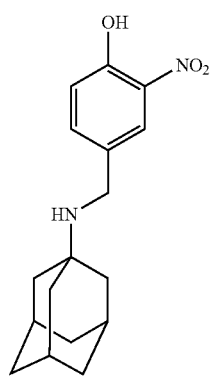 [SMILES: O=[N+]([O-])c1cc(CNC23CC4CC(CC(C4)C2)C3)ccc1O]

4-(Adamantan-1-ylaminomethyl)-2-nitro-phenol

Based on general procedure B, from adamantan-1-ylamine and 4-Hydroxy-3-nitro-benzaldehyde, a white solid (70%) is obtained. Data: MS m/z 303 [M+H]$^+$.

245

Example 53/IMX597

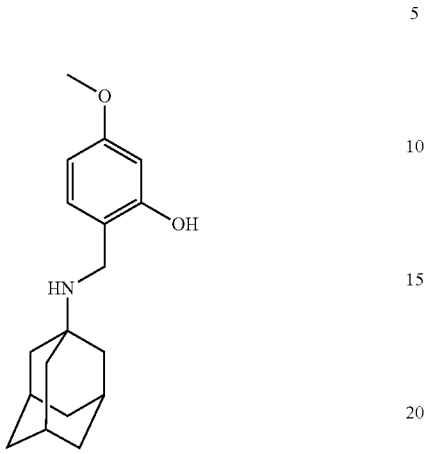

4-(Adamantan-1-ylaminomethyl)-3-methoxy-phenol

Based on general procedure A, from adamantan-1-ylamine and 2-Hydroxy-4-methoxy-benzaldehyde, a white solid (70%) is obtained. Data: LC/MS (ESR) m/z 288 [M+H]$^+$.

Example 54/IMX625

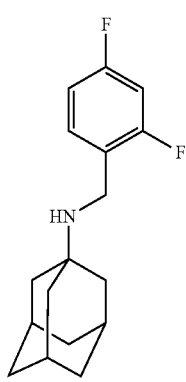 [SMILES: Fc1ccc(CNC23CC4CC(CC(C4)C2)C3)c(F)c1]

Adamantan-1-yl-(2,4-difluoro-benzyl)-amine

Based on general procedure A, from adamantan-1-ylamine and 2,4-difluoro-benzaldehyde, a white solid (70%) is obtained. Data: LC/MS (ESR) m/z 278 [M+H]$^+$.

246

Example 55/IMX620

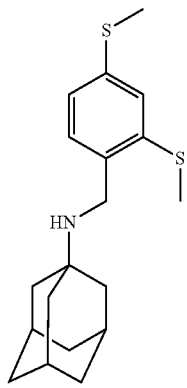 [SMILES: CSc1ccc(CNC23CC4CC(CC(C4)C2)C3)c(SC)c1]

Adamantan-1-yl-(2,4-bis-methylsulfanyl-benzyl)-amine

Treatment of adamantan-1-yl-(2,4-difluoro-benzyl)-amine (1.0 equiv) (based on general procedure A, from adamantan-1-ylamine and 2,4-difluoro-benzaldehyde) with CH$_3$SNa (3.0 equiv) in DMF at 170° C. for 20 h gave the title compound as a yellow solid (38%). Data: LC/MS (ESR) m/z 334 [M+H]$^+$.

Example 56/IMX 596

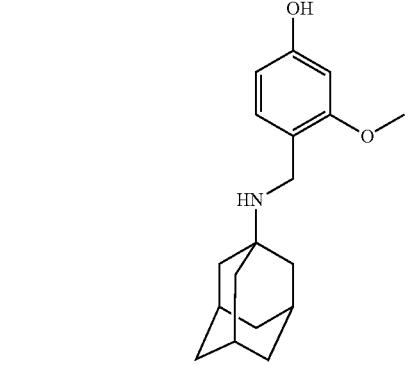 [SMILES: COc1cc(O)ccc1CNC12CC3CC(CC(C3)C1)C2]

4-(Adamantan-1-ylaminomethyl)-3-methoxy-phenol

Based on general procedure A, from adamantan-1-ylamine and 4-hydroxy-2-methoxy-benzaldehyde, a white solid (72%) is obtained. Data: LC/MS (ESR) m/z 288 [M+H]$^+$.

Example 57/IMX636

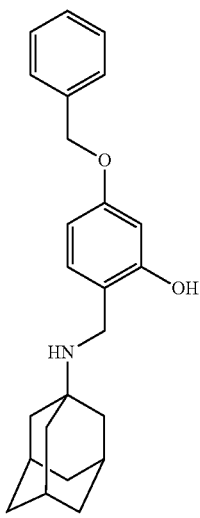 [SMILES: Oc1cc(OCc2ccccc2)ccc1CNC12CC3CC(CC(C3)C1)C2]

2-(Adamantan-1-ylaminomethyl)-5-benzyloxy-phenol

Based on general procedure A, from adamantan-1-ylamine and 4-benzyloxy-2-hydroxy-benzaldehyde, a white solid (72%) is obtained. Data: LC/MS (ESR) m/z 364 [M+H]$^+$.

Example 58/M2WJ279

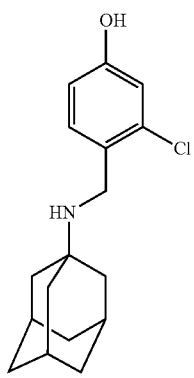

4-(Adamantan-1-ylaminomethyl)-3-chloro-phenol

Based on general procedure B, from adamantan-1-ylamine and 2-chloro-4-hydroxy-benzaldehyde (yield: 47%). Data: MS m/z 292 [M+H]$^+$.

Example 59/M2WJ296

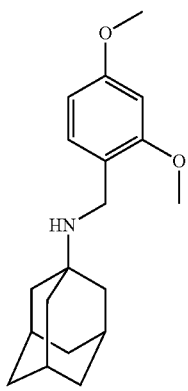 [SMILES: COc1ccc(CNC23CC4CC(CC(C4)C2)C3)c(OC)c1]

Adamantan-1-yl-(2,4-dimethoxy-benzyl)-amine

Based on general procedure B, from adamantan-1-ylamine and 2,4-dimethoxy-benzaldehyde (yield: 74%). Data: MS m/z 302 [M+H]$^+$.

Example 60/M2WJ307

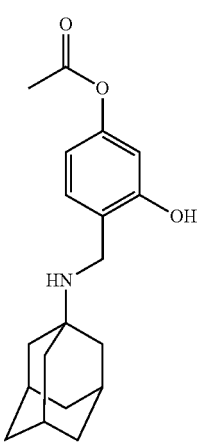

Acetic acid 4-(adamantan-1-ylaminomethyl)-3-hydroxy-phenyl ester Based on general procedure B, from adamantan-1-ylamine and acetic acid 4-formyl-3-hydroxy-phenyl ester (yield: 63%). Data: MS m/z 316 [M+H]$^+$.

Example 61 M2WJ290

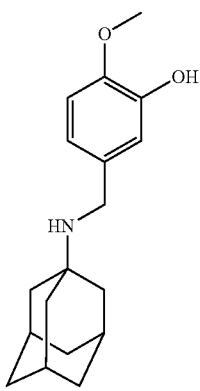 [SMILES: COc1ccc(CNC23CC4CC(CC(C4)C2)C3)cc1O]

5-(Adamantan-1-ylaminomethyl)-2-methoxy-phenol

Based on general procedure B, from adamantan-1-ylamine and 3-hydroxy-4-methoxy-benzaldehyde (yield: 55%). Data: MS m/z 288 [M+H]$^+$.

Example 62/M2WJ268

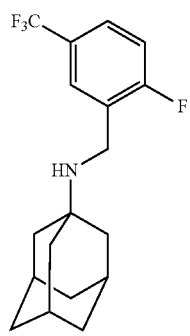 [SMILES: Fc1ccc(C(F)(F)F)cc1CNC12CC3CC(CC(C3)C1)C2]

Adamantan-1-yl-(2-fluoro-5-trifluoromethyl-benzyl)-amine

Based on general procedure B, from adamantan-1-ylamine and 2-Fluoro-5-trifluoromethyl-benzaldehyde (yield: 89%). Data: MS m/z 328 [M+H]$^+$.

Example 63/M2WJ277

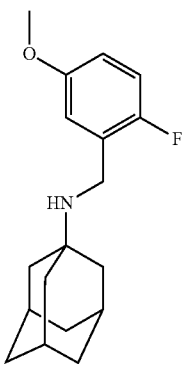 [SMILES: COc1ccc(F)c(CNC23CC4CC(CC(C4)C2)C3)c1]

Adamantan-1-yl-(2-fluoro-5-methoxy-benzyl)-amine

Based on general procedure B, from adamantan-1-ylamine and 2-Fluoro-5-methoxy-benzaldehyde (yield: 53%). Data: MS m/z 289 [M+H]$^+$.

Example 64

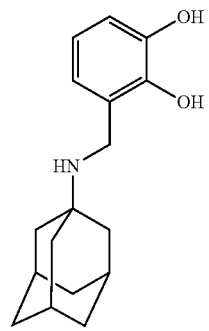 [SMILES: Oc1cccc(CNC23CC4CC(CC(C4)C2)C3)c1O]

3-(Adamantan-1-ylaminomethyl)-benzene-1,2-diol

Based on general procedure B, from adamantan-1-ylamine and 2,3-dihydroxy-benzaldehyde (yield: 36%). Data: MS m/z 274 [M+H]$^+$.

Example 65/IMX624

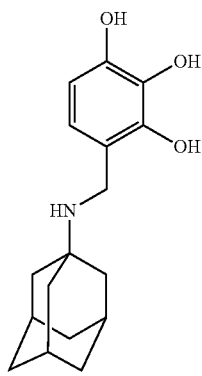

4-(Adamantan-1-ylaminomethyl)-benzene-1,2,3-triol

Based on general procedure A, from adamantan-1-ylamine and 2,3,4-trihydroxy-benzaldehyde, a white solid (68%) is obtained. Data: LC/MS (ESR) m/z 290 [M+H]$^+$.

Example 66/IMX595

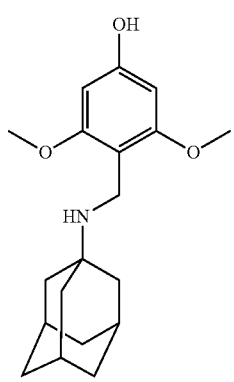

4-(Adamantan-1-ylaminomethyl)-3,5-dimethoxy-phenol

Based on general procedure A, from adamantan-1-ylamine and 4-hydroxy-2,6-dimethoxy-benzaldehyde, a off-white solid (79%) is obtained. Data: LC/MS (ESR) m/z 318 [M+H]$^+$.

Example 67/IMX611

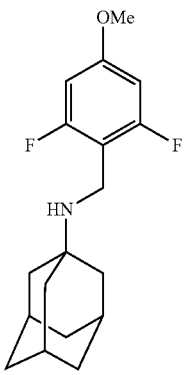 [SMILES: COc1cc(F)c(CNC23CC4CC(CC(C4)C2)C3)c(F)c1]

Adamantan-1-yl-(2,6-difluoro-4-methoxy-benzyl)-amine

Based on general procedure A, from adamantan-1-ylamine and 2,6-difluoro-4-methoxy-benzaldehyde, a white solid (71%) is obtained. Data: LC/MS (ESR) m/z 307 [M+H]$^+$.

Example 68/IMX568

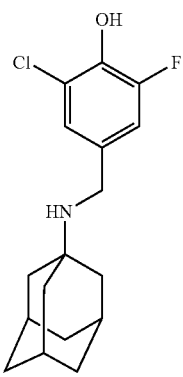 [SMILES: Oc1c(F)cc(CNC23CC4CC(CC(C4)C2)C3)cc1Cl]

4-(Adamantan-1-ylaminomethyl)-2-chloro-6-fluoro-phenol

Based on general procedure A, from adamantan-1-ylamine and 3-Chloro-5-fluoro-4-hydroxy-benzaldehyde, a white solid (61%) is obtained. Data: LC/MS (ESR) m/z 310 [M+H]$^+$.

253
Example 69/IMX612

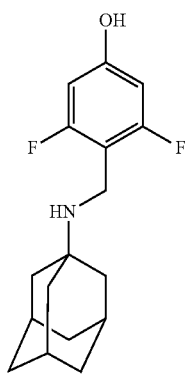 [SMILES: Oc1cc(F)c(CNC23CC4CC(CC(C4)C2)C3)c(F)c1]

4-(Adamantan-1-ylaminomethyl)-3,5-difluoro-phenol

Treatment of adamantan-1-yl-(2,6-difluoro-4-methoxy-benzyl)-amine (from adamantan-1-ylamine and 3-Chloro-5-fluoro-4-hydroxy-benzaldehyde) with $BBr_3$ at −78° C. gave the title compound as a solid (85%). Data: LC/MS (ESR) m/z 294 $[M+H]^+$.

Example 70/IMX594

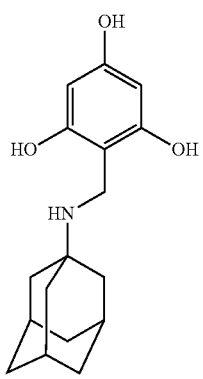 [SMILES: Oc1cc(O)c(CNC23CC4CC(CC(C4)C2)C3)c(O)c1]

2-(Adamantan-1-ylaminomethyl)-benzene-1,3,5-triol

Based on general procedure A, from adamantan-1-ylamine and 2,4,6-trihydroxy-benzaldehyde, an off-white solid (72%) is obtained. Data: LC/MS (ESR) m/z 290 $[M+H]^+$.

254
Example 71/M2WJ260

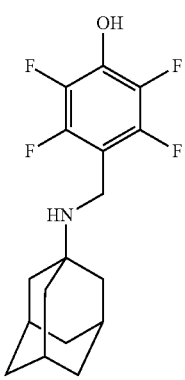 [SMILES: Oc1c(F)c(F)c(CNC23CC4CC(CC(C4)C2)C3)c(F)c1F]

4-(Adamantan-1-ylaminomethyl)-2,3,5,6-tetrafluoro-phenol

Based on general procedure B, from adamantan-1-ylamine and 2,3,5,6-tetrafluoro-4-hydroxybenzaldehyde, a solid (yield: 61%) is obtained. Data: MS m/z 195 $[M+H]^+$.

Example 72/IMX593

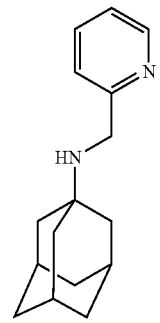 [SMILES: c1ccc(CNC23CC4CC(CC(C4)C2)C3)nc1]

Adamantan-1-yl-pyridin-2-ylmethyl-amine

Based on general procedure A, from adamantan-1-ylamine and pyridine-2-carbaldehyde, a white solid (73%) is obtained. Data: LC/MS (ESR) m/z 243 $[M+H]^+$.

Example 73/IMX592

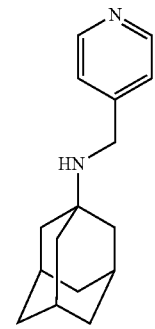 [SMILES: c1cc(CNC23CC4CC(CC(C4)C2)C3)ccn1]

255

Adamantan-1-yl-pyridin-4-ylmethyl-amine

Based on general procedure A, from adamantan-1-ylamine and pyridine-4-carbaldehyde, a white solid (71%) is obtained. Data: LC/MS (ESR) m/z 243 [M+H]$^+$.

Example 74/M2WJ306

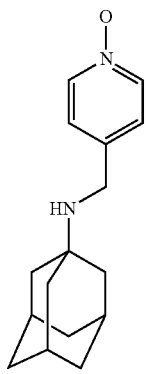

Adamantan-1-yl-(1-oxy-pyridin-4-ylmethyl)-amine

Based on general procedure B, from adamantan-1-ylamine and 1-Oxy-pyridine-4-carbaldehyde (yield: 79%). MS m/z 243 [M+H]$^+$.

Example 75/IMX587

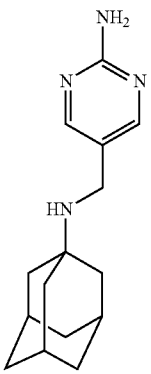

5-(Adamantan-1-ylaminomethyl)-pyrimidin-2-ylamine

Based on general procedure A, from adamantan-1-ylamine and 2-amino-pyrimidine-5-carbaldehyde, a white solid (65%) is obtained. Data: LC/MS (ESR) m/z 259 [M+H]$^+$.

256

Example 76/IMX641

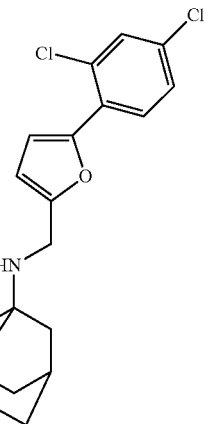

Adamantan-1-yl-[5-(2,4-dichloro-phenyl)-furan-2-ylmethyl]-amine

Based on general procedure A, from adamantan-1-ylamine and 5-(2,4-dichloro-phenyl)-furan-2-carbaldehyde, a white solid (XX %) is obtained. Data: LC/MS (ESR) m/z 377 [M+H]$^+$.

Example 77/IMX604

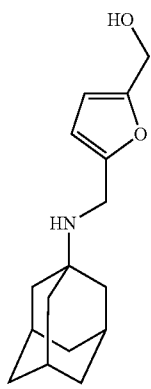 [SMILES: OCc1ccc(CNC23CC4CC(CC(C4)C2)C3)o1]

[5-(Adamantan-1-ylaminomethyl)-furan-2-yl]methanol

From adamantan-1-ylamine and 5-Hydroxymethyl-furan-2-carbaldehyde, a solid (81%) is obtained. Data: LC/MS (ESR) m/z 262 [M+H]$^+$.

Example 78/BC007

N-([2,2'-Bithiophen]-5-ylmethyl)adamantan-1-amine

Based on general procedure A, from adamantan-1-ylamine and [2,2'-bithiophene]-5-carbaldehyde, a yellow solid was obtained. Data: LC/MS (ESCi) m/z 330 [M+H]+.

Example 79/IMX606

Adamantan-1-yl-thieno[2,3-b]thiophen-2-ylmethyl-amine

Based on general procedure C, from adamantan-1-ylamine and thieno[2,3-b]thiophene-2-carboxylic acid, a yellow solid was obtained. Data: LC/MS (ESR) m/z 304 [M+H]+.

Example 80/IMX610

Adamantan-1-yl-(4H-thieno[3,2-b]pyrrol-5-ylmethyl)-amine

Based on general procedure C, from adamantan-1-ylamine and 4H-thieno[3,2-b]pyrrole-5-carboxylic acid, a yellow solid was obtained. Data: LC/MS (ESR) m/z 287 [M+H]+.

Example 81/IMX621

Adamantan-1-yl-thieno[3,2-b]thiophen-2-ylmethyl-amine

Based on general procedure C, from adamantan-1-ylamine and thieno[3,2-b]thiophene-2-carboxylic acid, an off-white solid was obtained. Data: LC/MS (ESR) m/z 304 [M+H]+.

Example 82/IMX634

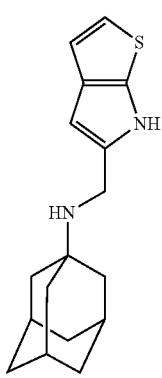 [SMILES: c1cc2cc(CNC34CC5CC(CC(C5)C3)C4)[nH]c2s1]

Adamantan-1-yl-(6H-thieno[2,3-b]pyrrol-5-ylmethyl)-amine

Based on general procedure C, from adamantan-1-ylamine and 6H-thieno[2,3-b]pyrrole-5-carboxylic acid, an off-white solid was obtained. Data: LC/MS (ESR) m/z 304 [M+H]⁺.

Example 83/IMX635

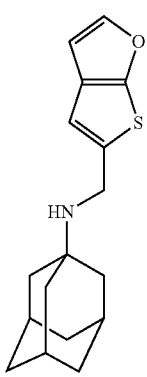 [SMILES: c1cc2cc(CNC34CC5CC(CC(C5)C3)C4)sc2o1]

Adamantan-1-yl-thieno[2,3-b]furan-5-ylmethyl-amine

Based on general procedure C, from adamantan-1-ylamine and thieno[2,3-b]furan-5-carboxylic acid, a pink solid was obtained. Data: LC/MS (ESR) m/z 288 [M+H]⁺.

Example 84/IMX648

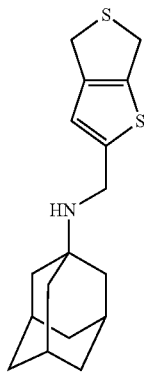 [SMILES: c1c(CNC23CC4CC(CC(C4)C2)C3)sc2c1CSC2]

Adamantan-1-yl-(4,6-dihydro-thieno[3,4-b]thiophen-2-ylmethyl)-amine Based on general procedure C, from adamantan-1-ylamine and 4,6-Dihydro-thieno[3,4-b]thiophene-2-carboxylic acid, a yellow solid was obtained. Data: LC/MS (ESR) m/z 306 [M+H]⁺.

Example 85/IMX644

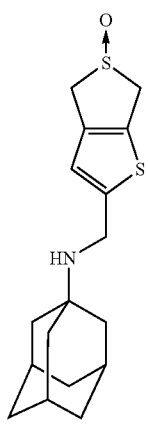 [SMILES: O=S1Cc2cc(CNC34CC5CC(CC(C5)C3)C4)sc2C1]

Adamantan-1-yl-(5-oxo-5,6-dihydro-4H-5M-thieno[3,4-b]thiophen-2-ylmethyl)-amine

Treatment of adamantan-1-yl-(4,6-dihydro-thieno[3,4-b]thiophen-2-ylmethyl)-amine (1.0 equiv) with mCPBA (1.2 equiv) at room temperature gave the title compound as an off-white solid (72%). Data: LC/MS (ESR) m/z 322 [M+H]⁺.

Example 86/M2WJ264

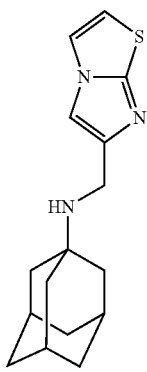 [SMILES: c1cn2cc(CNC34CC5CC(CC(C5)C3)C4)nc2s1]

Adamantan-1-yl-imidazo[2,1-b]thiazol-6-ylmethyl-amine

Based on procedure B, from adamantan-1-ylamine and imidazo[2,1-b]thiazole-6-carbaldehyde (68%). Data: MS m/z 288 [M+H]$^+$.

Example 87/M2WJ298

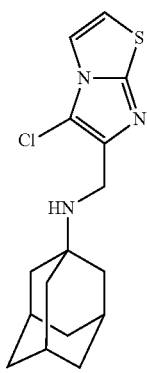

Adamantan-1-yl-(5-chloro-imidazo[2,1-b]thiazol-6-ylmethyl)-amine

Based on procedure B, from adamantan-1-ylamine and 5-chloro-imidazo[2,1-b]thiazole-6-carbaldehyde (yield: 58%). Data: MS m/z 322 [M+H]$^+$.

Example 88/IMX622

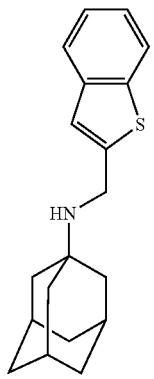 [SMILES: c1ccc2sc(CNC34CC5CC(CC(C5)C3)C4)cc2c1]

Adamantan-1-yl-benzo[b]thiophen-2-ylmethyl-amine

Based on procedure A, from adamantan-1-ylamine and benzo[b]thiophene-2-carbaldehyde, an off-white solid (76%) is obtained. Data: LC/MS (ESR) m/z 298 [M+H]$^+$.

Example 89/IMX631

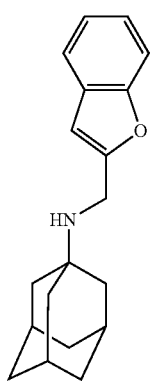 [SMILES: c1ccc2oc(CNC34CC5CC(CC(C5)C3)C4)cc2c1]

Adamantan-1-yl-benzofuran-2-ylmethyl-amine

Based on procedure A, from adamantan-1-ylamine and benzofuran-2-carbaldehyde, a white solid (71%) is obtained. Data: LC/MS (ESR) m/z 281 [M+H]$^+$.

Example 90/IMX626

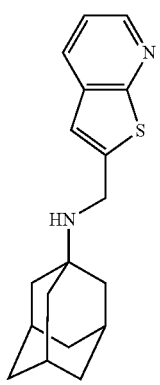 [SMILES: c1cnc2sc(CNC34CC5CC(CC(C5)C3)C4)cc2c1]

Adamantan-1-yl-thieno[2,3-b]pyridin-2-ylmethyl-amine

Based on procedure A, from adamantan-1-ylamine and thieno[2,3-b]pyridine-2-carbaldehyde, a white solid (70%) is obtained. Data: LC/MS (ESR) m/z 298 [M+H]$^+$.

Example 91/IMX632

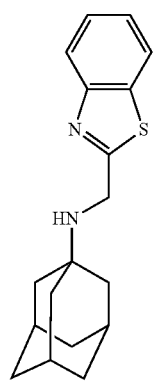 [SMILES: c1ccc2sc(CNC34CC5CC(CC(C5)C3)C4)nc2c1]

Adamantan-1-yl-benzothiazol-2-ylmethyl-amine

Based on procedure A, from adamantan-1-ylamine and benzothiazole-2-carbaldehyde, an off-white solid (69%) is obtained. Data: LC/MS (ESR) m/z 299 [M+H]$^+$.

Example 92/IMX633

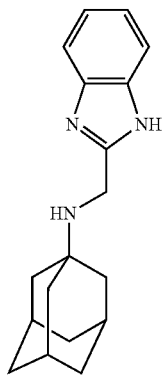

Adamantan-1-yl-(1H-benzoimidazol-2-ylmethyl)-amine

Based on procedure A, from adamantan-1-ylamine and 1H-benzoimidazole-2-carbaldehyde, a white solid (76%) is obtained. Data: LC/MS (ESR) m/z 282 [M+H]$^+$.

Example 93/IMX642

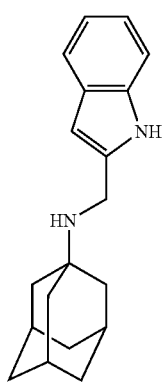 [SMILES: c1ccc2[nH]c(CNC34CC5CC(CC(C5)C3)C4)cc2c1]

Adamantan-1-yl-(1H-indol-2-ylmethyl)-amine

Based on procedure A, from adamantan-1-ylamine and 1H-indole-2-carbaldehyde, an off-white solid (73%) is obtained. Data: LC/MS (ESR) m/z 281 [M+H]$^+$.

Example 94/IMX623

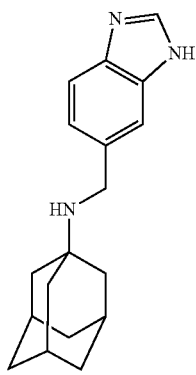 [SMILES: c1nc2ccc(CNC34CC5CC(CC(C5)C3)C4)cc2[nH]1]

Adamantan-1-yl-(3H-benzoimidazol-5-ylmethyl)-amine

Based on procedure A, from adamantan-1-ylamine and 3H-benzoimidazole-5-carbaldehyde, an off-white solid (75%) is obtained. Data: LC/MS (ESR) m/z 282 [M+H]+.

Example 95/M2WJ311

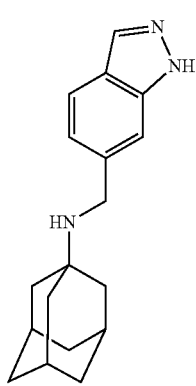 [SMILES: c1cc2cn[nH]c2cc1CNC12CC3CC(CC(C3)C1)C2]

Adamantan-1-yl-(1H-indazol-6-ylmethyl)-amine

Based on procedure B, from adamantan-1-ylamine and 1H-Indazole-6-carbaldehyde (yield: 63%). Data: MS m/z 282 [M+H]+.

Example 96/M2WJ303

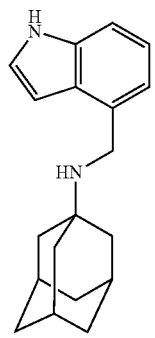 [SMILES: c1cc(CNC23CC4CC(CC(C4)C2)C3)c2cc[nH]c2c1]

Adamantan-1-yl-(1H-indol-4-ylmethyl)-amine

Based on procedure B, from adamantan-1-ylamine and 1H-Indole-4-carbaldehyde (yield: 71%). Data: MS m/z 281 [M+H]+.

Example 97/IMX639

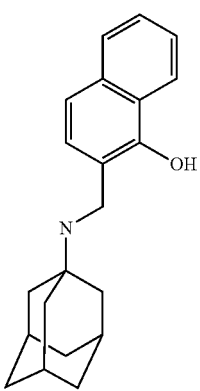 [SMILES: Oc1c(CNC23CC4CC(CC(C4)C2)C3)ccc2ccccc12]

2-(Adamantan-1-ylaminomethyl)-naphthalen-1-ol

Based on procedure A, from adamantan-1-ylamine and 1-hydroxy-naphthalene-2-carbaldehyde, a white solid (72%) is obtained. Data: LC/MS (ESR) m/z 308 [M+H]+.

Example 98/IMX640

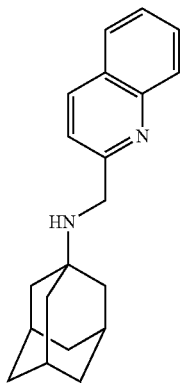 [SMILES: c1ccc2nc(CNC34CC5CC(CC(C5)C3)C4)ccc2c1]

Adamantan-1-yl-quinolin-2-ylmethyl-amine

Based on procedure A, from adamantan-1-ylamine and quinoline-2-carbaldehyde, a white solid (80%) is obtained. Data: LC/MS (ESR) m/z 293 [M+H]$^+$.

Example 99/M2WJ271

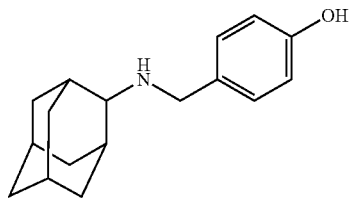 [SMILES: Oc1ccc(CNC2C3CC4CC(C3)CC2C4)cc1]

4-(Adamantan-2-ylaminomethyl)-phenol

Based on procedure B, from adamantan-2-ylamine and 4-hydroxy-benzaldehyde (yield: 65%). Data: MS m/z 258 [M+H]$^+$.

Example 100/M2WJ272

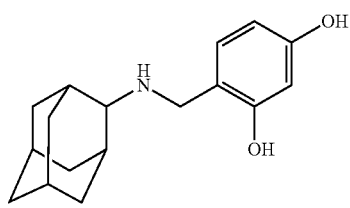 [SMILES: Oc1ccc(CNC2C3CC4CC(C3)CC2C4)c(O)c1]

4-(Adamantan-2-ylaminomethyl)-benzene-1,3-diol

Based on procedure B, from adamantan-2-ylamine and 2,4-dihydroxy-benzaldehyde (yield: 42%). Data: MS m/z 274 [M+H]$^+$.

Example 101/M2WJ273

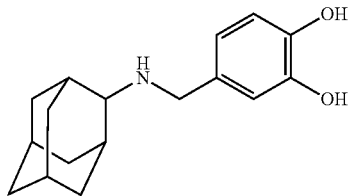 [SMILES: Oc1ccc(CNC2C3CC4CC(C3)CC2C4)cc1O]

4-(Adamantan-2-ylaminomethyl)-benzene-1,2-diol

Based on procedure B, from adamantan-2-ylamine and 3,4-dihydroxy-benzaldehyde (yield: 38%). Data: MS m/z 274 [M+H]$^+$.

Example 102/M2WJ286

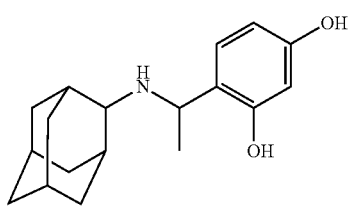 [SMILES: CC(NC1C2CC3CC(C2)CC1C3)c1ccc(O)cc1O]

4-[1-(Adamantan-2-ylamino)-ethyl]-benzene-1,3-diol

Based on procedure B, from adamantan-2-ylamine and 1-(2,4-dihydroxy-phenyl)-ethanone. Data: MS m/z 288 [M+H]$^+$.

Example 103/M2WJ297

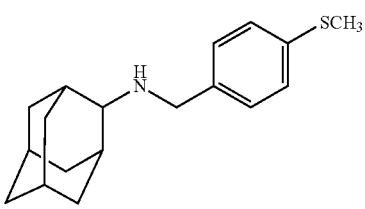 [SMILES: CSc1ccc(CNC2C3CC4CC(C3)CC2C4)cc1]

Adamantan-2-yl-(4-methylsulfanyl-benzyl)-amine

Based on procedure B, from adamantan-2-ylamine and 4-methylsulfanyl-benzaldehyde (yield: 68%). Data: MS m/z 288 [M+H]$^+$.

Example 104/M2WJ286

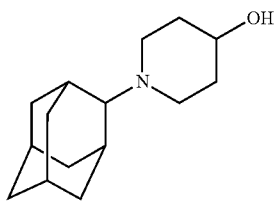 [SMILES: OC1CCN(C2C3CC4CC(C3)CC2C4)CC1]

1-Adamantan-2-yl-piperidin-4-ol

Based on procedure B, from Adamantan-2-one and Piperidin-4-ol. Data: MS m/z 236 [M+H]+.

Example 105/M2WJ299

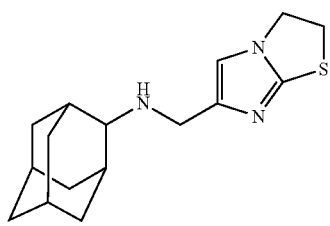 [SMILES: c1c(CNC2C3CC4CC(C3)CC2C4)nc2n1CCS2]

Adamantan-2-yl-(2,3-dihydro-imidazo[2,1-b]thiazol-6-ylmethyl)-amine

Based on procedure B, from adamantan-2-ylamine and 2,3-dihydro-imidazo[2,1-b]thiazole-6-carbaldehyde (yield: 68%). Data: MS m/z 290 [M+H]+.

Example 106/M2WJ302

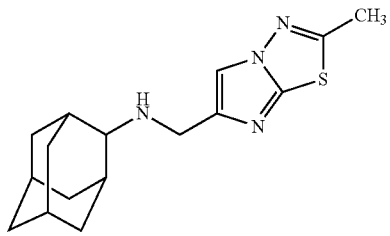 [SMILES: Cc1nn2cc(CNC3C4CC5CC(C4)CC3C5)nc2s1]

Adamantan-2-yl-(2-methyl-imidazo[2,1-b][1,3,4]thiadiazol-6-ylmethyl)-amine

Based on procedure B, from adamantan-2-ylamine and 2-Methyl-imidazo[2,1-b][1,3,4]thiadiazole-6-carbaldehyde (yield: 52%). Data: MS m/z 303 [M+H]+.

Example 107/M2WJ314

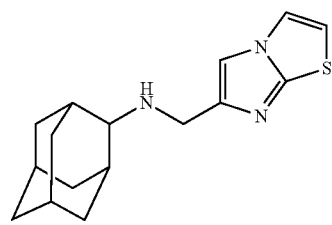 [SMILES: c1cn2cc(CNC3C4CC5CC(C4)CC3C5)nc2s1]

Adamantan-2-yl-imidazo[2,1-b]thiazol-6-ylmethyl-amine

Based on procedure B, from adamantan-2-ylamine and Imidazo[2,1-b]thiazole-6-carbaldehyde (yield: 71%). Data: MS m/z 288 [M+H]+.

Example 108/M2WJ282

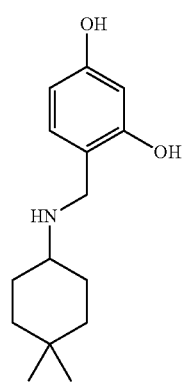 [SMILES: CC1(C)CCC(NCc2ccc(O)cc2O)CC1]

4-[(4,4-Dimethyl-cyclohexylamino)-methyl]-benzene-1,3-diol

Based on procedure B, from 4,4-dimethyl-cyclohexylamine and 2,4-Dihydroxy-benzaldehyde (yield: 43%). Data: MS m/z 250 [M+H]+.

Example 109/M2WJ294

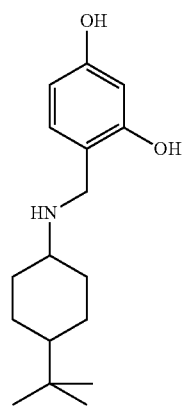 [SMILES: CC(C)(C)C1CCC(NCc2ccc(O)cc2O)CC1]

4-[(4-tert-Butyl-cyclohexylamino)-methyl]-benzene-1,3-diol

Based on procedure B, from 4-tert-Butyl-cyclohexylamine and 2,4-dihydroxy-benzaldehyde (yield: 57%). Data: MS m/z 278 [M+H]⁺.

Example 110/M2WJ285

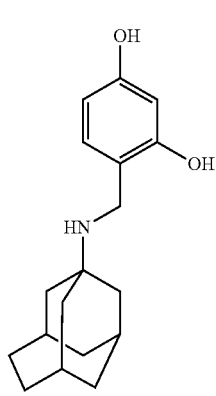 [SMILES: Oc1ccc(CNC23CC4CCC(CC(C4)C2)C3)c(O)c1]

4-(Tricyclo[4.3.1.1³,⁸]undec-1-ylaminomethyl)-benzene-1,3-diol

Based on procedure B, from tricyclo[4.3.1.1³,⁸]undec-1-ylamine and 2,4 dihydroxybenzaldehyde (yield: 37%). Data: MS m/z 288 [M+H]⁺.

Example 111/M2WJ284

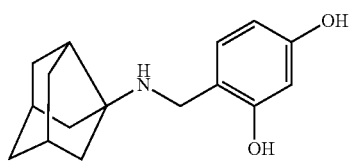 [SMILES: Oc1ccc(CNC23CC4CC(CC2C4)C3)c(O)c1]

4-[(Hexahydro-2,5-methano-pentalen-3a-ylamino)-methyl]-benzene-1,3-diol

Based on procedure B, from hexahydro-2,5-methano-pentalen-3a-ylamine and 2,4-dihydroxy-benzaldehyde (yield: 49%). Data: MS m/z 260 [M+H]⁺.

Example 112/M2WJ287

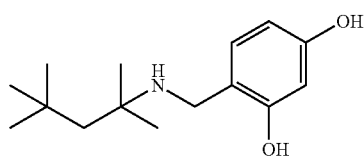 [SMILES: CC(C)(C)CC(C)(C)NCc1ccc(O)cc1O]

4-[(1,1,3,3-Tetramethyl-butylamino)-methyl]-benzene-1,3-diol

Based on procedure B, from 1,1,3,3-Tetramethyl-butylamine and 2,4-dihydroxy-benzaldehyde (yield: 74%). Data: MS m/z 252 [M+H]⁺.

Example 113/M2WJ283

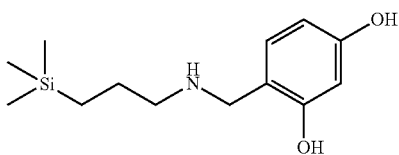 [SMILES: C[Si](C)(C)CCCNCc1ccc(O)cc1O]

4-[(3-Trimethylsilanyl-propylamino)-methyl]-benzene-1,3-diol

Based on procedure B, from 3-Trimethylsilanyl-propylamine and 2,4-dihydroxy-benzaldehyde (yield: 50%). Data: MS m/z 254 [M+H]⁺.

Example 114/M2WJ293

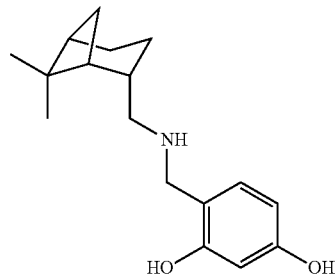 [SMILES: CC1(C)C2CCC(CNCc3ccc(O)cc3O)C1C2]

4-{[(6,6-Dimethyl-bicyclo[3.1.1]hept-2-ylmethyl)-amino]methyl}-benzene-1,3-diol Based on procedure B, from C-(6,6-Dimethyl-bicyclo[3.1.1]hept-2-yl)-methylamine and 2,4-dihydroxy-benzaldehyde (yield: 65%). Data: MS m/z 276 [M+H]⁺.

Example 115/M2WJ288

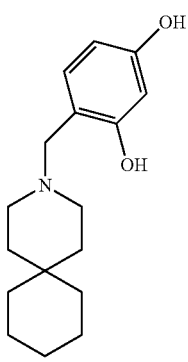 [SMILES: Oc1ccc(CN2CCC3(CCCCC3)CC2)c(O)c1]

4-(3-Aza-spiro[5.5]undec-3-ylmethyl)-benzene-1,3-diol

Based on procedure B, from 3-Aza-spiro[5.5]undecane and 2,4-dihydroxy-benzaldehyde (yield: 61%). Data: MS m/z 276 [M+H]$^+$.

Example 116/M2WJ292

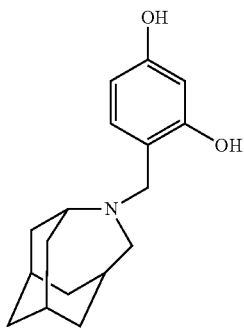 [SMILES: Oc1ccc(CN2CC3CC4CC(C3)CC2C4)c(O)c1]

4-(4-Aza-tricyclo[4.3.1.13,8]undec-4-ylmethyl)-benzene-1,3-diol

Based on procedure B, from 4-Aza-tricyclo[4.3.1.13,8]undecane and 2,4-dihydroxy-benzaldehyde (yield: 42%). Data: MS m/z 274 [M+H]$^+$.

Example 1a/IMX627

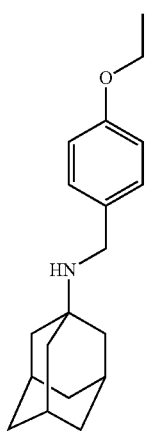 [SMILES: CCOc1ccc(CNC23CC4CC(CC(C4)C2)C3)cc1]

Adamantan-1-yl-(4-ethoxy-benzyl)-amine

Based on general procedure A, from 4-ethoxy-benzaldehyde and adamantan-1-ylamine, a white solid (70%) is obtained. Data: LC/MS (ESR) m/z 286 [M+H]$^+$.

Example 2a/BC063

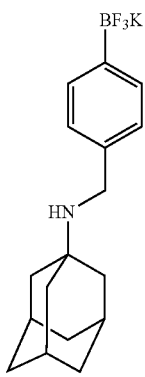

Potassium N-(4-adamantan-1-ylamino)methyl)phenyl)trifluoroborate (BC063)

See reference: Molander, G. A.; Trice, S. L. J.; Dreher, S. D. *J. Am. Chem. Soc.* 2010, 131, 17701-17703.

Example 3a/BC020

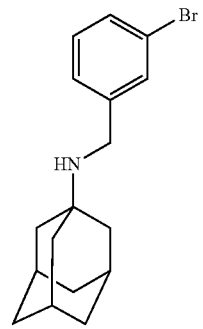

N-(3-Bromobenzyl)adamantan-1-amine (BC020)

Based on general procedure A, from adamantan-1-ylamine and 3-bromobenzaldehyde, a light yellow oil was obtained. Data: LC/MS (ESCi) m/z 320.08/322.09 [M+H]$^+$.

Example 4a/IMX673

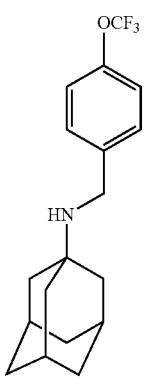

Adamantan-1-yl-(4-trifluoromethoxy-benzyl)-amine

Based on general procedure A, from 4-Trifluoromethoxy-benzaldehyde and adamantan-1-ylamine, a white solid (72%) is obtained. Data: LC/MS (ESR) m/z 326 [M+H]⁺.

Example 5a/IMX674

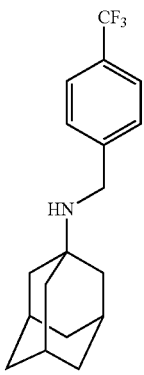

Adamantan-1-yl-(4-trifluoromethyl-benzyl)-amine

Based on general procedure A, from 4-trifluoromethyl-benzaldehyde and adamantan-1-ylamine, a white solid (72%) is obtained. Data: LC/MS (ESR) m/z 310 [M+H]⁺.

Example 6a/IMX676

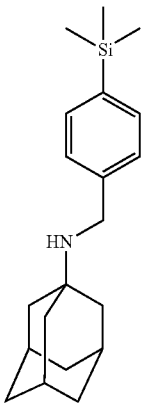 [SMILES: C[Si](C)(C)c1ccc(CNC23CC4CC(CC(C4)C2)C3)cc1]

Adamantan-1-yl-(4-trimethylsilanyl-benzyl)-amine

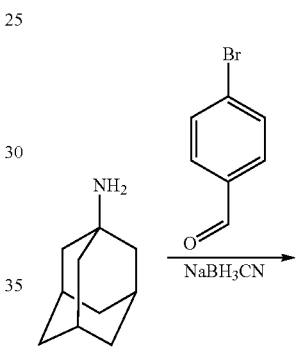

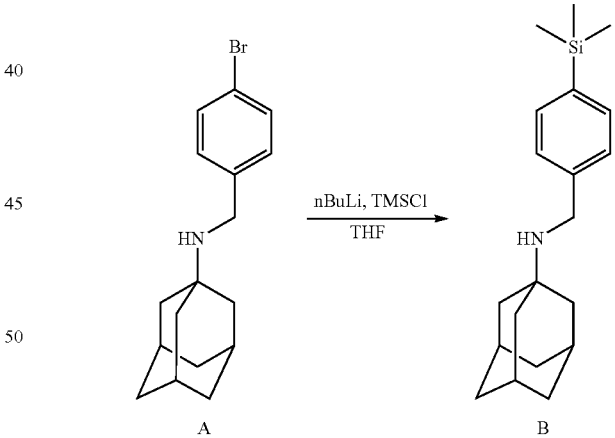

Follow procedure A, from 4-Bromo-benzaldehyde and adamantan-1-ylamine, adamantan-1-yl-(4-bromo-benzyl)-amine (A) was obtained as white solid (81%). Data: LC/MS (ESR) m/z 320 [M+H]⁺.

To a solution of adamantan-1-yl-(4-bromo-benzyl)-amine (A) (320 mg, 1 mmol) in anhydrous THF (10 mL) at N₂ atmosphere nBuLi (1.5 M in Hex, 1.0 mL, 2.5 mmol) was added dropwise at −78° C. After the mixture was stirred for 20 min TMSCl (140 mg, 1.2 mmol) was added. The mixture was stirred for 30 min before it was quenched with NH4Cl (sat'd) (5 mL). and the product was extracted with DCM (10 mL×3). The combined organic layer was dried over Na₂SO₄, and concentrated under reduced pressure. The crude product was separated by flash column chromatography (1-10% CH$_3$OH/CH$_2$Cl$_2$) to give adamantan-1-yl-(4-trimethylsilanyl-benzyl)-amine a white solid (219 mg, 71%). Data: LC/MS (ESR) m/z 314 [M+H]$^+$.

Example 7a/BC014

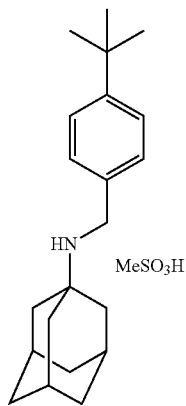 [SMILES: "MeSO3H" ; CC(C)(C)c1ccc(CNC23CC4CC(CC(C4)C2)C3)cc1]

N-(4-(tert-Butyl)benzyl)adamantan-1-amine methanesulfonate-(BC014)

Based on general procedure A, from adamantan-1-ylamine and 4-(tert-butyl)benzaldehyde. The pure free amine was dissolved in Et$_2$O and cooled to 0° C. and MeSO$_3$H (1 equiv) was added under N$_2$ and then mixture was stirred at 0° C. for 15 min and filtered to give a white solid. Data: LC/MS (ESCi) m/z 298.25 [M+H]$^+$.

Example 8a/BC076

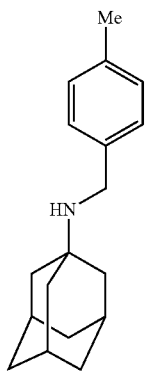

N-(4-Methylbenzyl)adamantan-1-amine

Based on general procedure F, from N-(4-bromobenzyl)adamantan-1-amine and potassium methyltrifluoroborate, a yellow solid was obtained. Data: LC/MS (ESCi) m/z 256.00 [M+H]$^+$.

Example 9a/BC080

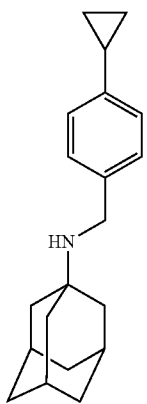 [SMILES: c1cc(C2CC2)ccc1CNC12CC3CC(CC(C3)C1)C2]

N-(4-Cyclopropylbenzyl)adamantan-1-amine (BC080)

Based on general procedure H, from adamantan-1-ylamine, and potassium cyclopropyltrifluoroborate, a white solid was obtained after column chromatography purification (0-10% MeOH/CH$_2$Cl$_2$). Data: LC/MS (ESCi) m/z 282.18 [M+H]$^+$.

Example 10a/IMX678

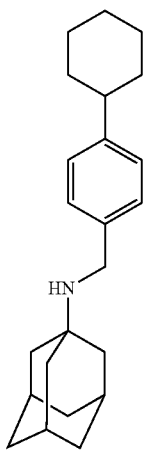 [SMILES: c1cc(C2CCCCC2)ccc1CNC12CC3CC(CC(C3)C1)C2]

Adamantan-1-yl-(4-cyclohexyl-benzyl)-amine

Based on general procedure A, 4-Cyclohexyl-benzaldehyde and Adamantan-1-ylamine, a white solid (70%) is obtained. Data: LC/MS (ESR) m/z 324 [M+H]$^+$.

Example 11a/WFD093

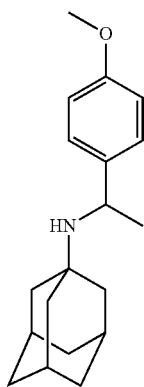 [SMILES: COc1ccc(C(C)NC23CC4CC(CC(C4)C2)C3)cc1]

N-(1-(4-methoxyphenyl)ethyl)adamantan-1-amine

Based on general procedure C, from adamantane-1-amine and 1-(4-methoxyphenyl)ethanone, a white solid is obtained. Data: HPLC retention time 7.3 min (77% B, Xterra RP-C18, 4.6×250 mm, 5 uM, mobile phase A: 10 mM NH4HCO3 buffer pH=9, mobile phase B: CH3CN, flow rate: 1.0 ml/min, 254 nm) LC/MS (ESR) m/z 286.3 [M+H]$^+$.

Example 12a/WFD023

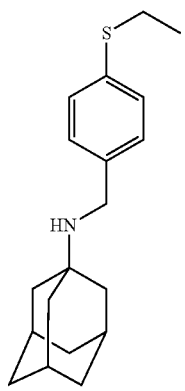 [SMILES: CCSc1ccc(CNC23CC4CC(CC(C4)C2)C3)cc1]

N-(4-(ethylthio)benzyl)adamantan-1-amine

Based on general procedure C, from adamantane-1-amine and 4-(ethylthio)benzaldehyde, a white solid is obtained. Data: HPLC retention time: 9.8 min (90% B, Xterra RP-C18, 4.6×250 mm, 5 uM, mobile phase A: 10 mM NH4HCO3 buffer pH=9, mobile phase B: CH3CN, flow rate: 1.0 ml/min, 254 nm) LC/MS (ESR) m/z 302.3 [M+H]$^+$.

Example 13a/IMX00657

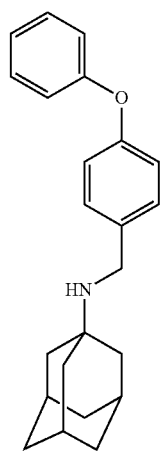 [SMILES: c1ccc(Oc2ccc(CNC34CC5CC(CC(C5)C3)C4)cc2)cc1]

Adamantan-1-yl-(4-phenoxy-benzyl)-amine

Based on general procedure A, 4-Phenoxy-benzaldehyde and Adamantan-1-ylamine, a white solid (71%) is obtained. Data: LC/MS (ESR) m/z 334 [M+H]$^+$.

Example 14a/IMX00649

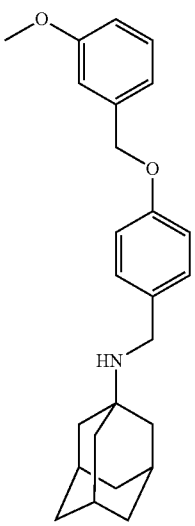 [SMILES: COc1cccc(COc2ccc(CNC34CC5CC(CC(C5)C3)C4)cc2)c1]

Adamantan-1-yl-[4-(3-methoxy-benzyloxy)-benzyl]-amine

Based on general procedure A, 4-(3-Methoxy-benzyloxy)-benzaldehyde and Adamantan-1-ylamine, a white solid (71%) is obtained. Data: LC/MS (ESR) m/z 378 [M+H]$^+$.

Example 15a/IMX00650

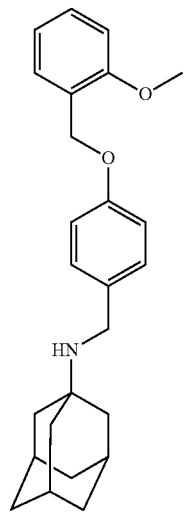 [SMILES: COc1ccccc1COc1ccc(CNC23CC4CC(CC(C4)C2)C3)cc1]

Adamantan-1-yl-[4-(2-methoxy-benzyloxy)-benzyl]-amine

Based on general procedure A, 4-(2-Methoxy-benzyloxy)-benzaldehyde and Adamantan-1-ylamine, a white solid (68%) is obtained. Data: LC/MS (ESR) m/z 378 [M+H]$^+$.

Example 16a/IMX00651

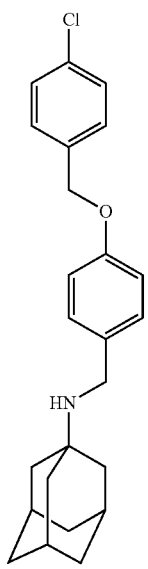 [SMILES: Clc1ccc(COc2ccc(CNC34CC5CC(CC(C5)C3)C4)cc2)cc1]

Adamantan-1-yl-[4-(4-chloro-benzyloxy)-benzyl]-amine

Based on general procedure A, 4-(4-Chloro-benzyloxy)-benzaldehyde and Adamantan-1-ylamine, a white solid (68%) is obtained. Data: LC/MS (ESR) m/z 382 [M+H]$^+$.

Example 17a/IMX00651

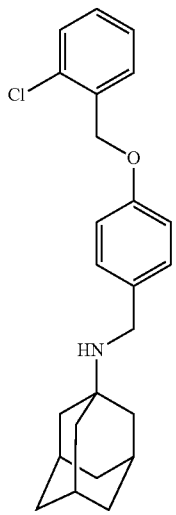 [SMILES: Clc1ccccc1COc1ccc(CNC23CC4CC(CC(C4)C2)C3)cc1]

Adamantan-1-yl-[4-(2-chloro-benzyloxy)-benzyl]-amine

Based on general procedure A, 4-(2-Chloro-benzyloxy)-benzaldehyde and Adamantan-1-ylamine, a white solid (68%) is obtained. Data: LC/MS (ESR) m/z 382 [M+H]$^+$.

Example 18a/IMX00653

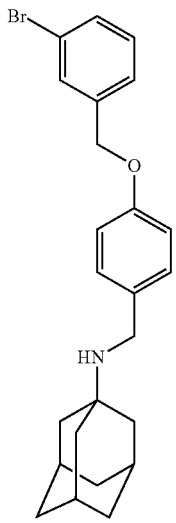 [SMILES: Brc1cccc(COc2ccc(CNC34CC5CC(CC(C5)C3)C4)cc2)c1]

Adamantan-1-yl-[4-(3-bromo-benzyloxy)-benzyl]-amine

Based on general procedure A, 4-(3-Bromo-benzyloxy)-benzaldehyde and Adamantan-1-ylamine, a white solid (68%) is obtained. Data: LC/MS (ESR) m/z 426 [M+H]$^+$.

Example 19a/IMX00654

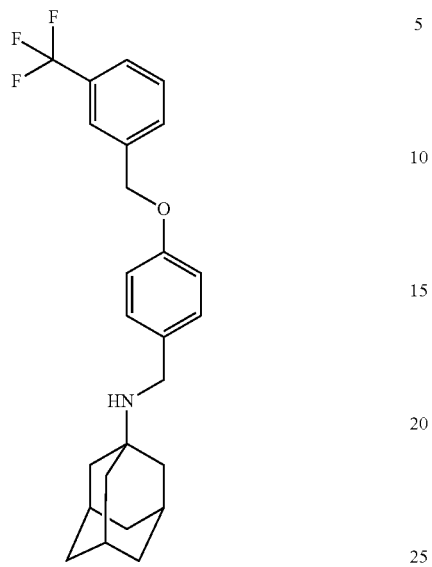

Adamantan-1-yl-[4-(3-trifluoromethyl-benzyloxy)-benzyl]-amine

Based on general procedure A, 4-(3-Trifluoromethyl-benzyloxy)-benzaldehyde and Adamantan-1-ylamine, a white solid (69%) is obtained. Data: LC/MS (ESR) m/z 416 [M+H]$^+$.

Example 20a/IMX00655

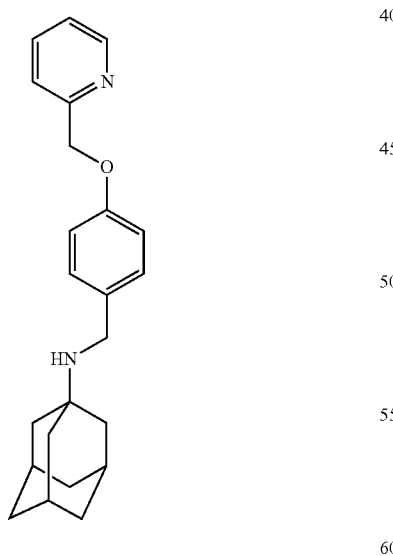

Adamantan-1-yl-[4-(pyridin-2-ylmethoxy)-benzyl]-amine

Based on general procedure A, 4-(Pyridin-2-ylmethoxy)-benzaldehyde and Adamantan-1-ylamine, a white solid (69%) is obtained. Data: LC/MS (ESR) m/z 349 [M+H]$^+$.

Example 21a/IMX00656

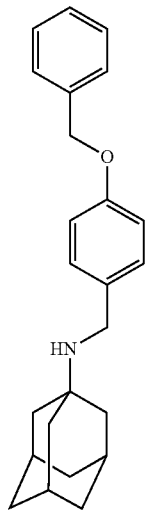 [SMILES: c1ccc(COc2ccc(CNC34CC5CC(CC(C5)C3)C4)cc2)cc1]

Adamantan-1-yl-(4-benzyloxy-benzyl)-amine

Based on general procedure A, Adamantan-1-yl-(4-benzyloxy-benzyl)-amine and Adamantan-1-ylamine, a white solid (69%) is obtained. Data: LC/MS (ESR) m/z 348 [M+H]$^+$.

Example 22a/IMX00629

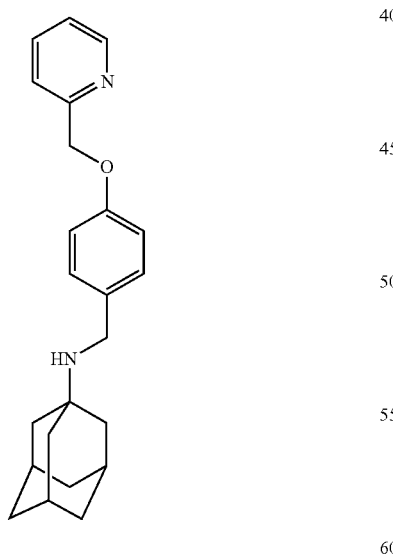

Adamantan-1-yl-[4-(furan-2-ylmethoxy)-benzyl]-amine

Based on general procedure A, 4-(Furan-2-ylmethoxy)-benzaldehyde and Adamantan-1-ylamine, a white solid (69%) is obtained. Data: LC/MS (ESR) m/z 338 [M+H]$^+$.

Example 23a/IMX00630

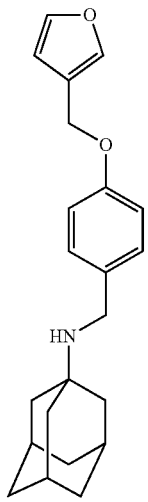 [SMILES: c1cc(COc2ccc(CNC34CC5CC(CC(C5)C3)C4)cc2)co1]

Adamantan-1-yl-[4-(furan-3-ylmethoxy)-benzyl]-amine

Based on general procedure A, 4-(Furan-3-ylmethoxy)-benzaldehyde and Adamantan-1-ylamine, a white solid (69%) is obtained. Data: LC/MS (ESR) m/z 338 [M+H]$^+$.

Example 24a/IMX00658

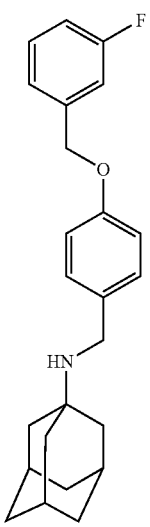 [SMILES: Fc1cccc(COc2ccc(CNC34CC5CC(CC(C5)C3)C4)cc2)c1]

Adamantan-1-yl-[4-(3-fluoro-benzyloxy)-benzyl]-amine

Based on general procedure A, 4-(3-Fluoro-benzyloxy)-benzaldehyde and Adamantan-1-ylamine, a white solid (69%) is obtained. Data: LC/MS (ESR) m/z 366 [M+H]$^+$.

Example 25a/IMX00659

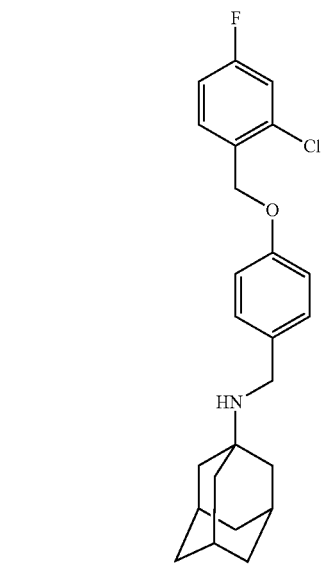

Adamantan-1-yl-[4-(2-chloro-4-fluoro-benzyloxy)-benzyl]amine

Based on general procedure A, from 4-(2-Chloro-4-fluoro-benzyloxy)-benzaldehyde and Adamantan-1-ylamine, a white solid (69%) is obtained. Data: LC/MS (ESR) m/z 400 [M+H]$^+$.

Example 26a/WFD097 and IMX00663

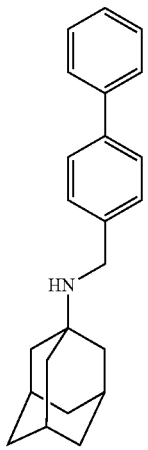

Adamantan-1-yl-biphenyl-4-ylmethyl-amine

Based on general procedure A, from Biphenyl-4-carbaldehyde and Adamantan-1-ylamine, a white solid (69%) is obtained. Data: LC/MS (ESR) m/z 318 [M+H]$^+$.

287
Example 27a/IMX00694

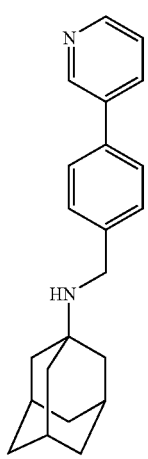 [SMILES: c1cncc(-c2ccc(CNC34CC5CC(CC(C5)C3)C4)cc2)c1]

Adamantan-1-yl-[4-(2-chloro-4-fluoro-benzyloxy)-benzyl]amine

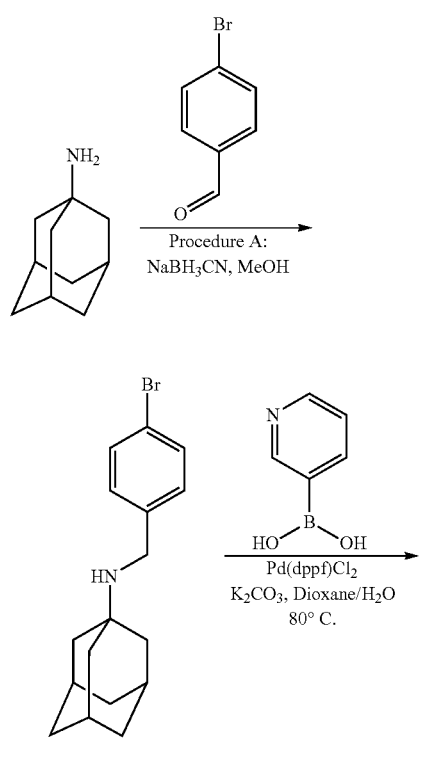

According to Procedure A, adamantan-1-yl-(4-bromo-benzyl)-amine was made from adamantan-1-ylamine and 4-bromo-benzaldehyde (76%). According to Procedure E, from adamantan-1-yl-(4-bromo-benzyl)-amine and 3-pyridylboronic acid, adamantan-1-yl-(4-pyridin-3-yl-benzyl)-amine as a white solid (69%) is obtained. Data: LC/MS (ESR) m/z 319 [M+H]$^+$.

288
Example 28a/IMX00695

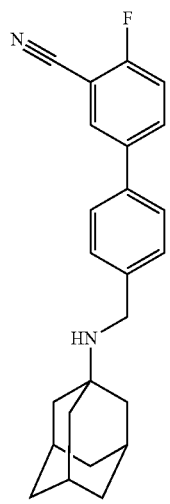 [SMILES: N#Cc1cc(-c2ccc(CNC34CC5CC(CC(C5)C3)C4)cc2)ccc1F]

Adamantan-1-yl-[4-(2-chloro-4-fluoro-benzyloxy)-benzyl]amine

Following the same sequence as example 27, from adamantan-1-ylamine, 4-bromo-benzaldehyde and (3-cyano-4-fluorophenyl)boronic acid, adamantan-1-yl-[4-(2-chloro-4-fluoro-benzyloxy)-benzyl]-amine (69%) is obtained as a white solid. Data: LC/MS (ESR) m/z 361 [M+H]$^+$.

Example 29a/BC018

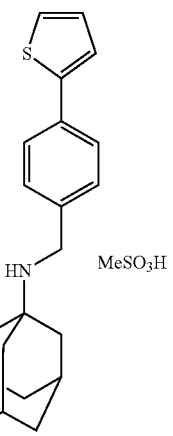

N-(4-(Thiophen-2-yl)benzyl)adamantan-1-amine methanesulfonate

Based on general procedure B, from N-(4-bromobenzyl)adamantan-1-amine (M2MJ325) and potassium (thiophen-2-yl)trifluoroborate. The pure free base was dissolved in Et$_2$O and then cooled to 0° C., MeSO$_3$H (1 equiv) was added under N$_2$. The mixture was stirred at 0° C. for 15 min and then filtered and dried in vacuo to provide a white solid. Data: LC/MS (ESCi) m/z 324.15 [M+H]$^+$.

Example 30a/BC026

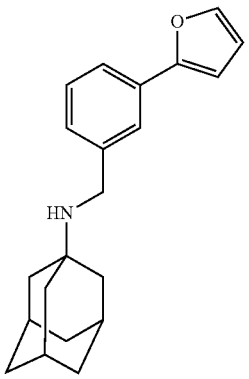 [SMILES: c1cc(CNC23CC4CC(CC(C4)C2)C3)cc(-c2ccco2)c1]

N-(3-(Furan-2-yl)benzyl)adamantan-1-amine

Based on general procedure B, from N-(3-bromobenzyl) adamantan-1-amine (BC020) and potassium furan-2-yltrifluoroborate, a brown solid was obtained. Data: LC/MS (ESCi) m/z 308.23 [M+H]$^+$.

Example 31a/BC032

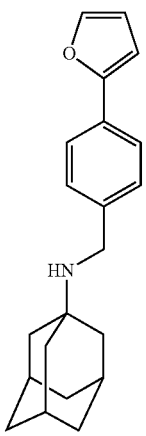 [SMILES: c1coc(-c2ccc(CNC34CC5CC(CC(C5)C3)C4)cc2)c1]

N-(4-(Furan-2-yl)benzyl)adamantan-1-amine (BC032)

Based on general procedure 2, from N-(4-bromobenzyl) adamantan-1-amine (BC005) and potassium furan-2-yltrifluoroborate, a yellow solid was obtained. Data: LC/MS (ESCi) m/z 308.16 [M+H]$^+$.

Example 32a/BC047

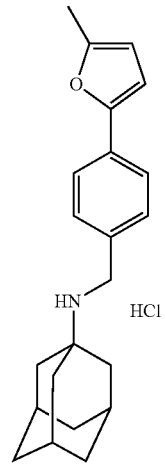 [SMILES: Cc1ccc(-c2ccc(CNC34CC5CC(CC(C5)C3)C4)cc2)o1 ; Cl]

N-(4-(5-Methylfuran-2-yl)benzyl)adamantan-1-amine hydrochloride (BC047)

Based on general procedure B, from N-(4-bromobenzyl) adamantan-1-amine (BC005) and potassium 5-methyl-(furan-2-yl)trifluoroborate. The pure free base was dissolved in Et$_2$O and then cooled to 0° C., 2M HCl in ether (5 equiv) was added. The mixture was stirred at 0° C. for 15 min and then concentrated and dried in vacuo to provide a white solid Data: LC/MS (ESCi) m/z 322.14 [M+H]$^+$.

Example 33a/BC046

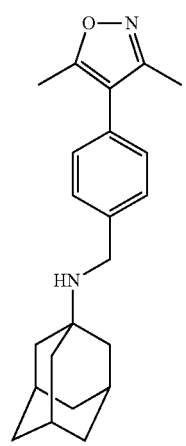 [SMILES: Cc1noc(C)c1-c1ccc(CNC23CC4CC(CC(C4)C2)C3)cc1]

N-(4-(3,5-Dimethylisoxazol-4-yl)benzyl)adamantan-1-amine (BC046)

Based on general procedure B, from 4-(bromobenzyl) adamantan-1-amine (BC005) and potassium (3,5-dimethylisoxazol-4-yl)trifluoroborate, a white solid was obtained. Data: LC/MS (ESCi) m/z 337.19 [M+H]$^+$.

Example 34a/BC025

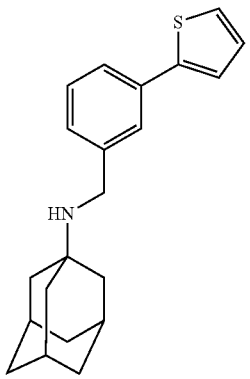 [SMILES: c1cc(CNC23CC4CC(CC(C4)C2)C3)cc(-c2cccs2)c1]

N-(3-(thiophen-2-yl)benzyl)adamantan-1-amine

Based on general procedure B, from 3-bromobenzyl) adamantan-1-amine (BC020) and potassium thiophen-2-yl-trifluoroborate, a light yellow oil was obtained. Data: LC/MS (ESCi) m/z 324.16 [M+H]+.

Example 35a/BC034

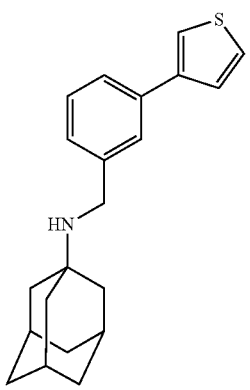 [SMILES: c1cc(CNC23CC4CC(CC(C4)C2)C3)cc(-c2ccsc2)c1]

N-(3-(Thiophen-2-yl)benzyl)adamantan-1-amine

Based on general procedure 2, from N-((3-bromobenzyl) adamantan-1-amine (BC020) and potassium thiophen-3-yl-trifluoroborate, a yellow solid was obtained. Data: LC/MS (ESCi) m/z 324.16 [M+H]+.

Example 36a/WFD029

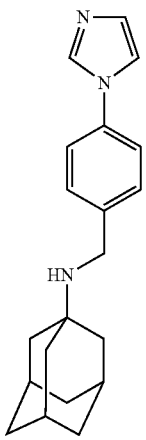 [SMILES: c1cn(-c2ccc(CNC34CC5CC(CC(C5)C3)C4)cc2)cn1]

N-(4-(1H-imidazol-1-yl)benzyl)adamantan-1-amine

Based on general procedure C, from adamantane-1-amine and 4-(1H-imidazol-1-yl)benzaldehyde, a white solid is obtained. Data: HPLC retention time: 6.5 min (70% B, Xterra RP-C18, 4.6×250 mm, 5 uM, mobile phase A: 10 mM NH4HCO3 buffer pH=9, mobile phase B: CH3CN, flow rate: 1.0 ml/min, 254 nm) LC/MS (ESR) m/z 308.3 [M+H]+.

Example 37a/IMX00636

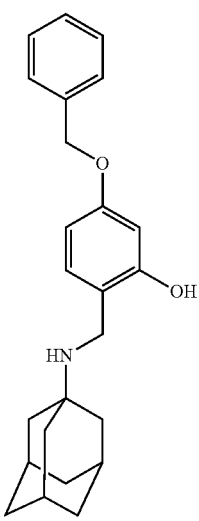 [SMILES: Oc1cc(OCc2ccccc2)ccc1CNC12CC3CC(CC(C3)C1)C2]

2-(Adamantan-1-ylaminomethyl)-5-benzyloxy-phenol

Based on general procedure C, 4-Benzyloxy-2-hydroxy-benzaldehyde and Adamantan-1-ylamine, a white solid (69%) is obtained. Data: LC/MS (ESR) m/z 364 [M+H]+.

Example 38a/M2WJ328

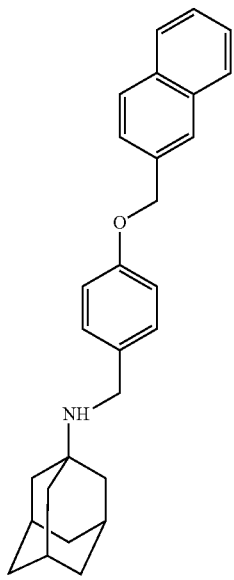 [SMILES: c1ccc2cc(COc3ccc(CNC45CC6CC(CC(C6)C4)C5)cc3)ccc2c1]

N-(4-(naphthalen-2-ylmethoxy)benzyl)adamantan-1-amine

Based on general procedure A, from amantadine and 4-(naphthalen-2-ylmethoxy)benzaldehyde, a yellow solid (70%) is obtained. Data: LC/MS (ESR) m/z 398.5 [M+H]$^+$.

Example 39a/IMX00681

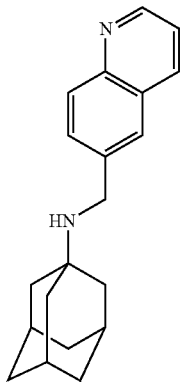 [SMILES: c1cnc2ccc(CNC34CC5CC(CC(C5)C3)C4)cc2c1]

Adamantan-1-yl-quinolin-6-ylmethyl-amine

Based on general procedure A, Quinoline-6-carbaldehyde and Adamantan-1-ylamine, a white solid (74%) is obtained. Data: LC/MS (ESR) m/z 293 [M+H]$^+$.

Example 40a/IMX00682

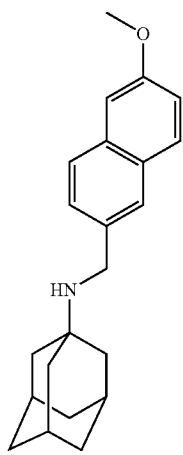 [SMILES: COc1ccc2cc(CNC34CC5CC(CC(C5)C3)C4)ccc2c1]

Adamantan-1-yl-(6-methoxy-naphthalen-2-ylm-ethyl)-amine

Based on general procedure A, 6-Methoxy-naphthalene-2-carbaldehyde and Adamantan-1-ylamine, a white solid (71%) is obtained. Data: LC/MS (ESR) m/z 322 [M+H]$^+$.

Example 41a/WFD115

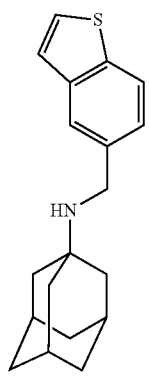 [SMILES: c1cc2cc(CNC34CC5CC(CC(C5)C3)C4)ccc2s1]

N-(benzo[b]thiophen-5-ylmethyl)adamantan-1-amine

Based on general procedure C, from adamantane-1-amine and benzo[b]thiophene-5-carbaldehyde, a white solid is obtained. Data: LC/MS (ES+) m/z 298.2 [M+H]$^+$.

Example 42a/WFD123

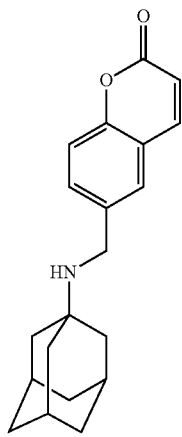 [SMILES: O=c1ccc2cc(CNC34CC5CC(CC(C5)C3)C4)ccc2o1]

6-((adamantan-1-ylamino)methyl)-2H-chromen-2-one

Based on general procedure C, from adamantane-1-amine and 2-oxo-2H-chromene-6-carbaldehyde, a white solid is obtained. Data: LC/MS (ES+) m/z 310.2 [M+H]$^+$.

Example 43a/WFD119

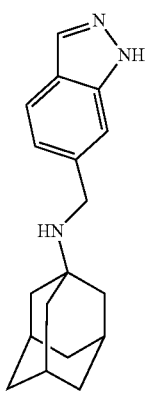 [SMILES: c1cc2cn[nH]c2cc1CNC12CC3CC(CC(C3)C1)C2]

N-((1H-indazol-6-yl)methyl)adamantan-1-amine

Based on general procedure C, from adamantane-1-amine and 1H-indazole-6-carbaldehyde, a white solid is obtained. Data: HPLC retention time: 5.5 min (70% B, Xterra RP-C18, 4.6×250 mm, 5 uM, mobile phase A: 10 mM NH4HCO3 buffer pH=9, mobile phase B: CH3CN, flow rate: 1.0 ml/min, 254 nm) LC/MS (ES+) m/z 282.3 [M+H]$^+$.

Example 44a/WFD008

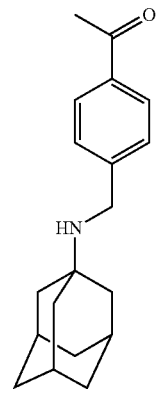 [SMILES: CC(=O)c1ccc(CNC23CC4CC(CC(C4)C2)C3)cc1]

1-(4-(adamantan-1-ylamino)methyl)phenyl)ethanone
Synthesis of ester precursor

Based on general procedure C, from adamantane-1-amine and methyl 4-formylbenzoate, methyl 4-(((3s,5s,7s)-adamantan-1-ylamino)methyl)benzoate (white solid, 60%) is obtained. Data: LC/MS (ES+) m/z 300.3 [M+H]$^+$.

Ketone Synthesis from the Ester Precursor

To a solution of methyl 4-formylbenzoate, methyl 4-(((3s,5s,7s)-adamantan-1-ylamino)methyl)benzoate (1 eq) in toluene was added N,N'-dimethylethylenediamine (DMEDA, 78.7 mg, 1.1 eq) and trimethylaluminum (12 eq, 2 M in toluene) dropwise under argon at room temperature. After the mixture was refluxed for 1 hour, it was quenched with water, and the products were extracted with ethyl acetate. The combined organic layers were washed with brine, and dried over Na$_2$SO$_4$. The filtered solvents were concentrated in vacuo, and the residue was purified by prep HPLC. Data: LC/MS (ES+) m/z 284.3 [M+H]$^+$

Example 45a/WFD014

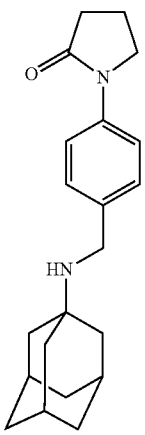 [SMILES: O=C1CCCN1c1ccc(CNC23CC4CC(CC(C4)C2)C3)cc1]

1-(4-((adamantan-1-ylamino)methyl)phenyl)pyrrolidin-2-one

Based on general procedure C, from adamantane-1-amine and 4-(2-oxopyrrolidin-1-yl)benzaldehyde, a white solid is obtained. Data: LC/MS (ES+) m/z 325.4 [M+H]$^+$.

Example 46a/BC090

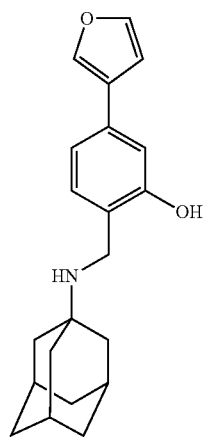 [SMILES: Oc1cc(-c2ccoc2)ccc1CNC12CC3CC(CC(C3)C1)C2]

The preparation of 2-(((-adamantan-1-ylamino)methyl)-5-(furan-3-yl)phenol (BC090)

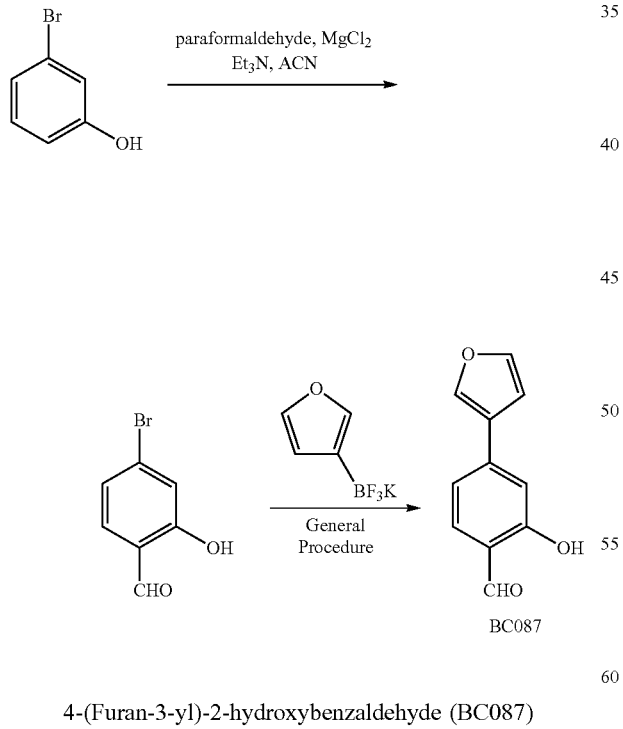

4-(Furan-3-yl)-2-hydroxybenzaldehyde (BC087)

A mixture of 2-bromophenol (58 mmol), anhydrous magnesium dichloride (87 mmol), and triethylamine (218 mmol) in acetonitrile (130 mL) was stirred at rt under N$_2$. Dry (P$_2$O$_5$) paraformaldehyde (235 mmol) was added to the mixture dropwise and after the addition was complete, the mixture was refluxed for 72 h. Then the mixture was acidified with 5% HCl and extracted with Et$_2$O (×3). The ethereal solution was washed with H$_2$O (×2) and brine and then dried over MgSO4, filtered, and concentrated in vacuo. The crude product was purified by column chromatography (0-10% ethyl acetate/hexane) to give 4-bromo-2-hydroxybenzaldehyde as an off-white solid in 42% yield. 4-(Furan-3-yl)-2-hydroxybenzaldehyde (BC087) was prepared based on general procedure 2, from 4-bromo-2-hydroxybenzaldehyde (M2WJ325) and furan-2yltrifluoroborate, a yellow solid in 86% yield (eluent 0-10% EtOAc/hexane).

2-(((-Adamantan-1-ylamino)methyl)-5-(furan-3-yl)phenol (BC090)

Based on general procedure C, from adamantan-1-amine and 4-(furan-3-yl)-2-hydroxybenzaldehyde (BC087), a light brown solid was obtained. Data: LC/MS (ESCi) m/z 324.22 [M+H]$^+$.

Example 47a/IMX00661

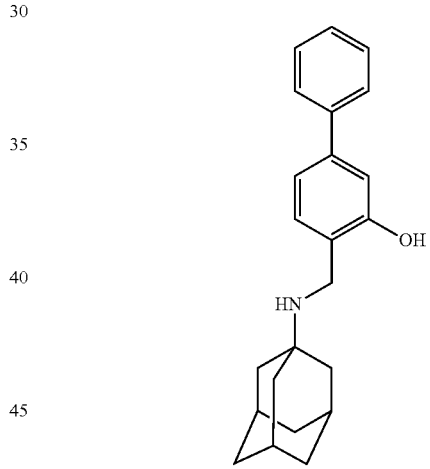

4-(Adamantan-1-ylaminomethyl)-biphenyl-3-ol

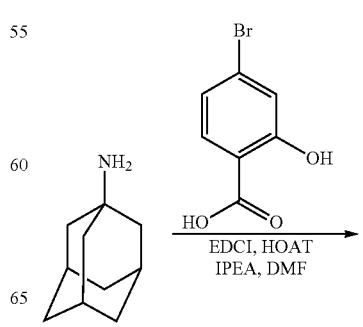

-continued

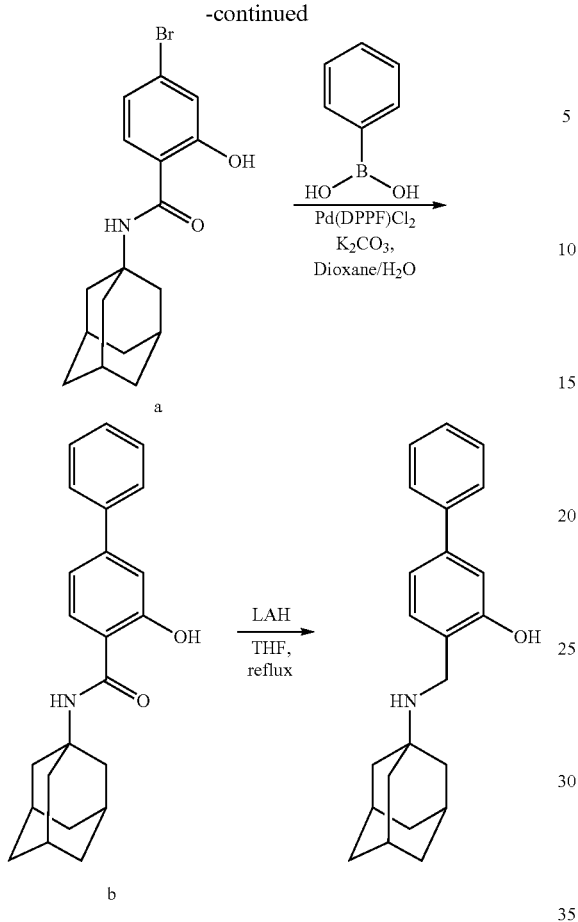

Acid (532 mg, 2 mmol) was added to a solution of HOAT (408 mg, 3 mmol) and EDCI (570 mg, 3 mmol) in anhydrous DMF (10 mL) and stirring was continued for 1 h. Then, amine (5 mL) was added and the reaction mixture was stirred at room temperature overnight. After the solvent was removed under reduced pressure, the residue was purified by flash column chromatography (1-10% CH$_3$OH/CH$_2$Cl$_2$) to give the tile amid 3 (558 mg, 80%). Data: LC/MS (ESR) m/z 350 [M+H]$^+$.

A mixture of 3 (347 mg), phenylboronic acid (144 mg, 1.2 mmol), K2CO3 (278 mg, 2.0 mmol), and Pd(dppf)Cl2 (73 mg, 10% mol) in dioxane/H$_2$O (v/v 5 mL:1 mL) was heated at 80° C. under inert environment for 2 h. The solution was evaporated to dryness and purified by flash column chromatography (1-10% CH$_3$OH/CH$_2$Cl$_2$) to give the title compound (173 mg, 50%). Data: LC/MS (ESR) m/z 348 [M+H]$^+$.

To a solution of above amide (170 mg, 0.48 mmol) in anhydrous THF (5 mL) was added dropwise of LiAlH$_4$ solution (2.0 M in THF, 1 mL) at 0° C. The resulting solution was stirred for 10 h at reflux. The solution was then cooled to 0° C. and quenched by H$_2$O/1N NaOH/H$_2$O protocol (76 uL H$_2$O, 152 uL 1N NaOH, 228 uL H$_2$O). After the mixture was stirred for 1 h, the solid was removed by filtration. The resulting solution was evaporated to dryness and purified by flash column chromatography (1-10% CH$_3$OH/CH$_2$Cl$_2$) to give 4-(Adamantan-1-ylaminomethyl)-biphenyl-3-ol (73 mg, 46%) as white solid. Data: LC/MS (ESR) m/z 334 [M+H]$^+$.

Example 48a/IMX00660

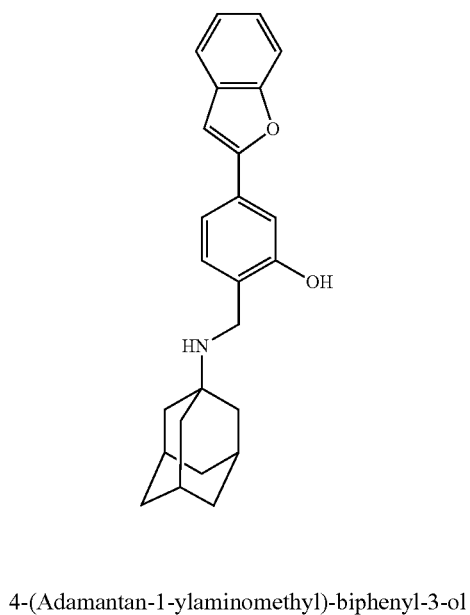

4-(Adamantan-1-ylaminomethyl)-biphenyl-3-ol

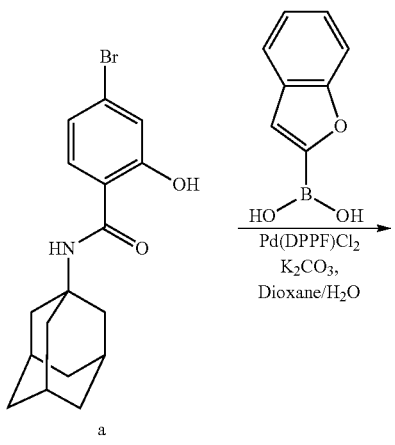

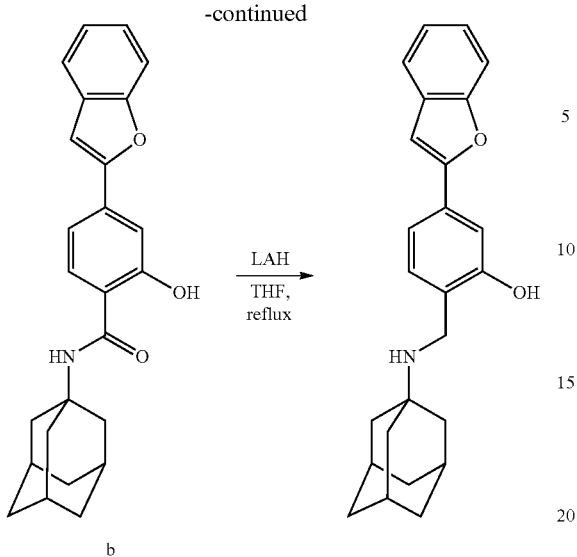

Follow the same procedure as example 47. Data: LC/MS (ESR) m/z 374 [M+H]⁺.

Example 49a/BC073

2-(-Adamantan-1-ylamino)thiophen-2yl)-5-methyl-phenol (BC073)

Based on general procedure B, from 2-(-adamantan-1-ylamino)methyl)-5-bromophenol (M2WJ325) and furan-3yltrifluoroborate, an off white solid was obtained. Data: LC/MS (ESCi) m/z 340.08 [M+H]⁺.

Example 50a/M2WJ325

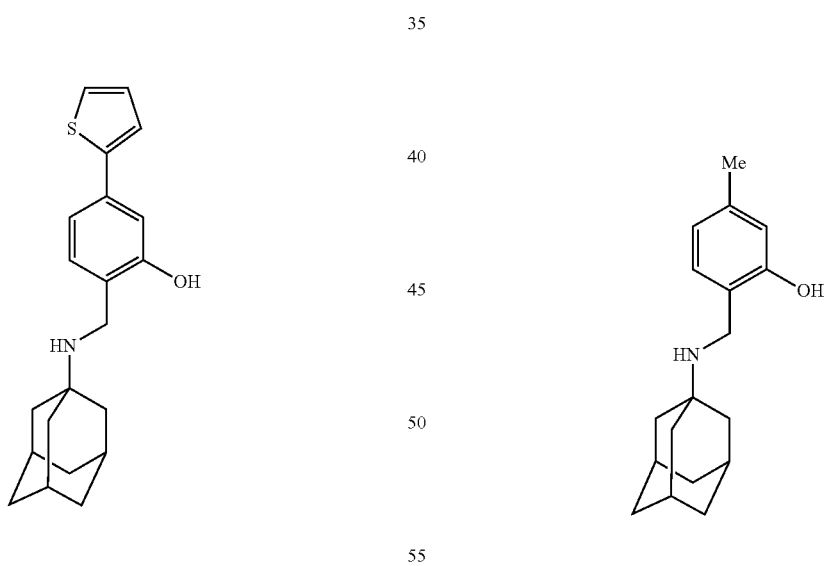

2-(((3s,5s,7s)-adamantan-1-ylamino)methyl)-5-bromophenol Based on general procedure C, from amantadine and 4-bromo-2-hydroxybenzaldehyde, a yellow solid (75%) is obtained. Data: LC/MS (ESR) m/z 337.3 [M+H]⁺.

Example 51a/BC081

Preparation of 2-(-Adamantan-1-ylamino)methyl)-5-methylphenol (BC081)

Based on general procedure F, from 2-(-adamantan-1-ylamino)methyl)-5-bromophenol (M2WJ325) and methyl-trifluoroborate, an off-white solid was obtained. Data: LC/MS (ESCi) m/z 272.23 [M+H]⁺.

Example 52a/M2WJ326

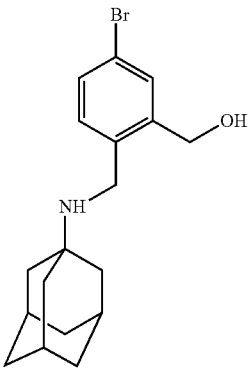 [SMILES: OCc1cc(Br)ccc1CNC12CC3CC(CC(C3)C1)C2]

[2-(Adamantan-1-ylaminomethyl)-5-bromo-phenyl]methanol

To a solution of amantadine (1.5 eq) in DCM was added dropwise a solution of Al(CH$_3$)$_3$ in hexane (1.5 eq). The mixture was stirred at r.t. for 15 mins, and then 5-bromophthalide (1 eq) was added in one portion. The mixture was then heated at 40° C. for 20 hours. After cooling to r.t., diluted HCl was added and the mixture was extracted with DCM (3×). The combined organic layers were then dried with MgSO$_4$, filtered and concentrated under reduced pressure to give the amide intermediate, which was used in the next step reduction without further purification. Amide (1 eq) was dissolved in anhydrous THF, and the solution was cooled to 0° C. using ice-bath, LiAlH$_4$ (4 eq, X gram) was added in small portions in 10 mins. The mixture was warmed to r.t. and stirred for 15 mins, then heated to reflux for 4 hours. After cooling to room temperature, H$_2$O (X ml), 15% NaOH (X ml) and H$_2$O (3× ml) were subsequently added, and the slurry was filtered. The filtrate was concentrated under reduced pressure and purified by HPLC.

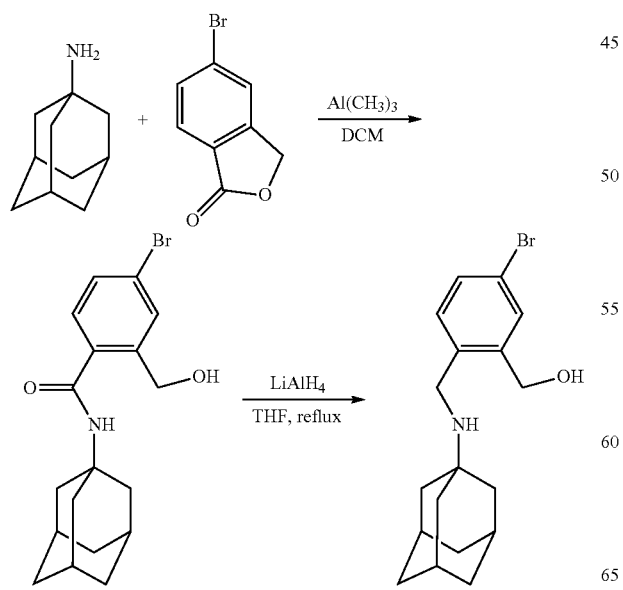

Example 53a/IMX00639

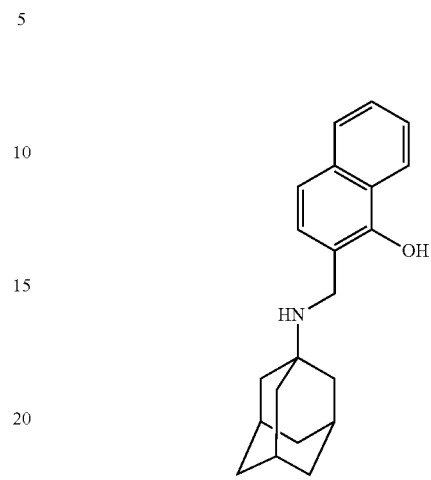

2-(Adamantan-1-ylaminomethyl)-naphthalen-1-ol

Based on general procedure A, 1-Hydroxy-naphthalene-2-carbaldehyde and Adamantan-1-ylamine, a white solid (69%) is obtained. Data: LC/MS (ESR) m/z 308 [M+H]$^+$.

Example 54a/IMX00710

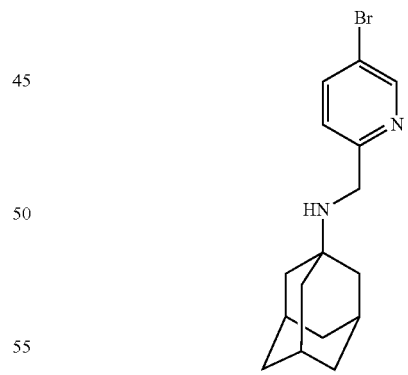

Adamantan-1-yl-(5-bromo-pyridin-2-ylmethyl)-amine

Based on general procedure A, 5-Bromo-pyridine-2-carbaldehyde and Adamantan-1-ylamine, a white solid (82%) is obtained. Data: LC/MS (ESR) m/z 322 [M+H]$^+$.

Example 55a/IMX00711

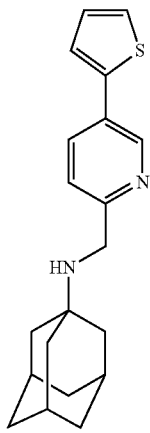

Adamantan-1-yl-(5-thiophen-2-yl-pyridin-2-ylmethyl)-amine

Based on general procedure E, from adamantan-1-yl-(5-bromo-pyridin-2-ylmethyl)-amine (IMX710) and 2-thiopheneboronic acid, Adamantan-1-yl-(5-thiophen-2-yl-pyridin-2-ylmethyl)-amine was obtained (46% two steps) as a white solid. Data: LC/MS (ESR) m/z 325 [M+H]$^+$.

Example 56a/IMX00640

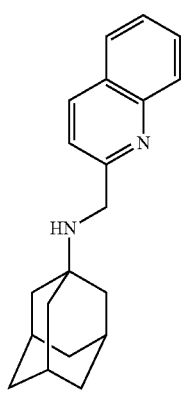 [SMILES: c1ccc2nc(CNC34CC5CC(CC(C5)C3)C4)ccc2c1]

Adamantan-1-yl-quinolin-2-ylmethyl-amine

Based on general procedure A, from Quinoline-2-carbaldehyde and Adamantan-1-ylamine, a white solid (82%) is obtained. Data: LC/MS (ESR) m/z 293 [M+H]$^+$.

Example 57a/M2WJ387

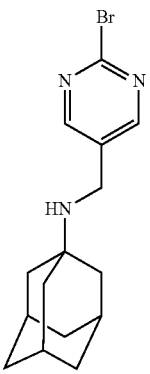 [SMILES: Brc1ncc(CNC23CC4CC(CC(C4)C2)C3)cn1]

N-((2-bromopyrimidin-5-yl)methyl)adamantan-1-amine

Based on general procedure C from amantadine and 2-bromopyrimidine-5-carbaldehyde, a brown solid (55%) is obtained. Data: LC/MS (ESR) m/z 323.2 [M+H]$^+$.

Example 58a/M2WJ383

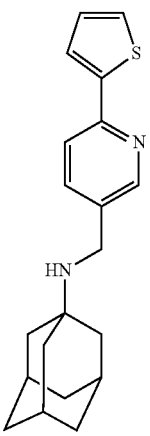 [SMILES: c1csc(-c2ccc(CNC34CC5CC(CC(C5)C3)C4)cn2)c1]

N-((6-(thiophen-2-yl)pyridin-3-yl)methyl)adamantan-1-amine

Based on general procedure C, from amantadine and 6-(thiophen-2-yl)nicotinaldehyde, a yellow solid (82%) is obtained. Data: LC/MS (ESR) m/z 325.5 [M+H]$^+$.

307

Example 59a/M2WJ385

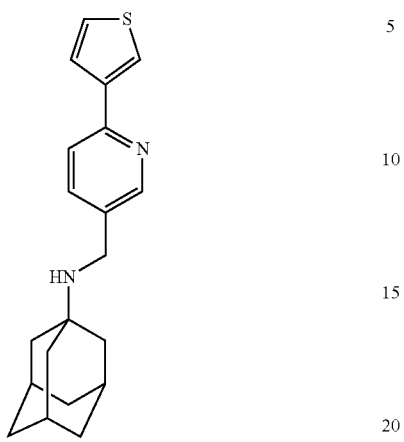

N-((6-(thiophen-3-yl)pyridin-3-yl)methyl)adamantan-1-amine

Based on general procedure C, from amantadine and 6-(thiophen-3-yl)nicotinaldehyde, a yellow solid (76%) is obtained. Data: LC/MS (ESR) m/z 325.5 [M+H]$^+$.

Example 60a/M2WJ329

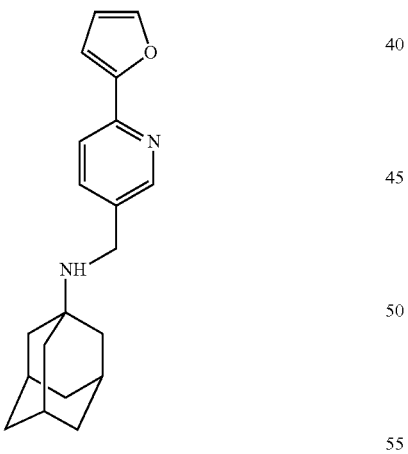

N-((6-(furan-2-yl)pyridin-3-yl)methyl)adamantan-1-amine

Based on general procedure C, from amantadine and 6-(furan-2-yl)nicotinaldehyde, a yellow solid (80%) is obtained. Data: LC/MS (ESR) m/z 309.4 [M+H]$^+$.

308

Example 61a/M2WJ330

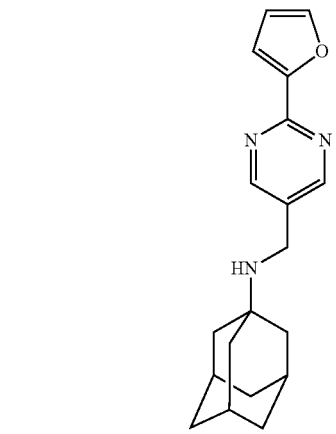

N-((2-(thiophen-2-yl)pyrimidin-5-yl)methyl)adamantan-1-amine

Based on general procedure C, from amantadine and 2-(thiophen-2-yl)pyrimidine-5-carbaldehyde, a yellow solid (81%) is obtained. Data: LC/MS (ESR) m/z 326.5 [M+H]$^+$.

Example 62a/M2WJ336

N-((2-(furan-2-yl)pyrimidin-5-yl)methyl)adamantan-1-amine

Based on general procedure C, from amantadine and 2-(furan-2-yl)pyrimidine-5-carbaldehyde, a yellow solid (72%) is obtained. Data: LC/MS (ESR) m/z 310.4 [M+H]$^+$

309
Example 63a/M2WJ391

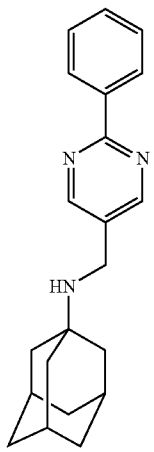

N-((2-phenylpyrimidin-5-yl)methyl)adamantan-1-amine

Based on general procedure C, from amantadine and 2-phenylpyrimidine-5-carbaldehyde, a yellow solid (85%) is obtained. Data: LC/MS (ESR) m/z 320.4 [M+H]$^+$.

Example 64a/M2WJ392

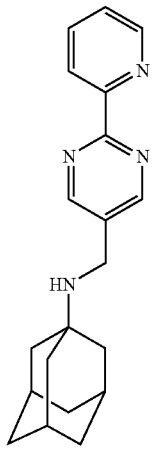

N-((2-(pyridin-2-yl)pyrimidin-5-yl)methyl)adamantan-1-amine

Based on general procedure C, from amantadine and 2-(pyridin-2-yl)pyrimidine-5-carbaldehyde, a yellow solid (71%) is obtained. Data: LC/MS (ESR) m/z 321.4 [M+H]$^+$.

310
Example 65a/M2WJ322

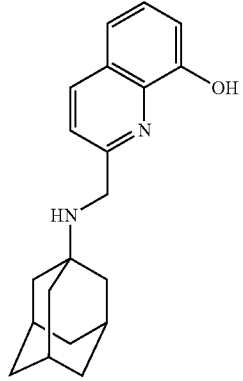 [SMILES: Oc1cccc2ccc(CNC34CC5CC(CC(C5)C3)C4)nc12]

2-((adamantan-1-ylamino)methyl)quinolin-8-ol

Based on general procedure C, from amantadine and 8-hydroxyquinoline-2-carbaldehyde, a white solid (64%) is obtained. Data: LC/MS (ESR) m/z 309.4 [M+H]$^+$.

Example 66a/IMX00616

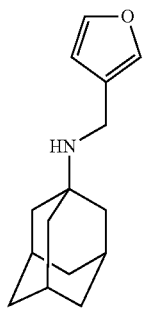

Adamantan-1-yl-furan-3-ylmethyl-amine

Based on general procedure A, From furan-3-carbaldehyde and Adamantan-1-ylamine, a white solid (82%) is obtained. Data: LC/MS (ESR) m/z 232 [M+H]$^+$.

Example 68a/IMX00617

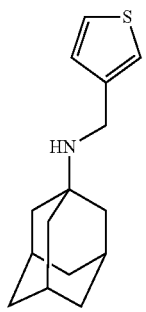

311
Adamantan-1-yl-thiophen-3-ylmethyl-amine

Based on general procedure A, from thiophene-3-carbaldehyde and adamantan-1-ylamine, a white solid (80%) is obtained. Data: LC/MS (ESR) m/z 248 [M+H]$^+$.

Example 69a/IMX00667 and WFD046

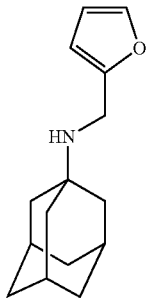 [SMILES: c1coc(CNC23CC4CC(CC(C4)C2)C3)c1]

Adamantan-1-yl-furan-2-ylmethyl-amine

Based on general procedure A, from furan-2-carbaldehyde and adamantan-1-ylamine, a white solid (80%) is obtained. Data: LC/MS (ESR) m/z 232 [M+H]$^+$.

Example 70a/IMX00668

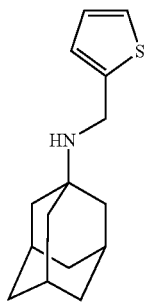 [SMILES: c1csc(CNC23CC4CC(CC(C4)C2)C3)c1]

Adamantan-1-yl-thiophen-2-ylmethyl-amine

Based on general procedure A, from thiophene-2-carbaldehyde and adamantan-1-ylamine, a white solid (80%) is obtained. Data: LC/MS (ESR) m/z 248 [M+H]$^+$.

Example 71a/WFD079 and IMX00669

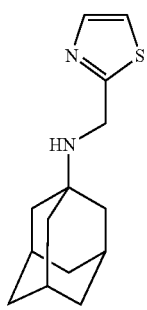 [SMILES: c1csc(CNC23CC4CC(CC(C4)C2)C3)n1]

312
Adamantan-1-yl-thiazol-2-ylmethyl-amine

Based on general procedure C, from thiazole-2-carbaldehyde and adamantan-1-ylamine, a white solid (70%) is obtained. Data: LC/MS (ESR) m/z 249 [M+H]$^+$.

Example 72a/IMX00697

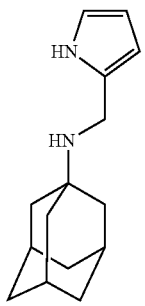 [SMILES: c1c[nH]c(CNC23CC4CC(CC(C4)C2)C3)c1]

Adamantan-1-yl-(1H-pyrrol-2-ylmethyl)-amine

Based on general procedure A, from 1H-Pyrrole-2-carbaldehyde and adamantan-1-ylamine, a white solid (70%) is obtained. Data: LC/MS (ESR) m/z 231 [M+H]$^+$.

Example 73a/M2WJ396

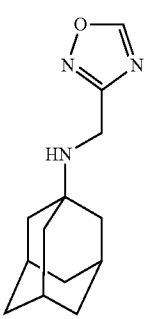

Adamantan-1-yl-[1,2,4]oxadiazol-3-ylmethyl-amine

Based on general procedure B, from amantadine and 3-(chloromethyl)-1,2,4-oxadiazole, a white solid (75%) is obtained. Data: $^1$HNMR (300 MHz, CD$_3$OD): δ 9.19 (s, 1H), 3.95 (s, 2H), 2.10-2.08 (m, 3H), 1.75-1.72 (m, 12H). EI-MS: m/z (M+H$^+$): 234.3 (calculated), 234.3 (found).

Example 74a/IMX00686

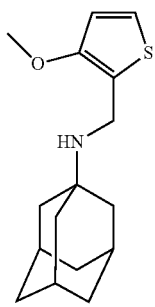 [SMILES: COc1ccsc1CNC12CC3CC(CC(C3)C1)C2]

Adamantan-1-yl-(3-methoxy-thiophen-2-ylmethyl)-amine

Based on general procedure A, from 3-methoxy-thiophene-2-carbaldehyde and adamantan-1-ylamine, a white solid (70%) is obtained. Data: LC/MS (ESR) m/z 278 [M+H]$^+$.

Example 75a/WFD050

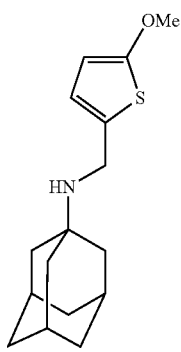 [SMILES: COc1ccc(CNC23CC4CC(CC(C4)C2)C3)s1]

N-((5-methoxythiophen-2-yl)methyl)adamantan-1-amine

Based on general procedure C, from adamantane-1-amine and 5-methoxythiophene-2-carbaldehyde, a white solid is obtained. Data: LC/MS (ES+) m/z 278.2 [M+H]$^+$.

Example 76a/WFD053

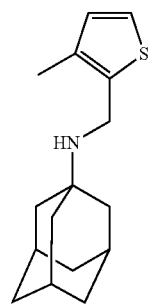 [SMILES: Cc1ccsc1CNC12CC3CC(CC(C3)C1)C2]

N-((3-methylthiophen-2-yl)methyl)adamantan-1-amine

Based on general procedure C, from adamantane-1-amine and 3-methylthiophene-2-carbaldehyde, a white solid is obtained. Data: LC/MS (ES+) m/z 262.2 [M+H]$^+$.

Example 77a/M2WJ338

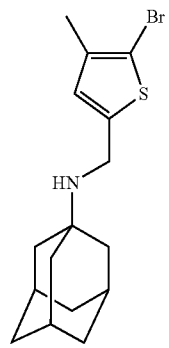 [SMILES: Cc1cc(CNC23CC4CC(CC(C4)C2)C3)sc1Br]

N-((5-bromo-4-methylthiophen-2-yl)methyl)adamantan-1-amine

Based on general procedure C, from amantadine and 5-bromo-4-methylthiophene-2-carbaldehyde, a yellow solid (65%) is obtained. Data: LC/MS (ESR) m/z 341.3 [M+H]$^+$.

Example 78a/WFD049

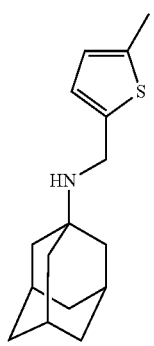

N-((5-methylthiophen-2-yl)methyl)adamantan-1-amine

Based on general procedure C, from adamantane-1-amine and 5-methylthiophene-2-carbaldehyde, a white solid is obtained. Data: LC/MS (ES+) m/z 262.1 [M+H]$^+$.

315

Example 79a/WFD052

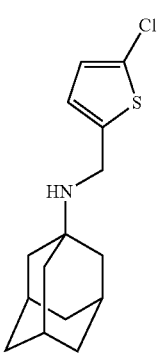 [SMILES: Clc1ccc(CNC23CC4CC(CC(C4)C2)C3)s1]

N-((5-chlorothiophen-2-yl)methyl)adamantan-1-amine

Based on general procedure C, from adamantane-1-amine and 5-chlorothiophene-2-carbaldehyde, a white solid is obtained. Data: LC/MS (ES+) m/z 282.2 [M+H]$^+$.

Example 80a/IMX00687

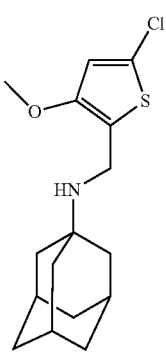 [SMILES: COc1cc(Cl)sc1CNC12CC3CC(CC(C3)C1)C2]

Adamantan-1-yl-(3-methoxy-thiophen-2-ylmethyl)-amine

Treatment of adamantan-1-yl-(3-methoxy-thiophen-2-yl-methyl)-amine (278 mg, 1.0 mmol) with NCS (150 mg, 1.2 eq) at 50° C. in DMF for 2 h. Solvent was removed under reduced pressure, the residue was purified by flash column chromatography (1-10% CH$_3$OH/CH$_2$Cl$_2$) to give the tile compound (215 mg, 66%) as a white solid. Data: LC/MS (ESR) m/z 312 [M+H]$^+$.

316

Example 81a/BC035

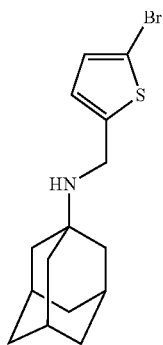

N-((5-Bromothiophen-2-yl)methyl)adamantan-1-amine

Based on general procedure A, adamantan-1-amine and 5-bromothiophene-2-carbaldehyde, a light yellow oil was obtained. Data: LC/MS (ESCi) m/z 328.00 [M+H]$^+$.

Example 82a/M2WJ341

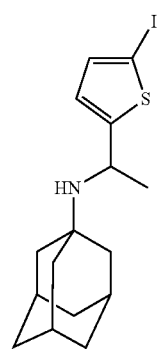 [SMILES: CC(NC12CC3CC(CC(C3)C1)C2)c1ccc(I)s1]

N-(1-(5-iodothiophen-2-yl)ethyl)adamantan-1-amine

Based on general procedure C, from amantadine and 1-(5-iodothiophen-2-yl)ethanone, a white solid (32%) is obtained. Data: LC/MS (ESR) m/z 388.3 [M+H]$^+$.

Example 83a/WFD082

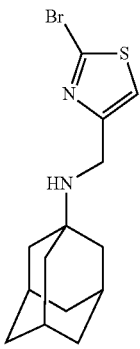 [SMILES: Brc1nc(CNC23CC4CC(CC(C4)C2)C3)cs1]

317

N-((2-bromothiazol-4-yl)methyl)adamantan-1-amine

Based on general procedure C, from adamantane-1-amine and 2-bromothiazole-4-carbaldehyde, a white solid is obtained. Data: LC/MS (ES+) m/z 327.09, 329.08 [M+H]$^+$.

Example 84a/WFD084

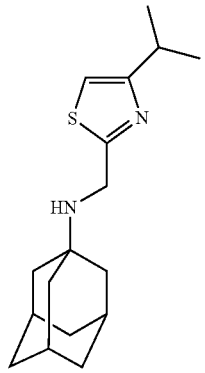 [SMILES: CC(C)c1csc(CNC23CC4CC(CC(C4)C2)C3)n1]

N-((4-isopropylthiazol-2-yl)methyl)adamantan-1-amine

Based on general procedure C, from adamantane-1-amine and 4-isopropylthiazole-2-carbaldehyde, a white solid is obtained. Data: LC/MS (ES+) m/z 291.3 [M+H]$^+$.

Example 85a/WFD073

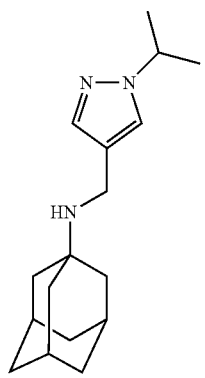 [SMILES: CC(C)n1cc(CNC23CC4CC(CC(C4)C2)C3)cn1]

N-((1-isopropyl-1H-pyrazol-4-yl)methyl)adamantan-1-amine

Based on general procedure C, from adamantane-1-amine and 1-isopropyl-1H-pyrazole-4-carbaldehyde, a white solid is obtained. Data: LC/MS (ES+) m/z 274.4 [M+H]$^+$.

318

Example 86a/IMX00671

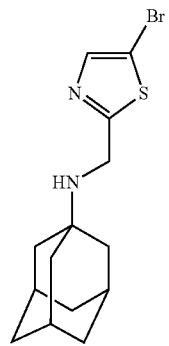 [SMILES: Brc1cnc(CNC23CC4CC(CC(C4)C2)C3)s1]

Adamantan-1-yl-(5-bromo-thiazol-2-ylmethyl)-amine

To adamantan-1-yl-thiazol-2-ylmethyl-amine (500 mg, 2.0 mmol) in THF (10 mL) at −78° C., was added nBuLi (2.5 M, 2.0 mL, 5 mmol). After 30 min, CBr$_4$ (784 mg, 2.4 mmol) was added. After stirred for 30 min at −10° C., the reaction was quenched with NH$_4$Cl (sat'd) (10 mL). The mixture was extracted with DCM (20 mL×3), and the combined organic layers was dried over Na$_2$SO$_4$ and solvent was removed under reduced pressure to give a residue, which was purified by flash column chromatography (1-10% CH$_3$OH/CH$_2$Cl$_2$) to give the tile compound (372 mg, 57%) as a white solid. Data: LC/MS (ESR) m/z 328 [M+H]$^+$.

Example 87a/IMX00688

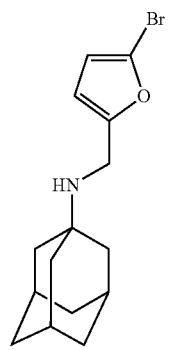

Adamantan-1-yl-(5-bromo-furan-2-ylmethyl)-amine

Based on general procedure A, 5-Bromo-furan-2-carbaldehyde and adamantan-1-ylamine, a white solid (70%) is obtained. Data: LC/MS (ESR) m/z 311 [M+H]$^+$.

Example 88a/IMX00698

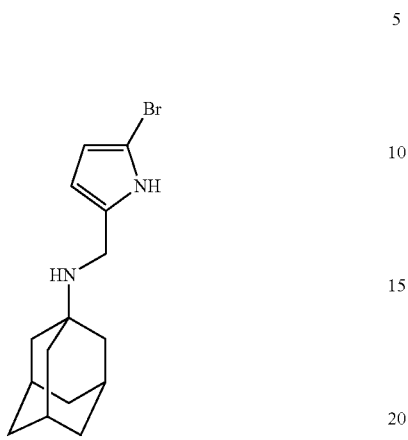

Adamantan-1-yl-(5-bromo-1H-pyrrol-2-ylmethyl)-amine

Based on general procedure A, 5-bromo-1H-pyrrole-2-carbaldehyde and adamantan-1-ylamine, a white solid (70%) is obtained. Data: LC/MS (ESR) m/z 310 [M+H]⁺.

Example 89a/IMX00701

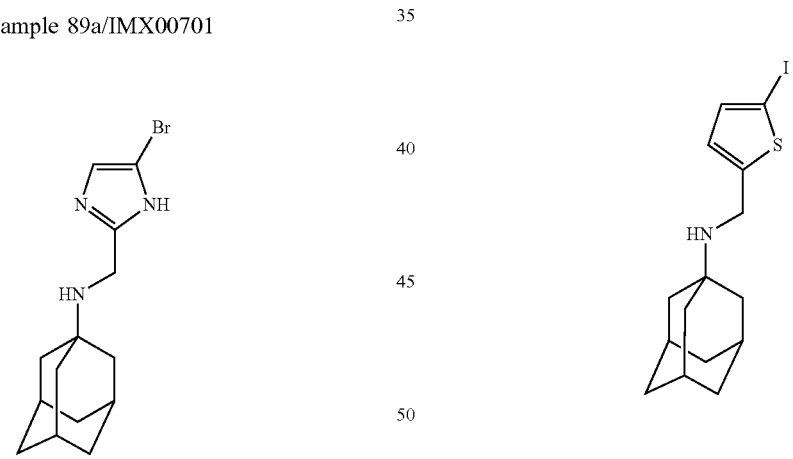

Adamantan-1-yl-(5-bromo-thiazol-2-ylmethyl)-amine

Treatment of Adamantan-1-yl-(1H-imidazol-2-ylmethyl)-amine (231 mg, 1.0 mmol) with NBS (180 mg, 1.1 eq) at 0° C. in DMF for 1 h. Solvent was removed under reduced pressure, the residue was purified by flash column chromatography (1-10% CH₃OH/CH₂Cl₂) to give the tile compound (71 mg, 23%) as a white solid. Data: LC/MS (ESR) m/z 311 [M+H]⁺.

Example 90a/M2WJP001 and IMX00689

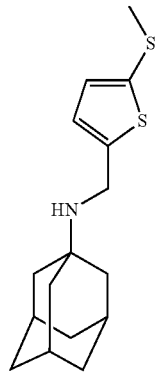 [SMILES: CSc1ccc(CNC23CC4CC(CC(C4)C2)C3)s1]

Adamantan-1-yl-(5-bromo-1H-pyrrol-2-ylmethyl)-amine

Based on general Procedure E, from 5-Methylsulfanyl-thiophene-2-carboxylic acid and adamantan-1-ylamine, a white solid (60%) is obtained. Data: LC/MS (ESR) m/z 294 [M+H]⁺.

Example 91a/BC067

N-((5-Iodothiophen-2-yl)methyl)adamantan-1-amine

A solution of N-((5-bromothiophen-2-yl)methyl)adamantan-1-amine (BC035) (1 mmol) in THF (12 mL) was added n-BuLi in hexane (2.5M 1.8 mL) at −78° C. under N₂. The reaction mixture was stirred for 30 min and then I₂ was added and stirred for 30 min at −78° C. The mixture was quenched with sodium thiosulfate, and the crude mixture was extracted with Et₂O (×3). The combined organic layers were dried over MgSO₄, filtered, and concentrated in vacuo. A light yellow solid was obtained. Data: LC/MS (ESCi) m/z 374.01 [M+H]⁺.

Example 92a/WFD058

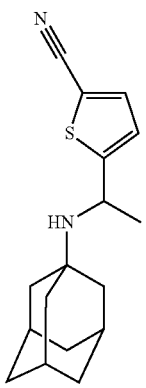 [SMILES: CC(NC12CC3CC(CC(C3)C1)C2)c1ccc(C#N)s1]

5-(1-(adamantan-1-ylamino)ethyl)thiophene-2-carbonitrile

Based on general procedure c, from adamantane-1-amine and 5-acetylthiophene-2-carbonitrile, a white solid is obtained. Data: LC/MS (ES+) m/z 287.2 [M+H]$^+$.

Example 93a/WFD085

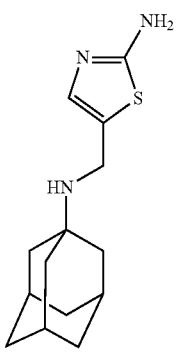 [SMILES: Nc1ncc(CNC23CC4CC(CC(C4)C2)C3)s1]

5-((adamantan-1-ylamino)methyl)thiazol-2-amine

Based on general procedure c, from adamantane-1-amine and 2-aminothiazole-5-carbaldehyde, a white solid is obtained. Data: LC/MS (ES+) m/z 264.2 [M+H]$^+$.

Example 94a/M2WJ364

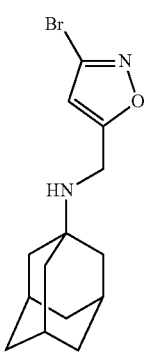

N-((3-bromoisoxazol-5-yl)methyl)adamantan-1-amine

Based on general procedure D, from amantadine and 3-bromo-5-(chloromethyl)isoxazole, a brown solid (80%) is obtained. Data: LC/MS (ESR) m/z 312.2 [M+H]$^+$.

Example 95a/M2WJ369

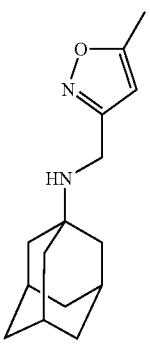

N-((5-methylisoxazol-3-yl)methyl)adamantan-1-amine

Based on general procedure C, from amantadine and 5-methylisoxazole-3-carbaldehyde, a yellow solid (83%) is obtained. Data: $^1$HNMR (300 MHz, CD$_3$OD): δ 6.19 (s, 1H), 3.77 (s, 2H), 2.40 (s, 3H), 2.09-2.07 (m, 3H), 1.73-1.69 (m, 12H). $^{13}$CNMR (75 MHz, CD$_3$OD): 171.11, 164.84, 102.39, 52.28, 42.78, 37.63, 37.08, 30.99, 11.98. EI-MS: m/z (M+H$^+$): 247.4 (calculated), 247.4 (found).

Example 96a/M2WJ405

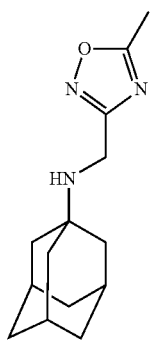 [SMILES: Cc1nc(CNC23CC4CC(CC(C4)C2)C3)no1]

N-((5-methyl-1,2,4-oxadiazol-3-yl)methyl)adamantan-1-amine

Based on general procedure D, from amantadine and 3-(chloromethyl)-5-methyl-1,2,4-oxadiazole, a white solid (77%) is obtained. Data: $^1$HNMR (300 MHz, CD$_3$OD): δ 3.85 (s, 2H), 2.58 (s, 3H), 2.10-2.08 (m, 3H), 1.76-1.66 (m, 12H). EI-MS: m/z (M+H$^+$): 248.3 (calculated), 248.4 (found).

Example 97a/WFD057

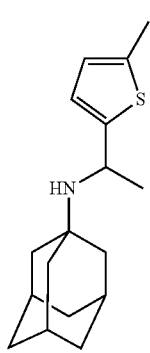

N-(1-(5-methylthiophen-2-yl)ethyl)adamantan-1-amine

Based on general procedure C, from adamantane-1-amine and 1-(5-methylthiophen-2-yl)ethanone, a white solid is obtained. Data: LC/MS (ES+) m/z 276.3 [M+H]$^+$.

Example 98a/hij-313

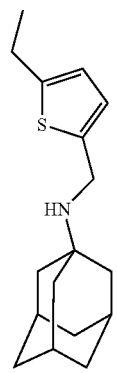 [SMILES: CCc1ccc(CNC23CC4CC(CC(C4)C2)C3)s1]

N-((5-ethylthiophen-2-yl)methyl)adamantan-1-amine

Based on general procedure C, from adamantane-1-amine and 5-ethylthiophene-2-carbaldehyde, a yellowish liquid is obtained by a silica gel column chromatography. Data: LC/MS (ES+) m/z 276.4 [M+H]$^+$.

Example 99a/WFD069

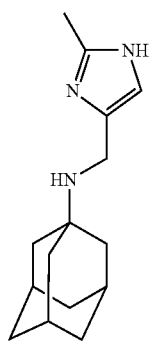 [SMILES: Cc1nc(CNC23CC4CC(CC(C4)C2)C3)c[nH]1]

N-((2-methyl-1H-imidazol-4-yl)methyl)adamantan-1-amine

Based on general procedure C, from adamantane-1-amine and 2-methyl-1H-imidazole-4-carbaldehyde, a yellowish liquid is obtained by a silica gel column chromatography. Data: LC/MS (ES+) m/z 246.3 [M+H]$^+$.

Example 100a/WFD061

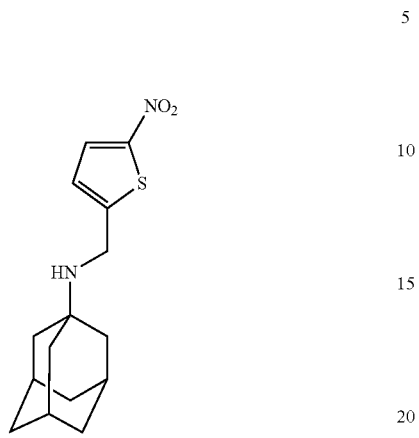

N-((5-nitrothiophen-2-yl)methyl)adamantan-1-amine

Based on general procedure C, from adamantane-1-amine and 5-nitrothiophene-2-carbaldehyde, a white solid is obtained. Data: LC/MS (ES+) m/z 293.2 [M+H]$^+$.

Example 101a/M2WJ305

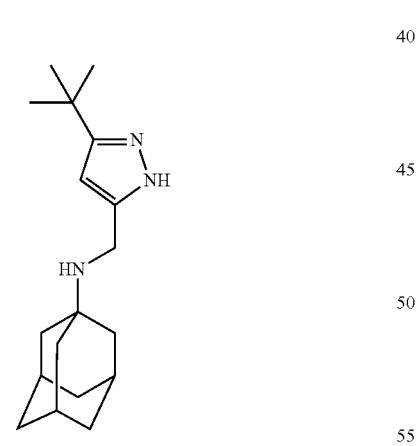

N-((3-(tert-butyl)-1H-pyrazol-5-yl)methyl)adamantan-1-amine

Based on general procedure C, from amantadine and 3-(tert-butyl)-1H-pyrazole-5-carbaldehyde, a yellow solid (80%) is obtained. Data: LC/MS (ESR) m/z 288.4 [M+H]$^+$.

Example 102a/M2WJ400

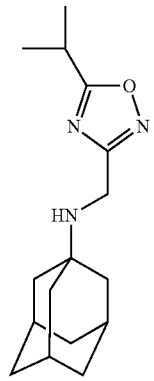 [SMILES: CC(C)c1nc(CNC23CC4CC(CC(C4)C2)C3)no1]

N-((5-isopropyl-1,2,4-oxadiazol-3-yl)methyl)adamantan-1-amine

Based on general procedure D, from amantadine and 3-(chloromethyl)-5-isopropyl-1,2,4-oxadiazole, a yellow solid (83%) is obtained. Data: $^1$HNMR (300 MHz, CD$_3$OD): δ 3.24 (q, J=6.99 Hz, 1H), 2.10-2.08 (m, 3H), 1.76-1.66 (m, 12H), 1.38 (d, J=6.99 Hz, 6H). EI-MS: m/z (M+H$^+$): 276.4 (calculated), 276.1 (found).

Example 103a/M2WJ401

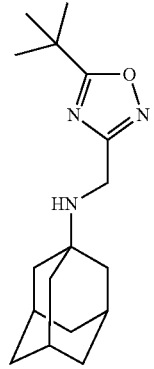 [SMILES: CC(C)(C)c1nc(CNC23CC4CC(CC(C4)C2)C3)no1]

N-((5-(tert-butyl)-1,2,4-oxadiazol-3-yl)methyl)adamantan-1-amine

Based on general procedure D, from amantadine and 5-(tert-butyl)-3-(chloromethyl)-1,2,4-oxadiazole, a white solid (79%) is obtained. Data: $^1$HNMR (300 MHz, CD$_3$OD): δ 3.86 (s, 2H), 2.10-2.08 (m, 3H), 1.76-1.66 (m, 12H), 1.47 (s, 9H). EI-MS: m/z (M+H$^+$): 290.4 (calculated), 290.2 (found).

Example 104a/M2WJ349

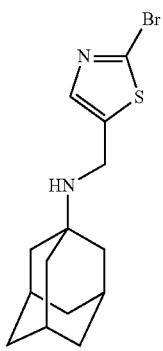

N-((2-bromothiazol-5-yl)methyl)adamantan-1-amine

Based on general procedure C, from amantadine and 2-(2-bromothiazol-5-yl)acetaldehyde, a white solid (62%) is obtained. Data: LC/MS (ESR) m/z 328.3 [M+H]$^+$.

Example 105a/M2WJ350

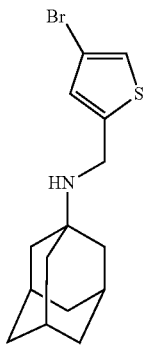 [SMILES: Brc1csc(CNC23CC4CC(CC(C4)C2)C3)c1]

N-((4-bromothiophen-2-yl)methyl)adamantan-1-amine

Based on general procedure C, from amantadine and 4-bromothiophene-2-carbaldehyde, a white solid (71%) is obtained. Data: LC/MS (ESR) m/z 327.3 [M+H]$^+$.

Example 106a/M2WJ371

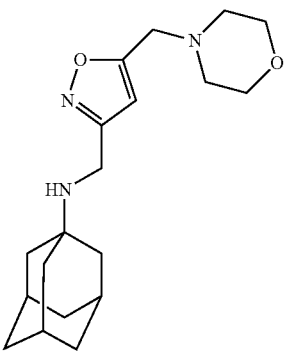 [SMILES: c1c(CNC23CC4CC(CC(C4)C2)C3)noc1CN1CCOCC1]

N-((5-(morpholinomethyl)isoxazol-3-yl)methyl)adamantan-1-amine

Based on general procedure D, from amantadine and 4-((3-(chloromethyl)isoxazol-5-yl)methyl)morpholine, a white solid (86%) is obtained. Data: $^1$HNMR (300 MHz, CD$_3$OD-d$_4$): δ 6.43 (s, 1H), 3.82 (s, 2H), 3.71 (s, 2H), 3.69 (t, J=4.68 Hz, 4H), 2.53 (t, J=4.68 Hz, 4H), 2.10-2.07 (m, 3H), 1.74-1.69 (m, 12H). EI-MS: m/z (M+H$^+$): 332.5 (calculated), 332.5 (found).

Example 107a/M2WJ379

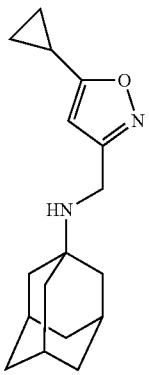

N-((5-cyclopropylisoxazol-3-yl)methyl)adamantan-1-amine

Based on general procedure D, from amantadine and 3-(chloromethyl)-5-cyclopropylisoxazole, a white solid (86%) is obtained. Data: LC/MS (ESR) m/z 273.4 [M+H]$^+$.

Example 108a/M2WJ395

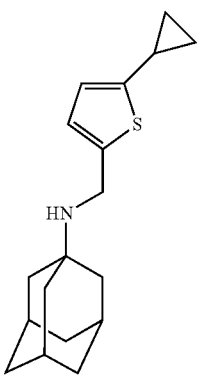 [SMILES: c1cc(C2CC2)sc1CNC12CC3CC(CC(C3)C1)C2]

N-((5-cyclopropylthiophen-2-yl)methyl)adamantan-1-amine

Based on general procedure I, a white solid (77% yield). Data: $^1$HNMR (300 MHz, CD$_3$OD): δ 7.03 (d, J=3.45 Hz, 1H), 6.75 (d, J=3.45 Hz, 1H), 4.31 (s, 2H), 2.23-2.21 (m, 3H), 2.14-2.09 (m, 1H), 1.98-1.96 (m, 6H), 1.84-1.72 (m, 6H), 1.05-1.02 (m, 2H), 0.71-0.69 (m, 2H). EI-MS: m/z (M+H⁺): 288.4 (calculated), 288.4 (found).

Example 109a/M2WJ403

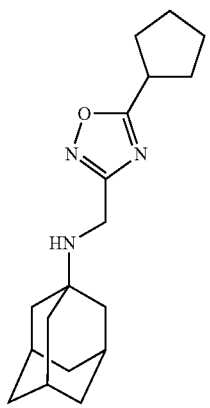

N-((5-cyclopentyl-1,2,4-oxadiazol-3-yl)methyl)adamantan-1-amine

Based on general procedure D, from amantadine and 3-(chloromethyl)-5-cyclopentyl-1,2,4-oxadiazole, a white solid (83%) is obtained. Data: ¹HNMR (300 MHz, CD₃OD): δ 3.86 (s, 2H), 3.45-3.30 (m, 1H), 2.25-2.02 (m, 5H), 1.98-1.62 (m, 18H). EI-MS: m/z (M+H⁺): 302.4

Example 110a/M2WJ358

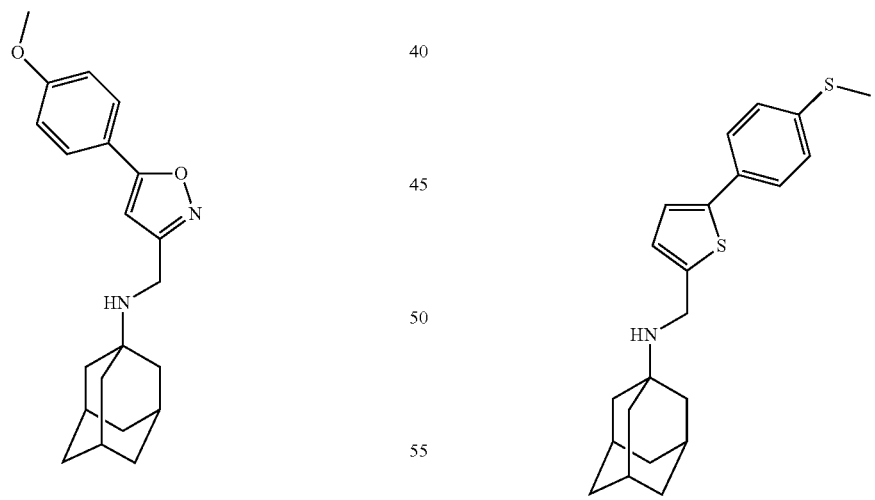

N-((5-(4-methoxyphenyl)isoxazol-3-yl)methyl)adamantan-1-amine

Based on general procedure C, from amantadine and 5-(4-methoxyphenyl)isoxazole-3-carbaldehyde, a yellow solid (75%) is obtained. Data: ¹HNMR (300 MHz, CD₃OD): δ 7.76-7.73 (m, 2H), 7.05-7.02 (m, 2H), 6.67 (s, 1H), 3.84 (s, 2H), 3.83 (s, 2H), 2.09-2.07 (m, 3H), 1.76-1.72 (m, 12H). ¹³CNMR (75 MHz, CD₃OD): 171.31, 165.34, 162.82, 128.37, 121.39, 115.54, 98.97, 55.89, 52.36, 42.80, 37.63, 37.16, 30.99. EI-MS: m/z (M+H⁺): 339.4 (calculated), 339.4 (found).

Example 111a/WFD060 and IMX00666

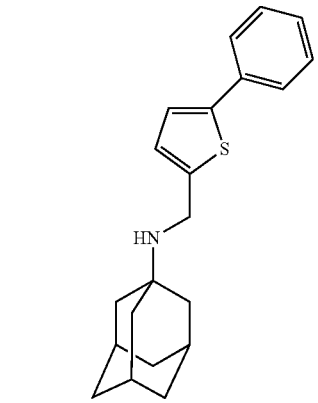 [SMILES: c1ccc(-c2ccc(CNC34CC5CC(CC(C5)C3)C4)s2)cc1]

Adamantan-1-yl-(5-bromo-thiophen-2-ylmethyl)-amine

Based on general procedure E, from Adamantan-1-yl-(5-bromo-thiophen-2-ylmethyl)-amine and pheneboronic acid, adamantan-1-yl-(5-bromo-thiophen-2-ylmethyl)-amine was obtained (66% two steps) as a white solid. Data: LC/MS (ESR) m/z 325 [M+H]⁺.

Example 112a/M2WJ343

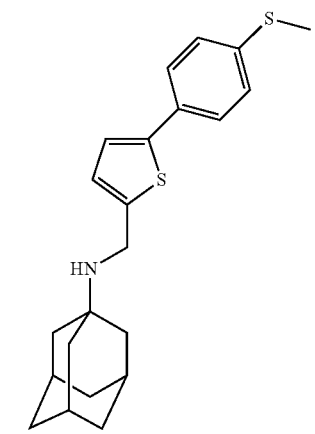

N-((5-(4-(methylthio)phenyl)thiophen-2-yl)methyl) adamantan-1-amine

Based on general procedure C, from amantadine and 5-(4-(methylthio)phenyl)thiophene-2-carbaldehyde, a white solid (72%) is obtained. Data: LC/MS (ESR) m/z 370.6 [M+H]

Example 113a/M2WJ344

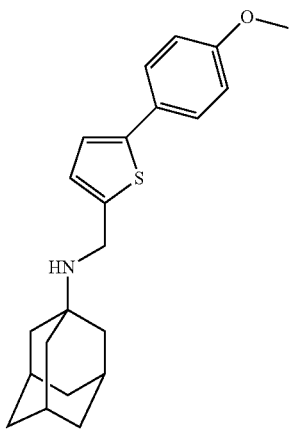

N-((5-(4-methoxyphenyl)thiophen-2-yl)methyl)adamantan-1-amine

Based on general procedure C, from amantadine and 5-(4-methoxyphenyl)thiophene-2-carbaldehyde, a white solid (71%) is obtained. Data: LC/MS (ESR) m/z 354.5 [M+H]$^+$.

Example 114a/WFD070

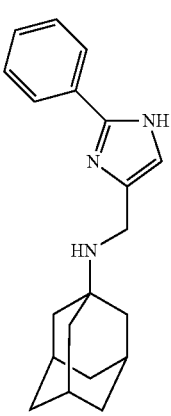 [SMILES: c1ccc(-c2nc(CNC34CC5CC(CC(C5)C3)C4)c[nH]2)cc1]

N-((2-phenyl-1H-imidazol-4-yl)methyl)adamantan-1-amine

Based on general procedure C, from adamantane-1-amine and 2-phenyl-1H-imidazole-4-carbaldehyde, a white solid is obtained. Data: LC/MS (ES+) m/z 308.3 [M+H]$^+$.

Example 115a/M2WJ351

N-((5-phenyl-1,3,4-oxadiazol-2-yl)methyl)adamantan-1-amine

Based on general procedure D, from amantadine and 2-(chloromethyl)-5-phenyl-1,3,4-oxadiazole, a yellow solid (78%) is obtained. Data: LC/MS (ESR) m/z 310.4 [M+H]$^+$.

Example 116a/M2WJ352

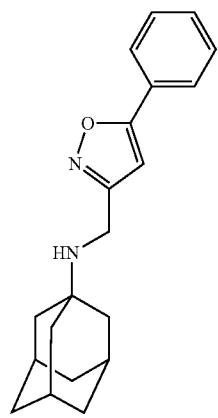 [SMILES: c1ccc(-c2cc(CNC34CC5CC(CC(C5)C3)C4)no2)cc1]

N-((5-phenylisoxazol-3-yl)methyl)adamantan-1-amine

Based on general procedure C, from amantadine and 5-phenylisoxazole-3-carbaldehyde, a white solid (89%) is obtained. Data: $^1$HNMR (300 MHz, DMSO-d$_6$): δ 7.90-7.87 (m, 2H), 7.56-7.53 (m, 3H), 7.02 (s, 1H), 3.80 (s, 2H), 2.07-2.05 (m, 3H), 1.66-1.64 (m, 12H). EI-MS: m/z (M+H$^+$): 309.4 (calculated), 309.3 (found).

Example 117a/M2WJ361

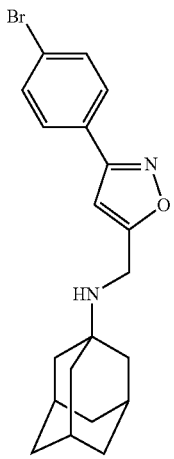

N-((3-(4-bromophenyl)isoxazol-5-yl)methyl)adamantan-1-amine

Based on general procedure C, from amantadine and 3-(4-bromophenyl)isoxazole-5-carbaldehyde, a brown solid (72%) is obtained. Data: $^1$HNMR (300 MHz, CD$_3$OD): δ 7.77-7.73 (m, 2H), 7.66-7.63 (m, 2H), 3.94 (s, 2H), 2.10-2.08 (m, 3H), 1.75-1.70 (m, 12H). EI-MS: m/z (M+H$^+$): 388.3 (calculated), 388.3 (found).

Example 118a/M2WJ366

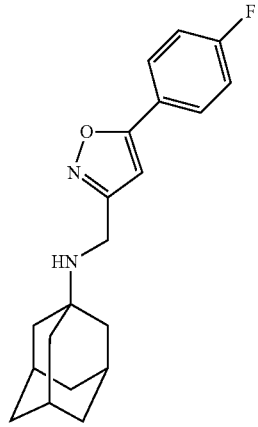 [SMILES: Fc1ccc(-c2cc(CNC34CC5CC(CC(C5)C3)C4)no2)cc1]

N-((5-(4-fluorophenyl)isoxazol-3-yl)methyl)adamantan-1-amine

Based on general procedure C, from amantadine and 5-(4-fluorophenyl)isoxazole-3-carbaldehyde, a yellow solid (69%) is obtained. Data: $^1$HNMR (300 MHz, DMSO-d$_6$): δ 7.92 (dd, J=8.21 Hz, 6.27 Hz, 2H), 7.36 (dd, J=5.79 Hz, 2.73 Hz, 2H), 6.97 (s, 1H), 3.75 (s, 2H), 2.02-2.00 (m, 3H), 1.63-1.61 (m, 12H). EI-MS: m/z (M+H$^+$): 327.4 (calculated), 327.2 (found).

Example 119a/M2WJ367

N-((5-(4-chlorophenyl)isoxazol-3-yl)methyl)adamantan-1-amine

Based on general procedure C, from amantadine and 5-(4-chlorophenyl)isoxazole-3-carbaldehyde, a white solid (80%) is obtained. Data: $^1$HNMR (300 MHz, CD$_3$OD): δ 7.82-7.78 (m, 2H), 7.53-7.49 (m, 2H), 6.84 (s, 1H), 3.86 (s, 2H), 2.10-2.08 (m, 3H), 1.75-1.71 (m, 12H). $^{13}$CNMR (75 MHz, CD$_3$OD): 169.98, 165.58, 137.26, 130.43, 128.25, 127.40, 100.97, 52.37, 42.82, 37.62, 37.15, 30.99. EI-MS: m/z (M+H$^+$): 343.9 (calculated), 343.4 (found).

Example 120a/M2WJ368

N-((5-(p-tolyl)isoxazol-3-yl)methyl)adamantan-1-amine

Based on general procedure C, from amantadine and 5-(p-tolyl)isoxazole-3-carbaldehyde, a yellow solid (88%) is obtained. Data: $^1$HNMR (300 MHz, DMSO-d$_6$): δ 7.73 (d, J=8.1 Hz, 2H), 7.33 (d, J=8.1 Hz, 2H), 6.90 (s, 1H), 3.75 (s, 2H), 2.36 (s, 3H), 2.02-2.00 (m, 3H), 1.63-1.60 (m, 12H). EI-MS: m/z (M+H$^+$): 323.4 (calculated), 323.4 (found).

Example 121a/M2WJ370

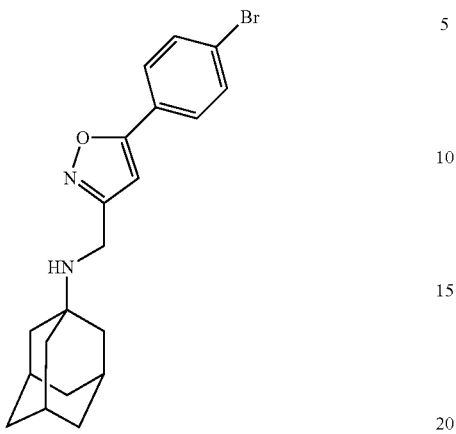

N-((5-(4-bromophenyl)isoxazol-3-yl)methyl)ada-
mantan-1-amine

Based on general procedure C, from amantadine and 5-(4-bromophenyl)isoxazole-3-carbaldehyde, a yellow solid (69%) is obtained. Data: $^1$HNMR (300 MHz, CD$_3$OD): δ 7.76-7.66 (m, 4H), 6.86 (s, 1H), 3.87 (s, 2H), 2.10-2.08 (m, 2H), 1.77-1.73 (m, 12H). EI-MS: m/z (M+H$^+$): 388 (calculated), 388.1 (found).

Example 122a/M2WJ386

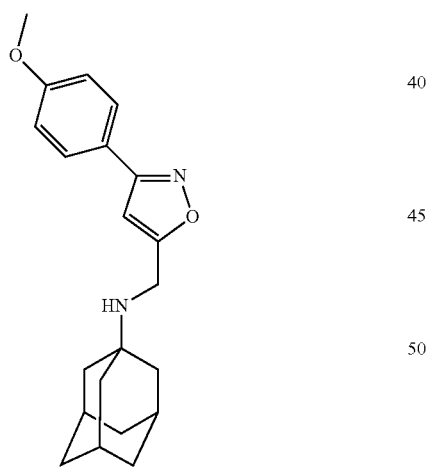

N-((3-(4-methoxyphenyl)isoxazol-5-yl)methyl)ada-
mantan-1-amine

Based on general procedure D, from amantadine and 5-(chloromethyl)-3-(4-methoxyphenyl)isoxazole, a white solid (80%) is obtained. Data: $^1$HNMR (300 MHz, DMSO-d$_6$): δ 7.78 (d, J=8.73 Hz, 2H), 7.06 (d, J=8.73 Hz, 2H), 6.82 (s, 1H), 3.81 (s, 3H), 3.73 (s, 2H), 2.10-2.08 (m, 3H), 1.64-1.60 (m, 12H). EI-MS: m/z (M+H$^+$): 339.4 (calculated), 339.2 (found).

Example 123a/M2WJ376

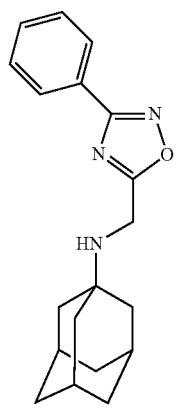 [SMILES: c1ccc(-c2noc(CNC34CC5CC(CC(C5)C3)C4)n2)cc1]

N-((3-phenyl-1,2,4-oxadiazol-5-yl)methyl)adaman-
tan-1-amine

Based on general procedure D, from amantadine and 5-(chloromethyl)-3-phenyl-1,2,4-oxadiazole, a white solid (74%) is obtained. Data: $^1$HNMR (300 MHz, DMSO-d$_6$): δ 8.02-7.99 (m, 2H), 7.58-7.56 (m, 3H), 4.06 (s, 2H), 2.02-2.00 (m, 3H), 1.62-1.55 (m, 12H). EI-MS: m/z (M+H$^+$): 310.4 (calculated), 310.6 (found).

Example 124a/M2WJ377

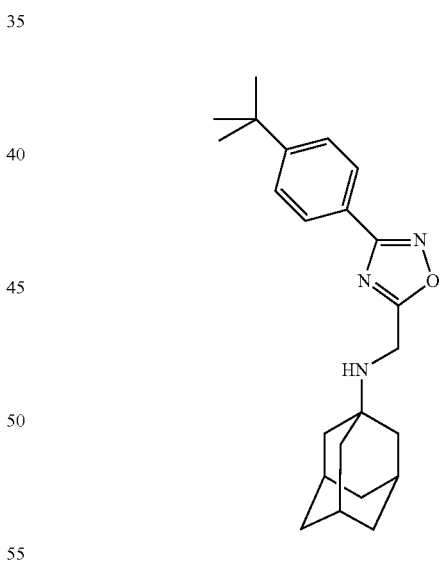

N-((3-(4-(tert-butyl)phenyl)-1,2,4-oxadiazol-5-yl)
methyl)adamantan-1-amine

Based on general procedure D, from amantadine and 3-(4-(tert-butyl)phenyl)-5-(chloromethyl)-1,2,4-oxadiazole, a white solid (89%) is obtained. Data: $^1$HNMR (300 MHz, DMSO-d$_6$): δ 7.92 (d, J=8.43 Hz, 2H), 7.57 (d, J=8.43 Hz, 2H), 4.05 (s, 2H), 2.02-2.00 (m, 3H), 1.59-1.52 (m, 12H), 1.31 (s, 9H). EI-MS: m/z (M+H$^+$): 366.5 (calculated), 366.3 (found).

Example 125a/M2WJ398

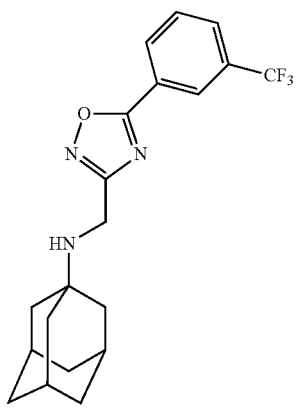 [SMILES: FC(F)(F)c1cccc(-c2nc(CNC34CC5CC(CC(C5)C3)C4)no2)c1]

N-((5-(3-(trifluoromethyl)phenyl)-1,2,4-oxadiazol-3-yl)methyl)adamantan-1-amine

Based on general procedure D, from amantadine and 3-(chloromethyl)-5-(3-(trifluoromethyl)phenyl)-1,2,4-oxadiazole, a yellow solid (91%) is obtained. Data: $^1$HNMR (300 MHz, CD$_3$OD): δ 8.43-8.40 (m, 2H), 8.00-7.97 (m, 1H), 7.86-7.80 (m, 1H), 3.99 (s, 2H), 2.11-2.08 (m, 3H), 1.79-1.72 (m, 12H). EI-MS: m/z (M+H$^+$): 378.4 (calculated), 378.4 (found).

Example 126a/M2WJ378

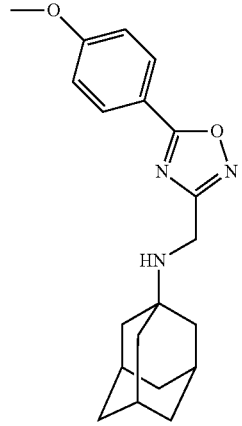

N-((5-(4-methoxyphenyl)-1,2,4-oxadiazol-3-yl)methyl)adamantan-1-amine

Based on general procedure D, from amantadine and 3-(chloromethyl)-5-(4-methoxyphenyl)-1,2,4-oxadiazole, a yellow solid (88%) is obtained. Data: $^1$HNMR (300 MHz, DMSO-d$_6$): δ 8.03 (d, J=8.82 Hz, 2H), 7.15 (d, J=8.82 Hz, 2H), 3.86 (s, 3H), 3.83 (s, 2H), 2.11-2.08 (m, 3H), 1.65-1.58 (m, 12H). EI-MS: m/z (M+H$^+$): 340.4 (calculated), 340.4 (found).

Example 127a/M2WJ356

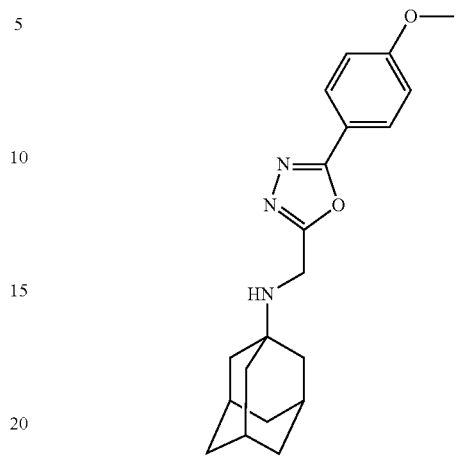

N-((5-(4-methoxyphenyl)-1,3,4-oxadiazol-2-yl)methyl)adamantan-1-amine

Based on general procedure D, from amantadine and 2-(chloromethyl)-5-(4-methoxyphenyl)-1,3,4-oxadiazole, a white solid (71%) is obtained. Data: LC/MS (ESR) m/z 340.4 [M+H]$^+$.

Example 128a/M2WJ393

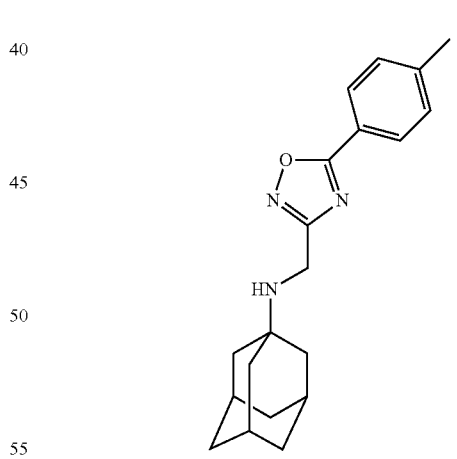

N-((5-(p-tolyl)-1,2,4-oxadiazol-3-yl)methyl)adamantan-1-amine

Based on general procedure D, from amantadine and 3-(chloromethyl)-5-(p-tolyl)-1,2,4-oxadiazole, a white solid (75%) is obtained. Data: $^1$HNMR (300 MHz, CD$_3$OD): δ 8.03 (d, J=8.25 Hz, 2H), 7.41 (d, J=8.25 Hz, 2H), 3.94 (s, 2H), 2.45 (s, 3H), 2.11-2.09 (m, 3H), 1.77-1.70 (m, 12H). EI-MS: m/z (M+H$^+$): 324.4 (calculated), 324.3 (found).

Example 129a/M2WJ397

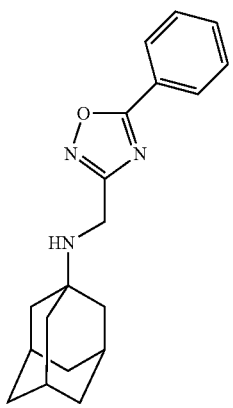

N-((5-(4-(trifluoromethyl)phenyl)-1,2,4-oxadiazol-3-yl)methyl)adamantan-1-amine

Based on general procedure D, from amantadine and 3-(chloromethyl)-5-(4-(trifluoromethyl)phenyl)-1,2,4-oxadiazole, a white solid (77%) is obtained. Data: $^1$HNMR (300 MHz, CD$_3$OD): δ 8.35 (d, J=8.55 Hz, 2H), 7.93 (d, J=8.55 Hz, 2H), 3.99 (s, 2H), 2.11-2.08 (m, 3H), 1.78-1.71 (m, 12H). EI-MS: m/z (M+H$^+$): 378.4 (calculated), 378.4 (found).

Example 130a/M2WJ398

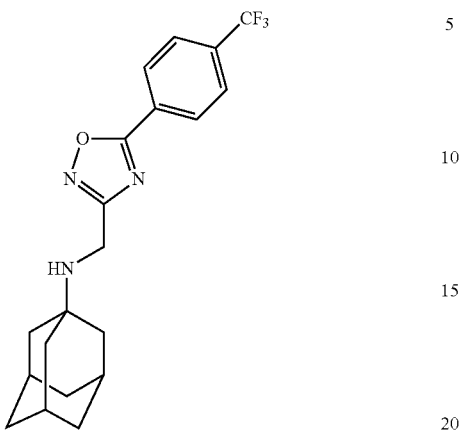

N-((5-(3-(trifluoromethyl)phenyl)-1,2,4-oxadiazol-3-yl)methyl)adamantan-1-amine

Based on general procedure B, from amantadine and 3-(chloromethyl)-5-(3-(trifluoromethyl)phenyl)-1,2,4-oxadiazole, a yellow solid (91%) is obtained. Data: $^1$HNMR (300 MHz, CD$_3$OD): δ 8.43-8.40 (m, 2H), 8.00-7.97 (m, 1H), 7.86-7.80 (m, 1H), 3.99 (s, 2H), 2.11-2.08 (m, 3H), 1.79-1.72 (m, 12H). EI-MS: m/z (M+H$^+$): 378.4 (calculated), 378.4 (found).

Example 131a/M2WJ399

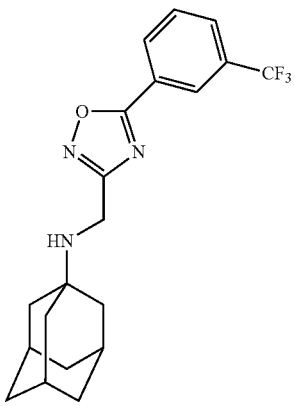 [SMILES: FC(F)(F)c1cccc(-c2nc(CNC34CC5CC(CC(C5)C3)C4)no2)c1]

N-((5-phenyl-1,2,4-oxadiazol-3-yl)methyl)adamantan-1-amine

Based on general procedure D, from amantadine and 3-(chloromethyl)-5-phenyl-1,2,4-oxadiazole, a white solid (84%) is obtained. Data: $^1$HNMR (300 MHz, CD$_3$OD): δ 8.17-8.13 (m, 2H), 7.69-7.57 (m, 3H), 3.96 (s, 2H), 2.11-2.08 (m, 3H), 1.78-1.70 (m, 12H). EI-MS: m/z (M+H$^+$): 310 (calculated), 310 (found).

Example 132a/M2WJ402

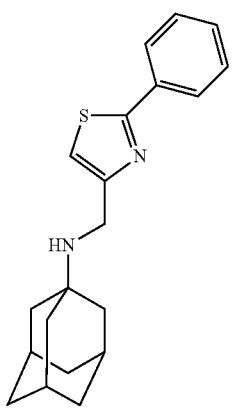

N-((2-phenylthiazol-4-yl)methyl)adamantan-1-amine

Based on general procedure D, from amantadine and 4-(chloromethyl)-2-phenylthiazole, a yellow solid (80%) is obtained. Data: LC/MS (ESR) m/z 325.5 [M+H]$^+$.

Example 133a/IMX00672

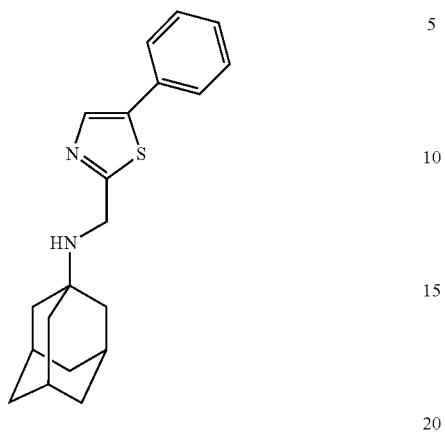

Adamantan-1-yl-(5-phenyl-thiazol-2-ylmethyl)-amine

Based on general procedure E, from adamantan-1-yl-(5-bromo-thiazol-2-ylmethyl)-amine (example 86) and phen-eboronic acid, adamantan-1-yl-(5-phenyl-thiazol-2-ylmethyl)-amine was obtained (46% two steps) as a white solid. Data: LC/MS (ESR) m/z 325 [M+H]$^+$.

Example 134a/M2WJ381

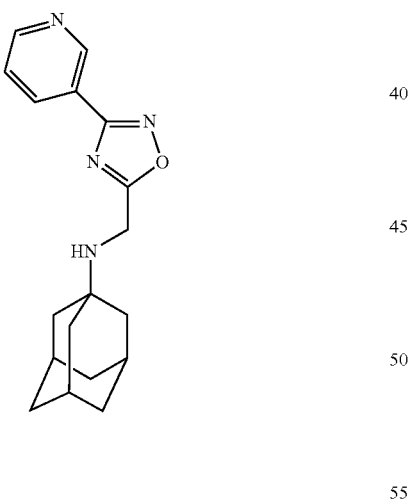

N-((3-(pyridin-3-yl)-1,2,4-oxadiazol-5-yl)methyl)adamantan-1-amine

Based on general procedure D, from amantadine and 5-(chloromethyl)-3-(pyridin-3-yl)-1,2,4-oxadiazole, a brown solid (73%) is obtained. Data: $^1$HNMR (300 MHz, DMSO-d$_6$): δ 9.18-9.16 (m, 1H), 8.79-8.77 (m, 1H), 8.38-8.36 (m, 1H), 7.64-7.62 (m, 1H), 4.09 (s, 2H), 2.07-2.04 (m, 3H), 1.62-1.55 (m, 12H). EI-MS: m/z (M+H$^+$): 311.4 (calculated), 311.5 (found).

Example 135a/M2WJ381

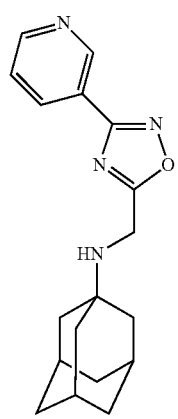 [SMILES: c1cncc(-c2noc(CNC34CC5CC(CC(C5)C3)C4)n2)c1]

Adamantan-1-yl-(3-pyridin-3-yl-[1,2,4]oxadiazol-5-ylmethyl)-amine

Example 136a/BC041

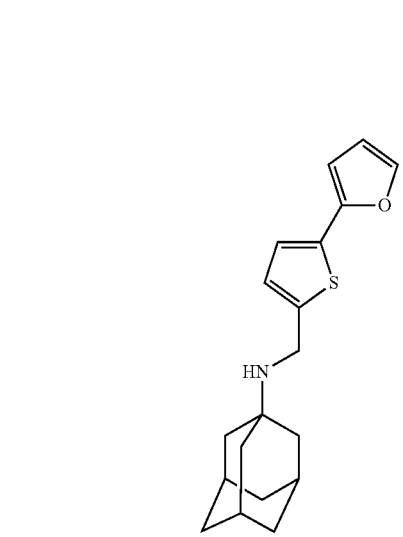 [SMILES: c1coc(-c2ccc(CNC34CC5CC(CC(C5)C3)C4)s2)c1]

N-((5-(Furan-2-yl)thiophen-2-yl)methyl)adamantan-1-amine

Based on general procedure B, from N-((5-bromothiophen-2-yl)methyl)adamantan-1-amine (BC035) and furan-2yl trifluoroborate, a light brown was obtained. Data: LC/MS (ESCi) m/z 314.02 [M+H]$^+$.

Example 137a/BC042

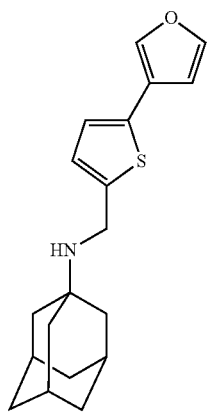 [SMILES: c1cc(-c2ccc(CNC34CC5CC(CC(C5)C3)C4)s2)co1]

N-((5-(Furan-3-yl)thiophen-2-yl)methyl)adamantan-1-amine

Based on general procedure B, from N-((5-bromothiophen-2-yl)methyl)adamantan-1-amine (BC035) and furan-3yl trifluoroborate, a light yellow solid was obtained. Data: LC/MS (ESCi) m/z 314.15 [M+H]$^+$.

Example 138a/IMX00703

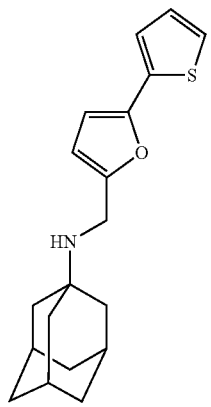 [SMILES: c1csc(-c2ccc(CNC34CC5CC(CC(C5)C3)C4)o2)c1]

Adamantan-1-yl-(5-thiophen-2-yl-furan-2-ylmethyl)-amine

Based on general procedure F, from Adamantan-1-yl-(5-bromo-furan-2-ylmethyl)-amine (example 87) and 2-thiopheneboronic, Adamantan-1-yl-(5-thiophen-2-yl-furan-2-ylmethyl)-amine was obtained (76% two steps) as a white solid. Data: LC/MS (ESR) m/z 314 [M+H]$^+$.

Example 139a/IMX00702

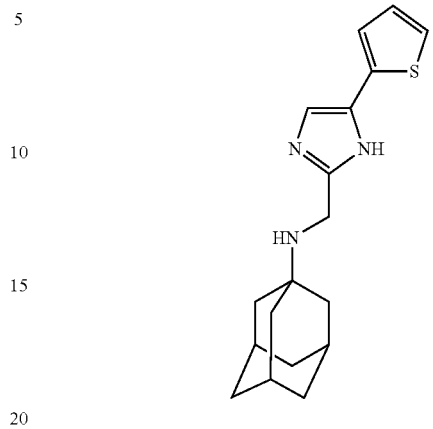

Adamantan-1-yl-(5-thiophen-2-yl-1H-imidazol-2-ylmethyl)-amine

Based on general procedure G, from Adamantan-1-yl-(5-bromo-1H-imidazol-2-ylmethyl)-amine (example 89) and 2-thiopheneboronic, adamantan-1-yl-(5-thiophen-2-yl-1H-imidazol-2-ylmethyl)-amine was obtained (76% two steps) as a white solid. Data: LC/MS (ESR) m/z 314 [M+H]$^+$.

Example 140a/M2WJ354

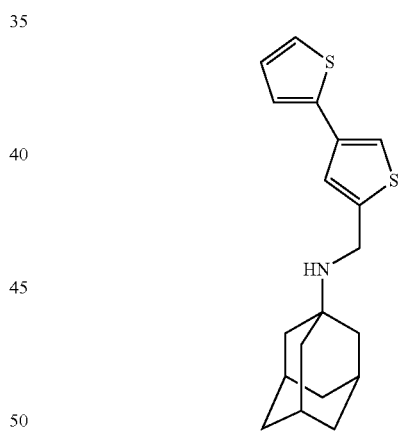

Adamantan-1-yl-[2,3']bithiophenyl-5'-ylmethyl-amine

A mixture of 4-bromothiophene-2-carbaldehyde (1 eq), thiophen-2-boronic acid (1.5 eq) and sodium carbonate (2 eq) in toluene, ethanol and water was degassed by bubbling with argon for 30 mins. Then Pd(Ph$_3$)$_4$ was added and the reaction was heated to reflux for overnight. The mixture was quenched with water, extracted with diethyl ether (3×), dried over MgSO$_4$, and concentrated to give the crude product. Flash column chromatography afforded the intermediate aldehyde as white powder. Subsequent reductive amination with amantadine following procedure A gave the final compound M2WJ354.

345

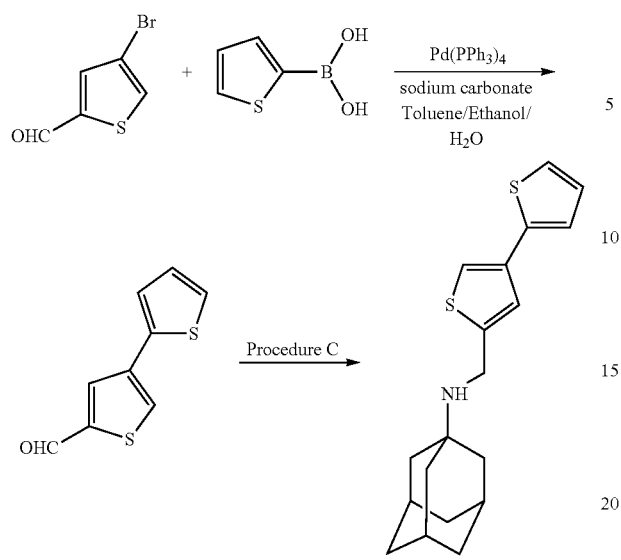

N-([2,3'-bithiophen]-5'-ylmethyl)adamantan-1-amine

White solid (65% yield). Data: ¹HNMR (300 MHz, CDCl$_3$): δ 7.51 (s, 1H), 7.46-7.44 (m, 1H), 7.35-7.34 (m, 1H), 7.25 (s, 1H), 7.10-7.07 (m, 1H), 3.92 (s, 2H), 2.07-2.03 (m, 3H), 1.68-1.62 (m, 12H). EI-MS: m/z (M+H$^+$): 330.5 (calculated), 330.5 (found).

Example 141a/M2WJ357

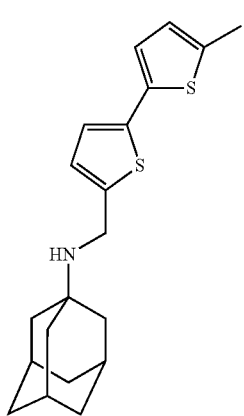 [SMILES: Cc1ccc(-c2ccc(CNC34CC5CC(CC(C5)C3)C4)s2)s1]

N-((5'-methyl-[2,2'-bithiophen]-5-yl)methyl)adamantan-1-amine

Based on general procedure C, from amantadine and 5'-methyl-[2,2'-bithiophene]-5-carbaldehyde, a yellow solid (72%) is obtained. Data: LC/MS (ESR) m/z 344.5 [M+H]$^+$.

346

Example 142a/M2WJ332

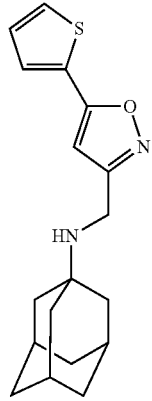

N-((5-(thiophen-2-yl)isoxazol-3-yl)methyl)adamantan-1-amine

Based on general procedure C, from amantadine and 5-(thiophen-2-yl)isoxazole-3-carbaldehyde, a yellow solid (75%) is obtained. Data: ¹HNMR (300 MHz, DMSO-d$_6$): δ 7.83 (d, J=4.59 Hz, 1H), 7.72 (d, J=4.59 Hz, 1H), 7.26 (dd, J=4.82 Hz, 3.84 Hz, 1H), 6.85 (s, 1H), 3.78 (s, 2H), 2.08-2.05 (m, 3H), 1.65-1.63 (m, 12H). EI-MS: m/z (M+H$^+$): 315.5 (calculated), 315.1 (found).

Example 143a/M2WJ359

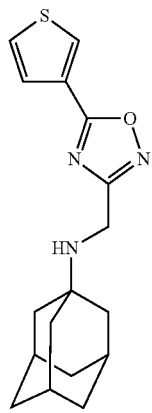

N-((5-(thiophen-3-yl)-1,2,4-oxadiazol-3-yl)methyl)adamantan-1-amine

Based on general procedure D, from amantadine and 3-(chloromethyl)-5-(thiophen-3-yl)-1,2,4-oxadiazole, a yellow solid (80%) is obtained. Data: LC/MS (ESR) m/z 316.4 [M+H]$^+$.

Example 144a/M2WJ360

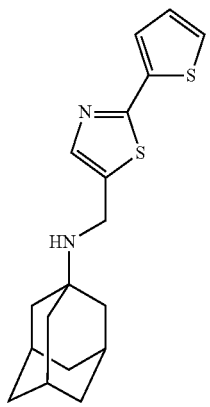 [SMILES: c1csc(-c2ncc(CNC34CC5CC(CC(C5)C3)C4)s2)c1]

N-((2-(thiophen-2-yl)thiazol-5-yl)methyl)adamantan-1-amine

Follow the procedure of example 140/M2WJ354. White solid (88% yield). Data: LC/MS (ESR) m/z 331.5 [M+H]⁺.

Example 145a/M2WJ384

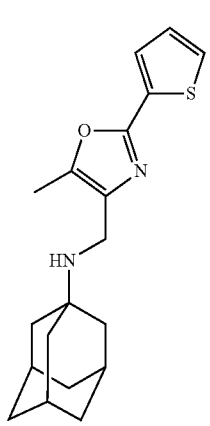 [SMILES: Cc1oc(-c2cccs2)nc1CNC12CC3CC(CC(C3)C1)C2]

N-((5-methyl-2-(thiophen-2-yl)oxazol-4-yl)methyl) adamantan-1-amine

Based on general procedure C, from amantadine and 5-methyl-2-(thiophen-2-yl)oxazole-4-carbaldehyde, a yellow solid (84%) is obtained. Data: LC/MS (ESR) m/z 329.5 [M+H]⁺.

Example 146a/M2WJ389

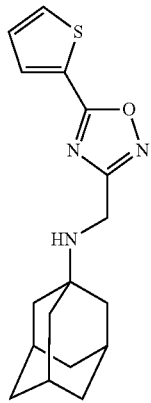

N-((5-(thiophen-2-yl)-1,2,4-oxadiazol-3-yl)methyl) adamantan-1-amine

Based on general procedure D, from amantadine and 3-(chloromethyl)-5-(thiophen-2-yl)-1,2,4-oxadiazole, a yellow solid (77%) is obtained. Data: $^1$HNMR (300 MHz, CD$_3$OD): δ 7.96 (dd, J=3.81 Hz, 1.17 Hz, 1H), 7.88 (dd, J=5.01 Hz, 1.14 Hz, 1H), 7.28 (dd, J=5.04 Hz, 3.84 Hz, 1H), 3.93 (s, 2H), 2.10-2.08 (m, 3H), 1.76-1.68 (m, 12H). EI-MS: m/z (M+H⁺): 316.4 (calculated), 316.2 (found).

Example 147a/M2WJ390

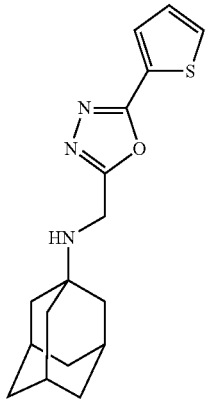

Adamantan-1-yl-(5-thiophen-2-yl-[1,3,4]oxadiazol-2-ylmethyl)-amine

General Procedure:

2-thiophenecarboxylic acid hydrazide (1 eq) and Et$_3$N (2 eq) were dissolved in CH$_2$Cl$_2$ at 0° C., methyl oxalate chloride (1 eq) was added dropwise. The reaction mixture was warmed slowly to room temperature and stirred for 6 hours. TsCl (1 eq) was added and stirred overnight. The mixture was diluted with CH$_2$Cl$_2$ and was washed with water, and saturated brine. The organic layer was dried over MgSO$_4$ and the solvent was removed under reduced pressure. The crude produce was purified by flash column chromatography to give the ester intermediate I.

349

General Procedure for Reduction:

Ester (1 eq) was dissolved in methanol and cooled down to 0° C. NaBH₄ (4 eq) was added in small portions to the solution over 10 mins. The mixture was warmed slowly to r.t. and stirred for 4 hours. Diluted HCl was added and the organic solvent was removed under reduced pressure. The resulting aqueous layer was extracted with ethyl acetate (3×), and the organic layers were combined, dried over MgSO₄ and the solvent was removed under reduced pressure. This alcohol intermediate II was used for the next step without further purification.

General Procedure for Brominaiton:

Alcohol (1 eq) was dissolved in anhydrous CH$_2$Cl$_2$ and cooled down to 0° C. PBr$_3$ (1 eq) was added dropwise over 5 mins. The mixture was slowly warmed to r.t. and stirred for 2 hrs. Solvent was removed under reduced pressure, and the residue was quenched with water. Ethyl acetate was added and the aqueous layer was extracted for three times. The combined organic layers were combined, dried over MgSO$_4$ and the solvent was removed under reduced pressure. Flash column chromatography gave the bromide intermediate II.

Final alkylation following procedure D gave M2WJ390.

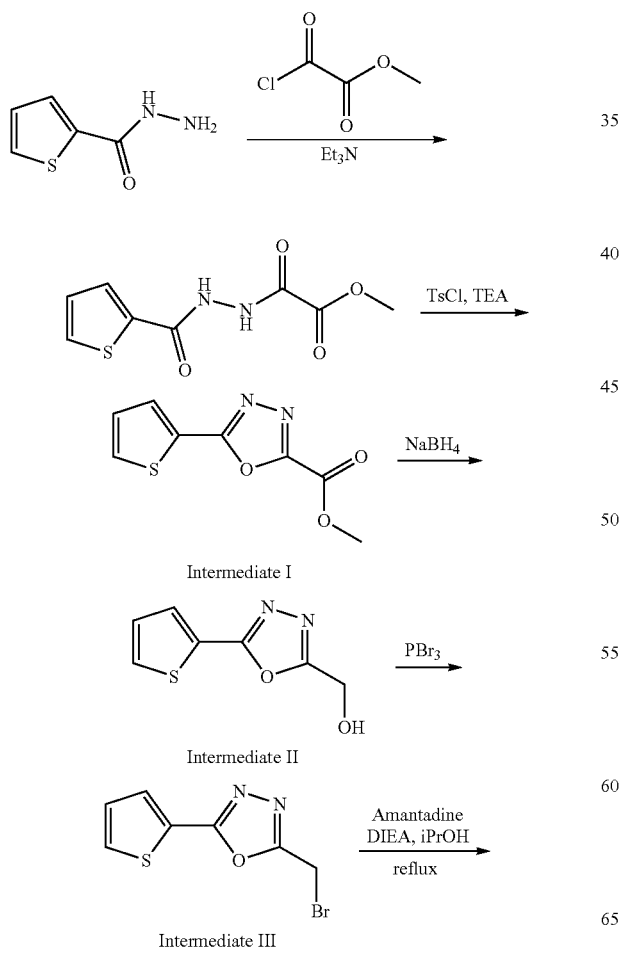

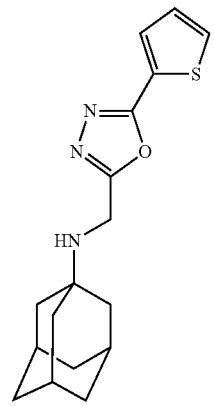 [SMILES: c1csc(-c2nnc(CNC34CC5CC(CC(C5)C3)C4)o2)c1]

M2WJ390

N-((5-(thiophen-2-yl)-1,3,4-oxadiazol-2-yl)methyl)adamantan-1-amine

White solid (35% yield). Data: ¹HNMR (300 MHz, DMSO-d6): δ 7.96-7.91 (m, 1H), 7.82-7.78 (m, 1H), 7.31-7.26 (m, 1H), 3.95 (s, 2H), 2.03-2.00 (m, 3H), 1.60-1.54 (m, 12H). EI-MS: m/z (M+H⁺): 316.4 (calculated), 316.5 (found).

Example 148a/M2WJ363

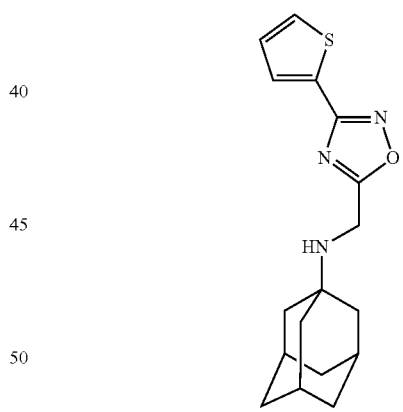

N-((3-(thiophen-2-yl)-1,2,4-oxadiazol-5-yl)methyl)adamantan-1-amine

Based on general procedure D, from amantadine and 5-(chloromethyl)-3-(thiophen-2-yl)-1,2,4-oxadiazole, a yellow solid (88%) is obtained. Data: ¹HNMR (300 MHz, DMSO-d$_6$): δ 7.90-7.86 (m, 1H), 7.82-7.78 (m, 1H), 7.27-7.24 (m, 1H), 4.03 (s, 2H), 2.02-2.00 (m, 3H), 1.59-1.50 (m, 12H). EI-MS: m/z (M+H⁺): 316.4 (calculated), 316.4 (found).

Example 149a/M2WJ372

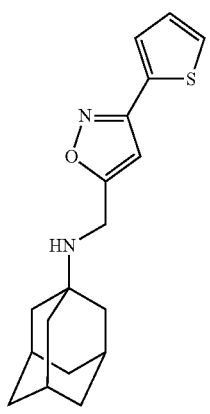 [SMILES: c1csc(-c2cc(CNC34CC5CC(CC(C5)C3)C4)on2)c1]

N-((3-(thiophen-2-yl)isoxazol-5-yl)methyl)adamantan-1-amine

Oximes were prepared according to previous published procedure. To a cooled solution (0° C. using ice bath) of oximes (1 eq), propargyl bromide/allyl bromide (1.2 eq), and triethylamine (1 eq) in CH$_2$Cl$_2$ was dropwise added 8% aqueous sodium hypochlorite. After addition, the solution was warmed to room temperature and stirred overnight. The mixture was separated, and the aqueous layer was extracted with CH$_2$Cl$_2$ twice. The organic layers were combined, dried over anhydrous magnesium sulfate, filtered and concentrated under reduced pressure. The mixture was then purified by silica gel flash column chromatography to give the intermediate isoxazole VII or isoxazoline VIII (10-40% ethyl acetate/hexane). The next step alkylation was performed according to the above general procedure as described in procedure B.

Brown solid (43% yield). Data: $^1$HNMR (300 MHz, DMSO-d6): δ 7.80-7.76 (m, 2H), 7.26-7.23 (m, 1H), 7.16 (s, 1H), 4.48 (s, 2H), 2.17-2.15 (m, 3H), 1.92-1.88 (m, 6H), 1.71-1.59 (m, 6H). EI-MS: m/z (M+H$^+$): 315.5 (calculated), 315.5 (found).

Example 150a/M2WJ374

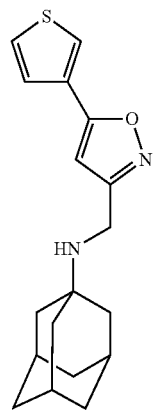

Adamantan-1-yl-(5-thiophen-3-yl-isoxazol-3-ylmethyl)-amine

EI-MS: m/z (M+H$^+$): 315

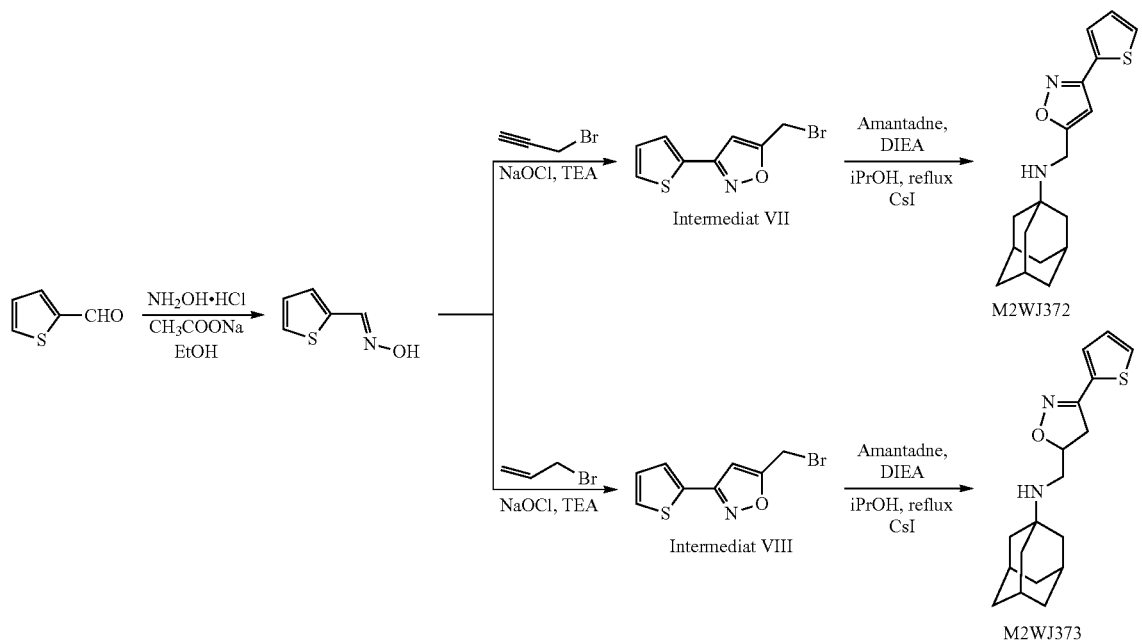

Example 151a/M2WJ375

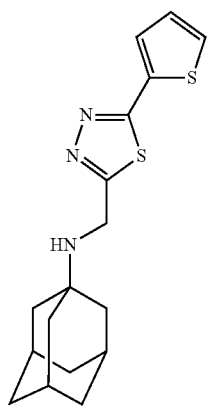 [SMILES: c1csc(-c2nnc(CNC34CC5CC(CC(C5)C3)C4)s2)c1]

N-((5-(thiophen-2-yl)-1,3,4-thiadiazol-2-yl)methyl)adamantan-1-amine

Yellow solid (22% yield). Data: ¹HNMR (300 MHz, DMSO-d6): δ 7.78-7.72 (m, 2H), 7.20-7.17 (m, 1H), 4.06 (s, 2H), 2.02-1.99 (m, 3H), 1.62-1.58 (m, 12H). EI-MS: m/z (M+H⁺): 332.5 (calculated), 332.5 (found).

Example 152a/M2WJ321

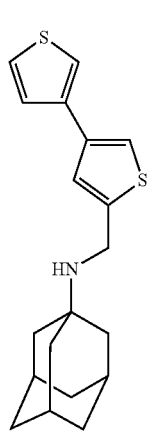 [SMILES: c1cc(-c2csc(CNC34CC5CC(CC(C5)C3)C4)c2)cs1]

N-([3,3'-bithiophen]-5-ylmethyl)adamantan-1-amine

Based on general procedure A, from amantadine and [3,3'-bithiophene]-5-carbaldehyde, a white solid (73%) is obtained. Data: LC/MS (ESR) m/z 330.5 [M+H]⁺.

Example 153a/M2WJ347

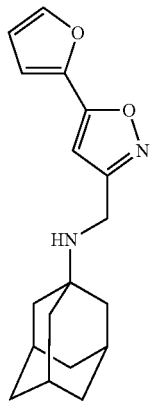

N-((5-(furan-2-yl)isoxazol-3-yl)methyl)adamantan-1-amine

Based on general procedure A, from amantadine and 5-(furan-2-yl)isoxazole-3-carbaldehyde, a yellow solid (62%) is obtained. Data: LC/MS (ESR) m/z 299.4 [M+H]⁺.

Example 154a/M2WJ348

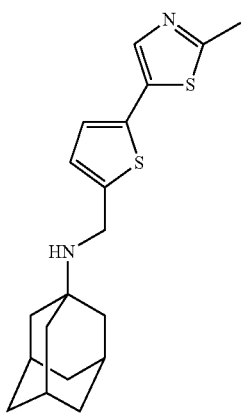 [SMILES: Cc1ncc(-c2ccc(CNC34CC5CC(CC(C5)C3)C4)s2)s1]

N-((5-(2-methylthiazol-5-yl)thiophen-2-yl)methyl)adamantan-1-amine

Based on general procedure A, from amantadine and 5-(2-methylthiazol-5-yl)thiophene-2-carbaldehyde, a yellow solid (87%) is obtained. Data: LC/MS (ESR) m/z 345.5 [M+H]⁺.

Example 155a/M2WJ340

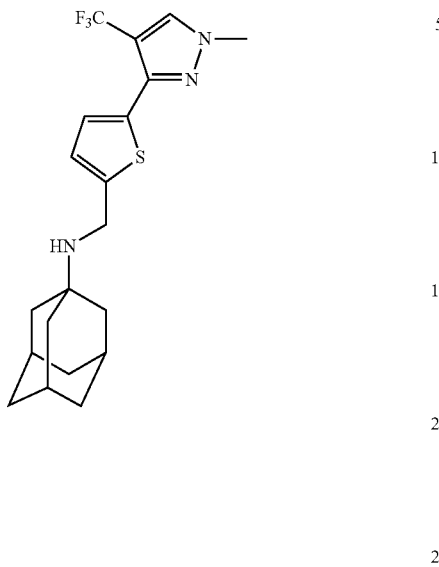

N-((5-(1-methyl-4-(trifluoromethyl)-1H-pyrazol-3-yl)thiophen-2-yl)methyl)adamantan-1-amine Based on general procedure C, from amantadine and 5-(1-methyl-4-(trifluoromethyl)-1H-pyrazol-3-yl)thiophene-2-carbaldehyde, a yellow solid (66%) is obtained. Data: LC/MS (ESR) m/z 396.5 [M+H]$^+$.

Example 156a/M2WJ362

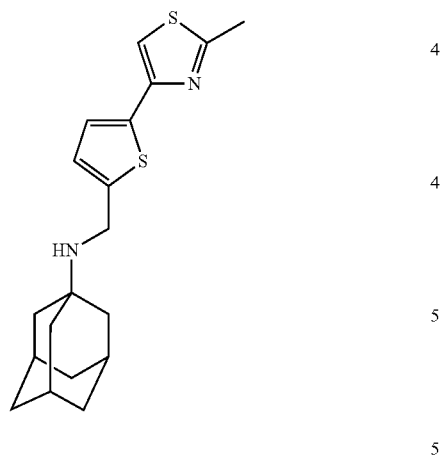

N-((5-(2-methylthiazol-4-yl)thiophen-2-yl)methyl)adamantan-1-amine

Based on general procedure C, from amantadine and 5-(2-methylthiazol-4-yl)thiophene-2-carbaldehyde, a yellow solid (79%) is obtained. Data: LC/MS (ESR) m/z 345.5 [M+H]$^+$.

Example 157a/M2WJ339

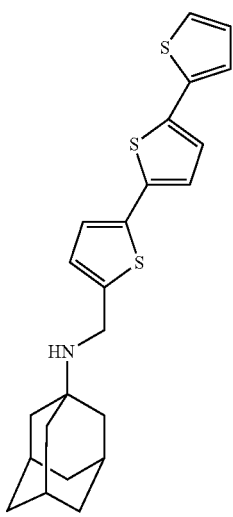 [SMILES: c1csc(-c2ccc(-c3ccc(CNC45CC6CC(CC(C6)C4)C5)s3)s2)c1]

N-([2,2':5',2''-terthiophen]-5-ylmethyl)adamantan-1-amine

Based on general procedure C, from amantadine and [2,2':5',2''-terthiophene]-5-carbaldehyde, a yellow solid (52%) is obtained. Data: LC/MS (ESR) m/z 412.6 [M+H]$^+$.

Example 158a/M2WJ331

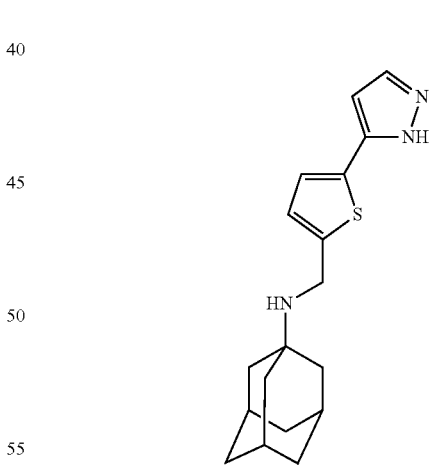

N-((5-(1H-pyrazol-5-yl)thiophen-2-yl)methyl)adamantan-1-amine

Based on general procedure C, from amantadine and 5-(1H-pyrazol-5-yl)thiophene-2-carbaldehyde, a white solid (68%) is obtained. Data: LC/MS (ESR) m/z 314.4 [M+H]$^+$.

Example 159a/M2WJ334

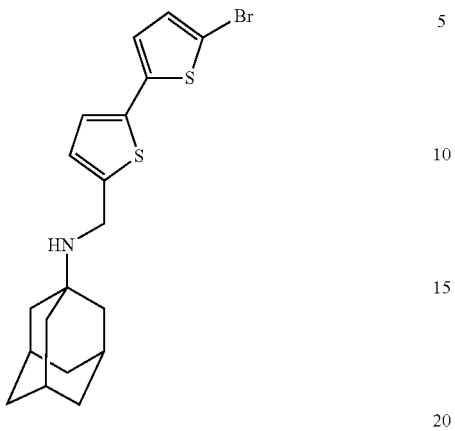

N-((5'-bromo-[2,2'-bithiophen]-5-yl)methyl)adamantan-1-amine

Based on general procedure C, from amantadine and 5'-bromo-[2,2'-bithiophene]-5-carbaldehyde, a yellow solid (81%) is obtained.

Example 160a/M2WJ394

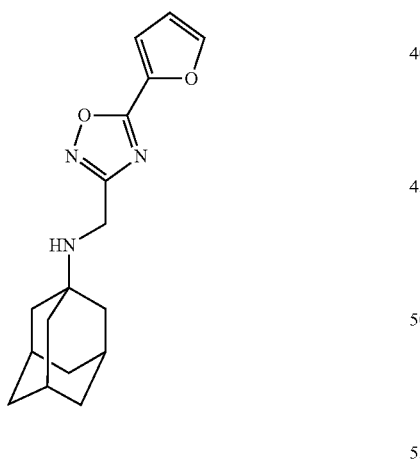

N-((5-(furan-2-yl)-1,2,4-oxadiazol-3-yl)methyl)adamantan-1-amine

Based on general procedure D, from amantadine and 3-(chloromethyl)-5-(furan-2-yl)-1,2,4-oxadiazole, a yellow solid (81%) is obtained. Data: LC/MS (ESR) m/z 300.4 [M+H]$^+$.

Example 161a/M2WJ365

N-((5-(1H-imidazol-1-yl)thiophen-2-yl)methyl)adamantan-1-amine

White solid (68% yield). Data: $^1$HNMR (300 MHz, CD$_3$OD): δ 9.25 (s, 1H), 7.91 (s, 1H), 7.69 (s, 1H), 7.45 (d, J=3.93 Hz, 1H), 7.33 (d, J=3.93 Hz, 1H), 4.50 (s, 2H), 2.26-2.24 (m, 3H), 2.04-2.01 (m, 6H), 1.86-1.74 (m, 6H). EI-MS: m/z (M+H$^+$): 314.5 (calculated), 314.5 (found).

Example 162a/M2WJ327

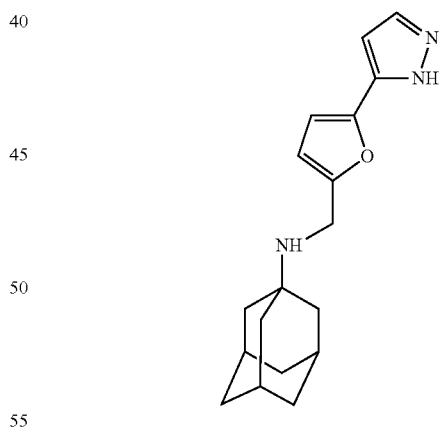

N-((5-(1H-pyrazol-5-yl)furan-2-yl)methyl)adamantan-1-amine

Based on general procedure A, from amantadine and 5-(1H-pyrazol-5-yl)furan-2-carbaldehyde, a white solid (81%) is obtained. Data: LC/MS (ESR) m/z 298.4 [M+H]$^+$.

Example 167a/M2WJ388

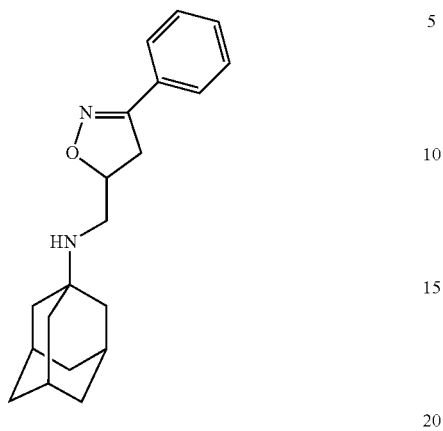

N-((3-phenyl-4,5-dihydroisoxazol-5-yl)methyl)adamantan-1-amine

Based on general procedure B, from amantadine and 5-(bromomethyl)-3-phenyl-4,5-dihydroisoxazole, a white solid (80%) is obtained. Data: ¹HNMR (300 MHz, CD$_3$OD): δ 7.70-7.67 (m, 2H), 7.44-7.42 (m, 3H), 4.87-4.76 (m, 1H), 3.51 (dd, J=17.01 Hz, 10.47 Hz, 1H), 3.18 (dd, J=17.01 Hz, 7.32 Hz, 1H), 2.80 (ddd, J=27.93 Hz, 12.00 Hz, 7.83 Hz, 1H), 2.08-2.06 (m, 3H), 1.71-1.68 (m, 12H). EI-MS: m/z (M+H$^+$): 311.4 (calculated), 311.4 (found).

Example 168a/M2WJ373

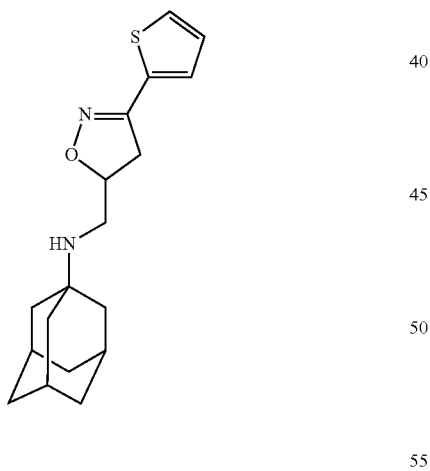

N-((3-(thiophen-2-yl)-4,5-dihydroisoxazol-5-yl)methyl)adamantan-1-amine

Follow the same procedure as Example 149/M2WJ372. Brown solid (52% yield). Data: ¹HNMR (300 MHz, CD$_3$OD): δ 7.53 (dd, J=5.10 Hz, 1.08 Hz, 1H), 7.32 (dd, J=3.66 Hz, 1.08 Hz, 1H), 7.10 (dd, J=5.10 Hz, 3.66 Hz, 1H), 4.87-4.75 (m, 1H), 3.52 (dd, J=16.80 Hz, 10.35 Hz, 1H), 3.20 (dd, J=16.80 Hz, 7.29 Hz, 1H), 2.80 (ddd, J=23.64 Hz, 12.09 Hz, 7.80 Hz, 1H), 2.09-2.06 (m, 3H), 1.74-164 (m, 12H). EI-MS: m/z (M+H$^+$): 317.5 (calculated), 317.5 (found).

Example 169a/WFD110

5-((adamantan-1-ylamino)methyl)pyrimidine-2,4 (1H,3H)-dione

Based on general procedure C, from adamantane-1-amine and 2,4-dioxo-1,2,3,4-tetrahydropyrimidine-5-carbaldehyde, a white solid is obtained. Data: LC/MS (ES+) m/z 276.3 [M+H]$^+$.

Example 170a/IMX00677

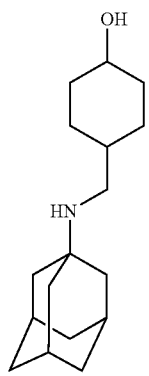 [SMILES: OC1CCC(CNC23CC4CC(CC(C4)C2)C3)CC1]

4-(Adamantan-1-ylaminomethyl)-cyclohexanol

Based on general Procedure E, from 4-hydroxy-cyclohexanecarboxylic acid and adamantan-1-ylamine, a white solid (76%) is obtained. Data: LC/MS (ESR) m/z 264 [M+H]$^+$.

Example 171a/IMX00683

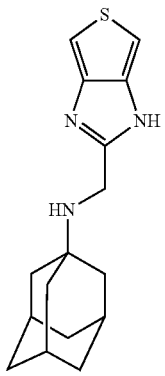 [SMILES: c1scc2[nH]c(CNC34CC5CC(CC(C5)C3)C4)nc12]

Adamantan-1-yl-(1H-thieno[3,4-d]imidazol-2-ylm-ethyl)-amine

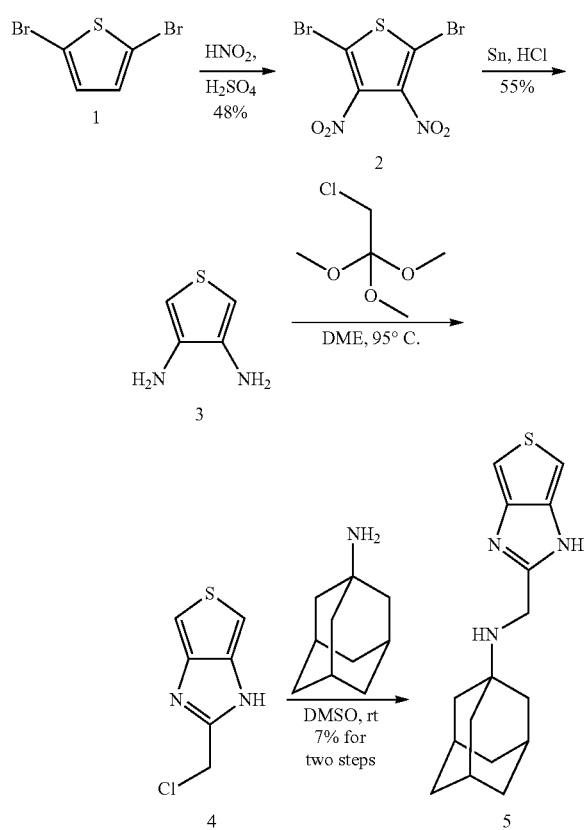

2,5-Dibromo-3,4-dinitrothiophene (2)

Concentrated sulfuric acid (13 mL), fuming sulfuric acid (20 mL), and fuming nitric acid (110 mL) were combined in a flask and cooled with an ice bath. 2,5-dibromothiophene (1) (3.5 mL, 7.5 g, 31.1 mmol) was added dropwise to maintain a temperature of 20-30° C. The mixture was allowed to react for a total of 3 hours and then poured over 90 g of ice. Upon the melting of the ice, the solid residue was recovered by vacuum filtration and recrystallized via hot methanol to give 5.1 g of product (48%), $^{13}$C NMR (300 MHz, CDCl$_3$): δ 113.7, 159.7.

3,4-Diaminothiophene (3)

Concentrated HCl (46 mL) and compound 2 (1.3 g, 3.8 mmol) were combined in a flask and cooled with an ice bath. Tin metal (3.2 g, 26.9 mmol) was added slowly to maintain a temperature of 25-30° C. After stabilizing at ~25° C., the reaction was allowed to continue until all the tin was consumed and then placed in a freezer overnight. The solid precipitate was recovered by vacuum filtration and washed with diethyl ether and acetonitrile until the wash was colorless to give the stable 3.2H+ salt. The 3.2H+ salt was dissolved in 50 mL of water, cooled with an ice bath, and the solution was made basic with 4 N Na$_2$CO$_3$. The product was extracted with diethyl ether, dried with anhydrous Na$_2$SO$_4$, and concentrated by rotary evaporation without heating to give 0.29 g (55%) of a white solid, $^1$HNMR (300 MHz, CDCl$_3$): δ 3.36 (br s, 4H), 6.16 (s, 2H).

2-Chloromethyl-1H-thieno[3,4-d]imidazole (4)

3,4-Diaminothiophene (0.29 g, 2.54 mmol) and 2-chloro-1,1,1-trimethoxy-ethane (0.5 g, 3.38 mmol) were combined in DME (5 mL) in a sealed tube and heated at 95° C. for overnight and concentrated to give a crude product to go to the next step without purification. LC-MS: m/z 173 [M+H]$^+$.

Adamantan-1-yl-(1H-thieno[3,4-d]imidazol-2-ylm-ethyl)-amine (5)

To above crude product (4) and adamantan-1-ylamine (755 mg, 5 mmol) were combined in DMSO (5 mL) and stirred at 25° C. for 12 h. The reaction was quenched with water (5 mL) and extracted with DCM (20 mL). After organic solvent was removed in vacuo, the residue was purified by flash column chromatography (1-10% CH$_3$OH/CH$_2$Cl$_2$) to give the Adamantan-1-yl-(1H-thieno[3,4-d]imidazol-2-ylmethyl)-amine (5) (51.1 mg, 7% over two steps). LC-MS: m/z 288 [M+H]$^+$. $^1$H NMR (300 MHz, CDCl$_3$) δ 6.75 (s, 2H), 5.74 (brs, 1H), 4.03 (s, 2H), 2.10-1.58 (m, 15H).

Example 172a/IMX685

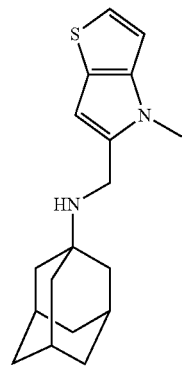 [SMILES: Cn1c(CNC23CC4CC(CC(C4)C2)C3)cc2sccc21]

Adamantan-1-yl-(4-methyl-4H-thieno[3,2-b]pyrrol-5-ylmethyl)-amine

Based on general procedure A, from 4-Methyl-4H-thieno[3,2-b]pyrrole-5-carbaldehyde and adamantan-1-ylamine, a white solid (71%) is obtained. Data: LC/MS (ESR) m/z 301 [M+H]⁺.

Example 173a/IMX00735

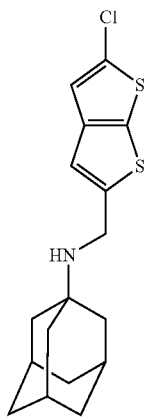 [SMILES: Clc1cc2cc(CNC34CC5CC(CC(C5)C3)C4)sc2s1]

Adamantan-1-yl-(5-chloro-thieno[2,3-b]thiophen-2-ylmethyl)-amine

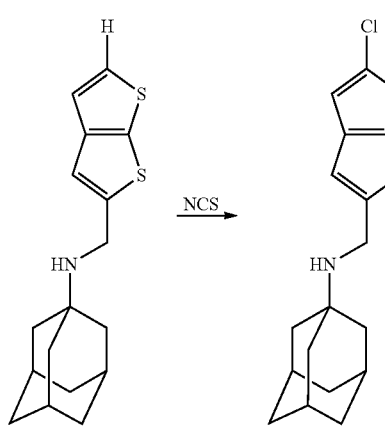

To a solution of Adamantan-1-yl-thieno[2,3-b]thiophen-2-ylmethyl-amine (150 mg, 0.5 mmol) was treated with NCS (67 mg, 0.5 mmol) in DMF (5 mL) at 0° C. for 2 h. The solvent was removed concentrated under reduced pressure. The crude product was separated by flash column chromatography (1-10% CH₃OH/CH₂Cl₂) to give the title compound (34 mg, 20%). Data: LC/MS (ESR) m/z 338 [M+H]⁺.

Example 174a/IMX00714

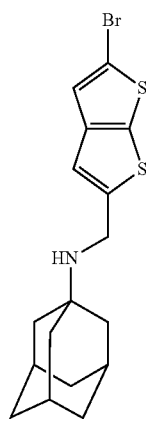

Adamantan-1-yl-(5-bromo-thieno[2,3-b]thiophen-2-ylmethyl)-amine

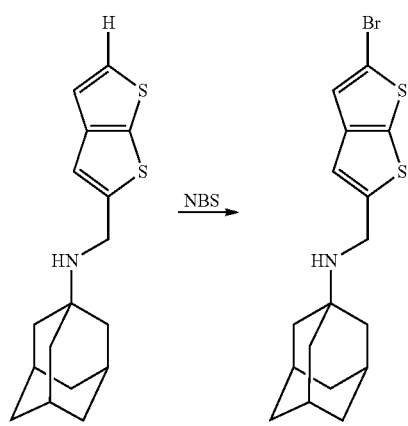

To a solution of Adamantan-1-yl-thieno[2,3-b]thiophen-2-ylmethyl-amine (150 mg, 0.5 mmol) was treated with NBS (90 mg, 0.5 mmol) in DMF (5 mL) at 0° C. for 2 h. The solvent was removed concentrated under reduced pressure. The crude product was separated by flash column chromatography (1-10% CH₃OH/CH₂Cl₂) to give the title compound (36 mg, 20%). Data: LC/MS (ESR) m/z 383 [M+H]⁺.

Example 177a/IMX00643

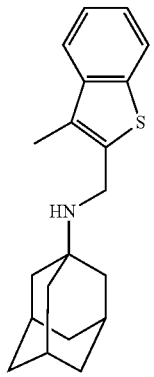 [SMILES: Cc1c(CNC23CC4CC(CC(C4)C2)C3)sc2ccccc12]

Adamantan-1-yl-(3-methyl-benzo[b]thiophen-2-ylmethyl)-amine

Based on general procedure A, from 3-Methyl-benzo[b]thiophene-2-carbaldehyde and adamantan-1-ylamine, a white solid (71%) is obtained. Data: LC/MS (ESR) m/z 312 [M+H]$^+$.

Example 178a/CMF004

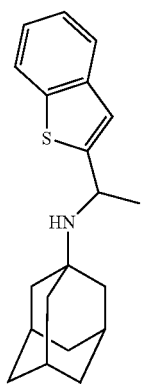 [SMILES: CC(NC12CC3CC(CC(C3)C1)C2)c1cc2ccccc2s1]

N-(1-(benzo[b]thiophen-2-yl)ethyl)adamantan-1-amine

Based on general procedure C, from adamantane-1-amine and 1-(benzo[b]thiophen-2-yl)ethanone, a white solid is obtained. Data: LC/MS (ES+) m/z 312.6 [M+H]$^+$.

Example 179a/IMX00705/M2WJ323 & Example 178a/IMX00696

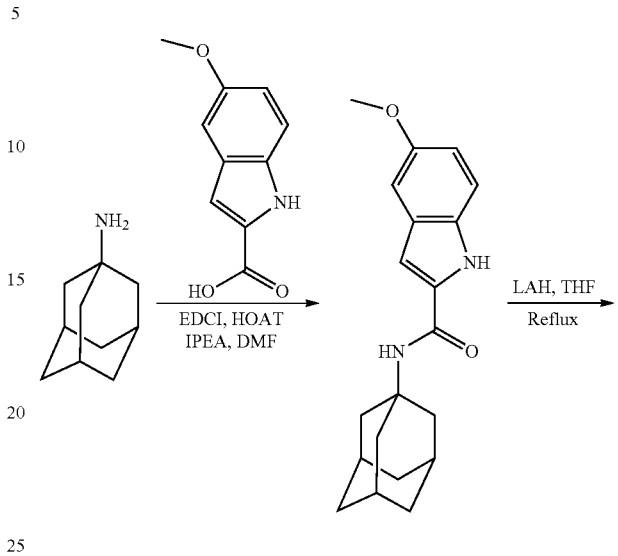

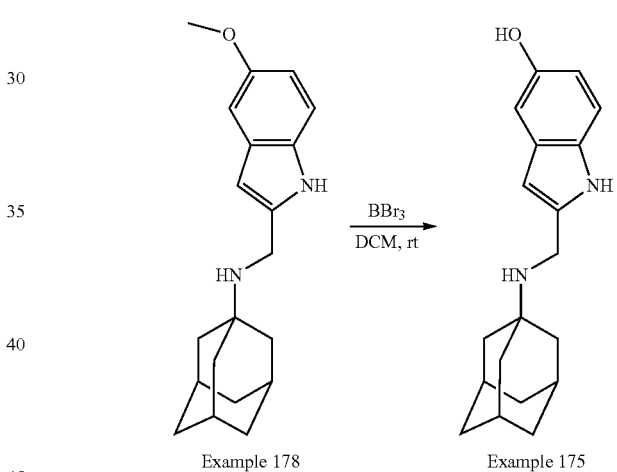

Example 178           Example 175

Based on general Procedure E, from 5-Methoxy-1H-indole-2-carboxylic acid and adamantan-1-ylamine, a white solid of example 178 adamantan-1-yl-(5-methoxy-1H-indol-2-ylmethyl)-amine (76%) is obtained. Data: LC/MS (ESR) m/z 311 [M+H]$^+$.

Treatment of adamantan-1-yl-(5-methoxy-1H-indol-2-ylmethyl)-amine (110 mg, 1.1 mmol) with BBr$_3$ (300 mg, 1.2 mmol) in DCM (5 mL) at −78° C. and then warm to rt for 2 h. The mixture was quenched with Na$_2$CO$_3$ (sat'd) (5 mL). The mixture was extracted with DCM (10 mL×3), and the combined organic layers was dried over Na$_2$SO$_4$ and solvent was removed under reduced pressure to give a residue, which was purified by flash column chromatography (1-10% CH$_3$OH/CH$_2$Cl$_2$) to give the tile compound example 175 (284 mg, 87%) as a white solid. Data: LC/MS (ESR) m/z 297 [M+H]$^+$.

367

Example 180a/IMX00692

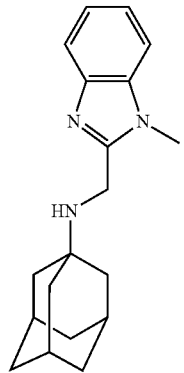 [SMILES: Cn1c(CNC23CC4CC(CC(C4)C2)C3)nc2ccccc21]

Adamantan-1-yl-(1-methyl-1H-benzoimidazol-2-ylmethyl)-amine

Based on general procedure A, from 1-Methyl-1H-benzoimidazole-2-carbaldehyde and adamantan-1-ylamine, a white solid (71%) is obtained. Data: LC/MS (ESR) m/z 296 [M+H]+.

Example 181a/IMX693

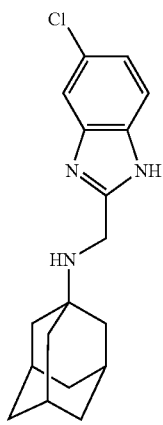 [SMILES: Clc1ccc2[nH]c(CNC34CC5CC(CC(C5)C3)C4)nc2c1]

Adamantan-1-yl-(5-chloro-1H-benzoimidazol-2-ylmethyl)-amine

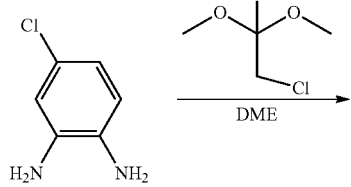

368

-continued

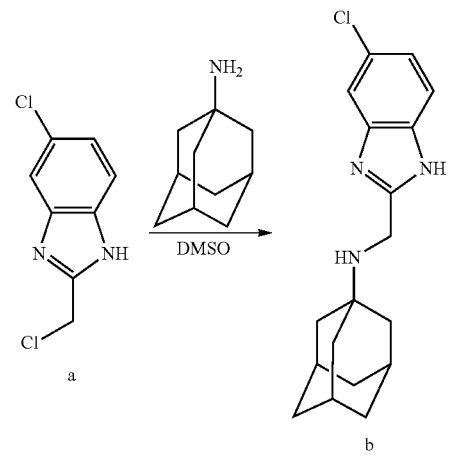

Follow the same procedure of Example 167/IMX00683 form 4-Chloro-benzene-1,2-diamine, a white solid (20% two step) is obtained. Data: LC/MS (ESR) m/z 316 [M+H]+.

Example 183a/IMX713

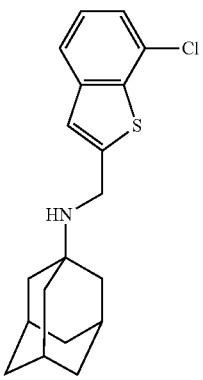 [SMILES: Clc1cccc2cc(CNC34CC5CC(CC(C5)C3)C4)sc12]

Adamantan-1-yl-(7-chloro-benzo[b]thiophen-2-ylmethyl)-amine

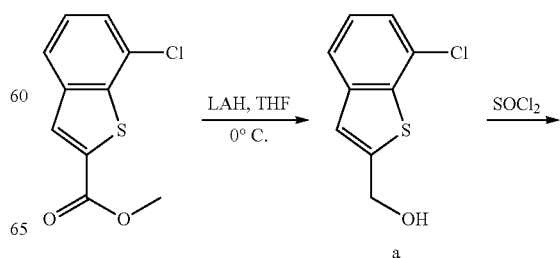

-continued

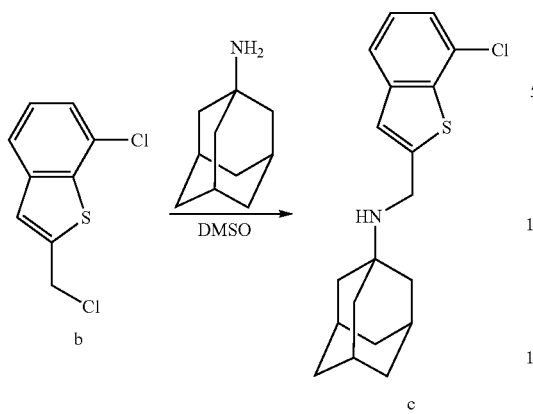

To a solution of 7-chloro-benzo[b]thiophene-2-carboxylic acid methyl ester (225 mg, 1 mmol) in anhydrous THF (5 mL) was added dropwise of LiAlH₄ solution (2.0 M in THF, 1 mL) at 0° C. The resulting solution was stirred for 2 h at 0° C. The solution was quenched by H₂O/1N NaOH/H₂O protocol (76 uL H₂O, 152 uL 1N NaOH, 228 uL H₂O). After the mixture was stirred for 1 h, the solid was removed by filtration. The resulting solution was evaporated to dryness and purified by flash column chromatography (1-10% CH₃OH/CH₂Cl₂) to give (7-Chloro-benzo[b]thiophen-2-yl)-methanol (150 mg, 76%). Data: LC/MS (ESR) m/z 199 [M+H]⁺. Above alcohol was dissolved in SOCl2 (2 mL) and the solution was heat at 80° C. for 1 h. The solvent was removed under reduced pressure. The residue (7-Chloro-benzo[b]thiophen-2-yl)-methanol was used directly to the next step without purification. Then the residue was taken to DMSo (5 mL) and Adamantan-1-ylamine (200 mg) was added. The mixture was stirred at rt for overnight and then was quenched with H₂O (5 mL). The mixture was extracted with DCM (10 mL×3), and the combined organic layers was dried over Na₂SO₄ and solvent was removed under reduced pressure to give a residue, which was purified by flash column chromatography (1-10% CH₃OH/CH₂Cl₂) to give the tile compound example 175 (15 mg, 10%) as a white solid. Data: LC/MS (ESR) m/z 332 [M+H]⁺.

Example 184a/IMX721

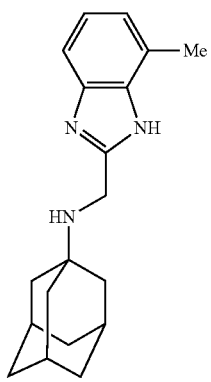 [SMILES: Cc1cccc2nc(CNC34CC5CC(CC(C5)C3)C4)[nH]c12]

Adamantan-1-yl-(7-methyl-1H-benzoimidazol-2-ylmethyl)-amine

Follow the same procedure as example 179, Adamantan-1-yl-(7-methyl-1H-benzoimidazol-2-ylmethyl)-amine was obtained as a white solid (21%). LC/MS (ESR) m/z 296 [M+H]⁺.

Example 185a/M2WJ345

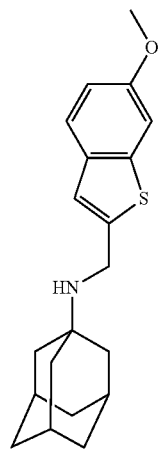 [SMILES: COc1ccc2cc(CNC34CC5CC(CC(C5)C3)C4)sc2c1]

N-((6-methoxybenzo[b]thiophen-2-yl)methyl)adamantan-1-amine

Based on general procedure C, from amantadine and 6-methoxybenzo[b]thiophene-2-carbaldehyde, a yellow solid (71%) is obtained. Data: LC/MS (ESR) m/z 328.4 [M+H]⁺.

Example 186a/M2WJ346

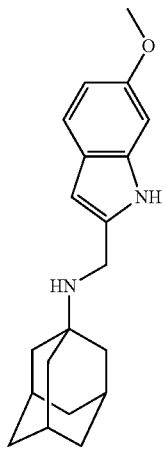 [SMILES: COc1ccc2cc(CNC34CC5CC(CC(C5)C3)C4)[nH]c2c1]

N-((6-methoxy-1H-indol-2-yl)methyl)adamantan-1-amine

Based on general procedure C, from amantadine and 6-methoxy-1H-indole-2-carbaldehyde, a yellow solid (61%) is obtained. Data: LC/MS (ESR) m/z 311.4 [M+H]⁺.

Example 187a/IMX684

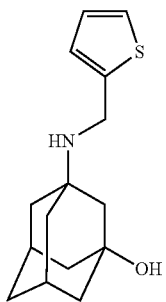 [SMILES: OC12CC3CC(C1)CC(NCc1cccs1)(C3)C2]

3-[(Thiophen-2-ylmethyl)-amino]adamantan-1-ol

Follow the procedure A, compound 3-[(Thiophen-2-ylmethyl)-amino]-adamantan-1-ol (a) (IMX680) was made from Thiophene-2-carbaldehyde and 3-Amino-adamantan-1-ol as a white solid (70%). LC/MS (ESR) m/z 264 [M+H]+.

Example 188a/IMX680

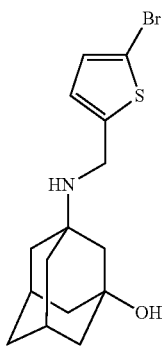 [SMILES: OC12CC3CC(C1)CC(NCc1ccc(Br)s1)(C3)C2]

3-[(5-Bromo-thiophen-2-ylmethyl)-amino]adamantan-1-ol

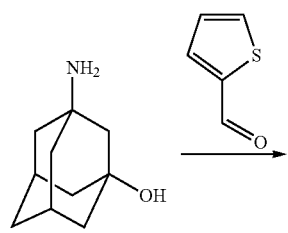

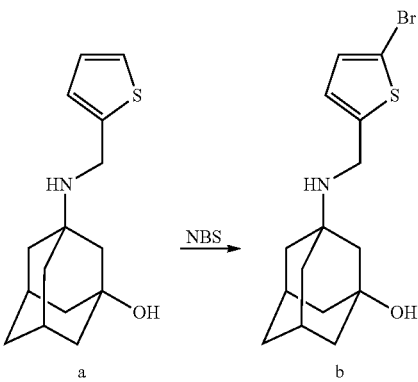

Treatment of 3-[(Thiophen-2-ylmethyl)-amino]-adamantan-1-ol (a) (example 183) (264 mg, 1.0 mmol) with NCS (150 mg, 1.2 eq) at 50° C. in DMF for 2 h. Solvent was removed under reduced pressure, the residue was purified by flash column chromatography (1-10% CH$_3$OH/CH$_2$Cl$_2$) to give the tile compound 3-[(5-Bromo-thiophen-2-ylmethyl)-amino]-adamantan-1-ol (215 mg, 66%) as a white solid. Data: LC/MS (ESR) m/z 343 [M+H]+.

Example 189a/IMX716

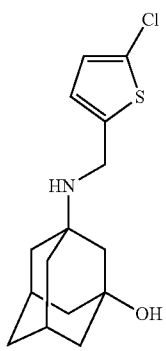 [SMILES: OC12CC3CC(C1)CC(NCc1ccc(Cl)s1)(C3)C2]

3-[(5-Chloro-thiophen-2-ylmethyl)-amino]adamantan-1-ol

Follow the same procedure except from NCS in the second step to give 3-[(5-Chloro-thiophen-2-ylmethyl)-amino]-adamantan-1-ol. Data: LC/MS (ESR) m/z 298 [M+H]+.

Example 190a/IMX00691

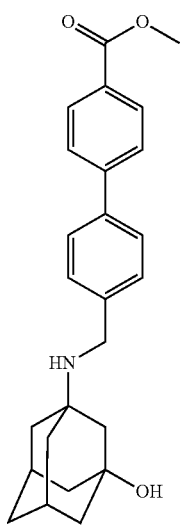 [SMILES: COC(=O)c1ccc(-c2ccc(CNC34CC5CC(CC(O)(C5)C3)C4)cc2)cc1]

4'-[(3-Hydroxy-adamantan-1-ylamino)-methyl]-biphenyl-4-carboxylic acid methyl ester

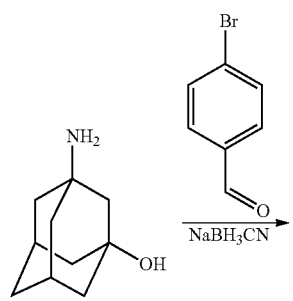

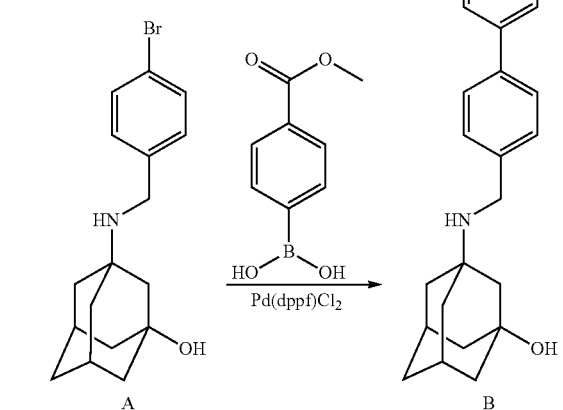

Follow the procedure A, compound A 3-(4-Bromo-benzylamino)-adamantan-1-ol was obtained as white solid (70%) from 3-Amino-adamantan-1-ol and 4-Bromo-benzaldehyde. Data: LC/MS (ESR) m/z 337 [M+H]⁺.

Follow the procedure E, 4'-[(3-Hydroxy-adamantan-1-ylamino)-methyl]-biphenyl-4-carboxylic acid methyl ester (B) was obtained as an off-white solid (60%). LC/MS (ESR) m/z 392 [M+H]⁺.

Example 191a/IMX00690

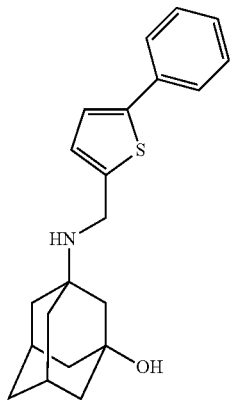 [SMILES: OC12CC3CC(C1)CC(NCc1ccc(-c4ccccc4)s1)(C3)C2]

3-[(5-Phenyl-thiophen-2-ylmethyl)-amino]adamantan-1-ol

Follow the procedure A, 3-[(5-Phenyl-thiophen-2-ylmethyl)-amino]-adamantan-1-ol Was obtained as white solid (70%) from 3-Amino-adamantan-1-ol and 5-Phenyl-thiophene-2-carbaldehyde. Data: LC/MS (ESR) m/z 340 [M+H]⁺.

Example 192a/IMX00706

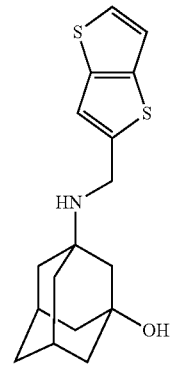 [SMILES: OC12CC3CC(C1)CC(NCc1cc4sccc4s1)(C3)C2]

3-[(Thieno[3,2-b]thiophen-2-ylmethyl)-amino]-adamantan-1-ol

Follow Procedure E, 3-[(Thieno[3,2-b]thiophen-2-ylmethyl)-amino]-adamantan-1-ol was obtained from Thieno[3,2-b]thiophene-2-carboxylic acid and 3-Amino-adamantan-1-ol as a white solid (40 two steps). Data: LC/MS (ESR) m/z 320 [M+H]⁺.

Example 193a/M2WJ404

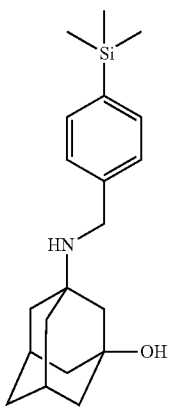 [SMILES: C[Si](C)(C)c1ccc(CNC23CC4CC(CC(O)(C4)C2)C3)cc1]

(1s,3r,5R,7S)-3-((4-(trimethylsilyl)benzyl)amino)adamantan-1-ol

Based on general procedure C, from 3-amino-1-adamantol and 4-(trimethylsilyl)benzaldehyde, a white solid (83%) is obtained. Data: LC/MS (ESR) m/z 330.6 [M+H]$^+$.

Example 194a/M2WJ382

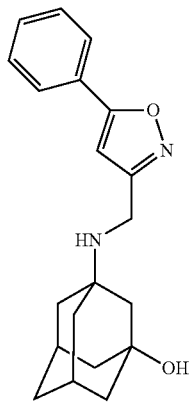 [SMILES: OC12CC3CC(C1)CC(NCc1cc(-c4ccccc4)on1)(C3)C2]

(1s,3r,5R,7S)-3-(((5-phenylisoxazol-3-yl)methyl)amino)adamantan-1-ol

Based on general procedure C, from 3-amino-1-adamantol and 5-phenylisoxazole-3-carbaldehyde, a white solid (82%) is obtained. Data: LC/MS (ESR) m/z 325.4 [M+H]$^+$.

Example 195a/IMX00733

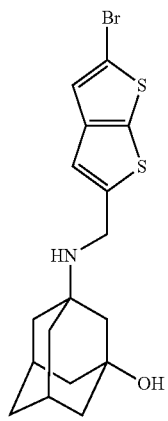 [SMILES: OC12CC3CC(C1)CC(NCc1cc4cc(Br)sc4s1)(C3)C2]

3-[(5-Bromo-thieno[2,3-b]thiophen-2-ylmethyl)-amino]-adamantan-1-ol

Based on general procedure A, from 3-amino-1-adamantol and 5-bromo-thieno[2,3-b]thiophene-2-carbaldehyde, a white solid (81%) is obtained. Data: LC/MS (ESR) m/z 398 [M+H]$^+$.

Example 196a/IM00727

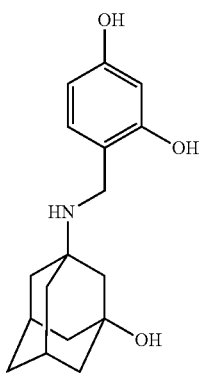 [SMILES: Oc1ccc(CNC23CC4CC(CC(O)(C4)C2)C3)c(O)c1]

4-[(3-Hydroxy-adamantan-1-ylamino)-methyl]-benzene-1,3-diol

Based on general procedure A, from 3-amino-1-adamantol and 2,4-dihydroxy-benzaldehyde, a off-white solid (83%) is obtained. Data: LC/MS (ESR) m/z 290 [M+H]$^+$.

Example 197a/IMX737

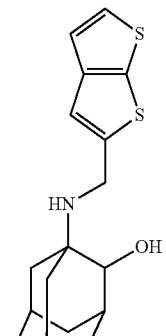

(±)-1-[(Thieno[2,3-b]thiophen-2-ylmethyl)-amino]adamantan-2-ol

Based on general procedure A, from (±)-1-amino-adamantan-2-ol (Armarego, W. L. F.; Tucker, P. G. Australian Journal of Chemistry, 1979, 32, 1805-17) and thieno[2,3-b]thiophene-2-carbaldehyde, a white solid (30%) is obtained. Data: LC/MS (ESR) m/z 320 [M+H]$^+$.

Example 198a/Hij306

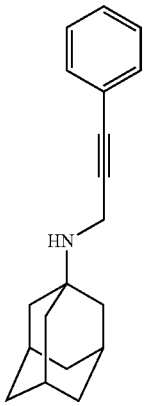 [SMILES: C(#Cc1ccccc1)CNC12CC3CC(CC(C3)C1)C2]

N-(3-phenylprop-2-yn-1-yl)adamantan-1-amine

Based on general procedure C, from adamantane-1-amine and 3-phenylpropiolaldehyde, a yellowish liquid was obtained by a silica gel column chromatography. Data: LC/MS (ES+) m/z 312.6 [M+H]$^+$.

Example 199a/CFM001

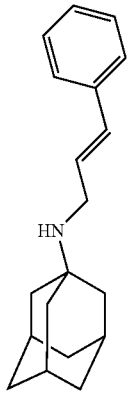 [SMILES: C(=C\c1ccccc1)/CNC12CC3CC(CC(C3)C1)C2]

N-cinnamyladamantan-1-amine

Based on general procedure C, from adamantane-1-amine and cinnamaldehyde, a yellowish liquid was obtained by a silica gel column chromatography. Data: LC/MS (ES+) m/z 268.3 [M+H]$^+$.

Example 200a/hij-307

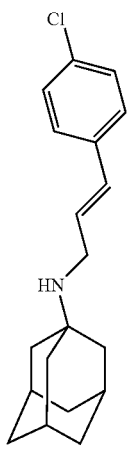 [SMILES: Clc1ccc(/C=C/CNC23CC4CC(CC(C4)C2)C3)cc1]

N-((E)-3-(4-chlorophenyl)allyl)adamantan-1-amine

Based on general procedure C, from adamantane-1-amine and (E)-3-(4-chlorophenyl)acrylaldehyde, a yellowish liquid was obtained by a silica gel column chromatography. Data: LC/MS (ES+) m/z 302.4 [M+H]$^+$.

Example 201a/IMX00732

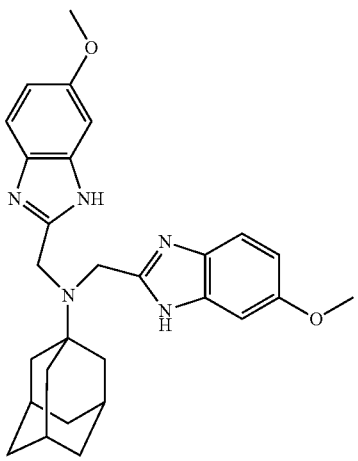 [SMILES: COc1ccc2nc(CN(Cc3nc4ccc(OC)cc4[nH]3)C34CC5CC(CC(C5)C3)C4)[nH]c2c1]

Adamantan-1-yl-bis-(6-methoxy-1H-benzoimidazol-2-ylmethyl)-amine

From amantadine (1 eq) and 2-Chloromethyl-6-methoxy-1H-benzoimidazole (3 eq), a white solid (43%) is obtained. Data: LC/MS (ESR) m/z 472 [M+H]$^+$.

Example 202a/M2WJ416

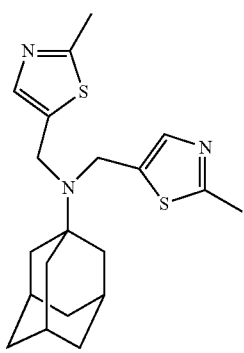 [SMILES: Cc1ncc(CN(Cc2cnc(C)s2)C23CC4CC(CC(C4)C2)C3)s1]

N,N-bis((2-methylthiazol-5-yl)methyl)adamantan-1-amine

Based on general procedure C, from amantadine (1 eq) and 5-(chloromethyl)-2-methylthiazole (3 eq), a white solid (80%) is obtained. Data: LC/MS (ESR) m/z 374.6 [M+H]$^+$.

Example 203a/IMX00709

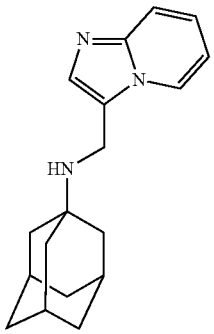 [SMILES: c1ccn2c(CNC34CC5CC(CC(C5)C3)C4)cnc2c1]

Adamantan-1-yl-imidazo[1,2-a]pyridin-3-ylmethyl-amine

Based on general procedure A, from imidazo[1,2-a]pyridine-3-carbaldehyde and Adamantan-1-ylamine, a white solid (69%) is obtained. Data: LC/MS (ESR) m/z 282 [M+H]$^+$.

Example 204a/BC059

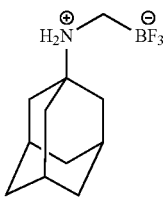

N-[(Trifluoro-4-boranyl)methyl]adamantan-1-aminium

See reference: Fleury-Bregeot, N.; Raushel, J.; Sandrock, D. L.; Molander G. A. Chem. Eur. J. 2012, 18, 9564-9570.

Example 205a/M2WJ324

N-([2,2'-bithiophen]-5-ylmethyl)adamantan-2-amine

Based on general procedure C, from 2-aminoadamantane and [2,2'-bithiophene]-5-carbaldehyde, a yellow solid (84%) is obtained. Data: LC/MS (ESR) m/z 330.5 [M+H]$^+$.

Example 1b/BC085

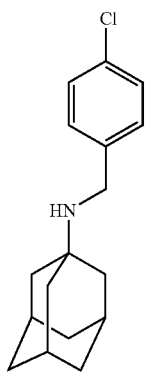

N-(4-Chlorobenzyl)adamantan-1-amine

Based on general procedure Cl, from adamantan-1-ylamine and 4-chlorobenzaldehdye, an off-white solid was obtained. Data: LC/MS (ESCi) m/z 276.14 [M+1]+.

Example 2b/BC089

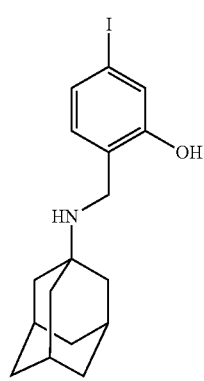

2-(-Adamantan-1-ylamino)methyl)-5-iodophenol

Based on general procedure Cl, from adamantan-1-ylamine and 2-hydroxy-4-iodobenzaldehyde (General Procedure L), a light brown solid was obtained. Data: LC/MS (ESCi) m/z 384.02 [M+1]+.

Example 3b/Hij339

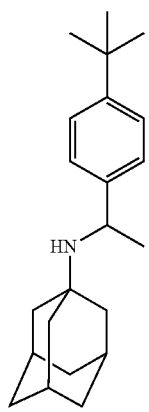 [SMILES: CC(NC12CC3CC(CC(C3)C1)C2)c1ccc(C(C)(C)C)cc1]

N-(1-(4-(tert-butyl)phenyl)ethyl)adamantan-1-amine

Based on general procedure C, from adamantan-1-ylamine and t-butylacetophenone, a white solid (30%) is obtained. Data: LC/MS (ESR) m/z 312 [M+H]+.

Example 4b/Hij339

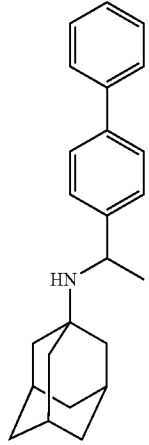 [SMILES: CC(NC12CC3CC(CC(C3)C1)C2)c1ccc(-c2ccccc2)cc1]

N-(1-([1,1'-biphenyl]-4-yl)ethyl)adamantan-1-amine

Based on general procedure C, from adamantan-1-ylamine and biphenylketone, a white solid (10%) is obtained. Data: LC/MS (ESR) m/z 332 [M+H]+.

Example 5b/BC045

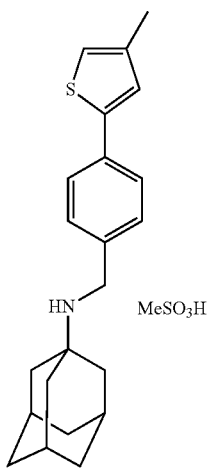 [SMILES: "MeSO3H" ; Cc1csc(-c2ccc(CNC34CC5CC(CC(C5)C3)C4)cc2)c1]

N-(4-(4-Methylthiophen-2-yl)benzyl)adamantan-1-amine

Based on general procedure Cl, from N-(4-bromobenzyl)adamantan-1-amine and potassium 4-methyl-(thiophen-2-yl)trifluoroborate. The free amine was dissolved in diethyl ether and cooled to 0° C. and MeSO$_3$H (1 equiv) was added under N$_2$, and then mixture was stirred at 0° C. for 15 min and filtered to give a white solid. Data: LC/MS (ESCi) m/z 338.13 [M+H]$^+$.

Example 6b/BC102

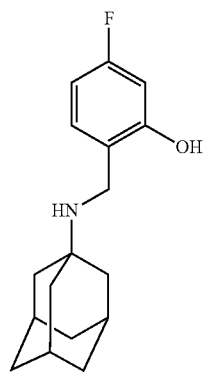

2-(-Adamantan-1-ylamino)methyl)-5-fluorophenol

Based on general procedure Cl, from adamantan-1-amine and 4-fluoro-2-hydroxybenzaldehdye (General Procedure L), an off-white solid was obtained Data: LC/MS (ESCi) m/z 276.14 [M+H]$^+$.

Example 7b/BC113

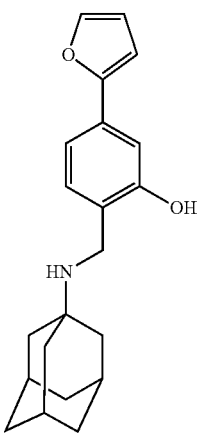

2-((-Adamantan-1-ylamino)methyl)-5-(furan-2-yl)phenol

Based on general procedure Cl, from adamantan-1-amine and 4-(furan-2-yl)-2-hydroxybenzaldehyde (general procedure F), an off-white solid was obtained Data: LC/MS (ESCi) m/z 324.28 [M+H]$^+$.

Example 8b/BC114

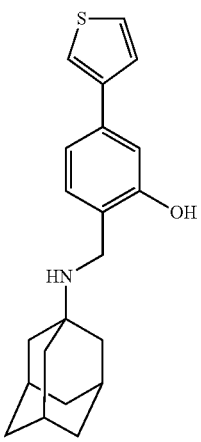

2-(((-Adamantan-1-ylamino)methyl)-5-(thiophen-3-yl)phenol

Based on general procedure Cl, from adamantan-1-amine and 4-(thiophen-3-yl)-2-hydroxybenzaldehyde (general procedure F), an off-white solid was obtained Data: LC/MS (ESCi) m/z 340.21 [M+H]$^+$.

Example 9b/BC100

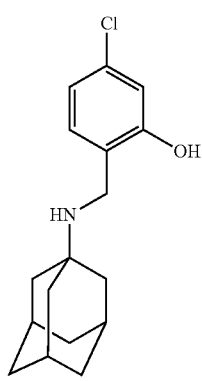 [SMILES: Oc1cc(F)ccc1CNC12CC3CC(CC(C3)C1)C2]

2-((-Adamantan-1-ylamino)methyl)-5-chlorophenol

Based on general procedure Cl, from adamantan-1-amine and 4-chloro-2-hydroxybenzaldehyde (General Procedure L), an off-white solid was obtained Data: LC/MS (ESCi) m/z 292.18 [M+1]$^+$.

Example 10b/M2WJ410

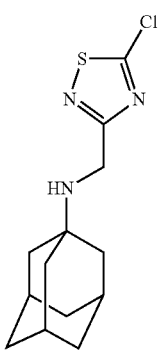 [SMILES: Clc1nc(CNC23CC4CC(CC(C4)C2)C3)ns1]

N-((5-chloro-1,2,4-thiadiazol-3-yl)methyl)adamantan-1-amine

Based on general procedure E, from adamantan-1-ylamine and 5-chloro-3-(chloromethyl)-1,2,4-thiadiazole, a yellow solid (72%) is obtained. Data: LC/MS (ESR) m/z 284 [M+H]$^+$.

Example 11b/M2WJ411

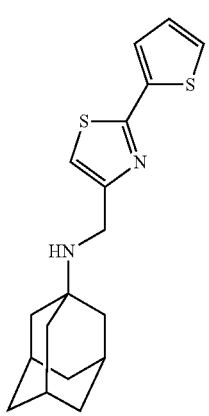

N-((2-(thiophen-2-yl)thiazol-4-yl)methyl)adamantan-1-amine

Based on general procedure E, from adamantan-1-ylamine and 4-(chloromethyl)-2-(thiophen-2-yl)thiazole, a yellow solid (78%) is obtained. Data: LC/MS (ESR) m/z 331 [M+H]$^+$.

Example 12b/M2WJ412

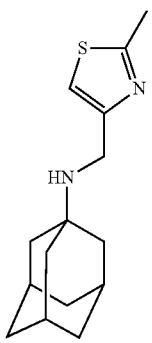 [SMILES: Cc1nc(CNC23CC4CC(CC(C4)C2)C3)cs1]

N-((2-methylthiazol-4-yl)methyl)adamantan-1-amine

Based on general procedure E, from adamantan-1-ylamine and 4-(chloromethyl)-2-methylthiazole, a yellow solid (82%) is obtained. Data: LC/MS (ESR) m/z 263 [M+H]$^+$.

Example 13b/M2WJ413

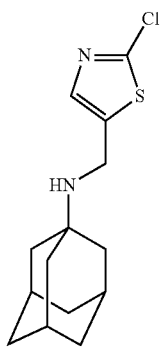 [SMILES: Clc1ncc(CNC23CC4CC(CC(C4)C2)C3)s1]

N-((2-chlorothiazol-5-yl)methyl)adamantan-1-amine

Based on general procedure E, from adamantan-1-ylamine and 2-chloro-5-(chloromethyl)thiazole, a yellow solid (75%) is obtained. Data: LC/MS (ESR) m/z 283 [M+H]$^+$.

Example 14b/M2WJ414

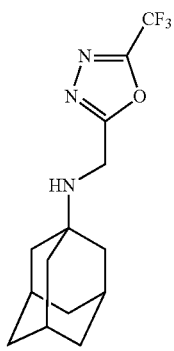 [SMILES: FC(F)(F)c1nnc(CNC23CC4CC(CC(C4)C2)C3)o1]

N-((5-(trifluoromethyl)-1,3,4-oxadiazol-2-yl)methyl) adamantan-1-amine

Based on general procedure E, from adamantan-1-ylamine and 2-(chloromethyl)-5-(trifluoromethyl)-1,3,4-oxadiazole, a yellow solid (83%) is obtained. Data: LC/MS (ESR) m/z 302 [M+H]$^+$.

Example 15b/M2WJ415

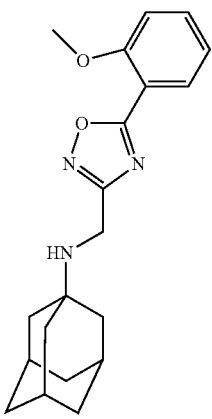 [SMILES: COc1ccccc1-c1nc(CNC23CC4CC(CC(C4)C2)C3)no1]

N-((5-(2-methoxyphenyl)-1,2,4-oxadiazol-3-yl) methyl)adamantan-1-amine

Based on general procedure E, from adamantan-1-ylamine and 3-(chloromethyl)-5-(2-methoxyphenyl)-1,2,4-oxadiazole, a yellow solid (78%) is obtained. Data: LC/MS (ESR) m/z 340 [M+H]$^+$.

Example 16b/M2WJ417

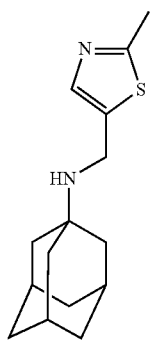 [SMILES: Cc1ncc(CNC23CC4CC(CC(C4)C2)C3)s1]

N-((2-methylthiazol-5-yl)methyl)adamantan-1-amine

Based on general procedure E, from adamantan-1-ylamine and 5-(chloromethyl)-2-methylthiazole, a yellow solid (88%) is obtained. Data: LC/MS (ESR) m/z 263 [M+H]$^+$.

Example 17b/M2WJ419

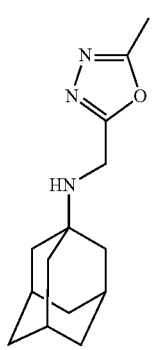

N-((5-methyl-1,3,4-oxadiazol-2-yl)methyl)adamantan-1-amine

Based on general procedure E, from adamantan-1-ylamine and 2-(chloromethyl)-5-methyl-1,3,4-oxadiazole, a yellow solid (72%) is obtained. Data: LC/MS (ESR) m/z 248 [M+H]$^+$.

Example 18b/M2WJ420

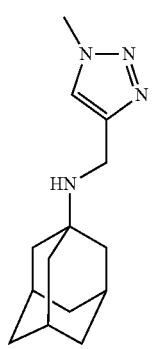 [SMILES: Cn1cc(CNC23CC4CC(CC(C4)C2)C3)nn1]

N-((1-methyl-1H-1,2,3-triazol-4-yl)methyl)adamantan-1-amine

Based on general procedure C, from adamantan-1-ylamine and 1-methyl-1H-1,2,3-triazole-4-carbaldehyde, a yellow solid (75%) is obtained. Data: LC/MS (ESR) m/z 247 [M+H]$^+$.

Example 19b/M2WJ421

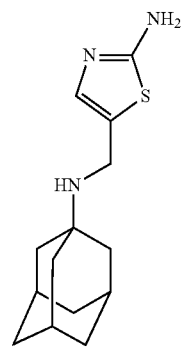 [SMILES: Nc1ncc(CNC23CC4CC(CC(C4)C2)C3)s1]

5-(adamantan-1-ylaminomethylthiazol-2-ylamine

Based on general procedure C, from adamantan-1-ylamine and 2-aminothiazole-5-carbaldehyde, a yellow solid (88%) is obtained. Data: LC/MS (ESR) m/z 264 [M+H]$^+$.

Example 20b/M2WJ422

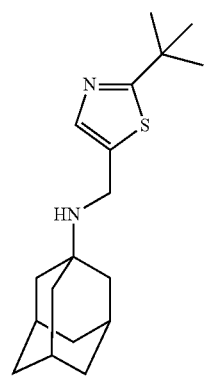 [SMILES: CC(C)(C)c1ncc(CNC23CC4CC(CC(C4)C2)C3)s1]

N-((2-(tert-butyl)thiazol-5-yl)methyl)adamantan-1-amine

Based on general procedure C, from adamantan-1-ylamine and 2-(tert-butyl)thiazole-5-carbaldehyde, a yellow solid (70%) is obtained. Data: LC/MS (ESR) m/z 305 [M+H]$^+$.

Example 21b/M2WJ423

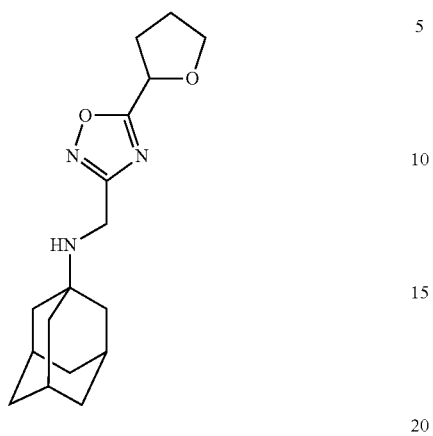

N-((5-(tetrahydrofuran-2-yl)-1,2,4-oxadiazol-3-yl)
methyl)adamantan-1-amine

Based on general procedure E, from adamantan-1-ylamine and 3-(chloromethyl)-5-(tetrahydrofuran-2-yl)-1,2,4-oxadiazole, a yellow solid (79%) is obtained. Data: LC/MS (ESR) m/z 304 [M+H]$^+$.

Example 22b/M2WJ424

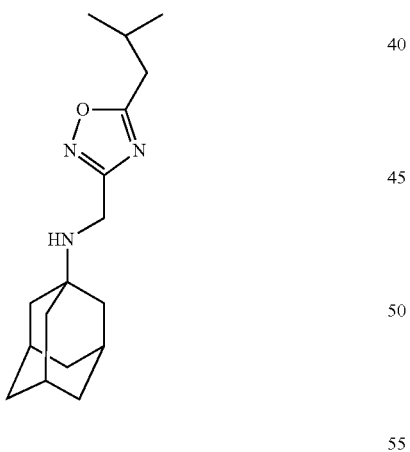

N-((5-isobutyl-1,2,4-oxadiazol-3-yl)methyl)adamantan-1-amine

Based on general procedure E, from adamantan-1-ylamine and 3-(chloromethyl)-5-isobutyl-1,2,4-oxadiazole, a yellow solid (72%) is obtained. Data: LC/MS (ESR) m/z 290 [M+H]$^+$.

Example 23b/M2WJ426

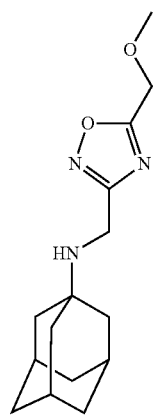

N-((5-(methoxymethyl)-1,2,4-oxadiazol-3-yl)
methyl)adamantan-1-amine

Based on general procedure E, from adamantan-1-ylamine and 3-(chloromethyl)-5-(methoxymethyl)-1,2,4-oxadiazole, a yellow solid (81%) is obtained. Data: LC/MS (ESR) m/z 278 [M+H]$^+$.

Example 24b/M2WJ428

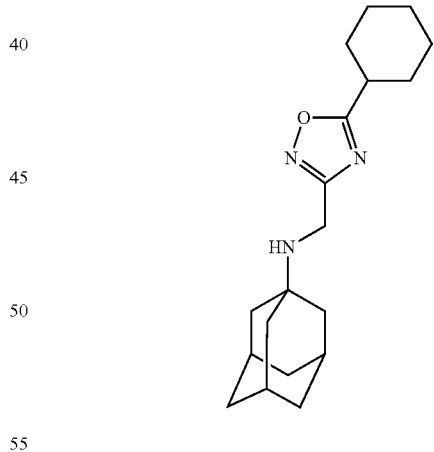

N-((5-(methoxymethyl)-1,2,4-oxadiazol-3-yl)
methyl)adamantan-1-amine

Based on general Procedure J, followed by general procedure E, from 2-chloro-N-hydroxyacetimidamide and cyclohexanecarbonyl chloride, a yellow solid (42%) is obtained. Data: LC/MS (ESR) m/z 316 [M+H]$^+$.

Example 25b/M2WJ430

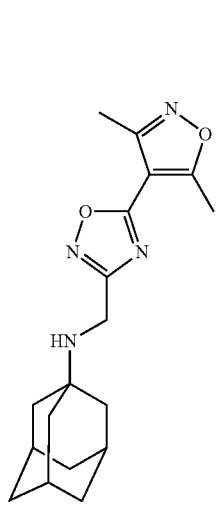 [SMILES: Cc1noc(C)c1-c1nc(CNC23CC4CC(CC(C4)C2)C3)no1]

N-((5-(3,5-dimethylisoxazol-4-yl)-1,2,4-oxadiazol-3-yl)methyl)adamantan-1-amine

Based on general procedure E, from adamantan-1-ylamine and 3-(chloromethyl)-5-(3,5-dimethylisoxazol-4-yl)-1,2,4-oxadiazole, a yellow solid (76%) is obtained. Data: LC/MS (ESR) m/z 329 [M+H]$^+$.

Example 26b/M2WJ431

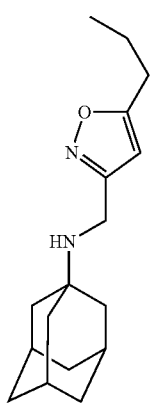 [SMILES: CCCc1cc(CNC23CC4CC(CC(C4)C2)C3)no1]

N-((5-propylisoxazol-3-yl)methyl)adamantan-1-amine

Based on general Procedure K, from pentan-2-one, a yellow solid (24%) is obtained. Data: LC/MS (ESR) m/z 275 [M+H]$^+$.

Example 27b/M2WJ432

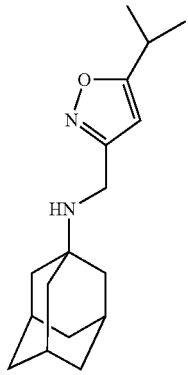 [SMILES: CC(C)c1cc(CNC23CC4CC(CC(C4)C2)C3)no1]

N-((5-isopropylisoxazol-3-yl)methyl)adamantan-1-amine

Based on general Procedure K, from 3-methylbutan-2-one, a yellow solid (23%) is obtained. Data: LC/MS (ESR) m/z 275 [M+H]$^+$.

Example 28b/M2WJ434

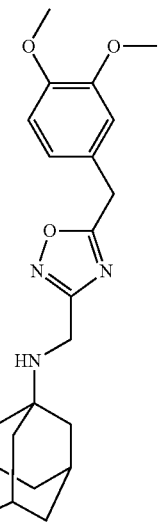

N-((5-(3,4-dimethoxybenzyl)-1,2,4-oxadiazol-3-yl)methyl)adamantan-1-amine

Based on general procedure E, from amantadine and 3-(chloromethyl)-5-(3,4-dimethoxybenzyl)-1,2,4-oxadiazole, a yellow solid (79%) is obtained. Data: LC/MS (ESR) m/z 384 [M+H]$^+$.

395

Example 29b/M2WJ437

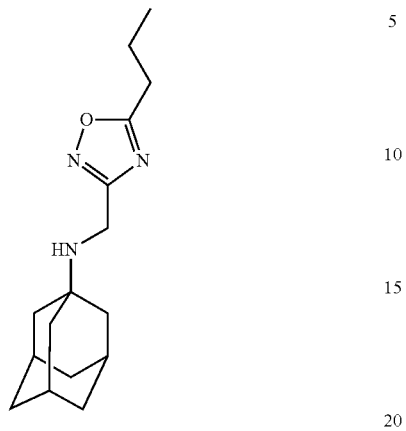

N-((5-propyl-1,2,4-oxadiazol-3-yl)methyl)adamantan-1-amine

Based on general procedure E, from amantadine and 3-(chloromethyl)-5-propyl-1,2,4-oxadiazole, a yellow solid (35%) is obtained. Data: LC/MS (ESR) m/z 276 [M+H]$^+$.

Example 30b/M2WJ438

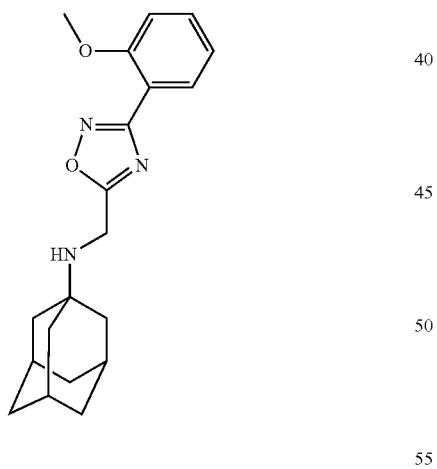

N-((3-(2-methoxyphenyl)-1,2,4-oxadiazol-5-yl)methyl)adamantan-1-amine

Based on general procedure E, from amantadine and 5-(chloromethyl)-3-(2-methoxyphenyl)-1,2,4-oxadiazole, a yellow solid (84%) is obtained. Data: LC/MS (ESR) m/z 340 [M+H]$^+$.

396

Example 31b/M2WJ439

N-((5-(2-chlorophenyl)-1,2,4-oxadiazol-3-yl)methyl)adamantan-1-amine

Based on general procedure E, from amantadine and 3-(chloromethyl)-5-(2-chlorophenyl)-1,2,4-oxadiazole, a yellow solid (81%) is obtained. Data: LC/MS (ESR) m/z 344 [M+H]$^+$.

Example 32b/M2WJ442

N-((5-cyclohexylisoxazol-3-yl)methyl)adamantan-1-amine

Based on general Procedure K, from 1-cyclohexylethanone, a yellow solid (23%) is obtained. Data: LC/MS (ESR) m/z 315 [M+H]$^+$.

397

Example 33b/M2WJ443

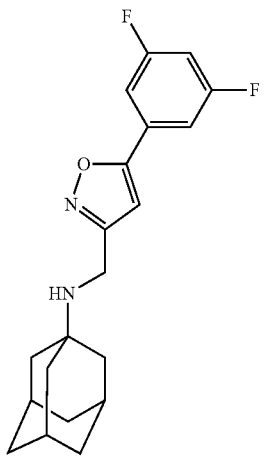 [SMILES: Fc1cc(F)cc(-c2cc(CNC34CC5CC(CC(C5)C3)C4)no2)c1]

N-((5-(3,5-difluorophenyl)isoxazol-3-yl)methyl)
adamantan-1-amine

Based on general Procedure K, from 1-(3,5-difluorophenyl)ethanone, a yellow solid (40%) is obtained. Data: LC/MS (ESR) m/z 345 [M+H]$^+$.

Example 34b/M2WJ444

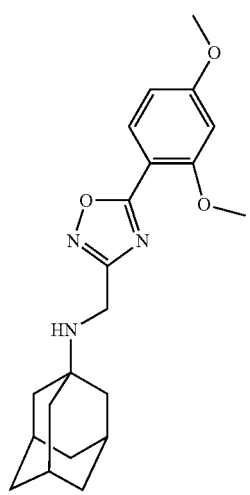 [SMILES: COc1ccc(-c2nc(CNC34CC5CC(CC(C5)C3)C4)no2)c(OC)c1]

N-((5-(2,4-dimethoxyphenyl)-1,2,4-oxadiazol-3-yl)
methyl)adamantan-1-amine

Based on general Procedure J, from 2,4-dimethoxybenzoyl chloride, a yellow solid (41%) is obtained. Data: LC/MS (ESR) m/z 370 [M+H]$^+$.

398

Example 35b/M2WJ445

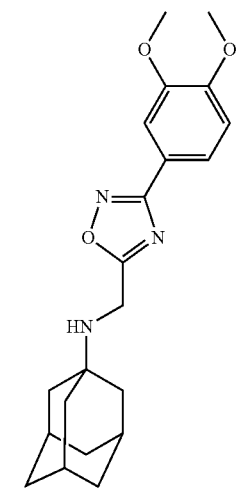 [SMILES: COc1ccc(-c2noc(CNC34CC5CC(CC(C5)C3)C4)n2)cc1OC]

N-((3-(3,4-dimethoxyphenyl)-1,2,4-oxadiazol-5-yl)
methyl)adamantan-1-amine

Based on general procedure E, from amantadine and 5-(chloromethyl)-3-(3,4-dimethoxyphenyl)-1,2,4-oxadiazole, a yellow solid (85%) is obtained. Data: LC/MS (ESR) m/z 370 [M+H]$^+$.

Example 36b/M2WJ446

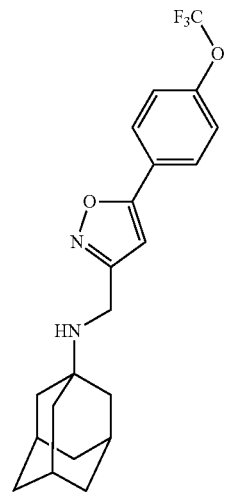 [SMILES: FC(F)(F)Oc1ccc(-c2cc(CNC34CC5CC(CC(C5)C3)C4)no2)cc1]

N-((5-(4-(trifluoromethoxy)phenyl)isoxazol-3-yl)
methyl)adamantan-1-amine

Based on general Procedure K, from 1-(4-(trifluoromethoxy)phenyl)ethanone, a yellow solid (41%) is obtained. Data: LC/MS (ESR) m/z 393 [M+H]$^+$.

Example 37b/M2WJ447

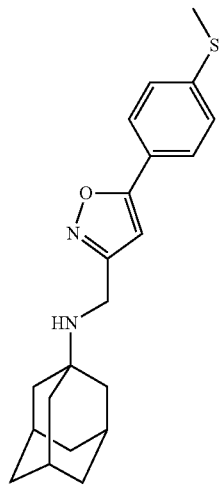 [SMILES: CSc1ccc(-c2cc(CNC34CC5CC(CC(C5)C3)C4)no2)cc1]

N-((5-(4-(methylthio)phenyl)isoxazol-3-yl)methyl)adamantan-1-amine

Based on general Procedure K, from 1-(4-(methylthio)phenyl)ethanone, a yellow solid (38%) is obtained. Data: LC/MS (ESR) m/z 355 [M+H]$^+$.

Example 38b/M2WJ448

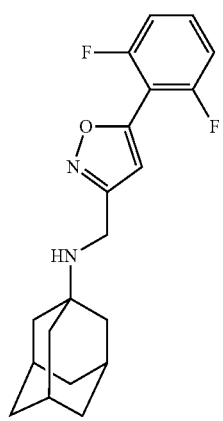 [SMILES: Fc1cccc(F)c1-c1cc(CNC23CC4CC(CC(C4)C2)C3)no1]

N-((5-(2,6-difluorophenyl)isoxazol-3-yl)methyl)adamantan-1-amine

Based on general Procedure K, from 1-(2,6-difluorophenyl)ethanone, a yellow solid (45%) is obtained. Data: LC/MS (ESR) m/z 345 [M+H]$^+$.

Example 39b/M2WJ449

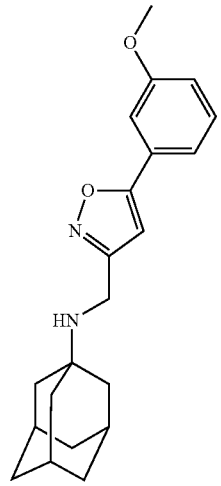 [SMILES: COc1cccc(-c2cc(CNC34CC5CC(CC(C5)C3)C4)no2)c1]

N-((5-(3-methoxyphenyl)isoxazol-3-yl)methyl)adamantan-1-amine

Based on general Procedure K, from 1-(3-methoxyphenyl)ethanone, a yellow solid (37%) is obtained. Data: LC/MS (ESR) m/z 339 [M+H]$^+$.

Example 40b/M2WJ451

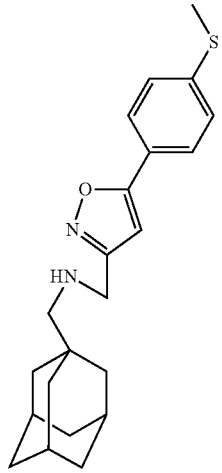 [SMILES: CSc1ccc(-c2cc(CNCC34CC5CC(CC(C5)C3)C4)no2)cc1]

1-((3r,5r,7r)-adamantan-1-yl)-N-((5-(4-(methylthio)phenyl)isoxazol-3-yl)methyl)methanamine Based on general procedure E, from (3r,5r,7r)-adamantan-1-ylmethanamine and 3-(chloromethyl)-5-(4-(methylthio)phenyl)isoxazole, a yellow solid (82%) is obtained. Data: LC/MS (ESR) m/z 369 [M+H]$^+$.

401

Example 41b/M2WJ452

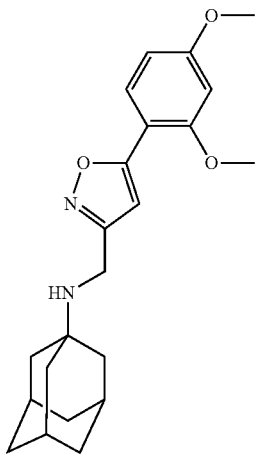 [SMILES: COc1ccc(-c2cc(CNC34CC5CC(CC(C5)C3)C4)no2)c(OC)c1]

N-((5-(2,4-dimethoxyphenyl)isoxazol-3-yl)methyl)
adamantan-1-amine

Based on general Procedure K, from 1-(2,4-dimethoxyphenyl)ethanone, a yellow solid (39%) is obtained. Data: LC/MS (ESR) m/z 369 [M+H]$^+$.

Example 42b/M2WJ454

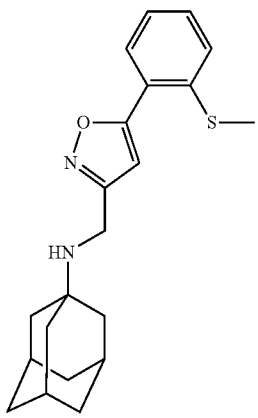

N-((5-(2-(methylthio)phenyl)isoxazol-3-yl)methyl)
adamantan-1-amine

Based on general Procedure K, from 1-(2-(methylthio)phenyl)ethanone, a yellow solid (41%) is obtained. Data: LC/MS (ESR) m/z 355 [M+H]$^+$.

402

Example 43b/M2WJ455

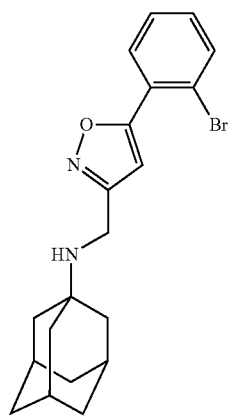 [SMILES: Brc1ccccc1-c1cc(CNC23CC4CC(CC(C4)C2)C3)no1]

N-((5-(2-bromophenyl)isoxazol-3-yl)methyl)adamantan-1-amine

Based on general Procedure K, from 1-(2-bromophenyl)ethanone, a yellow solid (40%) is obtained. Data: LC/MS (ESR) m/z 388 [M+H]$^+$.

Example 44b/M2WJ456

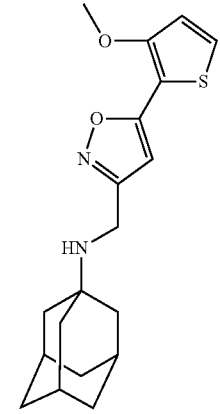 [SMILES: COc1ccsc1-c1cc(CNC23CC4CC(CC(C4)C2)C3)no1]

N-((5-(3-methoxythiophen-2-yl)isoxazol-3-yl)
methyl)adamantan-1-amine

Based on general Procedure K, from 1-(3-methoxythiophen-2-yl)ethanone, a yellow solid (32%) is obtained. Data: LC/MS (ESR) m/z 345 [M+H]$^+$.

Example 45b/M2WJ457

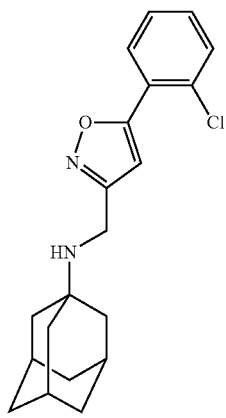

N-((5-(2-chlorophenyl)isoxazol-3-yl)methyl)adamantan-1-amine

Based on general Procedure K, from 1-(2-chlorophenyl)ethanone, a yellow solid (42%) is obtained. Data: LC/MS (ESR) m/z 343 [M+H]$^+$.

Example 46b/M2WJ458

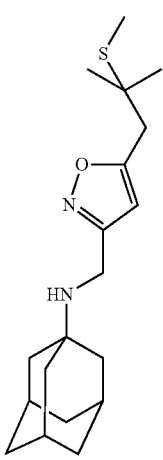 [SMILES: CSC(C)(C)Cc1cc(CNC23CC4CC(CC(C4)C2)C3)no1]

N-((5-(2-methyl-2-(methylthio)propyl)isoxazol-3-yl)methyl)adamantan-1-amine

Based on general Procedure K, from 4-methyl-4-(methylthio)pentan-2-one, a yellow solid (44%) is obtained. Data: LC/MS (ESR) m/z 335 [M+H]$^+$.

Example 47b/BC097

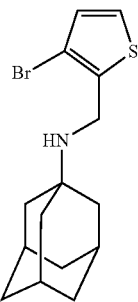 [SMILES: Brc1ccsc1CNC12CC3CC(CC(C3)C1)C2]

N-((3-Bromothiophen-2-yl)methyl)adamantan-1-amine

Based on general procedure Cl, from adamantan-1-amine and 3-bromothiophene-2-carbaldehyde, an off-white solid was obtained Data: LC/MS (ESCi) m/z 326.05/328.12 [M+1]$^+$.

Example 48/BC119

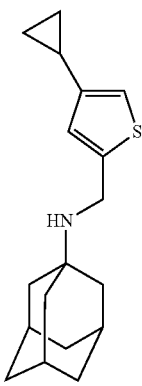 [SMILES: c1sc(CNC23CC4CC(CC(C4)C2)C3)cc1C1CC1]

N-((4-Cyclopropylthiophen-2-yl)methyl)adamantan-1-amine

Based on general procedure C, from adamantan-1-amine and 4-cyclopropylthiophen-2-carbaldehyde (General Procedure H), a light solid was obtained Data: LC/MS (ESCi) m/z 288.28 [M+1]$^+$.

Example 49b/BC120

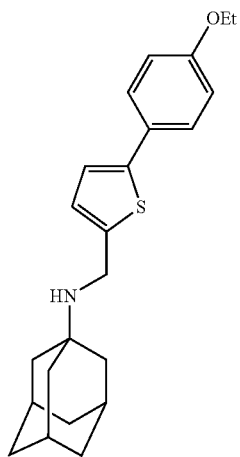 [SMILES: CCOc1ccc(-c2ccc(CNC34CC5CC(CC(C5)C3)C4)s2)cc1]

N-((5-(4-Ethoxyphenyl)thiophen-2-yl)methyl)adamantan-1-amine

Based on general procedure Cl, from adamantan-1-amine and 5-(4-ethoxyphenyl)thiophene-2-carbaldehyde (general procedure F), a white solid was obtained Data: LC/MS (ESCi) m/z 368.16 [M+1]$^+$.

Example 50b/BC121

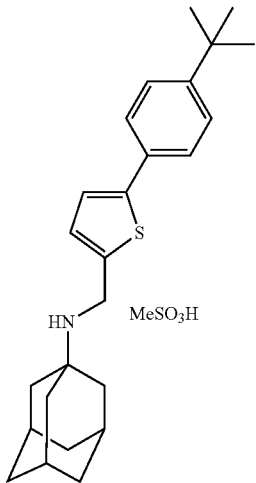 [SMILES: "MeSO3H" ; CC(C)(C)c1ccc(-c2ccc(CNC34CC5CC(CC(C5)C3)C4)s2)cc1]

N-((5-(4-(tert-Butyl)phenyl)thiophen-2-yl)methyl)adamantan-1-amine

Based on general procedure Cl, from adamantan-1-amine and 5-(4-(tert-butyl)phenyl)thiophene-2-carbaldehyde (general procedure F). The free amine was dissolved in diethyl ether and cooled to 0° C. and MeSO$_3$H (1 eq) was added under N$_2$, and then mixture was stirred at 0° C. for 15 min and filtered to give a white solid was obtained Data: LC/MS (ESCi) m/z 380.24 [M+1]$^+$.

Example 51b/BC070

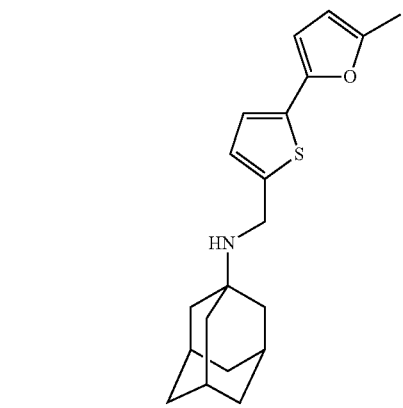

N-((4'-Methyl-[2,2'-bithiophen]-5-yl)methyl)adamantan-1-amine

Based on general procedure F, from N-((5-bromothiophen-2-yl)methyl)adamantan-1-amine and potassium 4-methyl(furan-2yl) trifluoroborate, a light brown oil was obtained Data: LC/MS (ESCi) m/z 344.24 [M+1]$^+$.

Example 52b/BC071

N-((5-(5-Methylfuran-2-yl)thiophen-2-yl)methyl)adamantan-1-amine

Based on general procedure F, from N-((5-bromothiophen-2-yl)methyl)adamantan-1-amine and potassium 5-methyl(furan-2-yl)trifluoroborate, a brown solid was obtained Data: LC/MS (ESCi) m/z 328.12 [M+1]$^+$.

Example 53b/Hij411

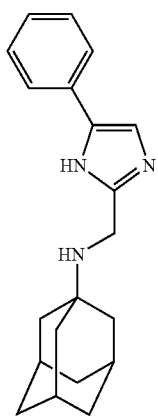 [SMILES: c1ccc(-c2cnc(CNC34CC5CC(CC(C5)C3)C4)[nH]2)cc1]

N-((5-phenyl-1H-imidazol-2-yl)methyl)adamantan-1-amine 4-phenyl-imidazole-2-carbaldehyde (2.7 g, 15.6 mmol) in DMF (15 mL) was treated with triethylamine (2 eq) and trityl chloride (1.3 eq) in DMF (10 mL). After completion of the reaction, the solution was diluted with ethyl acetate and washed with brine, sat. sodium carbonate and water to yield the yellow powder (3.3 g) after concentration under reduced pressure. A portion of the crude mixture (828 mg) was dissolved in methanol (10 mL) and sodium borohydride (2 eq) was added at room temperature for 3 h. The solution was concentrated and diluted with ethyl acetate and water. After washing with brine and concentration under reduced pressure, the crude mixture was concentrated. Based upon the general procedure I, the product was obtained after removal of trityl group 50% TFA/5% TIPS in DCM (10 mL). Data: LC/MS (ESR) m/z 308 [M+H]$^+$.

Example 54b/Hij372

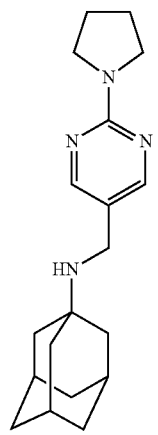

N-((2-(pyrrolidin-1-yl)pyrimidin-5-yl)methyl)adamantan-1-amine

Based on general procedure I, from adamantan-1-ylamine and 2-(pyrrolidin-1-yl)pyrimidin-5-yl) methanol, a white solid (30%) is obtained. Data: LC/MS (ESR) m/z 313 [M+H]$^+$.

Example 55b/Hij374

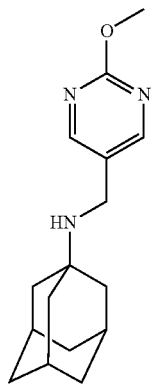

N-((2-methoxypyrimidin-5-yl)methyl)adamantan-1-amine

Based on general procedure I, from adamantan-1-ylamine and 2-methoxypyrimidin-5-yl)methanol, a white solid (30%) is obtained. Data: LC/MS (ESR) m/z 274 [M+H]$^+$.

Example 56b/Hij381

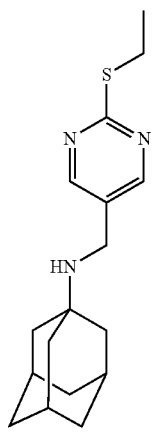 [SMILES: CCSc1ncc(CNC23CC4CC(CC(C4)C2)C3)cn1]

N-((2-(ethylthio)pyrimidin-5-yl)methyl)adamantan-1-amine

Based on general procedure I, from adamantan-1-ylamine and 2-(ethylthio)pyrimidin-5-yl)methanol, a white solid (20%) is obtained. Data: LC/MS (ESR) m/z 304 [M+H]$^+$.

Example 57b/Hij405

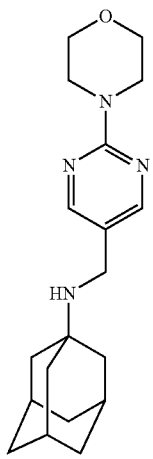 [SMILES: c1nc(N2CCOCC2)ncc1CNC12CC3CC(CC(C3)C1)C2]

N-((2-morpholinopyrimidin-5-yl)methyl)adamantan-1-amine

Based on general procedure I, from adamantan-1-ylamine and 2-(morpholino)pyrimidin-5-yl)methanol, a white solid (15%) is obtained. Data: LC/MS (ESR) m/z 329 [M+H]$^+$.

Example 58b/Hij382

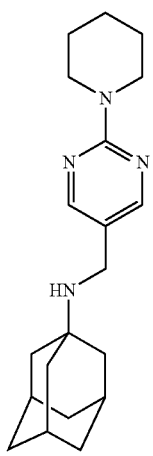

N-((2-(piperidin-1-yl)pyrimidin-5-yl)methyl)adamantan-1-amine

Based on general procedure I, from adamantan-1-ylamine and 2-(piperidin-1-yl)pyrimidin-5-yl)methanol, a white solid (20%) is obtained. Data: LC/MS (ESR) m/z 327 [M+H]$^+$.

Example 59b/WFD108

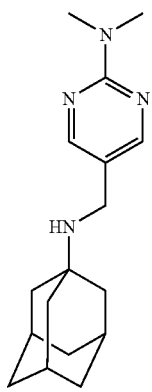 [SMILES: CN(C)c1ncc(CNC23CC4CC(CC(C4)C2)C3)cn1]

N-((2-dimethylaminopyrimidin-5-yl)methyl)adamantan-1-amine

Based on general procedure C, from adamantan-1-ylamine and N-((2-dimethylaminopyrimidin-5-yl) carbaldehyde, a white solid (30%) is obtained. Data: LC/MS (ESR) m/z 287 [M+H]$^+$.

Example 60b/Hij415

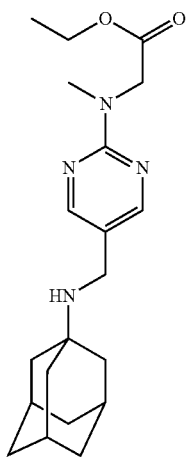 [SMILES: CCOC(=O)CN(C)c1ncc(CNC23CC4CC(CC(C4)C2)C3)cn1]

N-((2-methyl(ethylcarboxymethyl)aminopyrimidin-5-yl)methyl)adamantan-1-amine

Based on general procedure C, from adamantan-1-ylamine and N-((2-methyl(ethylcarboxymethyl)aminopyrimidin-5-yl)methyl) carbaldehyde, a white solid (30%) is obtained. Data: LC/MS (ESR) m/z 373 [M+H]$^+$.

Example 61b/Hij414

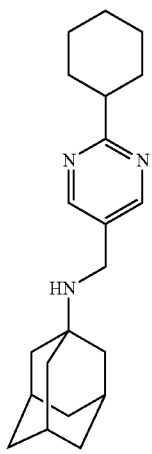

N-((2-cyclohexylpyrimidin-5-yl)methyl)adamantan-1-amine

Based on general procedure C, from adamantan-1-ylamine and N((2-cyclohexylpyrimidin-5-yl carbaldehyde, a white solid (15%) is obtained. Data: LC/MS (ESR) m/z 326 [M+H]$^+$.

Example 62b/Hij416

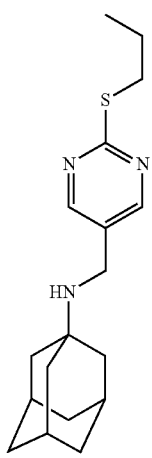 [SMILES: CCCSc1ncc(CNC23CC4CC(CC(C4)C2)C3)cn1]

N-((2-propylthiopyrimidin-5-yl)methyl)adamantan-1-amine

Based on general procedure C, from adamantan-1-ylamine and N((2-propylthiopyrimidin-5-yl) carbaldehyde, a white solid (60%) is obtained. Data: LC/MS (ESR) m/z 318 [M+H]$^+$.

Example 63b/Hij417

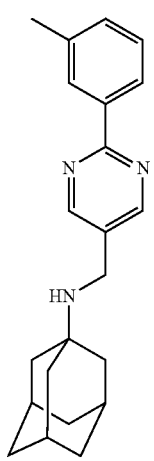 [SMILES: Cc1cccc(-c2ncc(CNC34CC5CC(CC(C5)C3)C4)cn2)c1]

N-((2-mtolylpyrimidin-5-yl)methyl)adamantan-1-amine

Based on general procedure C, from adamantan-1-ylamine and N-((2-mtolylpyrimidin-5-yl) carbaldehyde, a white solid (10%) is obtained. Data: LC/MS (ESR) m/z 334 [M+H]$^+$.

Example 64b/Hij406

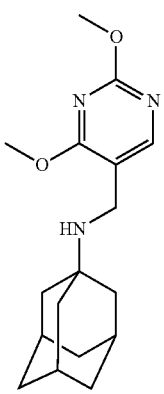 [SMILES: COc1ncc(CNC23CC4CC(CC(C4)C2)C3)c(OC)n1]

N-((2,4-dimethoxypyrimidin-5-yl)methyl)adamantan-1-amine

Based on general procedure C, from adamantan-1-ylamine and N-((2,4-dimethoxypyrimidin-5-yl) carbaldehyde, a white solid (10%) is obtained. Data: LC/MS (ESR) m/z 304 [M+H]$^+$.

Example 65b/IMX769

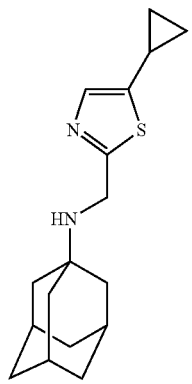 [SMILES: c1nc(CNC23CC4CC(CC(C4)C2)C3)sc1C1CC1]

Adamantan-1-yl-(5-cyclopropyl-thiazol-2-ylmethyl)-amine

Based on general procedure G, form adamantan-1-yl-(5-bromo-thiazol-2-ylmethyl)-amine (Example 86a) and cyclopropylboronic acid, an off-white solid was obtained (46%). Data: LC/MS (ESR) m/z 289 [M+H]$^+$.

Example 66b/IMX747

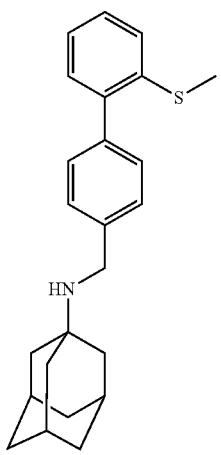 [SMILES: CSc1ccccc1-c1ccc(CNC23CC4CC(CC(C4)C2)C3)cc1]

Adamantan-1-yl-(2'-methylsulfanyl-biphenyl-4-ylmethyl)-amine

Based on general procedure G, form adamantan-1-yl-(4-bromo-benzyl)-amine (Example 41) and [2-(Methylsulfanyl)phenyl]boronic acid, a white solid was obtained (46%). Data: LC/MS (ESR) m/z 364 [M+H]$^+$.

Example 67b/IMX745

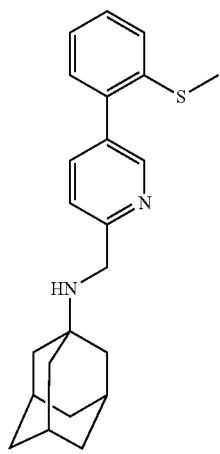

Adamantan-1-yl-[5-(2-methylsulfanyl-phenyl)-pyridin-2-ylmethyl]-amine

Based on general procedure G, form adamantan-1-yl-(5-bromo-pyridin-2-ylmethyl)-amine (Example 54a) and [2-(methylsulfanyl)phenyl]boronic acid, a white solid was obtained (56%). Data: LC/MS (ESR) m/z 365 [M+H]$^+$.

Example 68b/IMX746

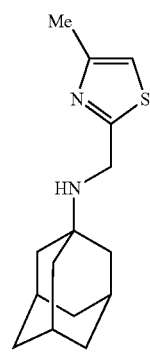 [SMILES: Cc1csc(CNC23CC4CC(CC(C4)C2)C3)n1]

Adamantan-1-yl-(4-methyl-thiazol-2-ylmethyl)-amine

Based on general procedure A, from 4-methyl-thiazole-2-carbaldehyde and adamantan-1-ylamine, a white solid (70%) is obtained. Data: LC/MS (ESR) m/z 263 [M+H]$^+$.

Example 69b/IMX744

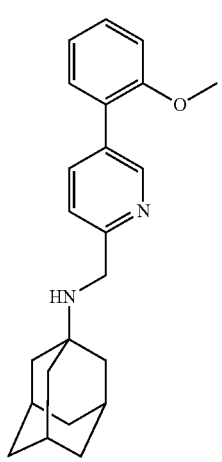

Adamantan-1-yl-[5-(2-methoxy-phenyl)-pyridin-2-ylmethyl]-amine

Based on general procedure G, form adamantan-1-yl-(5-bromo-pyridin-2-ylmethyl)-amine (Example 54a) and 2-methoxyphenylboronic acid, a white solid was obtained (66%). Data: LC/MS (ESR) m/z 349 [M+H]+

Example 70b/IMX747

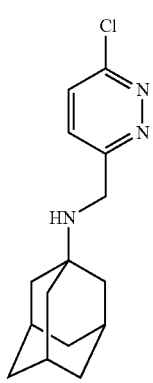

Adamantan-1-yl-(6-chloro-pyridazin-3-ylmethyl)-amine

Based on general procedure A, from 6-Chloro-pyridazine-3-carbaldehyde and adamantan-1-ylamine, an off-white solid (70%) is obtained. Data: LC/MS (ESR) m/z 278 [M+H]+.

Example 71b/IMX748

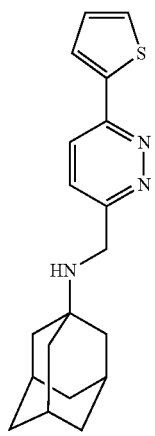 [SMILES: c1csc(-c2ccc(CNC34CC5CC(CC(C5)C3)C4)nn2)c1]

Adamantan-1-yl-(6-thiophen-2-yl-pyridazin-3-ylmethyl)-amine

Based on general procedure G, form adamantan-1-yl-(6-chloro-pyridazin-3-ylmethyl)-amine and 2-thiopheneboronic acid, a yellow solid was obtained (46%). Data: LC/MS (ESR) m/z 326 [M+H]+.

Example 72b/IMX755

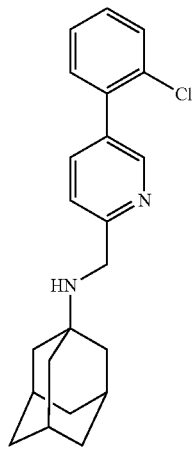

Adamantan-1-yl-[5-(2-chloro-phenyl)-pyridin-2-ylmethyl]-amine

Based on general procedure G, form adamantan-1-yl-(5-bromo-pyridin-2-ylmethyl)-amine (Example 54a) and 2-chlorophenylboronic acid, an off-white solid was obtained (56%). Data: LC/MS (ESR) m/z 353 [M+H]+.

Example 73b/IMX756

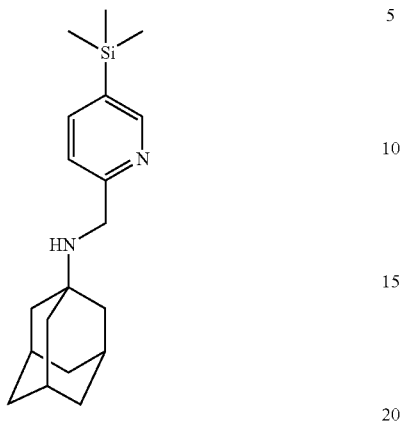

Adamantan-1-yl-(5-trimethylsilanyl-pyridin-2-ylmethyl)-amine

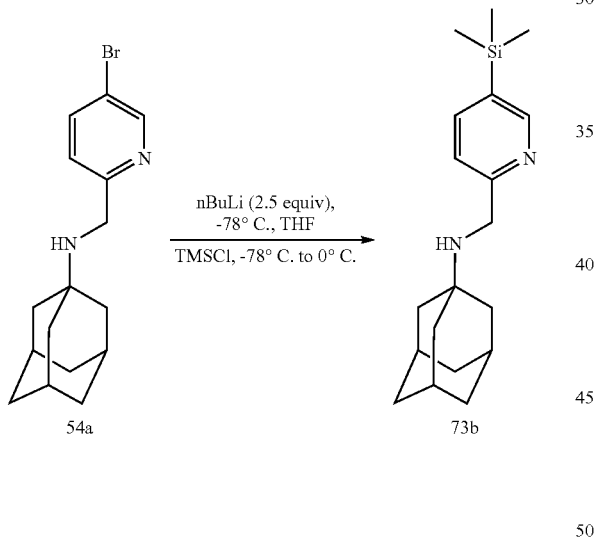

At −78° C., to adamantan-1-yl-(5-bromo-pyridin-2-ylmethyl)-amine Ma (321 mg, 1 mmol) in THF (10 mL) was added dropwise nBuLi (2.5 M in Hexane, 1.0 mL, 2.5 mmol). After the mixture was stirred at the same temperature for 10 min, TMSCl (130 mg, 1.2 mmol) was added dropwise. The resulting mixture was stirred for 30 min and warmed up to 0° C. over 1 h. The mixture was recooled to −78° C. and was quenched with NH$_4$Cl (sat'd) (5 ml). After the mixture was wormed to room temperature, it was extracted with DCM (10 mL×3). The organic layer was separated, dried over anhydrous magnesium sulfate, filtered and concentrated under reduced pressure. The mixture was then purified by silica gel flash column chromatography (1-10% CH$_3$OH/CH$_2$Cl$_2$) to give the title product 73b (174 mg, 56%) as a white solid. Data: LC/MS (ESR) m/z 315 [M+H]$^+$.

Example 74b/IMX757

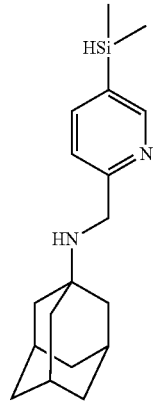

Adamantan-1-yl-(5-dimethylsilanyl-pyridin-2-ylmethyl)-amine

Based on the same procedure of example 73b excepting using chloro-dimethyl-silane instead of chloro-trimethyl-silane. A white solid (51%) was obtained. Data: LC/MS (ESR) m/z 301 [M+H]$^+$.

Example 75b/IMX734

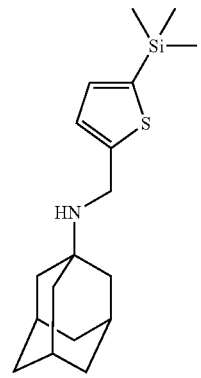

Adamantan-1-yl-(5-trimethylsilanyl-thiophen-2-ylmethyl)-amine

Based on the same procedure of example 73b excepting using adamantan-1-yl-(5-bromo-thiophen-2-ylmethyl)-amine (Example 81) instead of adamantan-1-yl-(5-bromo-pyridin-2-ylmethyl)-amine 54a. A white solid (41%) was obtained. Data: LC/MS (ESR) m/z 320 [M+H]$^+$.

Example 76b/IMX742

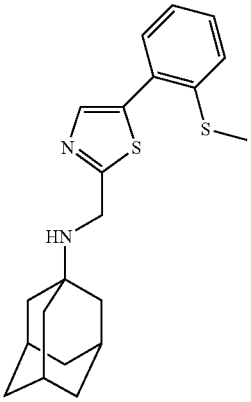 [SMILES: CSc1ccccc1-c1cnc(CNC23CC4CC(CC(C4)C2)C3)s1]

Adamantan-1-yl-[5-(2-methylsulfanyl-phenyl)-thiazol-2-ylmethyl]-amine

Based on general procedure G, form adamantan-1-yl-(5-bromo-thiazol-2-ylmethyl)-amine (Example 86a) and [2-(methylsulfanyl)phenyl]boronic acid, an off-white solid was obtained (45%). Data: LC/MS (ESR) m/z 371 [M+H]⁺.

Example 77b/IMX751

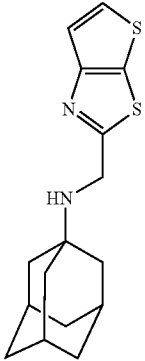 [SMILES: c1cc2nc(CNC34CC5CC(CC(C5)C3)C4)sc2s1]

Adamantan-1-yl-thieno[3,2-d]thiazol-2-ylmethyl-amine

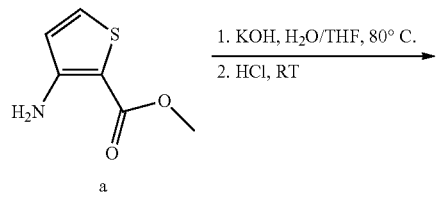

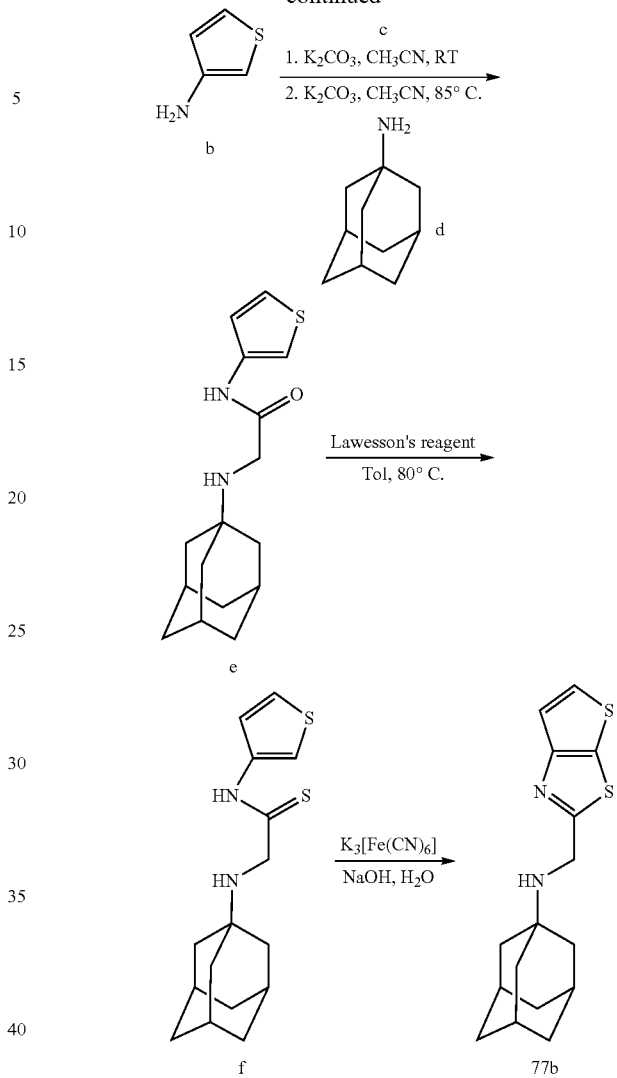

3-Amino-thiophene-2-carboxylic acid methyl ester (a) (1.57 g, 10 mmol), KOH (2.8 g, 50 mml) was dissolved in THF (50 mL) and water (5 mL). The mixture was heated at 80° C. overnight. The volatile was removed under vacuum and resulting mixture was treated with HCl (5 M, 10 mL, 50 mmol). Then the mixture was extracted with DCM (30 mL×3). The combined organic layer was dried over MgSO₄, and concentrated under reduced pressure after filtration to give a crude product thiophen-3-ylamine b (0.55 g, 56%). Data: LC/MS (ESR) m/z 100 [M+H]⁺. To a mixture of thiophen-3-ylamine b (0.5 g, 5.1 mmol) and K₂CO₃ (0.77 g, 5.6 mmol) in CH₃CN (10 mL), bromo-acetyl chloride (0.79 g, 5.1 mml) was added dropwise. The mixture was stirred overnight at room temperature. Then K₂CO₃ (0.77 g, 5.6 mmol) and adamantan-1-ylamine (0.92 g, 6.1 mmol) were added to the above mixture. After the mixture was heated at 85° C. for overnight, the mixture was filtered and the filter was concentrated. The crude residue was separated by flash column chromatography (1-10% CH₃OH/CH₂Cl₂) to give the tile compound 2-(adamantan-1-ylamino)-N-thiophen-3-yl-acetamide e (0.75 g, 51%) as a pink solid. Data: LC/MS (ESR) m/z 291 [M+H]⁺.

Lawesson's reagent (969.6 mg, 2.4 mmol) was added portions to a solution of 2-(adamantan-1-ylamino)-N-thiophen-3-yl-acetamide e (580 mg, 2.0 mmol) in toluene (10 mL) at 80° C. The mixture was heated for 2 h before the solvent was removed in vacuo. The crude residue was separated by flash column chromatography (1-10% CH₃OH/CH₂Cl₂) to give the tile compound 2-(adamantan-1-ylamino)-N-thiophen-3-yl-thioacetamide f (0.53 g, 87%) as a yellow solid. Data: LC/MS (ESR) m/z 307 [M+H]⁺.

To a solution of 2-(adamantan-1-ylamino)-N-thiophen-3-yl-thioacetamide f (0.52 g, 1.7 mmol) in ethanol (1 mL) was added 30% NaOH (1.6 mL, 12.0.0 mmol). The mixture was diluted to give 10% NaOH and stirred for 5 min. Portions of this mixture were added at 1 min intervals to a stirred solution of K3[Fe(CN)6] (2.0 g, 6.0 mmol) in H₂O (3 mL) at 85° C. The resulting mixture was further heated at 85° C. for 1 h. Solvent was removed in vacuo and the residue was extracted with DCM (5 mL×3). The combined organic layer was dried over MgSO₄, concentrated and separated by flash column chromatography (1-10% CH₃OH/CH₂Cl₂) to give the tile compound adamantan-1-yl-thieno[3,2-d]thiazol-2-ylmethyl-amine 77b/IMX751 (0.26 g, 52%) as a pink solid. Data: LC/MS (ESR) m/z 305 [M+H]⁺.

Example 78b/IMX738

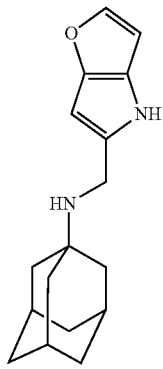 [SMILES: c1cc2[nH]c(CNC34CC5CC(CC(C5)C3)C4)cc2o1]

Adamantan-1-yl-(4H-furo[3,2-b]pyrrol-5-ylmethyl)-amine

Based on general procedure C, form adamantan-1-ylamine and 4H-Furo[3,2-b]pyrrole-5-carboxylic acid, an pink solid was obtained (26%). Data: LC/MS (ESR) m/z 271 [M+H]⁺.

Example 79b/IMX724

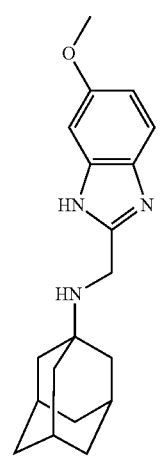 [SMILES: COc1ccc2nc(CNC34CC5CC(CC(C5)C3)C4)[nH]c2c1]

Adamantan-1-yl-(6-methoxy-1H-benzoimidazol-2-ylmethyl)-amine

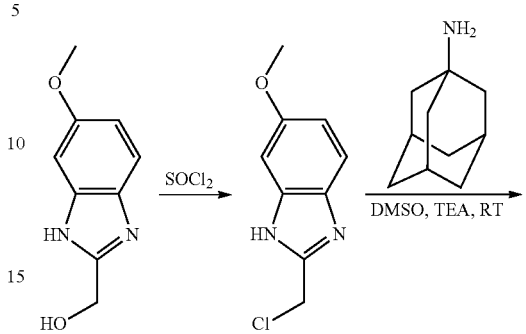

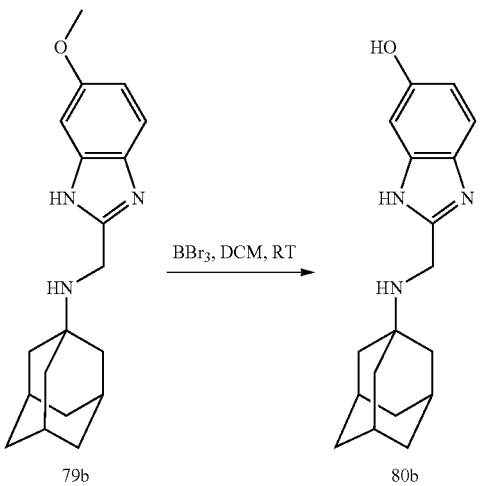

A solution of (6-methoxy-1H-benzoimidazol-2-yl)-methanol a (356 mg, 2.0 mmol) in SO₂Cl (2 mL) was heated at 70° C. for 1 h. Solvent was removed in vacuo and the resulting 2-chloromethyl-6-methoxy-1H-benzoimidazole b was used directly to the next step without further purification. To a solution of 6-methoxy-1H-benzoimidazole b in DMSO (5 mL) was added adamantan-1-ylamine (453 mg, 30.0 mmol) and TEA (0.5 mL). The solution was stirred for overnight before it was quenched with H₂O (5 mL). The mixture was extracted with DCM (10 mL×3). The combined organic layer was dried over MgSO₄, concentrated and separated by flash column chromatography (1-10% CH₃OH/CH₂Cl₂) to give the tile compound adamantan-1-yl-(6-methoxy-1H-benzoimidazol-2-ylmethyl)-amine 79b/IMX724 (0.23 g, 37%) as a white solid. Data: LC/MS (ESR) m/z 312 [M+H]⁺.

Example 80b/IMX725

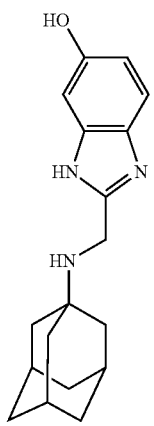 [SMILES: Oc1ccc2nc(CNC34CC5CC(CC(C5)C3)C4)[nH]c2c1]

2-(Adamantan-1-ylaminomethyl)-3H-benzoimidazol-5-ol

At −78° C., BBr₃ (1.0 M in DCM, 0.8 mL, 0.8 mmol) was added dropwise to a solution of adamantan-1-yl-(6-methoxy-1H-benzoimidazol-2-ylmethyl)-amine 79b/IMX724 (0.15 g, 0.48 mmol). The mixture was stirred at −78° C. for 30 min and warmed to rt. The mixture was quenched with NaHCO₃ (sat'd) (5 mL). The mixture was extracted with DCM (10 mL×3). The combined organic layer was dried over MgSO₄, concentrated and separated by flash column chromatography (1-10% CH₃OH/CH₂Cl₂) to give the tile compound 2-(adamantan-1-ylaminomethyl)-3H-benzoimidazol-5-ol 80b/IMX724 (0.12 g, 86%) as a white solid. Data: LC/MS (ESR) m/z 298 [M+H]⁺.

Example 81b/IMX722

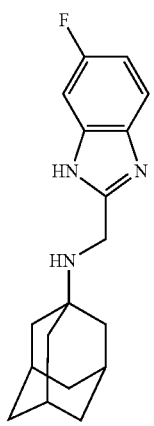 [SMILES: Fc1ccc2nc(CNC34CC5CC(CC(C5)C3)C4)[nH]c2c1]

Adamantan-1-yl-(6-fluoro-1H-benzoimidazol-2-ylmethyl)-amine

Followed the same procedure of Example 79b/IMX724 except using (6-fluoro-1H-benzoimidazol-2-yl)-methanol to replace (6-methoxy-1H-benzoimidazol-2-yl)-methanol. A white solid (38%). Data: LC/MS (ESR) m/z 300 [M+H]⁺.

Example 82b/M2WJ418

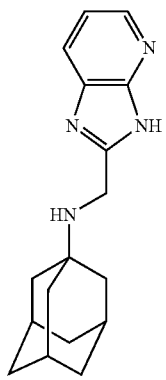

N-((3H-imidazo[4,5-b]pyridin-2-yl)methyl)adamantan-1-amine

Based on general procedure E, from amantadine and 2-(chloromethyl)-3H-imidazo[4,5-b]pyridine, a yellow solid (87%) is obtained. Data: LC/MS (ESR) m/z 283 [M+H]⁺.

Example 83b/IMX715

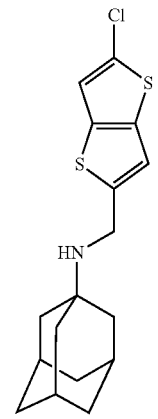 [SMILES: Clc1cc2sc(CNC34CC5CC(CC(C5)C3)C4)cc2s1]

Adamantan-1-yl-(5-chloro-thieno[3,2-b]thiophen-2-ylmethyl)-amine

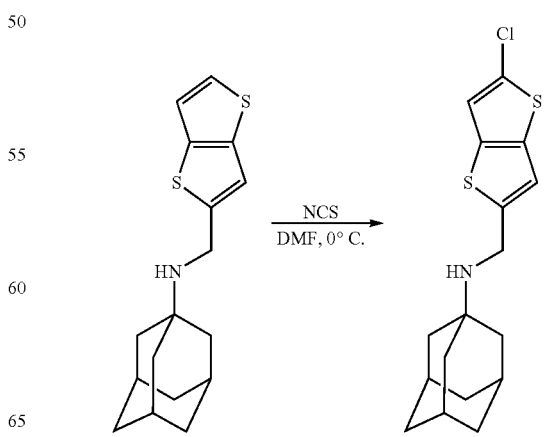

To a solution of Adamantan-1-yl-thieno[3,2-b]thiophen-2-ylmethyl-amine (150 mg, 0.5 mmol) was treated with NBS (90 mg, 0.5 mmol) in DMF (5 mL) at 0° C. for 2 h. The solvent was removed concentrated under reduced pressure. The crude product was separated by flash column chromatography (1-10% CH$_3$OH/CH$_2$Cl$_2$) to give the title compound (36 mg, 20%). Data: LC/MS (ESR) m/z 338 [M+1]$^+$.

Example 84b/M2WJ427

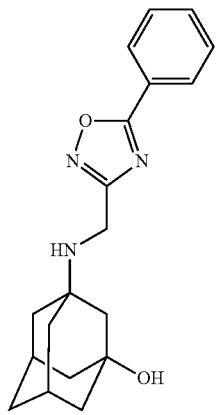 [SMILES: OC12CC3CC(C1)CC(NCc1noc(-c4ccccc4)n1)(C3)C2]

(1s,3r,5R,7S)-3-(((5-phenyl-1,2,4-oxadiazol-3-yl)methyl)amino)adamantan-1-61

Based on general procedure E, from (1s,3r,5R,7S)-3-aminoadamantan-1-ol and 3-(chloromethyl)-5-phenyl-1,2,4-oxadiazole, a yellow solid (88%) is obtained. Data: LC/MS (ESR) m/z 326 [M+H]$^+$.

Example 85b/M2WJ433

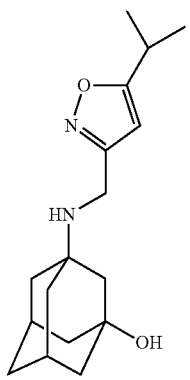 [SMILES: CC(C)c1cc(CNC23CC4CC(CC(O)(C4)C2)C3)no1]

(1s,3r,5R,7S)-3-(((5-isopropylisoxazol-3-yl)methyl)amino)adamantan-1-61

Based on general procedure E, from (1s,3r,5R,7S)-3-aminoadamantan-1-ol and 3-(bromomethyl)-5-isopropylisoxazole, a yellow solid (72%) is obtained. Data: LC/MS (ESR) m/z 291 [M+H]$^+$.

Example 86b/M2WJ429

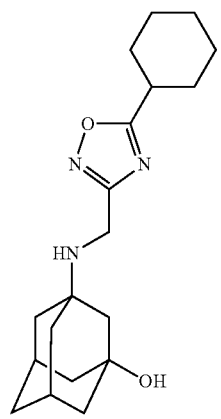 [SMILES: OC12CC3CC(C1)CC(NCc1noc(C4CCCCC4)n1)(C3)C2]

(1s,3r,5R,7S)-3-(((5-cyclohexyl-1,2,4-oxadiazol-3-yl)methyl)amino)adamantan-1-ol Based on general procedure E, from (1s,3r,5R,7S)-3-aminoadamantan-1-ol and 3-(bromomethyl)-5-cyclohexyl-1,2,4-oxadiazole, a yellow solid (75%) is obtained. Data: LC/MS (ESR) m/z 332 [M+H]$^+$.

Example 87b/Hij341

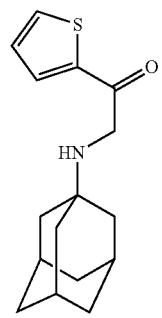 [SMILES: O=C(CNC12CC3CC(CC(C3)C1)C2)c1cccs1]

2-(adamantan-1-ylamino)-1-(thiophen-2-yl)ethanone

A mixture of adamantan-1-ylamine (2 mmol) and bromoacetylthiophen (1 mmol) in THF (6 mL) was stirred for 30 min at room temperature. The volatiles were removed and the crude mixture was purified by RP-HPLC. Data: LC/MS (ESR) m/z 276 [M+H]$^+$.

Example 88b/Hij350

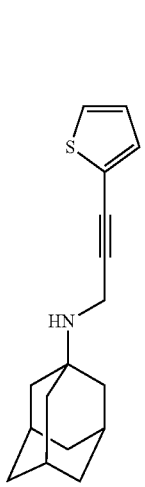 [SMILES: C(#Cc1cccs1)CNC12CC3CC(CC(C3)C1)C2]

N-((2,4-dimethoxypyrimidin-5-yl)methyl)adamantan-1-amine

Based on general procedure I, from adamantan-1-ylamine and 3-(thiophen-2-yl)prop-2-yn-1-ol, a white solid (20%) is obtained. Data: LC/MS (ESR) m/z 272 [M+H]$^+$.

Example 89b/IMX737

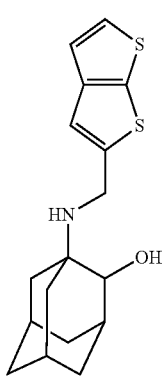 [SMILES: OC1C2CC3CC(C2)CC1(NCc1cc2ccsc2s1)C3]

(±)-1-[(Thieno[2,3-b]thiophen-2-ylmethyl)-amino] adamantan-2-ol

Based on general procedure A, from (±)-1-amino-adamantan-2-ol (Armarego, W. L. F. et al. *Australian Journal of Chemistry*, 1979, 32, 1805-17) and thieno[2,3-b]thiophene-2-carbaldehyde, a white solid (30%) is obtained. Data: LC/MS (ESR) m/z 320 [M+H]$^+$.

Example 90b/M2WJ450

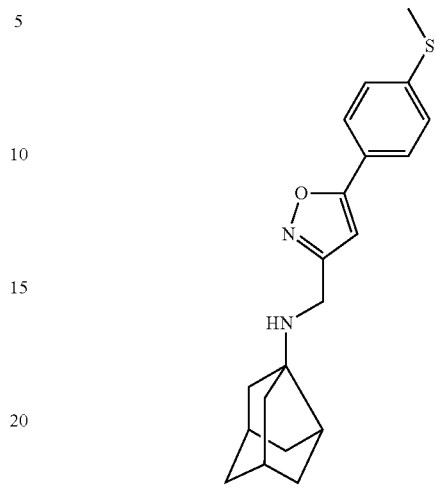

(2R,3as,5S,6as)-N-((5-(4-(methylthio)phenyl)isoxazol-3-yl)methyl)octahydro-2,5-methanopentalen-3a-amine Based on general procedure E, from (2R,3as,5S,6as)-octahydro-2,5-methanopentalen-3a-amine and 3-(bromomethyl)-5-(4-(methylthio)phenyl)isoxazole, a yellow solid (90%) is obtained. Data: LC/MS (ESR) m/z 341 [M+H]$^+$.

Example 91b/M2WJ453

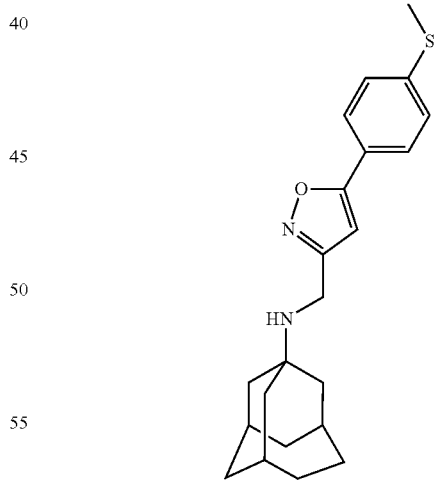

(1S,3R,8S)—N-((5-(4-(methylthio)phenyl)isoxazol-3-yl)methyl)tricyclo[4.3.1.13,8]undecan-1-amine Based on general procedure E, from (1S,3R,8S)-tricyclo [4.3.1.13,8]undecan-1-amine and 3-(bromomethyl)-5-(4-(methylthio)phenyl)isoxazole, a yellow solid (91%) is obtained. Data: LC/MS (ESR) m/z 369 [M+H]$^+$.

Example 92b/IMX800

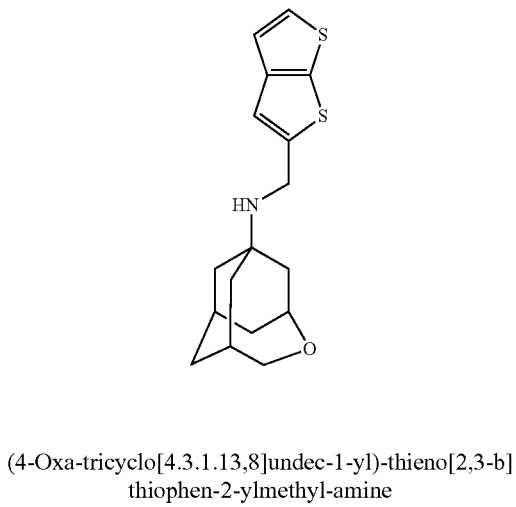

(4-Oxa-tricyclo[4.3.1.13,8]undec-1-yl)-thieno[2,3-b]thiophen-2-ylmethyl-amine

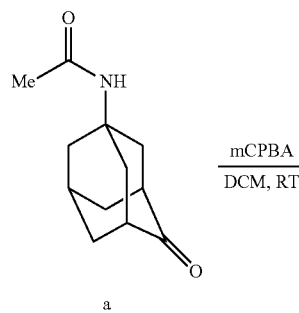

a

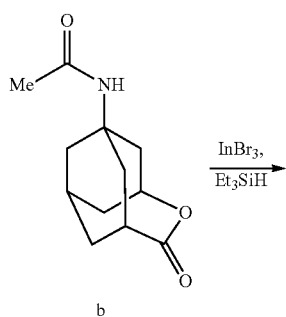

b

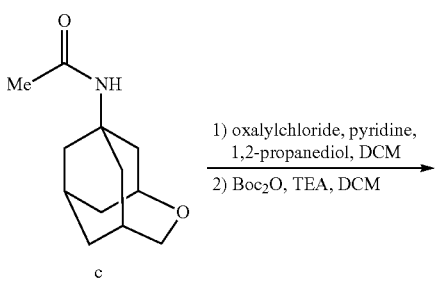

c

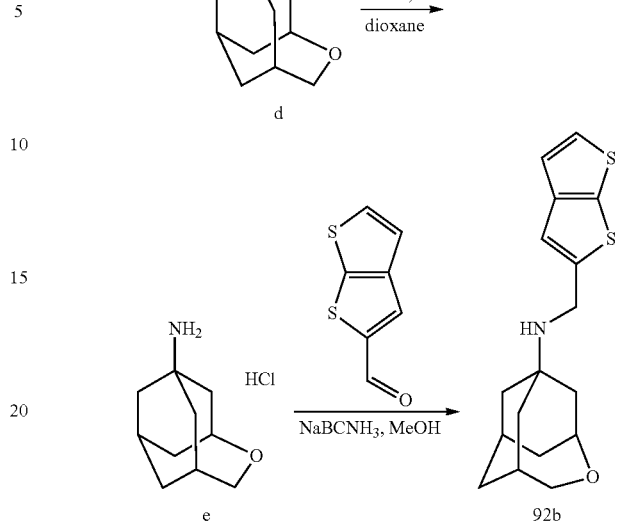

Solid mCPBA (551 mg, 2.4 mmol, 77% purity) were added to a solution of ketone a (414 mg, 2 mmol) in DCM (5 mL) at 0° C. The reaction mixture was allowed to warm to rt and was maintained for 1 h. The reaction mixture was diluted with a saturated, aqueous solution of sodium bisulfate (10 mL) and was extracted with DCM (3×10 mL). The combined organic layers were dried ($Na_2SO_4$) and concentrated. The residue was purified by silica gel chromatography (10/90 to 30/70 EtOAc/hexane) to provide lactone b in (401 mg, 90%). Data: LC/MS (ESR) m/z 224 [M+H]$^+$.

$InBr_3$ (700 mg, 2.0 mmol) and $Et_3SiH$ (1 mL) were successively added to a solution of lactone 16A (400 mg, 1.79 mmol) in $CHCl_3$ (10 mL) and the reaction mixture was heated at 60° C. for 1 h. The reaction mixture was allowed to cool to rt, was diluted with $H_2O$ (10 mL), and the layers were separated. The aqueous layer was extracted with DCM (3×10 mL) and the combined organic layers were dried ($Na_2SO_4$) and concentrated. The residue was purified by silica gel chromatography (10/90 to 30/70 EtOAc/hexane) to provide ether c (218 mg, 58%). Data: LC/MS (ESR) m/z 210 [M+H]$^+$.

A 2.0 M solution of oxalyl chloride in DCM (1.0 ml, 2.0 mmol) was added dropwise to a solution of amide c (210 mg, 1.0 mmol) in dry THF (5 mL) and pyridine (0.5 mL) at 0° C. The reaction mixture was maintained at 0° C. for 30 min when 1,2-propanediol (0.5 mL) was added in one portion and the reaction was allowed to warm to rt. The reaction mixture was diluted with EtOH (5 mL) and was concentrated. The crude oil was partitioned between 1 M aqueous HCl (2 mL) and TBME (5 mL) and the layers were separated. The organic phase was extracted with 1.0 M aqueous HCl solution (2×5 mL) and the pH of the combined aqueous layers was adjusted to pH 11 with 4 N aqueous NaOH. The aqueous layer was then extracted with DCM (3×5 mL) and the combined organic layers were dried ($Na_2SO_4$), and concentrated to provide the crude amine. Data: LC/MS (ESR) m/z 168 [M+H]$^+$.

Boc-anhydride (654 mg, 3.0 mmol) and TEA (1.0 mL) was added sequentially to a solution of the crude amine in DCM (5 mL) and the reaction mixture was maintained at rt for 2 h. The reaction mixture was diluted with a saturated, aqueous solution of NH₄Cl (1 mL) and the aqueous layer was extracted with DCM (3×10 mL). The combined organic layers were dried (Na₂SO₄) and concentrated. The residue was purified by silica gel chromatography (10/90 to 30/70 EtOAc/hexane) to provide the pure carbamate d (93.5 mg, 35% yield. Data: LC/MS (ESR) m/z 268 [M+H]⁺.

The carbamate d (90 mg, 0.34 mmol) in 1,4-dioxane (1 mL) was diluted with a solution of 4 N HCl in dioxane (1.0 mL, 1.0 mmol) and the reaction mixture was maintained at rt for 2 h. The reaction mixture was concentrated and the residue was dissolved in water (2 mL). The aqueous layer was washed with EtOAc (3×5 mL) and concentrated to provide 4-Oxa-tricyclo[4.3.1.1³,⁸]undec-1-ylamine e (57.9 mg, 85%) as a hydrochloric acid salt. Data: LC/MS (ESR) m/z 168 [M+H]⁺.

4-Oxa-tricyclo[4.3.1.1³,⁸]undec-1-ylamine e (50 mg, 0.25 mmol), TEA (0.2 mL) and thiophene-2-carbaldehyde (84 mg mg, 2.0 mmol) were mixed in methanol (1.0 mL) and then treated with sodium cyanoborohydride (188 mg, 3 mmol). The mixture was stirred at room temperature under a N₂ atmosphere overnight. The reaction mixture was quenched by adding water, and the product was extracted with butanol (5 mL×3). The combined organic layer was dried over Na₂SO₄, and concentrated under reduced pressure. The crude product was separated by flash column chromatography (1-10% CH₃OH/CH₂Cl₂) to give the title compound (4-Oxa-tricyclo[4.3.1.1³,⁸]undec-1-yl)-thieno[2,3-b]thiophen-2-ylmethyl-amine 92B/IMX800 (34.2 mg, 43%) as a white solid. Data: LC/MS (ESR) m/z 320 [M+H]⁺.

Example 93b/IMX797, example 94b/IMX798, and example 95b/IMX799

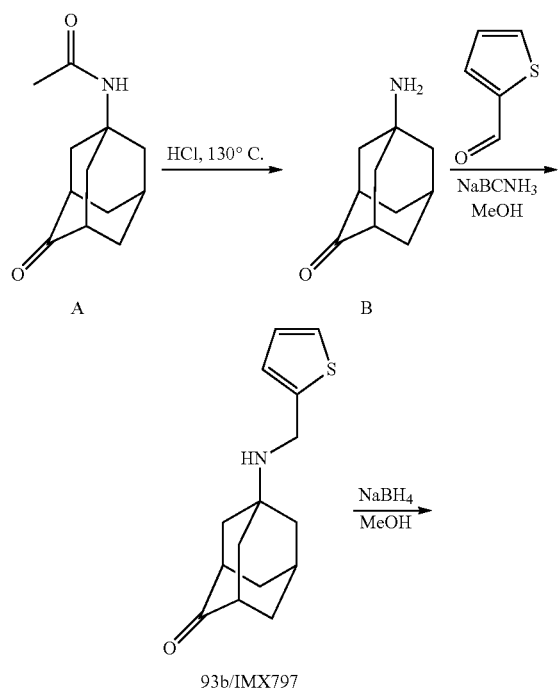

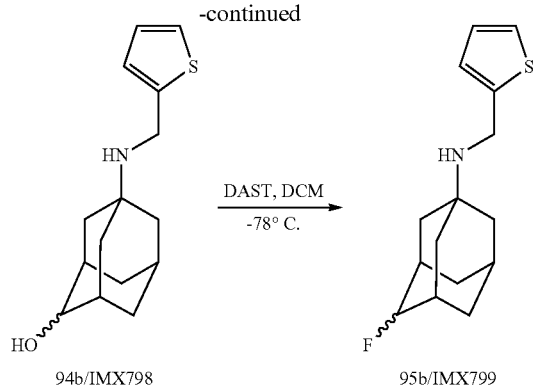

A solution of N-(4-oxoadamantan-1-yl)acetamide A (2.07 g, 10 mmol) in 100 mL of concentrated, aqueous HCl (12N) was heated in a sealed pressure tube at 130° C. for 20 h. The solvent was removed under reduced pressure to give 5-aminoadamantan-2-one B as an HCl salt (1.45 g, 90%) as an off-white solid. Data: LC/MS (ESR) m/z 166 [M+H]⁺.

Example 93b/IMX797

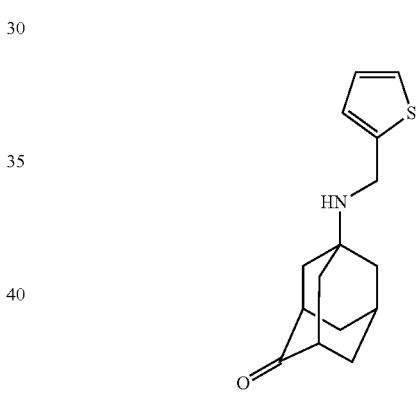

5-[(Thiophen-2-ylmethyl)-amino]-adamantan-2-one 5-aminoadamantan-2-one B (240 mg, 2.2 mmol) and thiophene-2-carbaldehyde (114 mg, 2.0 mmol) were mixed in methanol (5 mL) and then treated with sodium cyanoborohydride (376 mg, 6 mmol). The mixture was stirred at room temperature under a N₂ atmosphere overnight. The reaction mixture was quenched by adding water, and the product was extracted with butanol (10 mL×3). The combined organic layer was dried over Na₂SO₄, and concentrated under reduced pressure. The crude product was separated by flash column chromatography (1-10% CH₃OH/CH₂Cl₂) to give the title compound 5-[(thiophen-2-ylmethyl)-amino]-adamantan-2-one (201 mg, 38%) as a white solid. Data: LC/MS (ESR) m/z 262 [M+H]⁺.

Example 94b/IMX798

(±)5-[(Thiophen-2-ylmethyl)-amino]-adamantan-2-ol

Sodium borohydride (112 mg, 3.0 mmol) was added in one portion to a solution of ketone 93B (262 mg, 1.0 mmol) in MeOH (5 mL) at 0° C. The reaction mixture was allowed to warm to rt and was maintained at rt for 30 min. The solution was diluted with a saturated, aqueous NH$_4$Cl solution (5 mL) and the mixture was extracted with DCM (3×5 mL). The combined organic layers were dried (Na$_2$SO$_4$) and concentrated. The residue was purified by silica gel chromatography [0/100 to 5/95 MeOH/(50/50 DCM/Hexane)] to give alcohol 94b/IMX798 (241 mg, 92%) white solid. Data: LC/MS (ESR) m/z 264 [M+H]$^+$.

Example 95b/IMX799

(±) (4-Fluoro-adamantan-1-yl)-thiophen-2-ylmethyl-amine

A solution containing a mixture of alcohol (132 mg, 0.5 mmol) in DCM (1 mL) was added dropwise to a solution of (diethylamino)sulfur trifluoride (DAST) (97 mg, 0.6 mmol) in DCM (5 mL) at −78° C. The reaction mixture was allowed to warm to rt and was maintained for 1 h. The reaction mixture was diluted with a saturated, aqueous NH$_4$Cl solution (2 mL) and the mixture was extracted with DCM (3×5 mL). The combined organic extracts were dried (Na$_2$SO$_4$) and concentrated. The residue was purified by silica gel chromatography (0/100 to 30/70 EtOAc/hexane) to give fluoride (±) (4-Fluoro-adamantan-1-yl)-thiophen-2-ylm-ethyl-amine 95b/IMX799 (111 mg, 84%) as an off-white solid. Data: LC/MS (ESR) m/z 266 [M+1]$^+$.

Bioassay

In Vitro cRNA Transcription, Heterologous Expression, and Electrophysiological Recordings. The cDNA encoding to the influenza virus A/Udorn/72 a.m.2 protein was inserted into pGEMHJ (a gift from N. Dascal Tel-Aviv University, Israel) for expression on *Xenopus* oocytes. Plasmid was linearized with HindIII, and capped cRNA was transcribed in Vitro using T7 RNA polymerase (mMessage mMachine; Ambion, Austin, Tex.). The quality of transcripts was assessed by agarose gel electrophoresis and ethidium bromide staining and analytical UV spectroscopy. Stage V-VI *Xenopus laevis* oocytes were prepared as described previously (see Shimbo, K.; Brassard, D. L.; Lamb, R. A.; Pinto, L. H. Biophys. J. 1996, 70, 1335-1346). Oocytes were injected with 5-10 ng of cRNA in 50 nL/oocyte and assayed 2-3 days later. Two electrode voltage clamp recordings were carried out using TEV-200 (Dagan, Minneapolis, Minn.) connected to DIGIDATA 1440A and pCLAMP10 (Axon Instruments, Foster City, Calif.). Oocytes were superfused with Barth's solution containing 88 mM NaCl, 1 mM KCl, 2.4 mM NaHCO$_3$, 0.3 mM NaNO$_3$, 0.71 mM CaCl$_2$, 0.82 mM MgCl$_2$, and 15 mM HEPES for pH 8.5 or 15 mM MES for pH 5.5. Currents were recorded at −20 mV. Dose-inhibition curves were usually constructed by applying 1-3 concentrations per oocyte of antagonist mixed in recording pH 5.5 Barth's solution, and currents were normalized to the steady-state current obtained with pH 5.5 Barth's solution alone. Data were analyzed using the ORIGIN 8.0 software (OriginLab, Northampton, Mass.).

In Vitro cRNA Transcription, Heterologous Expression, and Electrophysiological Recordings. The cDNA encoding to the influenza virus A/Udorn/72 a.m.2 protein was inserted into pGEMHJ (a gift from N.Dascal Tel-Aviv University, Israel) for expression on *Xenopus* oocytes. Plasmid was linearized with HindIII, and capped cRNA was transcribed in Vitro using T7 RNA polymerase (mMessage mMachine; Ambion, Austin, Tex.). The quality of transcripts was assessed by agarose gel electrophoresis and ethidium bromide staining and analytical UV spectroscopy. Stage V-VI *Xenopus laevis* oocytes were prepared as described previously (see Shimbo, K.; Brassard, D. L.; Lamb, R. A.; Pinto, L. H. Biophys. J. 1996, 70, 1335-1346). Oocytes were injected with 5-10 ng of cRNA in 50 nL/oocyte and assayed 2-3 days later. Two electrode voltage clamp recordings were carried out using TEV-200 (Dagan, Minneapolis, Minn.) connected to DIGIDATA 1440A and pCLAMP10 (Axon Instruments, Foster City, Calif.). Oocytes were superfused with Barth's solution containing 88 mM NaCl, 1 mM KCl, 2.4 mM NaHCO3, 0.3 mM NaNO3, 0.71 mM CaCl2, 0.82 mM MgCl2, and 15 mM HEPES for pH 8.5 or 15 mM MES for pH 5.5. Currents were recorded at −20 mV. Dose-inhibition curves were usually constructed by applying 1-3 concentrations per oocyte of antagonist mixed in recording pH 5.5 Barth's solution, and currents were normalized to the steady-state current obtained with pH 5.5 Barth's solution alone. Data were analyzed using the ORIGIN 8.0 software (OriginLab, Northampton, Mass.).

Representative compounds of the present disclosure were tested for activity using the above protocol with results summarized in Tables 1-3, below. In the tables, S31 refers to AM2 virus that possesses the wild-type serine residue at the 31 position in the M2 protein, S31N refers to AM2 virus that possesses the serine→asparagine mutation at residue 31 in the M2 protein, and V27A refers to AM2 virus that possesses the valine→alanine mutation at residue 27 in the M2 protein. Activity range: (A)=31-95%, (B)=0-30%. ND: not determined.

TABLE 1

| Example Number | Compound Number | Structure | S31 OOcyte Inhibition at 100 uM (%) | S31N OOcyte Inhibition at 100 uM (%) | V27A OOcyte Inhibition at 100 uM (%) |
|---|---|---|---|---|---|
| 1 | IMX559 | 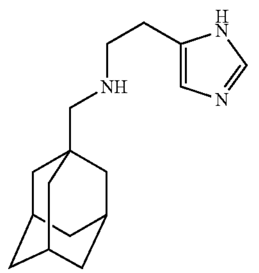 [SMILES: c1ncc(CCNCC23CC4CC(CC(C4)C2)C3)[nH]1] | B | B | B |
| 2 | IMX563 | 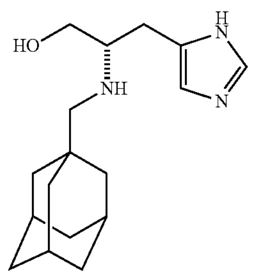 | B | B | B |
| 3 | IMX558 | 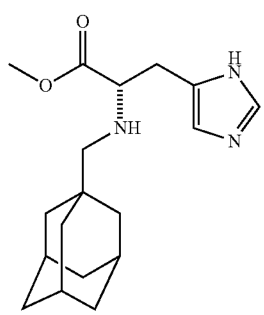 | B | B | B |
| 4 | IMX574 | 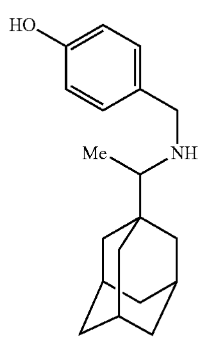 [SMILES: CC(NCc1ccc(O)cc1)C12CC3CC(CC(C3)C1)C2] | A | B | B |

TABLE 1-continued

| Example Number | Compound Number | Structure | S31 OOcyte Inhibition at 100 uM (%) | S31N OOcyte Inhibition at 100 uM (%) | V27A OOcyte Inhibition at 100 uM (%) |
|---|---|---|---|---|---|
| 5 | IMX603 | 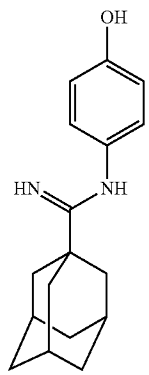 [SMILES: N=C(Nc1ccc(O)cc1)C12CC3CC(CC(C3)C1)C2] | A | B | B |
| 6 | IMX556 | 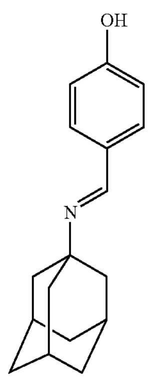 [SMILES: Oc1ccc(/C=N/C23CC4CC(CC(C4)C2)C3)cc1] | A | B | B |
| 7 | IMX 588 | 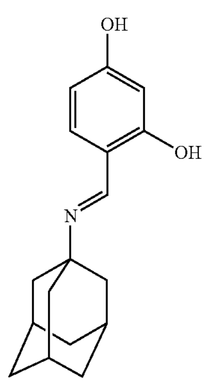 [SMILES: Oc1ccc(/C=N/C23CC4CC(CC(C4)C2)C3)c(O)c1] | A | B | A |
| 8 | IMX583 | 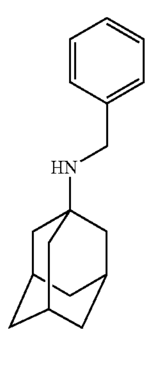 [SMILES: c1ccc(CNC23CC4CC(CC(C4)C2)C3)cc1] | A | B | B |

TABLE 1-continued

| Example Number | Compound Number | Structure | S31 OOcyte Inhibition at 100 uM (%) | S31N OOcyte Inhibition at 100 uM (%) | V27A OOcyte Inhibition at 100 uM (%) |
|---|---|---|---|---|---|
| 9 | IMX 557 | (4-hydroxybenzyl)(adamantan-1-yl)amine | A | A | B |
| 10 | IMX576 | (4-(methylamino)benzyl)(adamantan-1-yl)amine | ND | ND | ND |
| 11 | IMX 569 | (4-aminobenzyl)(adamantan-1-yl)amine | A | B | B |

TABLE 1-continued

| Example Number | Compound Number | Structure | S31 OOcyte Inhibition at 100 uM (%) | S31N OOcyte Inhibition at 100 uM (%) | V27A OOcyte Inhibition at 100 uM (%) |
|---|---|---|---|---|---|
| 12 | IMX579 | 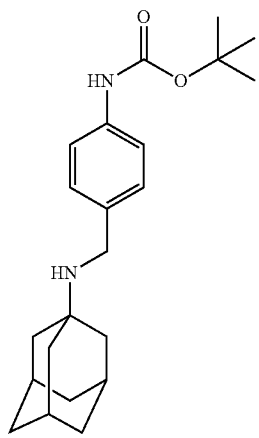 [SMILES: CC(C)(C)OC(=O)Nc1ccc(CNC23CC4CC(CC(C4)C2)C3)cc1] | B | B | B |
| 13 | IMX572 | 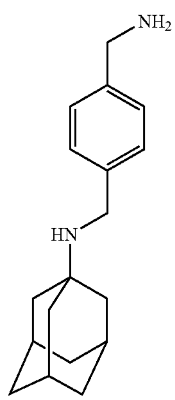 [SMILES: NCc1ccc(CNC23CC4CC(CC(C4)C2)C3)cc1] | B | B | A |
| 14 | IMX571 | 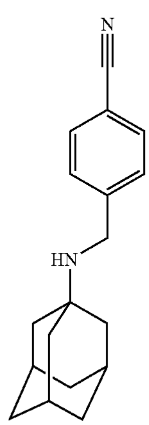 [SMILES: N#Cc1ccc(CNC23CC4CC(CC(C4)C2)C3)cc1] | A | B | B |

TABLE 1-continued

| Example Number | Compound Number | Structure | S31 OOcyte Inhibition at 100 uM (%) | S31N OOcyte Inhibition at 100 uM (%) | V27A OOcyte Inhibition at 100 uM (%) |
|---|---|---|---|---|---|
| 15 | IMX570 | 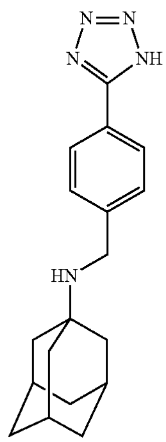 [SMILES: c1cc(-c2nnn[nH]2)ccc1CNC12CC3CC(CC(C3)C1)C2] | B | B | B |
| 16 | IMX586 | 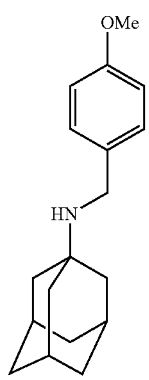 [SMILES: COc1ccc(CNC23CC4CC(CC(C4)C2)C3)cc1] | A | A | A |
| 17 | IMX584 | 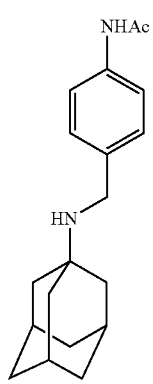 [SMILES: CC(=O)Nc1ccc(CNC23CC4CC(CC(C4)C2)C3)cc1] | B | A | B |

TABLE 1-continued

| Example Number | Compound Number | Structure | S31 OOcyte Inhibition at 100 uM (%) | S31N OOcyte Inhibition at 100 uM (%) | V27A OOcyte Inhibition at 100 uM (%) |
|---|---|---|---|---|---|
| 18 | IMX585 | 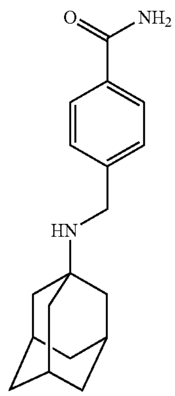 [SMILES: NC(=O)c1ccc(CNC23CC4CC(CC(C4)C2)C3)cc1] | B | B | B |
| 19 | IMX590/ M2WJ261 | 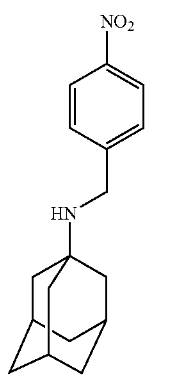 | A | B | B |
| 20 | IMX627 | 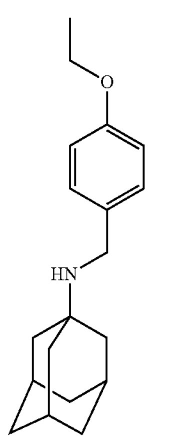 [SMILES: CCOc1ccc(CNC23CC4CC(CC(C4)C2)C3)cc1] | B | A | B |

TABLE 1-continued

| Example Number | Compound Number | Structure | S31 OOcyte Inhibition at 100 uM (%) | S31N OOcyte Inhibition at 100 uM (%) | V27A OOcyte Inhibition at 100 uM (%) |
|---|---|---|---|---|---|
| 21 | IMX629 | 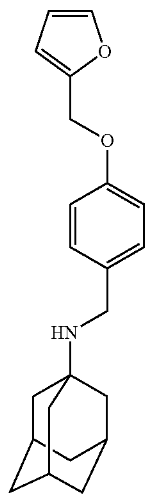 [SMILES: c1coc(COc2ccc(CNC34CC5CC(CC(C5)C3)C4)cc2)c1] | A | A | A |
| 22 | IMX630 | 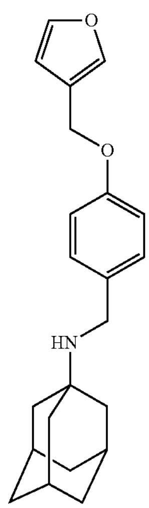 [SMILES: c1cc(COc2ccc(CNC34CC5CC(CC(C5)C3)C4)cc2)co1] | A | A | B |
| 23 | IMX613/ M2WJ275 | 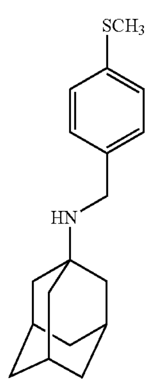 [SMILES: CSc1ccc(CNC23CC4CC(CC(C4)C2)C3)cc1] | B | A | B |

TABLE 1-continued

| Example Number | Compound Number | Structure | S31 OOcyte Inhibition at 100 uM (%) | S31N OOcyte Inhibition at 100 uM (%) | V27A OOcyte Inhibition at 100 uM (%) |
|---|---|---|---|---|---|
| 24 | IMX614 | 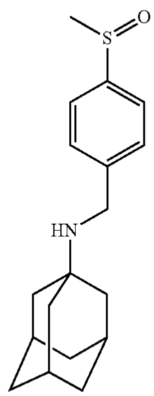 | B | B | B |
| 25 | M2WJ305 | 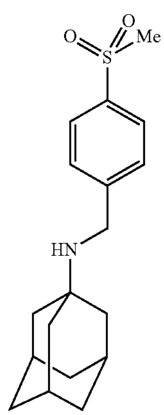 [SMILES: CS(=O)(=O)c1ccc(CNC23CC4CC(CC(C4)C2)C3)cc1] | A | B | B |
| 26 | IMX615/ M2WJ300 | 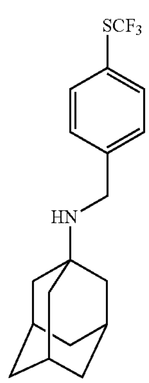 | B | A | B |

TABLE 1-continued

| Example Number | Compound Number | Structure | S31 OOcyte Inhibition at 100 uM (%) | S31N OOcyte Inhibition at 100 uM (%) | V27A OOcyte Inhibition at 100 uM (%) |
|---|---|---|---|---|---|
| 27 | IMX6 00 | 4-F-benzyl-adamantylamine | A | B | B |
| 28 | IMX599 | 2-OH-benzyl-adamantylamine | A | B | B |
| 29 | IMX598 | 2-OMe-benzyl-adamantylamine | B | B | B |
| 30 | IMX591 | 2-NO₂-benzyl-adamantylamine | A | B | B |

TABLE 1-continued

| Example Number | Compound Number | Structure | S31 OOcyte Inhibition at 100 uM (%) | S31N OOcyte Inhibition at 100 uM (%) | V27A OOcyte Inhibition at 100 uM (%) |
|---|---|---|---|---|---|
| 31 | IMX582 | 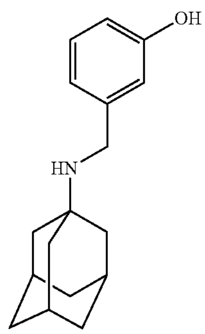 [SMILES: Oc1cccc(CNC23CC4CC(CC(C4)C2)C3)c1] | A | B | A |
| 32 | IMX637 | 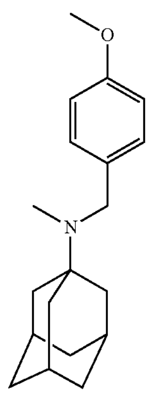 [SMILES: COc1ccc(CN(C)C23CC4CC(CC(C4)C2)C3)cc1] | A | B | B |
| 33 | M2WJ280 | 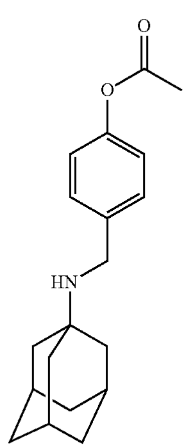 [SMILES: CC(=O)Oc1ccc(CNC23CC4CC(CC(C4)C2)C3)cc1] | A | A | B |

TABLE 1-continued
| Example Number | Compound Number | Structure | S31 OOcyte Inhibition at 100 uM (%) | S31N OOcyte Inhibition at 100 uM (%) | V27A OOcyte Inhibition at 100 uM (%) |
|---|---|---|---|---|---|
| 34 | M2WJ312 | 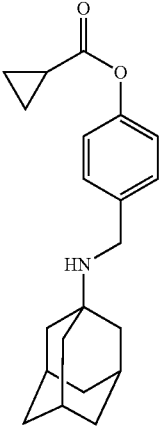 [SMILES: O=C(Oc1ccc(CNC23CC4CC(CC(C4)C2)C3)cc1)C1CC1] | B | B | B |
| 35 | M2WJ308 | 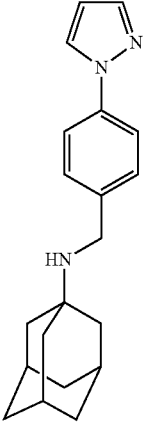 | B | B | B |
| 36 | M2WJ309 | 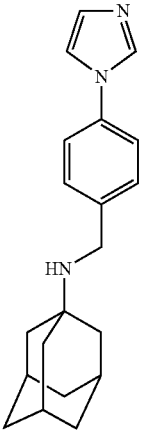 [SMILES: c1cn(-c2ccc(CNC34CC5CC(CC(C5)C3)C4)cc2)cn1] | B | B | B |

TABLE 1-continued
| Example Number | Compound Number | Structure | S31 OOcyte Inhibition at 100 uM (%) | S31N OOcyte Inhibition at 100 uM (%) | V27A OOcyte Inhibition at 100 uM (%) |
|---|---|---|---|---|---|
| 37 | M2WJ313 | 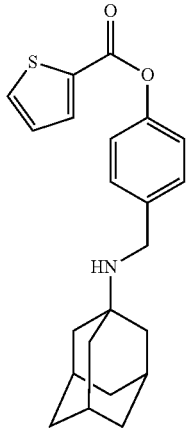 [SMILES: O=C(Oc1ccc(CNC23CC4CC(CC(C4)C2)C3)cc1)c1cccs1] | B | A | B |
| 38 | BC001 | 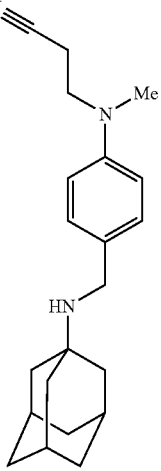 | B | A | B |
| 39 | BC002 | 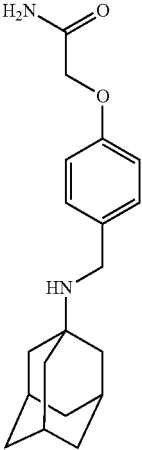 | B | B | B |

TABLE 1-continued

| Example Number | Compound Number | Structure | S31 OOcyte Inhibition at 100 uM (%) | S31N OOcyte Inhibition at 100 uM (%) | V27A OOcyte Inhibition at 100 uM (%) |
|---|---|---|---|---|---|
| 40 | BC004 | 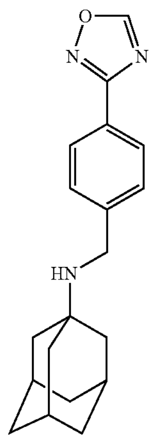 [SMILES: c1nc(-c2ccc(CNC34CC5CC(CC(C5)C3)C4)cc2)no1] | B | A | B |
| 41 | BC005 | 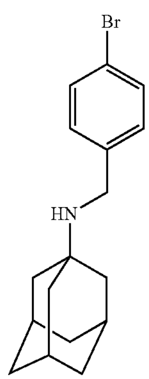 [SMILES: Brc1ccc(CNC23CC4CC(CC(C4)C2)C3)cc1] | A | A | B |
| 42 | BC015 | 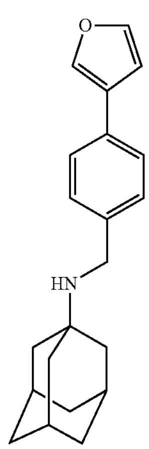 [SMILES: c1cc(-c2ccc(CNC34CC5CC(CC(C5)C3)C4)cc2)co1] | B | A | B |

TABLE 1-continued

| Example Number | Compound Number | Structure | S31 OOcyte Inhibition at 100 uM (%) | S31N OOcyte Inhibition at 100 uM (%) | V27A OOcyte Inhibition at 100 uM (%) |
|---|---|---|---|---|---|
| 43 | BC016 | 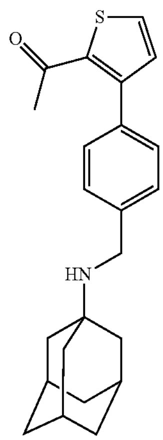 [SMILES: CC(=O)c1sccc1-c1ccc(CNC23CC4CC(CC(C4)C2)C3)cc1] | B | A | A |
| 44 | BC018 | 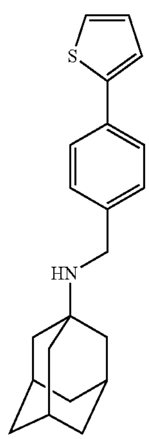 [SMILES: c1csc(-c2ccc(CNC34CC5CC(CC(C5)C3)C4)cc2)c1] | B | A | B |
| 45 | IMX564 | 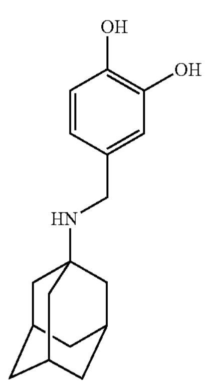 [SMILES: Oc1ccc(CNC23CC4CC(CC(C4)C2)C3)cc1O] | A | B | A |

TABLE 1-continued
| Example Number | Compound Number | Structure | S31 OOcyte Inhibition at 100 uM (%) | S31N OOcyte Inhibition at 100 uM (%) | V27A OOcyte Inhibition at 100 uM (%) |
|---|---|---|---|---|---|
| 46 | IMX589 | 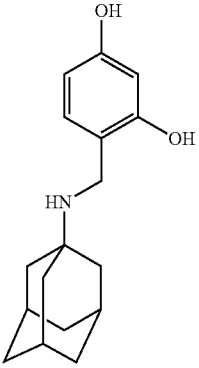 [SMILES: Oc1ccc(CNC23CC4CC(CC(C4)C2)C3)c(O)c1] | A | A | A |
| 47 | IMX 566 | 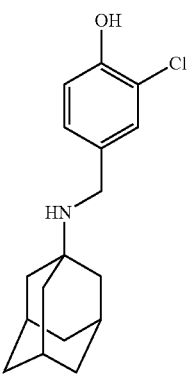 [SMILES: Oc1ccc(CNC23CC4CC(CC(C4)C2)C3)cc1Cl] | A | B | A |
| 48 | IMX 573 | 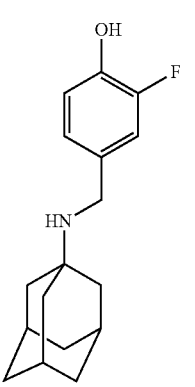 | A | A | A |
| 49 | IMX580 | 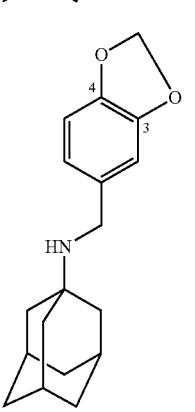 | A | B | B |

TABLE 1-continued

| Example Number | Compound Number | Structure | S31 OOcyte Inhibition at 100 uM (%) | S31N OOcyte Inhibition at 100 uM (%) | V27A OOcyte Inhibition at 100 uM (%) |
|---|---|---|---|---|---|
| 50 | IMX581 | 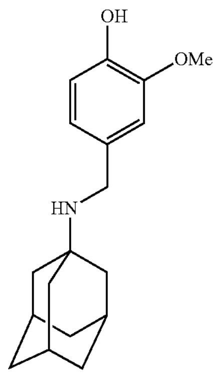 [SMILES: COc1cc(CNC23CC4CC(CC(C4)C2)C3)ccc1O] | A | B | A |
| 51 | IMX567 | 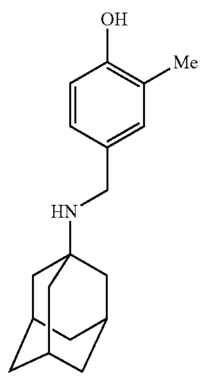 [SMILES: Cc1cc(CNC23CC4CC(CC(C4)C2)C3)ccc1O] | A | B | B |
| 52 | M2WJ259 | 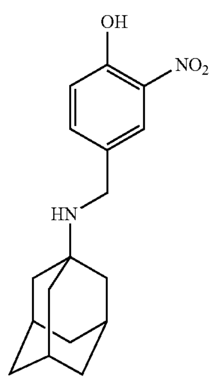 [SMILES: O=[N+]([O-])c1cc(CNC23CC4CC(CC(C4)C2)C3)ccc1O] | A | B | A |
| 53 | IMX597 | 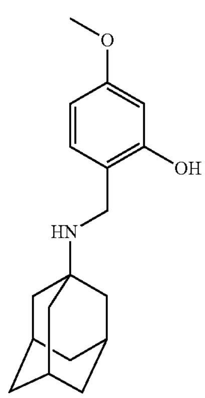 [SMILES: COc1ccc(CNC23CC4CC(CC(C4)C2)C3)c(O)c1] | A | A | B |

TABLE 1-continued

| Example Number | Compound Number | Structure | S31 OOcyte Inhibition at 100 uM (%) | S31N OOcyte Inhibition at 100 uM (%) | V27A OOcyte Inhibition at 100 uM (%) |
|---|---|---|---|---|---|
| 54 | IMX625 | *2,4-difluorobenzyl adamantan-1-amine* | A | B | B |
| 55 | IMX620 | *2,4-bis(methylthio)benzyl adamantan-1-amine* | B | B | B |
| 56 | IMX 596 | *4-hydroxy-2-methoxybenzyl adamantan-1-amine* | B | B | B |

TABLE 1-continued

| Example Number | Compound Number | Structure | S31 OOcyte Inhibition at 100 uM (%) | S31N OOcyte Inhibition at 100 uM (%) | V27A OOcyte Inhibition at 100 uM (%) |
|---|---|---|---|---|---|
| 57 | IMX636 | 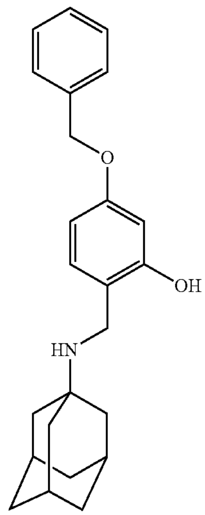 [SMILES: Oc1cc(OCc2ccccc2)ccc1CNC12CC3CC(CC(C3)C1)C2] | A | A | B |
| 58 | M2WJ279 | 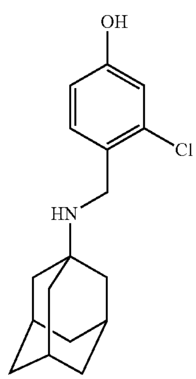 [SMILES: Oc1ccc(CNC23CC4CC(CC(C4)C2)C3)c(Cl)c1] | A | B | A |
| 59 | M2WJ296 | 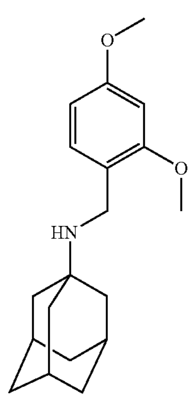 [SMILES: COc1ccc(CNC23CC4CC(CC(C4)C2)C3)c(OC)c1] | B | B | B |

TABLE 1-continued

| Example Number | Compound Number | Structure | S31 OOcyte Inhibition at 100 uM (%) | S31N OOcyte Inhibition at 100 uM (%) | V27A OOcyte Inhibition at 100 uM (%) |
|---|---|---|---|---|---|
| 60 | M2WJ307 | 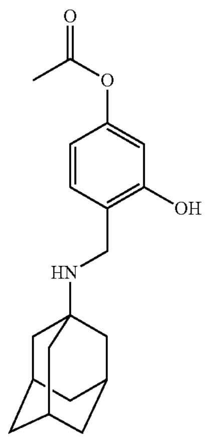 [SMILES: CC(=O)Oc1ccc(CNC23CC4CC(CC(C4)C2)C3)c(O)c1] | A | A | B |
| 61 | M2WJ290 | 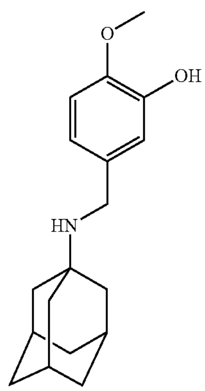 [SMILES: COc1ccc(CNC23CC4CC(CC(C4)C2)C3)cc1O] | A | B | A |
| 62 | M2WJ268 | 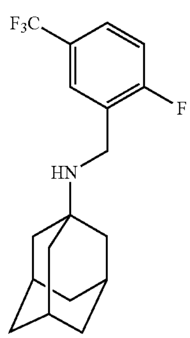 [SMILES: Fc1ccc(C(F)(F)F)cc1CNC12CC3CC(CC(C3)C1)C2] | B | B | B |
| 63 | M2WJ277 | 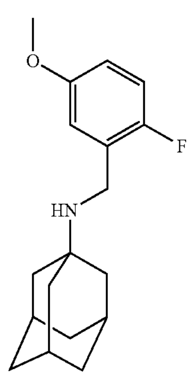 [SMILES: COc1ccc(F)c(CNC23CC4CC(CC(C4)C2)C3)c1] | A | B | B |

TABLE 1-continued

| Example Number | Compound Number | Structure | S31 OOcyte Inhibition at 100 uM (%) | S31N OOcyte Inhibition at 100 uM (%) | V27A OOcyte Inhibition at 100 uM (%) |
|---|---|---|---|---|---|
| 64 | M2WJ281 | 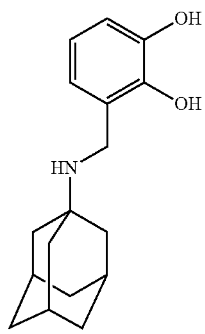 [SMILES: Oc1cccc(CNC23CC4CC(CC(C4)C2)C3)c1O] | A | B | A |
| 65 | IMX624 | 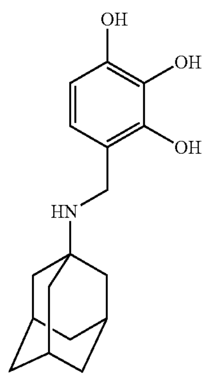 [SMILES: Oc1ccc(CNC23CC4CC(CC(C4)C2)C3)c(O)c1O] | B | B | A |
| 66 | IMX595 | 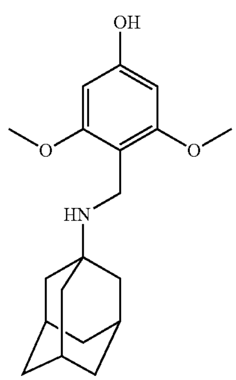 | A | B | B |
| 67 | IMX611 | 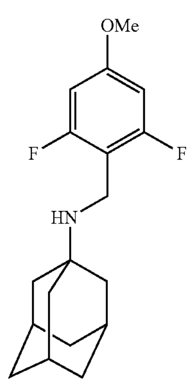 [SMILES: COc1cc(F)c(CNC23CC4CC(CC(C4)C2)C3)c(F)c1] | A | B | B |

TABLE 1-continued

| Example Number | Compound Number | Structure | S31 OOcyte Inhibition at 100 uM (%) | S31N OOcyte Inhibition at 100 uM (%) | V27A OOcyte Inhibition at 100 uM (%) |
|---|---|---|---|---|---|
| 68 | IMX568 | 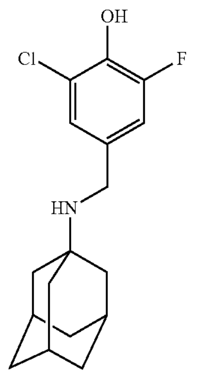 [SMILES: Oc1c(F)cc(CNC23CC4CC(CC(C4)C2)C3)cc1Cl] | A | B | B |
| 69 | IMX612 | 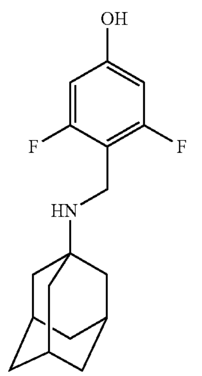 [SMILES: Oc1cc(F)c(CNC23CC4CC(CC(C4)C2)C3)c(F)c1] | A | B | A |
| 70 | IMX594 | 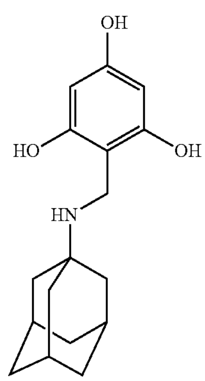 | B | B | B |
| 71 | M2WJ260 | 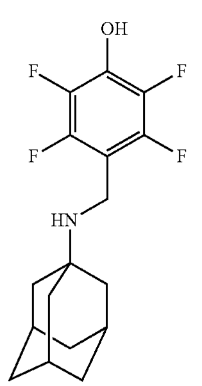 [SMILES: Oc1c(F)c(F)c(CNC23CC4CC(CC(C4)C2)C3)c(F)c1F] | B | B | A |

TABLE 1-continued

| Example Number | Compound Number | Structure | S31 OOcyte Inhibition at 100 uM (%) | S31N OOcyte Inhibition at 100 uM (%) | V27A OOcyte Inhibition at 100 uM (%) |
|---|---|---|---|---|---|
| 72 | IMX593 | 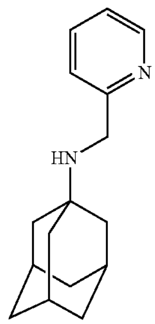 [SMILES: c1ccc(CNC23CC4CC(CC(C4)C2)C3)nc1] | B | B | B |
| 73 | IMX592 | 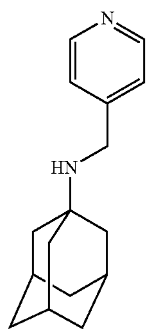 [SMILES: c1cc(CNC23CC4CC(CC(C4)C2)C3)ccn1] | A | B | B |
| 74 | M2WJ306 | 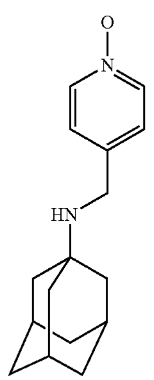 | B | B | B |
| 75 | IMX587 | 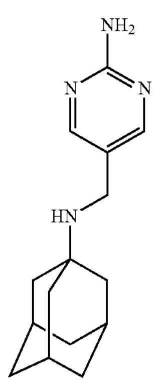 [SMILES: Nc1ncc(CNC23CC4CC(CC(C4)C2)C3)cn1] | A | B | B |

TABLE 1-continued

| Example Number | Compound Number | Structure | S31 OOcyte Inhibition at 100 uM (%) | S31N OOcyte Inhibition at 100 uM (%) | V27A OOcyte Inhibition at 100 uM (%) |
|---|---|---|---|---|---|
| 76 | IMX641 | 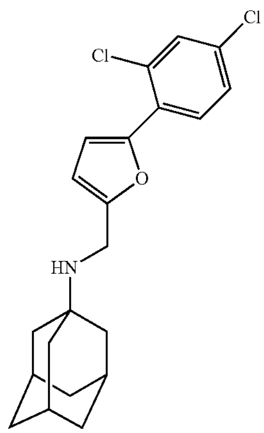 [SMILES: Clc1ccc(-c2ccc(CNC34CC5CC(CC(C5)C3)C4)o2)c(Cl)c1] | ND | ND | ND |
| 77 | IMX604 | 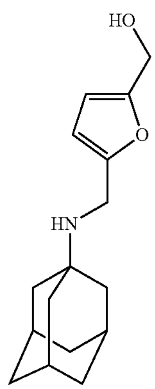 [SMILES: OCc1ccc(CNC23CC4CC(CC(C4)C2)C3)o1] | B | B | B |
| 78 | BC007 | 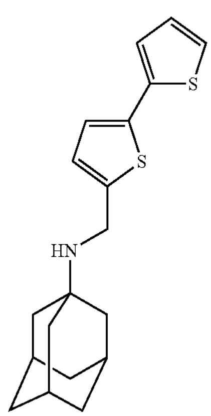 | B | A | B |

TABLE 1-continued

| Example Number | Compound Number | Structure | S31 OOcyte Inhibition at 100 uM (%) | S31N OOcyte Inhibition at 100 uM (%) | V27A OOcyte Inhibition at 100 uM (%) |
|---|---|---|---|---|---|
| 79 | IMX606 | 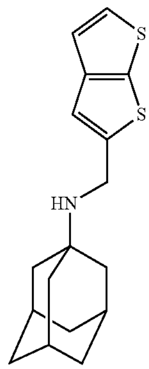 [SMILES: c1cc2cc(CNC34CC5CC(CC(C5)C3)C4)sc2s1] | A | A | B |
| 80 | IMX610 | 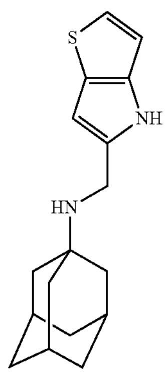 | A | A | B |
| 81 | IMX621 | 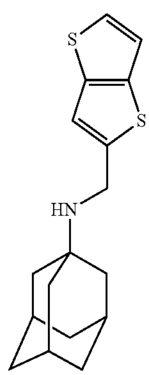 [SMILES: c1cc2sc(CNC34CC5CC(CC(C5)C3)C4)cc2s1] | A | A | B |
| 82 | IMX634 | 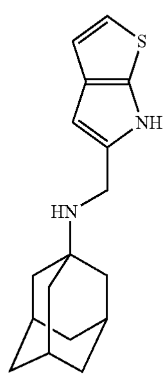 [SMILES: c1cc2cc(CNC34CC5CC(CC(C5)C3)C4)[nH]c2s1] | A | A | B |

TABLE 1-continued
| Example Number | Compound Number | Structure | S31 OOcyte Inhibition at 100 uM (%) | S31N OOcyte Inhibition at 100 uM (%) | V27A OOcyte Inhibition at 100 uM (%) |
|---|---|---|---|---|---|
| 83 | IMX635 | 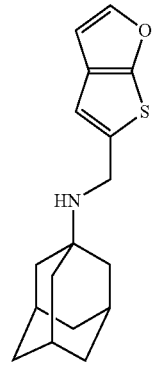 [SMILES: c1cc2cc(CNC34CC5CC(CC(C5)C3)C4)sc2o1] | A | A | B |
| 84 | IMX648 | 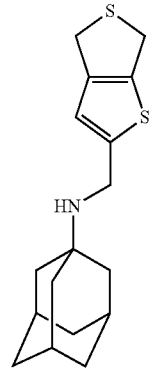 [SMILES: c1c(CNC23CC4CC(CC(C4)C2)C3)sc2c1CSC2] | A | A | B |
| 85 | IMX644 | 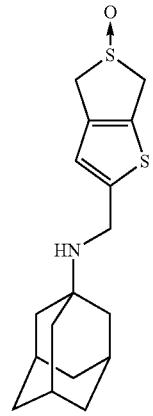 [SMILES: O=S1Cc2cc(CNC34CC5CC(CC(C5)C3)C4)sc2C1] | B | B | B |
| 86 | M2WJ264 | 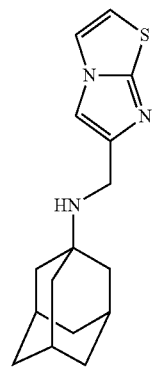 | A | A | B |

TABLE 1-continued
| Example Number | Compound Number | Structure | S31 OOcyte Inhibition at 100 uM (%) | S31N OOcyte Inhibition at 100 uM (%) | V27A OOcyte Inhibition at 100 uM (%) |
|---|---|---|---|---|---|
| 87 | M2WJ298 | 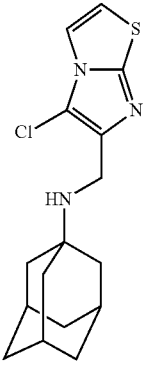 [SMILES: Clc1c(CNC23CC4CC(CC(C4)C2)C3)nc2sccn12] | B | B | B |
| 88 | IMX622 | 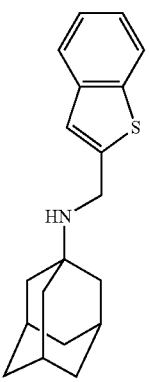 [SMILES: c1ccc2sc(CNC34CC5CC(CC(C5)C3)C4)cc2c1] | B | A | B |
| 89 | IMX631 | 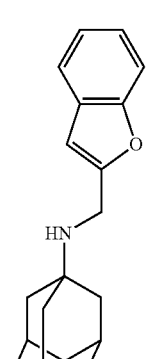 | B | A | B |
| 90 | IMX626 | 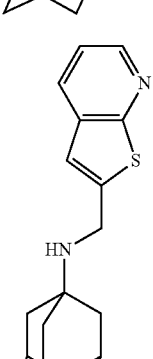 | B | B | B |

TABLE 1-continued
| Example Number | Compound Number | Structure | S31 OOcyte Inhibition at 100 uM (%) | S31N OOcyte Inhibition at 100 uM (%) | V27A OOcyte Inhibition at 100 uM (%) |
|---|---|---|---|---|---|
| 91 | IMX632 | 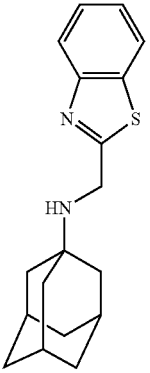 [SMILES: c1ccc2sc(CNC34CC5CC(CC(C5)C3)C4)nc2c1] | B | A | B |
| 92 | IMX633 | 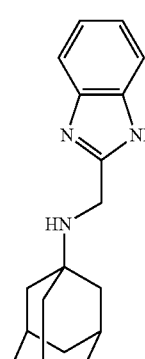 | B | A | B |
| 93 | IMX642 | 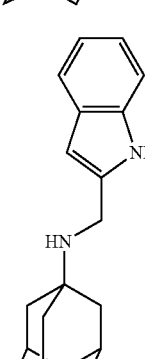 | B | A | B |
| 94 | IMX623 | 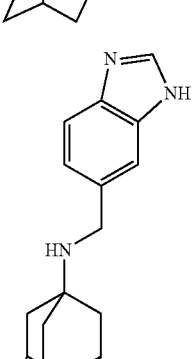 | B | B | B |

TABLE 1-continued

| Example Number | Compound Number | Structure | S31 OOcyte Inhibition at 100 uM (%) | S31N OOcyte Inhibition at 100 uM (%) | V27A OOcyte Inhibition at 100 uM (%) |
|---|---|---|---|---|---|
| 95 | M2WJ311 | 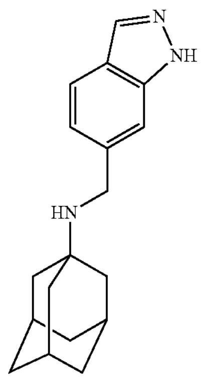 [SMILES: c1cc2cn[nH]c2cc1CNC12CC3CC(CC(C3)C1)C2] | A | B | A |
| 96 | M2WJ303 | 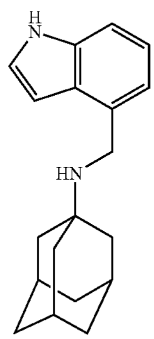 [SMILES: c1cc(CNC23CC4CC(CC(C4)C2)C3)c2cc[nH]c2c1] | A | B | A |
| 97 | IMX639 | 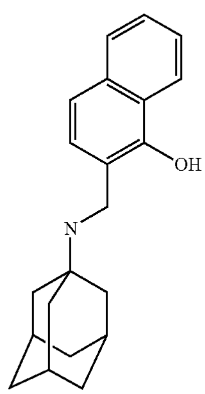 [SMILES: Oc1c(CNC23CC4CC(CC(C4)C2)C3)ccc2ccccc12] | A | A | B |
| 98 | IMX640 | 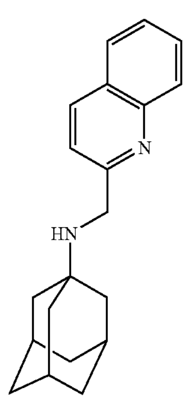 [SMILES: c1ccc2nc(CNC34CC5CC(CC(C5)C3)C4)ccc2c1] | A | A | B |

TABLE 1-continued
| Example Number | Compound Number | Structure | S31 OOcyte Inhibition at 100 uM (%) | S31N OOcyte Inhibition at 100 uM (%) | V27A OOcyte Inhibition at 100 uM (%) |
|---|---|---|---|---|---|
| 99 | M2WJ271 | 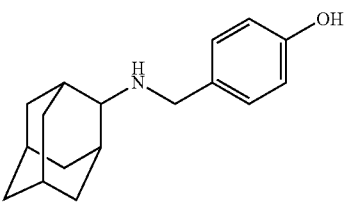 [SMILES: Oc1ccc(CNC2C3CC4CC(C3)CC2C4)cc1] | A | B | B |
| 100 | M2WJ272 | 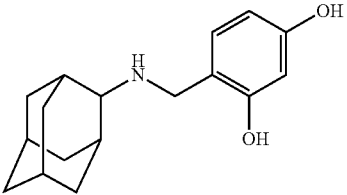 [SMILES: Oc1ccc(CNC2C3CC4CC(C3)CC2C4)c(O)c1] | A | B | A |
| 101 | M2WJ273 | 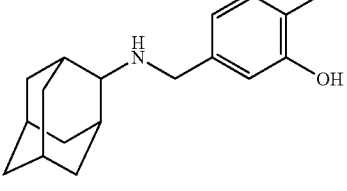 | A | B | B |
| 102 | M2WJ286 | 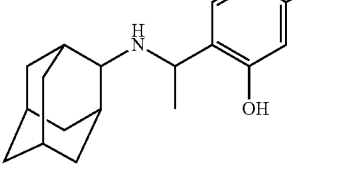 | A | B | A |
| 103 | M2WJ297 | 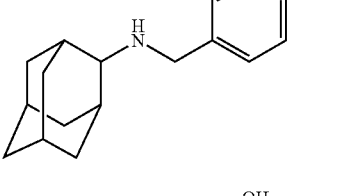 | B | A | A |
| 104 | M2WJ286 | 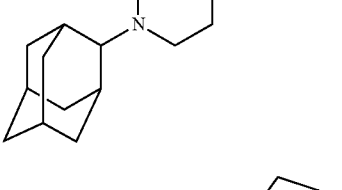 | B | B | B |
| 105 | M2WJ299 | 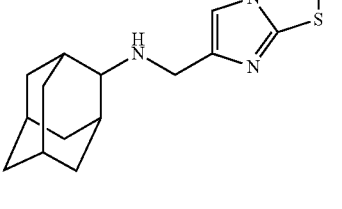 | A | B | B |

TABLE 1-continued

| Example Number | Compound Number | Structure | S31 OOcyte Inhibition at 100 uM (%) | S31N OOcyte Inhibition at 100 uM (%) | V27A OOcyte Inhibition at 100 uM (%) |
|---|---|---|---|---|---|
| 106 | M2WJ302 | 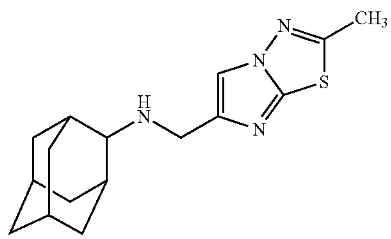 [SMILES: Cc1nn2cc(CNC3C4CC5CC(C4)CC3C5)nc2s1] | B | B | A |
| 107 | M2WJ314 | 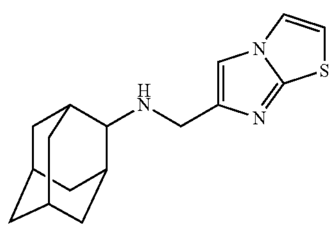 [SMILES: c1cn2cc(CNC3C4CC5CC(C4)CC3C5)nc2s1] | A | B | B |
| 108 | M2WJ282 | 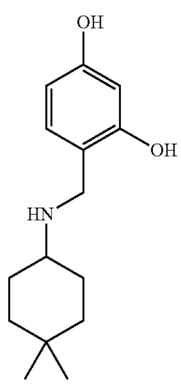 [SMILES: CC1(C)CCC(NCc2ccc(O)cc2O)CC1] | A | B | B |
| 109 | M2WJ294 | 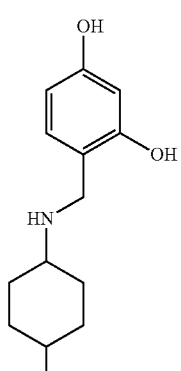 | A | B | A |

TABLE 1-continued

| Example Number | Compound Number | Structure | S31 OOcyte Inhibition at 100 uM (%) | S31N OOcyte Inhibition at 100 uM (%) | V27A OOcyte Inhibition at 100 uM (%) |
|---|---|---|---|---|---|
| 110 | M2WJ285 | 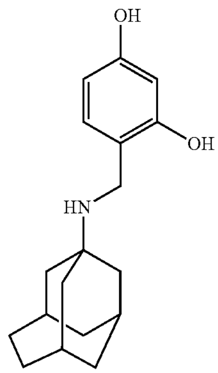 [SMILES: Oc1ccc(CNC23CC4CCC(CC(C4)C2)C3)c(O)c1] | A | A | A |
| 111 | M2WJ284 | 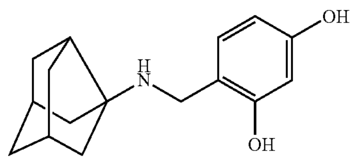 [SMILES: Oc1ccc(CNC23CC4CC(CC2C4)C3)c(O)c1] | A | A | B |
| 112 | M2WJ287 | 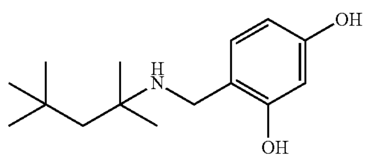 [SMILES: CC(C)(C)CC(C)(C)NCc1ccc(O)cc1O] | A | B | A |
| 113 | M2WJ283 | 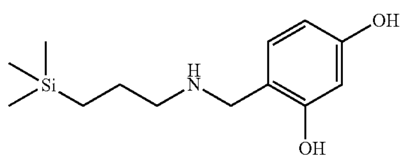 [SMILES: C[Si](C)(C)CCCNCc1ccc(O)cc1O] | A | B | B |
| 114 | M2WJ293 | 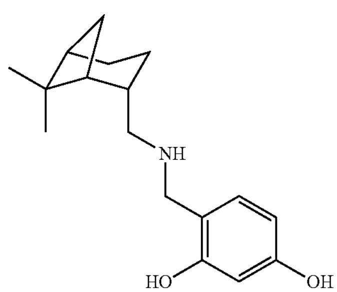 [SMILES: CC1(C)C2CCC(CNCc3ccc(O)cc3O)C1C2] | A | B | B |
| 115 | M2WJ288 | 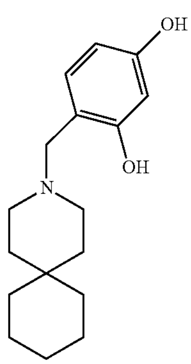 [SMILES: Oc1ccc(CN2CCC3(CCCCC3)CC2)c(O)c1] | A | B | B |

TABLE 1-continued
| Example Number | Compound Number | Structure | S31 OOcyte Inhibition at 100 uM (%) | S31N OOcyte Inhibition at 100 uM (%) | V27A OOcyte Inhibition at 100 uM (%) |
|---|---|---|---|---|---|
| 116 | M2WJ292 | 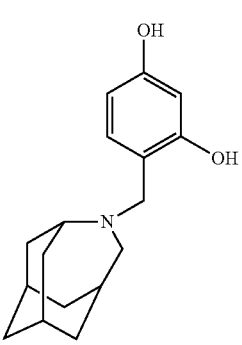 [SMILES: Oc1ccc(CN2CC3CC4CC(C3)CC2C4)c(O)c1] | A | B | A |
TABLE 2
| Example # | Batch External ID | Structure | S31 OOcyte Inhibition at 100 uM (%) | S31N OOcyte Inhibition at 100 uM (%) | V27A OOcyte Inhibition at 100 uM (%) |
|---|---|---|---|---|---|
| | | 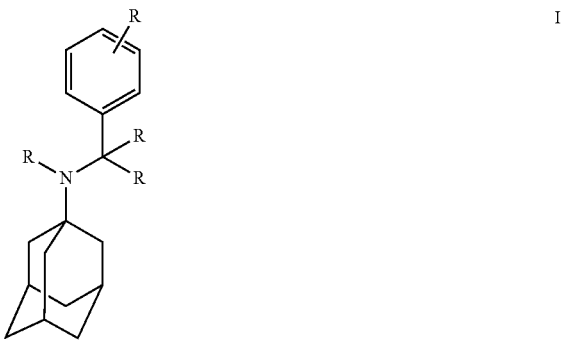 | | | I |
| 1a | IMX00627 | 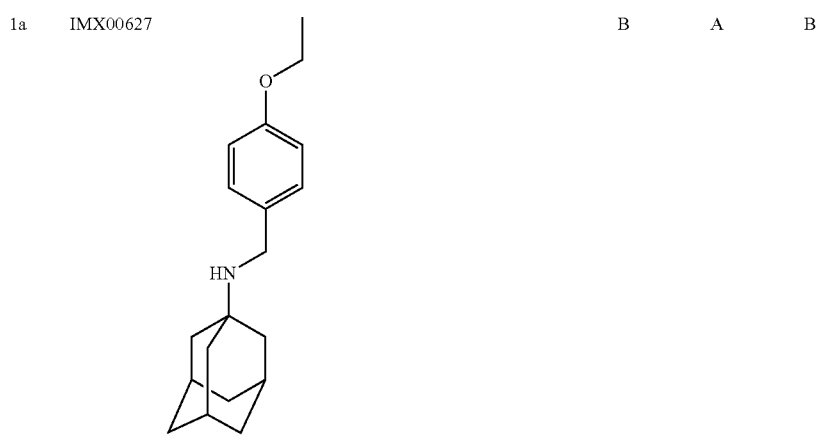 | B | A | B |

TABLE 2-continued

| Example # | Batch External ID | Structure | S31 OOcyte Inhibition at 100 uM (%) | S31N OOcyte Inhibition at 100 uM (%) | V27A OOcyte Inhibition at 100 uM (%) |
|---|---|---|---|---|---|
| 2a | BC063 | 4-BF₃K-C₆H₄-CH₂-NH-adamantyl | A | B | A |
| 3a | BC020 | 3-Br-C₆H₄-CH₂-NH-adamantyl | A | B | B |
| 4a | IMX00673 | 4-OCF₃-C₆H₄-CH₂-NH-adamantyl | B | B | B |
| 5a | IMX00674 | 4-CF₃-C₆H₄-CH₂-NH-adamantyl | B | B | B |

TABLE 2-continued

| Example # | Batch External ID | Structure | S31 OOcyte Inhibition at 100 uM (%) | S31N OOcyte Inhibition at 100 uM (%) | V27A OOcyte Inhibition at 100 uM (%) |
|---|---|---|---|---|---|
| 6a | IMX00676 | 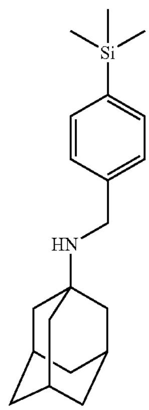 [SMILES: C[Si](C)(C)c1ccc(CNC23CC4CC(CC(C4)C2)C3)cc1] | B | A | B |
| 7a | BC014 | 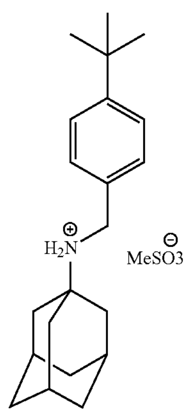 [SMILES: CC(C)(C)c1ccc(C[NH2+]C23CC4CC(CC(C4)C2)C3)cc1] | B | A | B |
| 8a | BC076 | 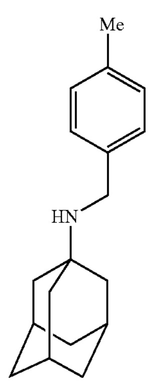 [SMILES: Cc1ccc(CNC23CC4CC(CC(C4)C2)C3)cc1] | A | B | ND |

TABLE 2-continued

| Example # | Batch External ID | Structure | S31 OOcyte Inhibition at 100 uM (%) | S31N OOcyte Inhibition at 100 uM (%) | V27A OOcyte Inhibition at 100 uM (%) |
|---|---|---|---|---|---|
| 9a | BC080 | 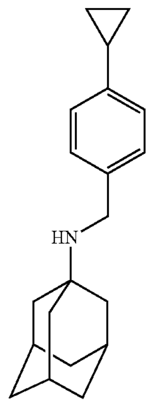 [SMILES: c1cc(C2CC2)ccc1CNC12CC3CC(CC(C3)C1)C2] | A | A | ND |
| 10a | IMX00678 | 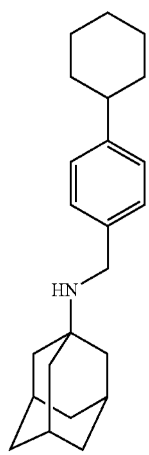 [SMILES: c1cc(C2CCCCC2)ccc1CNC12CC3CC(CC(C3)C1)C2] | B | A | B |
| 11a | WFD093, hij294 | 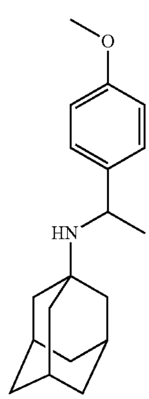 [SMILES: COc1ccc(C(C)NC23CC4CC(CC(C4)C2)C3)cc1] | A | A | A |

TABLE 2-continued

| Example # | Batch External ID | Structure | S31 OOcyte Inhibition at 100 uM (%) | S31N OOcyte Inhibition at 100 uM (%) | V27A OOcyte Inhibition at 100 uM (%) |
|---|---|---|---|---|---|
| 12a | WFD023 | 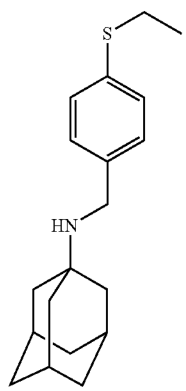 [SMILES: CCSc1ccc(CNC23CC4CC(CC(C4)C2)C3)cc1] | B | A | B |
| 13a | IMX00657 | 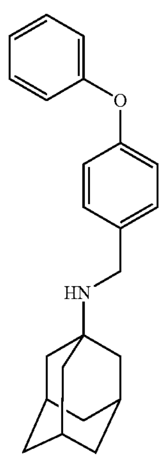 [SMILES: c1ccc(Oc2ccc(CNC34CC5CC(CC(C5)C3)C4)cc2)cc1] | A | A | B |
| 14a | IMX00649 | 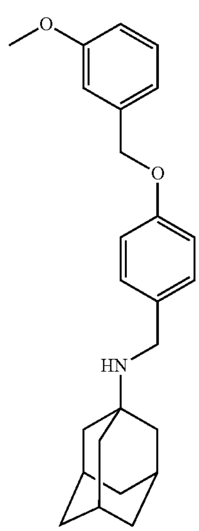 [SMILES: COc1cccc(COc2ccc(CNC34CC5CC(CC(C5)C3)C4)cc2)c1] | B | A | B |

TABLE 2-continued
| Example # | Batch External ID | Structure | S31 OOcyte Inhibition at 100 uM (%) | S31N OOcyte Inhibition at 100 uM (%) | V27A OOcyte Inhibition at 100 uM (%) |
|---|---|---|---|---|---|
| 15a | IMX00650 | 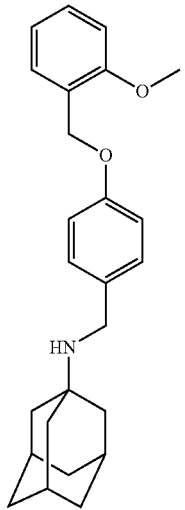 [SMILES: COc1ccccc1COc1ccc(CNC23CC4CC(CC(C4)C2)C3)cc1] | B | A | B |
| 16a | IMX00651 | 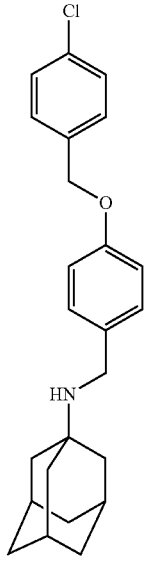 [SMILES: Clc1ccc(COc2ccc(CNC34CC5CC(CC(C5)C3)C4)cc2)cc1] | A | A | B |
| 29a | BC018_2 | 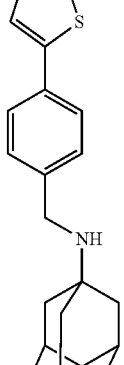 | B | A | B |

TABLE 2-continued
| Example # | Batch External ID | Structure | S31 OOcyte Inhibition at 100 uM (%) | S31N OOcyte Inhibition at 100 uM (%) | V27A OOcyte Inhibition at 100 uM (%) |
|---|---|---|---|---|---|
| 30a | BC026 | 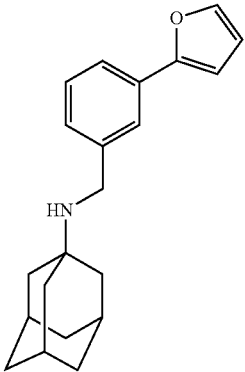 [SMILES: c1cc(CNC23CC4CC(CC(C4)C2)C3)cc(-c2ccco2)c1] | B | B | A |
| 31a | BC032 | 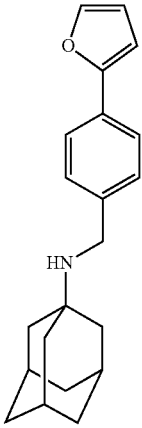 [SMILES: c1coc(-c2ccc(CNC34CC5CC(CC(C5)C3)C4)cc2)c1] | B | A | B |
| 32a | BC047 | 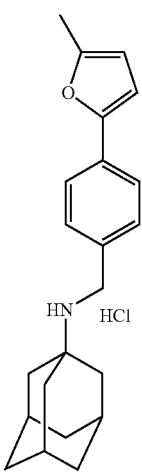 [SMILES: Cc1ccc(-c2ccc(CNC34CC5CC(CC(C5)C3)C4)cc2)o1 ; Cl] | B | A | B |

TABLE 2-continued

| Example # | Batch External ID | Structure | S31 OOcyte Inhibition at 100 uM (%) | S31N OOcyte Inhibition at 100 uM (%) | V27A OOcyte Inhibition at 100 uM (%) |
|---|---|---|---|---|---|
| 33a | BC046 | 3,5-dimethylisoxazol-4-yl phenyl CH2-NH-adamantyl | B | B | B |
| 34a | BC025 | 3-(thiophen-2-yl)phenyl CH2-NH-adamantyl | B | B | A |
| 35a | BC034 | 3-(thiophen-3-yl)phenyl CH2-NH-adamantyl | B | B | A |

TABLE 2-continued

| Example # | Batch External ID | Structure | S31 OOcyte Inhibition at 100 uM (%) | S31N OOcyte Inhibition at 100 uM (%) | V27A OOcyte Inhibition at 100 uM (%) |
|---|---|---|---|---|---|
| 36a | WFD029 | 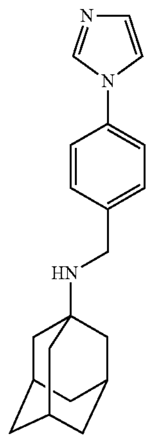 [SMILES: c1cn(-c2ccc(CNC34CC5CC(CC(C5)C3)C4)cc2)cn1] | 16.1 | 26.9 | ND |
| 37a | IMX00636 | 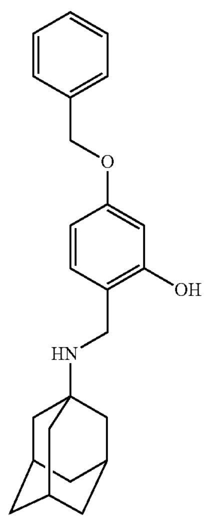 [SMILES: Oc1cc(OCc2ccccc2)ccc1CNC12CC3CC(CC(C3)C1)C2] | A | A | B |
| 38a | M2WJ328 | 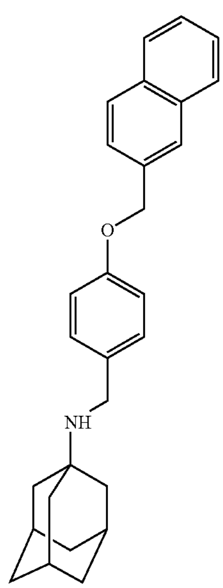 [SMILES: c1ccc2cc(COc3ccc(CNC45CC6CC(CC(C6)C4)C5)cc3)ccc2c1] | B | B | B |

TABLE 2-continued
| Example # | Batch External ID | Structure | S31 OOcyte Inhibition at 100 uM (%) | S31N OOcyte Inhibition at 100 uM (%) | V27A OOcyte Inhibition at 100 uM (%) |
|---|---|---|---|---|---|
| 39a | IMX00681 | 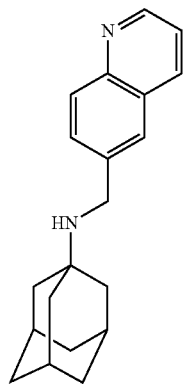 [SMILES: c1cnc2ccc(CNC34CC5CC(CC(C5)C3)C4)cc2c1] | B | A | B |
| 40a | IMX00682 | 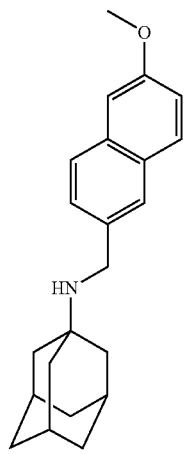 [SMILES: COc1ccc2cc(CNC34CC5CC(CC(C5)C3)C4)ccc2c1] | B | B | A |
| 41a | WFD115 | 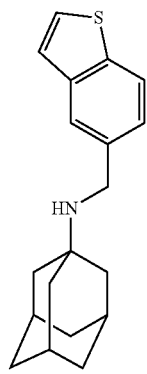 [SMILES: c1cc2cc(CNC34CC5CC(CC(C5)C3)C4)ccc2s1] | A | B | A |

TABLE 2-continued

| Example # | Batch External ID | Structure | S31 OOcyte Inhibition at 100 uM (%) | S31N OOcyte Inhibition at 100 uM (%) | V27A OOcyte Inhibition at 100 uM (%) |
|---|---|---|---|---|---|
| 42a | M2WJ337, WFD123 | 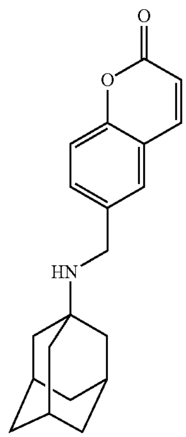 [SMILES: O=c1ccc2cc(CNC34CC5CC(CC(C5)C3)C4)ccc2o1] | B | B | B |
| 43a | WFD119 | 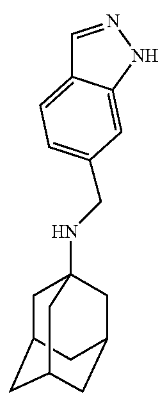 [SMILES: c1cc2cn[nH]c2cc1CNC12CC3CC(CC(C3)C1)C2] | A | B | ND |
| 44a | WFD008 | 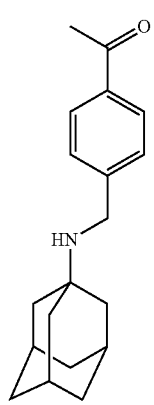 | B | B | B |

TABLE 2-continued

| Example # | Batch External ID | Structure | S31 OOcyte Inhibition at 100 uM (%) | S31N OOcyte Inhibition at 100 uM (%) | V27A OOcyte Inhibition at 100 uM (%) |
|---|---|---|---|---|---|
| 45a | WFD014 | 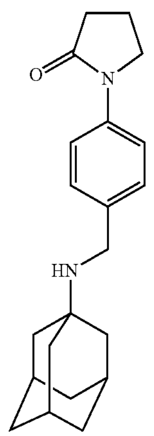 [SMILES: O=C1CCCN1c1ccc(CNC23CC4CC(CC(C4)C2)C3)cc1] | B | A | B |
| 46a | BC-090 | 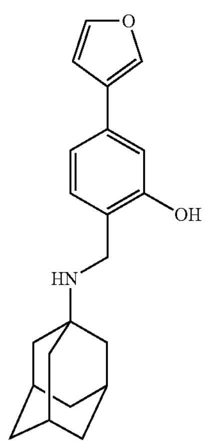 [SMILES: Oc1cc(-c2ccoc2)ccc1CNC12CC3CC(CC(C3)C1)C2] | B | A | ND |
| 47a | IMX00661 | 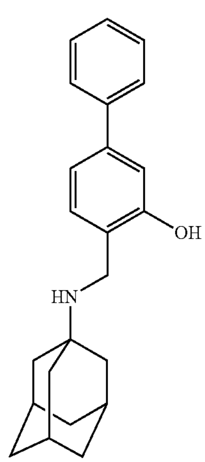 [SMILES: Oc1cc(-c2ccccc2)ccc1CNC12CC3CC(CC(C3)C1)C2] | B | A | B |

TABLE 2-continued
| Example # | Batch External ID | Structure | S31 OOcyte Inhibition at 100 uM (%) | S31N OOcyte Inhibition at 100 uM (%) | V27A OOcyte Inhibition at 100 uM (%) |
|---|---|---|---|---|---|
| 48a | IMX00660 | 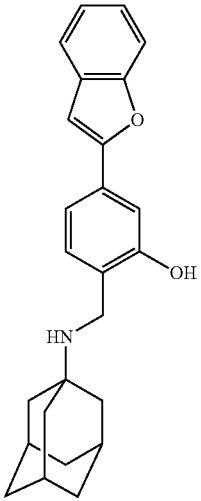 [SMILES: Oc1cc(-c2cc3ccccc3o2)ccc1CNC12CC3CC(CC(C3)C1)C2] | B | B | B |
| 49a | BC073 | 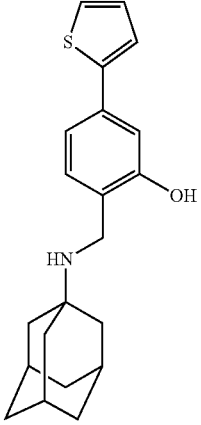 | B | B | ND |
| 50a | M2WJ325 | 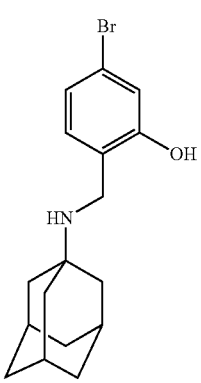 [SMILES: Oc1cc(Br)ccc1CNC12CC3CC(CC(C3)C1)C2] | A | A | B |

TABLE 2-continued

| Example # | Batch External ID | Structure | S31 OOcyte Inhibition at 100 uM (%) | S31N OOcyte Inhibition at 100 uM (%) | V27A OOcyte Inhibition at 100 uM (%) |
|---|---|---|---|---|---|
| 51a | BC081 | 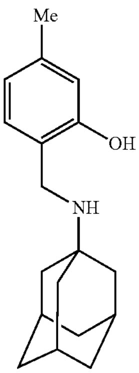 [SMILES: Cc1ccc(CNC23CC4CC(CC(C4)C2)C3)c(O)c1] | A | A | ND |
| 52a | M2WJ326 | 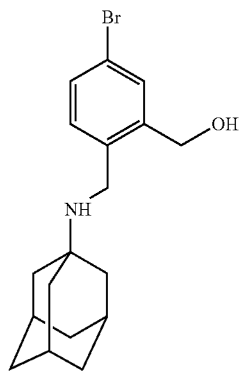 [SMILES: OCc1cc(Br)ccc1CNC12CC3CC(CC(C3)C1)C2] | B | B | B |
| 53a | IMX00639 | 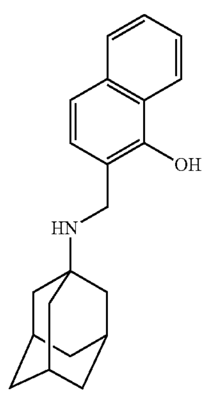 [SMILES: Oc1c(CNC23CC4CC(CC(C4)C2)C3)ccc2ccccc12] | A | A | B |

II

TABLE 2-continued
| Example # | Batch External ID | Structure | S31 OOcyte Inhibition at 100 uM (%) | S31N OOcyte Inhibition at 100 uM (%) | V27A OOcyte Inhibition at 100 uM (%) |
|---|---|---|---|---|---|
| 54a | IMX00710 | 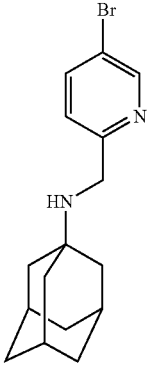 | A | A | ND |
| 55a | IMX00711 | 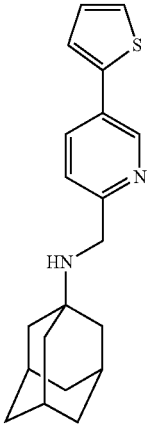 [SMILES: c1csc(-c2ccc(CNC34CC5CC(CC(C5)C3)C4)nc2)c1] | A | A | ND |
| 56a | IMX00640 | 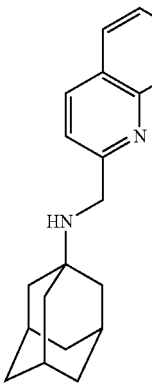 | A | A | B |

TABLE 2-continued
| Example # | Batch External ID | Structure | S31 OOcyte Inhibition at 100 uM (%) | S31N OOcyte Inhibition at 100 uM (%) | V27A OOcyte Inhibition at 100 uM (%) |
|---|---|---|---|---|---|
| 57a | M2WJ387 | 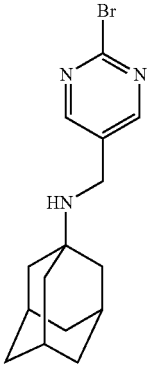 [SMILES: Brc1ncc(CNC23CC4CC(CC(C4)C2)C3)cn1] | B | B | ND |
| 58a | M2WJ383 | 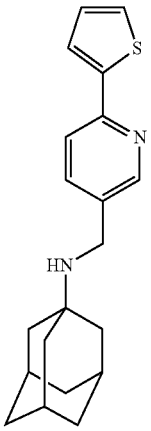 [SMILES: c1csc(-c2ccc(CNC34CC5CC(CC(C5)C3)C4)cn2)c1] | A | A | ND |
| 59a | M2WJ385 | 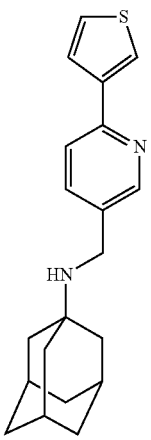 [SMILES: c1cc(-c2ccc(CNC34CC5CC(CC(C5)C3)C4)cn2)cs1] | B | A | ND |

TABLE 2-continued
| Example # | Batch External ID | Structure | S31 OOcyte Inhibition at 100 uM (%) | S31N OOcyte Inhibition at 100 uM (%) | V27A OOcyte Inhibition at 100 uM (%) |
|---|---|---|---|---|---|
| 60a | M2WJ329 | 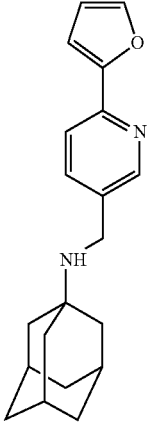 [SMILES: c1coc(-c2ccc(CNC34CC5CC(CC(C5)C3)C4)cn2)c1] | B | A | B |
| 61a | M2WJ330 | 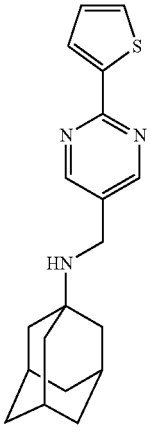 [SMILES: c1coc(-c2ncc(CNC34CC5CC(CC(C5)C3)C4)cn2)c1] | B | A | B |
| 62a | M2WJ336 | 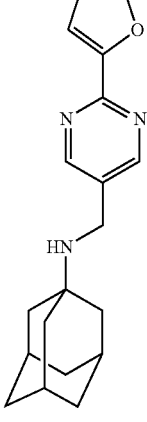 | B | A | B |

TABLE 2-continued
| Example # | Batch External ID | Structure | S31 OOcyte Inhibition at 100 uM (%) | S31N OOcyte Inhibition at 100 uM (%) | V27A OOcyte Inhibition at 100 uM (%) |
|---|---|---|---|---|---|
| 63a | M2WJ391 | 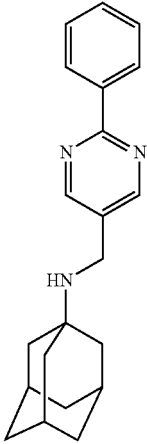 [SMILES: c1ccc(-c2ncc(CNC34CC5CC(CC(C5)C3)C4)cn2)cc1] | B | A | ND |
| 64a | M2WJ392 | 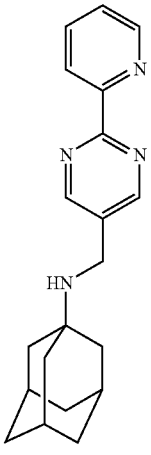 | B | B | ND |
| 65a | M2WJ322 | 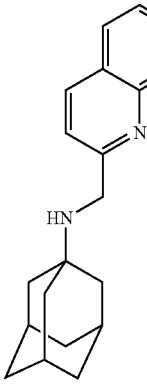 | A | B | B |

TABLE 2-continued

| Example # | Batch External ID | Structure | S31 OOcyte Inhibition at 100 uM (%) | S31N OOcyte Inhibition at 100 uM (%) | V27A OOcyte Inhibition at 100 uM (%) |
|---|---|---|---|---|---|
| 66a | IMX00616 | 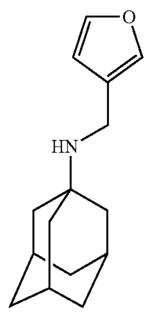 [SMILES: c1cc(CNC23CC4CC(CC(C4)C2)C3)co1] | A | B | B |
| 67a | WFD047 | 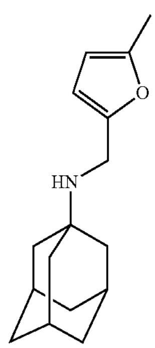 [SMILES: Cc1ccc(CNC23CC4CC(CC(C4)C2)C3)o1] | A | A | ND |
| 68a | IMX00617 | 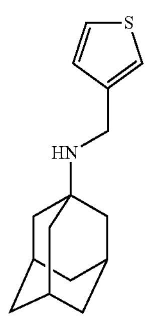 [SMILES: c1cc(CNC23CC4CC(CC(C4)C2)C3)cs1] | A | B | A |
| 69a | IMX00667 and WFD046 | 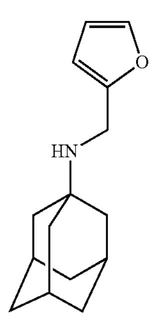 [SMILES: c1coc(CNC23CC4CC(CC(C4)C2)C3)c1] | A | B | B |

TABLE 2-continued

| Example # | Batch External ID | Structure | S31 OOcyte Inhibition at 100 uM (%) | S31N OOcyte Inhibition at 100 uM (%) | V27A OOcyte Inhibition at 100 uM (%) |
|---|---|---|---|---|---|
| 70a | IMX00668 | 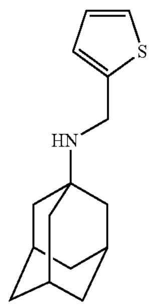 | A | B | B |
| 71a | WFD079 and IMX00669 | 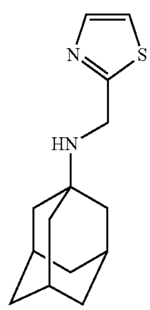 | A | A | B |
| 72a | IMX00697 | 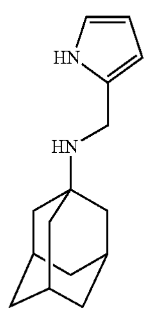 [SMILES: c1c[nH]c(CNC23CC4CC(CC(C4)C2)C3)c1] | A | B | ND |
| 73a | M2WJ396 | 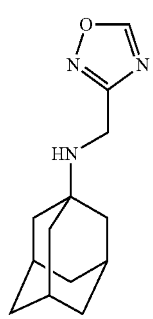 [SMILES: c1nc(CNC23CC4CC(CC(C4)C2)C3)no1] | A | A | ND |

TABLE 2-continued

| Example # | Batch External ID | Structure | S31 OOcyte Inhibition at 100 uM (%) | S31N OOcyte Inhibition at 100 uM (%) | V27A OOcyte Inhibition at 100 uM (%) |
|---|---|---|---|---|---|
| 74a | IMX00686 | (3-methoxy-thiophen-2-ylmethyl-adamantylamine) | A | A | B |
| 75a | WFD050 | (5-methoxy-thiophen-2-ylmethyl-adamantylamine) | A | A | B |
| 76a | WFD053 | (3-methyl-thiophen-2-ylmethyl-adamantylamine) | A | B | B |
| 77a | M2WJ338 | (5-bromo-4-methyl-thiophen-2-ylmethyl-adamantylamine) | A | A | A |

TABLE 2-continued
| Example # | Batch External ID | Structure | S31 OOcyte Inhibition at 100 uM (%) | S31N OOcyte Inhibition at 100 uM (%) | V27A OOcyte Inhibition at 100 uM (%) |
|---|---|---|---|---|---|
| 78a | WFD049 | 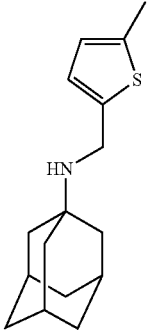 [SMILES: Cc1ccc(CNC23CC4CC(CC(C4)C2)C3)s1] | A | A | A |
| 79a | WFD052 | 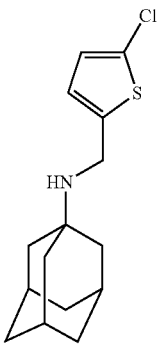 [SMILES: Clc1ccc(CNC23CC4CC(CC(C4)C2)C3)s1] | A | A | B |
| 80a | IMX00687 | 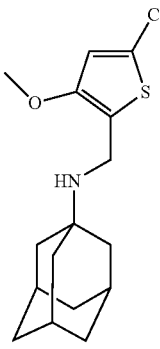 | A | B | B |
| 81a | BC035 | 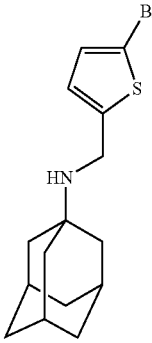 | A | A | B |

TABLE 2-continued
| Example # | Batch External ID | Structure | S31 OOcyte Inhibition at 100 uM (%) | S31N OOcyte Inhibition at 100 uM (%) | V27A OOcyte Inhibition at 100 uM (%) |
|---|---|---|---|---|---|
| 82a | M2WJ341 | 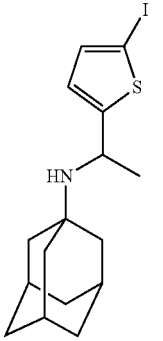 [SMILES: CC(NC12CC3CC(CC(C3)C1)C2)c1ccc(I)s1] | A | B | A |
| 83a | WFD082 | 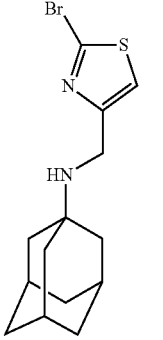 [SMILES: Brc1nc(CNC23CC4CC(CC(C4)C2)C3)cs1] | A | A | B |
| 84a | WFD084 | 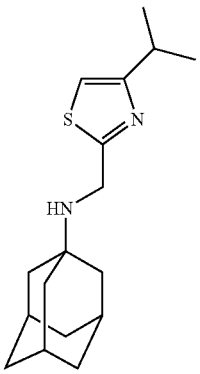 [SMILES: CC(C)c1csc(CNC23CC4CC(CC(C4)C2)C3)n1] | B | B | ND |
| 85a | WFD073 | 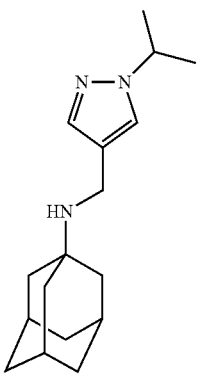 [SMILES: CC(C)n1cc(CNC23CC4CC(CC(C4)C2)C3)cn1] | B | B | ND |

TABLE 2-continued
| Example # | Batch External ID | Structure | S31 OOcyte Inhibition at 100 uM (%) | S31N OOcyte Inhibition at 100 uM (%) | V27A OOcyte Inhibition at 100 uM (%) |
|---|---|---|---|---|---|
| 86a | IMX00671 | 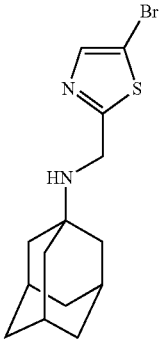 [SMILES: Brc1cnc(CNC23CC4CC(CC(C4)C2)C3)s1] | B | A | B |
| 87a | IMX00688 | 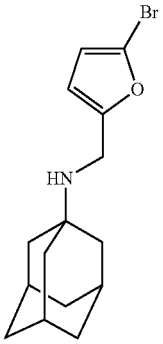 | A | B | B |
| 88a | IMX00698 | 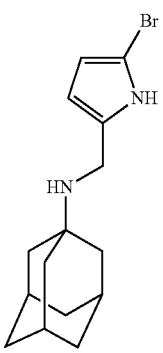 [SMILES: Brc1ccc(CNC23CC4CC(CC(C4)C2)C3)[nH]1] | A | A | ND |
| 89a | IMX00701 | 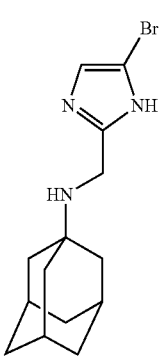 [SMILES: Brc1cnc(CNC23CC4CC(CC(C4)C2)C3)[nH]1] | A | A | ND |

TABLE 2-continued
| Example # | Batch External ID | Structure | S31 OOcyte Inhibition at 100 uM (%) | S31N OOcyte Inhibition at 100 uM (%) | V27A OOcyte Inhibition at 100 uM (%) |
|---|---|---|---|---|---|
| 90a | M2WJP001 and IMX00689 | 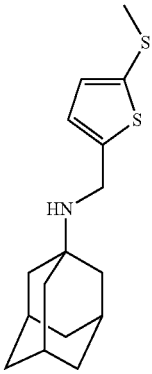 [SMILES: CSc1ccc(CNC23CC4CC(CC(C4)C2)C3)s1] | A | A | ND |
| 91a | BC067 | 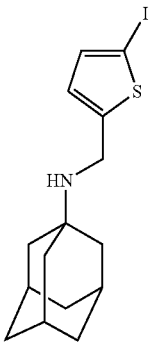 | A | A | ND |
| 92a | WFD058 | 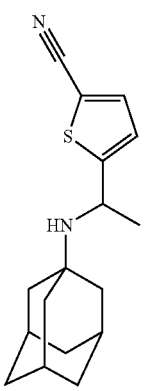 [SMILES: CC(NC12CC3CC(CC(C3)C1)C2)c1ccc(C#N)s1] | A | B | B |
| 93a | WFD085 | 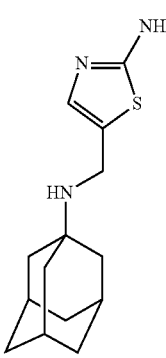 | A | B | ND |

TABLE 2-continued
| Example # | Batch External ID | Structure | S31 OOcyte Inhibition at 100 uM (%) | S31N OOcyte Inhibition at 100 uM (%) | V27A OOcyte Inhibition at 100 uM (%) |
|---|---|---|---|---|---|
| 94a | M2WJ364 | 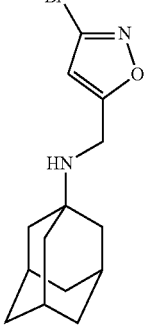 | B | A | ND |
| 95a | M2WJ369 | 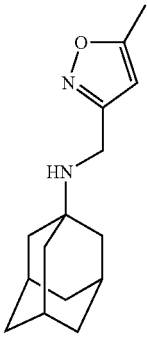 [SMILES: Cc1cc(CNC23CC4CC(CC(C4)C2)C3)no1] | A | A | ND |
| 96a | M2WJ405 | 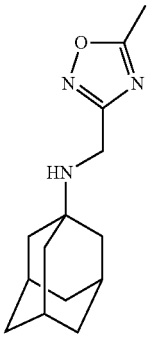 [SMILES: Cc1nc(CNC23CC4CC(CC(C4)C2)C3)no1] | A | A | ND |
| 97a | WFD057, hij-p011 | 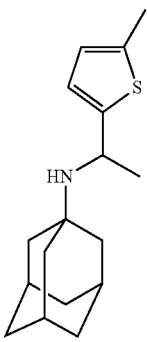 [SMILES: Cc1ccc(C(C)NC23CC4CC(CC(C4)C2)C3)s1] | B | B | B |

TABLE 2-continued

| Example # | Batch External ID | Structure | S31 OOcyte Inhibition at 100 uM (%) | S31N OOcyte Inhibition at 100 uM (%) | V27A OOcyte Inhibition at 100 uM (%) |
|---|---|---|---|---|---|
| 98a | hij-313 | 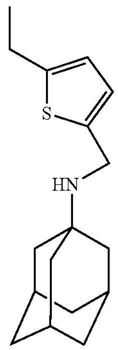 [SMILES: CCc1ccc(CNC23CC4CC(CC(C4)C2)C3)s1] | A | A | B |
| 99a | WFD069 | 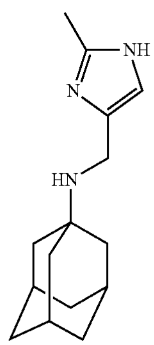 [SMILES: Cc1nc(CNC23CC4CC(CC(C4)C2)C3)c[nH]1] | B | B | B |
| 100a | WFD061 | 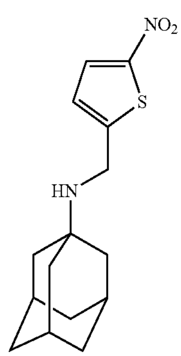 [SMILES: O=[N+]([O-])c1ccc(CNC23CC4CC(CC(C4)C2)C3)s1] | A | B | A |
| 101a | M2WJ335 | 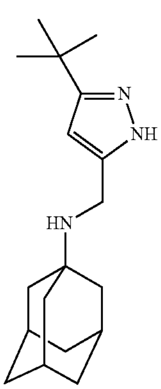 [SMILES: CC(C)(C)c1cc(CNC23CC4CC(CC(C4)C2)C3)[nH]n1] | B | B | B |

TABLE 2-continued
| Example # | Batch External ID | Structure | S31 OOcyte Inhibition at 100 uM (%) | S31N OOcyte Inhibition at 100 uM (%) | V27A OOcyte Inhibition at 100 uM (%) |
|---|---|---|---|---|---|
| 102a | M2WJ400 | 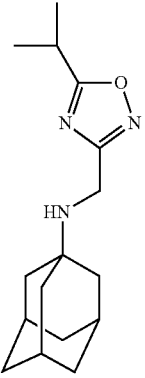 | B | A | ND |
| 103a | M2WJ401 | 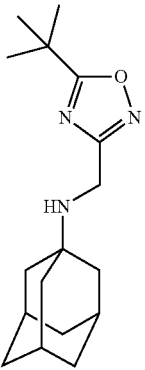 [SMILES: CC(C)(C)c1nc(CNC23CC4CC(CC(C4)C2)C3)no1] | B | A | ND |
| 104a | M2WJ349 | 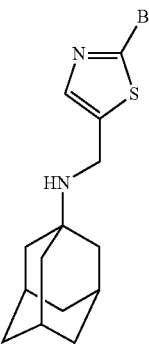 | B | A | B |
| 105a | M2WJ350 | 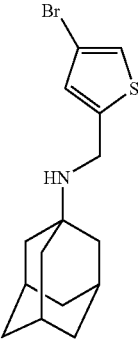 | A | A | B |

TABLE 2-continued
| Example # | Batch External ID | Structure | S31 OOcyte Inhibition at 100 uM (%) | S31N OOcyte Inhibition at 100 uM (%) | V27A OOcyte Inhibition at 100 uM (%) |
|---|---|---|---|---|---|
| 106a | M2WJ371 | 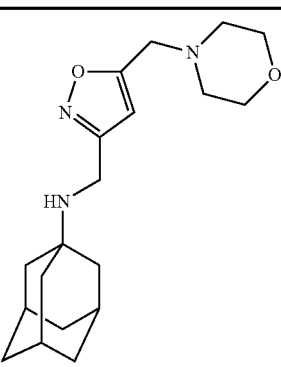 | B | B | ND |
| 107a | M2WJ379 | 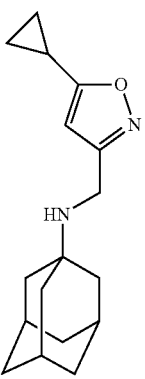 [SMILES: c1c(CNC23CC4CC(CC(C4)C2)C3)noc1C1CC1] | B | A | ND |
| 108a | M2WJ395 | 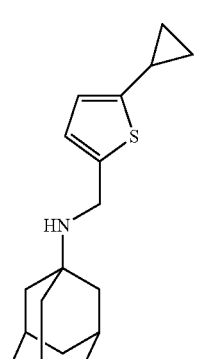 | B | A | ND |
| 109a | M2WJ403 | 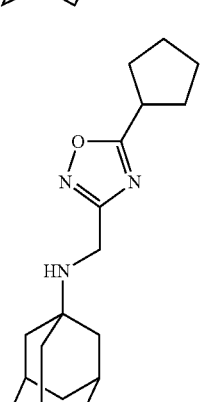 | B | A | ND |

TABLE 2-continued
| Example # | Batch External ID | Structure | S31 OOcyte Inhibition at 100 uM (%) | S31N OOcyte Inhibition at 100 uM (%) | V27A OOcyte Inhibition at 100 uM (%) |
|---|---|---|---|---|---|
| 110a | M2WJ358 | 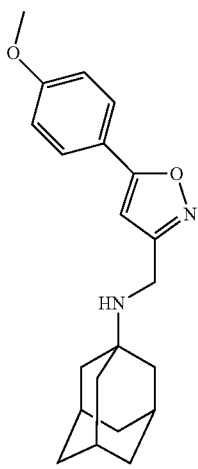 [SMILES: COc1ccc(-c2cc(CNC34CC5CC(CC(C5)C3)C4)no2)cc1] | B | A | B |
| 111a | WFD060 and IMX00666 | 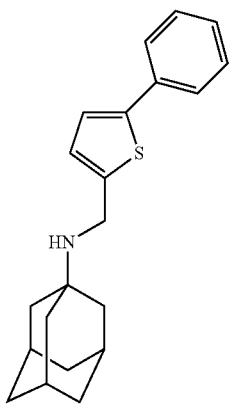 [SMILES: c1ccc(-c2ccc(CNC34CC5CC(CC(C5)C3)C4)s2)cc1] | B | A | A |
| 112a | M2WJ343 | 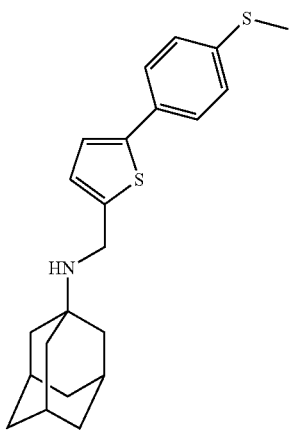 | B | A | B |

TABLE 2-continued

| Example # | Batch External ID | Structure | S31 OOcyte Inhibition at 100 uM (%) | S31N OOcyte Inhibition at 100 uM (%) | V27A OOcyte Inhibition at 100 uM (%) |
|---|---|---|---|---|---|
| 113a | M2WJ344 | 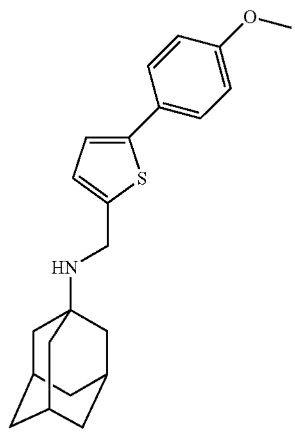 [SMILES: COc1ccc(-c2ccc(CNC34CC5CC(CC(C5)C3)C4)s2)cc1] | B | A | B |
| 114a | WFD070 | 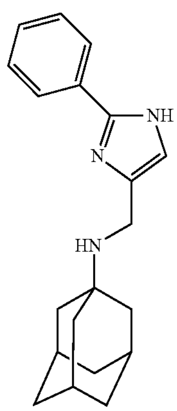 [SMILES: c1ccc(-c2nc(CNC34CC5CC(CC(C5)C3)C4)c[nH]2)cc1] | A | B | ND |
| 115a | M2WJ351 | 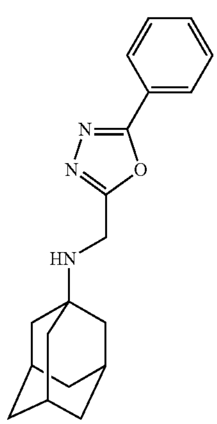 [SMILES: c1ccc(-c2nnc(CNC34CC5CC(CC(C5)C3)C4)o2)cc1] | B | A | B |

TABLE 2-continued
| Example # | Batch External ID | Structure | S31 OOcyte Inhibition at 100 uM (%) | S31N OOcyte Inhibition at 100 uM (%) | V27A OOcyte Inhibition at 100 uM (%) |
|---|---|---|---|---|---|
| 116a | M2WJ352 | 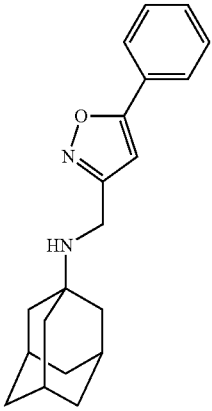 [SMILES: c1ccc(-c2cc(CNC34CC5CC(CC(C5)C3)C4)no2)cc1] | B | A | B |
| 117a | M2WJ361 | 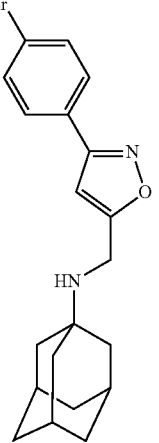 | B | B | ND |
| 118a | M2WJ366 | 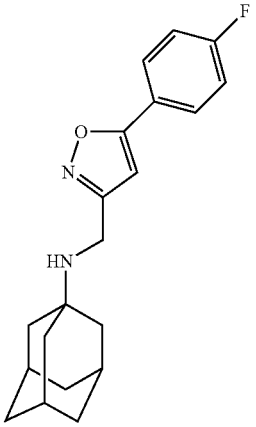 [SMILES: Fc1ccc(-c2cc(CNC34CC5CC(CC(C5)C3)C4)no2)cc1] | B | A | ND |

TABLE 2-continued

| Example # | Batch External ID | Structure | S31 OOcyte Inhibition at 100 uM (%) | S31N OOcyte Inhibition at 100 uM (%) | V27A OOcyte Inhibition at 100 uM (%) |
|---|---|---|---|---|---|
| 119a | M2WJ367 | (4-chlorophenyl-isoxazol-3-yl)methyl-adamantan-1-yl-amine | B | A | ND |
| 120a | M2WJ368 | (4-methylphenyl-isoxazol-3-yl)methyl-adamantan-1-yl-amine | B | A | ND |
| 121a | M2WJ370 | (4-bromophenyl-isoxazol-3-yl)methyl-adamantan-1-yl-amine | B | A | ND |

TABLE 2-continued

| Example # | Batch External ID | Structure | S31 OOcyte Inhibition at 100 uM (%) | S31N OOcyte Inhibition at 100 uM (%) | V27A OOcyte Inhibition at 100 uM (%) |
|---|---|---|---|---|---|
| 122a | M2WJ386 | 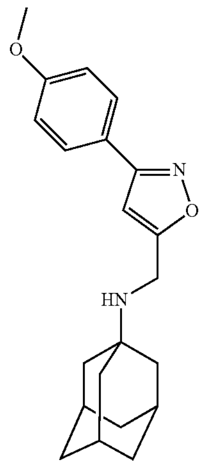 [SMILES: COc1ccc(-c2cc(CNC34CC5CC(CC(C5)C3)C4)on2)cc1] | B | A | ND |
| 123a | M2WJ376 | 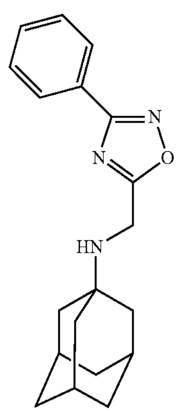 [SMILES: c1ccc(-c2noc(CNC34CC5CC(CC(C5)C3)C4)n2)cc1] | B | A | ND |
| 124a | M2WJ377 | 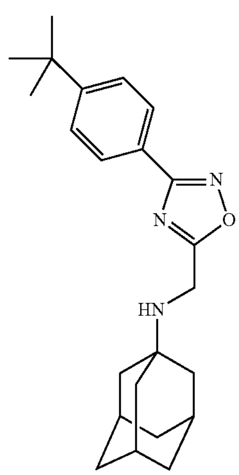 [SMILES: CC(C)(C)c1ccc(-c2noc(CNC34CC5CC(CC(C5)C3)C4)n2)cc1] | B | B | ND |

TABLE 2-continued

| Example # | Batch External ID | Structure | S31 OOcyte Inhibition at 100 uM (%) | S31N OOcyte Inhibition at 100 uM (%) | V27A OOcyte Inhibition at 100 uM (%) |
|---|---|---|---|---|---|
| 125a | M2WJ398 | 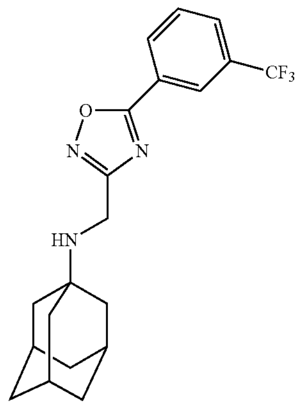 [SMILES: FC(F)(F)c1cccc(-c2nc(CNC34CC5CC(CC(C5)C3)C4)no2)c1] | B | A | ND |
| 126a | M2WJ378 | 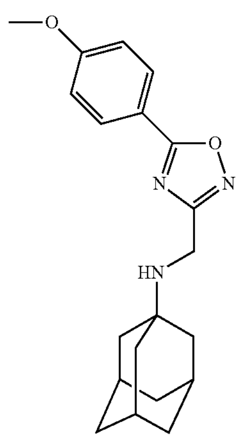 [SMILES: COc1ccc(-c2nc(CNC34CC5CC(CC(C5)C3)C4)no2)cc1] | B | A | ND |
| 127a | M2WJ356 | 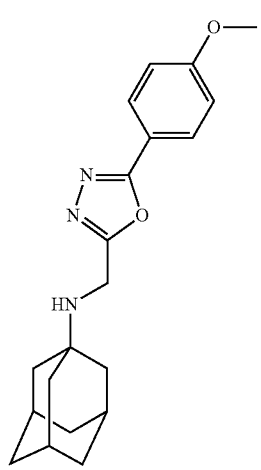 [SMILES: COc1ccc(-c2nnc(CNC34CC5CC(CC(C5)C3)C4)o2)cc1] | B | A | B |

TABLE 2-continued

| Example # | Batch External ID | Structure | S31 OOcyte Inhibition at 100 uM (%) | S31N OOcyte Inhibition at 100 uM (%) | V27A OOcyte Inhibition at 100 uM (%) |
|---|---|---|---|---|---|
| 128a | M2WJ393 | 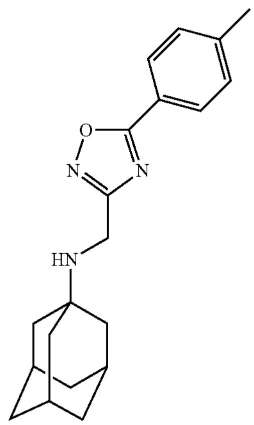 [SMILES: Cc1ccc(-c2nc(CNC34CC5CC(CC(C5)C3)C4)no2)cc1] | B | A | ND |
| 129a | M2WJ397 | 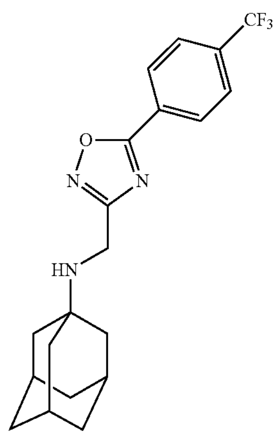 [SMILES: FC(F)(F)c1ccc(-c2nc(CNC34CC5CC(CC(C5)C3)C4)no2)cc1] | B | A | ND |
| 130a | M2WJ398 | 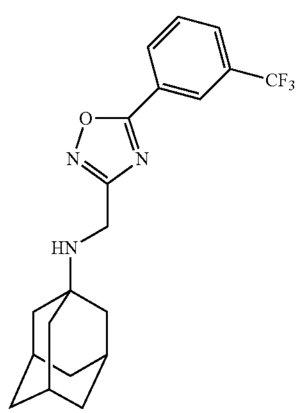 [SMILES: FC(F)(F)c1cccc(-c2nc(CNC34CC5CC(CC(C5)C3)C4)no2)c1] | B | A | ND |

TABLE 2-continued

| Example # | Batch External ID | Structure | S31 OOcyte Inhibition at 100 uM (%) | S31N OOcyte Inhibition at 100 uM (%) | V27A OOcyte Inhibition at 100 uM (%) |
|---|---|---|---|---|---|
| 131a | M2WJ399 | 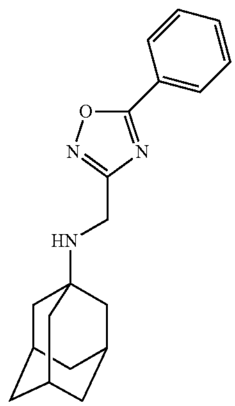 [SMILES: c1ccc(-c2nc(CNC34CC5CC(CC(C5)C3)C4)no2)cc1] | B | A | ND |
| 132a | M2WJ402 | 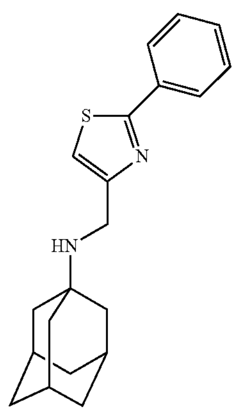 [SMILES: c1ccc(-c2nc(CNC34CC5CC(CC(C5)C3)C4)cs2)cc1] | B | B | ND |
| 133a | IMX00672 | 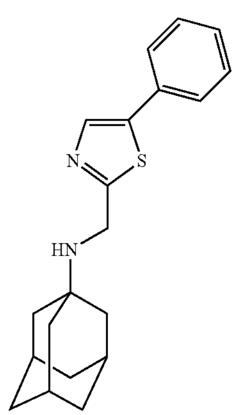 [SMILES: c1ccc(-c2cnc(CNC34CC5CC(CC(C5)C3)C4)s2)cc1] | ND | ND | ND |

TABLE 2-continued

| Example # | Batch External ID | Structure | S31 OOcyte Inhibition at 100 uM (%) | S31N OOcyte Inhibition at 100 uM (%) | V27A OOcyte Inhibition at 100 uM (%) |
|---|---|---|---|---|---|
| 134a | M2WJ380 | 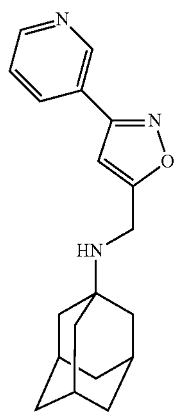 [SMILES: c1cncc(-c2cc(CNC34CC5CC(CC(C5)C3)C4)on2)c1] | B | A | ND |
| 135a | M2WJ381 | 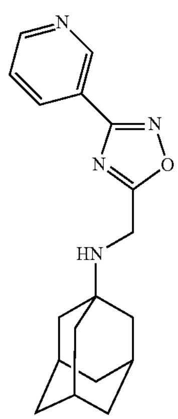 [SMILES: c1cncc(-c2noc(CNC34CC5CC(CC(C5)C3)C4)n2)c1] | B | A | ND |
| 136a | BC041 | 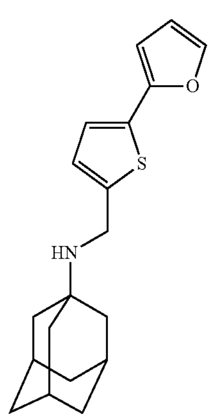 [SMILES: c1coc(-c2ccc(CNC34CC5CC(CC(C5)C3)C4)s2)c1] | B | A | B |

TABLE 2-continued

| Example # | Batch External ID | Structure | S31 OOcyte Inhibition at 100 uM (%) | S31N OOcyte Inhibition at 100 uM (%) | V27A OOcyte Inhibition at 100 uM (%) |
|---|---|---|---|---|---|
| 137a | BC042 | 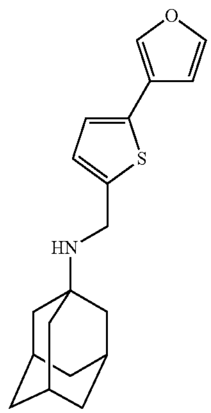 [SMILES: c1cc(-c2ccc(CNC34CC5CC(CC(C5)C3)C4)s2)co1] | B | A | B |
| 138a | IMX00703 | 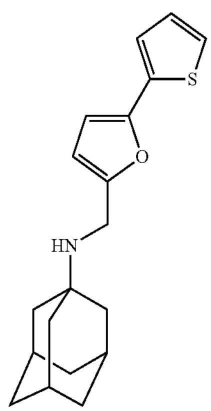 [SMILES: c1csc(-c2ccc(CNC34CC5CC(CC(C5)C3)C4)o2)c1] | B | A | ND |
| 139a | IMX00702 | 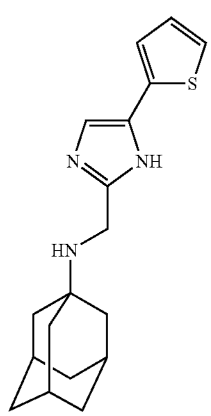 [SMILES: c1csc(-c2cnc(CNC34CC5CC(CC(C5)C3)C4)[nH]2)c1] | ND | ND | ND |

TABLE 2-continued

| Example # | Batch External ID | Structure | S31 OOcyte Inhibition at 100 uM (%) | S31N OOcyte Inhibition at 100 uM (%) | V27A OOcyte Inhibition at 100 uM (%) |
|---|---|---|---|---|---|
| 140a | M2WJ354 | 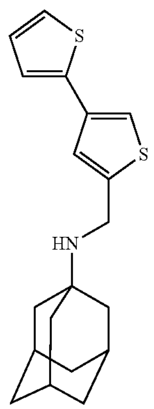 [SMILES: c1csc(-c2csc(CNC34CC5CC(CC(C5)C3)C4)c2)c1] | B | A | A |
| 141a | M2WJ357 | 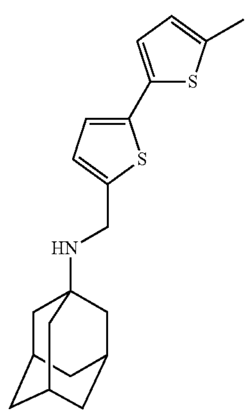 | B | A | B |
| 142a | M2WJ332 | 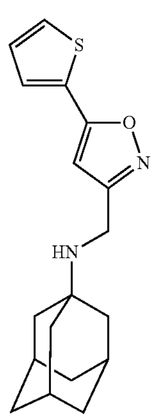 | B | A | B |

TABLE 2-continued
| Example # | Batch External ID | Structure | S31 OOcyte Inhibition at 100 uM (%) | S31N OOcyte Inhibition at 100 uM (%) | V27A OOcyte Inhibition at 100 uM (%) |
|---|---|---|---|---|---|
| 143a | M2WJ359 | 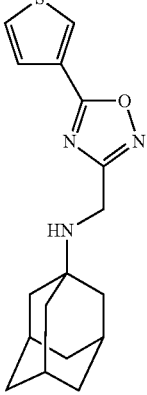 | B | A | B |
| 144a | M2WJ360 | 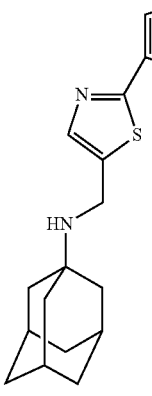 | B | A | B |
| 145a | M2WJ384 | 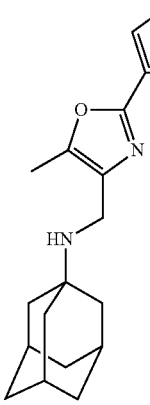 | B | B | ND |

TABLE 2-continued
| Example # | Batch External ID | Structure | S31 OOcyte Inhibition at 100 uM (%) | S31N OOcyte Inhibition at 100 uM (%) | V27A OOcyte Inhibition at 100 uM (%) |
|---|---|---|---|---|---|
| 146a | M2WJ389 | 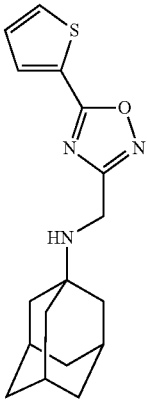 [SMILES: c1csc(-c2nc(CNC34CC5CC(CC(C5)C3)C4)no2)c1] | B | A | ND |
| 147a | M2WJ390 | 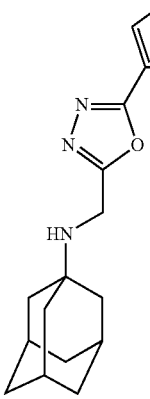 | B | A | |
| 148a | M2WJ363 | 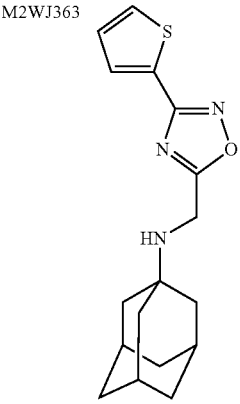 | B | A | ND |

TABLE 2-continued
| Example # | Batch External ID | Structure | S31 OOcyte Inhibition at 100 uM (%) | S31N OOcyte Inhibition at 100 uM (%) | V27A OOcyte Inhibition at 100 uM (%) |
|---|---|---|---|---|---|
| 149a | M2WJ372 | 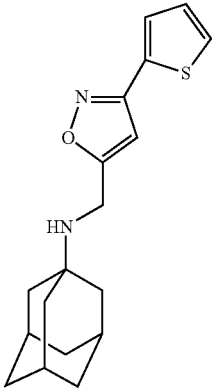 [SMILES: c1csc(-c2cc(CNC34CC5CC(CC(C5)C3)C4)on2)c1] | B | A | ND |
| 150a | M2WJ374 | 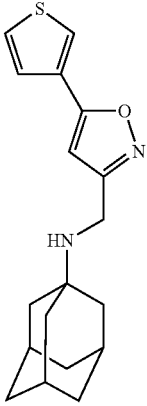 [SMILES: c1cc(-c2cc(CNC34CC5CC(CC(C5)C3)C4)no2)cs1] | B | A | ND |
| 151a | JZW036 and M2WJ375 | 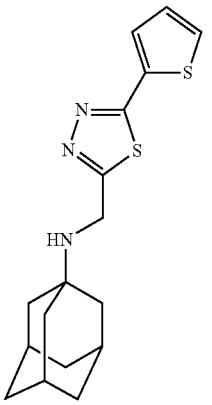 | B | A | ND |

TABLE 2-continued

| Example # | Batch External ID | Structure | S31 OOcyte Inhibition at 100 uM (%) | S31N OOcyte Inhibition at 100 uM (%) | V27A OOcyte Inhibition at 100 uM (%) |
|---|---|---|---|---|---|
| 152a | M2WJ321 | 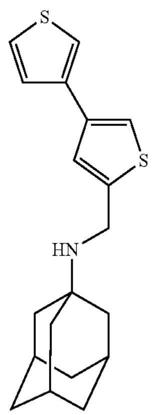 [SMILES: c1cc(-c2csc(CNC34CC5CC(CC(C5)C3)C4)c2)cs1] | B | B | A |
| 153a | M2347 | 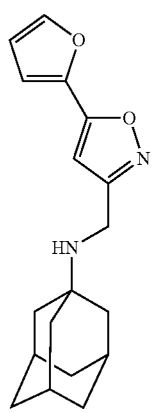 [SMILES: c1coc(-c2cc(CNC34CC5CC(CC(C5)C3)C4)no2)c1] | B | A | B |
| 154a | M2348 | 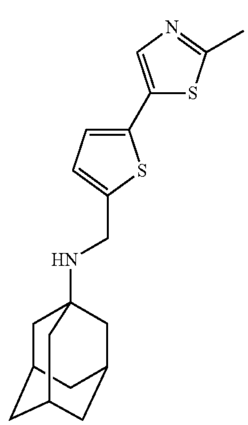 | B | A | A |

TABLE 2-continued

| Example # | Batch External ID | Structure | S31 OOcyte Inhibition at 100 uM (%) | S31N OOcyte Inhibition at 100 uM (%) | V27A OOcyte Inhibition at 100 uM (%) |
|---|---|---|---|---|---|
| 155a | M2WJ340 | 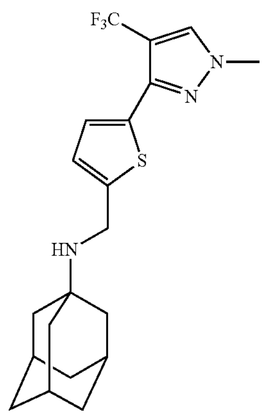 [SMILES: Cn1cc(C(F)(F)F)c(-c2ccc(CNC34CC5CC(CC(C5)C3)C4)s2)n1] | B | B | B |
| 156a | M2WJ362 | 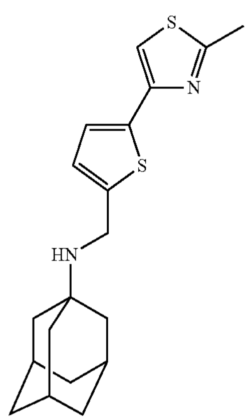 [SMILES: Cc1nc(-c2ccc(CNC34CC5CC(CC(C5)C3)C4)s2)cs1] | B | A | A |
| 157a | M2WJ339 | 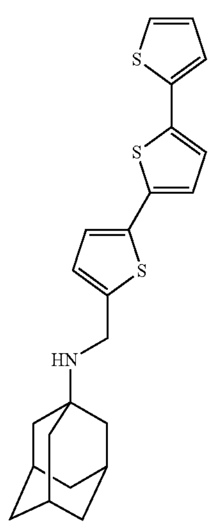 [SMILES: c1csc(-c2ccc(-c3ccc(CNC45CC6CC(CC(C6)C4)C5)s3)s2)c1] | B | B | B |

TABLE 2-continued

| Example # | Batch External ID | Structure | S31 OOcyte Inhibition at 100 uM (%) | S31N OOcyte Inhibition at 100 uM (%) | V27A OOcyte Inhibition at 100 uM (%) |
|---|---|---|---|---|---|
| 158a | M2WJ331 | 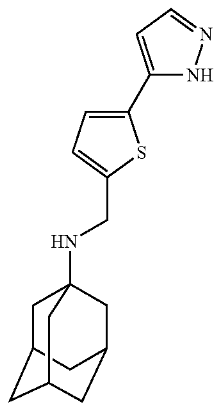 [SMILES: c1cc(-c2ccc(CNC34CC5CC(CC(C5)C3)C4)s2)[nH]n1] | B | A | A |
| 159a | M2WJ334 | 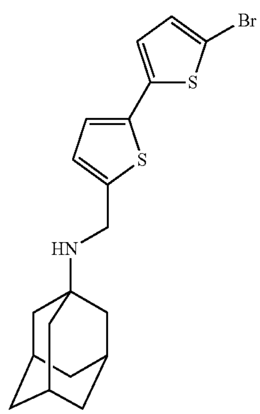 [SMILES: Brc1ccc(-c2ccc(CNC34CC5CC(CC(C5)C3)C4)s2)s1] | B | A | B |
| 160a | M2WJ394 | 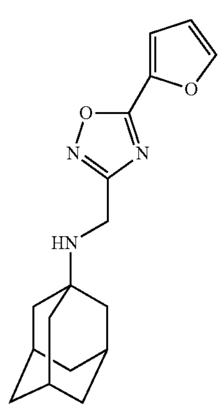 [SMILES: c1coc(-c2nc(CNC34CC5CC(CC(C5)C3)C4)no2)c1] | B | A | ND |

TABLE 2-continued

| Example # | Batch External ID | Structure | S31 OOcyte Inhibition at 100 uM (%) | S31N OOcyte Inhibition at 100 uM (%) | V27A OOcyte Inhibition at 100 uM (%) |
|---|---|---|---|---|---|
| 161a | M2WJ365 | 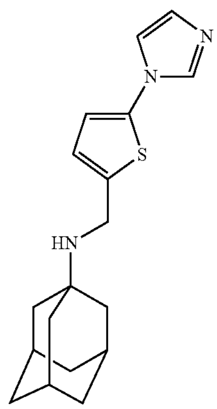 [SMILES: c1cn(-c2ccc(CNC34CC5CC(CC(C5)C3)C4)s2)cn1] | B | B | ND |
| 162a | M2WJ327 | 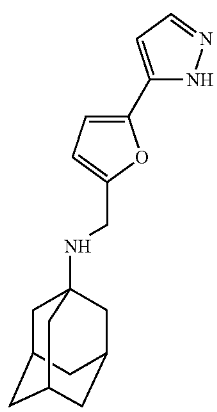 [SMILES: c1cc(-c2ccc(CNC34CC5CC(CC(C5)C3)C4)o2)[nH]n1] | B | B | B |
| 163a | M2WJ406 | 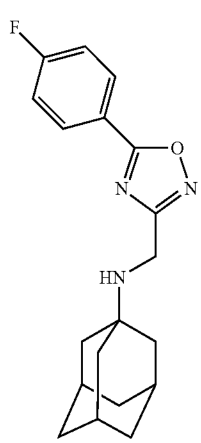 [SMILES: Fc1ccc(-c2nc(CNC34CC5CC(CC(C5)C3)C4)no2)cc1] | B | A | ND |

TABLE 2-continued
| Example # | Batch External ID | Structure | S31 OOcyte Inhibition at 100 uM (%) | S31N OOcyte Inhibition at 100 uM (%) | V27A OOcyte Inhibition at 100 uM (%) |
|---|---|---|---|---|---|
| 164a | M2WJ353 | 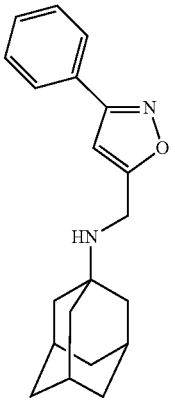 | B | A | ND |
| 165a | M2WJ408 | 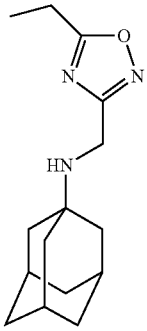 | A | A | ND |
| 166a | M2WJ409 | 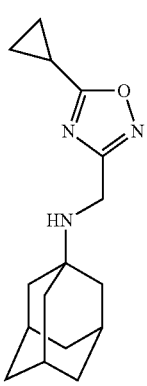 [SMILES: C(NC12CC3CC(CC(C3)C1)C2)c1noc(C2CC2)n1] | B | A | ND |
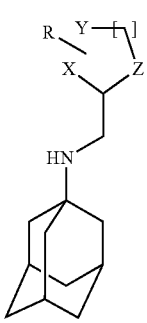
III TABLE 2-continued

| Example # | Batch External ID | Structure | S31 OOcyte Inhibition at 100 uM (%) | S31N OOcyte Inhibition at 100 uM (%) | V27A OOcyte Inhibition at 100 uM (%) |
|---|---|---|---|---|---|
| 167a | M2WJ388 | 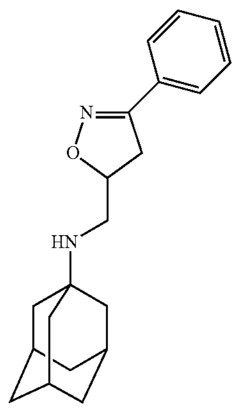 [SMILES: c1ccc(C2=NOC(CNC34CC5CC(CC(C5)C3)C4)C2)cc1] | B | A | ND |
| 168a | M2WJ373 | 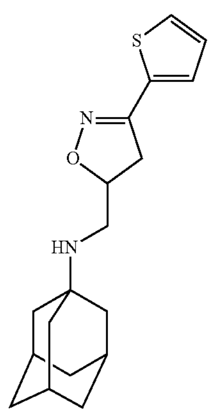 [SMILES: c1csc(C2=NOC(CNC34CC5CC(CC(C5)C3)C4)C2)c1] | B | A | ND |
| 169a | WFD110 | 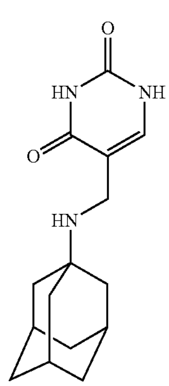 [SMILES: O=c1[nH]cc(CNC23CC4CC(CC(C4)C2)C3)c(=O)[nH]1] | B | B | B |

TABLE 2-continued
| Example # | Batch External ID | Structure | S31 OOcyte Inhibition at 100 uM (%) | S31N OOcyte Inhibition at 100 uM (%) | V27A OOcyte Inhibition at 100 uM (%) |
|---|---|---|---|---|---|
| 170a | IMX00677 | 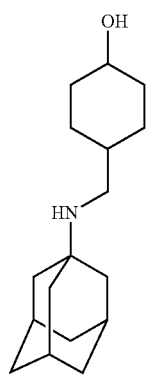 [SMILES: OC1CCC(CNC23CC4CC(CC(C4)C2)C3)CC1] | B | B | B |
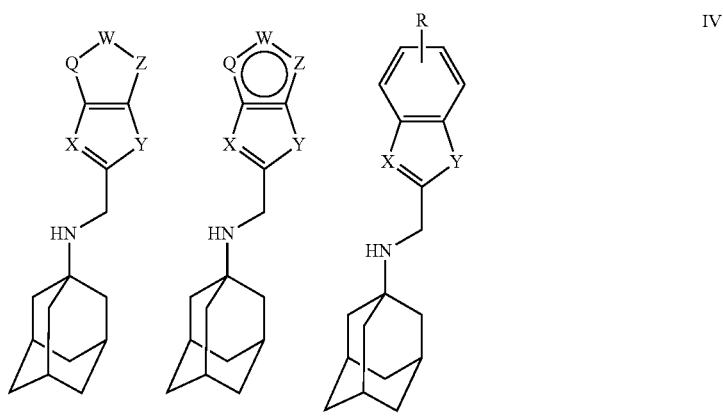    IV
X, Y, Z, Q, W, CR, NH, NR, O, S
| 171a | IMX00683 | 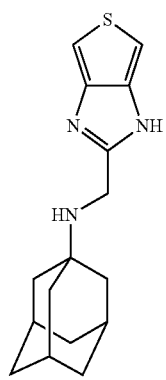 [SMILES: c1scc2[nH]c(CNC34CC5CC(CC(C5)C3)C4)nc12] | B | A | B |

TABLE 2-continued

| Example # | Batch External ID | Structure | S31 OOcyte Inhibition at 100 uM (%) | S31N OOcyte Inhibition at 100 uM (%) | V27A OOcyte Inhibition at 100 uM (%) |
|---|---|---|---|---|---|
| 172a | IMX00685 | 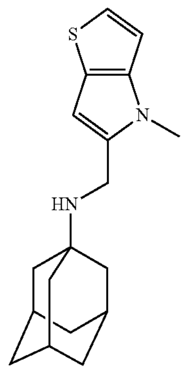 [SMILES: Cn1c(CNC23CC4CC(CC(C4)C2)C3)cc2sccc21] | B | B | B |
| 173a | IMX00735 | 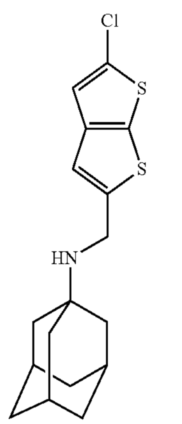 [SMILES: Clc1cc2cc(CNC34CC5CC(CC(C5)C3)C4)sc2s1] | A | A | TBD |
| 174a | IMX00714 | 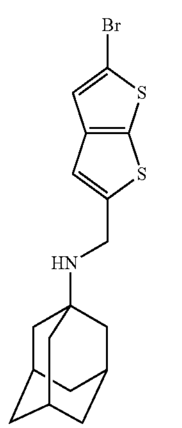 | ND | ND | ND |

TABLE 2-continued

| Example # | Batch External ID | Structure | S31 OOcyte Inhibition at 100 uM (%) | S31N OOcyte Inhibition at 100 uM (%) | V27A OOcyte Inhibition at 100 uM (%) |
|---|---|---|---|---|---|
| 175a | JZW162 | 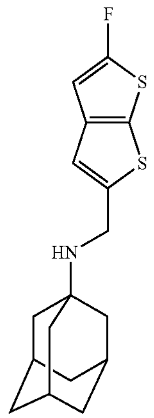 | ND | ND | ND |
| 176a | M2WJ333 | 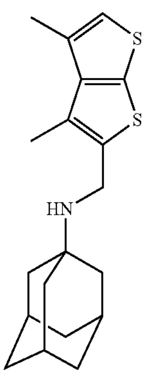 [SMILES: Cc1csc2sc(CNC34CC5CC(CC(C5)C3)C4)c(C)c12] | B | B | B |
| 177a | IMX00643 | 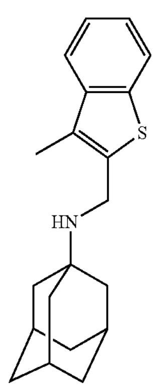 [SMILES: Cc1c(CNC23CC4CC(CC(C4)C2)C3)sc2ccccc12] | A | B | B |

TABLE 2-continued
| Example # | Batch External ID | Structure | S31 OOcyte Inhibition at 100 uM (%) | S31N OOcyte Inhibition at 100 uM (%) | V27A OOcyte Inhibition at 100 uM (%) |
|---|---|---|---|---|---|
| 178a | CMF004 | 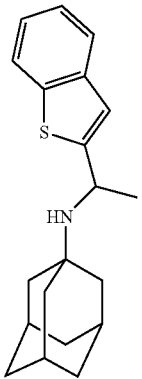 [SMILES: CC(NC12CC3CC(CC(C3)C1)C2)c1cc2ccccc2s1] | A | B | A |
| 179a | IMX00705/ M2WJ323 | 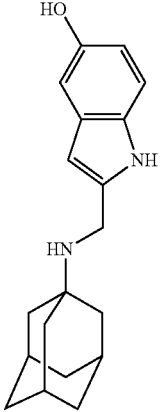 [SMILES: Oc1ccc2[nH]c(CNC34CC5CC(CC(C5)C3)C4)cc2c1] | B | B | B |
| 180a | IMX00692 | 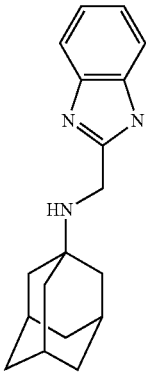 | B | B | ND |

TABLE 2-continued

| Example # | Batch External ID | Structure | S31 OOcyte Inhibition at 100 uM (%) | S31N OOcyte Inhibition at 100 uM (%) | V27A OOcyte Inhibition at 100 uM (%) |
|---|---|---|---|---|---|
| 181a | IMX00693 | 5-chloro-benzimidazol-2-yl-CH2-NH-(1-adamantyl) | B | A | ND |
| 182a | IMX00696 | 5-methoxy-1H-indol-2-yl-CH2-NH-(1-adamantyl) | B | A | ND |
| 183a | IMX00713 | 7-chloro-benzothiophen-2-yl-CH2-NH-(1-adamantyl) | A | B | ND |

TABLE 2-continued
| Example # | Batch External ID | Structure | S31 OOcyte Inhibition at 100 uM (%) | S31N OOcyte Inhibition at 100 uM (%) | V27A OOcyte Inhibition at 100 uM (%) |
|---|---|---|---|---|---|
| 184a | IMX00721 | 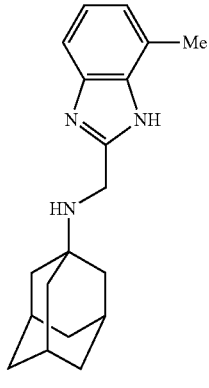 [SMILES: Cc1cccc2nc(CNC34CC5CC(CC(C5)C3)C4)[nH]c12] | B | A | ND |
| 185a | M2WJ345 | 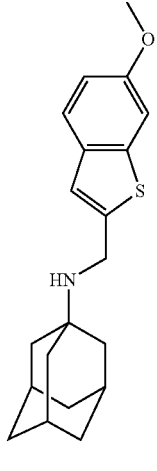 [SMILES: COc1ccc2cc(CNC34CC5CC(CC(C5)C3)C4)sc2c1] | B | A | B |
| 186a | M2WJ346 | 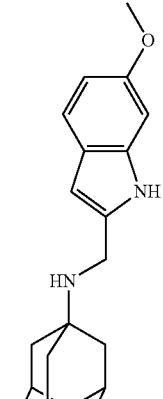 | B | A | B |

TABLE 2-continued
| Example # | Batch External ID | Structure | S31 OOcyte Inhibition at 100 uM (%) | S31N OOcyte Inhibition at 100 uM (%) | V27A OOcyte Inhibition at 100 uM (%) |
|---|---|---|---|---|---|
| | | 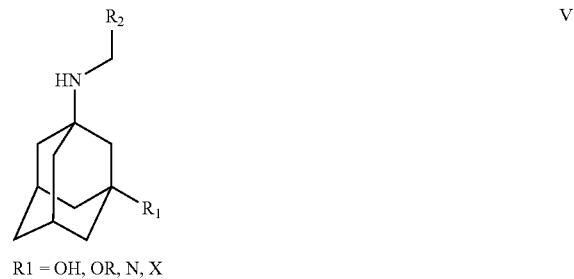<br>R1 = OH, OR, N, X | | | V |
| 187a | IMX00684 | 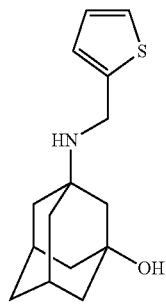 | B | A | B |
| 188a | IMX00680 | 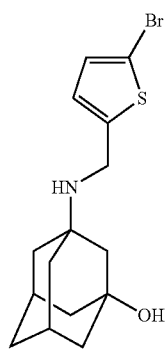 [SMILES: OC12CC3CC(C1)CC(NCc1ccc(Br)s1)(C3)C2] | B | A | ND |
| 189a | IMX00716 | 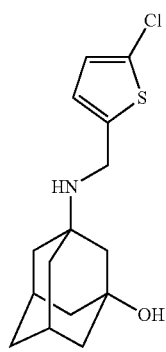 | B | B | TBD |

TABLE 2-continued

| Example # | Batch External ID | Structure | S31 OOcyte Inhibition at 100 uM (%) | S31N OOcyte Inhibition at 100 uM (%) | V27A OOcyte Inhibition at 100 uM (%) |
|---|---|---|---|---|---|
| 190a | IMX00691 | 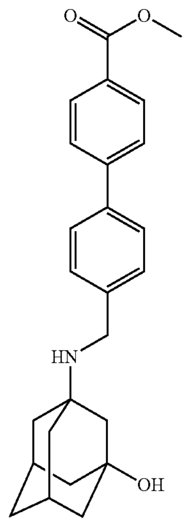 [SMILES: COC(=O)c1ccc(-c2ccc(CNC34CC5CC(CC(O)(C5)C3)C4)cc2)cc1] | B | A | ND |
| 191a | IMX00690 | 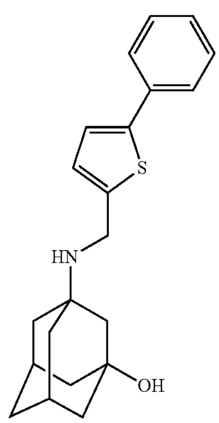 [SMILES: OC12CC3CC(C1)CC(NCc1ccc(-c4ccccc4)s1)(C3)C2] | B | A | B |
| 192a | IMX706 | 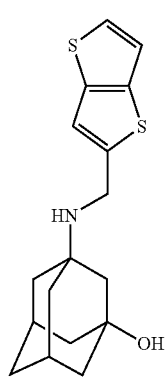 [SMILES: OC12CC3CC(C1)CC(NCc1cc4sccc4s1)(C3)C2] | B | A | ND |

TABLE 2-continued

| Example # | Batch External ID | Structure | S31 OOcyte Inhibition at 100 uM (%) | S31N OOcyte Inhibition at 100 uM (%) | V27A OOcyte Inhibition at 100 uM (%) |
|---|---|---|---|---|---|
| 193a | M2WJ404 | 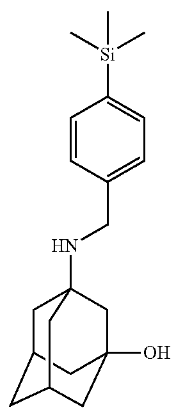 [SMILES: C[Si](C)(C)c1ccc(CNC23CC4CC(CC(O)(C4)C2)C3)cc1] | B | A | ND |
| 194a | M2WJ382 | 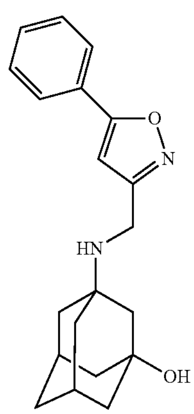 [SMILES: OC12CC3CC(C1)CC(NCc1cc(-c4ccccc4)on1)(C3)C2] | B | A | ND |
| 195a | IMX00733 | 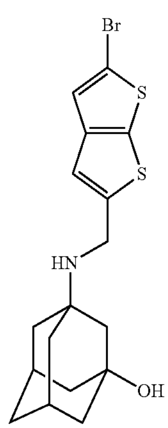 [SMILES: OC12CC3CC(C1)CC(NCc1cc4cc(Br)sc4s1)(C3)C2] | B | A | ND |

TABLE 2-continued
| Example # | Batch External ID | Structure | S31 OOcyte Inhibition at 100 uM (%) | S31N OOcyte Inhibition at 100 uM (%) | V27A OOcyte Inhibition at 100 uM (%) |
|---|---|---|---|---|---|
| 196a | Imx00727 | 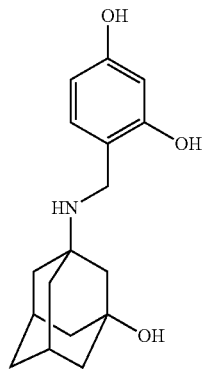 [SMILES: Oc1ccc(CNC23CC4CC(CC(O)(C4)C2)C3)c(O)c1] | B | A | ND |
| | | 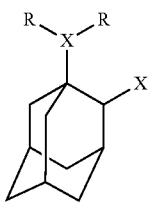<br>X = N, O | | | VI |
| 197a | IMX00737 | 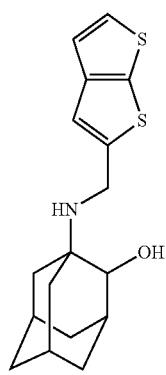 [SMILES: OC1C2CC3CC(C2)CC1(NCc1cc2ccsc2s1)C3] | ND | ND | ND |
| | | 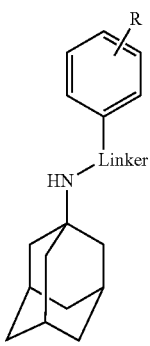 | | | VII |

TABLE 2-continued

| Example # | Batch External ID | Structure | S31 OOcyte Inhibition at 100 uM (%) | S31N OOcyte Inhibition at 100 uM (%) | V27A OOcyte Inhibition at 100 uM (%) |
|---|---|---|---|---|---|
| 198a | hij-306 | 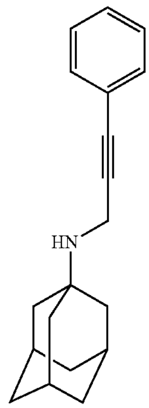 [SMILES: C(#Cc1ccccc1)CNC12CC3CC(CC(C3)C1)C2] | B | A | B |
| 199a | CFM001 | 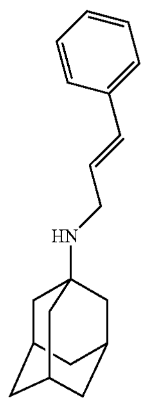 [SMILES: C(=C\c1ccccc1)/CNC12CC3CC(CC(C3)C1)C2] | B | A | B |
| 200a | hij-307 | 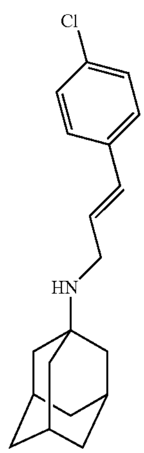 [SMILES: Clc1ccc(/C=C/CNC23CC4CC(CC(C4)C2)C3)cc1] | B | A | B |
| | | | | | VIII |

TABLE 2-continued
| Example # | Batch External ID | Structure | S31 OOcyte Inhibition at 100 uM (%) | S31N OOcyte Inhibition at 100 uM (%) | V27A OOcyte Inhibition at 100 uM (%) |
|---|---|---|---|---|---|
| 201a | IMX00732 | 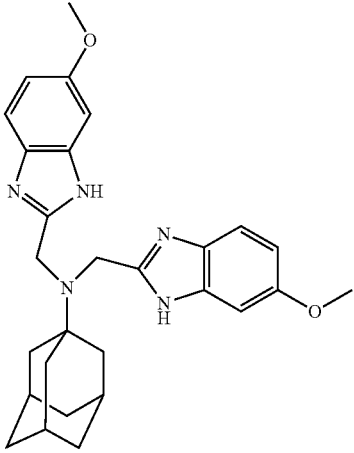 [SMILES: COc1ccc2nc(CN(Cc3nc4ccc(OC)cc4[nH]3)C34CC5CC(CC(C5)C3)C4)[nH]c2c1] | B | B | ND |
| 202a | M2WJ416 | 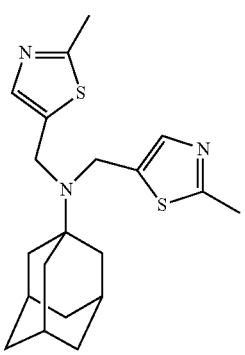 [SMILES: Cc1ncc(CN(Cc2cnc(C)s2)C23CC4CC(CC(C4)C2)C3)s1] | B | B | ND |
| Other |
| 203a | IMX00709 | 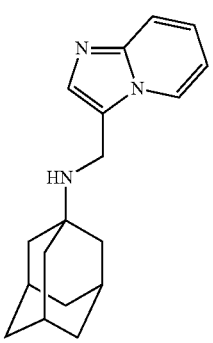 [SMILES: c1ccn2c(CNC34CC5CC(CC(C5)C3)C4)cnc2c1] | A | B | B |
| 204a | BC059 | 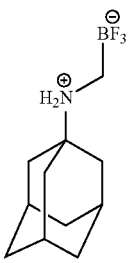 | A | B | B |

TABLE 2-continued
| Example # | Batch External ID | Structure | S31 OOcyte Inhibition at 100 uM (%) | S31N OOcyte Inhibition at 100 uM (%) | V27A OOcyte Inhibition at 100 uM (%) |
|---|---|---|---|---|---|
| | | | | | IX |
| 205a | M2WJ324 | 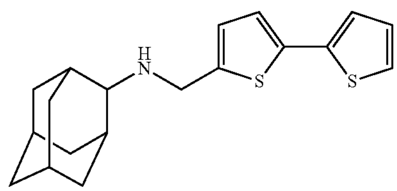 | B | A | B |
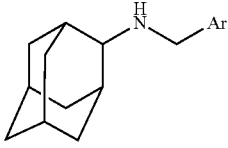
TABLE 3
| Example # | Batch External ID | Structure | S31 OOcyte Inhibition at 100 uM (%) | S31N OOcyte Inhibition at 100 uM (%) | V27A OOcyte Inhibition at 100 uM (%) |
|---|---|---|---|---|---|
| 1b | BC085 | 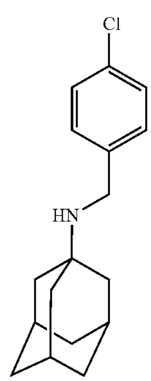 | A | A | ND |
| 2b | BC089 | 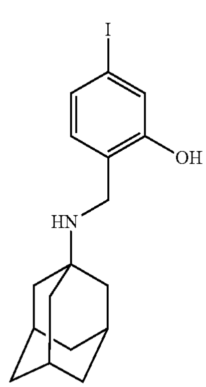 | A | A | ND |
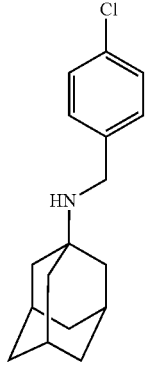
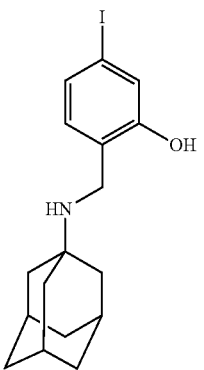

TABLE 3-continued

| Example # | Batch External ID | Structure | S31 OOcyte Inhibition at 100 uM (%) | S31N OOcyte Inhibition at 100 uM (%) | V27A OOcyte Inhibition at 100 uM (%) |
|---|---|---|---|---|---|
| 3b | Hij339-1 | 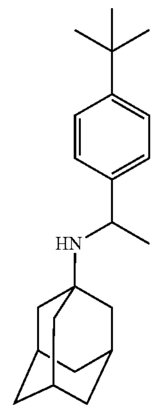 [SMILES: CC(NC12CC3CC(CC(C3)C1)C2)c1ccc(C(C)(C)C)cc1] | B | B | ND |
| 4b | Hij334-1 | 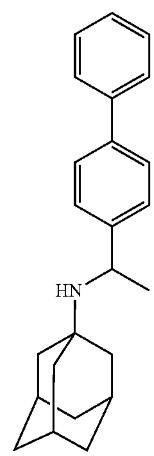 [SMILES: CC(NC12CC3CC(CC(C3)C1)C2)c1ccc(-c2ccccc2)cc1] | A | B | ND |
| 5b | BC045 | 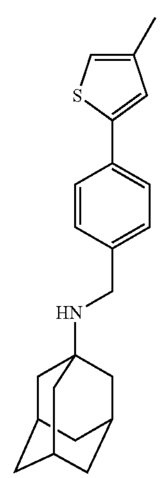 [SMILES: Cc1csc(-c2ccc(CNC34CC5CC(CC(C5)C3)C4)cc2)c1] | B | A | ND |

TABLE 3-continued

| Example # | Batch External ID | Structure | S31 OOcyte Inhibition at 100 uM (%) | S31N OOcyte Inhibition at 100 uM (%) | V27A OOcyte Inhibition at 100 uM (%) |
|---|---|---|---|---|---|
| 6b | BC102 | 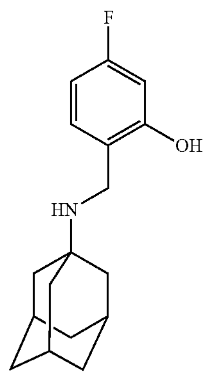 | A | A | ND |
| 7b | BC113 | 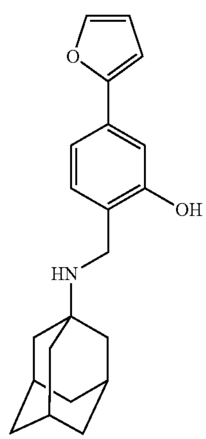 | B | A | ND |
| 8b | BC114 | 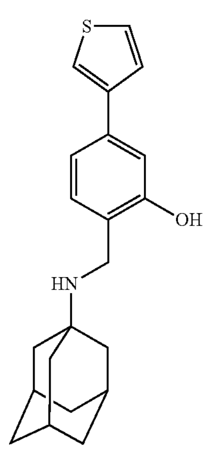 | B | A | ND |

TABLE 3-continued

| Example # | Batch External ID | Structure | S31 OOcyte Inhibition at 100 uM (%) | S31N OOcyte Inhibition at 100 uM (%) | V27A OOcyte Inhibition at 100 uM (%) |
|---|---|---|---|---|---|
| 9b | BC100 | 4-chloro-2-((adamantan-1-ylamino)methyl)phenol | A | A | ND |
| 10b | M2WJ410-1 | 5-chloro-3-((adamantan-1-ylaminomethyl))-1,2,4-thiadiazole | A | A | ND |
| 11b | M2WJ411-1 | 2-(thiophen-2-yl)-4-((adamantan-1-ylamino)methyl)thiazole | B | A | ND |
| 12b | M2WJ412-1 | 2-methyl-4-((adamantan-1-ylamino)methyl)thiazole | A | A | ND |

TABLE 3-continued

| Example # | Batch External ID | Structure | S31 OOcyte Inhibition at 100 uM (%) | S31N OOcyte Inhibition at 100 uM (%) | V27A OOcyte Inhibition at 100 uM (%) |
|---|---|---|---|---|---|
| 13b | M2WJ413-1 | 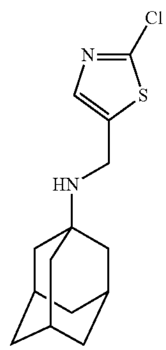 [SMILES: Clc1ncc(CNC23CC4CC(CC(C4)C2)C3)s1] | A | B | ND |
| 14b | M2WJ414-1 | 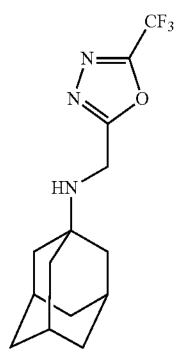 [SMILES: FC(F)(F)c1nnc(CNC23CC4CC(CC(C4)C2)C3)o1] | B | A | ND |
| 15b | M2WJ415-1 | 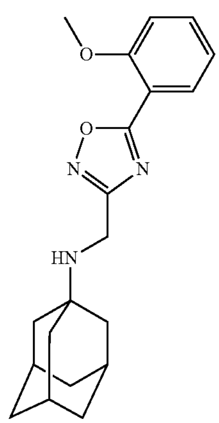 [SMILES: COc1ccccc1-c1nc(CNC23CC4CC(CC(C4)C2)C3)no1] | B | A | ND |
| 16b | M2WJ417-1 | 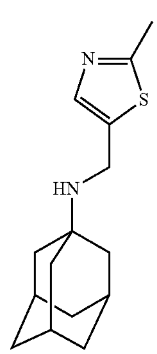 [SMILES: Cc1ncc(CNC23CC4CC(CC(C4)C2)C3)s1] | B | B | ND |

TABLE 3-continued
| Example # | Batch External ID | Structure | S31 OOcyte Inhibition at 100 uM (%) | S31N OOcyte Inhibition at 100 uM (%) | V27A OOcyte Inhibition at 100 uM (%) |
|---|---|---|---|---|---|
| 17b | M2WJ419-1 | 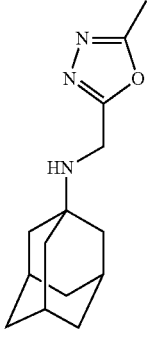 | B | A | ND |
| 18b | M2WJ420-1 | 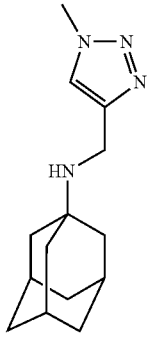 [SMILES: Cn1cc(CNC23CC4CC(CC(C4)C2)C3)nn1] | B | B | ND |
| 19b | M2WJ421-1 | 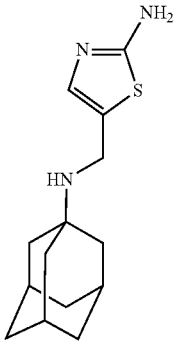 | B | B | ND |
| 20b | M2WJ422-1 | 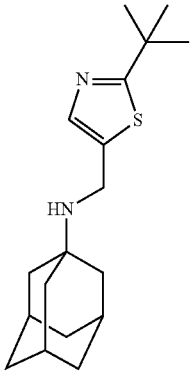 [SMILES: CC(C)(C)c1ncc(CNC23CC4CC(CC(C4)C2)C3)s1] | B | A | ND |

TABLE 3-continued

| Example # | Batch External ID | Structure | S31 OOcyte Inhibition at 100 uM (%) | S31N OOcyte Inhibition at 100 uM (%) | V27A OOcyte Inhibition at 100 uM (%) |
|---|---|---|---|---|---|
| 21b | M2WJ423-1 | 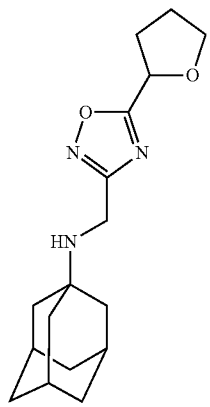 [SMILES: C1COC(c2nc(CNC34CC5CC(CC(C5)C3)C4)no2)C1] | B | A | ND |
| 22b | M2WJ4241 | 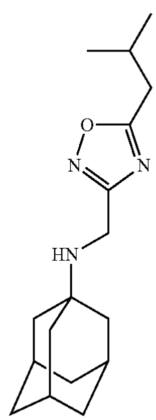 [SMILES: CC(C)Cc1nc(CNC23CC4CC(CC(C4)C2)C3)no1] | B | A | ND |
| 23b | M2WJ426-1 | 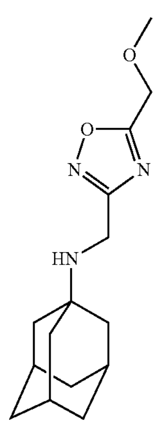 [SMILES: COCc1nc(CNC23CC4CC(CC(C4)C2)C3)no1] | B | A | ND |

TABLE 3-continued
| Example # | Batch External ID | Structure | S31 OOcyte Inhibition at 100 uM (%) | S31N OOcyte Inhibition at 100 uM (%) | V27A OOcyte Inhibition at 100 uM (%) |
|---|---|---|---|---|---|
| 24b | M2WJ428-1 | 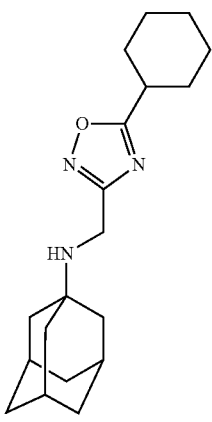 [SMILES: C1CCC(c2nc(CNC34CC5CC(CC(C5)C3)C4)no2)CC1] | A | A | ND |
| 25b | M2WJ430-1 | 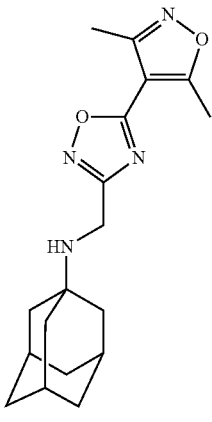 [SMILES: Cc1noc(C)c1-c1nc(CNC23CC4CC(CC(C4)C2)C3)no1] | B | B | ND |
| 26b | M2WJ431-1 | 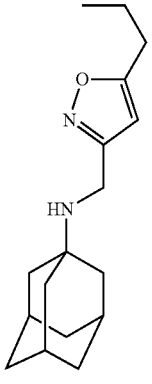 [SMILES: CCCc1cc(CNC23CC4CC(CC(C4)C2)C3)no1] | B | A | ND |

TABLE 3-continued
| Example # | Batch External ID | Structure | S31 OOcyte Inhibition at 100 uM (%) | S31N OOcyte Inhibition at 100 uM (%) | V27A OOcyte Inhibition at 100 uM (%) |
|---|---|---|---|---|---|
| 27b | M2WJ432-1 | 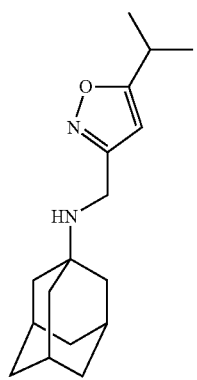 [SMILES: CC(C)c1cc(CNC23CC4CC(CC(C4)C2)C3)no1] | B | A | ND |
| 28b | M2WJ434-1 | 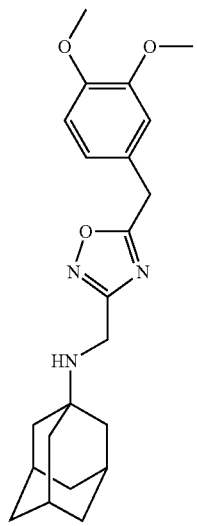 [SMILES: COc1ccc(Cc2nc(CNC34CC5CC(CC(C5)C3)C4)no2)cc1OC] | B | A | ND |
| 29b | M2WJ437-1 | 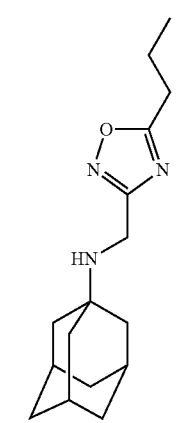 [SMILES: CCCc1nc(CNC23CC4CC(CC(C4)C2)C3)no1] | B | A | ND |

TABLE 3-continued

| Example # | Batch External ID | Structure | S31 OOcyte Inhibition at 100 uM (%) | S31N OOcyte Inhibition at 100 uM (%) | V27A OOcyte Inhibition at 100 uM (%) |
|---|---|---|---|---|---|
| 30b | M2WJ438-1 | 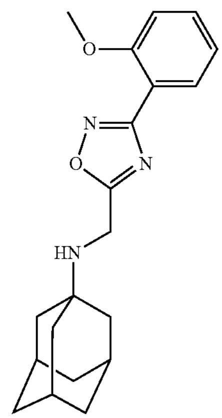 [SMILES: COc1ccccc1-c1noc(CNC23CC4CC(CC(C4)C2)C3)n1] | B | A | ND |
| 31b | M2WJ439-1 | 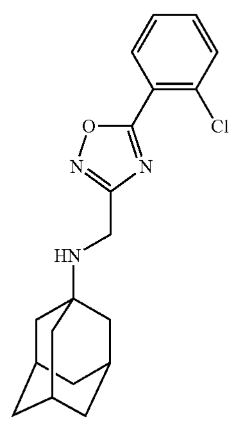 [SMILES: Clc1ccccc1-c1nc(CNC23CC4CC(CC(C4)C2)C3)no1] | B | A | ND |
| 32b | M2WJ442-1 | 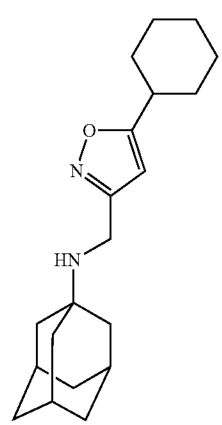 [SMILES: c1c(CNC23CC4CC(CC(C4)C2)C3)noc1C1CCCCC1] | B | A | ND |

TABLE 3-continued
| Example # | Batch External ID | Structure | S31 OOcyte Inhibition at 100 uM (%) | S31N OOcyte Inhibition at 100 uM (%) | V27A OOcyte Inhibition at 100 uM (%) |
|---|---|---|---|---|---|
| 33b | M2WJ442-1 | 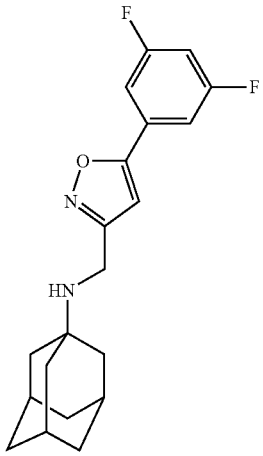 [SMILES: Fc1cc(F)cc(-c2cc(CNC34CC5CC(CC(C5)C3)C4)no2)c1] | B | A | ND |
| 34b | M2WJ444-1 | 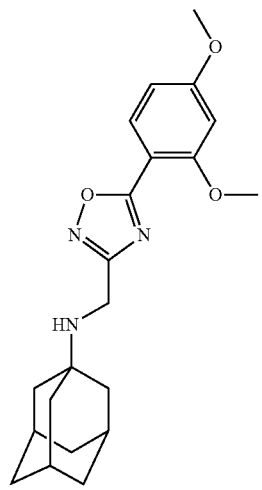 [SMILES: COc1ccc(-c2nc(CNC34CC5CC(CC(C5)C3)C4)no2)c(OC)c1] | B | A | ND |
| 35b | M2WJ445-1 | 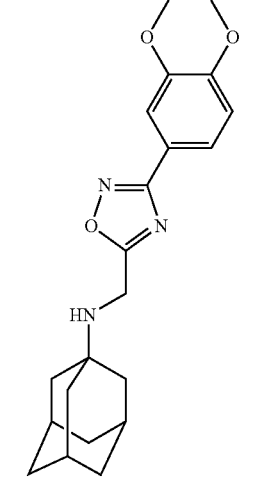 [SMILES: COc1ccc(-c2noc(CNC34CC5CC(CC(C5)C3)C4)n2)cc1OC] | B | A | ND |

TABLE 3-continued
| Example # | Batch External ID | Structure | S31 OOcyte Inhibition at 100 uM (%) | S31N OOcyte Inhibition at 100 uM (%) | V27A OOcyte Inhibition at 100 uM (%) |
|---|---|---|---|---|---|
| 36b | M2WJ446-1 | 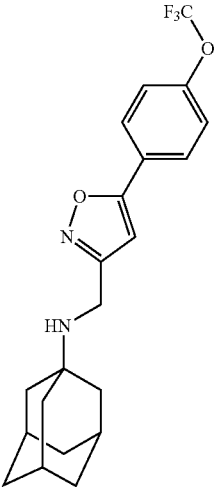 [SMILES: FC(F)(F)Oc1ccc(-c2cc(CNC34CC5CC(CC(C5)C3)C4)no2)cc1] | B | B | ND |
| 37b | M2WJ447-1 | 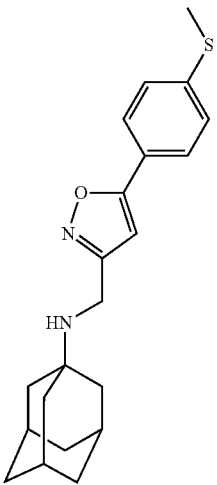 [SMILES: CSc1ccc(-c2cc(CNC34CC5CC(CC(C5)C3)C4)no2)cc1] | B | A | ND |
| 38b | M2WJ448-1 | 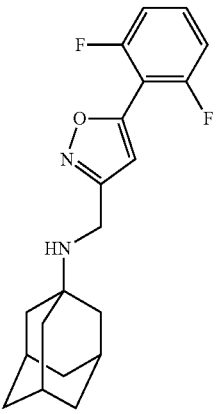 [SMILES: Fc1cccc(F)c1-c1cc(CNC23CC4CC(CC(C4)C2)C3)no1] | B | A | ND |

TABLE 3-continued

| Example # | Batch External ID | Structure | S31 OOcyte Inhibition at 100 uM (%) | S31N OOcyte Inhibition at 100 uM (%) | V27A OOcyte Inhibition at 100 uM (%) |
|---|---|---|---|---|---|
| 39b | M2WJ449-1 | 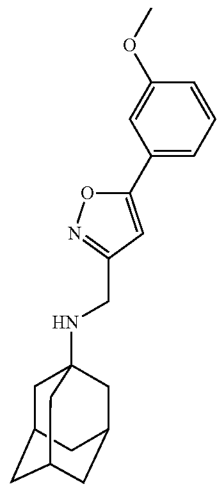 [SMILES: COc1cccc(-c2cc(CNC34CC5CC(CC(C5)C3)C4)no2)c1] | B | A | ND |
| 40b | M2WJ451-1 | 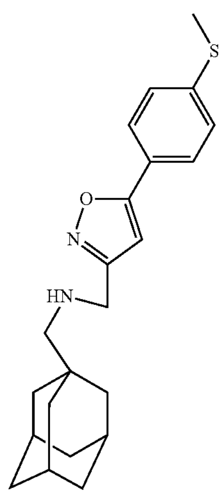 [SMILES: CSc1ccc(-c2cc(CNCC34CC5CC(CC(C5)C3)C4)no2)cc1] | B | A | ND |
| 41b | M2WJ452-1 | 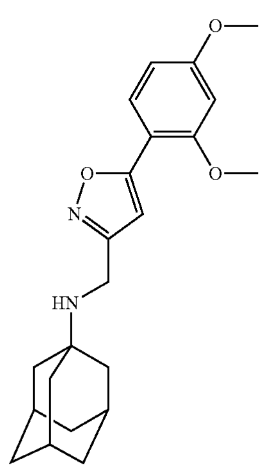 [SMILES: COc1ccc(-c2cc(CNC34CC5CC(CC(C5)C3)C4)no2)c(OC)c1] | B | A | ND |

TABLE 3-continued

| Example # | Batch External ID | Structure | S31 OOcyte Inhibition at 100 uM (%) | S31N OOcyte Inhibition at 100 uM (%) | V27A OOcyte Inhibition at 100 uM (%) |
|---|---|---|---|---|---|
| 42b | M2WJ454-1 | 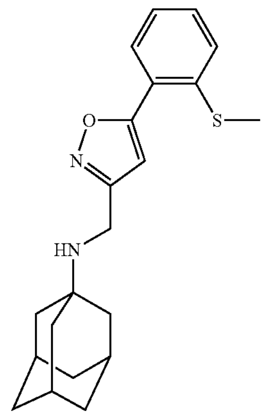 [SMILES: CSc1ccccc1-c1cc(CNC23CC4CC(CC(C4)C2)C3)no1] | B | A | ND |
| 43b | M2WJ455-1 | 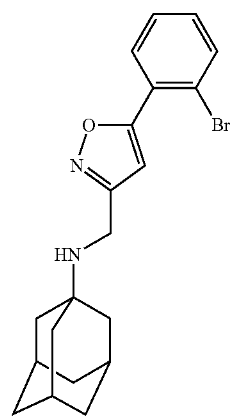 [SMILES: Brc1ccccc1-c1cc(CNC23CC4CC(CC(C4)C2)C3)no1] | B | A | ND |
| 44b | M2WJ456-1 | 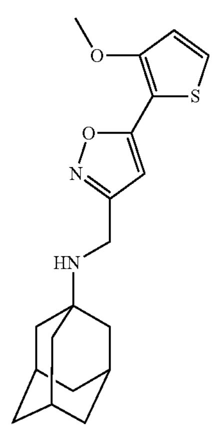 [SMILES: COc1ccsc1-c1cc(CNC23CC4CC(CC(C4)C2)C3)no1] | B | A | ND |

TABLE 3-continued
| Example # | Batch External ID | Structure | S31 OOcyte Inhibition at 100 uM (%) | S31N OOcyte Inhibition at 100 uM (%) | V27A OOcyte Inhibition at 100 uM (%) |
|---|---|---|---|---|---|
| 45b | M2WJ457-1 | 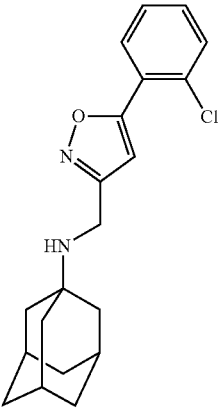 | B | A | ND |
| 46b | M2WJ458-1 | 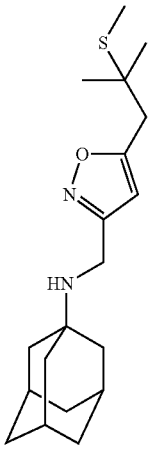 [SMILES: CSC(C)(C)Cc1cc(CNC23CC4CC(CC(C4)C2)C3)no1] | B | A | ND |
| 47b | BC097 | 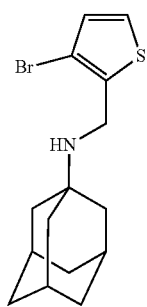 [SMILES: Brc1ccsc1CNC12CC3CC(CC(C3)C1)C2] | A | B | ND |

TABLE 3-continued
| Example # | Batch External ID | Structure | S31 OOcyte Inhibition at 100 uM (%) | S31N OOcyte Inhibition at 100 uM (%) | V27A OOcyte Inhibition at 100 uM (%) |
|---|---|---|---|---|---|
| 48b | BC119 | 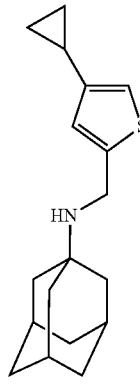 | B | A | ND |
| 49b | BC120 | 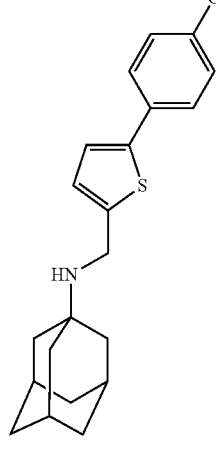 | B | A | ND |
| 50b | BC121 | 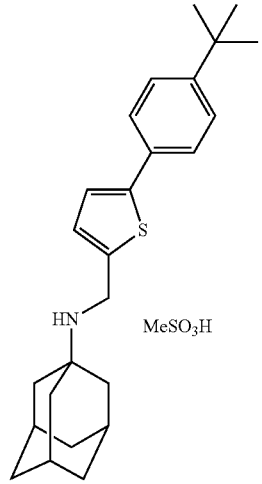 [SMILES: "MeSO3H" ; CC(C)(C)c1ccc(-c2ccc(CNC34CC5CC(CC(C5)C3)C4)s2)cc1] | B | A | ND |

TABLE 3-continued

| Example # | Batch External ID | Structure | S31 OOcyte Inhibition at 100 uM (%) | S31N OOcyte Inhibition at 100 uM (%) | V27A OOcyte Inhibition at 100 uM (%) |
|---|---|---|---|---|---|
| 51b | BC070 | 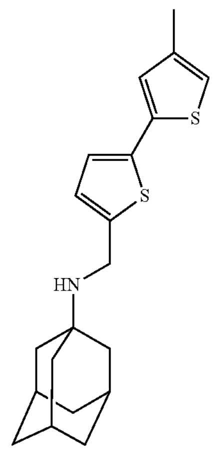 [SMILES: Cc1csc(-c2ccc(CNC34CC5CC(CC(C5)C3)C4)s2)c1] | B | A | ND |
| 52b | BC071 | 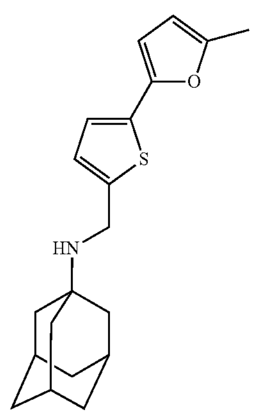 [SMILES: Cc1ccc(-c2ccc(CNC34CC5CC(CC(C5)C3)C4)s2)o1] | B | A | ND |
| 53b | Hij411-1/ JZW123 | 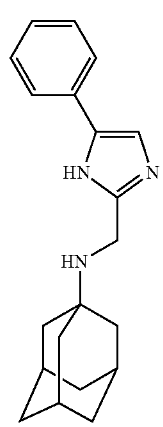 [SMILES: c1ccc(-c2cnc(CNC34CC5CC(CC(C5)C3)C4)[nH]2)cc1] | B | A | ND |

TABLE 3-continued

| Example # | Batch External ID | Structure | S31 OOcyte Inhibition at 100 uM (%) | S31N OOcyte Inhibition at 100 uM (%) | V27A OOcyte Inhibition at 100 uM (%) |
|---|---|---|---|---|---|
| 54b | Hij372-1 | 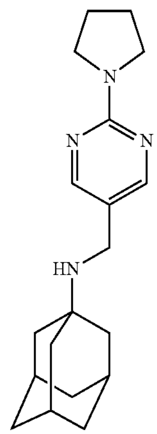 [SMILES: c1nc(N2CCCC2)ncc1CNC12CC3CC(CC(C3)C1)C2] | B | A | ND |
| 55b | Hij374-1 | 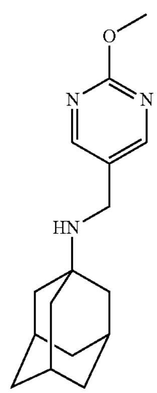 [SMILES: COc1ncc(CNC23CC4CC(CC(C4)C2)C3)cn1] | B | A | ND |
| 56b | Hij381-1 | 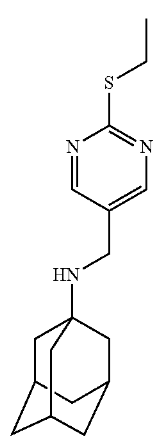 [SMILES: CCSc1ncc(CNC23CC4CC(CC(C4)C2)C3)cn1] | B | A | ND |

TABLE 3-continued

| Example # | Batch External ID | Structure | S31 OOcyte Inhibition at 100 uM (%) | S31N OOcyte Inhibition at 100 uM (%) | V27A OOcyte Inhibition at 100 uM (%) |
|---|---|---|---|---|---|
| 57b | Hij405-1 | 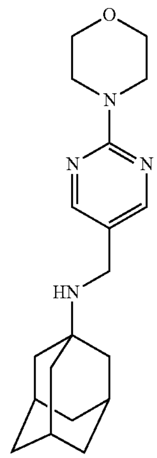 [SMILES: c1nc(N2CCOCC2)ncc1CNC12CC3CC(CC(C3)C1)C2] | B | A | ND |
| 58b | Hij382-1 | 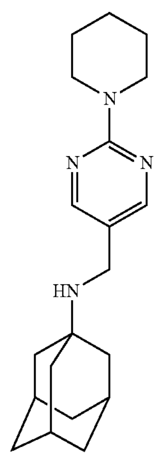 [SMILES: c1nc(N2CCCCC2)ncc1CNC12CC3CC(CC(C3)C1)C2] | B | A | ND |
| 59b | WFD108-1 | 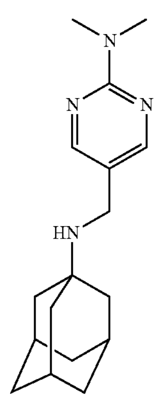 [SMILES: CN(C)c1ncc(CNC23CC4CC(CC(C4)C2)C3)cn1] | B | A | ND |

TABLE 3-continued

| Example # | Batch External ID | Structure | S31 OOcyte Inhibition at 100 uM (%) | S31N OOcyte Inhibition at 100 uM (%) | V27A OOcyte Inhibition at 100 uM (%) |
|---|---|---|---|---|---|
| 60b | Hij415-1 | 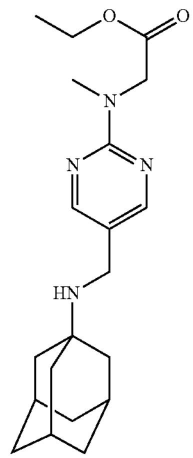 [SMILES: CCOC(=O)CN(C)c1ncc(CNC23CC4CC(CC(C4)C2)C3)cn1] | B | A | ND |
| 61b | Hij414-1 | 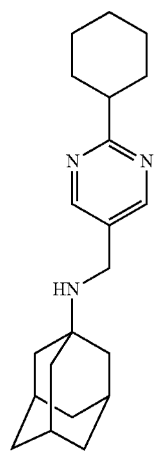 [SMILES: c1nc(C2CCCCC2)ncc1CNC12CC3CC(CC(C3)C1)C2] | B | A | ND |
| 62b | Hij416-1 | 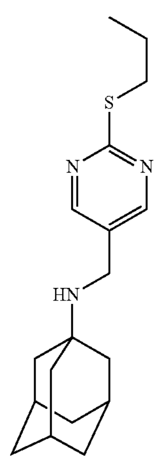 [SMILES: CCCSc1ncc(CNC23CC4CC(CC(C4)C2)C3)cn1] | B | A | ND |

TABLE 3-continued
| Example # | Batch External ID | Structure | S31 OOcyte Inhibition at 100 uM (%) | S31N OOcyte Inhibition at 100 uM (%) | V27A OOcyte Inhibition at 100 uM (%) |
|---|---|---|---|---|---|
| 63b | Hij417-1 | 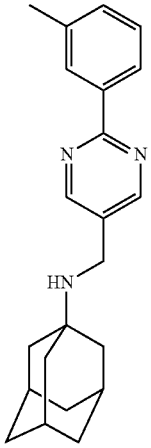 [SMILES: Cc1cccc(-c2ncc(CNC34CC5CC(CC(C5)C3)C4)cn2)c1] | B | A | ND |
| 64b | Hij406-1 | 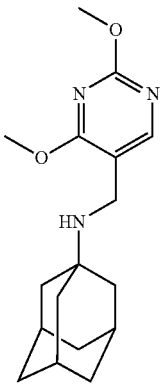 | B | B | ND |
| 65b | IMX760 | 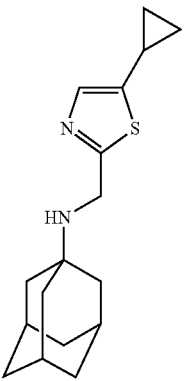 | B | A | ND |

TABLE 3-continued

| Example # | Batch External ID | Structure | S31 OOcyte Inhibition at 100 uM (%) | S31N OOcyte Inhibition at 100 uM (%) | V27A OOcyte Inhibition at 100 uM (%) |
|---|---|---|---|---|---|
| 66b | Imx747 | 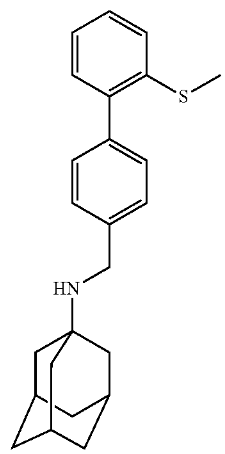 [SMILES: CSc1ccccc1-c1ccc(CNC23CC4CC(CC(C4)C2)C3)cc1] | B | A | TBD |
| 67b | IMX745 | 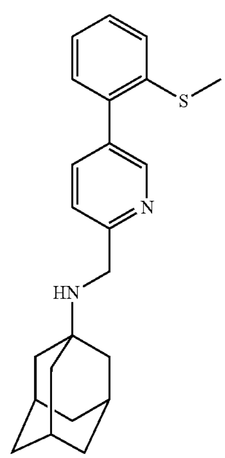 [SMILES: CSc1ccccc1-c1ccc(CNC23CC4CC(CC(C4)C2)C3)nc1] | A | A | ND |
| 68b | IMX746 | 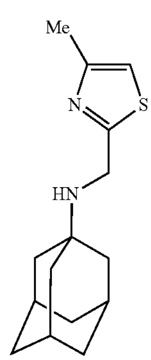 [SMILES: Cc1csc(CNC23CC4CC(CC(C4)C2)C3)n1] | A | A | ND |

TABLE 3-continued

| Example # | Batch External ID | Structure | S31 OOcyte Inhibition at 100 uM (%) | S31N OOcyte Inhibition at 100 uM (%) | V27A OOcyte Inhibition at 100 uM (%) |
|---|---|---|---|---|---|
| 69b | IMX744 | 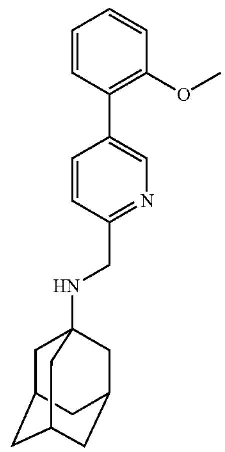 [SMILES: COc1ccccc1-c1ccc(CNC23CC4CC(CC(C4)C2)C3)nc1] | B | A | ND |
| 70b | IMX747 | 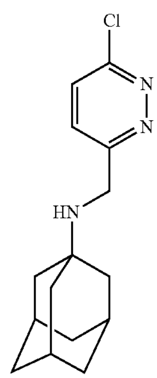 [SMILES: Clc1ccc(CNC23CC4CC(CC(C4)C2)C3)nn1] | A | B | ND |
| 71b | IMX748 | 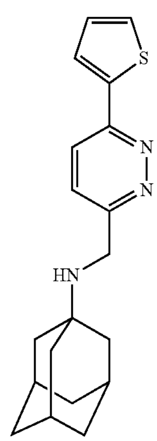 | B | A | ND |

TABLE 3-continued

| Example # | Batch External ID | Structure | S31 OOcyte Inhibition at 100 uM (%) | S31N OOcyte Inhibition at 100 uM (%) | V27A OOcyte Inhibition at 100 uM (%) |
|---|---|---|---|---|---|
| 72b | IMX755 | 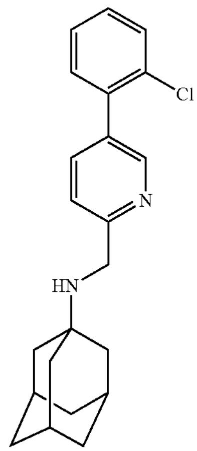 [SMILES: Clc1ccccc1-c1ccc(CNC23CC4CC(CC(C4)C2)C3)nc1] | B | A | ND |
| 73b | IMX756 | 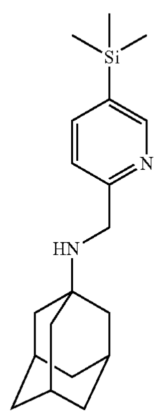 [SMILES: C[Si](C)(C)c1ccc(CNC23CC4CC(CC(C4)C2)C3)nc1] | ND | ND | ND |
| 74b | IMX757 | 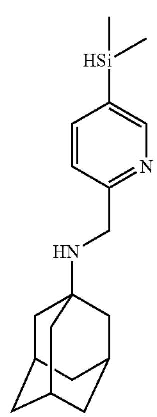 | ND | ND | ND |

TABLE 3-continued

| Example # | Batch External ID | Structure | S31 OOcyte Inhibition at 100 uM (%) | S31N OOcyte Inhibition at 100 uM (%) | V27A OOcyte Inhibition at 100 uM (%) |
|---|---|---|---|---|---|
| 75b | IMX734 | 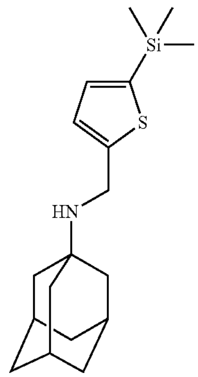 | B | A | ND |
| 76b | IMX742 | 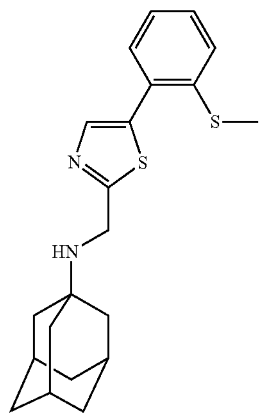 [SMILES: CSc1ccccc1-c1cnc(CNC23CC4CC(CC(C4)C2)C3)s1] | B | A | ND |
| 77b | IMX00751 | 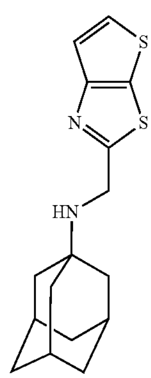 | B | A | ND |
| 78b | IMX738 | 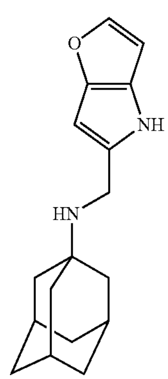 [SMILES: c1cc2[nH]c(CNC34CC5CC(CC(C5)C3)C4)cc2o1] | A | A | ND |

TABLE 3-continued
| Example # | Batch External ID | Structure | S31 OOcyte Inhibition at 100 uM (%) | S31N OOcyte Inhibition at 100 uM (%) | V27A OOcyte Inhibition at 100 uM (%) |
|---|---|---|---|---|---|
| 79b | IMX724 | 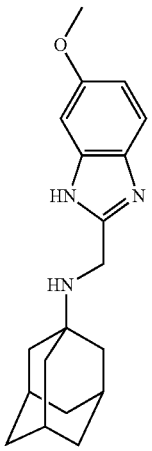 [SMILES: COc1ccc2nc(CNC34CC5CC(CC(C5)C3)C4)[nH]c2c1] | B | A | ND |
| 80b | IMX725 | 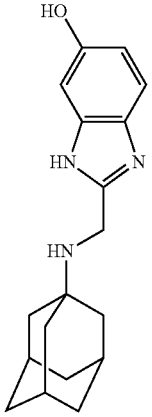 [SMILES: Oc1ccc2nc(CNC34CC5CC(CC(C5)C3)C4)[nH]c2c1] | ND | ND | ND |
| 81b | IMX722 | 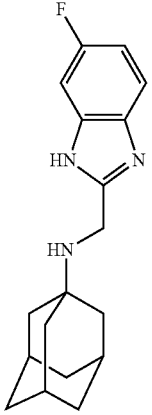 [SMILES: Fc1ccc2nc(CNC34CC5CC(CC(C5)C3)C4)[nH]c2c1] | ND | ND | ND |

TABLE 3-continued
| Example # | Batch External ID | Structure | S31 OOcyte Inhibition at 100 uM (%) | S31N OOcyte Inhibition at 100 uM (%) | V27A OOcyte Inhibition at 100 uM (%) |
|---|---|---|---|---|---|
| 82b | M2WJ418-1 | 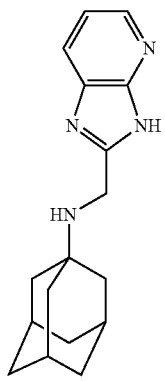 [SMILES: c1cnc2[nH]c(CNC34CC5CC(CC(C5)C3)C4)nc2c1] | B | A | ND |
| 83b | IMX715 | 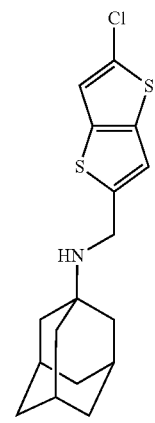 | TBD | TBD | TBD |
| 84b | M2WJ427-1 | 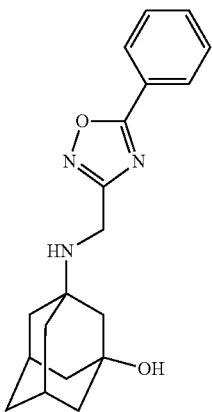 [SMILES: OC12CC3CC(C1)CC(NCc1noc(-c4ccccc4)n1)(C3)C2] | B | A | ND |

TABLE 3-continued

| Example # | Batch External ID | Structure | S31 OOcyte Inhibition at 100 uM (%) | S31N OOcyte Inhibition at 100 uM (%) | V27A OOcyte Inhibition at 100 uM (%) |
|---|---|---|---|---|---|
| 85b | M2WJ433-1 | *(isopropyl-isoxazole-CH2-NH-adamantane-OH)* | B | A | ND |
| 86b | M2WJ429-1 | *(cyclohexyl-oxadiazole-CH2-NH-adamantane-OH)* | B | A | ND |

VII

*(R-phenyl-Linker-NH-adamantane)*

| 87b | Hij341-1 | *(thiophene-C(O)-CH2-NH-adamantane)* | A | B | ND |

TABLE 3-continued
| Example # | Batch External ID | Structure | S31 OOcyte Inhibition at 100 uM (%) | S31N OOcyte Inhibition at 100 uM (%) | V27A OOcyte Inhibition at 100 uM (%) |
|---|---|---|---|---|---|
| 88b | Hij350-1 | 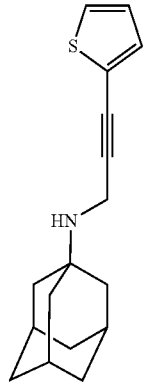 | B | A | ND |
| 89b | IMX00737 | 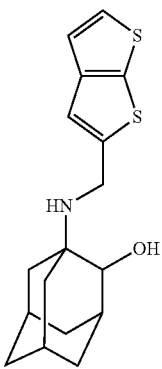 [SMILES: OC1C2CC3CC(C2)CC1(NCc1cc2ccsc2s1)C3] | | | ND |
| 90b | MSWJ450-1 | 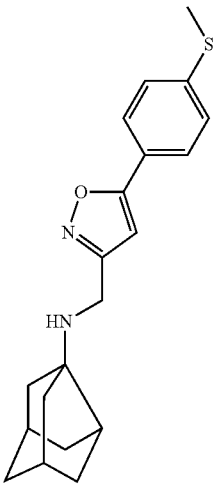 [SMILES: CSc1ccc(-c2cc(CNC34CC5CC(CC3C5)C4)no2)cc1] | B | A | ND |
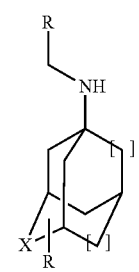

TABLE 3-continued
| Example # | Batch External ID | Structure | S31 OOcyte Inhibition at 100 uM (%) | S31N OOcyte Inhibition at 100 uM (%) | V27A OOcyte Inhibition at 100 uM (%) |
|---|---|---|---|---|---|
| 91b | MSWJ453-1 | 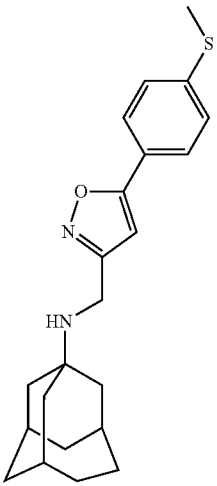 [SMILES: CSc1ccc(-c2cc(CNC34CC5CCC(CC(C5)C3)C4)no2)cc1] | B | A | ND |
| 92b | IMX800 | 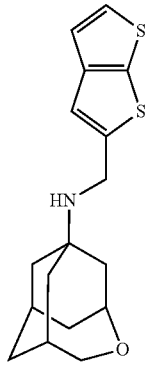 [SMILES: c1cc2cc(CNC34CC5COC(CC(C5)C3)C4)sc2s1] | ND | ND | ND |
| 93b | IMX797 | 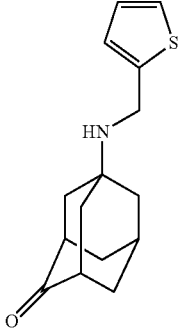 | ND | ND | ND |

TABLE 3-continued
| Example # | Batch External ID | Structure | S31 OOcyte Inhibition at 100 uM (%) | S31N OOcyte Inhibition at 100 uM (%) | V27A OOcyte Inhibition at 100 uM (%) |
|---|---|---|---|---|---|
| 94b | IMX798 | 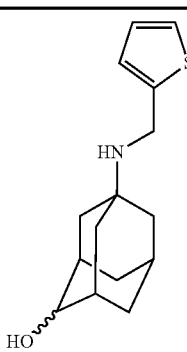 | ND | ND | ND |
| 95b | IMX799 | 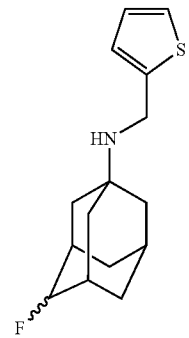 [SMILES: FC1C2CC3CC1CC(NCc1cccs1)(C3)C2] | ND | ND | ND |
What is claimed:
1. A compound that is selected from
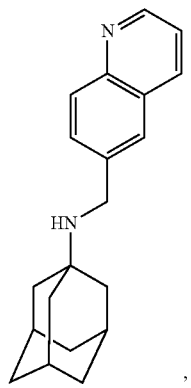 [SMILES: c1cnc2ccc(CNC34CC5CC(CC(C5)C3)C4)cc2c1]
,
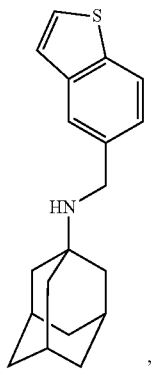
,

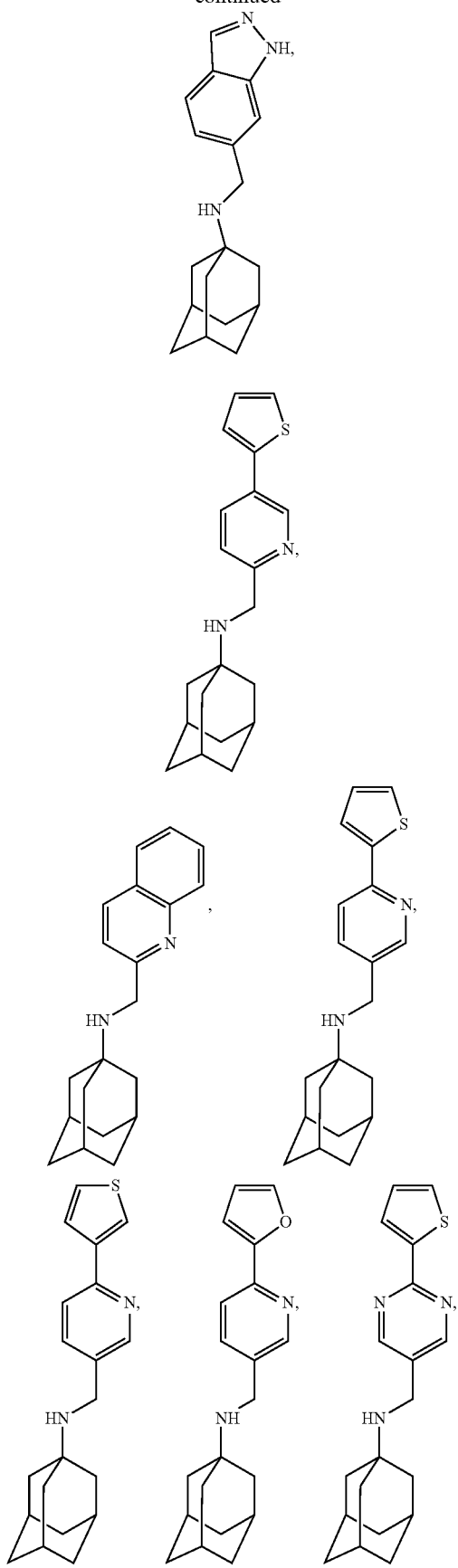
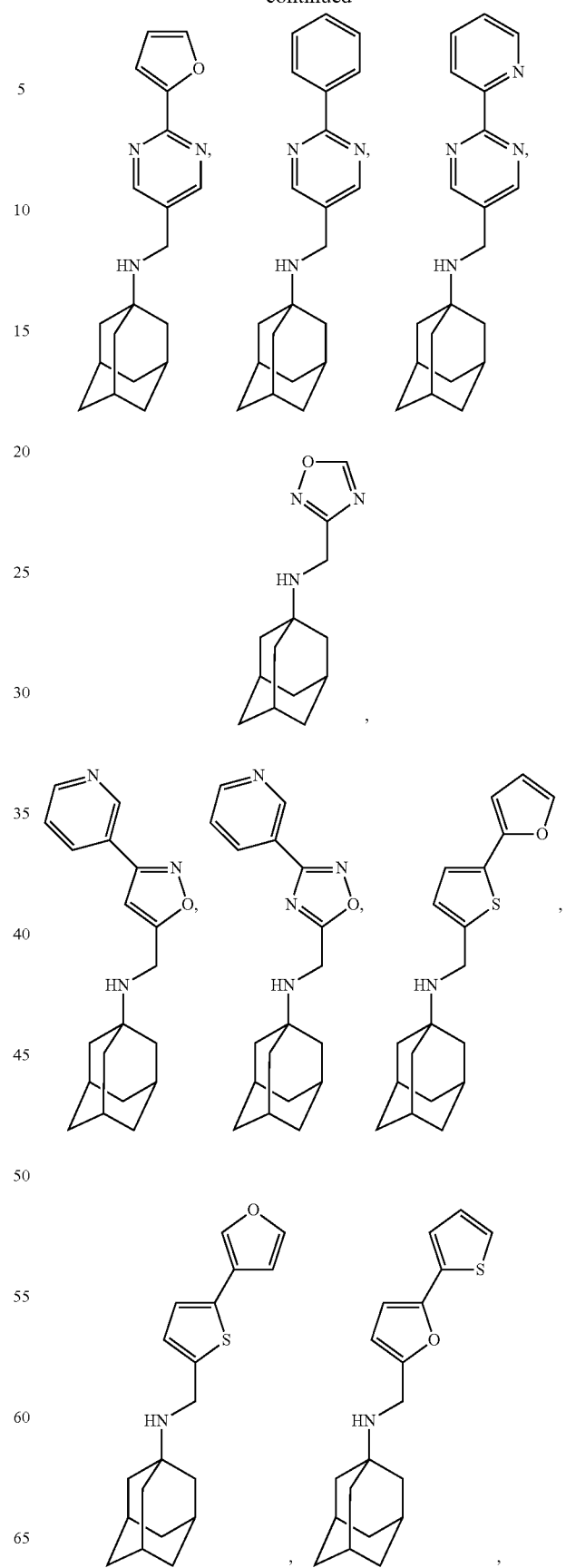

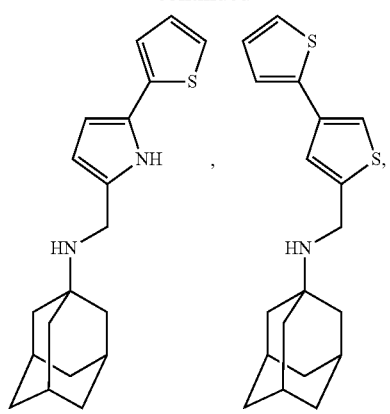
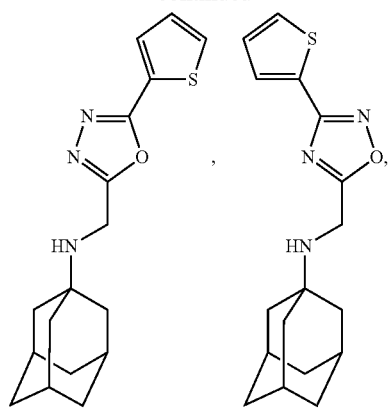
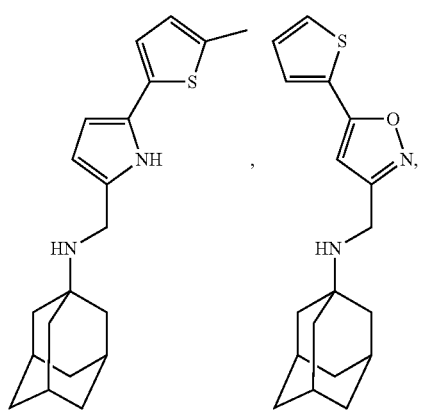
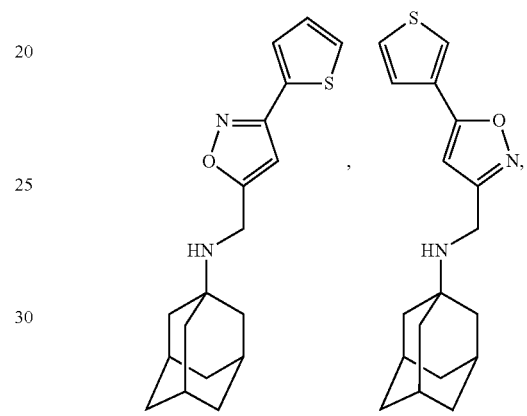
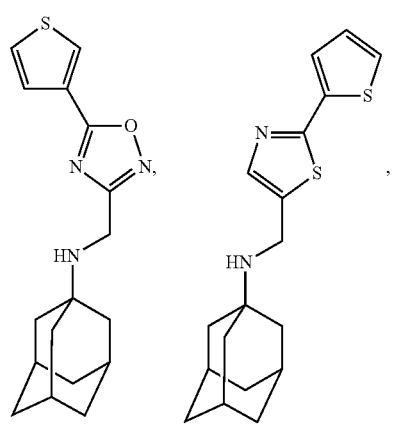
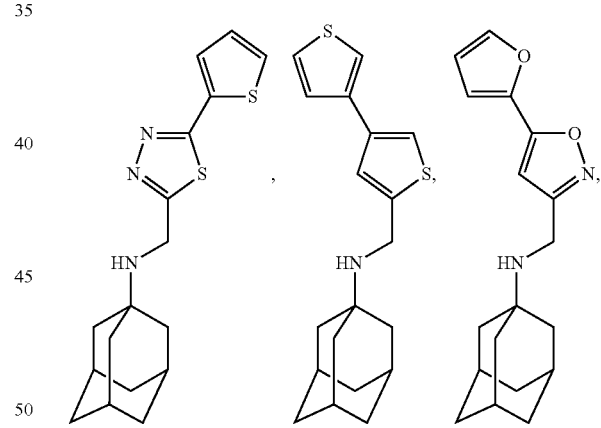
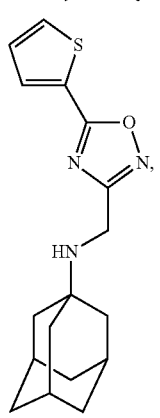
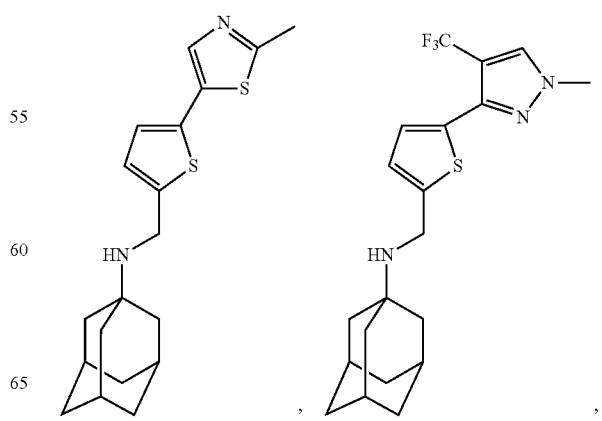

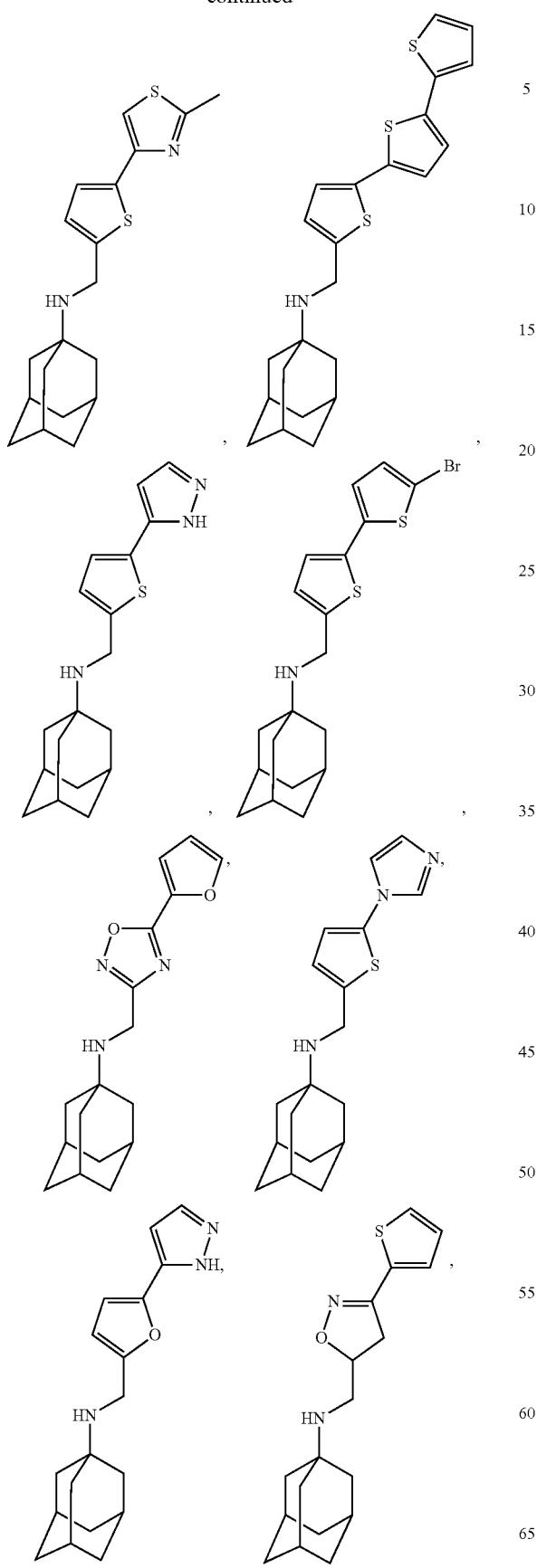
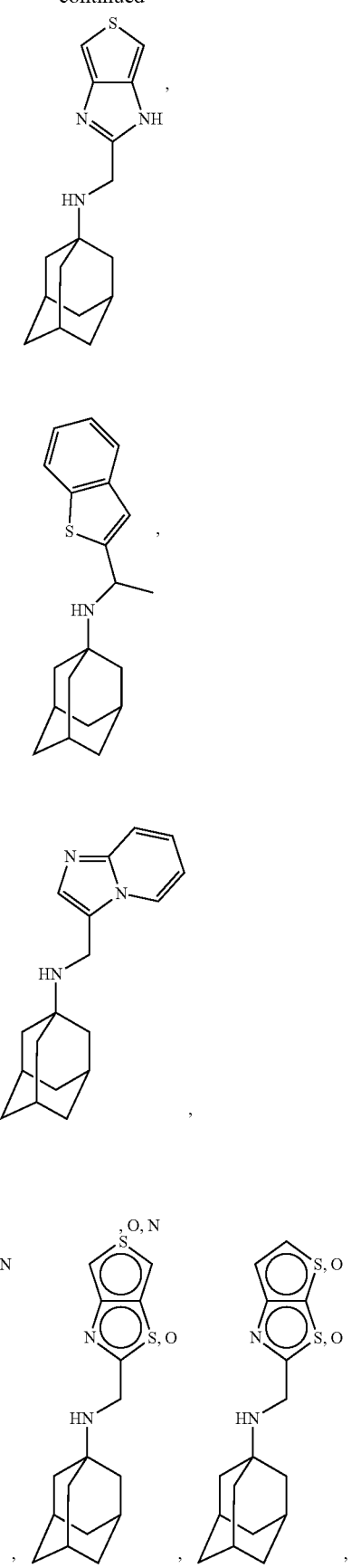

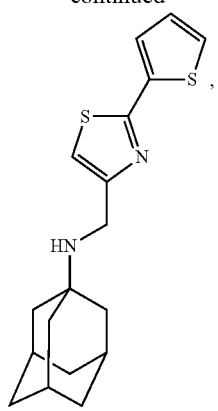
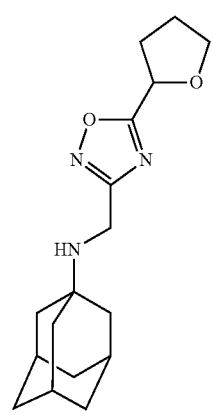
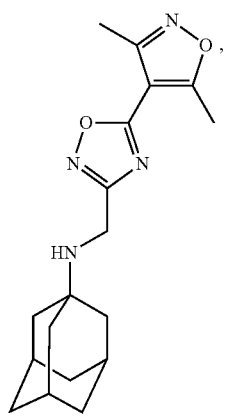
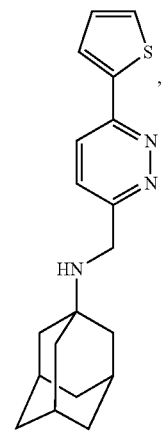 [SMILES: c1csc(-c2ccc(CNC34CC5CC(CC(C5)C3)C4)nc2)c1]
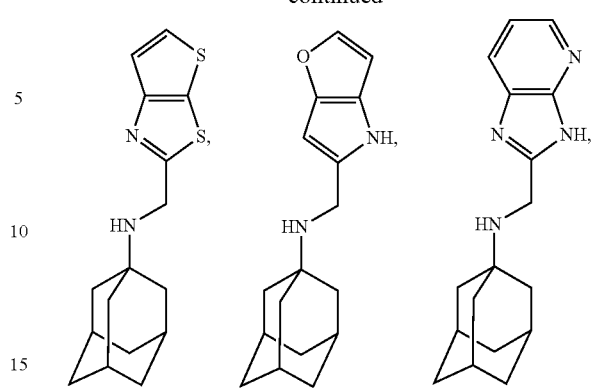
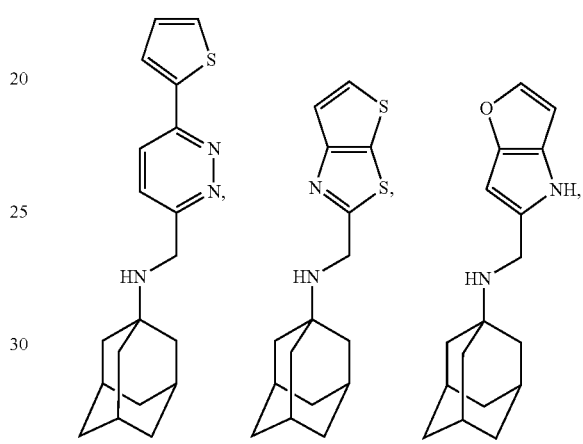
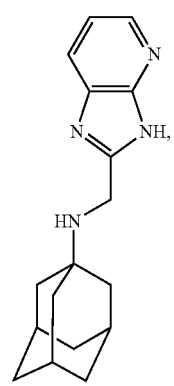
and
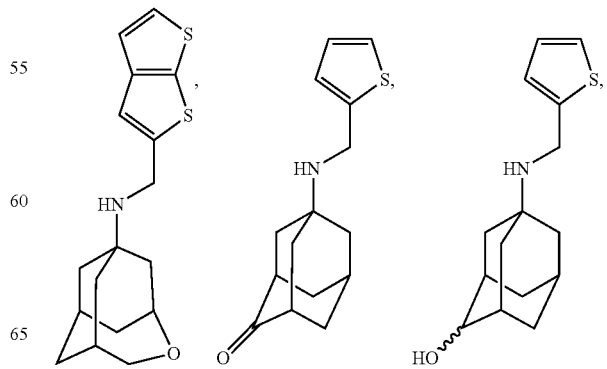

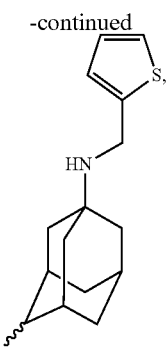
or a stereoisomer, isotopically substituted analogue, or pharmaceutically acceptable salt thereof.
* * * * *

UNITED STATES PATENT AND TRADEMARK OFFICE
CERTIFICATE OF CORRECTION

PATENT NO. : 9,884,832 B2
APPLICATION NO. : 14/363116
DATED : February 6, 2018
INVENTOR(S) : William F. DeGrado et al.

Page 1 of 1

It is certified that error appears in the above-identified patent and that said Letters Patent is hereby corrected as shown below:

Column 1, Lines 18-22, delete "Research leading to the disclosed invention was funded, in part, by the U.S. National Institutes of Health, Bethesda, Md., GM56423 and AI74571 (both to William F. DeGrado). Accordingly, the United States Government may have rights in the invention described herein." and insert --This invention was made with government support under grant number GM056423 and AI074571 awarded by the National Institutes of Health. The government has certain rights in the invention.--.

Signed and Sealed this
Twelfth Day of February, 2019

Andrei Iancu
*Director of the United States Patent and Trademark Office*